United States Patent [19]
Gordon et al.

[11] Patent Number: 5,760,036
[45] Date of Patent: Jun. 2, 1998

[54] AMINEDIOL PROTEASE INHIBITORS

[75] Inventors: Eric M. Gordon, Palo Alto, Calif.; Joel C. Barrish, Holland, Pa.; Gregory S. Bisacchi, Lawrenceville, N.J.; Chong-Oing Sun, East Windsor, N.J.; Joseph A. Tino, Lawrenceville, N.J.; Gregory D. Vite, Trenton, N.J.; Robert Zahler, Pennington, N.J.

[73] Assignee: E. R. Squibb & Sons, Inc., Princton, N.J.

[21] Appl. No.: 455,295

[22] Filed: May 31, 1995

Related U.S. Application Data

[60] Division of Ser. No. 79,978, Jun. 25, 1993, Pat. No. 5,559, 256, which is a continuation-in-part of Ser. No. 927,027, Aug. 6, 1992, abandoned, which is a continuation-in-part of Ser. No. 916,916, Jul. 20, 1992, abandoned.

[51] Int. Cl.$^6$ .................. A61K 31/445; A61K 31/535; C07D 295/192
[52] U.S. Cl. .................. 514/237.5; 514/330; 544/168; 546/226
[58] Field of Search .................. 544/168; 514/237.5, 514/330; 546/226

[56] References Cited

U.S. PATENT DOCUMENTS

| | | |
|---|---|---|
| 2,046,720 | 7/1936 | Bottoms . |
| 2,715,631 | 8/1955 | Croxall et al. . |
| 4,483,850 | 11/1984 | Patchett et al. . |
| 4,528,282 | 7/1985 | Preston et al. . |
| 4,602,002 | 7/1986 | Patchett et al. . |
| 4,644,055 | 2/1987 | Kettner et al. . |
| 4,665,055 | 5/1987 | Evans . |
| 4,719,288 | 1/1988 | Fuhrer et al. . |
| 4,727,060 | 2/1988 | Buhlmayer et al. . |
| 4,855,286 | 8/1989 | Wagner et al. . |
| 5,098,924 | 3/1992 | Poss . |
| 5,142,056 | 8/1992 | Kempe et al. . |
| 5,157,041 | 10/1992 | Handa et al. . |
| 5,169,952 | 12/1992 | Askin et al. . |
| 5,196,438 | 3/1993 | Martin et al. . |

FOREIGN PATENT DOCUMENTS

| | | |
|---|---|---|
| 89/46785 | 6/1990 | Australia . |
| 90/63221 | 4/1991 | Australia . |
| 90/68025 | 6/1991 | Australia . |
| 93/4468 | 10/1993 | Australia . |
| 2072785 | 1/1993 | Canada . |
| 2075547 | 2/1993 | Canada . |
| 0173481 A2 | 3/1986 | European Pat. Off. . |
| 229667 | 7/1987 | European Pat. Off. . |
| 0264795 A2 | 4/1988 | European Pat. Off. . |
| 0278158 A2 | 8/1988 | European Pat. Off. . |
| 0312157 A2 | 4/1989 | European Pat. Off. . |
| 0312158 A2 | 4/1989 | European Pat. Off. . |
| 0373549 A2 | 6/1989 | European Pat. Off. . |
| 0337714 A2 | 10/1989 | European Pat. Off. . |
| 0342541 A2 | 11/1989 | European Pat. Off. . |

(List continued on next page.)

OTHER PUBLICATIONS

Annual Drug Data Report, p. 801 (1987).
Billich et al., Arch. of Biochem. and Biophys., 290, pp. 186–190 (19910.
Blumenstein, et al., Synthetic Non–Peptide Inhibitors of HIV Protease; Biochemical and Biophysical Research Communications; vol. 163, No. 2, pp. 980–987 (1989).
Bone, et al., X–ray Crystal Structure of the HIV Protease Complex with L–700,417, an Inhibitor with Pseudo $C_2$ Symmetry; J. Am. Chem. Soc., 113, pp. 9382–9384 (1991).
Chenera, et al., Syntheis of $C_2$–Symmetric and Pseudosymmetric HIV–1 Protease Inhibitors from D–Mannitol and D–Arabitrol; Bioorganic & Medicinal Chemistry Letters, vol 1, No. 4, pp. 219–222 (1991).
Connolly, et al., Antiretroviral Therapy: Strategies Beyond Single–Agent Reverse Transcriptase Inhibition; Antimicrobial Agents and Chemotherapy, vol. 36, No. 3, pp. 509–520 (1992).
Copeland, et al., Substitution of Proline with Pipecolic Acid at the Scissile Bond Converts a Peptide Substrate of HIV Proteinase Into A Selective Inhibitor; Biochemical and Biophysical Research Communications; vol. 169, No. 1, pp. 310–314 (1990).
DeCamp, et al., Specific Inhibition of HIV–1 Protease by Boronated Porphyrins; J. Med. Chem., 35, pp. 3426–3428 (1992).
DesJarlais, et al., Structure–based Design of Nonpeptide Inhibitors Specific for the Human Immunodeficiency Virus 1 Protease; Proc. Natl. Acad. Sci., vol. 87, pp. 6644–6648 (1990).
deSolms, et al., Design and Synthesis of HIV Protease Inhibitors. Variations of the Carboxy Terminus of the HIV Protease Inhibitors L–682,679; J. Med. Chem., 34, pp. 2852–2857 (1991).
Dombrowski, et al., L–696,474, A Novel Cytochalasin as an Inhibitor of HIV–1 Protease 1. The Producing Organism and its Fermentation; J. of Antibiotics, vol. 45, No. 5, p. 671 (1992).
Dryer, et al., Hydroxyethylene Isostere Inhibitors of Human Immunodeficiency Virus–1 Protease: Structure–Activity Analysis Using Enzyme Kinetics, X–ray Crystallography, and Infected T–Cell Assays; Biochemistry, 31, pp. 6646–6659 (1992).
Dreyer, et al., Inhibition of Human Immunodeficiency Virus 1 Protease In vitro: Rational design of substrate analogue inhibitors; Proc. Natl. Acad. Sci., vol. 86, 1989; pp. 9752–9756 (1989).
Dwyer, et al., Amino Hemiketal Inhibitors of Aspartic Proteases, No. 11, American Chemical Society Meeting, San Francisco (Mar., 1992), abstract handout (2 pages).

(List continued on next page.)

Primary Examiner—Robert W. Ramsuer
Attorney, Agent, or Firm—Suzanne E. Babajko

[57] ABSTRACT

Novel aminediol compounds, pharmaceutical compositions containing these compounds, and methods of using these compounds in inhibiting retroviral protease, particularly useful in the treatment and/or prevention of HIV infection (AIDS).

16 Claims, No Drawings

FOREIGN PATENT DOCUMENTS

| | | |
|---|---|---|
| 0346847 A2 | 12/1989 | European Pat. Off. |
| 0352000 A2 | 1/1990 | European Pat. Off. |
| 0356223 A2 | 2/1990 | European Pat. Off. |
| 0356796 A2 | 3/1990 | European Pat. Off. |
| 0357332 A2 | 3/1990 | European Pat. Off. |
| 0357510 A1 | 3/1990 | European Pat. Off. |
| 0361341 A2 | 4/1990 | European Pat. Off. |
| 0364804 A1 | 4/1990 | European Pat. Off. |
| 0372537 A2 | 6/1990 | European Pat. Off. |
| 0374097 A2 | 6/1990 | European Pat. Off. |
| 0374098 A2 | 6/1990 | European Pat. Off. |
| 0386611 A2 | 9/1990 | European Pat. Off. |
| 0387231 A2 | 9/1990 | European Pat. Off. |
| 0393445 A2 | 10/1990 | European Pat. Off. |
| 0401675 A1 | 12/1990 | European Pat. Off. |
| 0401676 A1 | 12/1990 | European Pat. Off. |
| 0402646 A1 | 12/1990 | European Pat. Off. |
| 410260 | 1/1991 | European Pat. Off. |
| 416373 | 3/1991 | European Pat. Off. |
| 0428849 A2 | 5/1991 | European Pat. Off. |
| 0432595 A1 | 6/1991 | European Pat. Off. |
| 0432694 A2 | 6/1991 | European Pat. Off. |
| 0432695 A2 | 6/1991 | European Pat. Off. |
| 0434365 A2 | 6/1991 | European Pat. Off. |
| 0435059 A1 | 7/1991 | European Pat. Off. |
| 0437729 A2 | 7/1991 | European Pat. Off. |
| 0443559 A2 | 8/1991 | European Pat. Off. |
| 0443560 A2 | 8/1991 | European Pat. Off. |
| 0443573 A2 | 8/1991 | European Pat. Off. |
| 0456185 A2 | 11/1991 | European Pat. Off. |
| 0459465 A2 | 12/1991 | European Pat. Off. |
| 0472077 A2 | 2/1992 | European Pat. Off. |
| 0480714 A2 | 4/1992 | European Pat. Off. |
| 0482797 A1 | 4/1992 | European Pat. Off. |
| 0486948 A2 | 5/1992 | European Pat. Off. |
| 0490667 A2 | 6/1992 | European Pat. Off. |
| 0492136 A2 | 7/1992 | European Pat. Off. |
| 0498680 A1 | 8/1992 | European Pat. Off. |
| 0498784 | 8/1992 | European Pat. Off. |
| 521686 | 1/1993 | European Pat. Off. |
| 521827 | 1/1993 | European Pat. Off. |
| 528661 | 2/1993 | European Pat. Off. |
| 534511 | 3/1993 | European Pat. Off. |
| 541168 | 5/1993 | European Pat. Off. |
| 560268 | 9/1993 | European Pat. Off. |
| 560269 | 9/1993 | European Pat. Off. |
| 3721855 A1 | 9/1988 | Germany. |
| 3829594 A1 | 3/1990 | Germany. |
| 3840452 A1 | 6/1990 | Germany. |
| 4030350 A1 | 4/1991 | Germany. |
| 4039569 A1 | 6/1991 | Germany. |
| 4126485 | 2/1993 | Germany. |
| 83/3161 | 12/1983 | South Africa. |
| WO89/10752 | 11/1989 | WIPO. |
| WO89/10920 | 11/1989 | WIPO. |
| WO90/00399 | 1/1990 | WIPO. |
| 90/09191 | 8/1990 | WIPO. |
| WO91/10442 | 7/1991 | WIPO. |
| WO91/18866 | 12/1991 | WIPO. |
| WO92/00750 | 1/1992 | WIPO. |
| WO92/00956 | 1/1992 | WIPO. |
| WO92/06996 | 4/1992 | WIPO. |
| WO92/08688 | 5/1992 | WIPO. |
| WO92/08698 | 5/1992 | WIPO. |
| WO92/08699 | 5/1992 | WIPO. |
| WO92/08700 | 5/1992 | WIPO. |
| WO92/08701 | 5/1992 | WIPO. |
| WO92/09297 | 6/1992 | WIPO. |
| WO92/12123 | 8/1992 | WIPO. |
| WO92/14696 | 9/1992 | WIPO. |
| WO 92/17490 | 10/1992 | WIPO. |
| WO 93/01828 | 2/1993 | WIPO. |
| WO 93/02057 | 2/1993 | WIPO. |
| WO 93/04043 | 3/1993 | WIPO. |
| WO 93/18006 | 9/1993 | WIPO. |
| WO 93/23388 | 11/1993 | WIPO. |
| WO 94/02149 | 2/1994 | WIPO. |
| WO94/13629 | 6/1994 | WIPO. |

OTHER PUBLICATIONS

Erickson, et al., Design, Activity and 2.8 A Crystal Structure of a $C_2$ Symmetric Inhibitor Complexed to HIV–1 Protease; *Science*, vol. 249, pp. 527–533 (1990).

Ghosh, et al., Stereocontrolled Synthesis of HIV–1 Protease Inhibitors with $C_2$–Axis of Symmetry; *Tetrahedron Letters*, vol. 32, No. 41, pp. 5729–5732 (1991).

Goldman et al., L–696,229 Specifically Inhibits Human Immunodeficiency Virus Type 1 Reverse Transcriptase and Possesses Antiviral Activity In Vitro, *Antimicrobial Agents and Chemotherapy*, pp. 1019–1023 (1992) (abstract only).

Grobelny, et al., Selective Phosphinate Transition–State Analogue Inhibitors of the Protease of Human Immunodeficiency Virus; *Biochemical and Biophysical Research Communications;* vol. 169, No. 3, pp. 1111–1116 (1990).

Hui, et al., A Rational Approach in the Search for Potent Inhibitors Against HIV proteinase; *The FASEB Journal*, vol. 5, pp. 2606–2610 (1991).

Humber, et al., Penicillin Derived $C_2$–Symmetric Dimmers as Novel Inhibitors of HIV–1 Proteinase, *J. Med. Chem.*, 35, pp. 3080–3081 (1992).

Ikeda, et al., $\Psi[PO_2\text{-}CH_2N^+]$, a New Amide Bond Replacement: Potent Slow–Binding Inhibition of the HIV Protease, *J. Am. Chem. Soc.*, 114, pp. 7604–7606 (1992).

Kahn, et al., Examination of HIV–1 Protease Secondary Structure Specificity Using Conformationally Constrained Inhibitors; *J. Med. Chem.*, 34, pp. 3395–3399 (1991).

Kempf, et al., Structure–Based, $C_2$ Symmetric Inhibitors of HIV Protease; *J. Med. Chem.*, 33, pp. 2687–2689 (1990).

Kempf, et al., Antiviral and Pharmacokinetic Properties of $C_2$ Symmetric Inhibitors of the Human Immunodeficiency Virus Type 1 Protease; *Antimicrobial Agents and Chemotherapy*, vol. 35, No. 11, pp. 2209–2214 (1991).

Korant, et al., Virus–specified protease in poliovirus–infected HeLa cells; *Proc. Natl. Acad. Sci. USA*, vol. 76, No. 6, pp. 2992–2995 (1979).

Kotler, et al., Synthetic Peptides as Substrates and Inhibitors of a Retroviral Protease; *Proc. Natl. Acad. Sci.*, vol. 85, pp. 4185–4189 (1988).

Krohn, et al., Novel Binding Mode of Highly Potent HIV–Proteiinase Inhibitors Incorporating the (R)–Hydroxyethylamine Isostere; *J. Med. Chem.*, 34, pp. 3340–3342 (1991).

Lambert, et al., Human Immunodeficiency Virus Type 1 Protease Inhibitors Irreversibly Block Infectivity of Purified Virions from Chronically Infected Cells; *Antimicrobial Agents and Chemotherapy*, pp. 982–988 (1992) (abstract only).

Lingham, et al., HIV–1 Protease Inhibitory Activity of L–694,746, A Novel Metabolite of L–689,502; *Biochemical and Biophysical Research Comm.*, vol. 181, No. 3, pp. 1456–1461 (1991).

Lingham, et al., L–696,474, A Novel Cytochalasin as an Inhibitor of HIV–1 Proteae III. Biological Acitivity; *J. of Antibiotics*, p. 686 (1992).

Lyle, et al., Benzocycloalkyl Amines as Novel C–Termini for HIV Protease Inhibitors; *J. Med. Chem.*, 34, pp. 1228–1230 (1991).

McLeod, et al., Phosphonamidates and Phosphonamidate Esters as HIV–1 Protease Inhibitors; *Bioorganic & Medicinal Chemistry Letters*, vol. 1, No. 11, pp. 653–658 (1991).

Mimoto, et al., KNI–102 A Novel Tripeptide HIV Protease Inhibitor containing Allophenylnorstatine as a Transition-State Mimic; *Chem. Pharm. Bull.* vol. 39, No. 11, pp. 3088–3090 (1991).

Mimoto, et al., Rational Design and Synthesis of a Novel Class of Active Site-Targeted HIV Protease Inhibitors Containing a Hydroxymethylcarbonyl Isostere. Use of Phenylnorstatine or Allophenylnorstatine as a Transition-State Mimic; *Chem. Pharm. Bull.* vol. 39, No. 9, pp. 2465–2467 (1991).

Moore, et al., Peptide Substrates and Inhibitors of the HIV–1 Protease; *Biochemical and Biophysical Research Communications;* vol. 195, No. 2, pp. 420–425 (1989).

Ondeyka, et al., L–696,474, A Novel Cytochalasin as an Inhibitor of HIV–1 Protease II. Isolation and Structure; *J. of Antibiotics*, vol. 45, No. 5, p. 679 (1992).

Owens, et al., The Rapid Identification of HIV Protease Inhibitors Through the Synthesis and Screening of Defined Peptide Mixtures; *Biochemical and Biophysical Research Communications;* vol. 181, no. 1, pp. 402–408 (1991).

Peyman, et al., $C_2$–Symmetric Phosphinic Acid Inhibitors of HIV Protease; *Tetrahedron Letters*, vol. 33, No. 32, pp. 4549–4552 (1992).

Raju, et al., Substrate Analog Inhibitors of HIV–1 Protease Containing Phenylnorstatine as a Transition State Element; *Biochemical and Biophysical Research Communications;* vol. 180, No. 1, pp. 181–186 (1991).

Raju, et al., Investigating the Stereochemistry of Binding to HIV–1 Protease with Inhibitors Containing Isomers of 4–Amino–3–hydroxy–5–phenylpentanoic Acid, *Biochemical and Biophysical Research Communications*, vol. 180, No. 1, pp. 187–190 (1991).

Rich, et al., Hydroxyethylamine Analogues of the p17/;24 Substrate Cleavage Site Are Tight–Binding Inhibitors of HIV Protease; *J. Med. Chem.*, 33, pp. 1285–1288 (1990).

Rich, et al., Effect of Hydroxyl Group Configuration in Hydroxyethylamine Dipeptide Isosteres on HIV Protease Inhibition. Evidence for Multiple Binding Modes; *J. Med. Chem.*, 34, pp. 1222–1225 (1991).

Roberts, et al., Rational Design of Peptide–Based HIV Proteinase Inhibitors; *Science*, vol. 248, pp. 358–361 (1990).

Schramm, et al., Inhibition of HIV–1 Protease By Short Peptides Derived Fromt he Terminal Segments of the Protease; *Biochemical and Biophysical Research Comm.*, vol. 184, No. 2, pp. 980–985 (1992).

Sham, et al., Potent HIV–1 Protease Inhibitors with Antiviral Activities In Vitro; *Biochemical and Biophysical Research Communications;* vol. 175, No. 3, pp. 914–919 (1991).

Tam, et al., Intriguing Structure–Activity Relations Underlie the Potent Inhibition of HIV Protease by Norstatine–Based Peptides; *J. of Medicinal chemistry*, vol. 35, No. 7, pp. 1318–1320 (1992).

Thaisrivongs, et al., Inhibitors of the Protease from Human Immunodeficiency Virus: Design and Modeling of a Compound Containing a Dihydroxyethylene Isostere Insert with High Binding Affinity and Effective Antiviral Activity; *J. Med. Chem.*, 34, pp. 2344–2356 (1991).

Thompson, et al., Synthesis and Antiviral Activity of a Series of HIV–1 Protease Inhibitors with Functionality Tethered to the $P_1$ or $P_1$' Phenyl Substituents: X–ray Crystal Structure Assisted Design; *J. Med. Chem.*, 35, pp. 1685–1701 (1992).

Tomasselli, et al., Specificity and Inhibition of Protease from Human Immunodeficiency Viruses 1 and 2; *The Journal of Biological Chemistry*, vol. 265, pp. 14675–14693 (1990).

Tucker, et al., A. Series of Potent HIV–1 Protease Inhibitors Containing a Hydroxyethyl Secondary Amine Transition State Isostere: Synthesis, Enxyme Inhibition, and Antiviral Acitivity, *J. Med. Chem.*, 35, 2525–2533 (1992).

Urban, et al., Reduced–bond Tight–Binding Inhibitors of HIV–1 Protease, Fine Tuning of the Enzyme Subsite Specificity; *FEBS Letters*, vol. 298, No. 1, pp. 9–13 (1992).

Vacca, et al., L–687,908, a Potent Hydroxyethylene–Containing HIV Protease Inhibitor; *J. Med. Chem.*, 34, pp. 1225–1228 (1991).

Young, et al., HIV–1 Protease Inhibitors Based on Hydroxyethylene Dipeptide ISosteres: An Investigation into the Role of the $P_1$' Side Chain on Structure–Acitivity; *J. Med. Chem.*, 35, pp. 1702–1709 (1992).

Ghosh et al., 3–Tetrahydrofuran and Pyran Urethanes as High–Affinity $P_2$–Ligands for HIV–1 Protease Inhibitors, *J. Med. Chem.*, 36, 292–294 (1993).

Getman et al., Discovery of a Novel Class of Potent HIV–1 Protease Inhibitors Containing the (R)–(Hydroxyethyl)urea Isostere, *J. Med. Chem.*, 36, 288–291 (1993).

Ghosh et al., Cyclic Sulfolanes as Novel and High Affinity $P_2$ Ligands for HIV–1 Protease Inhibitors, *J. Med. Chem.*, 36, 924–927 (1993).

Martin, *Antiviral. Res.*, 17, 265–278 (1992).

Gordon et al., *Biochem. Biophys. Res. Commun.*, 126(1), 419–426 (1985).

Richards et al., *FEBS letters*, 247(9), 113–117 (1989).

Barrish et al., *J. Med. Chem.*, 37, 1758–1768 (1994).

CA95:102820: Bechtold et al., "Antiviral Properties of Aminodiol Inhibitors against Human Immunodeficiency Virus and Protease", *Antimicrobial Agents and Chemotherapy*, pp. 374–379 (Feb. 1995).

CA94:281362: Bechtold et al., "Antiviral Properties of BMS 182,193, an Aminoalcohol Inhibitor of HIV Protease", *Antiviral Research 23 (Supp. 1), Seventh International Conference on Antiviral Research, Charleston, S.C.* (Feb. 27—mar. 4, 1994).

CA94:281361:Ahmad et al., "Potent Inhibitors of HIV Protease: $P_2$ and $P_3$ Extended Analogs of BMS–182,193", *Antiviral Research 23 (Supp. 1), Seventh International Converence on Antiviral Research, Charleton, S.C.* (Feb. 27—Mar. 4, 1994).

CA94:281344: Bechtold et al., "Antiviral Properties of MS 182,193 an Aminoalcohol Inhibitor of HIV Protease", *Antiviral Research 23 (Supp. 1), Seventh International Conference on Antiviral Research, Charleston, S.C.* (Feb. 27—Mar. 4, 1994).

CA94:281338: Barrish et al., "Novel Aminoalcohol Inhibitors of HIV Protease: Design, Synthesis, and Characterization", *Antiviral Research 23 (Supp. 1), Seventh International Conference on Antiviral Research, Charleston, S.C.* (Feb. 27—Mar. 4, 1994).

CA94:361189: Wlodawer, "Rational Drug Design: The Proteinase Inhibitors", *Pharmacotherapy*, 14/6 II, pp. 9S–20S (1994).

CA94:463934: Tino et al., "Novel Aminodiol Inhibitors of HIV Protease. Design, Synthesis, and Characterization", *Abstracts of Papers American Chemical Society 208 (1–2) (1994) or 208th National Meeting of the American Chemical Society, Washington, DC* (Aug. 21–25, 1994).

March, J., "Advanced Organic Chemistry" 1985, J. Wiley & Sons, New York, pp. 270, 664, 726 and 727.

Eds. L. Kaudy, J. F. Rounsaville, G. Schultz: "Ullmann's Encyclopedia of Industrial Chemistry, 5th Edition", VCH, Weinheim, pp. 531–545.

AMINEDIOL PROTEASE INHIBITORS

This is a division of U.S. patent application Ser. No. 08/079,978, filed Jun. 25, 1993, now U.S. Pat. No. 5,559,256 which is a continuation-in-part of U.S. patent application Ser. No. 07/927,027, filed Aug. 6, 1992, now abandoned, which is a continuation-in-part of U.S. patent application Ser. No. 07/916,916, filed Jul. 20, 1992, now abandoned; wherein said U.S. patent application Ser. Nos. 07/927,027 and 07/916,916, are incorporated by reference herein in their entirety.

FIELD OF THE INVENTION

The present invention relates to novel aminediol compounds, to pharmaceutical compositions containing these compounds, and to methods of using these compounds in inhibiting the replication of retroviruses. The present invention particularly relates to novel aminediol compounds useful in the treatment and/or prevention of Acquired Immunodeficiency Syndrome (AIDS).

SUMMARY OF THE INVENTION

The present invention provides compounds of the following formula I:

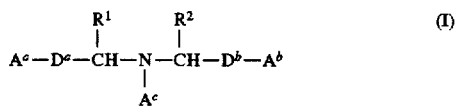

where $A^a$, $A^b$ and $A^c$ are independently:
(1) hydrogen;
(2) alkyl, especially lower alkyl;

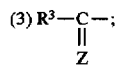

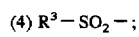

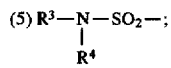

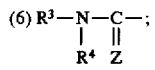

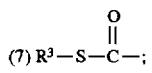

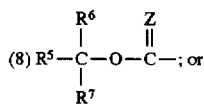

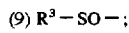

$D^a$ and $D^b$ are independently selected from groups of the formula:

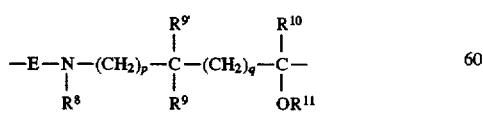

where $D^a$ and $D^b$ are bonded to the groups $A^a$ and $A^b$, respectively, through the moiety —E—N($R^8$)—, where E is a single bond or a peptide chain containing 1 to 4 amino acids, the N-terminus of which is bonded to $A^a$ when E is part of $D^a$ or to $A^b$ when E is part of $D^b$;

$R^1$ and $R^2$ are independently:
(1) hydrogen;
(2) alkyl, especially lower alkyl;
(3) alkenyl, especially lower alkenyl;
(4) aryl;
(5) heterocyclo; or
(6) carbocyclo, such as cycloalkyl;

$R^3$ and $R^4$ are independently:
(a) hydrogen;
(b) alkyl, especially lower alkyl;
(c) aryl;
(d) heterocyclo;
(e) carbocyclo, such as cycloalkyl;
(f) when $R^3$ and $R^4$ are bonded to a common nitrogen atom, $R^3$ and $R^4$ may be joined, together with that nitrogen atom, to form a heterocyclic ring system, such as a 5 to 7 membered heterocyclic ring; or
(g) when E is a single bond and $R^3$ is part of $A^a$ or $A^b$, $R^3$ may, together with $R^8$, form an alkylene group, for example, having one to five carbons, such as wherein $R^3$ and $R^8$, together with the atoms to which they are bonded, form the cyclic moiety:

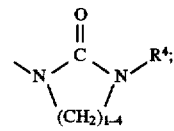

$R^5$, $R^6$ and $R^7$ are independently:
(a) hydrogen;
(b) alkyl, especially lower alkyl;
(c) aryl;
(d) carbocyclo, such as cycloalkyl;
(e) fluorenyl;
(f) heterocyclo;
(g) $R^5$, $R^6$ and $R^7$ may, independently, be joined, together with the carbon atom to which they are bonded, to form a mono-, bi- or tricyclic carbocyclic ring system, especially wherein each ring contains 3 to 7 carbon atoms, or a mono-, bi- or tricyclic heterocyclic ring system;
(h) alkynyl;
(i) alkenyl; or
(j) when E is a single bond and $R^5$, $R^6$ and $R^7$ are part of $A^a$ or $A^b$, one of $R^5$, $R^6$, or $R^7$ may, together with $R^8$, form an alkylene group, for example, having one to three carbons, such as wherein $R^5$ and $R^6$ are methyl and $R^7$ and $R^8$, together with the atoms to which they are bonded, form the cyclic moiety:

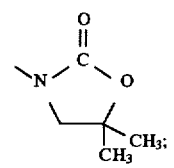

$R^8$ is:
(a) hydrogen;
(b) alkyl, especially unsubstituted lower alkyl or aryllower alkyl;
(c) $R^8$ and $R^9$ may be joined, together with the atoms to which they are bonded, to form a heterocyclic ring system, for example, a 5 to 7 membered monocyclic heterocyclic ring;

(d) $R^8$ may be joined together with $R^5$, $R^6$ or $R^7$ as described above;

(e) $R^8$ may be joined together with $R^3$ as described above; or (f) $R^8$ and $R^{11}$ may be joined, together with the atoms to which they are bonded, to form a heterocyclic ring system, such as where $R^8$ and $R^{11}$ together are an alkylene group;

$R^9$ and $R^{9'}$ are independently:
(a) hydrogen;
(b) alkyl, especially lower alkyl;
(c) alkenyl, especially lower alkenyl;
(d) alkynyl;
(e) aryl;
(f) heterocyclo;
(g) carbocyclo, such as cycloalkyl;
(h) $R^9$ may be joined together with $R^8$ as described above; or
(i) $R^9$ and $R^{9'}$ may be joined, together with the carbon atom to which they are bonded, to form a carbocyclic group, such as 5- or 6-membered carbocyclic ring;

$R^{10}$ is:
(a) hydrogen;
(b) alkyl, such as unsubstituted lower alkyl or hydroxy-lower alkyl, cycloalkyl-lower alkyl, aryl-lower alkyl or heterocyclo-lower alkyl;
(c) alkenyl, especially lower alkenyl;
(d) alkynyl;
(e) carbocyclo, such as cycloalkyl;
(f) aryl; or
(g) $R^{10}$ and $R^{11}$ taken together may form a bond to give a keto (C=O) group;

$R^{11}$ is:
(a) hydrogen;
(b) a hydroxyl protecting group, such as alkyl;
(c) $R^{11}$ may be joined together with $R^8$ as described above; or
(d) $R^{11}$ may, together with $R^{10}$, form a bond to give a keto group as described above;

z is oxygen or sulfur; and p and q are, independently, integers from 0 to 4; and salts, preferably pharmaceutically acceptable salts, thereof.

The compounds of the present invention inhibit the replication of retroviruses. The present invention thus also provides methods, and pharmaceutical compositions, for the treatment and/or prevention of diseases caused by such pathogenic organisms.

DETAILED DESCRIPTION OF THE INVENTION

The terms "alk" or "alkyl", as employed herein alone or as part of another group, denote both straight and branched chain, optionally substituted saturated radicals, for example, containing 1 to 12 carbons, most preferably 1 to 8 carbons, in the normal chain. It is understood, therefore, that throughout this specification the terms "alk" and "alkyl" denote both unsubstituted groups such as methyl, ethyl, n-propyl, iso-propyl, n-butyl, iso-butyl, sec-butyl, tert-butyl, n-pentyl, 1-methylbutyl, 2,2-dimethylbutyl, 2-methylpentyl, n-hexyl and the like, as well as substituted groups such as phenyl-methyl and the like. Exemplary substituents may include one or more, such as 1, 2 or 3, of the following:

(1) hydroxy (or protected hydroxy);
(2) oxo (i.e. =O), with the proviso that the carbon bearing the oxo group is not adjacent to a heteroatom;
(3) carboxy;
(4) halo (especially to form trihaloalkyl, particularly trifluoromethyl);
(5) alkoxy, such as phenyl-lower alkoxy or

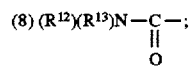

where m is an integer from 2 to 5; n is an integer from 1 to 5; and $R^{16}$ is:
(a) hydrogen;
(b) alkyl, especially unsubstituted lower alkyl or alkoxy-lower alkyl;
(c) aryl; or
(d) heterocyclo;

(6) aryloxy;
(7) alkoxycarbonyl;

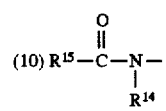

where $R^{12}$ and $R^{13}$ are independently:
(a) hydrogen;
(b) alkyl, especially lower alkyl;
(c) aryl;
(d) heterocyclo;
(e) carbocyclo, such as cycloalkyl;
(f) $R^{12}$ and $R^{13}$ may be joined, together with the nitrogen atom to which they are bonded, to form a 5 to 7 membered heterocyclic ring;

(9) $(R^{12})$ $(R^{13})N$—, such as amino $(H_2N-)$;

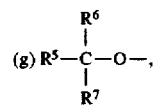

where $R^{14}$ is:
(a) hydrogen;
(b) alkyl, especially lower alkyl;
(c) aryl;
(d) heterocyclo;
(e) carbocyclo, such as cycloalkyl; or
(f) $R^{14}$ and $R^{15}$ may be joined to form an alkylene group of three to five carbon atoms; and $R^{15}$ is:
(a) hydrogen;
(b) alkyl, especially lower alkyl;
(c) alkenyl, especially lower alkenyl;
(d) aryl;
(e) heterocyclo;
(f) carbocyclo, such as cycloalkyl;

wherein $R^5$, $R^6$ and $R^7$ are, independently, those groups (a) through (i) recited for $R^5$, $R^6$ and $R^7$ above; or (h) $R^{15}$ may be joined together with $R^{14}$ as described above;

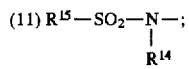

(12) carbocyclo, such as cycloalkyl;
(13) heterocyclo;
(14) heterocyclooxy;
(15) aryl;
(16) alkylcarbonyloxy, such as lower alkylcarbonyloxy;
(17) arylcarbonyloxy;
(18) cyano;
(19) mercapto;
(20) alkenyl;
(21) alkynyl, such as ethynyl (e.g., forming a propargyl group);
(22) alkylthio;
(23) arylthio;
(24) trialkylsilyl, such as trimethylsilyl;
(25) azo (i.e., $R^{16}O-N=$ where $R^{16}$ is as defined above, preferably hydrogen (to form an oxime group (HO—N=)) or unsubstituted alkyl (to form an unsubstituted alkoxyimino group (alkyl-O—N=)); or
(26) $(R^{12})$ $(R^{13})N-C(O)-O-$, where $R^{12}$ and $R^{13}$ are as defined above.

The term "alkoxy" denotes an alkyl group bonded through an oxygen bridge (—O—); the term "alkylthio" denotes an alkyl group bonded through a sulfur bridge (—S—); the term "alkoxycarbonyl" (also referred to as "carboalkoxy") denotes an alkoxy group attached to a carbonyl group to form an ester; the term "alkylcarbonyloxy" denotes an alkyl group bonded to a carbonyl group which is in turn bonded through an oxygen bridge; the term "aminocarbonyloxy" denotes an amino group bonded through a carbonyl group which is, in turn, bonded through an oxygen bridge; the term "alkylaminocarbonyloxy" denotes an alkyl group bonded through an aminocarbonyloxy group as described above; the term "alkylaminocarbonyl" denotes an alkyl group bonded through an amino group which is, in turn, bonded through a carbonyl group; and the term "alkylene" denotes a divalent alkyl group. With respect to exemplary alkyl groups which are substituted, the term "alkoxy-alkyl" specifically denotes an alkoxy group bonded through an alkyl group; the term "aryl-alkyl" specifically denotes an aryl group bonded through an alkyl group; the term "heterocyclo-alkyl" specifically denotes a heterocyclo group bonded through an alkyl group; the term "cycloalkyl-alkyl" specifically denotes a cycloalkyl group bonded through an alkyl group; and the term "hydroxy-alkyl" specifically denotes one or more hydroxyl groups attached to an alkyl group. In each of the aforementioned terms, "alkyl" may be further substituted, or unsubstituted, as defined above. Likewise, "fluorenylalkyl" specifically denotes a fluorenyl group bonded through alkyl. Similarly, the terms "arylalkoxy", "alkoxyalkoxy", "hydroxyalkoxy", "heterocycloalkoxy", "aminoalkoxy", "aminocarbonyloxyalkoxy", "heterocyclocarbonylalkoxy", "heterocyclooxyalkoxy", "alkoxycarbonylalkoxy" and "carboxyalkoxy" specifically denote alkoxy substituted by aryl, alkoxy, hydroxy, heterocyclo, amino, aminocarbonyloxy, heterocyclocarbonyl, heterocyclooxy, alkoxycarbonyl and carboxy, respectively.

The term "lower alkyl", as employed herein alone or as part of another group, denotes optionally substituted groups as described above for alkyl containing 1 to 6 carbon atoms in the normal chain. Lower alkyl groups are preferred alkyl groups.

The term "alkenyl", as employed herein alone or as part of another group, denotes both straight and branched chain, optionally substituted radicals, for example, containing 2 to 12 carbons in the normal chain, most preferably 2 to 8 carbons, which contain at least one carbon to carbon double bond and which are directly attached through one of the carbons composing the double bond. It is understood, therefore, that throughout this specification, the term "alkenyl" denotes both unsubstituted groups such as ethenyl, propenyl, butenyl, pentenyl, hexenyl, and the like, as well as substituted groups. Exemplary substituents may include one or more, such as 1, 2 or 3, of the following:

(1) alkyl, especially lower alkyl;
(2) aryl;
(3) carbocyclo, such as cycloalkyl;
(4) heterocyclo;
(5) carboxy;
(6) halo;

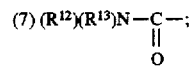

(8) cyano;
(9) alkoxycarbonyl;
(10) trialkylsilyl; or
(11) alkynyl.

The term "lower alkenyl", as employed herein alone or as part of another group, denotes optionally substituted groups as described above for alkenyl containing 2 to 6 carbon atoms in the normal chain. Lower alkenyl groups are preferred alkenyl groups.

The term "alkynyl", as employed herein alone or as part of another group, denotes both straight and branched chain, optionally substituted radicals, for example, containing 2 to 12 carbons in the normal chain, most preferably 2 to 8 carbons, which contain at least one carbon to carbon triple bond and which are directly attached through one of the carbons composing the triple bond. It is understood, therefore, that throughout this specification, the term "alkynyl" denotes both unsubstituted groups such as ethynyl, methyl-ethynyl, and the like, as well as substituted groups. Exemplary substituents may include one or more, such as 1, 2 or 3, of the following:

(1) alkyl, especially lower alkyl;
(2) aryl;
(3) carbocyclo, such as cycloalkyl;
(4) heterocyclo;
(5) carboxy;

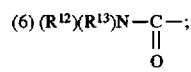

(7) cyano;
(8) alkoxycarbonyl;
(9) alkenyl; or
(10) trialkylsilyl.

The terms "carbocyclo", "carbocyclic" or "carbocyclic ring system", as employed herein alone or as part of another group, denote an optionally substituted, saturated or partially unsaturated, homocyclic carbon ring system, such as a cycloalkenyl ring system, which is partially unsaturated, or most preferably, a cycloalkyl ring system, which is fully saturated, wherein the aforementioned cycloalkenyl and cycloalkyl ring systems are, according to the above definition, optionally substituted. Such cyclic groups preferably contain from 1 to 3 rings and from 3 to 12, most preferably from 3 to 7, carbons per homocyclic ring. It is understood, therefore, that throughout this specification the terms "carbocyclo", "carbocyclic" and "carbocyclic ring system" denote both unsubstituted groups exemplified by monocyclic groups such as cyclopropyl, cyclobutyl, cyclopentyl, cyclohexyl and cycloheptyl; bicyclic groups such as octahydropentalenyl, decalin, norbornyl, spirocycloheptyl (e.g., spiro[2.4]heptyl), spirocyclooctyl (e.g., spiro [3.4]octyl), spirocyclononyl (e.g. spiro[4.4]nonyl), and the like; and tricyclic groups such as adamantyl, as well as substituted groups. Exemplary substituents may include one or more, such as 1, 2 or 3, of the following:

(1) alkyl, especially lower alkyl;
(2) hydroxy (or protected hydroxy);
(3) halo;
(4) mercapto;
(5) cyano;
(6) carboxy;
(7) alkoxycarbonyl;

(8) 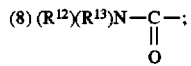

(9) alkylcarbonyloxy, such as lower alkylcarbonyloxy;
(10) arylcarbonyloxy;
(11) $(R^{12})$ $(R^{13})N—$, such as amino $(H_2N—)$;
(12) alkoxy;
(13) aryl, such as where said aryl group is bonded through a single bond or is fused to said carbocyclo group (e.g. to form a tetrahydronaphthyl, indanyl or indenyl group), and wherein, in each case, the aryl-carbocyclo moiety so formed is bonded through the carbocyclo group;
(14) heterocyclo;
(15) heterocyclooxy;
(16) oxo (=O);
(17) aryloxy;
(18) alkylthio;
(19) arylthio;

(20) 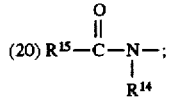

(21) alkenyl;
(22) alkynyl; or
(23) trialkylsilyl.

The terms "ar" or "aryl", as employed herein alone or as part of another group, denote homocyclic, optionally substituted aromatic groups, preferably monocyclic or bicyclic groups containing from 6 to 12 carbons in the ring portion, such as phenyl, naphthyl, tetrahydronaphthyl, indanyl, biphenyl and the like. It is understood, therefore, that throughout this specification, the terms "ar" and "aryl" denote unsubstituted as well as substituted groups. Exemplary substituents may include one or more, such as 1, 2 or 3, of the following:

(1) alkyl, especially lower alkyl;
(2) alkoxy;
(3) hydroxy (or protected hydroxy);
(4) halo;
(5) $(R^{12})$ $(^{13})N—$, such as amino $(H_2N—)$
(6) alkylthio;
(7) mercapto;
(8) nitro;
(9) cyano;
(10) carboxy;
(11) carboalkoxy;
(12) carbocyclo, such as where said carbocyclo group is bonded through a single bond, or is fused to said aryl group (e.g. to form a tetrahydronaphthyl, indanyl or indenyl group), and wherein, in each case, the carbocyclo-aryl moiety so formed is bonded through the aryl group;

(13) 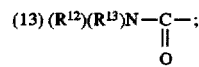

(14) $(R^{12})(R^{13})N—SO_2—$; 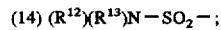

(15) 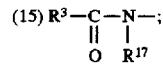

where $R^{17}$ is:
(a) hydrogen;
(b) alkyl, especially lower alkyl;
(c) aryl;
(d) heterocyclo;
(e) carbocyclo, such as cycloalkyl; or
(f) $R^{17}$ may, together with $R^3$, form an alkylene group of three to five carbons;

(16) 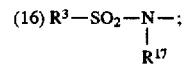

(17) phenyl;
(18) alkylcarbonyloxy, such as lower alkylcarbonyloxy;
(19) arylcarbonyloxy;
(20) arylthio;
(21) heterocyclooxy;
(22) aryloxy;
(23) alkylthio; or
(24) alkenyl.

The terms "arylcarbonyloxy" or "aroyloxy" denote an aryl group which is bonded through a carbonyl group which is, in turn, bonded through an oxygen bridge; the term "aryloxy" denotes on aryl group bonded through an oxygen bridge; the term "arylcarbonyl" denotes an aryl group bonded through a carbonyl group; the term "arylaminocarbonyl" denotes an aryl group bonded through an amino group which is, in turn, bonded through a carbonyl group; and the term "arylthio" denotes an aryl group bonded through a sulfur bridge.

The terms "halogen" or "halo", as employed herein alone or as part of another group, refer to chlorine, bromine, fluorine and iodine.

The terms "heterocyclo", "heterocyclic" or "heterocyclic ring system", as employed herein alone or as part of another group, denote an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclo group containing a heteroatom may have 1, 2 or 3 heteroatoms selected from nitrogen atoms, oxygen atoms or sulfur atoms, where the nitrogen and sulfur heteroatoms may optionally be oxidized and the nitrogen heteroatoms may optionally be quaternized. The heterocyclo group may be attached at any heteroatom or carbon atom.

Exemplary monocyclic heterocyclo groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazoyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane, and tetrahydro-1,1-dioxothienyl, and the like.

Exemplary bicyclic heterocyclo groups include indolyl, benzothiazolyl, benzoxazolyl, benzothienyl, quinuclidinyl, quinolinyl, tetrahydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, dihydroindazolyl such as the group:

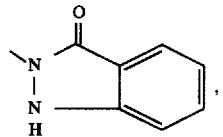

furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), and the like.

Exemplary tricyclic heterocyclo groups include carbazolyl, benzindolyl, phenanthrolinyl, acridinyl, phenanthridinyl, xanthenyl, and the like.

It is understood that throughout this specification the terms "heterocyclo", "heterocyclic" and "heterocyclic ring system" denote both unsubstituted as well as substituted groups. Exemplary heterocyclo substituents may include one or more, such as 1, 2 or 3, of the following:

(1) alkyl, especially lower alkyl;
(2) hydroxy (or protected hydroxy);
(3) halo;
(4) oxo (i.e. =O);
(5) $(R^{12})(R^{13})N$—, such as amino ($H_2N$—)
(6) alkoxy;
(7) carbocyclo, such as cycloalkyl;
(8) carboxy;
(9) heterocyclooxy;
(10) alkoxycarbonyl, such as unsubstituted lower alkoxycarbonyl;

(11) 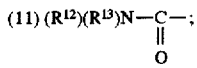

(12) mercapto;
(13) nitro;
(14) cyano;
(15) carboalkoxy;

(16) $(R^{12})(R^{13})N-SO_2-$;

(17) $R^3-\underset{\underset{O}{\|}}{C}-\underset{\underset{R^{17}}{|}}{N}-$;

(18) $R^3-SO_2-\underset{\underset{R^{17}}{|}}{N}-$;

(19) aryl;
(20) alkylcarbonyloxy;
(21) arylcarbonyloxy;
(22) arylthio;
(23) aryloxy;
(24) alkylthio; or
(25) formyl.

The term "heterocyclooxy" denotes a heterocyclo group bonded through an oxygen bridge; and the term "heterocyclocarbonyl", denotes a heterocyclo group bonded through a carbonyl group.

The term "hydroxyl protecting group", as used herein, denotes any group known as or capable of functioning as a hydroxyl protecting group, such as those groups so described in "Protective Groups in Organic Synthesis" by T. W. Greene, John Wiley and Sons, 1991, or Fieser & Fieser. Exemplary hydroxyl protecting groups include benzyl, trialkylsilyl, acetate and benzoate.

The term "carboxy", as used herein alone or as part of another group, denotes the carboxylic acid group —COOH.

The term "amino acid", as used herein alone or as part of another group, preferably denotes the group:

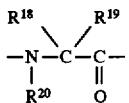

where $R^{18}$ and $R^{19}$ are independently:
(1) hydrogen;
(2) alkyl, especially lower alkyl;
(3) alkenyl, especially lower alkenyl;
(4) aryl;
(5) heterocyclo;
(6) carbocyclo, such as cycloalkyl;
(7) $R^{18}$ and $R^{19}$ may be joined, together with the carbon atom to which they are bonded, to form a carbocyclo group, such as a 4- to 7-membered cycloalkyl ring; or
(8) $R^{18}$ and $R^{20}$ may be joined as described in the definition of $R^{20}$ following;

$R^{20}$ is:
(1) hydrogen;
(2) alkyl, especially lower alkyl;
(3) aryl;
(4) heterocyclo;

(5) carbocyclo, such as cycloalkyl; or
(6) $R^{18}$ and $R^{20}$ may be joined, together with the atoms to which they are bonded, to form a heterocyclic group, such as a 4 to 7 membered, saturated monocyclic heterocyclic ring which may be unsubstituted or substituted by groups such as:
(i) hydrogen;
(ii) alkyl, especially lower alkyl;
(iii) alkenyl, especially lower alkenyl;
(iv) aryl, for example, where said aryl group is bonded through a single bond, or is fused to said monocyclic heterocyclic ring to form an unsaturated bicyclic heterocyclo ring system;
(v) heterocyclo;
(vi) mercapto;
(vii) alkoxy;
(viii) carbocyclo, such as cycloalkyl, for example, where said cycloalkyl group is bonded through a single bond, or is fused or spirofused to said monocyclic heterocyclic ring to form a saturated bicyclic heterocyclic ring system;
(ix) hydroxyl (or protected hydroxyl);
(x) aryloxy;
(xi) alkylthio;
(xii) arylthio; or
(xiii) oxo.

The amino acid moiety described above includes, for example, such moieties as may be found in D and L alanine, asparagine, aspartic acid, arginine, cysteine, glycine, glutamine, glutamic acid, histidine, isoleucine, leucine, lysine, methionine, phenylalanine, serine, homoserine, threonine, tryptophan, tyrosine, valine, hydroxyvaline, norleucine, norvaline, phenylglycine, cyclohexylalanine, t-butylglycine (t-leucine), hydroxy-t-butylglycine, amino butyric acid, ornithine, and cycloleucine, and preferably, when $R^{18}$ and $R^{20}$ are joined, together with the atoms to which they are bonded, proline, 4-hydroxyproline, pyroglutamic acid, azetidine carboxylic acid, pipecolinic acid, indoline-2-carboxylic acid, tetrahydro-3-isoquinoline carboxylic acid,

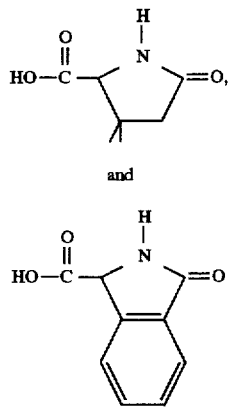

The term "peptide chain", as used herein, denotes two or more amino acids as described above bonded through a peptide linkage

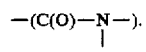

The "N-terminus" of the above-described amino acid(s) denotes the —$N(R^{20})$— group.

The term "salt(s)", as employed herein, denotes acidic and/or basic salts formed with inorganic and/or organic acids and bases. Zwitterions (internal or inner salts) are included within the term "salt(s)" as used herein, as are quaternary ammonium salts such as alkylammonium salts. The nontoxic, pharmaceutically acceptable salts are preferred, although other salts may be useful, for example, in isolation or purification steps which may be employed during preparation.

Exemplary acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pectinate, persulfate, 3-phenylpropionate, picrate, pivalate, propionate, succinate, tartrate, thiocyanate, tosylate, and undecanoate.

Exemplary basic salts include ammonium salts, alkali metal salts such as sodium, lithium, and potassium salts, alkaline earth metal salts such as calcium and magnesium salts, salts with organic bases such as dicyclohexylamine, N-methyl-D-glucamine, and salts with amino acids such as arginine, lysine and so forth. The basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

The present invention contemplates all compounds containing the moiety:

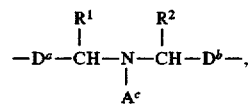

particularly such compounds capable of inhibiting retroviral, preferably HIV, protease.

Prodrugs and solvates of the inventive compounds are also contemplated herein. The term "prodrug", as employed herein, denotes a compound which, upon administration to a subject, undergoes chemical conversion by metabolic or chemical processes to yield a compound of the formula I, or a salt and/or solvate thereof. See H. Bundgaard, "Drugs of the Future", 16 (5), 443–458 (1991); and H. Bundgaard (Ed), "Design of Prodrugs" 1985 Elsevier (Amsterdam), both incorporated herein by reference.

Solvates of the compounds of formula I are preferably hydrates. Tautomers of the inventive compounds are also contemplated, such as hemiketals of hydroxyketones, the enol form of ketones, and the like.

The initial definition provided for a group or term herein applies to that group or term throughout the present specification, unless otherwise indicated. It is to be understood that "exemplary" groups recited herein are illustrative and not limiting. It is particularly advantageous to employ those groups preceded by the terms "especially" or "preferably". Throughout this specification, groups and substituents thereof may be chosen to provide stable moieties and compounds.

All stereoisomers of the present compounds are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

A description of exemplary methods for obtaining the compounds of the present invention follows. The reaction conditions of these methods, such as temperature, amount of reagent, pressure, reaction time, atmosphere and solvent employed may readily be ascertained by one of ordinary skill in the art.

In the following Reaction Schemes:

$Q^1$ and $Q^2$ are independently:

$$R^3-\underset{Z}{\overset{\|}{C}}-; \quad (1)$$

$$R^3-SO_2-; \quad (2)$$

$$R^3-\underset{R^4}{N}-SO_2-; \quad (3)$$

$$R^3-\underset{R^4}{N}-\underset{Z}{\overset{\|}{C}}-; \quad (4)$$

$$R^3-S-\overset{O}{\overset{\|}{C}}-; \quad (5)$$

$$R^5-\underset{R^7}{\overset{R^6}{C}}-O-\overset{Z}{\overset{\|}{C}}-; \quad (6)$$

or $$R^3-SO-. \quad (7)$$

The above $Q^1$ and $Q^2$ groups are preferably employed where indicated as they render the nitrogen atoms to which they are bonded non-basic. Where compounds of the invention are desired in which $A^a$ and/or $A^b$ are one of the above groups (1) to (7), the $Q^1$ or $Q^2$ groups of the following Reaction Schemes need not be removed. Where compounds of the invention are desired in which $A^a$ and/or $A^b$ are other than the above groups (1) to (7), $Q^1$ or $Q^2$, for example, can be:

$$R^3-\overset{O}{\overset{\|}{C}}- \quad \text{or} \quad R^5-\underset{R^7}{\overset{R^6}{C}}-O-\overset{O}{\overset{\|}{C}}-$$

(especially t-butoxycarbonyl (Boc) or carbobenzyloxy (Cbz) ), forming amide and carbamate groups, respectively. These latter groups can be removed, and replaced with the desired $A^a$ and/or $A^b$ groups, by methods known in the art. With the exception of the conditions used for their optional removal, $Q^1$ and $Q^2$ groups are chosen that are stable to the conditions used in the following Reaction Schemes.

$Q^3$ is:

(1) hydrogen; or
(2) alkyl.

The above $Q^3$ groups are preferably employed where indicated as they render the nitrogen atom to which they are bonded basic. Exemplary $Q^3$ groups are hydrogen, unsubstituted lower alkyl, alkenyl-lower alkyl, and aryl-lower alkyl. Where compounds of the invention are desired in which $A^c$ is one of the above groups (1) or (2), the $Q^3$ group employed in the following Reaction Schemes need not be removed. Where compounds of the invention are desired in which $A^c$ is other than the above groups (1) or (2), $Q^3$ can, for example, be a benzyl group. The benzyl group may be removed and replaced by the desired $A^c$ group by methods known in the art. With the exception of the conditions used for their removal, $Q^3$ groups are chosen that are stable to the conditions used in the following Reaction Schemes.

In the following Reaction Schemes, where it is desired to remove $Q^1$, $Q^2$ and/or $Q^3$ groups and to couple the amine groups so formed with another of the groups of $A^a$, $A^b$ and/or $A^c$, methods known to those of ordinary skill in the art may be employed (as exemplified by Methods (D), (E) and (F) of Reaction Scheme 11). For examples of amine protecting groups and their removal see Greene, "Protective Groups in Organic Synthesis," John Wiley (1991).

Reaction Scheme 1
Preparation of Intermediate Materials

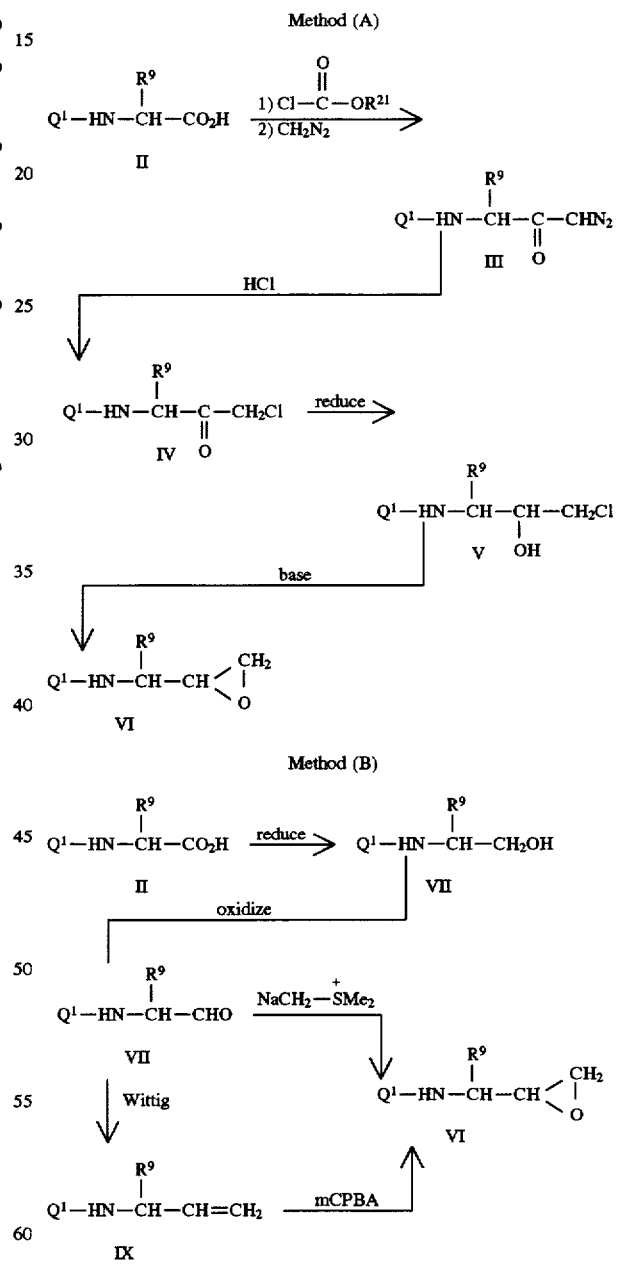

Intermediate materials for the preparation of compounds of the formula I may be prepared by Methods (A) or (B) as shown in Reaction Scheme 1 above. Starting compounds II may readily be prepared by one of ordinary skill in the art by known methods, such as those described in Greene.

In Method (A), an N-protected amino acid II is converted to a reactive intermediate (not shown), such as to an acid chloride by reaction with thionyl chloride or oxalyl chloride, or to a mixed anhydride by reaction with a chloroformate of the formula Cl—C(O)—OR$^{21}$ where R$^{21}$ is an unsubstituted lower alkyl group, and then treated with diazomethane to give the diazoketone III. Treatment of III with HCl gives the (α-chloroketone IV, which may be converted to the chlorohydrin V by reduction, and then to the epoxide VI by reaction with a base by methods known in the art (see Handa et al., Eur. Pat. Appl. 346,847;Rich et al., J. Med. Chem., 34, 1222 (1991)). For example, the α-chloroketone IV may be reduced with a hydride reducing agent such as lithium aluminum hydride, sodium borohydride, lithium and/or potassium-selectride, potassium borohydride, diisobutylaluminum hydride, and the like to give the chlorohydrin V, which can be converted to the epoxide VI by treatment with a base such as sodium or potassium hydroxide, sodium or potassium hydride, or an alkylamine base such as triethylamine. Compound III may, alternatively, be treated with HBr to give the α-bromoketone corresponding to α-chloroketone IV. The corresponding α-bromoketone may be prepared or employed wherever the α-chloroketone IV is prepared or employed in the present Reaction Schemes (for example, to prepare the bromohydrin corresponding to chlorohydrin V).

An alternate procedure, Method (B), based upon methods known in the art (see Desolms et al., European Patent 356,223) may also be employed. This method involves reduction of the protected amino acid II to the alcohol VII using a reagent such as lithium aluminum hydride or borane (Brown et al., J. Amer. Chem. Soc., 82, 3866 (1960)) or via reduction of a mixed anhydride intermediate (formed as described above) with a hydride reducing agent such as sodium borohydride (Corey et al., J. Amer. Chem. Soc., 98, 6417 (1976)). The alcohol VII can be oxidized to the aldehyde VIII with a chromium (VI) reagent (Evans et al., J. Org. Chem., 47, 3016 (1982)), or via a Moffatt (Albright et al., J. Org. Chem., 30, 1107 (1965)) or Swern (Swern et al., J. Org. Chem., 43, 2480 (1978)) procedure. The aldehyde VIII may be converted directly to the epoxide VI via reaction with a sulfonium or arsonium ylide (Corey et al., J. Amer. Chem. Soc., 87, 1353 (1965); Still et al., J. Amer. Chem. Soc., 103, 1283 (1981)), or indirectly by a Wittig or Peterson (Peterson, J. Org. Chem., 33, 780 (1968)) reaction to give the olefin IX, followed by epoxidation with a reagent such as meta-chloroperbenzoic acid (mCPBA), peracetic acid, or the like.

In Method (B), the aldehyde VIII may also be produced from a carboxylic acid ester of the acid II (not shown) by reduction with diisobutylaluminum hydride (Ito et al., Chem. Pharm. Bull., 23, 3081 (1975)), or via reduction of the methyl hydroxamate with lithium aluminum hydride (Castro et al., Synthesis, 676 (1983)), and the aldehyde VIII converted to the epoxide VI as described above.

Reaction Scheme 2
Preparation of Compounds I where A$^a$ = A$^b$ and D$^a$ = D$^b$

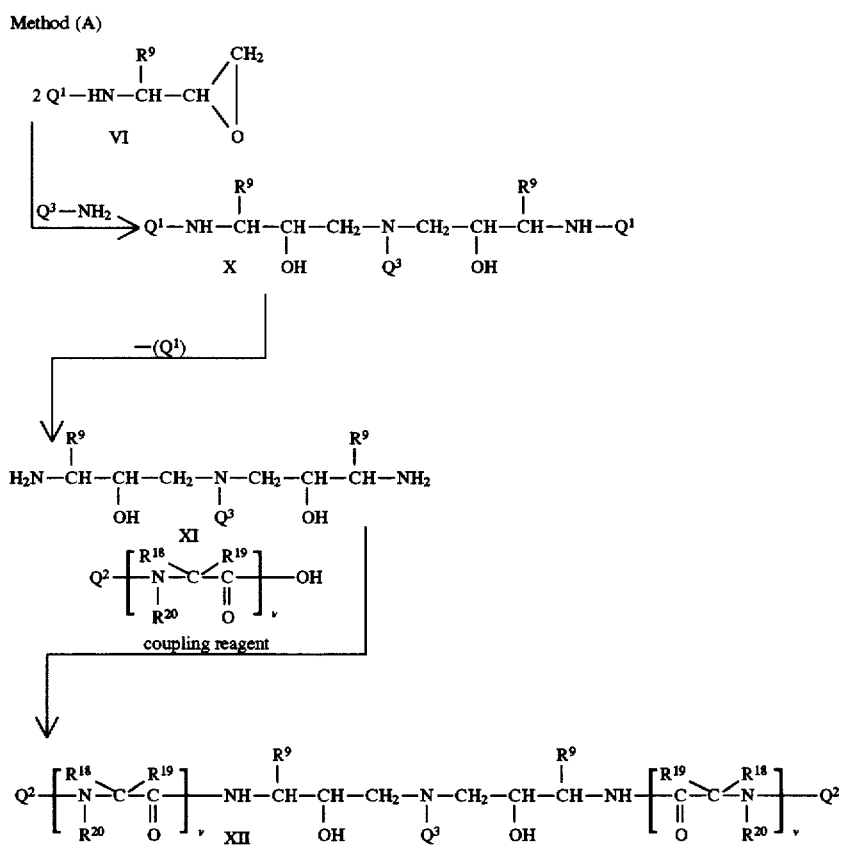

-continued
Reaction Scheme 2
Preparation of Compounds I where $A^a = A^b$ and $D^a = D^b$
Method (B)
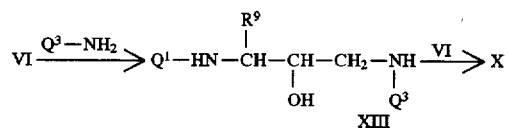
Method (C)
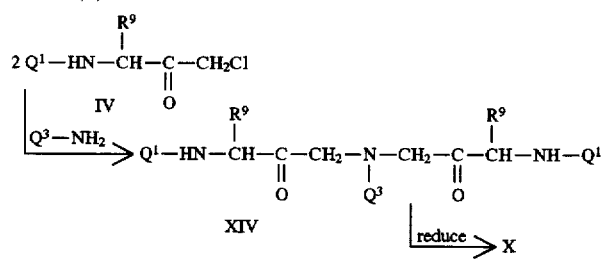
Method (D)
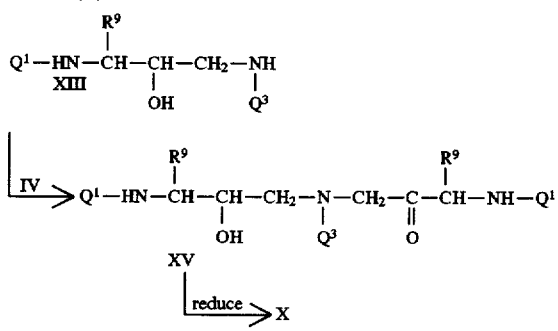
Method (E)
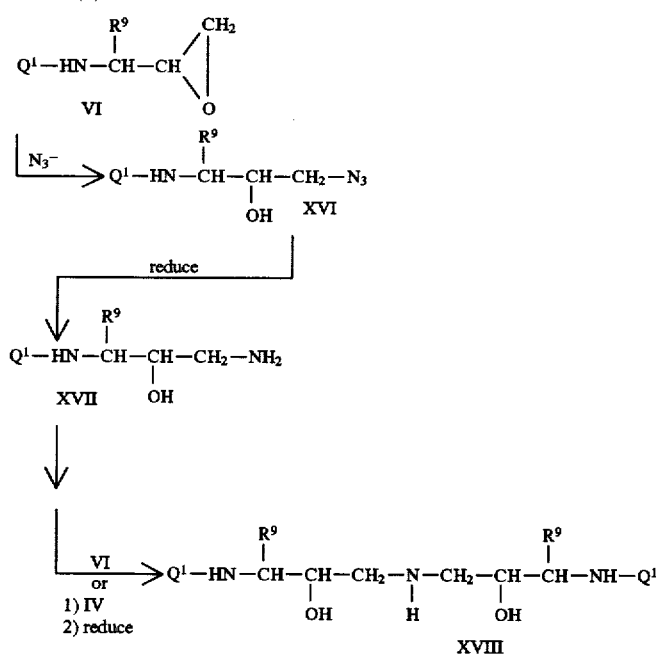

-continued
Reaction Scheme 2
Preparation of Compounds I where $A^a = A^b$ and $D^a = D^b$ Method (F)

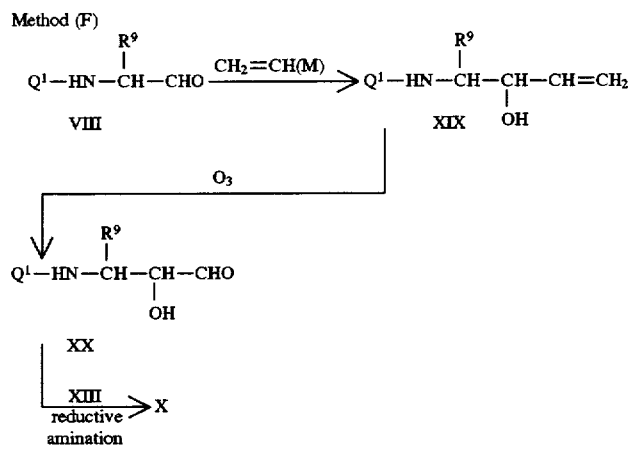

Reaction Scheme 2 above illustrates Methods (A) through (F), which may be used to prepare compounds of the formula I where $A^a$ is the same as $A^b$ and $D^a$ is the same as $D^b$ ("symmetrical" compounds).

Method (A) begins by treating two equivalents of the epoxide VI with one equivalent of $Q^3$—$NH_2$, where $Q^3$ is preferably hydrogen, unsubstituted lower alkyl, alkenyl-lower alkyl (e.g. allyl) or aryl-lower alkyl (e.g. benzyl), particularly benzyl as described above, and heating in a solvent such as methanol or dimethylformamide (Parker et al., Chem. Rev., 59, 737 (1959); for alternative conditions, see Posner et al., J. Amer. Chem. Soc., 99, 8208 (1977); Overman, J. Org. Chem., 50, 4154 (1985); Tetrahedron Lett., 27, 2451 (1986)), giving the aminediol X.

The terminal groups $Q^1$ of the aminediol X may optionally be removed by methods known to the skilled artisan (Greene), and the resulting bis-amine XI coupled to an N-protected amino acid or peptide chain (prepared using standard solid or solution phase techniques as described in Bodanszky and Bodanszky, The Practice of Peptide Chemistry; pp. 89–150, Springer-Verlag, 1984, where $Q^2$ is described above and is compatible with the conditions used in the coupling reaction), using a coupling reagent such as dicyclohexylcarbodiimide (DCC), 3-ethyl-3'-(dimethylamino)propylcarbodiimide (EDCI), bis-(2-oxo-3-oxazolidinyl)-phosphinic chloride (BOP-Cl), benzotriazol-1-yloxy-tris(dimethylamino)phosphonium hexafluorophosphate (BOP reagent), diphenylphosphoryl azide (DPPA) and the like, to give the aminediol XII. (For other methods see Bodanszky, Principles of Peptide Synthesis, pp. 9–58, Springer-Verlag (1984)). In the N-protected amino acid or peptide chain, v is an integer from 1 to 4. Where, in the bis-amine XI, $Q^3$ is hydrogen, the central nitrogen atom to which it is bonded ("central amine") may optionally be protected. Here, and in the following Reaction Schemes where appropriate, the central amine may be protected by nitrogen protecting groups known in the art, for example, by an aryl-alkyl group such as benzyl or trityl, an alkenyl-alkyl group such as allyl, as well as groups forming, together with the central nitrogen atom, a carbamate or amide group.

Methods (B) through (F), described following, illustrate alternate routes for obtaining compound X, which may optionally be further treated as described above in Method (A).

In Method (B), the process may be carried out in a step-wise fashion by treatment of one equivalent of the epoxide VI with one equivalent or an excess of the primary amine or ammonia ($Q^3$—$NH_2$) to give the amino alcohol XIII, which in turn may be coupled again to the epoxide VI to give X.

In Method (C), the process may be carried out by reaction of two equivalents of the chloroketone IV (or the corresponding bromoketone) with one equivalent of the aforementioned primary amine or ammonia ($Q^3$—$NH_2$, where $Q^3$ is preferably benzyl), to form the diketoamine XIV, which may be reduced to the aminediol X with a hydride reducing agent such as lithium aluminum hydride, sodium or potassium borohydride, lithium or potassium selectride (i.e., lithium or potassium tri-sec-butylborohydride), diisobutylaluminum hydride, and the like.

In Method (D), a step-wise procedure can be carried out by coupling the aforementioned amino alcohol XIII with the chloroketone IV (or the corresponding bromoketone) (Gordon et al., J. Org. Chem., 51, 3073 (1986)) to give the ketohydroxyamine XV, which may be reduced by methods described above.

In Method (E), the epoxide VI may be opened with azide anion, such as by treatment with sodium azide, to give the azidoalcohol XVI (Ingham et al., J. Org. Chem., 21, 373 (1956); Rosenberg et al., J. Med. Chem., 32, 1371 (1989); Saito et al., Tetrahedron Lett., 30, 4153 (1989)). The azido moiety may be reduced to the amine by, for example, hydrogenation over Pd/C or by treatment with triphenylphosphine (Vaultier et al., Tetrahedron Lett., 24, 763 (1983)). The resulting aminoalcohol 20 XVII can be coupled to the epoxide VI, or to the chloroketone IV (or the corresponding bromoketone) followed by reduction, as described above to give the aminodiol XVIII. The central amine may optionally be protected as described above, and the $Q^1$ groups optionally removed and the resulting amines coupled to amino acids or peptide chains, also as described above.

In Method (F), the aminoaldehyde VIII can be reacted with a vinyl organometallic reagent of the formula $CH_2$=$CH(M)$, where M is a metal-containing moiety, such as vinyl lithium, vinyl magnesium bromide and the like to give the allylic alcohol XIX. The olefin moiety may be oxidatively cleaved to the aldehyde by ozonolysis, or the compound XIX converted to the corresponding diol (not shown) with osmium tetraoxide or potassium permanganate, followed by cleavage of the diol with sodium periodate (Lemieux et al., J. Org. Chem., 21, 478 (1956)) to form the aldehyde. The aldehyde XX can then be reacted with the aminoalcohol XIII under reductive amination conditions (for example, hydrogenation over Pd/C or reaction with sodium cyanoborohydride where $Q^3$ is hydrogen or benzyl; see Hudlicky, Reductions in Organic Chemistry, pp. 134–136, John Wiley, 1984) to give compound X.

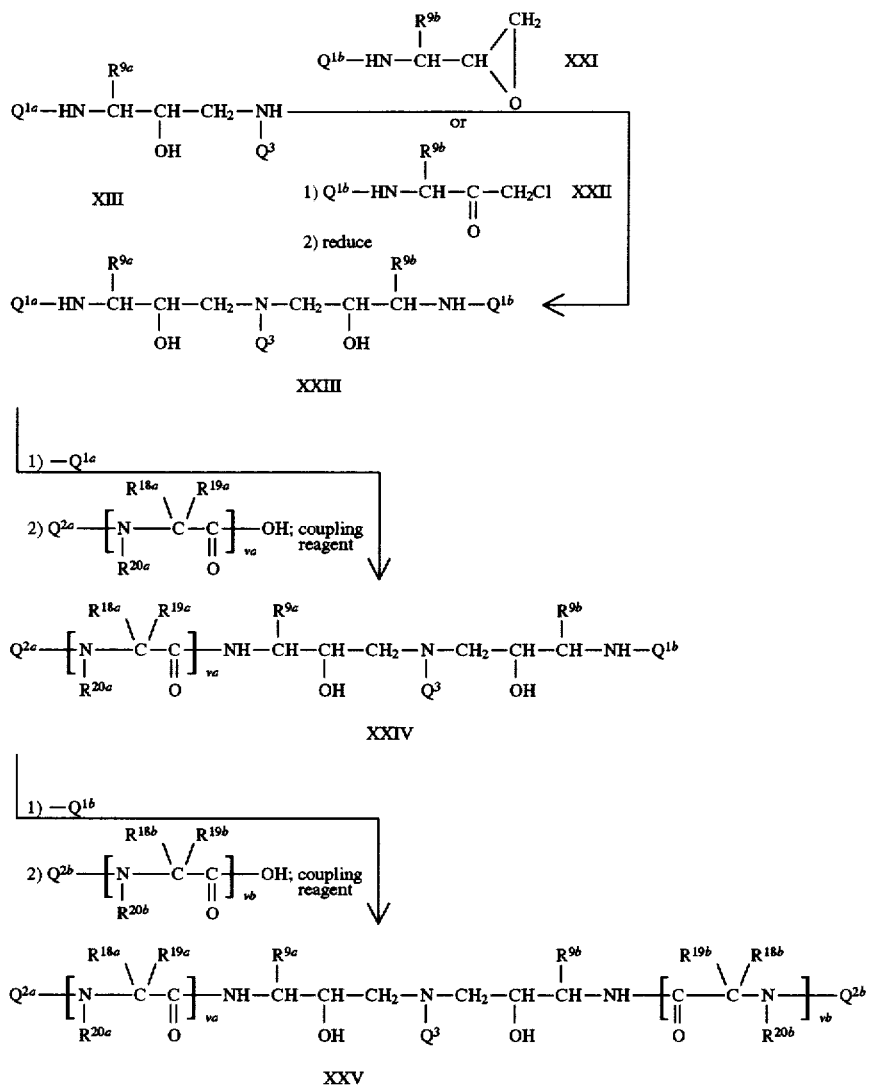

Reaction Scheme 3
Preparation of Compounds I where $A^a \neq A^b$ and/or $D^a \neq D^b$ Method (A)

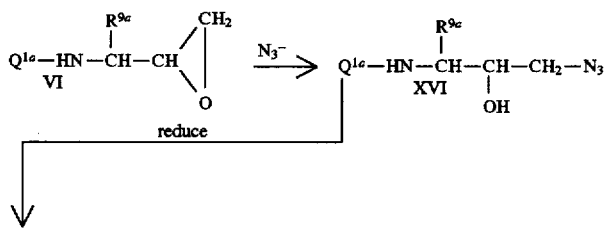

Method (B)

-continued
Reaction Scheme 3
Preparation of Compounds I where $A^a \neq A^b$
and/or $D^a \neq D^b$

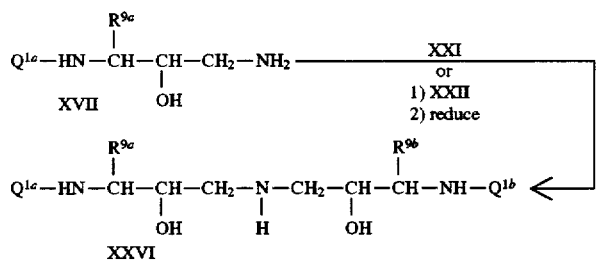

Method (C)

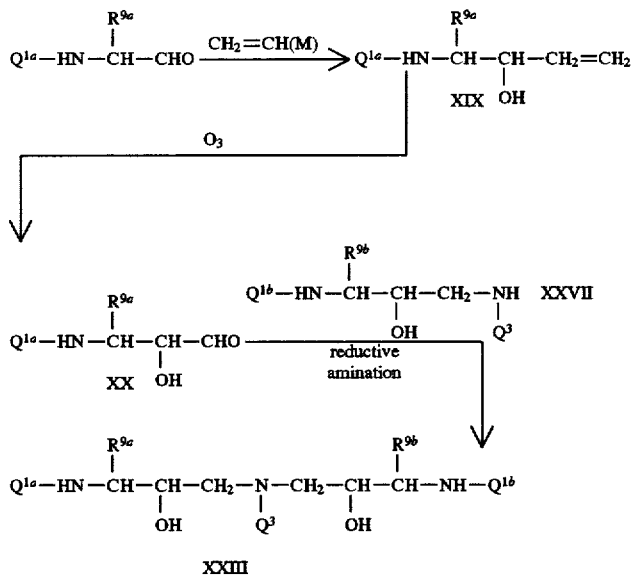

Reaction Scheme 3 above illustrates Methods (A) through (C), which may be used to prepare compounds of the formula I where $A^a$ differs from $A^b$ and/or $D^a$ differs from $D^b$ ("asymmetrical", compounds) by procedures analogous to those of Reaction Scheme 2. In Reaction Scheme 3, and hereinafter, the symbols "a" or "b" added to a moiety (e.g. $R^{9a}$) denote those groups ultimately forming a part of the moiety $A^a$-$D^a$- or $A^b$-$D^b$-, respectively, in the compounds of formula I, or, in the case of $Q^{1a}$ or $Q^{2a}$ and $Q^{1b}$ or $Q^{2b}$, denote those groups on the corresponding side of the molecule. Moieties to which the symbols "a" or "b" are added are otherwise defined as above (e.g., $R^{9a}$ is defined as for $R^9$), although said moieties may be defined independently of each other (e.g., $R^{9a}$ may be defined independently of $R^{9b}$).

Method (A) of Reaction Scheme 3 begins by coupling the aminoalcohol XIII to the epoxide XXI (see Method (A) of Reaction Scheme 1 for preparation of epoxide XXI), or to the chloroketone XXII (see Method (A) of Reaction Scheme 1 for preparation of chloroketone XXII; the corresponding bromoketone may also be prepared and employed as described therein) followed by reduction, to give the asymmetric aminediol XXIII. Optionally, the groups $Q^{1a}$ and $Q^{1b}$ may be sequentially removed and the resulting amines coupled to N-protected amino acids or peptide chains to give the compound XXV. Where $Q^3$ is hydrogen, the central amine to which it is bonded may optionally be protected as described above.

Such compounds as are prepared above may also be prepared by employing Methods (B) or (C) of Reaction Scheme 3 using procedures analogous to those of Reaction Scheme 2. In particular, Method (B) of Reaction Scheme 3 may be carried out by procedures analogous to those of Method (E) of Reaction Scheme 2; Method (C) of Reaction Scheme 3 may be carried out by procedures analogous to those of Method (F) of Reaction Scheme 2. The asymmetrical diols XXVI and XXIII may optionally be deprotected and coupled as described above. Where $Q^3$ is hydrogen, the central amine group to which it is bonded may, in each case, be optionally protected as described above.

Reaction Scheme 4
Preparation of Compounds I where $R^1$
and/or $R^2 \neq$ Hydrogen
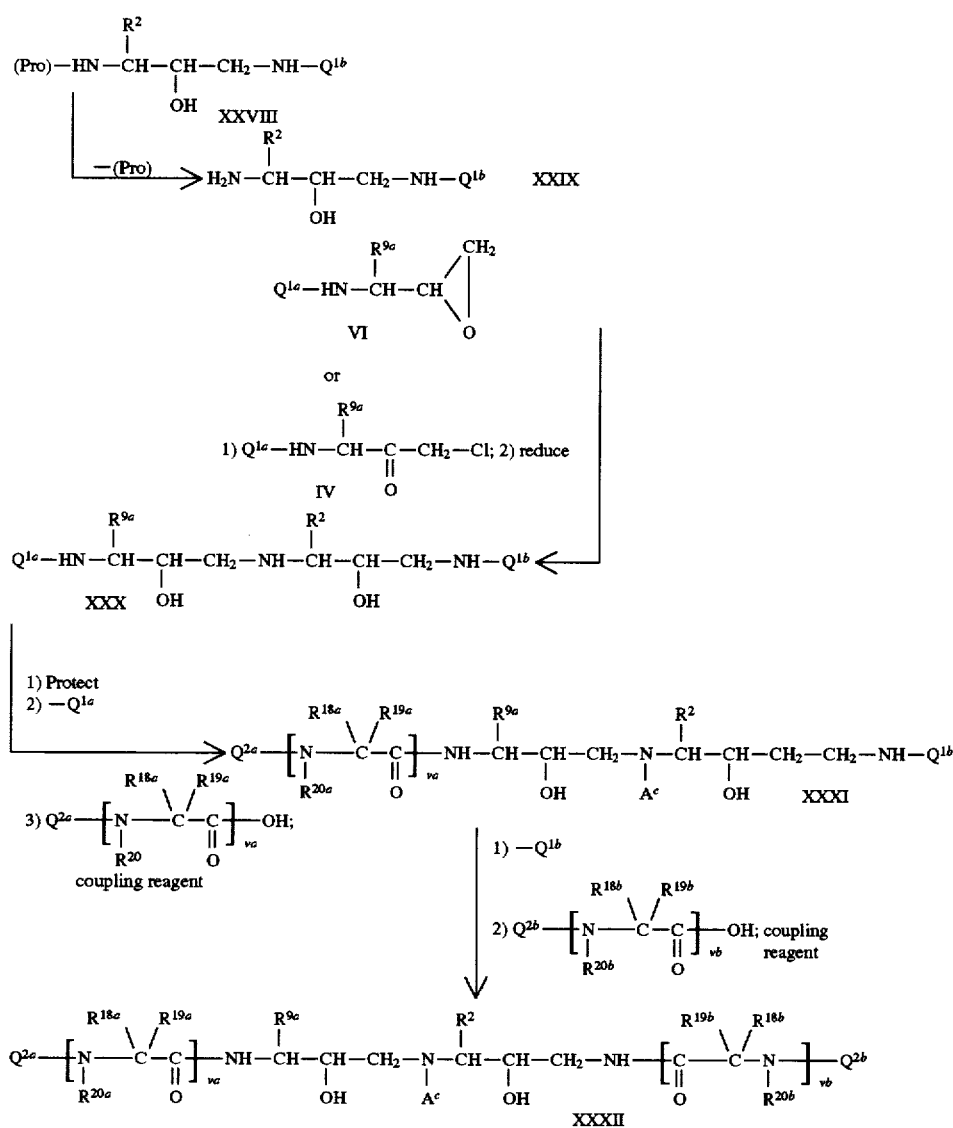
Method (B)
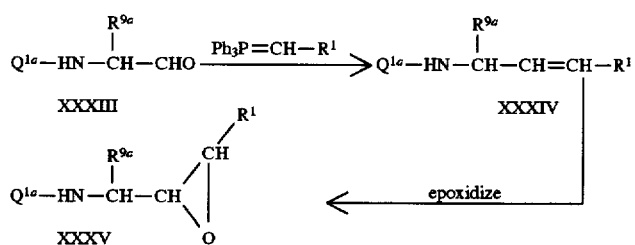

5,760,036
27
28
-continued
Reaction Scheme 4
Preparation of Compounds I where $R^1$
and/or $R^2 \neq$ Hydrogen
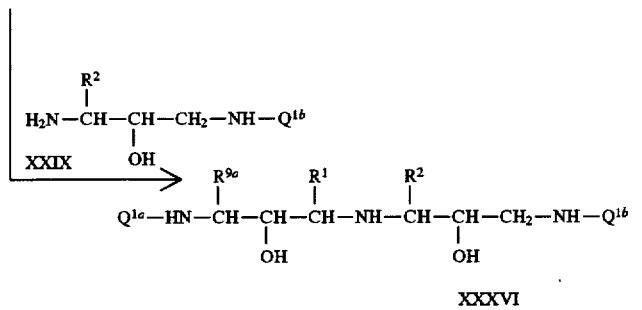
1) Protect
2) $-Q^{1a}$
3) $Q^{2a}$—[...]—OH; coupling reagent
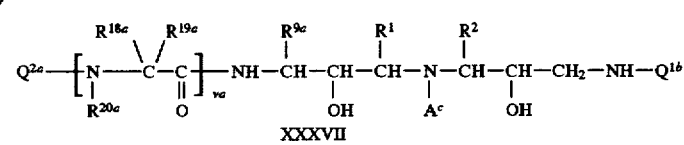
1) $-Q^{1b}$
2) $Q^{2b}$—[...]—OH; coupling reagent
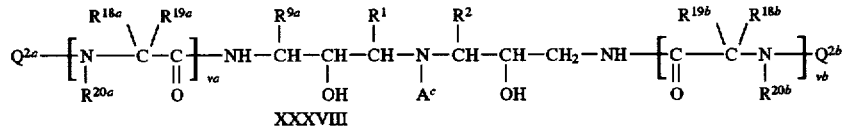
Method (C)
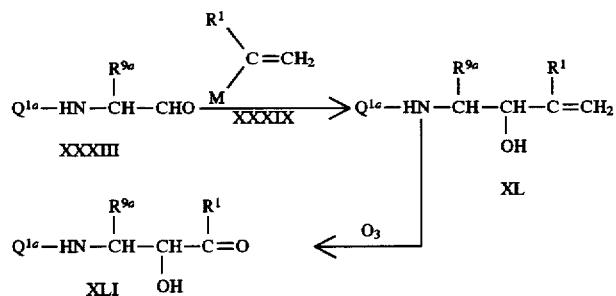

-continued
Reaction Scheme 4
Preparation of Compounds I where $R^1$ and/or $R^2 \neq$ Hydrogen

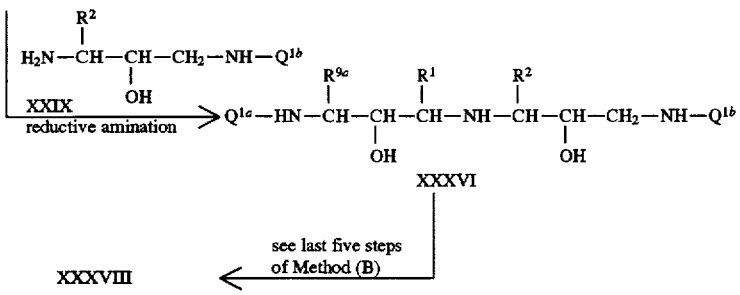

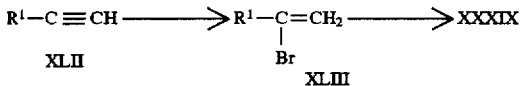

Method (D)

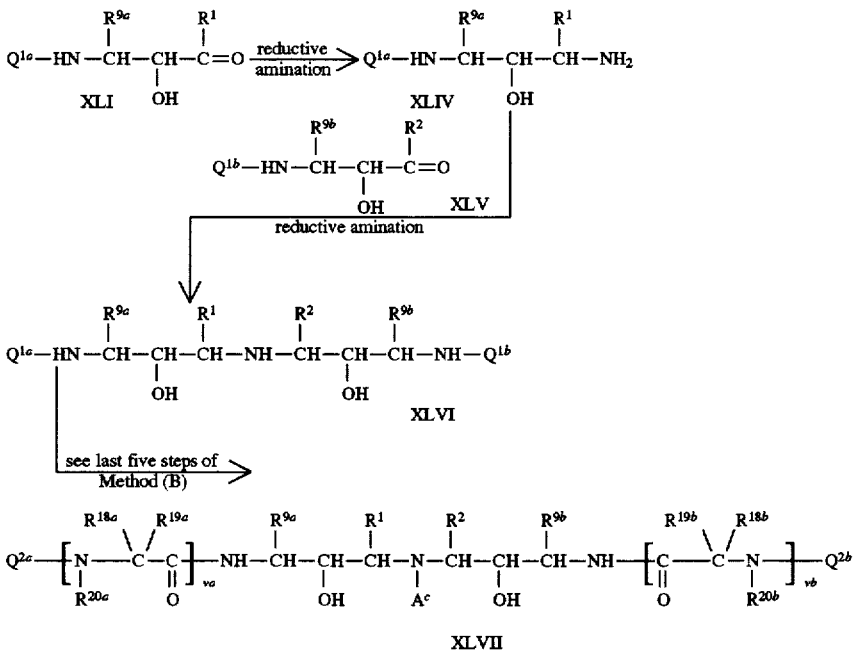

Reaction Scheme 4 above illustrates Methods (A) to (D) which may be used to prepare compounds of the formula I where $R^1$ and/or $R^2$ are not hydrogen.

As shown above in Method (A), selective removal of the protecting group (Pro) of compound XXVIII (which compound may be prepared by methods analogous to those employed in the preparation of compound XIII described above) is conducted, where (Pro) is independently chosen from those groups defined for $Q^1$, followed by coupling of the resulting amine XXIX with epoxide VI, or chloroketone IV (or corresponding bromoketone) followed by reduction, giving the aminediol XXX. Optionally, where $A^c$ is hydrogen, the central amine group to which it is bonded may be protected as described above, and the $Q^{1a}$ and/or $Q^{1b}$ N-terminal groups may then be sequentially or simultaneously removed and the resulting amines coupled to N-protected amino acids or peptide chains by methods described above.

Alternatively, as shown in Method (B), the aldehyde XXXIII (see Method (B) of Reaction Scheme 1 for preparation) may be converted to the olefin XXXIV by Wittig or Peterson methodology, and the olefin XXXIV in turn epoxidized by methods analogous to those described above (see Reaction Scheme 1, Method (B)) to yield compound XXXV. The epoxide XXXV may be coupled with the amine XXIX to give the aminediol XXXVI, which optionally may be protected at the central amine when $A^c$ is hydrogen as described above, and the $Q^{1a}$ and/or $Q^{1b}$ N-terminal groups may be sequentially or simultaneously deprotected and coupled to N-protected amino acids or peptide chains to give aminediol XXXVIII.

The aminediol XXXVIII may also be prepared as shown in Method (C) by reaction of the aldehyde XXXIII with the vinyl organometallic reagent XXXIX, where M is a metal-containing moiety such as magnesium bromide, lithium, $CeCl_2$, and the like, to give the allylic alcohol XL. The double bond may then be oxidatively cleaved by methods described above to give the ketone XLI, which can then undergo reductive amination in the presence of the amine XXIX, by methods also described above, to give compound XXXVI. The compound XXXVI may be converted to the aminediol XXXVIII by the methods described above in Method (B). The reagent XXXIX employed above in Method (C) may be prepared from the corresponding acetylene XLII via the vinyl bromide XLIII (Pollet et al., Syn. Commun., 10, 805 (1980); Suzuki et al., Tetrahedron Lett., 24, 731 (1983)).

Alternatively, as shown in Method (D), the ketone XLI may undergo reductive amination by methods described above, in the presence of ammonia, to give the aminoalcohol XLIV, which in turn can undergo reductive amination in the presence of the ketone XLV (see Method (C) for a method for preparation thereof) to give the aminediol XLVI. The aminediol XLVI may then be optionally protected, and sequentially deprotected and coupled to N-protected amino acids or peptide chains as described above in Method (B) to give compound XLVII.

Reaction Scheme 5
Preparation of Compounds I where $R^{10} \neq$ Hydrogen

Method (A)

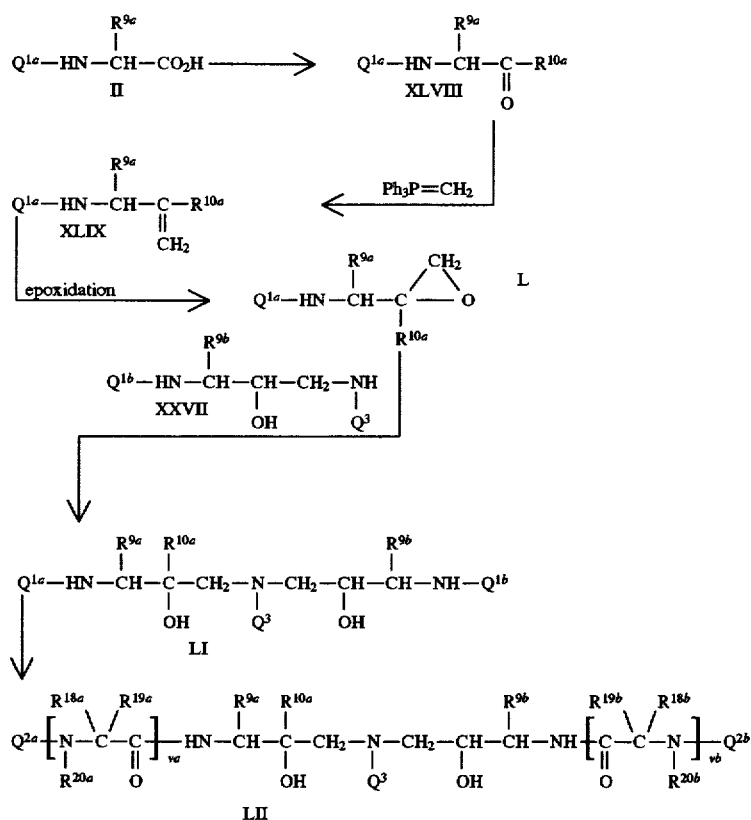

Reaction Scheme 5
Preparation of Compounds I where $R^{10} \neq$ Hydrogen Method (B)

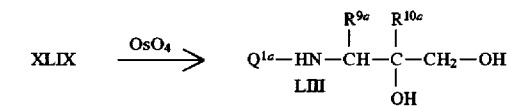

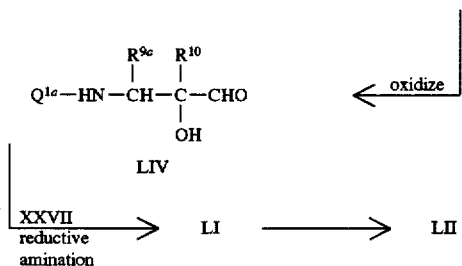

Method (C)

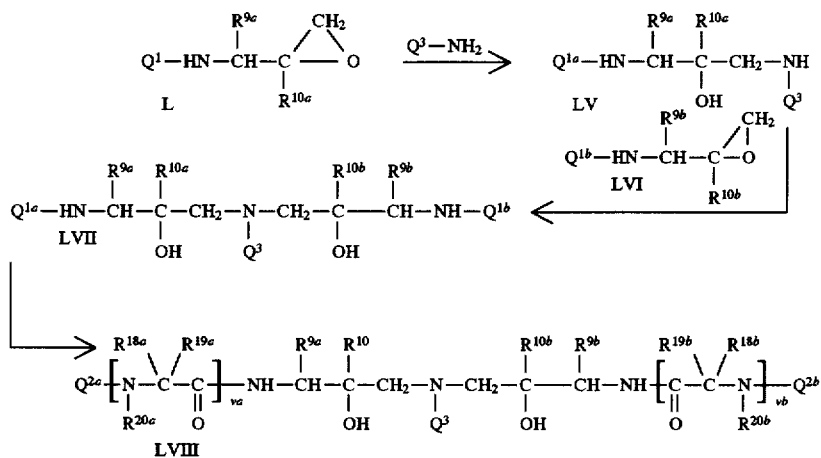

Method (D)

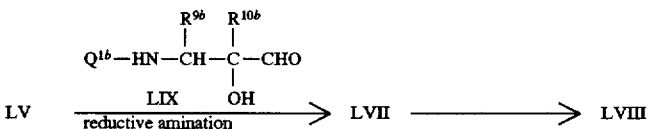

Reaction Scheme 5 above illustrates Methods (A) to (D), which may be used to prepare compounds of the formula I where $R^{10}$ is not hydrogen.

In Method (A), the protected amino acid II can be converted to the ketone XLVIII by methods known in the art (see, e.g., Gordon et al., Tetrahedron Lett., 28, 1603 (1987)). For example, conversion of amino acid II to an intermediate pyridyl ester or methyl hydroxamate (Weinreb et al., Tetrahedron Lett., 22, 3815 (1981)) (not shown), followed by reaction with an organolithium or organomagnesium reagent provides ketone XLVIII. The ketone obtained may then be converted to the olefin XLIX via a Wittig or Peterson reaction, which can be followed by epoxidation using methods as described above. The epoxide L so formed may be coupled with the aminoalcohol XXVII to give the aminediol LI. Optionally, the $Q^1$ groups may then be sequentially or simultaneously deprotected and coupled to N-protected amino acids or peptide chains using methods as described above to give compound LII.

Alternatively, as shown in Method (B), the olefin XLIX may be converted directly to the cis diol LIII using osmium tetraoxide or potassium permanganate (Kochi et al., Metal Catalyzed Oxidations of Organic Compounds, pp. 162-171, 294-296, Academic Press (1981)), and the diol LIII in turn oxidized to the aldehyde LIV by methods described above. The aldehyde LIV may then undergo reductive amination in the presence of the aminoalcohol XXVII to give the aminediol LI, and the latter compound converted to the aminediol LII, by methods described above.

Another route is shown in Method (C). In Method (C), the epoxide L may be coupled to a primary amine or ammonia $Q^3$—$NH_2$ by methods described above to give the aminoalcohol LV, which can be coupled to the epoxide LVI (see Method (A) for preparation thereof), to give the aminediol LVII. As described above, the $Q^1$ protecting groups may optionally be sequentially or simultaneously removed and the resulting amino groups coupled to N-protected amino acids or peptide chains to give compound LVIII.

Alternatively, as shown in Method (D), the aminoalcohol LV may undergo reductive amination in the presence of the aldehyde LIX (see Method (B) for preparation) by methods described above to give compound LVII, and the latter converted to compound LVIII by methods also described above, for example, in Method (C).

Reaction Scheme 6
Preparation of Compounds I where $R^8 \neq$ Hydrogen

Method (A)

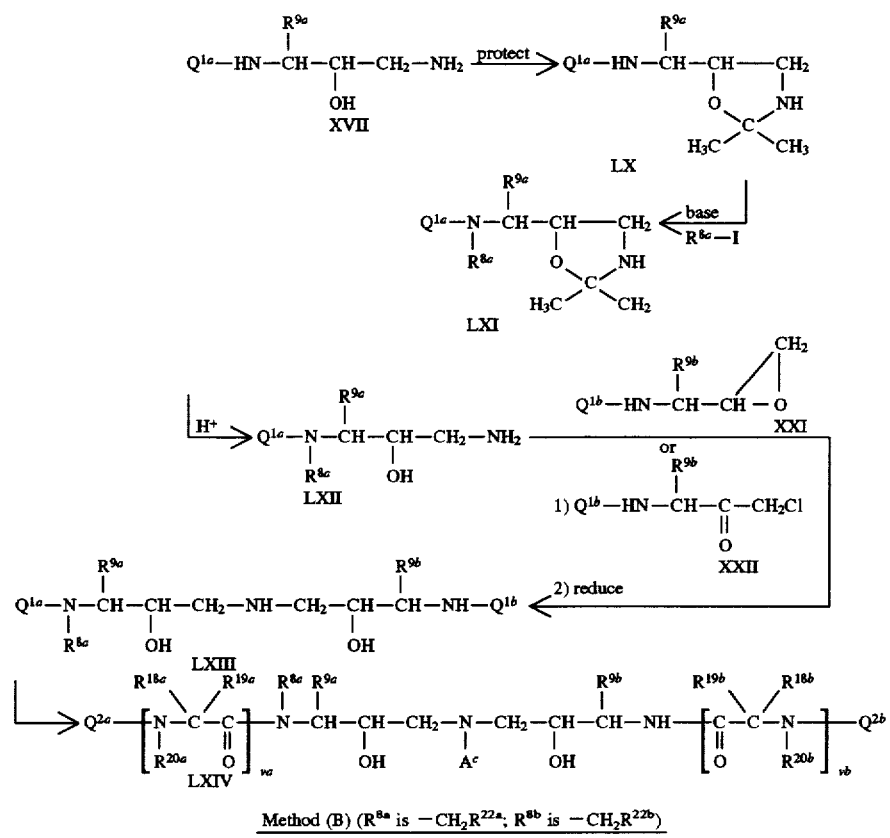

Method (B) ($R^{8a}$ is —$CH_2R^{22a}$; $R^{8b}$ is —$CH_2R^{22b}$)

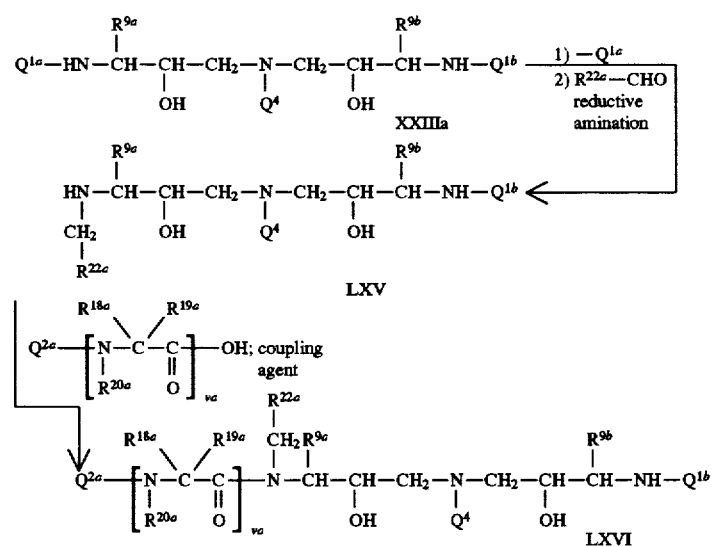

-continued
Reaction Scheme 6
Preparation of Compounds I where $R^8 \neq$ Hydrogen

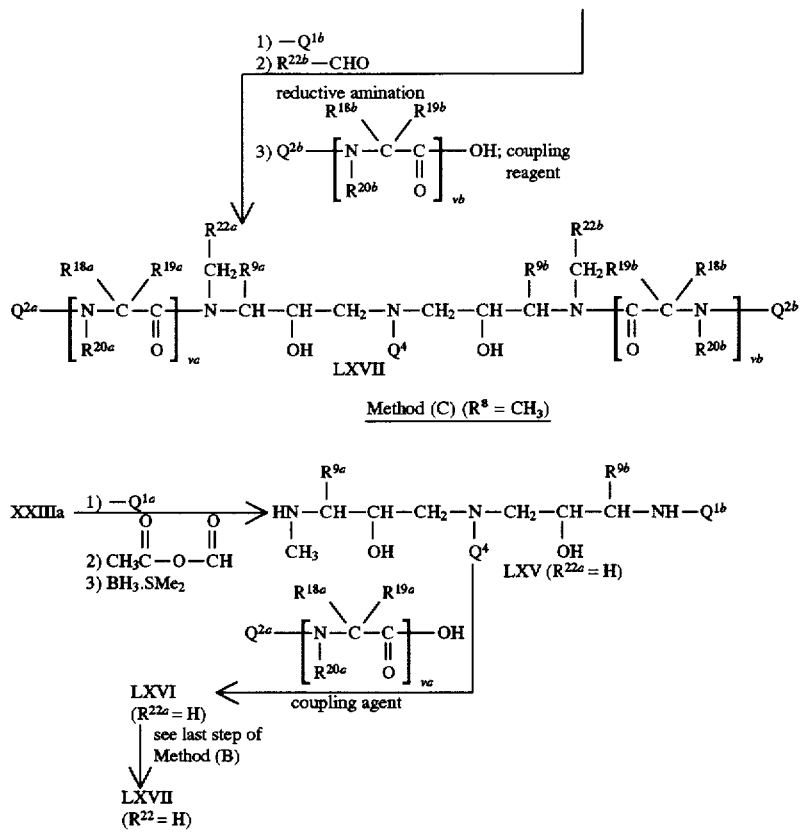

Reaction Scheme 6 above illustrates Methods (A), (B) and (C) which may be used to prepare compounds of the formula I where $R^8$ is not hydrogen.

In Method (A), the aminoalcohol XVII can be protected as shown yielding compound LX (Bergmann, Chem. Rev., 53, 309 (1953)) and the non-basic nitrogen alkylated (Benoiton et al., Can. J. Chem., 49, 1968 (1971)) by treatment with a base such as sodium or potassium hydride, sodium or potassium hexamethyldisilazide, or the like, followed by, for example, an alkylating agent such as an alkyl iodide, bromide, chloride, tosylate, triflate, or the like. $Q^{1a}$ is an activating group which renders the hydrogen on the nitrogen atom to which it is bonded acidic and easily removed with a base as described above, such as a group forming, together with —$N(R^{8a})$, a carbamate or amide group. The aminoalcohol LXI formed can then be deprotected to form compound LXII, and the latter coupled to an epoxide XXI, or to a chloroketone XXII (the corresponding bromoketone may be employed as described above) followed by reduction, by methods described above to give an aminediol LXIII, which optionally may be protected at the central amine and the $Q^1$ groups sequentially or simultaneously deprotected and coupled to N-protected amino acids or peptide chains to give LXIV.

Alternatively, as shown in Method (B), an aminediol such as XXIIIa (which may be prepared from aminediol XXIII by methods known to one of ordinary skill in the art) may be monodeprotected at $Q^{1a}$ or $Q^{1b}$ and the resulting amine reacted under reductive amination conditions in the presence of a compound of the formula $R^{22a}$—CHO where $R^{22a}$ is hydrogen or alkyl, by methods described above to give LXV. $Q^4$ is defined to include alkyl and those groups included in the definition of $Q^1$. The resulting amine may be optionally coupled by methods described above to give compound LXVI. A similar process may optionally be carried out at the other end of the molecule to produce an aminediol such as LXVII.

In Method (C), compounds where $R^8$ is a methyl group may be prepared by deprotecting an aminediol XXIIIa, where $Q^4$ is not formyl; formylating the deprotected amine; and reducing the resulting formamide to the methylated amine using borane-dimethyl sulfide complex (Krishnamurthy, Tetrahedron Lett., 23, 3315 (1982)). The methylated amine LXV ($R^{22a}$=H) may optionally be coupled to an N-protected amino acid or peptide chain to give the compound LXVI ($R^{22a}$=H), and the compound LXVI converted to compound LXVII ($R^{22}$=H) as described above.

Reaction Scheme 7
Preparation of Compounds I where
p and/or q ≠ zero
Method (A)
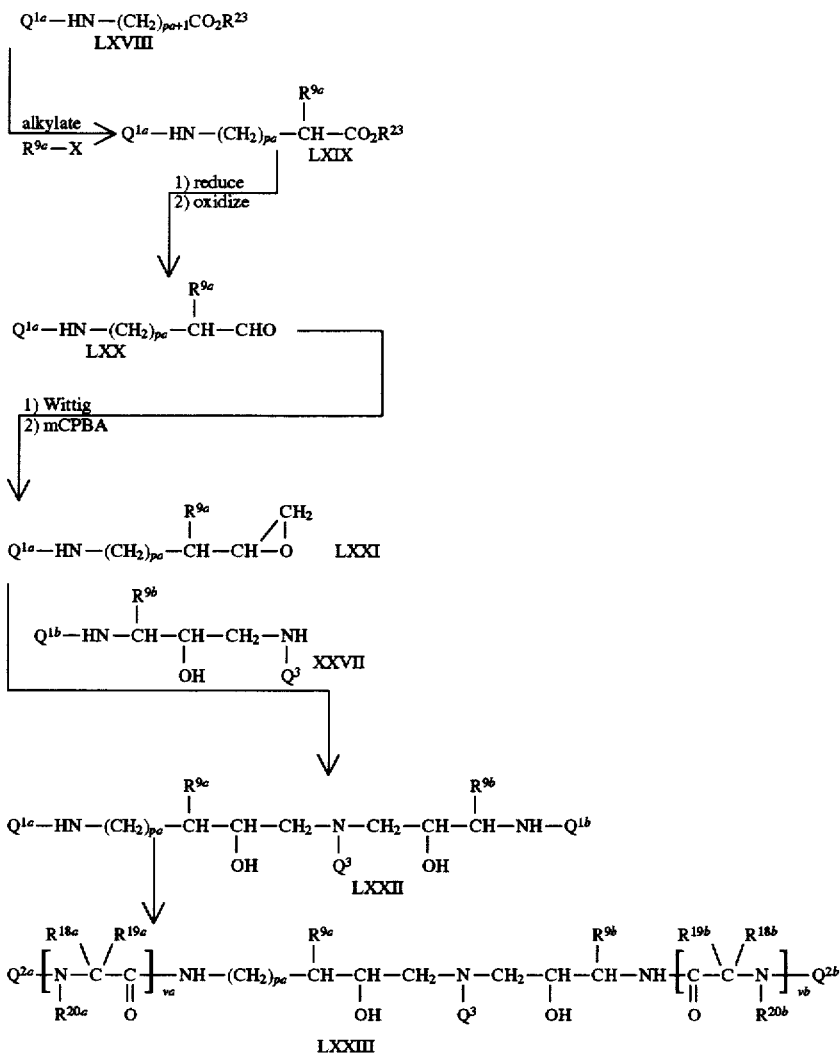
Method (B)
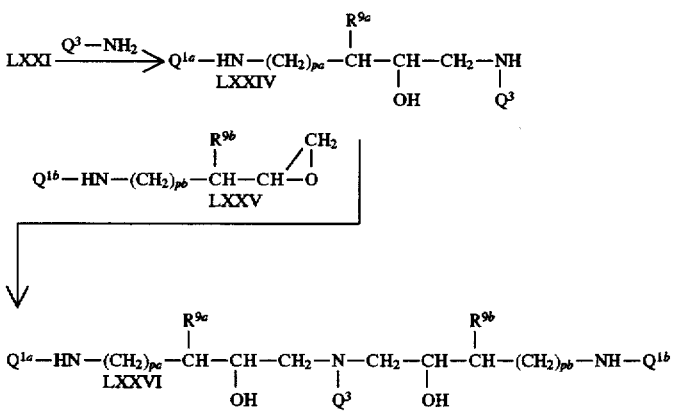

-continued
Reaction Scheme 7
Preparation of Compounds I where
p and/or q ≠ zero
Method (C)
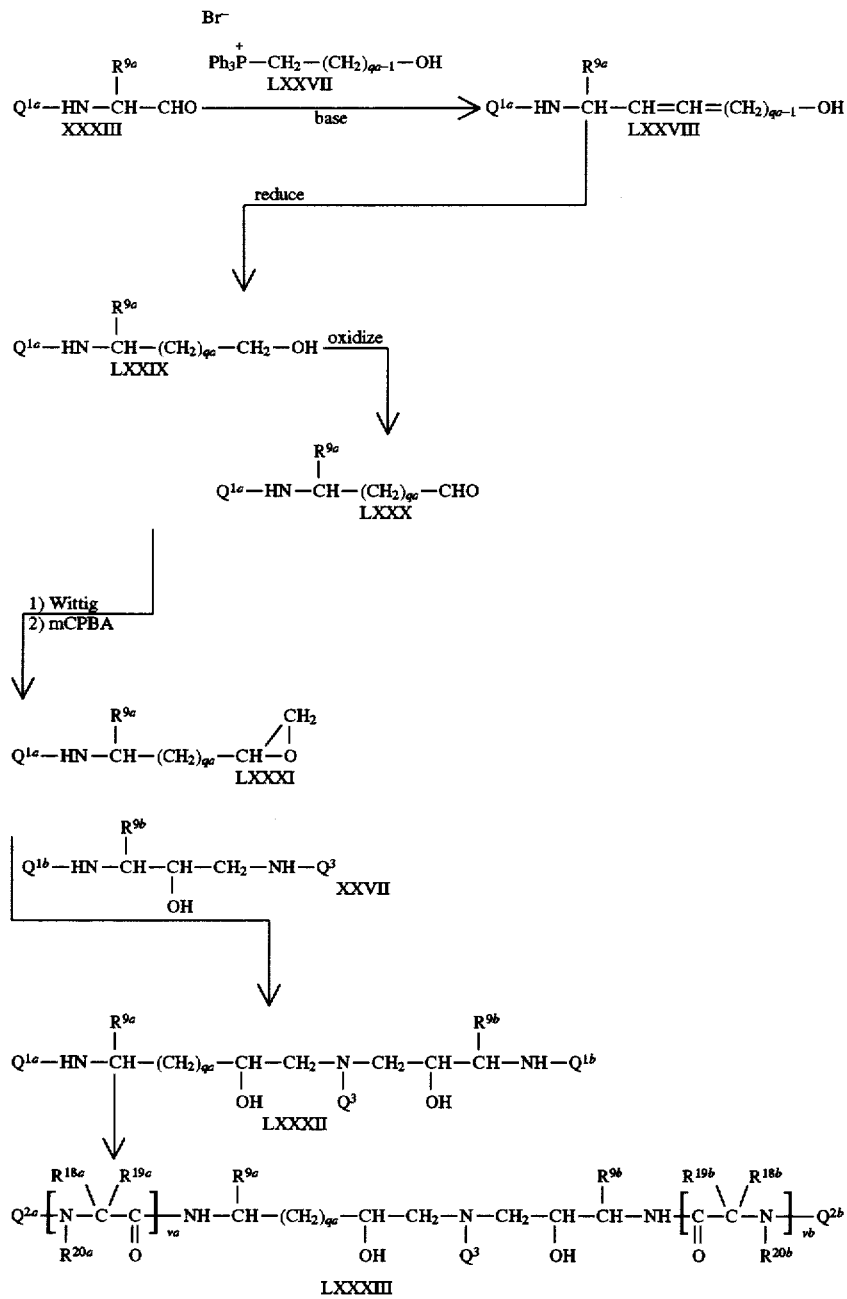
Method (D)
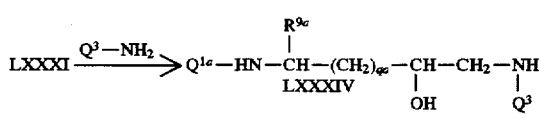

-continued
Reaction Scheme 7
Preparation of Compounds I where
p and/or q ≠ zero

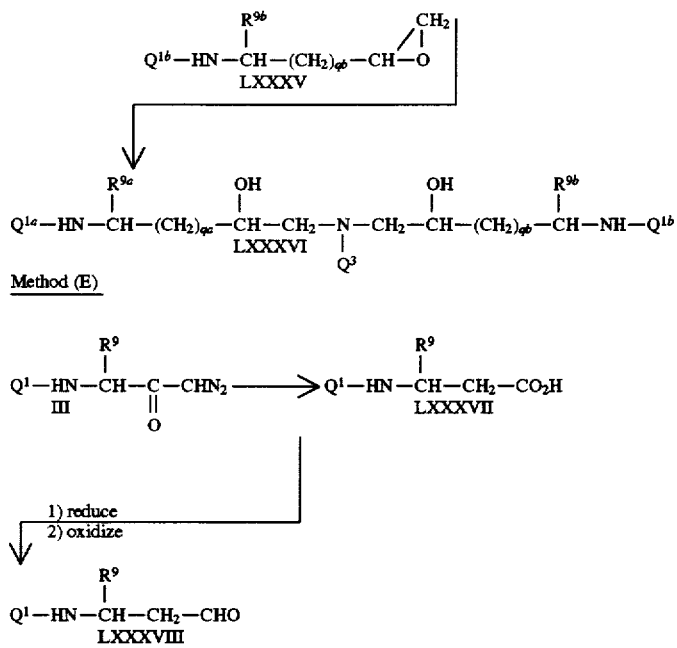

Method (E)

Reaction Scheme 7 above illustrates Methods (A) to (E), which may be used to prepare compounds of the formula I where p and/or q are not zero.

In Method (A), the protected amino ester LXVIII ($R^{23}$ may be unsubstituted lower alkyl, aryl or aryl-lower alkyl) where $P_a$=1–4 and q=0 can be alkylated via its enolate anion (formed by treatment of the ester with a base such as lithium diisopropylamide, lithium bis(trimethylsilyl)amide or the like) with $R^{9a}$-X, where X is halogen, tosylate, mesylate or the like to give the ester LXIX. The ester may be reduced directly to the aldehyde LXX with diisobutylaluminum hydride or in two steps by conversion to the primary alcohol with a hydride reducing agent and then oxidation to the aldehyde as described above. The aldehyde can be converted directly to the epoxide LXXI via reaction with a sulfonium or arsonium ylide or by a Wittig or Peterson reaction to give the corresponding olefin (not shown), followed by epoxidation as described above. The epoxide may be coupled to the amino alcohol XXVII to give the aminediol LXXII, which optionally may then be sequentially or simultaneously deprotected and coupled to N-protected amino acids or peptide chains as described above to give the compound LXXIII. The starting ester LXVIII of Method (A) may be obtained by methods known to those skilled in the art such as those methods described in J. March, "Advanced Organic Chemistry", John Wiley (1985) (see pages 1157–1158).

Method (B) illustrates a method for obtaining compounds where both $P_a$ and $P_b$>zero. In this method, the epoxide LXXI is reacted with ammonia or a primary amine $Q^3$—$NH_2$ to give the compound LXXIV, followed by coupling with the epoxide LXXV (which may be prepared by a method analogous to that for preparing the epoxide LXXI above) to give compound LXXVI. The compound LXXVI may optionally then be sequentially or simultaneously deprotected and coupled to N-protected amino acids or peptide chains as described above.

Method (C) illustrates a method for obtaining compounds where $q_a$=2–4 and p=zero. In Method (C), Wittig reaction of the hydroxy-phosphorane LXXVII with the protected amino aldehyde XXXIII gives the olefin LXXVIII which can be reduced to the saturated alcohol LXXIX under catalytic hydrogenation conditions. Oxidation of the alcohol LXXIX to the aldehyde LXXX may be followed by conversion to the epoxide LXXXI, the latter achieved by a Wittig reaction followed by treatment with m-chloroperoxybenzoic acid (mCPBA). The epoxide LXXXI is then coupled with the amino alcohol XXVII to give the aminediol LXXXII as described above. The aminediol may then optionally and sequentially be deprotected and coupled to N-protected amino acids or peptide chains to give compound LXXXIII. The hydroxyphosphorane starting material LXXVII may be prepared by reaction of the appropriate haloalcohol with triphenylphosphine under standard conditions.

Method (D) illustrates a method where compounds in which $q_a$ and $q_b$ are both >1 and p=0 may be prepared by reaction of the epoxide LXXXI with ammonia or a primary amine $Q^3$—$NH_2$ to give compound LXXXIV. The latter compound may then be coupled with the epoxide LXXXV (prepared, e.g., by the method employed above for preparation of the epoxide LXXXI) to yield the aminediol LXXXVI. The aminediol LXXXVI may optionally then be sequentially or simultaneously deprotected and coupled to N-protected amino acids or peptide chains as described above.

Method (E) illustrates a method for preparing intermediate compounds which may be employed in preparing aminediols where q=1 and p=0. In Method (E), the intermediate aldehyde LXXXVIII may be prepared by an Arndt-Eistert reaction (Meier and Zeller, Angew. Chem. Int. Ed. Engl., 14, 32 (1975)) on the diazoketone III to give the carboxylic acid LXXXVII. Conversion of the carboxylic acid to the aldehyde may be conducted by reduction and oxidation as described above. The aldehyde may then be converted to the desired aminediol as described in Methods (C) and (D).

Reaction Scheme 8
Preparation of Compounds I where R[9'] ≠ Hydrogen

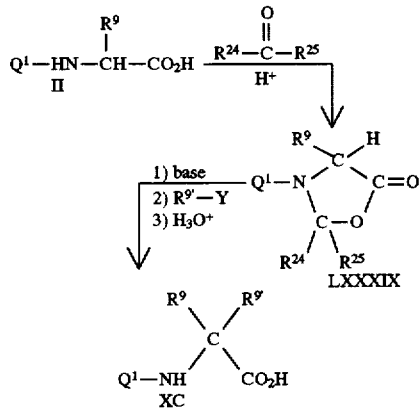

Reaction Scheme 8 illustrates a method for the preparation of compounds of the formula I where $R^{9'}$ is not hydrogen.

An N-protected amino acid II may be converted into an acetal LXXXIX where $R^{24}$ and $R^{25}$ are independently hydrogen or unsubstituted lower alkyl as shown. Treatment of the acetal LXXXIX with a base such as lithium diisopropyl amide, followed by reaction with a compound $R^{9'}$-Y where Y may be Cl, Br, I or triflate, and hydrolysis of the acetal gives the α-substituted amino acid XC. The amino acid XC may be converted to amine diols of the formula I by those methods described in Schemes 1 to 7 above. Unnatural, optically active α-amino acids can be prepared by methods such as those described in Evans et al., *J. Am. Chem. Soc.*, 112, 4011 (1990); and Oppolzer et al., *Tetrahedron Lett.*, 30, 5603, 6009 (1989). Alternative methods are also described in Williams, R. M., *Synthesis of Optically Active α-Amino Acids*, Pergamon Press: Oxford (1989).

Reaction Scheme 9
Alternative Methods for
Preparation of Intermediate Materials

Method (A)

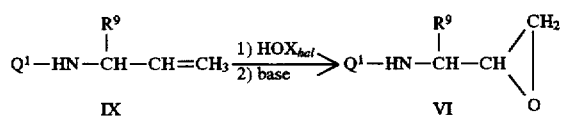

-continued
Reaction Scheme 9
Alternative Methods for
Preparation of Intermediate Materials Method (B)

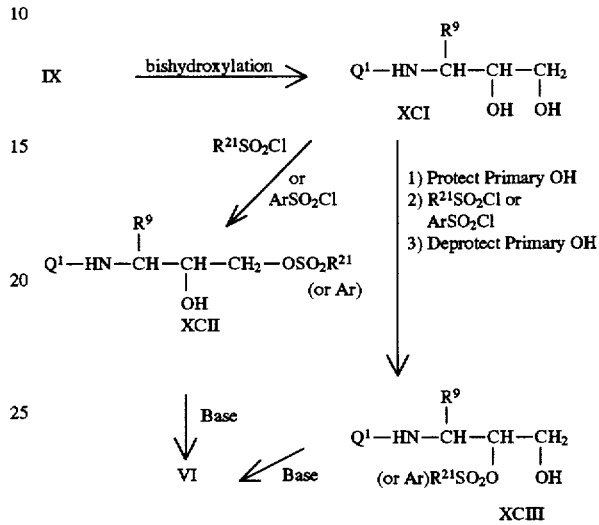

Method (C)

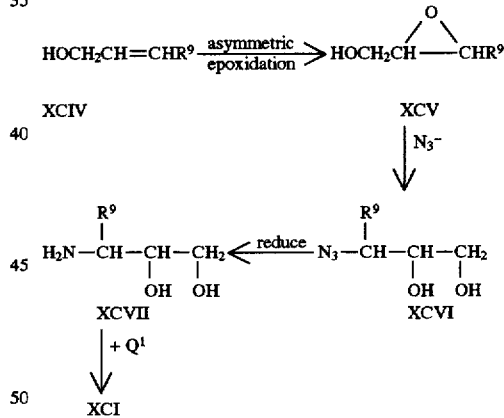

-continued
Reaction Scheme 9
Alternative Methods for Preparation of Intermediate Materials

Method (D)

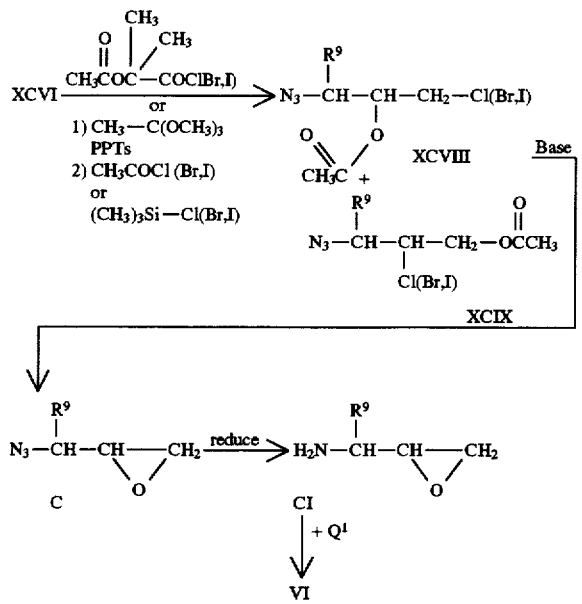

Method (E)

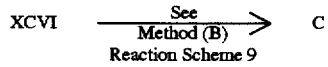

Method (F)

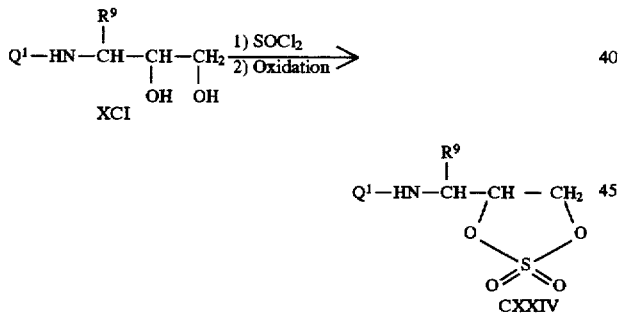

Intermediate materials for the preparation of compounds of the formula I may alternatively be prepared by methods (A) to (F) as shown in Reaction Scheme 9 above.

In this regard, the present invention provides a novel method for the preparation of a halohydrin of the following formula:

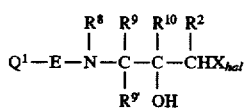

where $Q^1$, E, $R^2$, $R^8$, $R^9$, $R^{9'}$ and $R^{10}$ are as defined above, particularly where $R^9$ is not the same as $R^{9'}$ (most preferably, where one of $R^9$ or $R^{9'}$ is hydrogen), and $X_{hal}$ is chloro or bromo, comprising the step of contacting an olefin of the following formula:

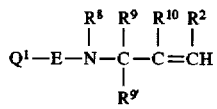

with the compound $HOX_{hal}$.

The compound $HOX_{hal}$ may be formed in situ for use in the method of the present invention, such as by contacting N-chlorosuccinimide, N-bromosuccinimide, $Br_2$ or $Cl_2$ with water. Preferred molar ratios of the compound $HOX_{hal}$ to the olefin starting material are from about 1:1 to about 3:1.

In a preferred embodiment, the novel method of the present invention comprises the optional further step of preparing an epoxide of the following formula:

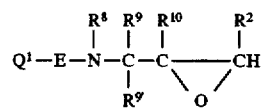

by contacting the above halohydrin with a base.

The base employed may be any basic compound providing conversion of the halohydrin to the epoxide, such as alkali metal (e.g., sodium or potassium) hydroxides, alkali metal (e.g., sodium or potassium) hydrides, alkali metal (e.g., sodium or potassium) carbonates, or amine bases (e.g., trialkylamines). Preferred molar ratios of the base to the halohydrin are from about 1:1 to about 5:1.

The temperature employed during the above steps for halohydrin and, optionally, epoxide formation is preferably from about −78° C. to about 50° C. The steps are preferably conducted in an organic solvent such as dioxane or tetrahydrofuran. An alcohol (for example, methanol) is preferably employed during epoxide formation, such as by addition to the aforementioned organic solvent when a single pot is employed, particularly where the base is other than an amine base. Times employed are those sufficient for halohydrin and, optionally, epoxide formation.

The above novel method of the present invention preferentially (that is, in a greater than 1:1 molar ratio) provides halohydrins of the following relative stereoconfiguation:

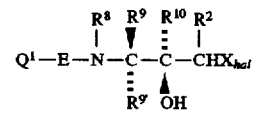

relative to the corresponding stereoisomers thereof:

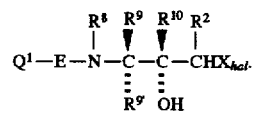

Thus, the above method of the present invention comprising the preferred further step of epoxide formation is particularly advantageous where epoxides having the following relative stereoconfiguration are sought:

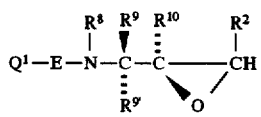

as such compounds are formed preferentially (that is, in a greater that 1:1 molar ratio) relative to the corresponding stereoisomers thereof:

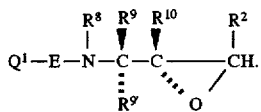

The starting olefins may be prepared by methods such as those described by Luly et al., *J. Org. Chem.*, 52, 1487–1482 (1987).

Method (A) illustrates the novel method of the present invention. In Method (A), olefin IX is converted to the halohydrin (not shown) by treatment with aqueous bromine or N-bromosuccinimide or N-chlorosuccinimide, and then treated with base, such as potassium carbonate or potassium or sodium hydroxide or the like to give epoxide VI.

As shown in Method (B), olefin IX may be converted to the diol XCI by treatment with osmium tetroxide or potassium permanganate, or other methods known in the art (Kochi, et al., Metal Catalyzed Oxidations of Organic Compounds, pp. 162–171, 294–296, Academic Press (1981); Jacobsen, et al., J. Am. Chem. Soc., 110, 1968 (1988); Sharpless, et al., J. Org. Chem., 57, 2768 (1992)). Diol XCI may be treated with a sulfonyl chloride (e.g., methanesulfonyl chloride or p-toluenesulfonyl chloride; Ar denotes aryl) to give the sulfonate XCII; or, alternatively, the primary hydroxyl group of XCI may be selectively protected (see Greene, Protective Groups in Organic Synthesis), and the secondary hydroxyl group sulfonylated, followed by deprotection of the primary hydroxyl group, to give XCIII. The sulfonate esters XCII or XCIII may be independently converted to the epoxide VI by treatment with base, such as sodium or potassium hydroxide, or an alkylamine base such as triethylamine; the latter reaction from XCIII occurs with inversion of the configuration of the secondary hydroxyl group.

In Method (C) (see Thompson, et. al., *J. Am. Chem. Soc.*, 115, 801 (1993) and Bennett, et. al., *JCS Chem. Commun.*, 737 (1993)), the olefin XCIV may be converted to the epoxide XCV by asymmetric epoxidation (Gao, et al., J. Am. Chem. Soc., 109, 5765 (1987)). Starting olefin XCIV may readily be prepared by one of ordinary skill in the art by known methods (e.g., Wittig reaction, March, Advanced Organic Reactions, pp 839–841 and pp 845–854 (Third Edition)). Epoxide XCV can be converted to the azidodiol XCVI by treatment with azide anion, such as treatment with sodium azide and titanium bisisopropoxide (Caron, et al., J. Org. Chem., 53, 5185 (1988); Omaka, et al., Chem. Lett., 1327 (1986)). The azidodiol can be reduced by methods described above in Reaction Scheme 2, Method (E) to give the aminodiol XCVII. Protection of the amine by methods known in the art, such as those described in Greene, Protective Groups in Organic Synthesis, may provide Compound XCI.

Alternatively, as described in Method (D), azidodiol XCVI may be converted to the mixture of haloacetates XCVIII and XCIX by treatment with 2-acetoxyisobutyryl halide, or treatment with trimethyl orthoacetate and PPTs followed by acetyl halide (e.g., acetyl bromide) or trimethylsilyl halide (e.g., trimethylsilyl chloride) (Russel, et al., J. Am. Chem. Soc., 95, 4025 (1973); Thompson, et al., ibid, 115, 801 (1993); Kolb, et al, Tetrahedron, 48, 10515 (1992)). The haloacetates XCVIII and XCIX may be treated with base such as sodium methoxide or sodium or potassium carbonate, to give the azidoepoxide C. Reduction of the azidoepoxide C to the aminoepoxide CI followed by protection of the amine by methods known in the art provides epoxide VI.

Alternatively, as shown in Method (E), the azidodiol XCVI may be converted to the epoxide C by methods analogous to those described above (Reaction Scheme 9, Method (B)).

In Method (F), diol XCI may be converted to the cyclic sulfate CXXIV by treatment, first with thionyl chloride to give the cyclic sulfite (structure not shown), and then oxidation with potassium permanganate or ruthenium trichloride/sodium periodate, and the like (Lohray, Synthesis, 1035 (1992); Gao, et al., J. Am. Chem. Soc., 110, 7538 (1988)). Compound CXXIV, or the intermediate sulfite, may be converted to aminediols by methods described above for the conversion of epoxides VI and/or XXI.

Reaction Scheme 10

Alternative Methods for

Preparation of Compounds I where $A^a = A^b$ and $D^a = D^b$

Method (A)

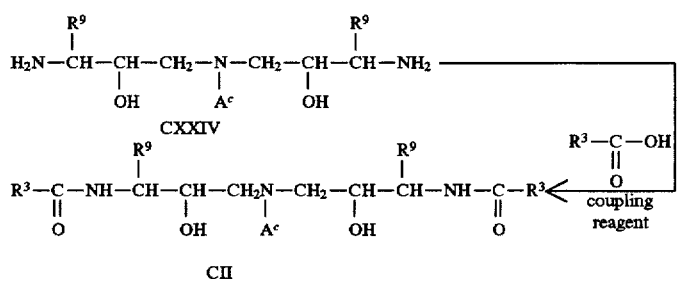

CII

-continued
Reaction Scheme 10
Alternative Methods for
Preparation of Compounds I where $A^a = A^b$
and $D^a = D^b$ Method (B)

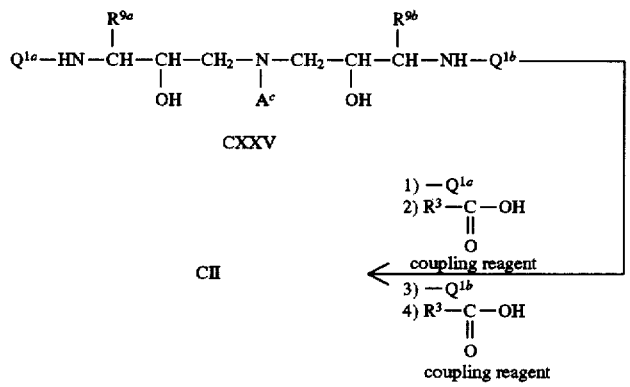

Method (C)

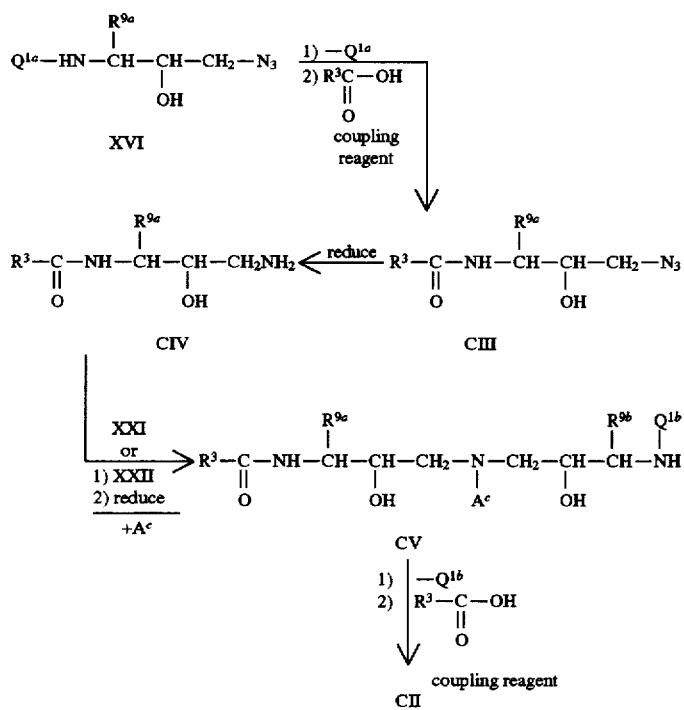

Reaction Scheme 10 above illustrates Methods (A) through (C), which may be used to prepare compounds of the formula I where $A^a$ is the same as $A^b$ and $D^a$ is the same as $D^b$ ("symmetrical" compounds.

In Method (A), one equivalent of the bis-amine CXXIV (prepared as for XI where $A^c$ replaces $Q^3$) is coupled to a carboxylic acid (prepared by standard techniques, where $R^3$ is described above and is compatible with the conditions used in the coupling reaction), using a coupling reagent such as DCC, EDCI, BOP reagent, BOP-Cl, DPPA, and the like, as described earlier (for alternative coupling conditions see Bodanszky, "Principles of Peptide Synthesis"; pp. 9–58, Springer-Verlag, (1984)) to give the aminediol CII. Where, in the bis-amine CXXIV, $A^c$ is hydrogen, the central amine to which it is bonded may optionally be protected as described above.

In Method (B), the process may be carried out in a step-wise fashion. The groups $Q^{1a}$ and $Q^{1b}$ in CXXV (prepared as for XXIII where $A^c$ replaces $Q^3$) may be sequentially removed and the resulting amines coupled to a carboxylic acid to give the compound CII. Where $A^c$ is hydrogen, the central amine to which it is bonded may optionally be protected as described above.

Method (C) begins with removal of the group $Q^{1a}$ and coupling of the resulting amine with a carboxylic acid to give the azidoalcohol CIII. The azido moiety may be reduced and the resulting aminoalcohol CIV can be coupled to the epoxide XXI or the haloketone XXII, followed by reduction, to give the aminediol CV (see Reaction Scheme 3). The central amine may optionally be protected with $A^c$. Removal of the group $Q^{1b}$ and coupling with a carboxylic acid as described above gives CII.

Reaction Scheme 11
Alternative Methods for
Preparation of Compounds I where $A^a \neq A^b$ and/or $D^a \neq D^b$ Method (A)

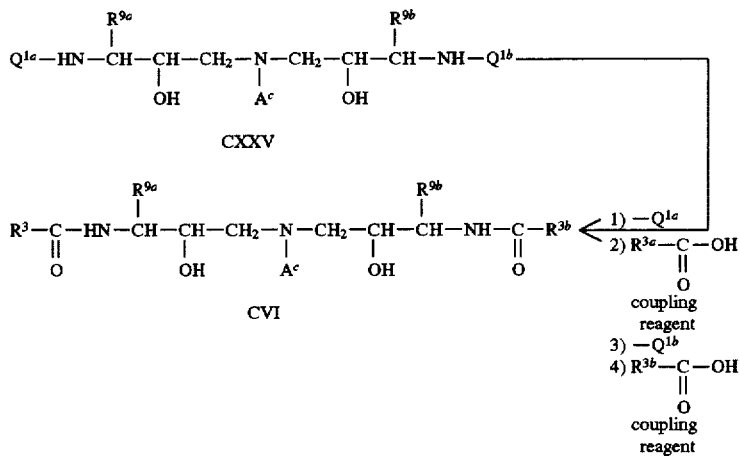

Method (B)

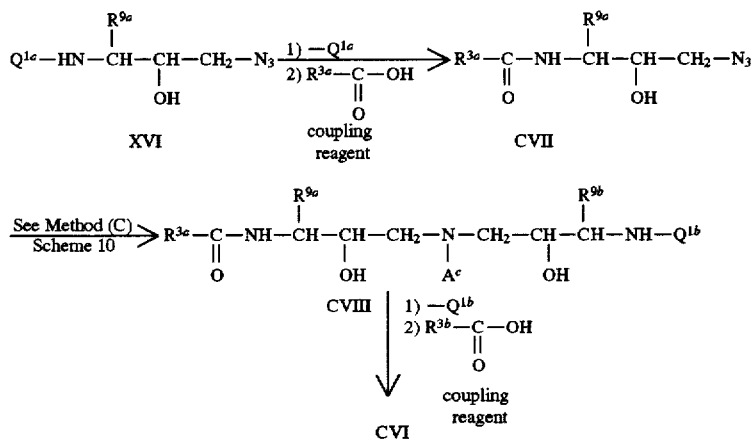

Method (C)

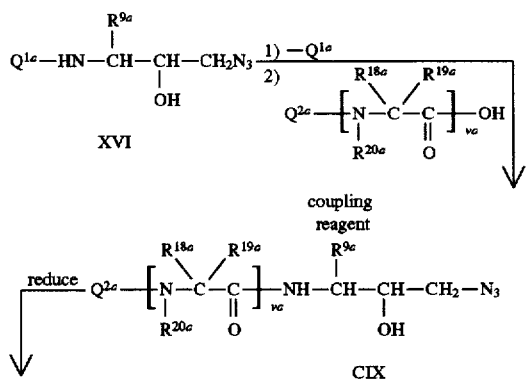

-continued
Reaction Scheme 11
Alternative Methods for
Preparation of Compounds I where $A^a \neq A^b$
and/or $D^a \neq D^b$
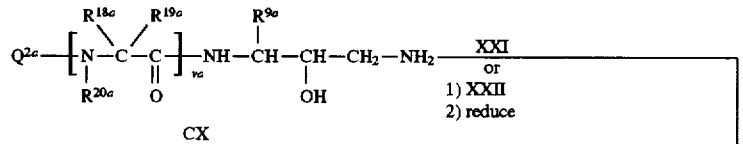
CX
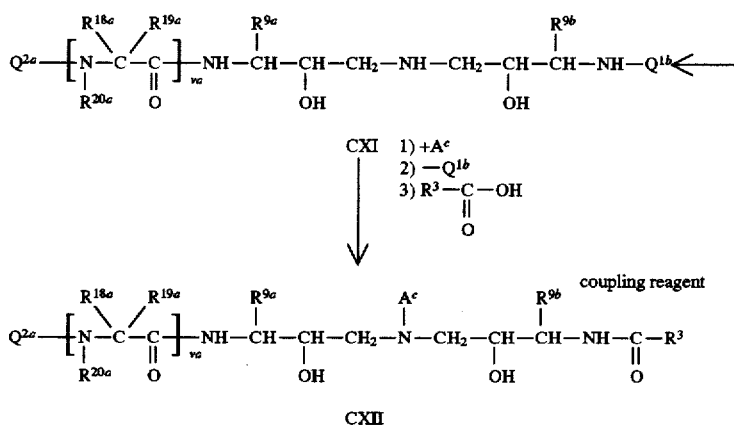
CXII
Method (D)
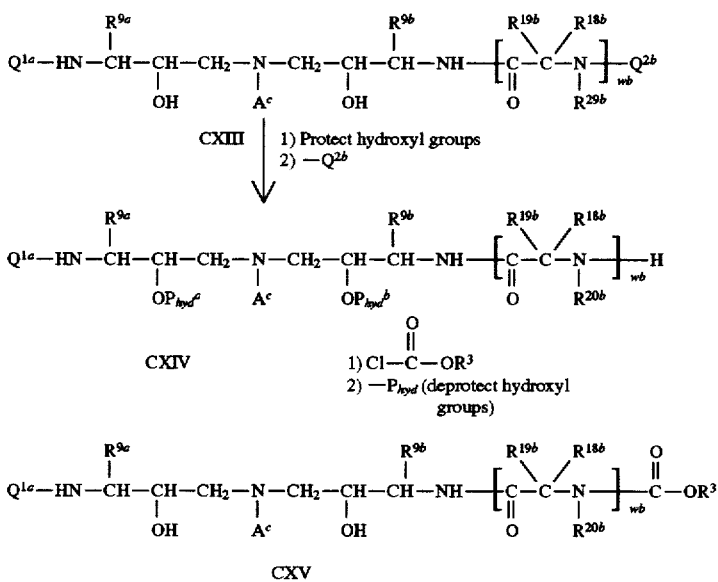
CXV
Method (E)
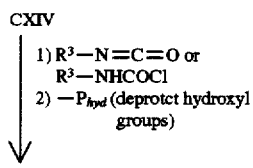

-continued
Reaction Scheme 11
Alternative Methods for
Preparation of Compounds I where $A^a \neq A^b$
and/or $D^a \neq D^b$

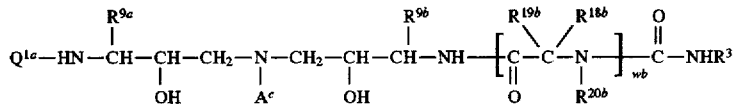

CXVI

Method (F)

CXIV

1) $R^3-\underset{\underset{O}{\|}}{C}-OH$
   coupling agent
2) deprotect hydroxyl groups

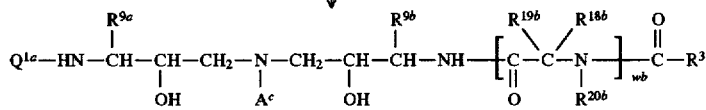

CXVII y

Reaction Scheme 11 above illustrates Methods (A) through (F) which may be used to prepare compounds of the formula I where $A^a$ differs from $A^b$ and/or $D^a$ differs from $D^b$ ("non-symmetrical" compounds).

According to Methods (A) and (B), non-symmetrical compounds may be prepared by procedures analogous to those of Scheme 10. In Method (A), the groups $Q^{1a}$ and $Q^{1b}$ may be sequentially removed and the resulting amines coupled to carboxylic acids to give Compound CVI. Where $A^c$ is hydrogen, the central amine to which it is bonded may optionally be protected as described above. Such compounds may also be prepared by employing Method (B), starting from azidoalcohol XVI and using procedures analogous to those of Method (C) of Reaction Scheme 10.

According to Method (C), non-symmetrical compounds may be prepared by procedures analogous to those of Reaction Schemes 2, 3 and 10. The method begins by removing the group $Q^{1a}$ and coupling the resulting amine to N-protected amino acids or peptide chains to give the compound CIX. The azido moiety may be reduced and the resulting aminoalcohol CX can be coupled to the epoxide XXI, or to the haloketone XXII followed by reduction, as described in Methods (C) through (E) of Reaction Scheme 2, to give the aminodiol CXI. Optionally, the central amine may be protected and the $Q^{1b}$ group may be removed and the resulting amine coupled to a suitable carboxylic acid by procedures analogous to those of Method (A) of Reaction Scheme 10 to give the aminodiol CXII.

Method (D) starts from compound CXIII (prepared as for XXIV where $A^c$ replaces $Q^3$) where w=0–4. The hydroxyl groups may optionally be protected such as with an ethoxyethyl group as described in Greene, Protective Groups in Organic Synthesis ($P_{hyd}$ denotes a hydroxyl protecting group). The $Q_{2b}$ group may then be removed and the resulting amine CXIV coupled with a chloroformate to afford, after removal of the hydroxyl protecting groups, the carbamate CXV. Where $A^c$ is hydrogen, the central amine to which it is bonded may be protected as described above.

In Method (E), the amine CXIV may be coupled with an isocyanate compound or a carbamoyl chloride to provide, after removal of the hydroxyl protecting groups, the urea CXVI. Where $A^c$ is hydrogen, the central amine to which it is bonded may be protected as described above.

In Method (F), the amine CXIV may be coupled with a carboxylic acid, using methods described in Scheme 10, to give, after removal of the hydroxyl protecting groups, the amide CXVII. Where $A^c$ is hydrogen, the central amine to which it is bonded may optionally be protected as described above.

Reaction Scheme 12
Preparation of Compounds I where $R^9$ = a
Substituted (Hydroxyphenyl)methyl analog

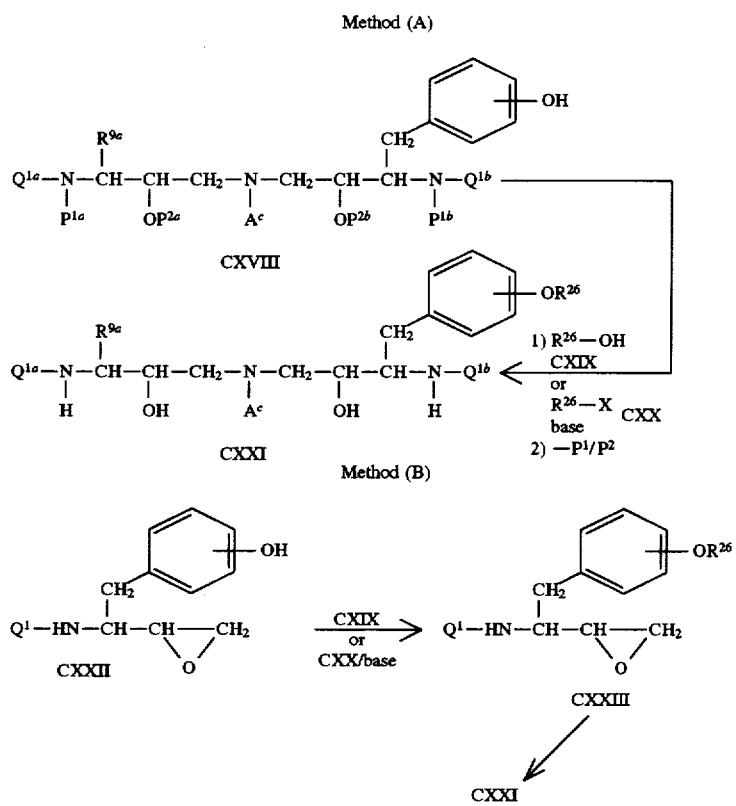

Reaction Scheme 12 above illustrates Methods (A) and (B) which may be used to prepare compounds of the formula I where $R^9$ is a substituted (hydroxyphenyl)methyl group.

Compound CXVIII in which the nitrogens bear $P^{1a}$ or $P^{1b}$ ($P^1$ denotes a nitrogen protecting group) and in which the hydroxyl groups are protected ($P^2$ denotes a hydroxyl protecting group) of Method (A) may be prepared by methods described in Greene, Protective Groups in Organic Synthesis. In particular, the aforementioned nitrogen and hydroxyl oxygen may be connected by a one carbon linker to form an oxazolidine ring. The phenol may then be reacted with a suitable alcohol CXIX (where $R^{26}$ is a lower alkyl group) in the presence of a phosphine (e.g., triphenylphosphine) and a reagent, such as diethyl- or diisopropylazodicarboxylate to give, after deprotection, the substituted phenol CXXI (Mitsunobu, Synthesis, 1 (1981); Varasi, et al., J. Org. Chem., 52, 4235 (1987)). Alternatively, phenol CXVIII may be treated with a base, such as potassium carbonate, sodium or potassium hydride, sodium or potassium bis (trimethylsilyl)amide, or the like, and a suitable activated alkyl compound CXX where X can be a halogen, such as bromo, chloro, or iodo, or a sulfonate ester such as trifluoromethyl sulfonate (i.e. —O—SO$_2$—CF$_3$) to give CXXI. Compound CXX can be prepared by methods known to those skilled in the art.

The aminediol CXXI may also be prepared as shown in Method (B). Procedures analogous to those of Method (A) above may be used to convert phenol CXXII (see Reaction Scheme 1 and Methods (A) and (B) of Reaction Scheme 9 for preparation) to epoxide CXXIII. Compound CXXIII may be converted to aminediol CXXI by procedures analogous to those of Methods (A), (B) and (E) of Reaction Scheme 2 and Methods (A) and (B) of Reaction Scheme 3.

Compounds of the formula I where $R^{11}$ is not hydrogen may be obtained, for example, by methods known in the art for adding a hydroxyl protecting group, such as those described in Greene (referred to above).

Modifications to the processes of the above Reaction Schemes 1 to 12 may be made by one of ordinary skill in the art to obtain any of the compounds of the present invention. For example, protection and deprotection of groups may be suitably employed during such preparation.

PREFERRED COMPOUNDS

Preferred compounds of the formula I are those compounds containing the preferred groups described following.

$A^a$ and $A^b$ are preferably, independently,
(A) hydrogen;
(B) alkyl such as unsubstituted lower alkyl or hydroxyalkyl;
(C) the group:

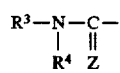

where Z is sulfur or, most preferably, oxygen;
$R^3$ is preferably alkyl such as unsubstituted lower alkyl (e.g., methyl or tert-butyl), arylalkyl (e.g., benzyl), or heterocycloalkyl (e.g., pyridylmethyl or benzimidazolylmethyl); and
$R^4$ is preferably alkyl such as unsubstituted lower alkyl (e.g., methyl) or, most preferably, $R^4$ is hydrogen;

(D) the group:

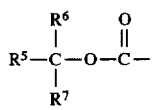

where

R[5] is preferably hydrogen; carbocyclo (e.g., indenyl); alkyl such as unsubstituted lower alkyl (e.g., methyl, ethyl or tert-butyl) or alkyl which is substituted by one or more of amino, substituted amino (e.g., amino substituted by formyl, phenyl, benzyl or benzyloxycarbonyl), halo (e.g., fluoro), aryl (e.g., phenyl), hydroxy (e.g., mono or dihydroxy) or protected hydroxy, heterocyclo (e.g., dihydroindazolyl (optionally substituted by oxo and/or benzyl)), alkoxy (such as unsubstituted lower alkoxy (e.g., methoxy) or arylalkoxy (e.g., benzyloxy)), aryloxy (e.g., phenoxy), or arylaminocarbonyl (e.g., phenylaminocarbonyl); aryl (e.g., phenyl or biphenyl); heterocyclo (e.g., imidazolyl (optionally substituted by trityl and/or phenyl), oxazolyl (optionally substituted by phenyl), 2-furo[2, 3-c]pyridinyl, 2-furo[3,2-b]pyridinyl, 2-furo[2,3-b]pyridinyl, quinoxalinyl, benzothiazolyl, quinolinyl, benzimidazolyl (optionally substituted by benzyloxymethyl), pyridyl, indolyl, oxazolidinyl (optionally substituted by oxo), dihydroisoindolyl (optionally substituted by oxo), 1,3-dioxolane (optionally substituted by methyl groups), dihydroquinazolinyl (optionally substituted by oxo), or benzoxazolyl); or alkynyl (e.g., phenylalkynyl); R[5] is most preferably hydrogen, alkyl (unsubstituted or substituted, in the latter case preferably hydroxyalkyl), aryl or heterocyclo;

R[6] and R[7] are preferably hydrogen, or alkyl such as unsubstituted lower alkyl (e.g., methyl) or hydroxyalkyl; or two of R[5], R[6] and R[7], together with the carbon atom to which they are bonded, form a carbocyclo group (e.g., cyclobutyl or cyclopentyl (optionally substituted by hydroxy), or indanyl (optionally further substituted by hydroxy or protected hydroxy)), or a heterocyclo group (e.g., oxetanyl, tetrahydrofuryl (optionally substituted by hydroxy), tetrahydro-1,1-dioxothienyl, tetrahydropyranyl, or benzimidazolyl (optionally substituted by methyl));

(E) the group:

where

Z is sulfur or, most preferably, oxygen;

R[3] is preferably hydrogen; aryl (e.g., phenyl or naphthyl); alkyl which is unsubstituted (e.g., ethyl or tert-butyl) or substituted by one or more of oxo, hydroxy (e.g., mono- or dihydroxy) or protected hydroxy, aryloxy (e.g., phenoxy or naphthyloxy), alkoxy (e.g., methoxy, benzyloxy, or benzimidazolylpropoxy), aryl (e.g., phenyl), heterocyclo (e.g., benzimidazolyl, 1,3-dioxolane (optionally substituted by methyl groups), indolyl, pyridyl, or dihydroindazolyl (optionally substituted by oxo)), oxime, alkoxyimino (e.g., methoxyimino), amino or substituted amino (e.g., benzyloxycarbonylamino), alkylaminocarbonyl (e.g., N-methylaminocarbonyl), arylaminocarbonyl (e.g., phenylaminocarbonyl), alkylaminocarbonyloxy (e.g., N-methylaminocarbonyloxy), or fluoro (e.g., to form trifluoromethyl); carbocyclo (e.g., cyclopentyl or cyclohexyl (optionally substituted by methyl and/or hydroxy groups), or indanyl (optionally further substituted by hydroxy); or heterocyclo (e.g., quinolinyl, pyrrolidinyl (optionally substituted by methyl and/or oxo groups), oxazolidinyl (optionally substituted by methyl and/or oxo groups), dihydroisoindolyl (optionally substituted by formyl), tetrahydrofuryl (optionally substituted by hydroxy and/or methyl groups), or benzimidazolyl); R[3] is most preferably carbocyclo or alkyl wherein the carbocyclo or alkyl groups are substituted, particularly by one or more of hydroxy, aryl, heterocyclo, alkylaminocarbonyl or fluoro (especially to form trifluoromethyl); or (F) the groups:

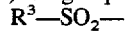

or

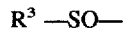

where R[3] is alkyl, especially unsubstituted lower alkyl.

The above groups (C), (D) and (E) are most preferred as $A^a$ or $A^b$ substituents.

$A^c$ is most preferably hydrogen. Where $A^c$ is other than hydrogen, preferred $A^c$ groups are alkyl-O—C(O)—, such as trialkylsilylalkyl-O—C(O)— (e.g., trimethylsilylethoxycarbonyl), fluorenylalkyl-O—C(O)— (e.g., fluorenylmethoxycarbonyl) or arylalkyl-O—C(O)— (e.g., benzyloxycarbonyl); arylalkyl (e.g., benzyl); or unsubstituted lower alkyl (e.g., methyl).

E is preferably a single bond or a peptide chain containing 1 or 2 amino acids. Preferred amino acids are those wherein, in the formula:

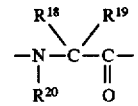

R[18] is hydrogen or unsubstituted lower alkyl (e.g., methyl);

R[19] is hydrogen, aryl (e.g., phenyl), or, most preferably, R[19] is lower alkyl which is unsubstituted (e.g., methyl, isopropyl, or tert-butyl) or which is substituted, particularly by one or more of hydroxy (or protected hydroxy), amino, aminocarbonyl, fluoro (e.g., to form trifluoromethyl), phenyl, or hydroxyphenyl; or R[18] and R[19], together with the carbon atom to which they are bonded, form a cycloalkyl group (e.g., cyclopentyl); and R[20] is hydrogen or unsubstituted lower alkyl (e.g., methyl).

R[1] and R[2] are most preferably hydrogen.

Where R[1] and R[2] are other than hydrogen, preferred R[1] and R[2] groups are arylalkyl (e.g., benzyl).

R[8] is preferably hydrogen; alkyl, especially unsubstituted lower alkyl (e.g., methyl); R[8] and R[9], together with the atoms to which these groups are bonded, form a heterocyclo group (e.g., pyrrolidinyl or tetrahydroisoquinolinyl); R[8] and R[11], together with the atoms to which these groups are bonded, form a heterocyclo group (e.g., 2,2-dimethyloxazolidinyl); or R[8] and $A^a$ or $A^b$ (as described above), together with the atoms to which these groups are bonded, form a heterocyclo group (e.g., 5,5-dimethyl-2-oxooxazolidinyl). R[8] is most preferably hydrogen.

$R^9$ is most preferably alkyl, especially unsubstituted lower alkyl (e.g., sec-butyl or isobutyl); or substituted lower alkyl, particularly:

(A) cycloalkylalkyl (e.g., cyclohexylmethyl);
(B) heterocycloalkyl, especially heterocyclomethyl (e.g., indolylmethyl, pyridylmethyl, or quinolinylmethyl);
(C) arylalkenylalkyl, particularly where aryl is substituted by a group Ar(sub) defined below; or
(D) arylalkyl, for example, phenylethyl, or, especially, a group of the formula:

where Ar(sub) is:
(i) hydrogen;
(ii) hydroxy;
(iii) alkenyl (e.g., ethenyl);
(iv) unsubstituted lower alkyl (e.g., ethyl); or
(v) alkoxy, especially:
  unsubstituted lower alkoxy (e.g., methoxy);
  alkoxyalkoxy (e.g., methoxyethoxy, methoxybutoxy, benzyloxyethoxy, or benzyloxypropoxy);
  hydroxyalkoxy (e.g., hydroxyethoxy, hydroxypropoxy, or hydroxybutoxy);
  arylalkoxy (e.g., benzyloxy);
  heterocycloalkoxy (e.g., morpholinylpropoxy, morpholinylethoxy, 3-oxo-morpholinylethoxy, pyridylethoxy, benzoxazolylmethoxy, benzoxazolylpropoxy, imidazolylethoxy, 2-oxo-oxazolidinylethoxy, 3-methyl-2-oxo-imidazolidinylethoxy, 2-hydroxy-2-pyridylethoxy);
  aminoalkoxy (e.g., aminoethoxy) or aminocarbonyloxyalkoxy (e.g., aminocarbonyloxyalkoxy), especially where the amino moiety is unsubstituted or mono- or disubstituted by alkyl (e.g., methyl) or aryl (e.g., tolyl);
  heterocyclocarbonylalkoxy (e.g., morpholinylcarbonylethoxy, morpholinylcarbonylmethoxy or piperidinylcarbonylmethoxy);
  heterocyclooxyalkoxy (e.g., pyridyloxyethoxy);
  alkoxycarbonylalkoxy (e.g., ethoxycarbonylmethoxy); or
  carboxyalkoxy (e.g., carboxymethoxy).

Where $R^9$ is other than alkyl, preferred $R^9$ groups are hydrogen; aryl; alkenyl; carbocyclo; or $R^9$ and $R^8$, together with the atoms to which these groups are bonded, form a heterocyclo group (e.g., pyrrolidinyl or tetrahydroisoquinolinyl).

$R^{9'}$ is preferably hydrogen.

$R^{10}$ is most preferably hydrogen. Where $R^{10}$ is other than hydrogen, preferred $R^{10}$ groups are arylalkyl (e.g., benzyl); unsubstituted lower alkyl (e.g., methyl); or $R^{10}$ and $R^{11}$ together form a keto group.

$R^{11}$ is most preferably hydrogen. Where $R^{11}$ is other than hydrogen, preferred $R^{11}$ groups are alkoxyalkyl (e.g., ethoxyethyl); unsubstituted lower alkyl (e.g., methyl); $R^{11}$ and $R^8$, together with the atoms to which these groups are bonded, form a heterocyclo group (e.g., 2,2-dimethyloxazolidinyl); or $R^{11}$ and $R^{10}$ together form a keto group.

p and q are preferably 0.

Particularly preferred compounds of the present invention are the following compounds, and salts and/or stereoisomers thereof, prepared as the title compounds of the following Examples of this specification: 2, 21, 76, 93, 104, 162, 175, 178, 209, 224, 226, 234, 246, 257, 262, 271, 282, 293, 297, 298, 304, 308, 311, 322, 327, 331, 333, 334, 336, 339, 344, 352, 355, 356, 359, 366, 368, 377 and 383.

PREFERRED UTILITY

Proteases are enzymes which cleave proteins at specific peptide bonds and, in living systems, mediate or control a broad spectrum of biological functions, such as cleaving precursors to form active proteins in post-translational processing of polypeptides. For example, retroviral proteases cleave large precursor polypeptides, produced in infected cells, into smaller protein components, or subunits, which are subsequently assembled to form functional virus structures. As proteases encoded by the viral genome play a critical role in the replication of a virus, these enzymes represent targets for therapeutic agents.

Retroviruses are viruses which contain two copies of their RNA genome, each of which is copied into a double strand of DNA using a retroviral enzyme reverse transcriptase (RT). A second retroviral enzyme, ribonuclease H, is part of the RT protein and facilitates the synthesis of the DNA:DNA duplex. A third retroviral enzyme called integrase splices the double stranded DNA copy of the virus into the chromosome of the host cell. A fourth retroviral enzyme cell protease is critical to the process of viral replication by cleaving polypeptide precursors into required enzymes and structural proteins.

The compounds of the present invention inhibit retroviral proteases, thereby inhibiting viral replication, and are thus especially useful in the treatment and/or prevention of retroviral infections caused by such pathogenic organisms.

Exemplary protease-encoding retroviruses, the replication of which may be inhibited by the compounds of the present invention include the human T-cell lymphotrophic viruses, HTLV-I and HTLV-II, the human immunodeficiency viruses, for example, HIV-1, HIV-2 or mutants thereof (AIDS pathogens), feline leukemia virus and simian immunodeficiency virus. Protease inhibition may be assayed by methods such as those described below in the Examples section of the present specification. The compounds of the present invention may, of course, be used to simultaneously inhibit the replication of two or more retroviruses, as well as to inhibit the replication of a single retrovirus.

The compounds of the present invention are particulary useful in the inhibition of human immunodeficiency virus (HIV) protease, and thus in the prevention and/or treatment of infection by HIV viruses (HIV-1, HIV-2, and mutants thereof), including the treatment of consequent pathological conditions such as AIDS.

HIV protease is a retroviral protease which processes the gag polyprotein precursor into core proteins and the pol polyprotein precursor into reverse transcriptase, integrase, and the protease itself. HIV protease is essential for the correct processing of these polyproteins and the production of infectious viral particles, as evidenced by the fact that mutations of the protease gene result in non-infectious viral particles with an immature morphology. Inhibition of HIV protease is thus a highly attractive target for anti-HIV therapy.

Use of the compounds of the present invention in inhibiting HIV protease includes, but is not limited to, treating a wide range of states of HIV infection such as treating or preventing AIDS or ARC (AIDS related complex), treating both symptomatic and asymptomatic HIV-infected patients, and treating actual or potential exposure to HIV. For example, the compounds of this invention are useful in treating infection by HIV after suspected past exposure to HIV by, e.g., blood transfusion, accidental needle stick, or exposure to patient blood during surgery.

As indicated above, the compounds of the present invention may also be useful in the treatment and/or prevention of infections caused by other retroviruses. Exemplary retroviruses that are pathogenic in man in addition to the human immunodeficiency viruses are HTLV-1 and HTLV-2. Exemplary viruses pathogenic in other species are feline leukemia virus and simian immunodeficiency virus.

The present invention also provides pharmaceutical compositions comprising at least one of the inventive compounds capable of inhibiting retroviral protease in an amount effective therefor, and a pharmaceutically acceptable vehicle or diluent. The compositions of the present invention may be formulated, for example, by employing conventional solid or liquid vehicles or diluents, as well as pharmaceutical additives of a type appropriate to the mode of desired administration. The compounds may, for example, be administered orally, such as in the form of tablets, capsules, granules or powders; parenterally, such as by subcutaneous, intravenous, intramuscular, or intrasternal injection or infusion techniques (e.g. as sterile injectable aqueous or non-aqueous solutions or suspensions); nasally such as by inhalation spray; or rectally such as in the form of suppositories; in dosage unit formulations containing non-toxic, pharmaceutically acceptable vehicles or diluents. The present compounds may, for example, be administered liposomally.

When administered orally, the compositions may be prepared according to techniques well known in the art of pharmaceutical formulation. As a suspension they may, for example, contain microcrystalline cellulose for imparting bulk, alginic acid or sodium alginate as a suspending agent, methylcellulose as a viscosity enhancer, and sweeteners or flavoring agents known in the art. As immediate release tablets, the present compositions may contain microcrystalline cellulose, dicalcium phosphate, starch, magnesium stearate and/or lactose and/or other excipients, binders, extenders, disintegrants, diluents and lubricants known in the art.

When administered by nasal aerosol or inhalation, the compositions may be prepared according to techniques well known in the art of pharmaceutical formulation and may be prepared as solutions in saline, employing benzyl alcohol or other suitable preservatives, absorption promoters to enhance bioavailability, and/or other solubilizing or dispersing agents known in the art.

When administered as injectable solutions or suspensions, the present compositions may be formulated according to techniques well known in the pharmaceutical art, using suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

When rectally administered in the form of suppositories, these compositions may be prepared by techniques well known in the pharmaceutical art by mixing the drug with a suitable non-irritating excipient, such as cocoa butter, synthetic glyceride esters or polyethylene glycols, which are solid at ordinary temperatures, but liquify and/or dissolve in the rectal cavity to release the drug.

The pharmaceutical compositions of the present invention may contain an amount of the inventive compound(s) effective for the inhibition of retroviral replication, and preferably an amount effective for the treatment and/or prevention of infection by HIV. The effective amount of a compound of the present invention may be determined by one of ordinary skill in the art, and includes amounts such as those from about 1 to 150 mg/kg of body weight of active compound per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

Viral hosts which are preferred subjects for treatment and/or prevention of retroviral infections include animals, most preferably mammalian species such as humans, and domestic animals such as dogs, cats and the like. A dose for adult humans is preferably between about 10 and about 50 mg/kg of body weight per day, which may be administered in a single dose or in the form of individual divided doses, such as from 1–4 times per day.

The compounds of the present invention may be employed alone or in combination with other suitable therapeutic agents useful in the treatment of retroviral infections such as AIDS, such as other antiviral agents, immunomodulators, antibiotics or vaccines.

Other therapeutic agents may include, but are not restricted to the following: antivirals exemplified by AL-721, interferon beta, polymannoacetate, ganciclovir, DDC (dideoxycytidine), d4T, DDI (dideoxyinosine), Foscarnet (trisodium phosphonoformate), HPA-23, eflornithine, Peptide T (octapeptide sequence), Reticulose (nucleophosphoprotein), AZT, ansamycin LM 427, trimetrexate, UA-001, ribavirin, α-interferon, acyclovir, 3TC, PMEA, nevirapine, pyridinones (e.g. L-697,661), BHAPs (e.g. U-90152), alpha-APA derivatives (e.g. R 18893), TIBO derivatives (e.g. R 82913), and Ro 31-8959; immunomodulators exemplified by bropirimine, Ampligen (mismatched RNA), Anti-human alpha interferon antibody, Colony Stimulating Factor (GM-CSF), CL246,738, IMREG-1, IMREG-2, diethyl dithio carbamate, interleukin-2, inosine pranobex, methionine enkephalin, MTP-PE (muramyl-tripeptide), Thymypentin (TP-5) (thymic compound), recombinant erythoropoietin, naltrexone, TNF (tumor necrosis factor); and antibiotics exemplified by Pentam 300 (pentamidine isethionate).

In particular, the HIV protease inhibitors of the present invention may be used in combination with other anti-retroviral therapies for the treatment of AIDS. Such combined therapies may include, but are not limited to, a compound of the present invention in combination with: other (e.g., those other than inhibitors of the present invention) HIV protease inhibitors (e.g. Ro 31-8959); nucleoside and non-nucleoside reverse transcriptase inhibitor(s), preferably nucleoside reverse transcriptase inhibitors such as AZT, DDI, d4T, DDC, 3TC or PMEA, and non-nucleoside reverse transcriptase inhibitors such as nevirapine, pyridinones (e.g. L-697,661), BHAPs (e.g. U-90152), alpha-APA derivatives (e.g., R 18893), and TIBO derivatives (e.g. R 82913); inhibitor(s) of tat such as R024-7429; drug(s) which inhibit binding of the virus to $CD_4$ receptors; inhibitor(s) of RNase, integrase, or rev; and immunomodulator(s) such as IFN-α (α-interferon).

The above compounds to be employed in combination with the compounds of the present invention will be used, for example, in amounts as indicated in the Physicians' Desk Reference (PDR) or as otherwise determined by one of ordinary skill in the art. The aforementioned combined therapies may, for example, be conducted simultaneously or sequentially.

The instant invention also provides methods for the inhibition of retroviral proteases by contacting said protease with a compound of the present invention capable of said inhibition, and particularly for the treatment and/or prevention of retroviral infections. Treatment and/or prevention of infection by the human imunodeficiency viruses is preferred. The methods of the present invention preferably comprise the step of administering to a subject in need thereof one or more of the present compounds capable of treatment and/or prevention of retroviral infection in an amount effective therefor. Other therapeutic agents such as those described above may be employed with the inventive compounds in the present methods.

The compounds of the present invention are also useful in the preparation of other compounds of the formula I. Thus, for example, one compound of the present invention may be employed in the preparation of another compound of the present invention, where the latter compound has greater potency against the same or a different retrovirus than the former.

The following Examples will serve to illustrate the preparation of compounds of the present invention, and are not intended to limit the scope or spirit of the instant claims. The following abbreviations are employed in the Examples:

ABBREVIATIONS

Ph=phenyl
Bn=benzyl
t-Bu=tertiary-butyl
Me=methyl
Et=ethyl
Ts=tosyl (p-toluenesulfonyl)
Bz=benzoyl
Phe=phenylalanine
Val=valine
TMS=trimethylsilyl
TBS or TBDMS=tert-butyldimethylsilyl
FMOC=fluorenylmethoxycarbonyl
Teoc=trimethylsilylethoxycarbonyl
Boc=tert-butoxycarbonyl
Cbz or Z=carbobenzoxy (or carbobenzyloxy or benzyloxycarbonyl)
THF=tetrahydrofuran
Et$_2$O=diethylether
EtOAc=ethyl acetate
DMF=dimethylformamide
MeOH=methanol
EtOH=ethanol
i-PrOH=iso-propanol
t-BuOH=tert-butanol
DMSO=dimethylsulfoxide
DME=1,2-dimethoxyethane
HMPA=hexamethylphosphoric triamide
HOAc or AcOH=acetic acid
TFA=trifluoroacetic acid
i-Pr$_2$NEt=diisopropylethylamine
Et$_3$N=triethylamine
DMAP=4-dimethylaminopyridine
MeLi=methyl lithium
n-BuLi=n-butyllithium
s-BuLi=sec-butyllithium
n-Bu$_4$NF·nH$_2$O=tetra-n-butylammonium fluoride hydrate
n-Bu$_4$NBr=tetra-n-butylammonium bromide
n-Bu$_4$NI=tetra-n-butylammonium iodide
EDC (or EDC·HCl) or EDCI (or EDCI·HCl)=3-ethyl-3'-(dimethylamino)propylcarbodiimide hydrochloride (or 1-(3-dimethylaminopropyl)-3-ethylcarbodiimide hydrochloride)
HOBT or HOBT·H$_2$O=1-hydroxybenzotriazole hydrate
KN(TMS)$_2$=potassium bis(trimethylsilyl)amide
NaN(TMS)$_2$=sodium bis(trimethylsilyl)amide
Boc-ON=[2-(tert-butoxycarbonyloxyimino)-2-phenyl-acetonitrile]
AcCl=acetyl chloride
BOP-Cl=Bis(2-oxo-3-oxazolidinyl)phosphinic chloride
BOP reagent=benzotriazol-1-yloxy-tris(dimethylamino) phosphonium hexafluorophosphate
PPh$_3$=triphenylphosphine
DEAD=diethylazodicarboxylate
Me$_2$S=dimethylsulfide
Ti(i-Pro)$_4$=titanium(IV) isopropoxide
KOAc=potassium acetate
Dibal or DIBAL-H=diisobutylaluminum hydride
Cbz-Cl=carbobenzoxy chloride (benzyl chloroformate)
PMA=phosphomolybdic acid
min=minute(s)
h or hr=hour(s)
L=liter
ml or mL=milliliter
μl or μL=microliter
g=gram(s)
mg=milligram(s)
mol=mole(s)
mmol=millimole(s)
RT=room temperature
sat. or sat'd.=saturated
aq.=aqueous
TLC=thin layer chromatography
HPLC=high performance liquid chromatography
UV=ultraviolet
MS or Mass Spec.=mass spectrometry
NMR=nuclear magnetic resonance
mp=melting point
hex=hexane
Tf=triflate
NaHB(OAc)$_3$=sodium triacetoxyborohydride
p-TsOH=p-toluenesulfonic acid
m-CPBA=metachloroperbenzoic acid
DCC=dicyclohexylcarbodiimide
NBS=N-bromosuccinimide
PPTs=Pyridinium p-tosylate
PCC=pyridinium chlorochromate
BF$_3$·Et$_2$O=boron trifluoride etherate Compounds in the following Examples are referred to by the step and number of the Example in which they are prepared. For example, "Compound 1c" denotes the compound prepared in step (c) of Example 1; "Compound 39" denotes the compound prepared in Example 39, which Example contains a single step.

EXAMPLE 1

Preparation of [1S-[1R*,2S*(2S*,3R*)]]-[3-[[3-[[(1,1-Dimethylethoxy)carbonyl]amino]-2-hydroxy-4-phenylbutyl](phenylmethyl)amino]-2-hydroxy-1-(phenylmethyl)propyl]carbamic acid, 1,1-dimethylethyl ester (Compound 1c)

(a) Compound 1a(iv)

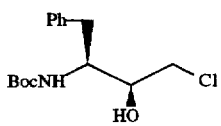

(i) Diazomethane-Et$_2$O solution

To the mixture of 40% aqueous KOH (75 ml) and Et$_2$O (255 ml) cooled at 0° C. was added 1-methyl-3-nitro-1-nitrosoguanidine (23.85 g, 162.2 mmol) portionwise. The mixture was swirled several times during each addition. After 10 min, the resulting yellow Et$_2$O layer was decanted over KOH pellets at 0° C. and dried for 2.0 h at 0° C.

(ii) Compound 1a(ii)

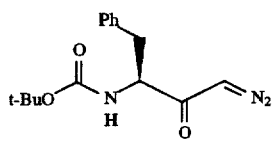

To the solution of N-Boc-L-phenylalanine (14.34 g, 54.05 mmol) in dry THF (80 ml) cooled at −20° C. to −25° C. (dry ice-CCl$_4$ bath) was added isobutyl chloroformate (7.01 ml, 54.05 mmol) over 5 min, followed by 4-methylmorpholine (5.94 ml, 54.05 mmol) and the mixture was stirred for 20 min. The white precipitate was removed by filtration under argon atmosphere and washed with ca. 70 ml of dry THF. The combined THF solution of mixed anhydride was cooled to −5° C. and poured into the above prepared diazomethane in Et$_2$O solution at 0° C. The resulting yellow solution was kept at 0° C. for 2.0 h, then RT overnight. N$_2$ was then bubbled through the light-yellow solution for 30 min, and Et$_2$O (400 ml) then added. The solution was washed with H$_2$O (400 ml), saturated NaHCO$_3$ (300 ml) and brine (300 ml), and was dried over anhydrous MgSO$_4$. Concentration in vacuo afforded a yellow residue, which was triturated with hexane to give, after drying over P$_2$O$_5$ overnight under high vacuum, 14.72 g (94%) of the title α-diazoketone as a pale yellow solid. This material was used immediately in the reaction of the next step without further purification.

(iii) Compound 1a(iii)

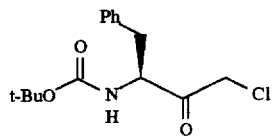

To the solution of the crude α-diazoketone prepared above (14.72 g, 50.87 mmol) in dry Et$_2$O (500 ml) cooled at 0° C. was added, dropwise, a solution of 4N HCl in dioxane (12.72 ml, 50.87 mmol) while maintaining the temperature below 5° C. The reaction mixture was then stirred at 0° C. for 1.0 h. TLC (hexane-EtOAc 4:1) showed trace amounts of the starting α-diazoketone remained. Additional 4N HCl in dioxane (636 µl, 0.05 eq., 2.54 mmol) was added and the mixture was stirred at 0° C. for one additional hour.

Concentration in vacuo gave a residue which was dissolved in hot Et$_2$O (60 ml). Hexane (200 ml) was slowly added and the mixture allowed to stand for 2.0 h at 5° C. The solid was filtered and dried over P$_2$O$_5$ under high vacuum to afford 9.58 g (first crop) of the title α-chloroketone. The filtrate was concentrated to dryness and the residue was again recrystallized from Et$_2$O-hexane to give an additional 4.41 g (second crop) of the above α-chloroketone. Total yield: 13.99 g (92%).

(iv) Compound 1a(iv)

NaBH$_4$ (1.59 g; 42 mmol) was added to a solution of the α-chloroketone prepared above (5 g; 16.8 mmol) in 84 ml of THF and 9 ml of H$_2$O at 0° C. After stirring at 0° C. for 45 min the reaction mixture was concentrated to dryness. The residue was stirred at 0° C. with EtOAc (150 ml) and H$_2$O (25 ml) while saturated KHSO$_3$ solution was carefully added until the pH was ~1.5. This mixture was then diluted with 350 ml of EtOAc and the layers were separated. The organic layer was washed with H$_O$ (100 ml) and brine (100 ml). After drying over MgSO$_4$, the organic layer was concentrated to a white solid. A portion of this solid (4.89 g) was recrystallized from 70 ml of hot EtOAc to afford 2.47 g (50%) of Compound 1a(iv) as a white solid containing a few percent of its diastereomer, the following Compound 1a(v):

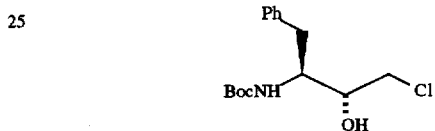

(b) Compound 1b(i)

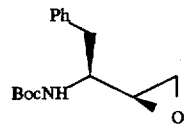

0.71M KOH in EtOH (14.7 ml; 10.4 mmol) was added to a suspension of Compound 1a(iv) (2.6 g; 8.67 mmol) in 87 ml of EtOH at RT. The reaction was stirred 1.5 h at RT, during which time the thick suspension became a fine powdery one. At this time, the EtOH was removed in vacuo and the residue was partitioned between EtOAc (200 ml) and H$_2$O (200 ml). The organic layer was washed with saturated NH$_4$Cl solution (2×100 ml), H$_2$O (2×100 ml), and brine (100 ml). After drying over MgSO$_4$, the EtOAc was removed in vacuo and the solid white residue was recrystallized by dissolving in 10 ml of refluxing EtOAc and adding 190 ml of hexane. The resulting crystalline suspension was allowed to cool to −40° C. and stand overnight. Filtration, rinsing with hexane, and drying under high vacuum for two hours afforded 1.92 g (84%) of Compound 1b(i) as a colorless crystalline solid. This material was 99.1% diastereomerically pure by HPLC.

Compound 1b(ii)

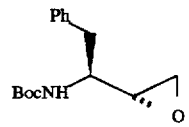

The diastereomeric epoxide 1b(ii) is prepared by a procedure analogous to the one used for 1b(i) starting from the minor diastereomeric chlorohydrin isolated by column chromatography from 1a(iv) above.

Alternatively, to a solution of the compound:

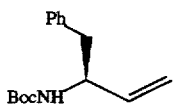

(for preparation, see Luly et al., *J. Org. Chem.*, 52, 1487–1492 (1987)) in dioxane at 0° C. was added a suspension of NBS in H$_2$O. After 5 min, the reaction mixture was warmed to RT and stirred for 2.0 h. The reaction mixture was then diluted with MeOH and K$_2$CO$_3$ was added. After 3.0 h, the volatiles were removed in vacuo and the residue was partitioned between CH$_2$Cl$_2$ and H$_2$O. The organic layer was concentrated in vacuo to give a mixture of Compounds 1b(i) and 1b(ii) (3:1 mixture, 1b(i): 1b(ii)) as a colorless solid.

(c) Compound 1c

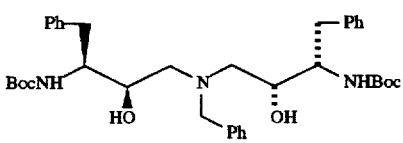

A DMF (2.5 mL) solution of Compound 1b(i) (1.97 g, 7.48 mmol) and benzyl amine (0.41 mL, 3.74 mmol) was heated under argon for 7 h at 105°–108° C., then stirred overnight at RT. After heating an additional 1.5 h at 105°–108° C., the volatiles were evaporated in vacuo. The resulting residue was co-evaporated twice with MeOH/CH$_2$Cl$_2$ and purified by flash column chromatography (silica gel, 5 by 19 cm), eluting with 0.5, 1,2,3,4,7, and then 10% MeOH:CH$_2$Cl$_2$ to give Compound 1c (1.39 g, 56% yield) as a colorless solid.

Anal. Calc. for C$_{37}$H$_{51}$N$_3$O$_5$·1.63 H$_2$O: C, 68.68; H, 8.45; N, 6.49; Found: C, 68.35; H, 8.10; N, 6.82

EXAMPLE 2

Preparation of [1S-[1R*,2S*(2S*,3R*)]]-[3-[[3-[[(1,1-Dimethylethoxy)carbonyl]amino]-2-hydroxy-4-phenylbutyl]amino]-2-hydroxy-1-(phenylmethyl) propyl]carbamic acid, 1,1-dimethylethyl ester (Compound 2)

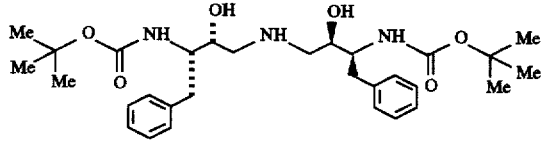

To an EtOH (5 mL) solution of Compound 1c (90 mg, 0.142 mmol) and cyclohexene (2.5 mL) at RT was added Pd(OH)$_2$ (41 mg, 20% on carbon). The reaction mixture was refluxed at 90° C. for 1 h, filtered hot through Celite, and the volatiles were removed in vacuo to leave a colorless solid (74 mg). The residue was purified by flash chromatography (silica gel, 1 by 12.5 cm), eluting with 0.5, 2, 4, 8, and then 9% MeOH:CH$_2$Cl$_2$ to give the title Compound 2 (53 mg, 69% yield) as a colorless solid. m.p. 178°–179.5° C.; [α]$_D$=−7.07° (c 0.1, MeOH). MS: 544 (M+H).

Anal. Calc. for C$_{30}$H$_{45}$N$_3$O$_6$·0.8 H$_2$O: C, 64.57; H, 8.42; N, 7.53; Found: C, 64.53; H, 8.30; N, 7.57

EXAMPLE 3

Preparation of [1S-[1R*,2R*(2R*,3R*)]]-[3-[[3-[[(1,1-Dimethylethoxy)carbonyl]amino]-2-hydroxy-4-phenylbutyl]amino]-2-hydroxy-1-(phenylmethyl) propyl]carbamic acid, 1,1-dimethylethyl ester (Compound 3)

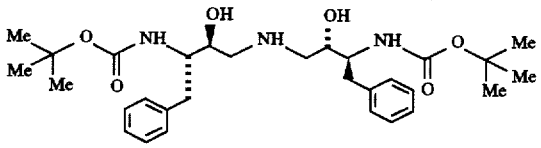

Compound 1b(ii) was converted to the title Compound 3 by procedures analogous to those described for Compounds 1c and 2.

m.p. 140°–141° C.; [α]$_D^{25}$=−42.38° (c 0.29, MeOH). MS: 544 (M+H). Anal. Calc. for C$_{30}$H$_{45}$N$_3$O$_6$·1.45 H$_2$O: C, 63.24; H, 8.47; N, 7.37; Found: C, 63.25; H, 8.36; N, 7.36

EXAMPLE 4

Preparation of [1S-[1R*,2S*(2R*,3R*)]]-[3-[[3-[[(1,1-Dimethylethoxy)carbonyl]amino]-2-hydroxy-4-phenylbutyl](phenylmethyl)amino]-2-hydroxy-1-(phenylmethyl)propyl]carbamic acid, 1,1-dimethylethyl ester (Compound 4b)

(a) Compound 4a

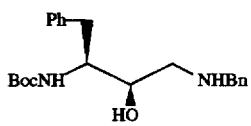

A DMF (0.4 mL) solution of Compound 1b(i) (75 mg, 0.285 mmol) and benzyl amine (0.025 mL, 0.229 mmol) was heated for 18 h at 85° C. and the volatiles were evaporated in vacuo at 30° C. The solid residue (100 mg) was purified by flash column chromatography (silica gel, 1.5 by 11 cm), eluting with 0.5, 4, and then 8% MeOH:CH$_2$Cl$_2$ to give Compound 4a (50 mg, 41% yield) as a colorless solid.

(b) Compound 4b

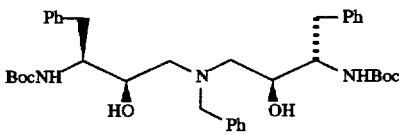

A DMF (0.3 mL) solution of Compound 4a (48 mg, 0.11 mmol) and Compound 1b(ii) (55 mg, 0.21 mmol) was heated for 7 h at 105°–110° C., then stored at −40° C. overnight. After warming to RT, the volatiles were evaporated in vacuo at 30° C. The oily-solid residue (120 mg) was purified by flash column chromatography (silica gel, 1 by 16 cm), eluting with 0.5, 1, 1.5, and then 2% MeOH:CH$_2$Cl$_2$ to give Compound 4b (74 mg, ~100% yield) as a colorless solid. R$_f$=0.69 (7% MeOH:CH$_2$Cl$_2$).

EXAMPLE 5

Preparation of [1S-[1R*,2S*(2R*,3R*)]]-[3-[[(1,1-Dimethylethoxy)carbonyl]amino]-2-hydroxy- 4-phenylbutyl]amino]-2-hydroxy-1-(phenylmethyl)propyl]carbamic acid, 1,1-dimethylethyl ester (Compound 5)

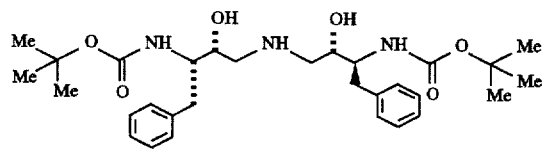

Compound 4b was deprotected using a procedure analogous to that for Compound 2 to give the title Compound 5.

m.p. 151°–153° C.; $[\alpha]_D^{25}$=–22.93° (c 0.23, MeOH). MS: 544 (M+H). Anal. Calc. for $C_{30}H_{45}N_3O_6 \cdot 0.67\ H_2O$: C, 64.83; H, 8.40; N, 7.56; Found: C, 64.84; H, 8.37; N, 7.55

EXAMPLE 6

Preparation of (2S)-2,2'-[(Phenylmethyl)imino-bis[1-hydroxy-2,1-ethanediyl]bis-1-pyrrolidinecarboxylic acid], bis(1,1-dimethylether)ester, sinale isomer (A) (Compound 6b)

(a) Compounds 6a(i) and 6a(ii)

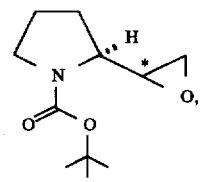

Compound 6a(i) faster moving isomer Compound 6a(ii) slower moving isomer

Compounds 6a(i) and 6a(ii) (unknown stereochemistry) were prepared by a procedure analogous to the synthesis of Compounds 1b(i) and 1b(ii) in which Boc-(L)-proline was employed in place of N-Boc-L-phenylalanine.

(b) Compound 6b

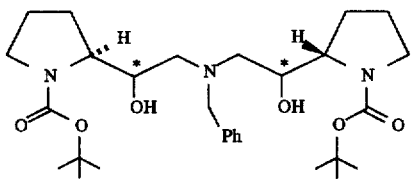

Compound 6a(ii) was converted to the title Compound 6b by opening with benzyl amine and then reacting with another molecule of 6a(ii) analogous to the two-step procedure used for the preparation of Compound 4b. $R_f$=0.36 (3:1 EtOAc/hexane) (oil).

EXAMPLE 7

Preparation of (2S)-2,2'-[Iminobis(1-hydroxy-2,1-ethanediyl]bis-(1-pyrrolidinecarboxylic acid), bis(1,1-dimethylether)ester, single isomer (A) (Compound 7)

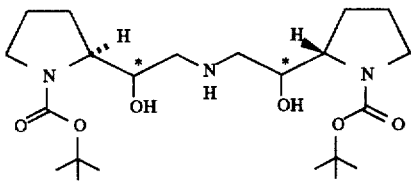

A suspension of 0.069 g (0.13 mmol) of Compound 6b and 10 mg of Pd(OH)$_2$ in 1.5 ml of MeOH was stirred under a H$_2$ atmosphere (balloon) at RT overnight. The mixture was filtered through a micropore fritted funnel (MeOH wash) and evaporated. The crude product was purified by flash chromatography (20 mm×6"; 10% MeOH/CH$_2$Cl$_2$+1% NH$_4$OH) to give 41 mg (<72%) of slightly impure material. This material was combined with 41 mg of material from a previous reaction and recrystallized from EtOAc/Hexane to give 32 mg of the title Compound 7 as a white solid.

m.p.=181°–184° C.; $[\alpha]_D^{25}$=–86° (c 0.1, MeOH). MS: 444 (M+H). Anal. Calc. for $C_{22}H_{41}N_3O_6 \cdot 0.52\ H_2O$: C, 58.34; H, 9.35; N, 9.28; Found: C, 58.39; H, 9.44; N, 9.23.

EXAMPLE 8

Preparation of [S-(R*,R*)]-2-[2-[[[S-(R*,S*)]- 2-[1-[(1,1-Dimethylethoxy)carbonyl]-pyrrolidinyl]-2-hydroxyethyl]amino]-hydroxyethyl]-1-pyrrolidinecarboxylic acid, (1,1-dimethylethyl) ester (Compound 8)

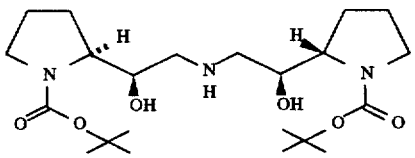

Compounds 6a(i) and 6a(ii) were converted to the title Compound 8 (white solid) by procedures analogous to those used for the synthesis of Compound 7 except that epoxide 6a(ii) was opened with 2 equivalents of benzyl amine and the resulting product was reacted with epoxide 6a(i) by a procedure analogous to that used for Compound 4b.

m.p. 44°–48° C.; $[\alpha]_D$=–67.30 (c 0.26, CHCl$_3$); Mass Spec. 444 (M+H); Anal. Calc. for $C_{22}H_{41}N_3O_6 \cdot 0.56\ H_2O$: C, 58.24; H, 9.36; N, 9.26; Found: C, 58.50; H, 9.63; N, 9.00

EXAMPLE 9

Preparation of [S-(R*,R*)]-3,3-[[(Phenylmethyl)imino]bis(1-hydroxy-2,1-ethanediyl)]bis[2(1H)-isoquinolinecarboxylic acid, bis(1,1-dimethylethyl) ester (Compound 9b)

(a) Compound 9a(i)

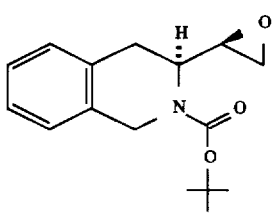

and

Compound 9a(ii)

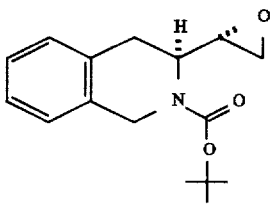

Compounds 9a(i) (major) and 9a(ii) (minor) were prepared by a procedure analogous to the synthesis of Compounds 1b(i) and 1b(ii) in which Boc-(L)-tetrahydroisoquinoline-2-carboxylic acid (see J. Am. Chem. Soc., 70, 180 (1948); ibid 84, 4487 (1962)) was employed in place of N-Boc-L-phenylalanine.

(b) Compound 9b

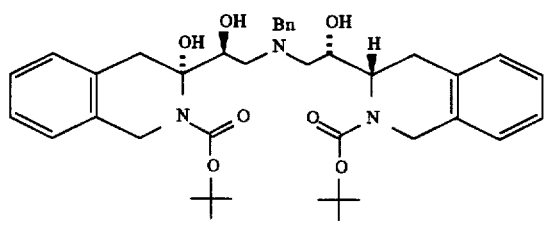

Compound 9a(i) was converted to the title Compound 9b (light-yellow oil) by opening with 2 equivalents of benzyl amine and then reacting with another molecule of 9a(i) analogous to the two-step procedure used for the preparation of Compound 4b.

$^1$H NMR (CD$_3$OD): δ 1.43–1.46 (brs's, 18H), 2.45 (m, 4H), 2.61 (m, 2H), 2.87 (m, 2H), 3.43 (m, 1H), 3.55 (m, 3H), 4.22 (m, 4H), 4.71 (m, 2H), 7.00–7.25 (m, 13H).

EXAMPLE 10

Preparation of [S-(R*,R*)]-3,3'-[Iminobis(1-hydroxy-2,1-ethanediyl)]-bis[2(1H)-isoquinolinecarboxylic acid], bis(1,1-dimethylethyl) ester (Compound 10)

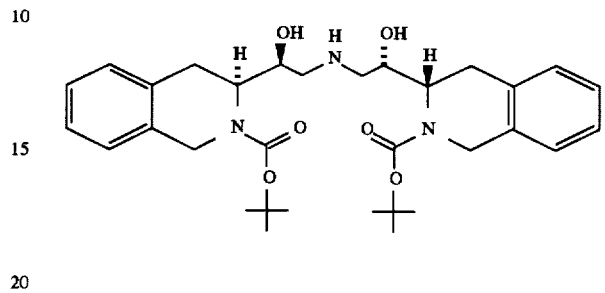

Compound 9b was deprotected by a procedure analogous to that used for Compound 7 to give the title Compound 10 (white solid).

mp 70°–76° C.; [α]$_D$=+33.6° (c 0.25, MeOH); Mass Spec: 568 (M+H); Analysis calc. for C$_{32}$H$_{45}$N$_3$O$_6$·0.69H$_2$O: C, 66.25; H, 8.06; N, 7.24; Found: C, 66.45; H, 7.96; N, 7.04.

EXAMPLE 11

Preparation of [R-(R*,R*)]-3,3'[Iminobis(1-hydroxy-2,1-ethanediyl)]-bis[2(1H)-isoquinolinecarboxylic acid], bis(1,1-dimethylethyl) ester (Compound 11)

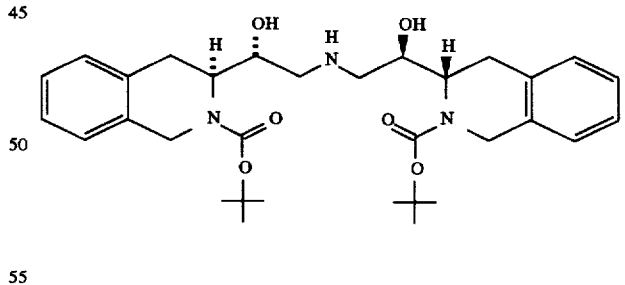

Compound 11 (white solid) was prepared from Compound 9a(ii) by procedures analogous to those used for the synthesis of Compound 10.

mp 68°–76° C.; [α]$_D$=+34.00 (c 0.05, MeOH). Mass Spec.: 568 (M+H); Analysis calc. for C$_{32}$H$_{45}$N$_3$O$_6$·0.91H$_2$O: C, 65.81; H, 8.08; N, 7.19; Found: C, 65.96; H, 8.15; N, 7.04.

EXAMPLE 12

Preparation of [S-(R*,R*)]-3-[2-[[[-(R*,S*)]-2-[2-[(1,1-Dimethylethoxy)carbonyl]-1,2,3,4-tetrahydro-3-isoquinolinyl]-2-hydroxyethyl]amino]-1-hydroxyethyl]-3,4-dihydro-2(1H)-isoquinolinecarboxylic acid, (1,1-dimethylethyl) ester (Compound 12)

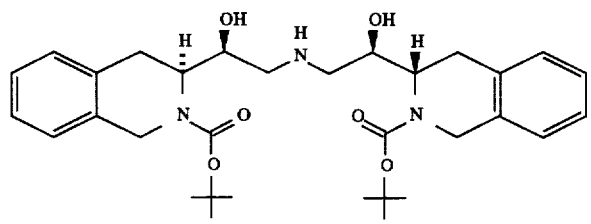

Compounds 9a(i) and 9a(ii) were converted to the title Compound 12 (white solid) by procedures analogous to those used for the synthesis of Compound 10 except that epoxide 9a(i) was opened with benzyl amine and the resulting product was reacted with epoxide 9a(ii) by a procedure analogous to that used for Compound 4b.

mp 65°–72° C.; [α]$_D$=+20.5° (c 0.19, MeOH). Mass Spec.: 568 (M+H); Analysis calc. for $C_{32}H_{45}N_3O_6 \cdot 1.13H_2O$: C, 65.35; H, 8.10; N, 7.15; Found: C, 65.68; N, 7.94; N, 6.82.

EXAMPLE 13

Preparation of [R-(R*,S*)]-[Iminobis[2-hydroxy-1-(1-methylpropyl)-3,1-proyanediyl]]biscarbamic acid, 1,1-dimethylethyl ester (Compound 13)

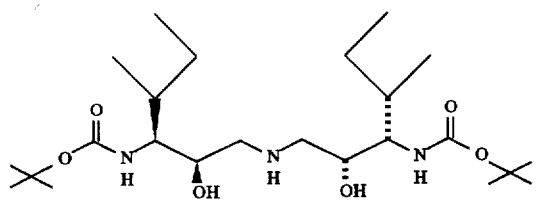

Starting from N-Boc-L-isoleucine in place of N-Boc-L-phenylalanine, the title Compound 13 (colorless oil) was prepared using procedures analogous to those described for Compounds 1b(i), 4b, and 7.

TLC, Rf=0.10, $CH_2Cl_2$:MeOH:$NH_4OH$, 95.5:4.9:0.1, (PMA). $^{13}$C NMR ($CD_3OD$): δ12.1, 16.7, 24.1, 28.8, 36.1, 52.8, 59.6, 69.6, 80.1, 158.9. Mass Spec. (M+H)$^+$ @476

EXAMPLE 14

Preparation of [R-(R*,S*)]-[Iminobis[1-(cyclohexylmethyl)-2-hydroxy-3,1-propanediyl]]-biscarbamic acid, bis(1,1-dimethylethyl) ester (Compound 14)

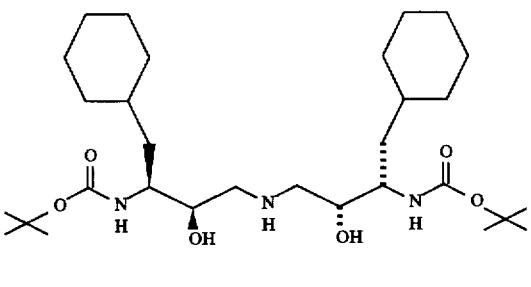

Starting from N-Boc-L-cyclohexylalanine in place of N-Boc-L-phenylalanine, the title Compound 14 (white solid) was prepared using procedures analogous to those described for Compounds 1b(i), 4b, and 7.

[α]$_D$=−33.70° (c 0.18, MeOH). $^{13}$C NMR (CDCl$_3$): δ26.1, 26.4, 26.5, 28.4, 32.3, 34.2, 34.3, 38.1, 51.0, 51.6, 72.7, 79.5, 156.4. Mass Spec. (M+H)$^+$ @ 556. High Resolution FAB; exact mass calcd. for $C_{30}H_{58}O_6N_3$ (M+H)$^+$, 556.4325; Found 556.4304.

EXAMPLE 15

Preparation of [1S-[1R*,2S*(2S*,3R*)]]-[3-[[4-Cyclohexyl-3-[[(1,1-dimethylethoxy)carbonyl]-amino]-2-hydroxybutyl]amino-2-hydroxy-1-(phenylmethyl)propyl]carbamic acid, 1,1-dimethylethyl ester (Compound 15)

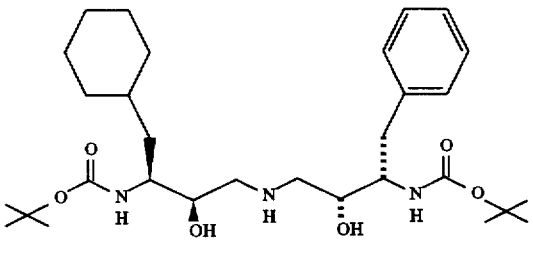

Compound 4a and the epoxide prepared in Example 14 (i.e., in the step analogous to that for Compound 1b(i)) were converted to the title Compound 15 by procedures analogous to those used for Compounds 4b and 7.

mp 120°–125° C.; [α]$_D$=−15.0° (c 0.10, MeOH). Mass Spec. (M+H)$^+$ @ 550. Analysis calc. for $C_{30}H_{51}N_3O_6 \cdot 0.32H_2O$: C, 64.99; H, 9.20; N, 7.58; Found: C, 65.08; H, 9.46; N, 7.49.

EXAMPLE 16

Preparation of [2S-[2R*,[S*(2S*,3R*)]]-[1-Hydroxy-3-[[(1,1-dimethylethoxy)carbonyl]-amino]-2-hydroxy-4-phenylbutyl]amino]ethyl-2-methylbutyl]carbamic acid, phenylmethyl ester (Compound 16c)

(a) Compound 16a

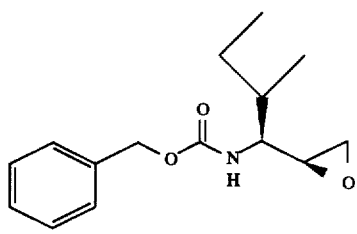

Compound 16a was prepared by procedures analogous to those used for the synthesis of Compound 1b(i) in which N-Cbz-L-isoleucine was employed in place of N-Boc-L-phenylalanine.

(b) Compound 16b

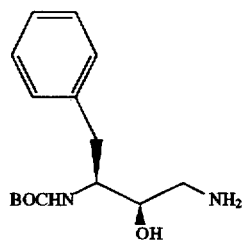

Compound 1b(i) (15.0 g; 56.96 mmol) dissolved in 350 ml of EtOH was added, with stirring, over 1 h to 350 ml of concentrated NH$_4$OH at 0° C. NH$_3$ gas was bubbled through the reaction mixture during the addition and for 1 h after. The reaction was then warmed to RT and stirred overnight. The resulting slurry was diluted with 800 ml EtOAc and the organic layer washed repeatedly with brine. The organic extracts were dried (MgSO$_4$) and concentrated to give a white solid which was triturated with 10% i-PrOH/EtOAc to give 4.37 g of Compound 16b. The mother liquors were evaporated and triturated again as above to give an additional 5.73 g of Compound 16b (total yield: 10.1 g; 63%).

(c) Compound 16c

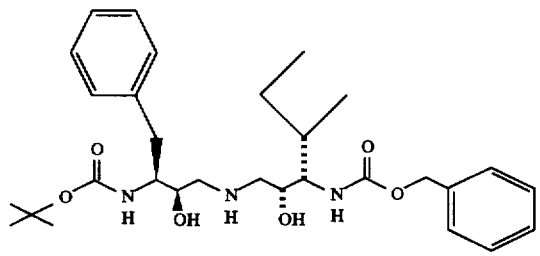

Compounds 16a and 16b were reacted by a procedure analogous to that used for the preparation of Compound 4b to give the title Compound 16c.

mp 155°–157° C.; [α]$_D$=+1.36° (c 0.22, MeOH). Mass Spec. (M+H)$^+$ @544. Analysis calc. for C$_{30}$H$_{45}$N$_3$O$_6$·0.38H$_2$O; C, 65.46 H, 8.38 N, 7.63; Found: C, 65.48 H, 8.29 N, 7.61

EXAMPLE 17

Preparation of [1S-[1R*,2S*(2S*,3R*)]]-[3-[[3-[[(1,1-Dimethylethoxy)carbonyl]amino]2-hydroxy-4-phenylbutyl]amino]-2-hydroxy-1-[[4-(phenylmethoxy)phenyl]methyl]propyl]carbamic acid, phenylmethyl ester (Compound 17b)

(a) Compound 17a

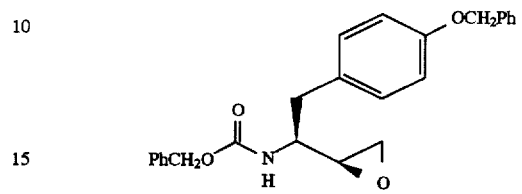

Compound 17a was prepared by procedures analogous to those used for the synthesis of Compound 1b(i) where N-Cbz-O-benzyl-L-tyrosine was employed in place of N-Boc-L-phenylalanine.

(b) Compound 17b

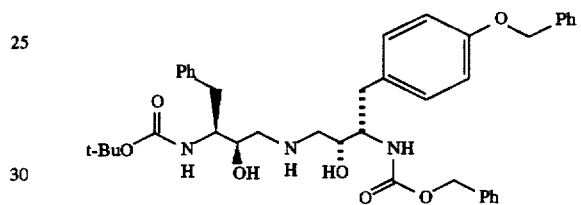

Compounds 17a and 16b were reacted by a procedure analogous to that used for the preparation of Compound 4b to give the title Compound 17b.

m.p.: 154°–155.5° C. [α]$_D$=–19.09° (c 0.24, DMSO). MS (FAB): 684$^+$ (M+H)$^+$. Anal. Calc. for C$_{40}$H$_{49}$N$_3$O$_7$·0.87H$_2$O: C, 68.68; H, 7.31; N, 6.01. Found: C, 68.84; H, 7.18; N, 5.85.

EXAMPLE 18

Preparation of [1S-[1R*,2S*(2S*,3R*)]]-[3-[[3-[[(1,1-Dimethylethoxy)carbonyl]amino]-2-hydroxy-4-phenylbutyl][[2-(trimethylsilyl)ethoxylcarbonyl]amino]-2-hydroxy-1-[[4-(phenylmethoxy)phenyl]methylpropyl]carbamic acid, phenylmethyl ester (Compound 18)

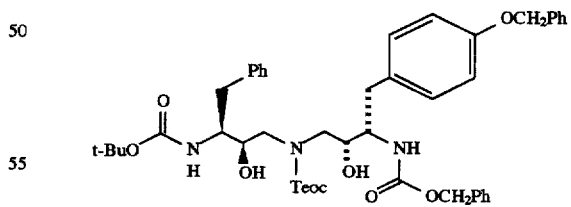

To the mixture of Compound 17b (342 mg, 0.5 mmol) and i-Pr$_2$NEt (140 μl, 0.8 mmol) in dry DMF (3.8 ml) cooled at 0° C. was added 2-trimethylsilylethyl chloroformate (125 μl 0.55 mmol). The mixture was stirred at 0° C. for 1.0 hr and diluted with EtOAc (70 ml). H$_2$O (50 ml) was added and the mixture was extracted with additional EtOAc (2×20 ml). The combined organic layers were washed with saturated NaHCO$_3$ (40 ml) and brine (40 ml) and dried over anhydrous Na$_2$SO$_4$. Concentration in vacuo followed by flash chromatography (100% CHCl₃ to 2:1 CHCl₃-EtOAc) afforded 401 mg (97%) of Compound 18 as a white foam. ¹H-NMR (400 MHz, CDCl₃): 7.17–7.44 (m, 15H), 7.08 (d, J=8.12, 2H), 6.85 (d, J=8.12, 2H), 4.99 (s, 2H), 4.58 and 4.72 (bs, 2H), 4.14 (t, J=8.77, 2H), 3.70–4.00 (m, 4H), 3.15–3.55 (m, 4H), 2.70–3.00 (m, 4H), 1.32 (s, 9H), 0.94 (m, 2H), 0.00 (s, 9H).

EXAMPLE 19

Preparation of [1S-[1R*,2S*(2S*,3R*)]]-[3-[[3-Amino-2-hydroxy-4-(4-hydroxyphenyl)butyl][[2-(trimethylsilyl)ethoxy]carbonyl]amino]-2-hydroxy-1-(phenylmethyl)propyl]carbamic acid 1,1-dimethylethyl ester (Compound 19)

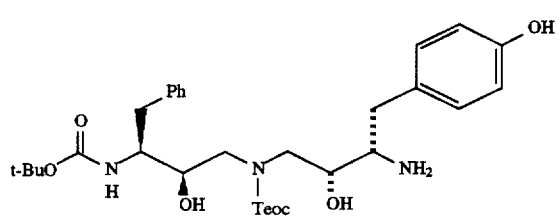

To the solution of Compound 18 (401 mg, 0.485 mmol) in 17 ml of 100% EtOH was added 200 mg of Pd(OH)₂. The mixture was stirred under a H₂ atmosphere overnight (>16 hrs). The catalyst was removed by filtration through a small plug of Celite and washed several times with MeOH. Concentration in vacuo afforded an oily residue, which after recrystallization from CHCl₃ (2.0 ml) and hexane (25 ml) gave 272 mg (93%) of Compound 19 as an off-white solid. This material was immediately used in the next Example.

EXAMPLE 20

Preparation of [1S-[1R*,2S*(2S*,3R*)]]-[3-[[3-[[(1,1-Dimethylethoxy)carbonyl]amino]-2-hydroxy-4-(4-hydroxyphenyl)butyl][[2-(trimethylsilyl)-ethoxy]carbonyl]amino]-2-hydroxy-1-(phenylmethyl)-propyl]carbamic acid, 1,1-dimethylethyl ester (Compound 20)

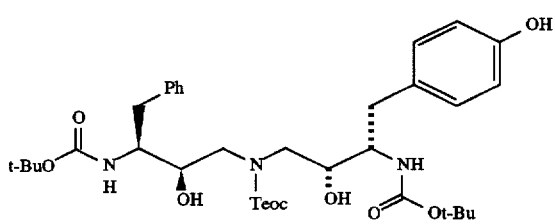

To the solution of Compound 19 (121 mg, 0.20 mmol) in 1,4-dioxane-water (1:1, 0.6 ml) was added Et₃N (42 μl, 0.30 mmol), followed by Boc-ON (59 mg, 0.24 mmol). The mixture was stirred at RT overnight. The reaction mixture was diluted with EtOAc (25 ml) and washed with H₂O (2×10 ml). The aqueous layer was extracted with EtOAc (2×25 ml). The combined organic layers were washed with saturated NaHCO₃ (20 ml) and brine (20 ml) and dried over anhydrous Na₂SO₄. Concentration in vacuo followed by flash chromatography (100% CHCl₁₃ to 95:5 CHCl₃—MeOH) on a silica gel column (190×20 mm) afforded 132 mg of Compound 20 as a glassy solid, which was triturated with hexane to give 126 mg (94%) of Compound 20 as a white solid.

MS (FAB): 704⁺ (M+H)⁺.

EXAMPLE 21

Preparation of [1S-[1R*,2S*(2S*,3R*)]]-3-[[3-[[(1,1-Dimethylethoxy)carbonyl]amino]-2-hydroxy-4-(4-hydroxyphenyl)butyl]amino]-2-hydroxy-1-(phenylmethyl)propyl]carbamic acid, 1,1-dimethylethyl ester (Compound 21)

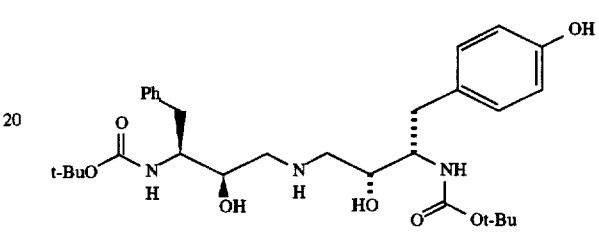

The mixture of Compound 20 (124 mg, 0.176 mmol) and solid n-Bu₄NF·nH₂O (138 mg, 0.529 mmol) in dry THF (0.75 ml) was heated at 50° C. for 4.0 hrs. After cooling to room temperature, Celite (1.0 g) was added and the solvent was removed under reduced pressure. Flash chromatography (100% CHCl₃ to CHCl₃—MeOH—NH₄OH: 92:8:0.8) on silica gel column (20×200 mm) afforded 79 mg (81%) of Compound 21 as a white solid.

m.p.: 151.0°–152.5° C. [α]_D=−1.53° (c 0.196, CHCl₃). MS (FAB): 560⁺ (M+H)⁺. Anal. Calc. for C₃₀H₄₅N₃O₇·0.70H₂O: C, 62.96; H, 8.17; N, 7.34. Found: C, 63.03; H, 8.08; N, 7.27.

EXAMPLE 22

Preparation of [1S-[1R*,2S*(2S*,3R*)]]-[3-[[3-[[(1,1-Dimethylethoxy)carbonyl]amino]-2-hydroxy-4-ehenylbutyl]amino]-2-hydroxy-1-[(1H-indol-3-yl)methyl]propyl]carbamic acid, phenylmethyl ester (Compound 22b)

(a) Compound 22a

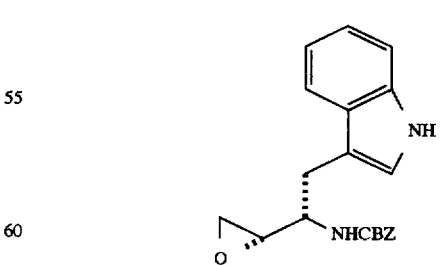

Compound 22a was prepared by procedures analogous to those used for the synthesis of Compound 1b(i) in which N-Cbz-L-tryptophan was employed in place of N-Boc-L-phenylalanine.

(b) Compound 22b

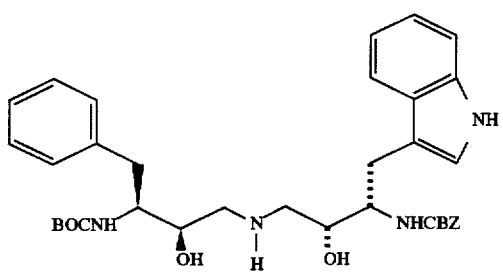

Compounds 22a and 16b were reacted by a procedure analogous to that used for the preparation of Compound 4b to give the title Compound 22b (white solid).

m.p. 170–171° C.; [α]$_D$ = 21.1° (c = 0.48, MeOH)
Elemental Analysis (%)
C$_{35}$H$_{44}$N$_4$O$_6$·0.89 H$_2$O

|   | Calc. | Found |
|---|---|---|
| C | 67.62 | 67.53 |
| H | 7.22  | 7.14  |
| N | 9.01  | 9.10  |

EXAMPLE 23

Preparation of [1S-[1R*,2S*(2S*,3R*)]]-[3-[[3-[[(1,1-Dimethylethoxy)carbonyl]amino]-2-hydroxy-4-(1H-indol-3-ylmethyl)butyl]amino]-2-hydroxy-1-(phenylmethyl)propyl]carbamic acid, 1,1-dimethylethyl ester (Compound 23)

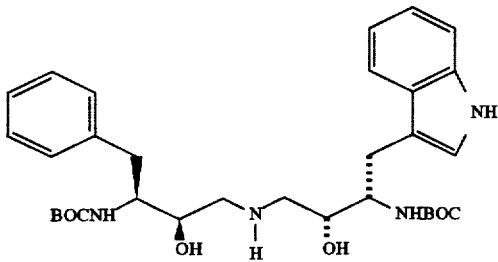

Compound 22b was converted to the title Compound 23 (white solid) using procedures analogous to those for the synthesis of Compounds 18 through 21 (di-tert-butyldicarbonate was used instead of BOC-ON to put on the Boc group).

m.p. 168–169° C.; [α]$_D$ = −14.4° (c = 0.21, MeOH)
Elemental Analysis (%)
for C$_{32}$H$_{46}$N$_4$O$_6$·1.09 H$_2$O

|   | Calc. | Found |
|---|---|---|
| C | 65.24 | 65.31 |
| H | 7.99  | 8.18  |
| N | 9.51  | 9.44  |

EXAMPLE 24

Preparation of [1S-[1R*,2S*((2S*,3R*)]]-[3-[[3-[[(1,1-Dimethylethoxy)carbonyl]amino-2-hydroxy-4-phenylbutyl]amino]-2-hydroxy-1-(2-phenylethyl)propyl]carbamic acid, phenylmethyl ester (Compound 24b)

(a) Compound 24a

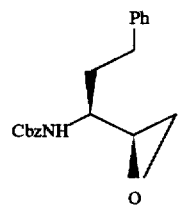

Compound 24a was prepared by procedures analogous to those used for the synthesis of Compound 1b(i), in which N-Cbz-L-homophenylalanine was employed in place of N-Boc-L-phenylalanine.

(b) Compound 24b

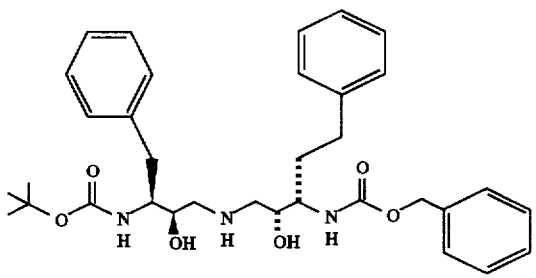

Compounds 24a and 16b were reacted by a procedure analogous to that used for the preparation of Compound 4b to give the title Compound 24b.

mp 150°–151° C. [α]$^n_D$=−9.1° (c 0.2, MeOH). Mass Spec. [M+H]$^+$=592. Analysis calc. for C$_{34}$H$_{45}$N$_3$O$_6$·0.43 H$_2$O: C, 68.13; H, 7.71; N, 7.01; Found: C, 68.15; H, 7.58; N, 6.99.

EXAMPLE 25

Preparation of [1S-[1R*,2S*(2S*,3R* )]]-[3-[[3-[[(1,1-Dimethylethoxy)carbonyl]amino]-2-hydroxy-4-phenylbutyl]amino]-2-hydroxy-1-(2-phenylethyl))propyl]carbarmic acid, 1,1-dimethylethyl ester (Compound 25)

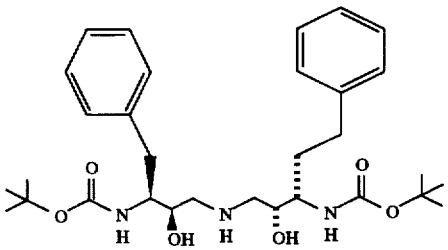

Compound 24b was converted to the title Compound 25 using procedures analogous to those for the synthesis of Compounds 18 through 21.

mp 145°–148° C.; [α]$_D$=−6° (c 0.3, MeOH). Mass Spec: Fab (M+H)$^+$: 558. Analysis calculated for $C_{31}H_{47}N_3O_6 \cdot 0.44H_2O$: C; 65.82; H; 8.53; N; 7.43; Found: C; 65.69: H;8.40; N; 7.56.

EXAMPLE 26

Preparation of [1R-[1R*,2R*(2R*,3S*)]]-3-[[3-[[(1,1-Dimethylethoxy)carbonyl]amino]-2-hydroxy-4-phenylbutyl]amino]-2-hydroxy-1-(phenylmethyl) propyl]carbamic acid, 1,1-dimethylethyl ester (Compound 26b(i)) and Preparation of [1R-[1R*,2S*(2R*,3S*)]]-3-[[3-[[(1,1-Dimethylethoxy)carbonyl]amino]-2-hydroxy-4-phenylbutyl]amino]-2-hydroxy-1-(phenylmethyl)-propyl]carbamic acid, 1,1-dimethylethyl ester (Compound 26b(ii))

(a) Compound 26a(i)

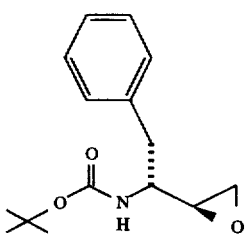

and
Compound 26a(ii)

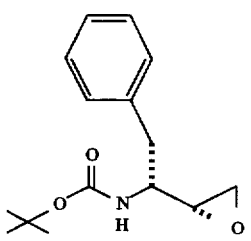

Compounds 26a(i) and 26a(ii) were prepared by procedures analogous to those used for the synthesis of Compounds 1b(i) and 1b(ii), in which N-Boc-D-phenylalanine was employed in place of N-Boc-L-phenylalanine.

(b) Compound 26b(i)

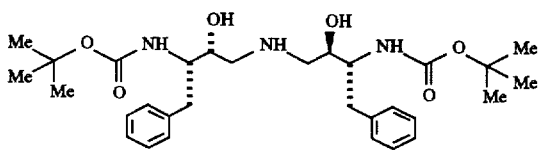

and
Compound 26b(ii)

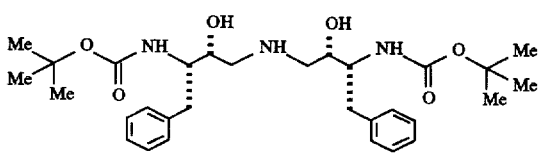

A mixture of Compounds 26a(i) and 26a(ii) were reacted with Compound 16b by a procedure analogous to that used for the preparation of Compound 4b (except that MeOH at 55° was used in place of DMF) to give, after separation by silica gel chromatography the title Compounds 26b(i) and 26b(ii).

Compound 26b(i)

m.p. 158°–160° C.; $[\alpha]_D^{25}=+14.9°$ (c 0.35, MeOH). MS: (CI/NH$_3$): 544 (M+H). Anal. Calc. for $C_{30}H_{45}N_3O_6 \cdot 0.67$ H$_2$O; C, 64.84; H, 8.40; N, 7.56; Found: C, 64.66; H, 8.25; N, 7.74

Compound 26b(ii)

m.p. 200°–201° C.; $[\alpha]_D^{25}=+6.0°$ (c 0.1, DMSO). MS: (FAB): 544 (M+H). Anal. Calc. for $C_{30}H_{45}N_3O_6 \cdot 0.32$ H$_2$O; C, 65.58; H, 8.37; N, 7.65; Found: C, 65.44; H, 8.38; N, 7.79

EXAMPLE 27

Preparation of [1S-[1R*,2R*(3S*)]]-[3-[[3-[[(1,1-Dimethylethoxy)carbonyl]amino]-2-hydroxy-4-phenylbutyl]amino]-2-hydroxy-1-(phenylmethyl) propyl]-carbamic acid 1,1-dimethylethyl ester (Compound 27b)

(a) Compound 27a

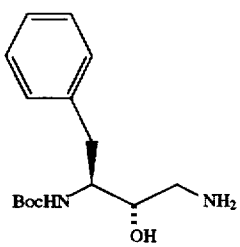

Compound 1b(ii) was converted to Compound 27a by a procedure analogous to the one used for the preparation of Compound 16b.

(b) Compound 27b

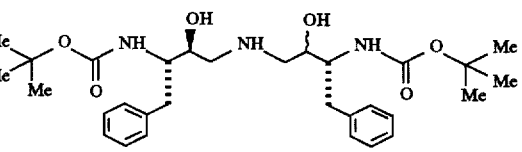

A mixture of Compounds 26a(i) and 26a(ii) were reacted with Compound 27a by a procedure analogous to that used for the preparation of Compound 4b (except that MeOH at 55° was used in place of DMF) to give the title Compound 27b as a mixture of diastereomers.

m.p. 156°–159° C.; MS: (CI/NH$_3$): 544 (M+H). Anal. Calc. for $C_{30}H_{45}N_3O_6 \cdot 0.16$ H$_2$O; C, 65.91; H, 8.36; N, 7.69; Found: C, 65.89; H, 8.34; N, 7.71

EXAMPLE 28

Preparation of [1S-[1R*,2S*(2S*,3R*)]]-[3-[[3-[[(1,1-Dimethylethoxy)-carbonyl]amino]-2-hydroxy-4-phenylbutyl]amino]-2-hydroxy-1-[[3-(phenylmethoxy)phenyl]methyl]propyl]carbamic acid, 1,1-dimethylethyl ester (Compound 28g)

(a) Compound 28a

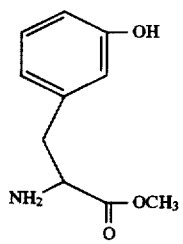

SOCl₂ (1.28 ml) was added dropwise to a solution of DL-meta-tyrosine (3.2 g, 17.7 mmol) in 4.4 ml MeOH at −15° C. and the resulting solution was stirred at 0° C. for 2 h, and at RT overnight. The reaction mixture was concentrated in vacuo and the residue was washed with Et₂O, filtered, and dried in vacuo to yield 3.2 g (94%) of the HCl salt of methyl ester Compound 28a.

(b) Compound 28b

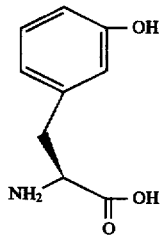

Compound 28a (1.54 g, 6.65 mmol) in 70 ml of 0.2N NaHCO₃ was added to a 100 ml aqueous solution of Subtilisin (protease type VIII from baccilus licheniformis, 3.8 mg) and the reaction mixture was stirred slowly at RT for 40 min. The pH of this solution was maintained at pH 8.0 with the occasional addition of 1N NaOH. Unreacted methyl ester of D-m-tyrosine was extracted 5× with 100 ml portions of EtOAc. The aqueous solution was acidified with 1N HCl to pH 6.0 and concentrated to 5 ml. The resulting solid was filtered, washed with 1 ml of cold H₂O and dried to yield 0.45 g of Compound 28b. The filtrate was passed through 20 ml of Dowex AG50 in H⁺ form, followed by the elution of desired material with 2% pyridine in H₂O to yield an additional 0.14 g of Compound 28b (total 0.59 g, 98%). This crude product was carried on to the next step.

(c) Compound 28c

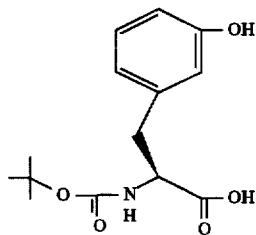

Compound 28b (0.473 g, 2.61 mmol) was reacted with BOC-anhydride (0.613 g, 2.81 mmol) in 20 ml of absolute EtOH overnight at RT. The reaction mixture was concentrated in vacuo, and the residue was dissolved in EtOAc (400 ml) and washed with H₂O, brine, dried (Na₂SO₄), filtered and concentrated in vacuo. The crude product was chromatographed through 80 g of silica gel using a (2:1:97) MeOH:HOAc:CHCl₃ solvent system. The resulting product was crystallized from CHCl₃ (15 ml) to yield 0.41 g (59%) of Compound 28c.

[α]_D=+10.8 (MeOH, c=1.0)

(d) Compound 28d

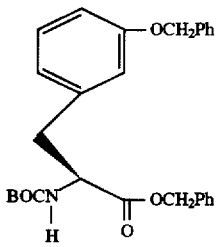

Compound 28c (0.41 g, 1.46 mmol), benzyl bromide (0.51 g, 2.98 mmol) and Cs₂CO₃ (0.97 g, 2.96 mmol) were stirred in DMF (2.5 ml) overnight. The reaction mixture was diluted with 200 ml of EtOAc and the organic solution was washed with water, brine, dried (Na₂SO₄) and concentrated in vacuo. The product was crystallized from 10 ml of (1:1) Et₂O:hexane to yield 0.54 g (81%) of Compound 28d.

(e) Compound 28e

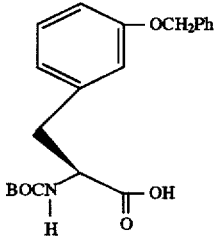

Compound 28d (1.147 g; 2.49 mmol) was dissolved in 2.5 ml of THF and 2.5 ml of 1N LiOH and stirred at RT for 20 min. An additional 2.0 ml of THF was added and the reaction was stirred for 40 more min. The reaction mixture was neutralized with 2.5 ml of 1N HCl at 0° C. and concentrated in vacuo to 4 ml. The product was extracted with EtOAC and this solution was washed with brine, dried (Na₂SO₄), and concentrated in vacuo. The residue was redissolved in 50 ml of saturated NaHCO₃ and washed with Et₂O (3×). The bicarbonate solution was neutralized with 1N HCl and the product was extracted with EtOAc. The organic extracts were washed with brine, dried (Na₂SO₄) and concentrated in vacuo to yield Compound 28e (0.84 g, 91%).

(f) Compound 28f

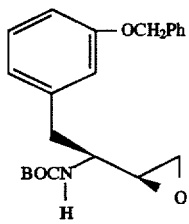

Compound 28e was converted into Compound 28f by procedures analogous to those used for the synthesis of Compound 1b(i).

(g) Compound 28g

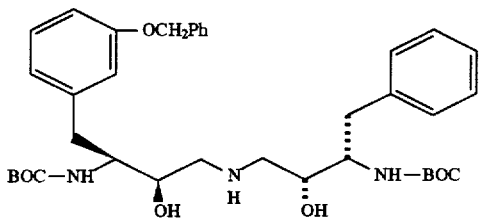

Compounds 28f and 16b were reacted by a procedure analogous to that used for the preparation of Compound 4b to give the title Compound 28g.

mp=125°–145° C. High Resolution mass spec: (M+H)⁺= 650.3802; theory=650.3805.

EXAMPLE 29

Preparation of [1S-[1R*,2S*(2S*,3R*)]]-[3-[[3-[[(1,1-Dimethylethoxy)-carbonyl]amino]-2-hydroxy-4-(3-hydroxyphenyl)butyl]-amino]-2-hydroxy-1-(phenylmethyl)propyl]carbamic acid, 1,1-dimethylethyl ester (Compound 29)

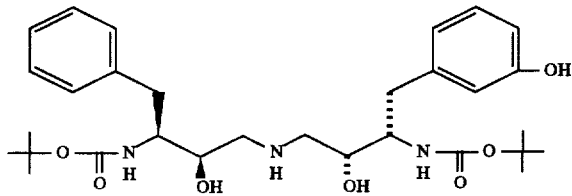

The benzyl group of Compound 28g (0.177 mmol) was removed by hydrogenolysis (MeOH, cat. Pd(OH)₂, H₂) by a procedure analogous to that used for the preparation of Compound 7 to give, after silica gel chromatography, 53 mg (51%) of the title Compound 29.

m.p.=193°–196° C., [α]$_D$=–5.650 (MeOH, c=0.23); High Resolution mass spec: (M+H)⁺ 560.3343; theory=560.3336.

EXAMPLE 30

Preparation of [1S-[1R*,2S*( 2S*,3R*)]]-[3-[[3-[[(1,1-Dimethylethoxy)-carbonyl]amino]-2-hydroxy-4-phenylbutyl]amino]-2-hydroxy-1-(4-pyridinylmethyl)propyl]carbamic acid, 1,1-dimethylethyl ester (Compound 30g)

(a) Compound 30a

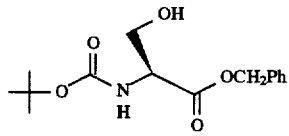

Boc-L-serine (4.03 g, 19.6 mmol) and benzyl bromide (3.35 g, 19.6 mmol) were stirred with Cs₂CO₃ (7.5 g, 23.0 mmol) in 20 ml of DMF at 5° C. for 4 h. The reaction was diluted with Et₂O (500 ml) and the resulting mixture was washed with H₂O , brine, dried (Na₂SO₄) and concentrated in vacuo. The resulting residue solidified and was triturated with hexane, filtered, and dried in vacuo to yield Compound 30a as a white solid (mp 62°–64° C., 5.02 g, 86%).

(b) Compound 30b

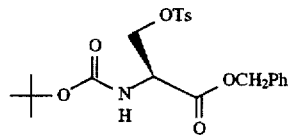

Compound 30a (5.0 g, 16.9 mmol) was dissolved in 10 ml of pyridine, and the reaction was cooled to –10° C. Tosyl chloride (3.24 g, 17.0 mmol) was added portionwise and the reaction mixture was stirred at –10° C. for 4 h. Crushed ice was added to the reaction mixture which was stirred until the product solidified. The solid was filtered and washed thoroughly with water and finally dried over P₂O₅ overnight to give Compound 30b (mp 88°–90° C., 6.8 g, 80%).

c) Compound 30c

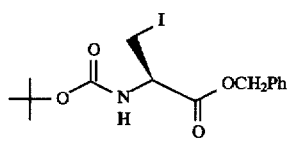

Compound 30b (5.0 g, 11.12 mmol) was partially dissolved in 26 ml of acetone. NaI (1.9 g, 12.75 mmol) was added and the reaction mixture was stirred for 48 h. The reaction mixture was filtered and the filtrate was concentrated in vacuo. The resulting residue was chromatographed on 200 g of silica gel using (5:95) acetone:hexane to give Compound 30c as a white solid (mp 78°–80° C., 3.6 g, 82%).

(d) Compound 30d

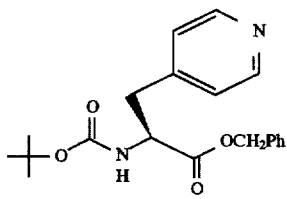

Three grams of zinc dust and 3 g of copper (II) acetate monohydrate were suspended in 6 ml of glacial HOAc and this mixture was stirred until it solidified (15 min). The mixture was triturated with Et₂O and transferred to a filter funnel under a stream of argon. The solid was washed with Et₂O (200 ml) followed by benzene (50 ml). The resulting Zn/Cu couple reagent was dried in vacuo over P₂O₅ for 2 h; 0.54 g of it was suspended in 3 ml of benzene and 0.6 ml of dimethylacetamide, and sonicated while a solution of Compound 30c (1.82 g, 4.06 mmol) in 7 ml of benzene was added slowly. The reaction mixture was sonicated for 45 min and then diluted with 4 ml of benzene. 4-Bromopyridine (0.64 g, 4.06 mmol) and Pd((Ph)₃P)₂Cl₂ (0.23 g) was added and the reaction mixture was stirred at 40° C. for 1 h. The reaction mixture was diluted with EtOAc (200 ml) and filtered. The filtrate was stirred with 50 ml of 0.1N HCl then neutralized with saturated NaHCO₃. The organic layer was separated, washed with H₂O , brine, dried (Na₂SO₄) and concentrated. The crude product was chromatographed on 80 g of silica gel using (2:8) acetone:hexane to give Compound 30d (0.71 g, 49%).

(e) Compound 30e

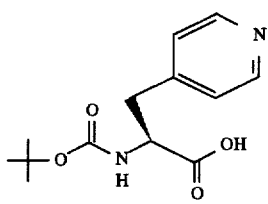

Compound 30d (1.2 mmol) was saponified with aqueous LiOH (1.3 ml of 1N solution) in 1.2 ml THF using a procedure analogous to the one used for Compound 28e to give 0.28 g of the title Compound 30e (m.p.=218° C.).
(f) Compound 30f

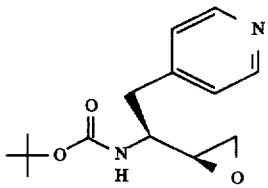

Compound 30e was converted into Compound 30f by procedures analogous to those used for the synthesis of Compound 1b(i).
(g) Compound 30g

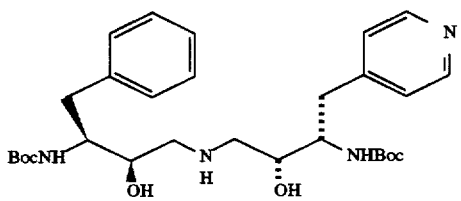

Compounds 30f and 16b were reacted by a procedure analogous to that used for the preparation of Compound 4b to give the title Compound 30g.

High Resolution mass spec(M+H)⁺ 545.3347⁺; Theoretical (M+H)⁺ 545.3339⁺; $^1$H (CD$_3$OD, 300MHz, 50° C.): δ 8.39–8.37 (m, 2H), 7.31–7.14 (m, 7H), 3.76–3.59 (m, 4H), 3.05–3.27 (m, 2H), 2.60–2.85 (m, 6H), 1.29 (br s, 9H).

EXAMPLE 31

Preparation of [1S-[1R*,2S*(2S*,3R*)]]-[3-[[3-[[(1,1-Dimethylethoxy)-carbonyl]amino]-2-hydroxy-4-phenylbutyl]amino-2-hydroxy-1-(6-quinolinylmethyl)propyl]carbamic acid, 1,1-dimethylethyl ester (Compound 31i)

(a) Compound 31a

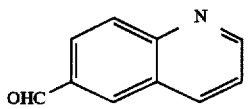

6-Methylquinoline (7.0 g, 49 mmol) and selenium oxide (6.0 g, 54 mmol) were heated at 150° C. for 1 h and at 220° C. for 30 min. The reaction mixture was cooled to RT and the residue was triturated with MeOH and filtered. The filtrate was concentrated in vacuo, and the crude product was chromatographed on 250 g of silica gel using 3:7 EtOAc:Hexane. The appropriate fractions were combined and concentrated to yield 3.8 g (49%) of Compound 31a as a white solid. m.p. 93°–95° C.

(b) Compound 31b

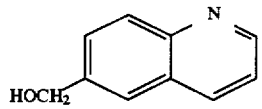

Compound 31a (1.65 g, 10.5 mmol) was dissolved in 50 ml of MeOH, cooled to 5° C. and NaBH$_4$ (0.397g, 10.5 mmol) was added and the reaction mixture was stirred for 15 min. After the addition of 10 ml saturated NH$_4$Cl, the reaction mixture was concentrated to 10 ml and extracted with EtOAc. The organic layer was washed with H$_2$O, brine, dried (Na$_2$SO$_4$), and concentrated in vacuo to yield a viscous oil which on standing solidified (74°–78° C.). This material was dissolved in Et$_2$O and 4N HCl was added until acidic. The HCl salt that precipitated was filtered and dried to yield 1.56 g (76%) of Compound 31b as its hydrochloride salt.

(c) Compound 31c

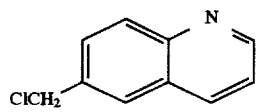

SOCl$_2$ (4.5 ml) was added to Compound 31b (1.46 g, 7.5 mmol). The reaction mixture was heated at 110° C. for 1 h, and excess SOCl$_2$ was distilled off. The residue was dissolved in H$_2$O and 1N KOH was added until basic (pH 12). The product was extracted with EtOAc and this solution was washed with H$_2$O, brine, dried (Na$_2$SO$_4$) and concentrated to yield Compound 31c (1.22 g, 91%) as a crystalline solid. m.p. 65°–68° C.

(d) Compound 31d

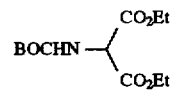

Diethylaminomalonate (4.23 g, 20 mmol), di-tert-butyldicarbonate (4.4 g, 20 mmol) and Et$_3$N (2.8 ml, 20 mmol) were dissolved and stirred in 150 ml of absolute EtOH for 24 h. The reaction mixture was concentrated in vacuo and the residue was dissolved in EtOAc (300 ml). This was washed with aqueous KHSO$_4$ (10%), brine, dried (Na$_2$SO$_4$), filtered and concentrated in vacuo to yield Compound 31d (4.3 g, 78%) as an oil.

(e) Compound 31e

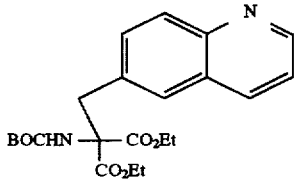

Sodium ethoxide (4.27M in EtOH, 3.0 ml, 12.8 mmol) was added to an EtOH (5 ml) solution of Compound 31d (3.52 g, 12.8 mmol), followed by the addition of Compound 31c (1.13 g, 6.4 mmol). The reaction mixture was refluxed for 3.5 h. Celite (2 g) was added and the mixture was concentrated and chromatographed on 80 g of Merck silica gel to yield Compound 31e (2.03 g, 76%) as a crystalline solid. m.p. 110°–113° C.

(f) Compound 31f

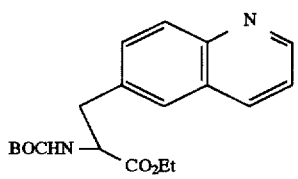

Compound 31e (0.8 g, 1.9 mmol) was dissolved in 1 ml of THF and 2.2 ml of 1N LiOH. The reaction mixture was stirred at 40° C. for 4 hr, concentrated down to 2 ml and HOAc was added until pH 4 was reached. The mono-acid precipitated and was filtered. Without further purification this material was suspended in dioxane and the reaction mixture was heated at reflux for 2 hr . The reaction was concentrated and the resulting residue was chromatographed on 50 g of Merck silica gel using (3:7) acetone:hexane to afford Compound 31f (0.52 g, 80%). m.p. 92°–95° C.

(g) Compound 31g

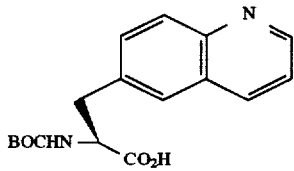

Compound 31f (1.8 g, 5.2 mmol) in 45 ml of DMF was added dropwise to 700 ml of $H_2O$ containing 10 mg of Subtlisin protease VII and 50 ml of 0.2N $NaHCO_3$. After the addition, the pH was maintained at 7.5 to 8.0 with the occasional addition of 0.1N NaOH. After 2.5 h the solution was extracted with EtOAc and the aqueous layer was acidified to pH 4 with HOAc. The aqueous layer was concentrated in vacuo and the crude product was chromatographed on 80 g of Merck silica gel using 16:1.5:0.25 $CH_2Cl_2$:MeOH:HOAc to afford Compound 31g (0.82 g, 90%). m.p. 184°–189° C. (dec);

$[\alpha]_D$=+29.0° (c 0.77, MeOH)

(h) Compound 31h

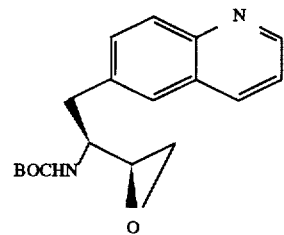

Compound 31h was prepared from Compound 31g by a multi-step procedure analogous to that used for the conversion of N-Boc-L-phenylalanine to Compound 1b(i). m.p. 136°–140° C.

(i) Compound 31i

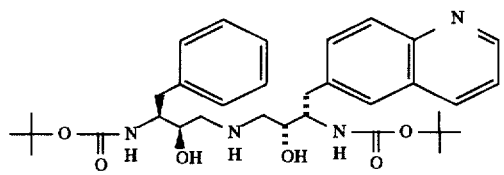

Compound 31h (100.9 mg, 0.321 mmol) was reacted with Compound 16b (90 mg, 0.321 mmol) by a procedure analogous to that of Example 4b to afford the title Compound 31i (0.113 g; 59%) as a white solid. m.p. 105°–112° C.; $[\alpha]_D$= +4.55° (c 0.88, MeOH).

EXAMPLE 32

Preparation of [2R-(2R*,3S*)]1,1'-(Phenylmethyl)-iminobis(3-amino-4-phenyl-2-butanol)hydrochloride salt (Compound 32)

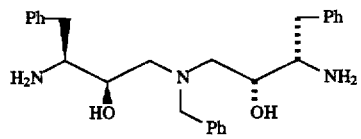

To neat Compound 1c (117 mg, 0.185 mmol) at 0° C. was added HCl in dioxane (2.0 mL, 4M). The reaction mixture was stirred at 0° C. for 15 min and then 1.15 h at RT. The volatiles were then removed in vacuo and the residue co-evaporated with dry $Et_2O$. The resulting solid was dried under high vacuum ($P_2O_5$) for 4 h to give the title Compound 32 as a colorless solid (91 mg), which was used without further purification as the tri-HCl salt.

$R_f$=0.53 (20:7:80, MeOH:$NH_4OH$:$CHCl_3$)

EXAMPLE 33

Preparation of [S-(1R*,2S*)]-N,N'-[(Phenylmethyl) iminobis[2-hydroxy-1-(phenylmethyl)-3,-propanediyl]]bis-[$N^2$-[(1,1-dimethylethoxy) carbonyl]-L-valinamide] (Compound 33)

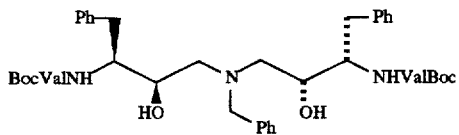

To a solution of Compound 32 (≦0.185 mmol) and Boc-(L)-valine (87 mg, 0.40 mmol) in $CH_2Cl_2$ (2.0 mL) at 0° C. under argon was added EDCI (85 mg, 0.44 mmol), HOBT (93 mg, 0.69 mmol), and 4-methylmorpholine (0.065 mL). After 20 min at 0° C., the reaction mixture was stirred at RT for 68 h. The reaction mixture was partitioned between EtOAc and saturated $NaHCO_3$. The organic layer was extracted with brine, dried over $Na_2SO_4$, and the volatiles were evaporated in vacuo to give an oily-solid residue. This residue (140 mg) was purified by flash column chromatography (silica gel, 2.5 by 13 cm), eluting with 0.5, 1, 2, 3, 4 and then 12% MeOH:$CH_2Cl_2$ to give the title Compound 33 (29.6 mg, 19% yield for the 2 steps) as a colorless solid.

$R_f$=0.59 (15% MeOH:$CH_2Cl_2$).

EXAMPLE 34

Preparation of [S-(1R*,2S*)]-N,N'-[Iminobis[2-hydroxy-1-(phenylmethyl)-3,1-propanediyl]]bis[$N^2$-[(1,1-dimethylethoxy)carbonyl]-L-valinamide] (Compound 34)

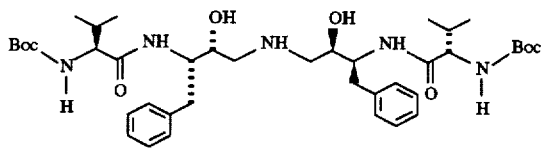

Compound 33 was converted to the title Compound 34 by a procedure analogous to the one used for the synthesis of Compound 7.

m.p. 216°–222° C.; $[\alpha]_D^{25}$=–28.55° (c 0.16, MeOH). MS: 742 (M+H). Anal. Calc. for $C_{40}H_{63}N_5O_8 \cdot 0.27 H_2O$: C, 64.32; H, 8.58; N, 9.38; Found: C, 63.90; H, 8.49; N, 9.80

EXAMPLE 35

Preparation of [S-(1R*,2S*)]-N,N'-[[(Phenylmethyl)imino]bis[2-hydroxy-1-(phenylmethyl)-3,1-DroDanediyl]]bisbenzamide (Compound 35)

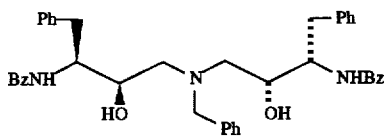

To a suspension of Compound 32 (≦0.168 mmol) in $CH_2Cl_2$ (1.5 mL) was added i-$Pr_2NEt$ (0.09 mL), resulting in a homogeneous solution. To the stirring reaction mixture at 0° C. was added 0.04 ml of benzoyl chloride. A second portion of $CH_2Cl_2$ (1.5 mL) and i-$Pr_2NEt$ (0.09 mL) was added after 30 min at 0° C. and the reaction mixture was stirred at RT for 1.5 h. At 0° C., the reaction mixture was quenched with saturated $NaHCO_3$ and the aqueous layer was saturated with NaCl and extracted with EtOAc and $CH_2Cl_2$. The combined organic layers were dried ($Na_2SO_4$) and the volatiles were evaporated in vacuo to a slightly yellow solid residue which was purified by silica gel chromatography (2 by 10 cm), eluting with 8:2 EtOAc:$CH_2Cl_2$, then EtOAc to give the title Compound 35 (96 mg, 93% yield) as a colorless solid. $R_f$=0.60 (20:7:80 MeOH:$NH_4OH$:$CHCl_3$).

EXAMPLE 36

Preparation of [S-(1R*,2S*)]-N,N'-[Iminobis[2-hydroxy-1-(phenylmethyl)-3,1-propanediyl]] bisbenzamide (Compound 36)

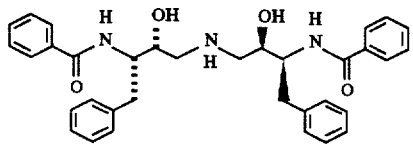

A mixture of Compound 35 (96 mg, 0.157 nmol) and Pd(OH)$_2$ (45 mg, 20% on carbon) in aqueous HOAc (3 mL, 90%) at RT was stirred under a $H_2$ atmosphere. After 7 h, a second portion of Pd(OH)$_2$ (6 mg) was added. The reaction mixture was stirred for an additional 45 min and filtered through Celite, washing the filter pad thoroughly with aqueous HOAc. The volatiles were removed in vacuo to give a colorless solid which was triturated twice with hot $Et_2O$ and once with hot EtOAc. The resulting residue was purified by flash chromatography (silica gel, 1 by 11 cm), eluting with MeOH:$NH_4OH$:$CH_2Cl_2$ (1:0.1:9) to give the title Compound 36 (50 mg, 58% yield) as a colorless solid.

m.p. dec. 227°–231° C.; $[\alpha]_D^{25}$=83.950 (c 0.21, DMSO); MS: 552 (M+H). Anal. Calc. for $C_{34}H_{37}N_3O_4$: C, 74.02; H, 6.76; N, 7.62; Found: C, 73.88; H, 6.70; N, 7.62

EXAMPLE 37

Preparation of [S-(1R*,2S*)]-[[(Phenylmethyl)imino]bis[2-hydroxy-1-(phenylmethyl)-3,1-propanediyl]]bisiminobis[$N^2$-[(1,1-dimethylethoxy)carbonyl]-L-phenylalaninamide] (Compound 37)

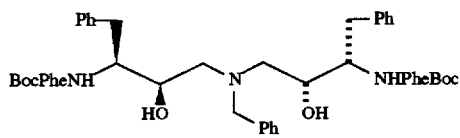

Compound 32 was coupled with Boc-L-phenylalanine by a procedure analogous to the one used for the synthesis of Compound 33 (1:1 $CH_2Cl_2$:DMF was used) to give the title Compound 37.

$R_f$=0.78 (10% MeOH:$CH_2Cl_2$).

EXAMPLE 38

Preparation of [S-(1R*,2S*)]-[Iminobis[2-hydroxy-1-(phenylmethyl)-3,1-propanediyl]]-bisimino-bis[$N^2$-[(1,1-dimethylethoxy)carbonyl]-L-phenylalaninamide] (Compound 38)

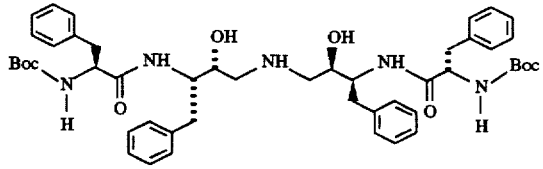

Compound 37 was converted to the title Compound 38 by a procedure analogous to the one used for the synthesis of Compound 36.

m.p. dec. 206°–212° C.; $[\alpha]_D^{25}$=–14.28° (c 0.13, DMSO); MS: (CI/$NH_3$): 838 (M+H). Anal. Calc. for $C_{48}H_{63}N_5O_8 \cdot 1.07 H_2O$: C, 67.24; H, 7.66; N, 8.17; Found: C, 67.23; H, 7.26; N, 8.18

EXAMPLE 39

Preparation of [S-(1R*,2S*)]-N,N'-[[[(9H-Fluoren-9-ylmethoxy)carbonyl]imino]-bis[2-hydroxy-1-(phenylmethyl)-3,1-propanediyl]biscarbamic acid, bis(1,1-dimethylethyl) ester (Compound 39)

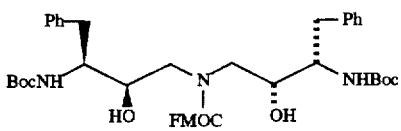

To a mixture of Compound 2 (192 mg, 0.354 mmol) in i-Pr$_2$NEt (0.08 mL) and DMF (2 mL) at 0° C. was added 9-fluorenylmethyl chloroformate (100 mg, 0.386 mmol). After 1 h at 0° C., the reaction mixture was stirred at RT for 2 h, quenched at 0° C. with saturated NaHCO$_3$, and extracted with EtOAc. The organic layer was dried (Na$_2$SO$_4$) and the volatiles removed in vacuo to leave an oily-foam which was purified by flash chromatography (silica gel, 2.5 by 12 cm), eluting with 30% EtOAc:CH$_2$Cl$_2$ to give the title Compound 39 (251 mg, containing 8% by weight of EtOAc by $^1$H NMR analysis, 85% yield) as an oily foam. R$_f$=0.33 (35:65, EtOAc:CH$_2$Cl$_2$).

EXAMPLE 40

Preparation of [R-(R*,S*)]-N,N-Bis(3-amino-2-hydroxy-4-phenylbutyl)carbamic acid, 9H-fluoren-9-ylmethyl ester, hydrochloride salt (Compound 40)

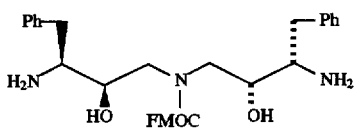

Compound 39 was converted to the title Compound 40 by a procedure analogous to the one used for the synthesis of Compound 32. R$_f$=0.56 (20:6:80, MeOH:NH$_4$OH:CHCl$_3$).

EXAMPLE 41

Preparation of [S-(1S*,2R*)]-N,N'-[[[(9H-Fluoren-9-ylmethoxy)carbonyl]imino]bis-[2-hydroxy-1-(phenylmethyl)-3,1-propanediyl]bis[N$^2$-[(phenylmethoxy)carbonyl]-L-valinamide] (Compound 41)

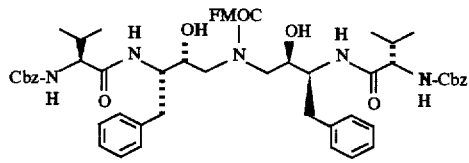

Compound 40 was coupled with Cbz-L-valine by a procedure analogous to the one used for the synthesis of Compound 33 (DMF was used) to give the title Compound 41. R$_f$=0.69 (1:9, MeOH:CH$_2$Cl$_2$).

EXAMPLE 42

Preparation of [1S-(1R*,2S*)]-N,N'-[Iminobis[2-hydroxy-1-(phenylmethyl)-3,1-proanediyl]bis[N$^2$-[(phenylmethoxy)carbonyl]-L-valinamide] (Compound 42)

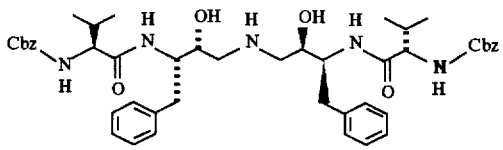

To a mixture of Compound 41 (110 mg, 0.107 mmol) in DMF (4 mL) at RT was added piperidine (0.20 mL). After 50 min, the reaction mixture was diluted with H$_2$O and the resulting solid was collected by filtration and washed with H$_2$O and hexanes. The resulting residue was purified by flash chromatography (silica gel, 2 by 13 cm), eluting with MeOH:NH$_4$OH:CH$_2$Cl$_2$ (7:0.7:92.3, 8:0.8:91.2, and then 9:0.9:90.1) to give the title Compound 42 (65 mg, 75% yield) as a colorless solid.

m.p. dec. 217°–221° C.; [α]$_D^{25}$=−14.14° (c 0.21, DSMO); MS: 810 (M+H). Anal. Calc. for C$_{46}$H$_{59}$N$_5$O$_8$·0.56 H$_2$O: C, 67.37; H, 7.39; N, 8.54; Found: C, 67.43; H, 7.17; N, 8.48

EXAMPLE 43

Preparation of [S-(1S*,2R*)]-N,N'-[Iminobis[2-hydroxy-1-(phenylmethyl)-3,1-propanediyl]]bis-L-valinamide (Compound 43)

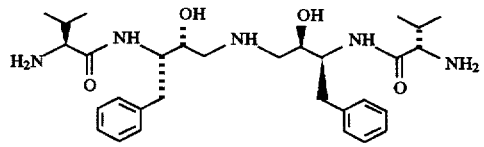

A mixture of Compound 42 (65 mg, 81 μmol) and Pd(OH)$_2$ (23 mg) in aqueous HOAc (3 mL, 90%) at RT was stirred under an H$_2$ for 2.5 h, filtered through Celite, washing the filter pad with aqueous HOAc, and the volatiles were removed in vacuo. The resulting oily-residue was co-evaporated with dry Et$_2$O to give a colorless solid (60 mg). This residue was dissolved in H$_2$O, basified to pH 9–10 with saturated aqueous K$_2$CO$_3$ and purified by CHP-20P resin chromatography, eluting with H$_2$O, then CH$_3$CN:NH$_4$OH:H$_2$O and the column flushed with MeOH:NH$_4$OH:H$_2$O to give the title Compound 43 (29 mg, ~62% yield) as a slightly colored solid. m.p. 115°–116° C. MS: 542 (M+H).

EXAMPLE 44

Preparation of [R-(R*,S*)]-Iminobis[2-hydroxy-1-(phenylmethyl)-3,1-propandiyl]]biscarbamic acid, bis(phenylmethyl) ester (Compound 44c)

(a) Compound 44a

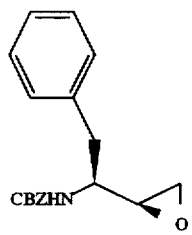

Compound 44a was prepared by procedures analogous to those used for the synthesis of Compound 1b(i), in which N-Cbz-L-phenylalanine was employed in place of N-Boc-L-phenylalanine.

(b) Compound 44b

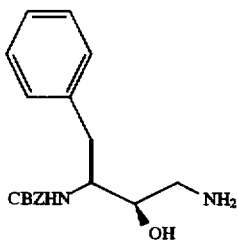

Compound 44a was converted into Compound 44b by a procedure analogous to the one used for the synthesis of Compound 16b except that the reaction was done in MeOH saturated with $NH_3$ at 55° C. for 40 h in a sealed bottle.

(c) Compound 44c

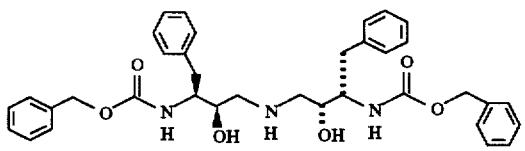

Compounds 44a and 44b (1 equivalent of each) were reacted by a procedure analogous to that used for the preparation of Compound 4b to give the title Compound 44c (white solid).

mp 167°–171° C.; $[\alpha]_D=-27.7°$ (c 0.13, AcOH); Mass Spec. 612 (M+H). Analysis Calc. for $C_{36}H_{41}N_3O_6 \cdot 1.43H_2O$: C, 67.82; H, 6.93; N, 6.59; Found: C, 68.12; H, 6.56; N, 6.29.

EXAMPLE 45

Preparation of [R-(R*,S*)]-[Iminobis[2-hydroxy-1-(phenylmethyl)-3,1-propandiyl]biscarbamic acid, 1,1-dimethylethyl phenylmethyl ester (Compound 45)

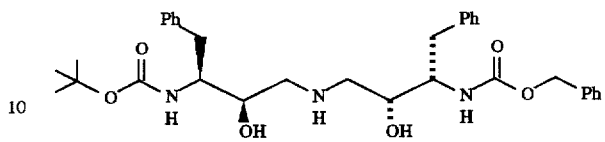

To a solution of lithium perchlorate (16.4 g, 0.155 mol) in 500 ml $CH_3CN$ was added Compound 16b (43.5 g, 0.155 mol) as a solid followed by Compound 44a (41.2 g, 0.139 mole) in 150 ml $CH_3CN$. The resulting mixture was stirred at 30° C. for 2 h and at 40° C. for 30 h at which point it was cooled to RT then added to 1.5L of $H_2O$. The resulting precipitate was filtered and triturated with i-PrOH followed by 1:1 EtOAc:i-PrOH (2×) to give 42.1 g (52%) of Compound 45 as a white solid.

m.p. 169°–173°; $[\alpha]_D=-13.9°$ (c 1.3, MeOH).

EXAMPLE 46

Preparation of [R-(R*,S*)]-N,N"-[[(9H-Fluoren-9-ylmethoxy)carbonyl]iminobis-[2-hydroxy-1-(phenylmethyl)-3,1-propanediyl]]bis[N'-(1,1-dimethylethyl)urea] (Compound 46)

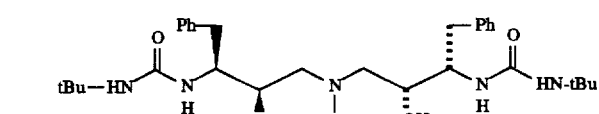

To a suspension of Compound 40 (59 mg, 92 μmol) in $CH_2Cl_2$ (1 mL) was added $Et_3N$ (40 μL) followed by tert-butylisocyanate (20 mg, 0.201 mmol). After 3 h, a second portion of tert-butylisocyanate (4.3 mg, 0.044 mmol) was added and after a further 2 h the volatiles were removed in vacuo to leave a colorless solid. The residue was purified by flash chromatography (silica gel, 1 by 14 cm), eluting with 0.5, 3, and then 4% $MeOH:CH_2Cl_2$ to give the title Compound 46 (55 mg, 79% yield) as a colorless solid. $R_f=0.56$ (10:90, $MeOH:CH_2Cl_2$) (PMA); Mass Spec.(FAB): 764 (M+H).

EXAMPLE 47

Preparation of [R-(R*,S*)]-N,N"-[Iminobis[2-hydroxy-1-(phenylmethyl)-3,1-propanediyl]-bis[N'-(1,1-dimethylethyl)urea] (Compound 47)

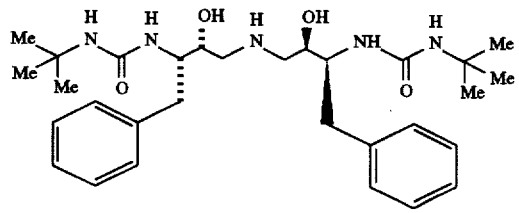

Compound 46 was converted to the title Compound 47 by a procedure analogous to the one used for the synthesis of Compound 42.

m.p. 108°–110° C.; $[\alpha]_D^{25}$=+1.930° (c 0.19, MeOH).

MS: (CI): 542 (M+H). Anal. Calc. for $C_{30}H_{47}N_5O_4 \cdot 0.84$ $H_2O$: C, 64.70; H, 8.81; N, 12.58; Found: C, 64.85; H, 8.71; N, 12.43

EXAMPLE 48

Preparation of [1S-[1R*,2S*(2S*,3R*)]]-[3-[(3-Amino-2-hydroxy-4-phenylbutyl)-[[2-(trimethylsilyl)ethoxy]carbonyl]amino]-2-hydroxy-1-(phenylmethyl)propyl]carbamic acid, 1,1-dimethylethyl ester (Compound 48)

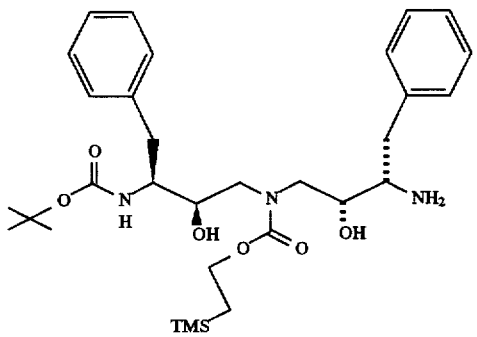

Compound 45 was converted to the title Compound 48 by a two-step procedure analogous to the coversion of Compound 17b to Compound 19 (MeOH was used in removing the carbobenzyloxy group).

$^1$H NMR (CD$_3$OD): δ0.05 (s, 9H), 1.03 (m, 2H), 1.30 (s, 9H), 2.60 (m, 2H), 3.00 (m, 3H), 3.21 (m, 1H), 3.45–3.82 (m's, 6H), 4.12 (m, 2H), 7.11–7.28 (m, 10H).

EXAMPLE 49

Preparation of [1S-[1R*,2S*(2S*,3R*)]]-[3-[[3-[[[(1,1-Dimethylethyl)amino]carbonyl]amino]-2-hydroxy-4-phenylbutyl][2-(trimethylsilyl)-ethoxy]carbonyl]amino]-2-hydroxy]-1-(phenylmethyl)propyl]carbamic acid, 1,1-dimethylethyl ester (Compound 49)

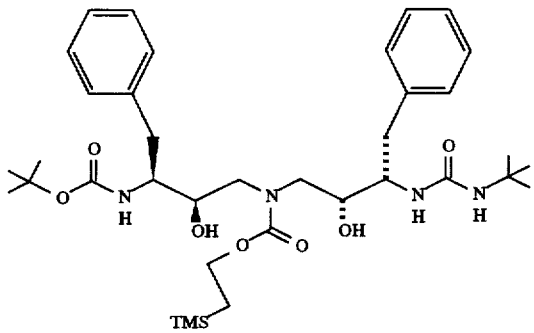

Compound 48 was converted to the title Compound 49 by a procedure analogous to that used for the synthesis of Compound 46.

$^1$H NMR (CD$_3$OD): δ0.05 (s, 9H), 0.98 (m, 2H), 1.20 (s, 9H), 1.27 (s, 9H), 2.65 (m, 2H), 3.05 (m, 2H), 3.25 (m, 2H), 3.60–3.85 (m's, 6H), 4.15 (m, 2H), 7.10–7.30 (m, 10OH).

EXAMPLE 50

Preparation of [1S-[1R*,2S*(2S*,3R*)]]-[3-[[3-[[[(1,1-Dimethylethyl)amino]carbonyl]amino]-2-hydroxy-4-phenylbutyl]amino]-2-hydroxy-1-(phenylmethyl)propyl]carbamic acid, 1,1-dimethylethyl ester (Compound 50)

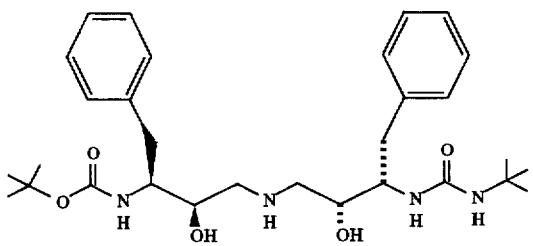

Compound 49 was deprotected by a procedure analogous to the one used for the synthesis of Compound 21 to give the title Compound 50.

mp 110°–112° C.; $[\alpha]_D$=–3.5° (c 0.2, MeOH). Mass Spec.: 543 (M+H). Analysis calc. for $C_{30}H_{46}N_4O_5 \cdot 1.39H_2O$: C, 63.46; H, 8.66; N, 9.87; Found: C, 63.78; H, 8.21; N, 9.55.

EXAMPLE 51

Preparation of [S-[1R*,2S*(2S*,3R*)]]-N-[3-[[3-[[[(1,1-Dimethylethoxy)carbonyl]amino]-2-hydroxy-4-phenylbutyl][[2-(trimethylsilyl)ethoxylcarbonyl]amino]-2-hydroxy-1-(phenylmethyl)propyl]-N$^2$-[(phenylmethoxy)carbonyl-L-valinamide (Compound 51)

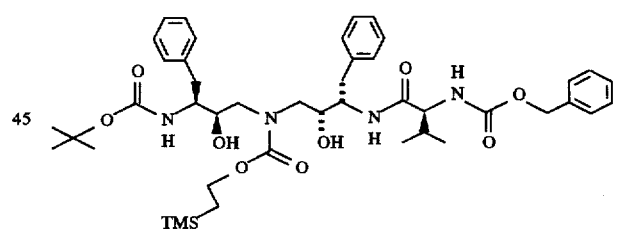

EDC (44 mg; 0.23 mmol) was added to a solution of Cbz-valine (54 mg; 0.23 mmol) and HOBT (35 mg; 0.23 mmol) in 1 ml of DMF at 0° C. After stirring at 0° C. for 1 h, Compound 48 (124 mg; 0.21 mmol) was added, followed by N-methylmorpholine (28 ml; 0.25 mmol). The reaction mixture was allowed to warm to RT and stir for 20 h, after which time it was partitioned between EtOAc (30 ml) and H$_2$O (30 ml). The organic layer was washed with saturated aqueous KHSO$_4$ (2×), H$_2$O, 1N NaOH (2×), H$_2$O and brine. The organic layer was dried (MgSO4), concentrated, and the resulting residue purified by silica gel column chromatography (2.5×12 cm), eluting with 1:1 EtOAc:hexane to afford 137 mg (80%) of Compound 51 as a white foam.

Mass Spec.: 821 (M+H).

EXAMPLE 52

Preparation of [S-[1R*,2S*(2S*, 3R*)]-N-[3-[[3-[[(1,1-Dimethylethoxy)carbonyl]amino]-2-hydroxy-4-phenylbutyl]-amino]-2-hydroxy-1-(phenylmethyl) propyl- N²-[(phenylmethoxy)carbonyl]-L-valinamide (Compound 52)

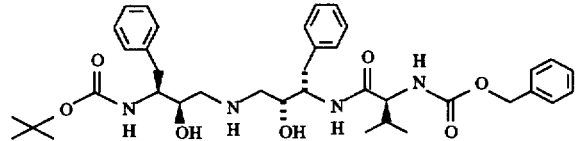

Compound 51 was deprotected by a procedure analogous to the one used for the synthesis of Compound 21 to give the title Compound 52 (white solid).

mp 202°–204° C.; [α]$_D$=–31.4° (c 0.07, AcOH). Mass Spec.: 677 (M+H). Analysis calc. for $C_{38}H_{52}N_4O_7 \cdot 0.22H_2O$: C, 67.04; H, 7.76; N, 8.23; Found: C, 67.01; H, 7.79; N, 8.26.

EXAMPLE 53

Preparation of [1S-[1R*,2S*(2S*3R*)]]-N-[3-[[3-[[(1,1-Dimethylethoxy)-carbonyl]amino]-2-hydroxy-4-phenylbutyl]amino]-2-hydroxy-1-(phenylmethyl) propyl]-N²[(phenylmethoxy)-carbonyl]-L-aspartamide (Compound 53)

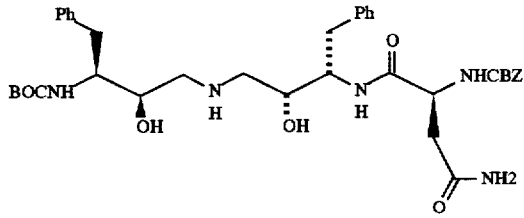

The title Compound 53 was prepared from Compound 48 by a two-step procedure analogous to that used for the synthesis of Compound 52 except that Cbz-asparagine was used.

mp 182°–185° C.; [α]$_D$=–26.7° (c 0.4, AcOH); High Resolution mass spec.(M+H): 692.3665; calc'd for $C_{37}H_{50}N_5O_8$: 692.3659.

EXAMPLE 54

Preparation of [1S-[1R*,2S*(2S*,3R*)]-[3-[(3-Amino-2-hydroxy-4-phenylbutyl)amino]-2-hydroxy-1-(phenylmethyl)propyl]carbamic acid, 1,1-dimethylethyl ester (Compound 54)

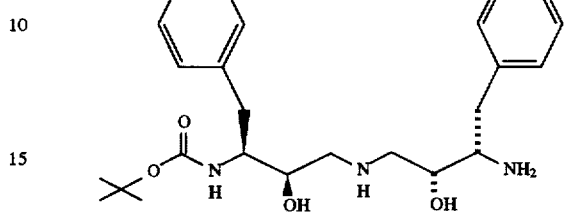

A suspension of 1.0 g (1.73 mmol) of Compound 45 in 12 ml of EtOH and 6 ml of cyclohexene along with 0.1 g of Pd(OH)$_2$/C was stirred at reflux (oil bath temp.=85°) for 1 h. The reaction mixture was cooled to RT and filtered through a plug of Celite on a nylon-66 filter and the filtrate evaporated to dryness to give 0.705 g (92%) of a white solid containing the title Compound 54.

¹H NMR (CD$_3$OD): δ1.30 (s, 9H), [1.18—rotamer], 2.45–2.64 (m, 2H), 2.65–2.84 (m, 4H), 2.93–3.15 (m, 3H), 3.56–3.73 (m, 3H), 7.10–7.36 (m, 10H).

EXAMPLE 55

Preparation of [1R*,2S*(2S*,3R*)]-N-[[3-[[(1,1-Dimethylethoxy)carbonyl]amino]-2-hydroxy-4-phenylbutyl]amino]-2-hydroxy-1-(phenylmethyl) propyl]-N²-[(phenylmethoxy)carbonyl]-L-phenylalaninamide (Compound 55)

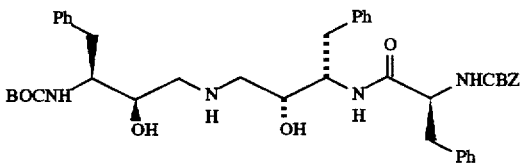

EDC (38.4 mg, 0.20 mmol) was added to a solution of Cbz-phenylalanine (57.0 mg, 0.19 mmol) and HOBT (33.0 mg, 0.24 mmol) in CH$_2$Cl$_2$ (0.8 mL) at 0° C. under argon. After stirring at 0° C. for 1 hr, Compound 54 (77.0 mg, 0.17 mmol) was added in dry DMF (1.0 mL). The reaction mixture was allowed to warm to RT and stirred overnight. The reaction was diluted with CH$_2$Cl$_2$ (40 mL) and washed with saturated NaHCO$_3$ solution (15 mL), H$_2$O (15 mL), and brine (15 mL), dried over MgSO4, filtered, and concentrated. The crude material was purified by flash chromatography (silica gel; 1.5×15 cm) eluting with CH$_2$Cl$_2$:MeOH:NH$_4$OH (gradient from 98.9:1:0.1 to 89:9:1) to give 76 mg of the title Compound 55 (62%).

mp 185–188° C.; [α]$_D$=–27.80 (c 0.2, MeOH); High Resolution mass spec. (M+H)⁺: 725.3906; Calc'd for $C_{42}H_{53}N_4O_7$: 725.3914.

EXAMPLE 56

Preparation of [S-[1R*,2S*(2S*,3R*)]-N²-[(1,1-Dimethylethoxy)carbonyl]-N-[3-[[3-[[(1,1-dimethlethoxy)carbonyl]amino]-2-hydroxy-4-phenylbutyl]-amino]-2-hydroxy-1-(phenylmethyl)propyl]-L-phenylalaninamide (Compound 56)

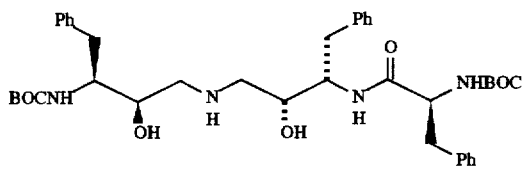

The title Compound 56 was prepared from Compound 54 and Boc-phenylalanine by a procedure analogous to that used for the synthesis of Compound 55.

mp 179–182° C.; $[\alpha]_D$=−14.4° (c 0.6, MeOH); Mass Spec.: (M+H)=691; Analysis calculated for $C_{39}H_{54}N_4O_7$·0.47 $H_2O$: C, 66.90 H, 7.92 N, 8.01; Found: C, 67.00 H, 7.64 N, 7.99

EXAMPLE 57

Preparation of [1R*,2S*(2S*,3R*)]-[2-Hydroxy-3-[[2-hydroxy-4-phenyl-3-[[[(phenylmethyl)amino]-carbonyl]amino]butyl]amino]-1-(phenylmethyl)-propyl]carbamic acid, 1,1-dimethylethyl ester (Compound 57)

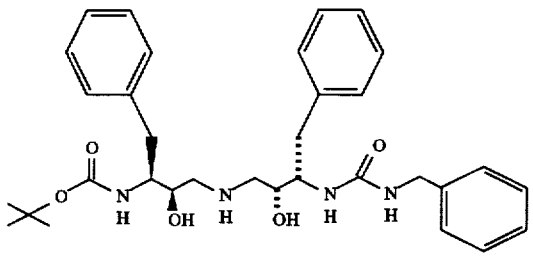

The title Compound 57 was prepared from Compound 48 by a two-step procedure analogous to the one used for the synthesis of Compound 50 except that benzylisocyanate was used in place of tert-butylisocyanate.

mp 161°–165° C.; $[\alpha]_D$=−11.90°(c 0.5, MeOH); Mass Spec. (M+H) 577; Analysis calculated for $C_{33}H_{44}N_4O_5$·0.40 $H_2O$: C, 67.88; H, 7.73; N, 9.60; Found: C, 67.90; H, 7.59; N, 9.58.

EXAMPLE 58

Preparation of [S-[1R*,2S*(2S*,3R*)]-N-[3-[[3-[[(1,1-Dimethylethoxy)carbonyl]amino]-2-hydroxy-4-phenylbutyl]amino]-2-hydroxy-1-(phenylmethyl)-propyl-N²-[(1,1-dimethylethoxy)-carbonyl]-L-valinamide (Compound 58)

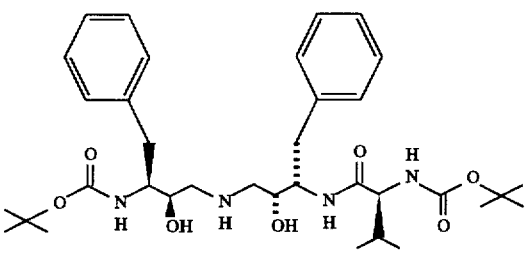

The title Compound 58 (white solid) was prepared from Compound 48 by a two-step procedure analogous to that used for the synthesis of Compound 52 except that Boc-valine was used.

mp 182°–187° C.; $[\alpha]_D$=−11.70° (c 0.06, AcOH). Mass Spec.: 642 (M+H). Analysis calc. for $C_{35}H_{54}N_4O_7$ •0.26$H_2O$: C, 64.93; H, 8.49; N, 8.65; Found: C, 64.80; H, 8.35; N, 8.78.

EXAMPLE 59

Preparation of [S-[1R*,2S*(2S*,3R*)-N-[3 [[3-[[(1,1-Dimethylethoxy) carbonyl]amino]-2-hydroxy-4-phenylbutyl]amino]-2-hydroxy-1-(phenylmethyl)-propyl-L-valinamide (Compound 59)

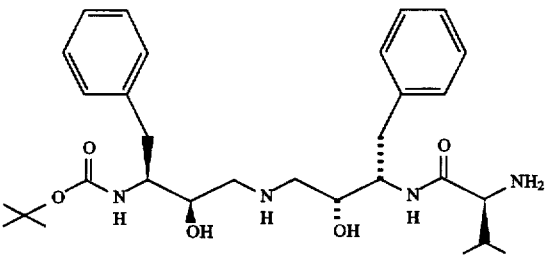

The title Compound 59 (white solid) was prepared from Compound 52 by a procedure analogous to the one used for the preparation of Compound 43.

mp 131°–137° C.; $[\alpha]_D$=+6.0° (c 0.2, MeOH). Mass Spec.: 543 (M+H). Analysis calc. for $C_{30}H_{46}N_4O_5$•1.14$H_2O$: C, 63.97; H, 8.64; N, 9.95; Found: C, 63.96; H, 8.39; N, 9.96.

EXAMPLE 60

Preparation of [1S-[1R*,2S*(2S*,3R*)]]-[3 [[3-[(3,3-Dimethyl-1-oxybutyl)amino]-2-hydroxy-4-phenylbutyl]amino]-2-hydroxy-1-(phenylmethyl)-propyl]carbamic acid, 1,1-dimethylethyl ester (Compound 60)

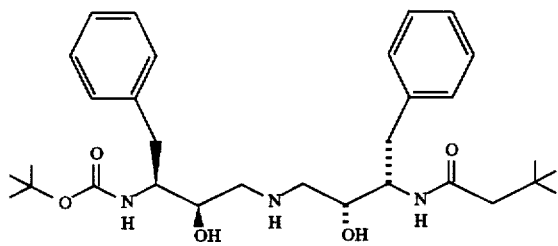

The title Compound 60 was prepared from Compound 48 by a two-step procedure analogous to that used for the synthesis of Compound 52 except that tert-butylacetic acid was used in place of Cbz-valine ($CH_2Cl_2$ replaced DMF and no N-methyl morpholine was used in the EDC coupling).

mp 153°–156° C.; $[\alpha]^r{}_D = -3.3°$ (c 0.1, MeOH). Mass Spec.: 542 (M+H). Analysis calc. for $C_{31}H_{47}N_3O_5 \cdot 0.54\ H_2O$: C, 67.52; H, 8.79; N, 7.62; Found: C, 67.88; H, 8.80; N, 7.26.

EXAMPLE 61

Preparation of [1S-[1R*,2S*(2S*,3R*)]]-N-[3-[[3-[(1,1-Dimethylethoxy)carbonyl]amino]-2-hydroxy-4-phenylbutyl][[2-(trimethylsilyl)ethoxy]-carbonylamino]-2-hydroxy-1-(phenylmethyl)1propyl]1-L-valinamide (Compound 61)

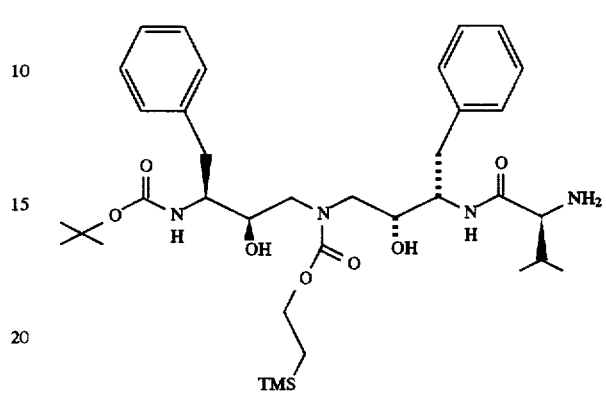

A suspension of Compound 51 (385 mg; 0.47 mmol) and 110 mg of $Pd(OH)_2/C$ in 5 ml of MeOH was stirred at RT under a $H_2$ atmosphere for 1.5 h. The reaction mixture was filtered through a Nylon-66, 0.45 micron filter to remove the catalyst and the filtrate was concentrated to dryness. The residue was chromatographed on a 2.5×20 cm silica gel column, using 5% $MeOH/CH_2Cl_2$ as the mobile phase to afford 306 mg (95%) of the title Compound 61 as a white foam.

$^1H$ NMR (DMSO-$d^6$; 60° C.): δ0.02 (s, 9H), 0.56 (J=7 Hz, 3H), 0.74 (d, J=7 Hz, 3H), 0.95 (t, J=7.5, 9.5 Hz, 2H), 1.25 (s, 9H), 1.48 (brs, 2H), 1.80 (m, 1H), 2.62 (m, 2H), 2.87 (d, J=4.5 Hz, 1H), 2.97 (m, 2H), 3.59 (m, 3H), 3.69 (m, 2H), 3.94 (m, 1H), 4.06 (dd, J=7.5, 14.5 Hz, 2H), 4.87 (m, 1H), 4.97 (m, 1H), 6.37 (brs, 1H), 7.14 (m, 2H), 7.20 (m, 10H), 7.57 (d, J=9 Hz, 1H).

EXAMPLE 62

Preparation of [1S-[1R*,2S*(2S*,3R*)]-N-[3-[[3-[[(1,1-Dimethylethoxy)carbonyl]amino]-2-hydroxy-4-phenylbutyl]amino]-2-hydroxy-1-(phenyl-methyl)propyl]-$N^2$-[(phenylmethoxy)carbonyl]-L-phenylalanyl]-L-valinamide (Compound 62)

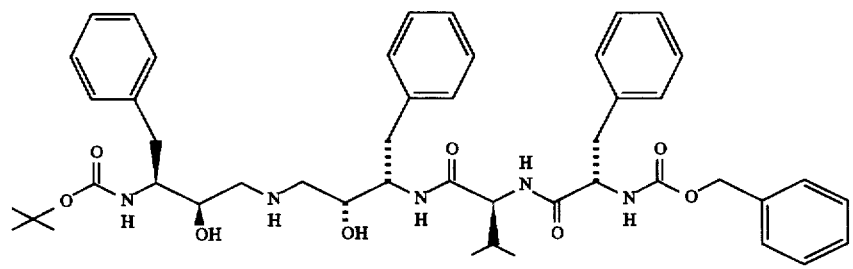

The title Compound 62 (white solid) was prepared from Compound 61 and Cbz-phenylalanine by a two-step procedure analogous to that used for the conversion of Compound 48 to Compound 52.

mp 215°–218° C.; [α]$_D$=–20.7° (C 0.15, AcOH). Mass Spec.: (M+H=824). Analysis calc. for C$_{47}$H$_{61}$N$_5$O$_8$•0.90 H$_2$O: C, 67.19; H, 7.53; N, 8.33; Found: C, 67.25; H, 7.25; N, 8.27.

EXAMPLE 63

Preparation of [1S-[1R*,2S*(2S*,3R*)]]-[2-Hydroxy-3-[[2-hydroxy-3-[[(1-naphthalenyloxy)-acetyl]amino]-4-phenylbutyl]amino]-1-(phenyl-methyl)propyl]carbamic acid, 1,1-dimethylethyl ester (Compound 63)

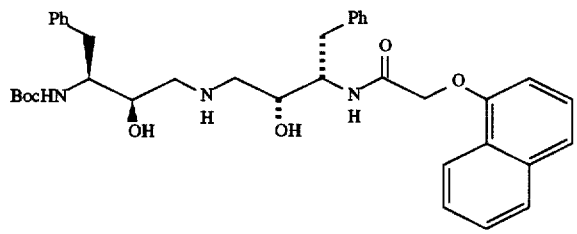

The title Compound 63 was prepared from Compound 48 by a two-step procedure analogous to that used for the synthesis of Compound 52 except that (1-naphthoxy)acetic acid was used.

m.p. 182°–185° C.; [α]$_D$=–58.50 (c=0.19, MeOH). High Resolution Mass Spec: (M+H=628.3397; C$_{37}$H$_{46}$N$_3$O$_6$; 1.7 ppm error).

EXAMPLE 64

Preparation of [1S-[1R*,2S*(2S*,3R*)]]-[2-Hydroxy-3-[[2-hydrox-3-[(2-naphthalenyl-carbonyl)amino]-4-phenylbutyl]amino]-1-(phenylmethyl)propyl]carbamic acid, 1,1-dimethylethyl ester (Compound 64)

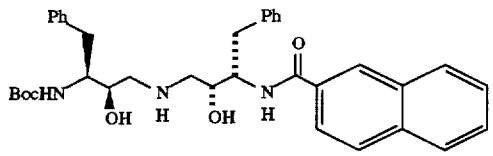

The title Compound 64 was prepared from Compound 48 by a two-step procedure analogous to that used for the synthesis of Compound 52 except that 2-naphthoic acid was used.

m.p. 188°–192° C.; [α]$_D$=–64.1° (c=0.19, MeOH). High Resolution Mass Spec: (M+H=598.3292; C$_{36}$H$_{44}$N$_3$O$_5$; 1.8 ppm error).

EXAMPLE 65

Preparation of [1S-[1R*,2S*(2S*,3R*)]]-[2-Hydroxy-3-[[2-hydroxy-4-phenyl-3-[(2-quinolinylcarbonyl)-amino]butyl]amino]-1-(phenylmethyl)propyl]carbamic acid, 1,1-dimethylethyl ester (Compound 65)

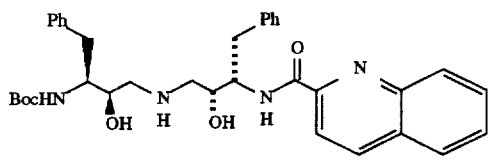

The title Compound 65 was prepared from Compound 48 by a two-step procedure analogous to that used for the synthesis of Compound 52 except that quinaldic acid was used.

m.p. 192°–196° C.; [α]$_D$=–67.2° (c=3.75, MeOH). High Resolution Mass Spec: (M+H=599.3257; C$_{35}$H$_{43}$N$_4$O$_5$; 4 ppm error).

EXAMPLE 66

Preparation of [S-[1R*,2S*(2S*,3R*)]]-N-[3-[[3-[(1,1-Dimethylethoxy)carbonyl)amino]-2-hydroxy-4-[phenylbutyl]amino]-2-hydroxy-1-(phenylmethyl)propyl]-N$^2$-methyl-N$^2$[(phenylmethoxy)-carbonyl]-L-valinamide (Compound 66b)

(a) Compound 66a

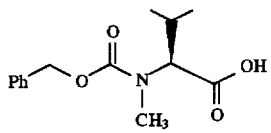

To a solution of N-Cbz-L-valine (2.51 g, 10.0 mmol) and CH$_3$I (5.0 mL, 80.0 mmol) in dry THF (30 mL) cooled at 0° C. was added NaH (0.90 g of 80% dispersion in mineral oil, 30.0 mmol) in portions. After the addition, the suspension was stirred at RT for 12 h at which time additional CH$_3$I (1.5 mL, 24.0 mmol) was added, followed by 0.25 g of NaH (80%, 8.3 mmol). After the suspension was stirred for an additional 24 h, EtOAc (50 mL) was added. The mixture was stirred for 30 min at RT, and then cooled down to 0° C. H$_2$O was added dropwise to destroy NaH. The solvents were removed in vacuo, the oily residual partitioned between H$_2$O and Et$_2$O, and the aqueous layer extracted with Et$_2$O. The combined Et$_2$O solution was extracted with 40% aqueous NaHCO$_3$ and the combined aqueous phase acidified with 4N HCl to pH 2 and extracted with EtOAc. The EtOAc extracts were washed with H$_{2O}$, 5% aqueous NaS$_2$O$_3$, H$_2$O, dried over MgSO$_4$ and evaporated in vacuo to dryness to give a pale yellow oil, which was crystallized from Et$_2$O and pentane to afford white crystalline Compound 66a. (2.97g, 97%).

mp. 66°–67° C.

(b) Compound 66b

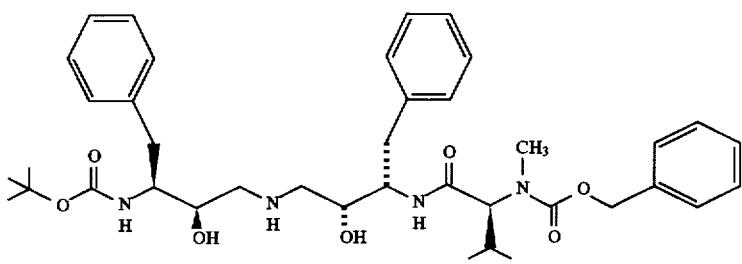

The title Compound 66b was prepared from Compounds 54 and 66a by a procedure analogous to the one used for the synthesis of Compound 55 (1 eq. of N-methylmorpholine was added along with Compound 54).

mp 67°–70° C.; [α]″$_D$=–59.3° (c 0.8, MeOH). Mass Spec. FAB [M+H]$^+$: 691. Analysis calc. for $C_{39}H_{54}N_4O_7 \cdot 1.15 \, H_2O$: C, 65.84; H, 7.97; N, 7.87; Found: C, 65.94; H, 7.62; N, 7.77.

EXAMPLE 67

Preparation of [S-[1R*,2S*(2S*,3R*)]]-N$^2$-[[2,3-Dihydro-1H-inden-1-yl)oxy]carbonyl]-N-[3-[[3-[[(1,1-dimethylethoxy)carbonyl]amino]-2-hydroxy-4-phenylbutyl]amino]-2-hydroxy-1-(phenylmethyl)propyl]-L-valinamide (Compound 67c)

(a) Compound 67a

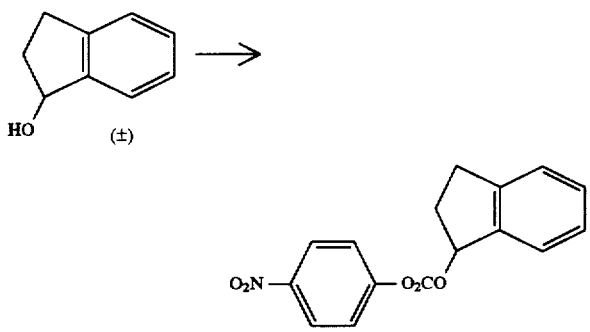

To a solution of 537 mg (4.00 mmol) of (±)-1-indanol in 20 ml of dry CH$_2$Cl$_2$ at 0° C. were added 1.01 g (5.00 mmol) of p-nitrophenyl chloroformate and 0.70 mL of Et$_3$N. The mixture was stirred for 2 h at 0° C. and for 2 h at RT. The reaction mixture was diluted with 100 mL of CH$_2$Cl$_2$, and washed with 5% KHSO$_4$ (50 mL), 0.1N NaOH (2×50 mL) and saturated NaCl (50 mL). The organic layer was dried over Na$_2$SO$_4$, filtered, and concentrated in vacuo. Flash chromatography of the residue on silica gel (CC-7; buffered, pH=7), eluting with 0–10% EtOAc-hexane, provided 1.24 g (~100%) of Compound 62a, as a white solid.

(b) Compound 67b

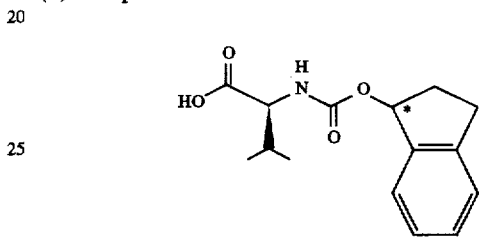

A suspension of 117 mg (1.00 mmol) of L-valine in 1 mL of 1.0N NaOH was stirred for 30 min and then treated with a solution of 299 mg (1.00 mmol) of Compound 67a in 2 mL of t-butanol and 1 mL of dioxane. The reaction mixture was stirred at RT overnight. 0.2 mL of Et$_3$N was added to the mixture to increase the rate of the reaction and stirring was continued for 48 h. The reaction mixture was diluted with 50 mL of EtOAc, and washed with 5% KHSO$_4$ (2×25 mL), and saturated NaCl (25 mL). The organic layer was dried over Na$_2$SO$_4$, filtered, and concentrated in vacuo to provide 355 mg of crude acid. Flash chromatography on silica gel, eluting with 50% EtOAc-hexane and then 50% EtOAc-hexane with 0.5% HOAc, afforded 209 mg (75%) of Compound 67b, as a white solid. (c) Compound 67c

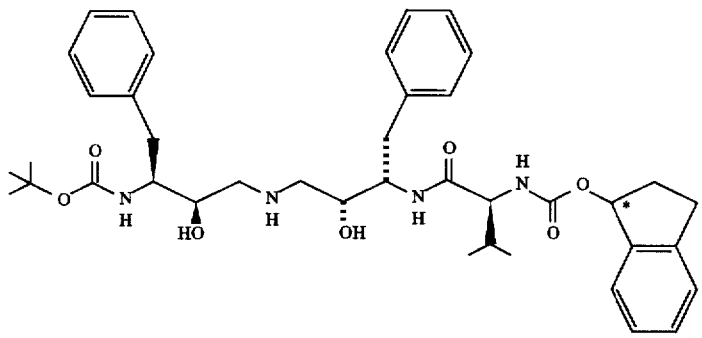

The title Compound 67c was prepared as a mixture of diastereomers from Compound 54 and Compound 67b by a procedure analogous to that used for the synthesis of Compound 55.

mp 202-206° C.; $[\alpha]^{20}_D = -15°$ (c = 0.071, $CH_3OH$)
Mass spec. 703 (M + H)$^+$
Elemental Analysis (%)
$C_{40}H_{54}N_4O_7$

|   | Calc. | Found |
|---|-------|-------|
| C | 68.35 | 68.13 |
| H | 7.74  | 7.84  |
| N | 7.97  | 7.70  | mp 208-211° C.; $[\alpha]^{20}_D = -19°$ (c = 0.077, $CH_3OH$)
Mass spec. 753 (M + H)$^+$
Elemental Analysis (%)
$C_{44}H_{56}N_4O_7$

|   | Calc. | Found |
|---|-------|-------|
| C | 70.19 | 69.91 |
| H | 7.50  | 7.48  |
| N | 7.44  | 7.23  |

EXAMPLE 68

Preparation of [S-[1R*,2S*(2S*,3R*)]]-$N^2$-[((1,1-Biphenyl]-4-ylmethoxy]carbonyl-N-[3-[[3-[[(1,1-dimethylethoxy)carbonyl]amino]-2-hydroxy-4-phenylbutyl]amino]-2-hydroxy-1-(phenylmethyl)[propyl]-L-valinamide (Compound 68)

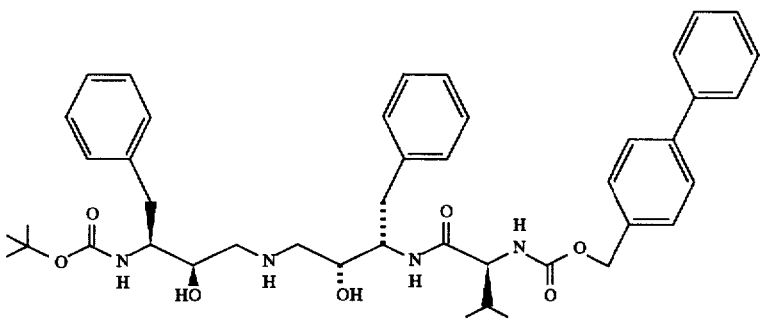

The title Compound 68 was prepared from Compound 54 by a three-step procedure analogous to that used for the synthesis of Compound 67c except that 4-biphenylmethanol was used in the first step and 1.1 eq. of $Et_3N$ (no t-BuOH) was used in the second step.

EXAMPLE 69

Preparation of [1S-[1R*,2S*(2S*,3R*)]]-2-Hydrox3-[[2-hydroxy-3-[[[methyl(phenylmethyl)-amino]carbonyl]amino]-4-phenylbutyl]amino]-1-(phenylmethyl)propyl]carbamic acid, 1,1-dimethylethyl ester (Compound 69)

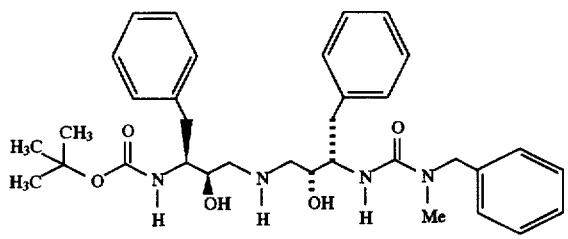

The title Compound 69 (white solid) was prepared from Compound 48 and N-benzyl-N-methyl carbamoyl chloride (Bull. Chem. Soc. Jpn., 50, 1872 (1977)) by a two-step procedure analogous to that used for the synthesis of Compound 50.

mp 97–99° C.; $[\alpha]_D$ = –18.8° (c 0.5, $CH_3OH$).
Mass spec. FAB $(M + H)^+$ = 591
Analysis calc. for $C_{34}H_{46}N_4O_5 \cdot 0.89H_2O$:

| | | | |
|---|---|---|---|
| Calculated | C, 67.31; | H, 7.94; | N, 9.23; |
| Found: | C, 67.42; | H, 7.83; | N, 9.12. |

EXAMPLE 70

Preparation of [S-[1R*,2S*(2S*,3R*)]]-N-[3-[[3-[[(1,1-Dimethylethoxy)carbonyl]amino]-2-hydroxy-4-phenylbutyl]amino]-2-hydroxy-1-(phenylmethyl)-propyl]-$N^2$-(2-pyridinylmethoxy)carbonyl]-L-valinamide (Compound 70d)

(a) Compounds 70a(i) and 70a(ii)

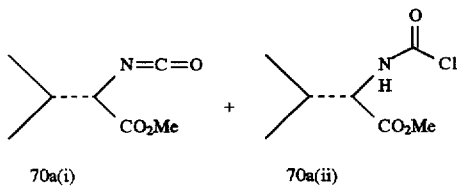

To a solution of L-valine methyl ester hydrochloride (2.5 g; 14.9 mmol) in 14.9 mL of dry dioxane was added trichloromethyl chloroformate (1.5 g; 7.6 mmol) at RT. The mixture was heated at 60° C. for 3.5 h. The clear solution was cooled to RT and concentrated in vacuo to give an oil, which was azeotroped from dry toluene (2×10 mL) to give Compounds 70a(i) and 70a(ii).

(b) Compound 70b

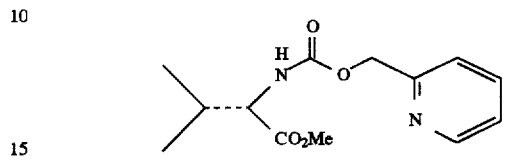

To a solution of the crude Compounds 70a(i) and 70a(ii) (2.3 g; 14.9 mmol) in 48 mL of dry toluene was added 1.6 g (14.9 mmol) of 2-pyridylcarbinol. The mixture was heated to reflux for 12 h and then concentrated in vacuo to a residue. Purification by flash chromatography (silica gel; 25% acetone-hexane) afforded 1.08 g (27% over two steps) of Compound 70b.

(c) Compound 70c

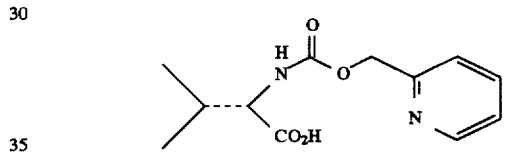

To a solution of Compound 70b (223 mg; 0.83 mmol) in 3.3 mL of dry dioxane was added 3.0 mL of 0.5M LiOH. After 12 h at RT, the reaction mixture was acidified with 1N HCl (1.5 ml) and then evaporated to dryness. Further drying over $P_2O_5$ under vacuum at RT gave 300 mg (~100%) of a brown residue containing Compound 70c.

(d) Compound 70d

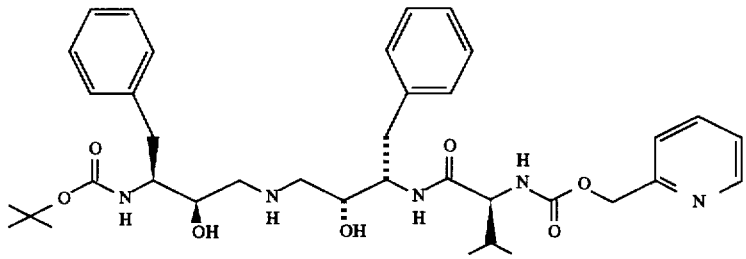

The title Compound 70d was prepared from Compounds 54 and crude 70c by a procedure analogous to that used for the synthesis of Compound 55 (1 eq. of N-methylmorpholine was used).

m.p. 175–178° C.; $[\alpha]^{rt}_D = -16.0°$ (c 0.13, MeOH).
Mass spec. (M + H) 678
Elemental Analysis (%)
$C_{37}H_{51}N_5O_7 \cdot 2.90 \, H_2O$

|   | Calc. | Found |
|---|-------|-------|
| C | 60.87 | 60.84 |
| H | 7.54  | 7.30  |
| N | 9.59  | 9.57  |

EXAMPLE 71

Preparation of [R-[1S*,2R*(2R*, 3S*)]]-N-[3-[[3-[[(1,1-Dimethylethoxy)carbonyl]amino]2- hydroxy-4-phenylbutyl]amino]-2-hydroxy-1-phenylmethyl)propyl]-$N^2$-[(phenylmethoxy)-carbonyl]-D-valinamide (Compound 71)

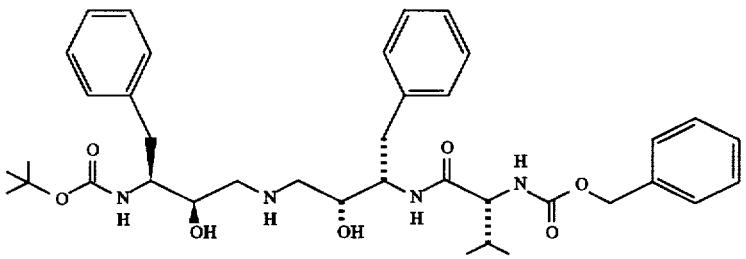

The title Compound 71 was prepared from Compounds 54 and N-Cbz-D-valine by a procedure analogous to that used for the synthesis of Compound 55.

mp 185°–187° C.; $[\alpha]^{rt}_D = +16.25°$ (c 0.16, MeOH). Mass Spec. FAB [M+H]$^+$: 677. Analysis calc. for $C_{38}H_{52}N_4O_7 \cdot 1.63 \, H_2O$: C, 64.63; H, 7.89; N, 7.93; Found: C, 64.63; H, 7.70; N, 8.12.

EXAMPLE 72

Preparation of 1S-[1R*,2S*(2S*,3R*)]]-[2-Hydroxy-3-[[2-hydroxy-3-[(phenoxyacetyl)amino]-4-phenylbutyl]amino]-1-(phenylmethyl)propyl] carbamic acid, 1,1-dimethylethyl ester (Compound 72)

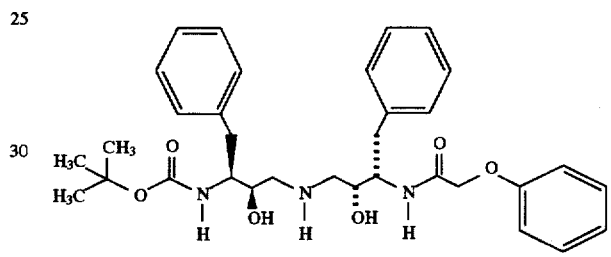

The title Compound 72 (white solid) was prepared from Compounds 54 and phenoxyacetic acid by a procedure analogous to that used for the synthesis of Compound 55 (1 eq. of N-methylmorpholine was used).

mp 162°–165 C.; $[\alpha]_D = -17.6°$ (c 0.5, CH$_3$OH). Mass Spec. (FAB) (M+H)$^+$=578; Analysis calc. for $C_{33}H_{43}N_3O_6$: Calculated C, 68.61; H, 7.50; N, 7.27; Found: C, 68.59; H, 7.58; N, 7.33.

EXAMPLE 73

Preparation of [(S,R)-3-[[(R,S)-3-[[2-[[(Phenyl-methoxy)carbonyl]amino]-2,3-dimethyl-1-oxy-butyl]amino]-2-hydroxy-4-phenylbutyl]amino]-2-hydroxy-1-(phenylmethyl)-propyl]carbamic acid, 1,1-dimethylethyl ester (Compound 73d)

(a) Compound 73a

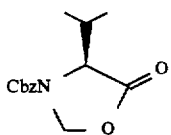

A suspension of N-Cbz-L-Valine (2.51 g, 10.0 mmol), paraformaldehyde (2.0 g) and p-toluene-sulfonic acid (0.2 g) in 200 mL of toluene was heated to reflux for 2 h. After being cooled down to RT, the reaction mixture was washed with saturated NaHCO₃, brine and dried over MgSO₄. The filtrate was concentrated in vacuo to afford 2.32 g (88%) of Compound 73a as a light yellow solid.

(b) Compound 73b

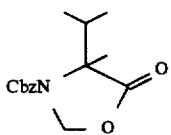

To a solution of crude Compound 73a (0.76 g; 2.88 mmol) in 10 ml of dry THF cooled at −78° C. was added 6.62 ml (3.31 mmol) of KN(TMS)₂ (0.5M solution in toluene) dropwise over 15 min. The reaction mixture was stirred at the same temperature for 15 min, then CH₃I (0.216 ml, 3.46 mmol) was added dropwise. The mixture was stirred at −78° C. for 20 min, −20° C. for 20 min, then at 0° C. for 1 h. The reaction was quenched with 10 ml pH 7 buffer, and extracted with CH₂Cl₂ (2×50 ml). The combined organics were washed with H₂O, brine and dried over MgSO₄. The filtrate was concentrated to dryness and the oily residue purified by flash chromatography (silica gel), using 20% EtOAc/hexane as the mobile phase to afford 0.487 g (61%) of Compound 73b as a colorless oil.

(c) Compound 73c

A solution of Compound 73b (0.46 g, 1.66 [nmol] in 5 ml of MeOH and 5 ml of 1N NaOH was heated at 55° C. for 30 min. After removal of MeOH, the aqueous phase was acidified to pH 1–2 with 1L HCl and extracted with CH₂Cl₂ (2×30 ml). The combined CH₂Cl₂ phase was washed with water, brine and dried over MgSO₄ to give after concentrating in vacuo 0.44 g (100%) of Compound 73c as a colorless oil.

(d) Compound 73d

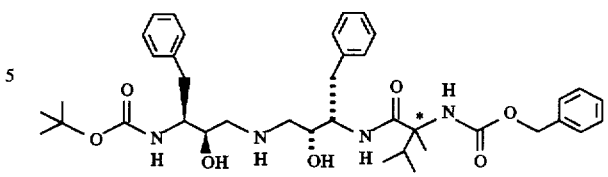

The title Compound 73d was prepared as a 1:1 mixture of diastereomers from Compounds 54 and 73c by a procedure analogous to that used for the synthesis of Compound 55. mp 66°–68° C.; [α]$^{rt}_D$=−5.6° (c 0.25, MeOH). Mass Spec. [M+H]⁺: 691. Analysis calc. for $C_{39}H_{54}N_4O_7$–0.46 $H_2O$: C, 67.00; H, 7.92; N, 8.01; Found: C, 66.88; H, 7.88; N, 8.13. The diastereomers (at position indicated by an asterisk) were then separated by HPLC.

EXAMPLE 74

Preparation of [[R-(R*,S*)]-1,1'-Iminobis(3-amino-4-phenyl-2-butanol), trihydrochloride (Compound 74)

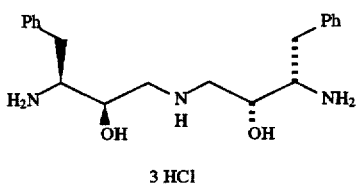

The title Compound 74 was prepared from Compound 2 by a procedure analogous to that used for the synthesis of Compound 32. $R_f$=0.054 (20:2:78 MeOH:NH₄OH:CH₂Cl₂).

EXAMPLE 75

Preparation of [S-(1R*,2S*)]-N,N'-[Iminobisr[2-hydroxy-1-(phenylmethyl)-3,1-propanediyl]bisr[N²-[[methyl(2-pyridinylmethyl)amino]carbonyl]-L-valinamide (Compound 75f)

(a) Compound 75a

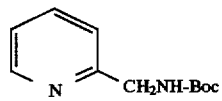

To a solution of di-tert-butyldicarbonate (63 g, 0.29 mole) in 600 ml of CH₂Cl₂ at 0° C. was added a solution of 2-(aminomethyl)pyridine (31.36 g, 0.29 mole) in 150 ml of CH₂Cl₂ in a dropwise manner. After the addition was complete the mixture was allowed to slowly warm to RT and stir overnight. The reaction was washed with H₂O (3×800 ml), brine (800 ml) and dried (Na₂SO₄) to give, after concentration, 58.6 g (97%) of Compound 75a as a pale yellow oil.

(b) Compound 75b

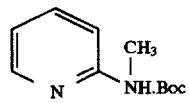

Compound 75a was converted to Compound 75b by a procedure analogous to that used for the synthesis of Compound 66a except that DMF was used in place of THF.

(c) Compound 75c

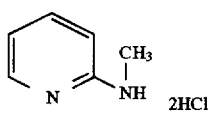

Compound 75b was converted to Compound 75c by a procedure analogous to that used for the synthesis of Compound 32 except that the reaction was run at 40° C.

(d) Compound 75d

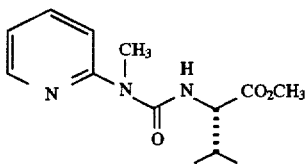

Compound 75c was converted to Compound 75d by a procedure analogous to that used for the synthesis of Compound 70b except that $CH_2Cl_2$ replaced toluene and 2.5 eq. of N-methylmorpholine was added.

(e) Compound 75e

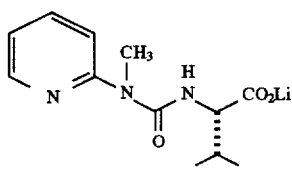

Compound 75d was converted to Compound 75e by a procedure analogous to that used for the synthesis of Compound 70c (the reaction was quenched with one equivalent of 1N HCl).

(f) Compound 75f

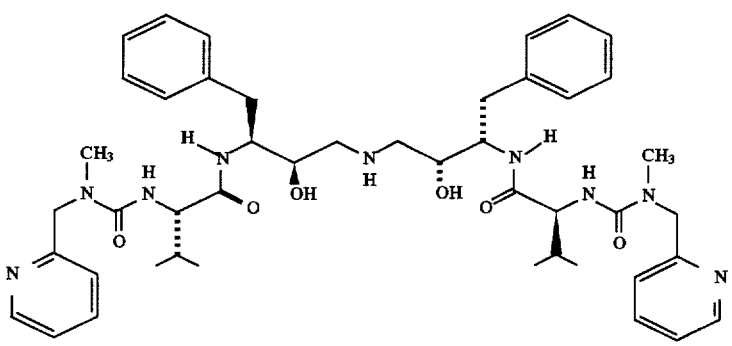

A mixture of Compound 74 (136 mg, 0.25 mmol), HOBT (84 mg, 0.55 mmol), and Compound 75e (148 mg, 0.55 mmol) in 0.6 ml of dry DMF was cooled to 0° C. EDCI (108 mg, 0.55 mmol) was added followed by 6 eq. of N-methylmorpholine (167 mg, 3.3 mmol). The mixture was stirred at 0C for several hours and was then allowed to slowly warm to RT and stir overnight. The DMF was removed in vacuo and the residue was partitioned between saturated $NaHCO_3$ (10 ml) and EtOAc (15 ml). The EtOAc layer was washed with additional saturated NaHCO3, brine, dried over $MgSO_4$ and evaporated to give a crude yellow solid which purified on a 30 ml silica column (CC-7, $pH_{6.8}$) eluting with 5% –10% $MeOH/CH_2Cl_2$ +0.1% $NH_4OH$ to afford 86 mg (41%) of the title Compound 75f as a colorless solid.

m.p. 178°–182° C.; $[\alpha]_D$=–22.4° (c,0.25, MeOH); Analysis calc. for $C_{46}H_{63}N_9O_6$ •2.0 $H_2O$: C, 63.21; H, 7.73; N, 14.42; Found: C, 63.51; H, 7.52; N, 14.12.

EXAMPLE 76

Preparation of [S-[1R*,2S*(2S*,3R*)]]-N-[3-[[3-[[(1,1-Dimethylethoxy) carbonyl amino]-2-hydroxy-4-phenylbutyl]amino]-2-hydroxy-1-(phenylmethyl) propyl]-$N^2$[[methyl(2-pyridinyl -methyl)amino] carbonyl]-L-valinamide (Compound 76)

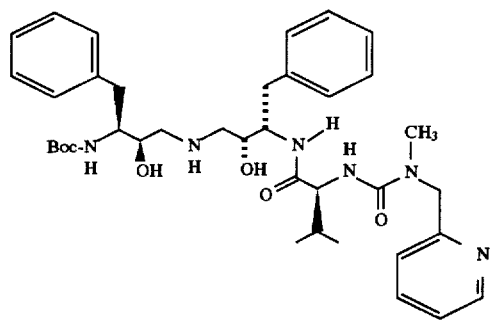

To a solution of Compound 54 (111 mg, 0.25 mmol), HOBT (42 mg, 0.275 mmol), and Compound 75e (74 mg, 0.275 mmol) in dry DMF (0.5 ml) at 0° C. was added EDCI (53 mg, 0.275 mmol) followed immediately by N-methylmorpholine (91 μl, 83 mg, 0.825 mmol). The reaction was stirred several hours at 0° C. and was then slowly warmed to RT and stirred overnight.

The DMF was removed in vacuo and the resulting residue was partitioned between EtOAc (10 ml) and $H_2O$ (10 ml). The organic layer was washed with saturated $NaHCO_3$ and brine, dried over $MgSO_4$ and concentrated to give a crude product which was purified on a 20 ml CC-7 silica column (Silica pH 6.8) eluting with 3%→10% $MeOH/CH_2Cl_2$+ 0.1% $NH_4OH$ to afford a glasslike residue.

Lyophilization from dioxane/$H_2O$ gave 48 mg (28%) of Compound 76 as a colorless solid.

m.p. 184°–188° C.; $[\alpha]_D$=–16.4° (c=0.2, MeOH); High Resolution Mass Spec. (FAB): $C_{38}H_{55}N_6O_6$=691.4183; Δ=0.35 ppm.

EXAMPLE 77

Preparation of [S-[1R*,2S*(2S*,3R*,N²R*]]-N-[3-[[3-[[(1,-Dimethylethoxy)carbonyl]amino]-2-hydroxy-4-phenylbutyl]amino]-2-hydroxy-(phenyyl-methyl)propyl]N²-(2-hydroxy-1-oxo-3-phenyl-propyl)-L-valinamide (Compound 77)

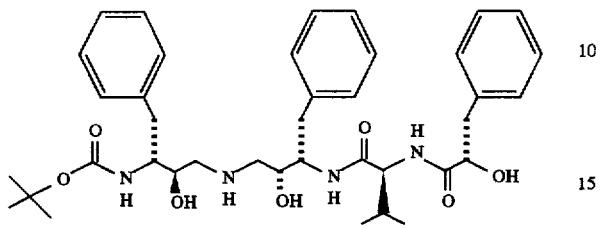

The title Compound 77 (white solid) was prepared from Compound 61 and L-phenyllactic acid by a two-step procedure analogous to that used for the conversion of Compound 48 to Compound 52.

mp 176°–178° C.; $[\alpha]_D = -49.5°$ (C 0.16, MeOH). Mass Spec. FAB+ion : (M+H)=691. Analysis calc. for $C_{39}H_{54}N_4O_7 \cdot 0.61\ H_2O$: C, 66.75; H, 7.93; N, 7.98; Found: C, 66.81; H, 7.69; N, 7.92.

EXAMPLE 78

Preparation of [S-[1R*,2S*[2S*,3R*,N1S*]-N-[3-[[3-[[(1,1-Dimethylethoxy)carbonyl]amino]-2-hydroxy-4-phenylbutyl]amino]-2-hydroxy-1-(phenylmethyl)[propyl]-N²-(2-hydroxy-1-oxo-3-phenyl-propyl)-L-valinamide (Compound 78)

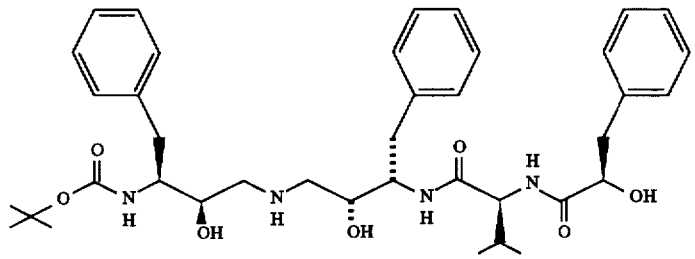

The title Compound 78 (white solid) was prepared from Compound 61 and D-phenyllactic acid by a two-step procedure analogous to that used for the conversion of Compound 48 to Compound 52.

mp 188°–194° C.; $[\alpha]_D = +7.6°$ (c 0.17, MeOH). Mass Spec. FAB+ion : (M+H)=691. Analysis calc. for $C_{39}H_{54}N_4O_7 \cdot 1.42\ H_2O$: C, 65.38; H, 8.00; N, 7.82; Found: C, 65.26; H, 7.84; N, 7.94.

EXAMPLE 79

Preparation of [S-[1R*,2S*(2S*,3R*)]]-N-[3-[[3-[[(1,1-Dimethylethoxy) carbonyl]amino]-2-hydroxy-4-phenylbutyl]amino]-2-hydroxy-1-(phenylmethyl) propyl]-N²(2-naphthalenylcarbonyl)-L-valinamide The title Compound 79 was prepared from Compound 61 and 2-naphthoic acid by a two-step procedure analogous to that used for the conversion of Compound 48 to Compound 52.

m.p. 192°–196° C.; $[\alpha]_D=-12.6°$ (c=0.18, MeOH); Analysis: calc. for $C_{41}H_5N_4O_6 \cdot 0.6\ H_2O$: C, 69.59; H, 7.58; N, 7.92; Found: C, 69.64; H, 7.59; N, 7.87.

EXAMPLE 80

Preparation of [S-[1R*,2S*(2S*,3R*)]]-N-[3-[[3-[[(1,1-Dimethylethoxy)carbonyl]amino]-2-hydroxy-4-phenylbutyl]amino]-2-hydroxy-1-(phenylmethyl) propyl]-$N_2$-(2-quinolinylcarbonyl)-L-valinamide (Compound 80)

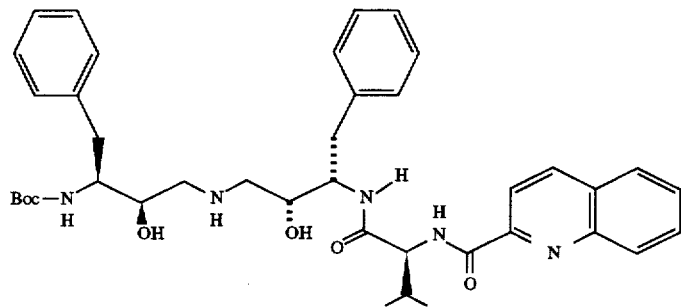

The title Compound 80 was prepared from Compound 61 and quinaldic acid by a two-step procedure analogous to that used for the conversion of Compound 48 to Compound 52.

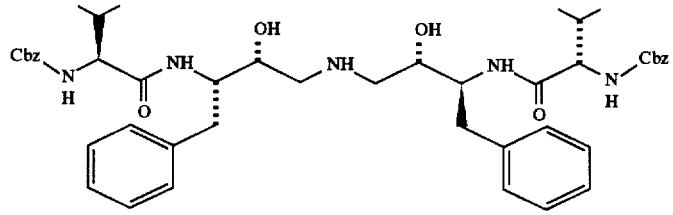

m.p. 192°–194° C.; $[\alpha]_D=-14.5°$ (c=0.24, MeOH); Analysis calc. for $C_{40}H_{51}N_5O_6 \cdot 0.64\ H_2O$: C, 67.73; H, 7.43; N, 9.87; Found: C, 67.98; H, 7.56; N, 9.62.

EXAMPLE 81

Preparation of [2R-[2R*(2S*,3S*),3S*]]-1,1'-Iminobis(3-amino-4-phenyl-2-butanol) hydrochloride (Compound 81)

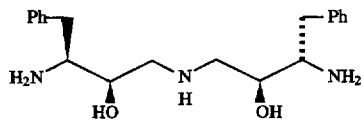

The title Compound 81 was prepared as a tri-HCl salt from Compound 5 by a procedure analogous to that used for the synthesis of Compound 32.

$R_f=0.07$ (15:1.5:84.5 $MeOH:NH_4OH:CH_2Cl_2$).

EXAMPLE 82

Preparation of [S-[1R*,2R*(2S*,3R*)]]-N-[2-Hydroxy-3-[[2-hydroxy-4-phenyl-3-[[[N-(phenylmethoxy)carbonyl]-L-valyl]amino]butyl] amino]-1-(phenylmethyl)propyl]-$N$-$^2$-[ (phenylmethoxy)carbonyl]-L-valinamide (Compound 82)

The title Compound 82 was prepared from Compound 81 and Cbz-L-valine by a procedure analogous to that used for the synthesis of Compound 75f.

m.p. 216°–219° C.; $[\alpha]_D^{25}=-34.8°$ (c 0.28, DMSO). Mass Spec.: (FAB): 810 (M+H). Anal. Calc. for $C_{46}H_{59}N_5O_8$: C, 68.21; H, 7.34; N, 8.65; Found: C, 67.88; H, 7.50; N, 8.64

EXAMPLE 83

Preparation of [R-(R*,S*)]-N,N'-[Iminobis[2-hydroxy-1-(phenylmethyl)-3,1-propanediyl [bisbenzeneacetamide (Compound 83)

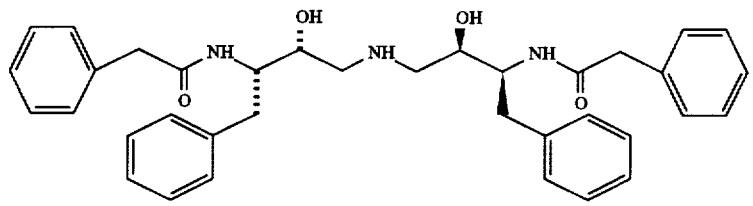

The title Compound 83 was prepared from Compound 74 and phenylacetic acid by a procedure analogous to that used for the synthesis of Compound 75f.

m.p. dec. 216°–221° C.; $[\alpha]_D^{25}$=+11.4° (c 0.22, DMSO). MS: (CI/NH$_3$): 580 (M+H). Anal. Calc. for $C_{36}H_{41}N_3O_4 \cdot 0.3$ H$_2$O: C, 73.90; H, 7.17; N, 7.18; Found: C, 73.88; H, 7.03; N, 7.20

EXAMPLE 84

Preparation of [S-[1R*,2S*(2S*,3R*)]-N-[3-[[3-[[(1,1-Dimethylethoxy)carbonyl]amino]-2-hydroxy-4-phenylbutyl]amino]-2-hydroxy-1-(phenylmethyl) propyl)-L-valyl]-L-phenylalanamide, fumarate (2:3) salt

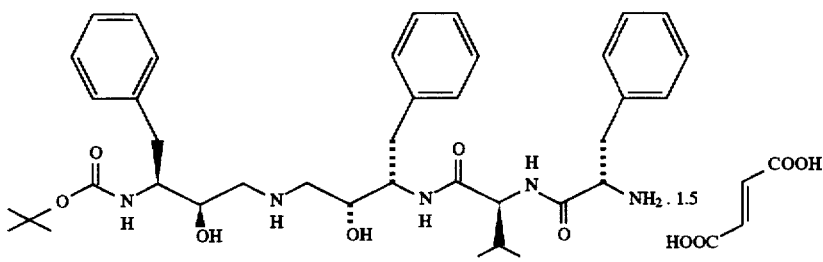

A solution of Compound 62 (153 mg; 0.185 mmol) in 2 ml of HOAc was stirred for 1 h over 20% Pd(OH)$_2$/C (50 mg) at RT under a H$_2$ atmosphere (balloon). The catalyst was removed by filtration through a 0.45 micron Nylon-66 filter and the filtrate was concentrated to dryness. The residue was dissolved in 5 ml of MeOH and fumaric acid (43 mg; 0.370 mmol) was added as a solution in hot MeOH. The MeOH was removed in vacuo and the residual HOAc was azeotroped with heptane. After drying under high vacuum for several hours, the solid was dissolved in ~2 ml of MeOH and Et$_2$O (~12 ml) was added dropwise with rapid stirring. The resulting suspension was filtered and dried under high vacuum at 60° C. for 48 h to give 149 mg (93%) of Compound 84 as a white powder.

mp 125°–136° C.; $[\alpha]_D$=–20.7 (c 0.15, MeOH). Mass Spec. FAB+ions: M+H=690. Analysis calc. for $C_{39}H_{55}N_5O_6 \cdot 1.5$ $C_4H_4O_4 \cdot 0.52$ H$_2$O: C, 61.89; H, 7.16; N, 8.02; Found: C, 61.91; H, 7.23; N, 8.00.

EXAMPLE 85

Preparation of [S-(1R*,2S*,3R*)]-N$^2$-[3-[[(Phenylmethoxy)carbonyl]amino]-1-oxo-3-phenylpropyl)-N-[3-[[3-[[(1,1-dimethylethoxy) carbonyl]amino]-2-hydroxy-4-phenyl-butyl]amino]-2-hydroxy-1-(phenylmethyl)-propyl]-L-valinamide (Compound 85b)

(a) Compound 85a

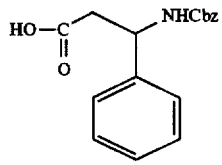

Benzylchloroformate (1.0 ml; 6.70 mmol) and 2N NaOH (3.1 ml; 6.2 mmol) were alternately added over 5 min to a vigorously stirred solution of 3-amino-3-phenylpropionic acid (1.0 g; 6.05 mmol) in 3.05 ml of 2N NaOH at 0° C. The mixture was stirred for 30 min at 0° C. and 30 min at RT. 1N NaOH (10 ml) and water (50 ml) were added and the reaction mixture was washed with Et₂O (3×50 ml). After acidifying the aqueous layer to pH <1 with 6N HCl, it was extracted with Et₂O. The Et₂O layer was washed with H₂O and brine, dried over MgSO₄, and concentrated to a white solid which was recrystallized from EtOAc:hexane, 1:1 to afford 1.02 g (61%) of Compound 85a.

(b) Compound 85b

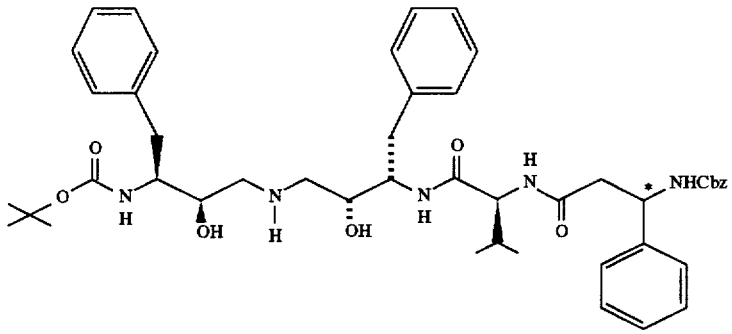

The title Compound 85b (white solid) was prepared as a mixture of diastereomers (at carbon marked with an asterisk) from Compounds 61 and 85a by a two-step procedure analogous to that used for the conversion of Compound 48 to Compound 52.

¹H NMR (DMSO-d⁶; 700° C.): δ 0.57 (d, J=7 Hz, 1.5H) 0.63 (d, J=7 Hz, 1.5H), 0.69 (d, J=7 Hz, 1.5H), 0.72 (d, J=7 Hz, 1.5H), 1.25 (s, 9H), 2.56 (m, 8H), 2.95 (m, 2H), 3.43 (m, 2H), 3.57 (m, 1H), 3.91 (m, 1H), 4.04 (m, 2H), 4.55 (brs, 1H), 4.97 (m, 3H), 6.33 (brs, 1H), 7.25 (m, 20H), 7.50 (m, 2H), 7.56 (d, 8.5 Hz, 1H).

EXAMPLE 86

Preparation of [S-[1R*,2S*(2S*,3R*)]-N²(3-Amino-1-oxo-3-phenylpropyl)-N-[3-[[3-[[(1,1-dimethylethoxy)carbonyl]amino]-2-hydroxy-4-phenylbutyl]amino-[-2-hydroxy-1-(-phenylmethyl) propyl]-L-valinamide, fumarate (2:3) salt (Compound 86)

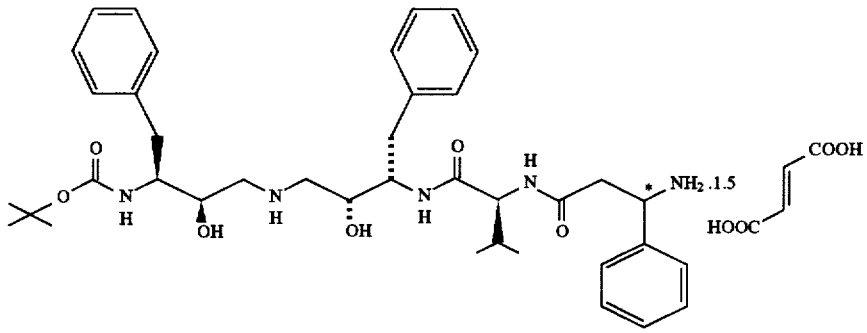

Compound 85b was converted to the title Compound 86 (white solid) by a procedure analogous to that used for the synthesis of Compound 84.

mp 138°–146° C.; [α]_D=−13.0 (c 0.2, MeOH). Mass Spec. FAB+ion : (M+H)=690. Analysis calc. for C₃₉H₅₅N₅O₆·1.5 C₄H₄O₄·0.92 H₂O: C, 61.98; H, 7.15; N, 8.03; Found: C, 61.95; H, 7.21; N, 8.06.

EXAMPLE 87

Preparation of [1S-[1R*,2S*(2S*,3R*)]]-[2-Hydroxy 3-[[2-hydroxy-3-[[[1-[[(phenylmethoxy)-carbonyl]amino]cycloyentyl]carbonyl]amino]-4-phenylbutyl]-amino]-1-(phenylmethyl)propoyl] carbamic acid, 1,1-dimethylethyl ester (Compound 87b)

(a) Compound 87a

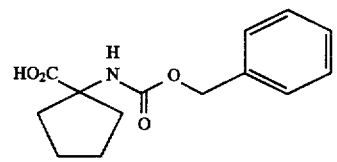

Compound 87a was prepared from 1-aminocyclopentanecarboxylic acid (cycloleucine) by a procedure analogous to that used for the synthesis of Compound 85a.

(b) Compound 87b

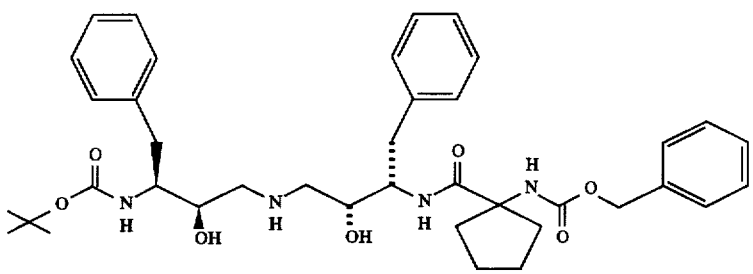

The title Compound 87b was prepared from Compounds 54 and 87a by a procedure analogous to that used for the synthesis of Compound 55.

mp 70°–73° C.; [α]$_D$=+9° (c 0.2, MeOH). Mass Spec: FAB (M+H)+: 689. Analysis calculated for C$_{38}$H$_{52}$N$_4$O$_7$·0.65 H$_2$O: C, 66.87; H, 7.67; N, 8.00; Found: C, 66.82; H, 7.58; N, 8.05.

EXAMPLE 88

Preparation of [1S-[1R*-[1R*,2S*(2S*,3R*)]]]- 2,2-Dimethyl-1-[[[3-[[3-[[(1,1-Dimethylethoxcy)-carbonylamino]-2-hydroxy-4-phenylbutyl]amino]-2-hydroxy-1-(phenylmethyl),propyl]amino]-carbonyl] propoyl]carbamic acid, phenylmethyl ester (Compound 88b)

(a) Compound 88a

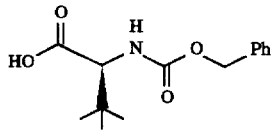

Compound 88a was prepared from L-tert-leucine by a procedure analogous to that used for the synthesis of Compound 85a.

(b) Compound 88b

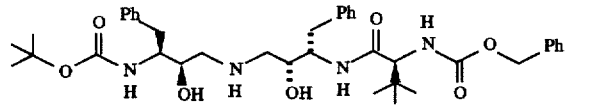

The title Compound 88b was prepared from Compounds 54 and 88a by a procedure analogous to that used for the synthesis of Compound 55 (DMF only was used along with 1 equivalent of N-methylmorpholine).

m.p. 144°–147°; [α]$_D^{25}$=−14.8° (c 0.15, MeOH); {[α]$_{365}$=−62.7° (c 0.15, MeOH)}. Mass Spec.: (FAB/SIMS): 691 (M+H). Analysis Calc. For C$_{39}$H$_{54}$N$_4$·0.13 H$_2$O: C, 67.58; H, 7.89; N, 8.08; Found: C, 67.32; H, 7.76; N, 8.34

EXAMPLE 89

Preparation of [S-[1R*,2S*(2S*,3R*)][-N-[3-[[3-[[(1,1-Dimethylethoxy)carbonyl]amino]-2-hydroxy-4-phenylbutyl]amino]-2-hydroxy-1-(phenylmethyl)-propyl]-N$_2$-[(phenylmethoxy)carbonyl]-L-lysinamide (Compound 89b)

(a) Compound 89a

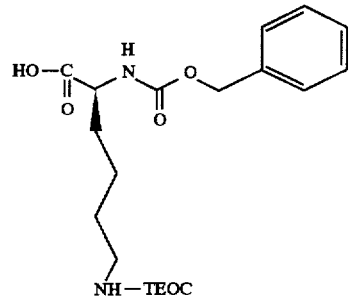

Compound 89a was prepared from α-N-Cbz-L-lysine and trimethylsilylethylchloroformate by a procedure analogous to that used for the synthesis of Compound 85a.

(b) Compound 89b

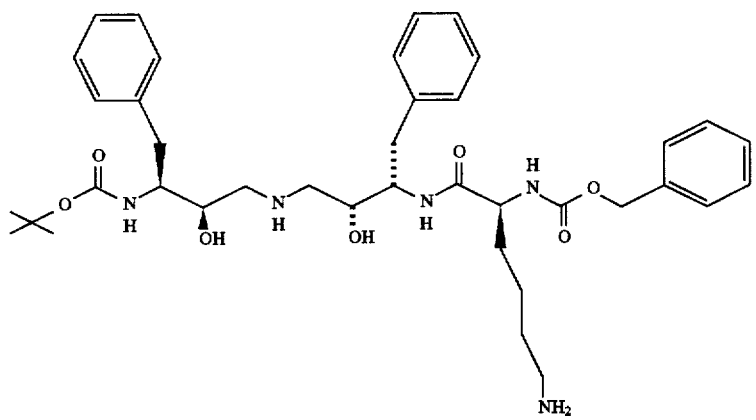

The title Compound 89b (white solid) was prepared from Compounds 48 and 89a by a two-step procedure analogous to that used for the synthesis of Compound 52 (6 equivalents of n-Bu$_4$NF was used).

mp 129°–131° C.; $[\alpha]_D = -19.4°$ (c 0.35, MeOH). Mass Spec. FAB+ion: (M+H)=706. Analysis calc. for C$_{39}$H$_{55}$N$_5$O$_7$·1.49 H$_2$O: C, 63.93; H, 7.98; N, 9.56; Found: C, 64.01; H, 7.68; N, 9.48.

EXAMPLE 91

Preparation of [S-(1R*,2S*)[-N,N'-[Iminobis[2-hydroxy-1-(phenylmethyl)-3,1-pro-anediyl]]bis[N$^2$-[N-[(1,1-dimethoxyethyl)carbonyl]-L-phenylalanyl]-L-valinamide] (Compound 91)

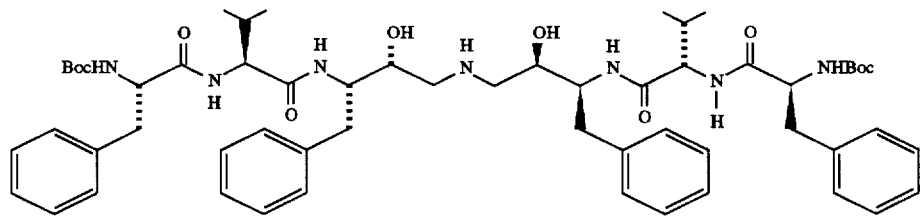

EXAMPLE 90

Preparation of [S-(1R*,2S*)]-N,N'-[Iminobis[2-hydroxy-1-(phenylmethyl)-3,1-propanediyl]]bis[L-valinamide], trihydrochloride (Compound 90)

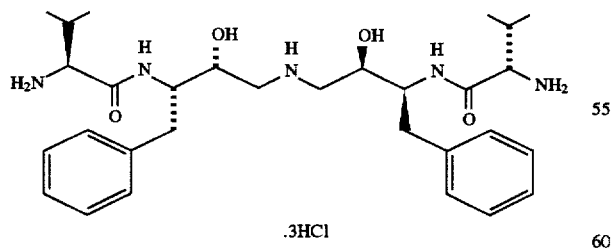

The title Compound 90 was prepared from Compound 34 by a procedure analogous to that used for the synthesis of Compound 32. R$_f$=0.29 (20:2:78 MeOH:NH$_4$OH:CH$_2$Cl$_2$).

The title Compound 91 was prepared from Compound 90 and Boc-L-phenylalanine by a procedure analogous to that used for the synthesis of Compound 75f. R$_f$=0.31 (10:1:89; MeOH:NH$_4$OH:CH$_2$Cl$_2$). MS: (FAB): 1036 (M+H).

EXAMPLE 92

Preparation of [S-(1R*,2S*)]-N,N'-[Iminobis[2-hydroxy-1-(phenylmethyl)-3,1-propanediyl]bis[N²-(L-phenylalanyl)-L-valinamide],trihydrochloride (Compound 92)

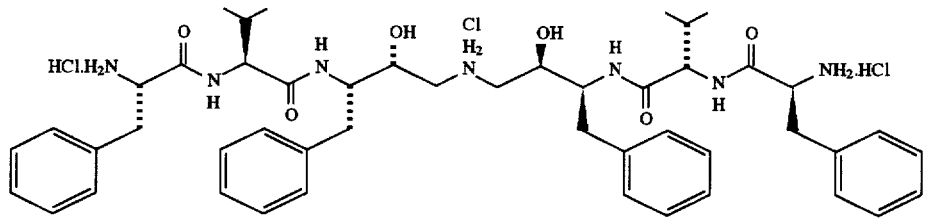

Compound 91 (81 mg; 78.2 μmol) was stirred with methanolic HCl (1 ml of 2.09M solution) at 0°C. for 30 min and at RT for 2 h. The volatiles were removed and the residue evaporated from Et₂O and dried under high vacuum overnight. The resulting solid was dissolved in MeOH and precipitated with Et₂O after which it was triturated with Et₂O and EtOAc to give 62 mg (86%) of a light-orange colored solid.

m.p. dec. 180°–187° C.; $[\alpha]_D^{25}$=–16.5° (c 0.12, MeOH); MS: (FAB): 836 (M+H). Anal. Calc. for $C_{48}H_{68}Cl_3N_7O_6$·2.58 $H_2O$: C, 58.13; H, 7.43; N, 9.88; Found: C, 58.20; H, 7.33; N, 9.81

EXAMPLE 93

Preparation of [S-[1R*,2S*(2S*,3R*)][-N-[3-[[3-[[(1,1-Dimethylethoxy)carbonyl]amino]-2-hydroxy-4-phenylbutyl]amino]-2-hydroxy-1-(phenylmethyl)propyl]-N₂-]-(1H-benzimidazol-2-ylmethoxy) carbonyl]-L-valinamide (Compound 93f)

(a) Compound 93a

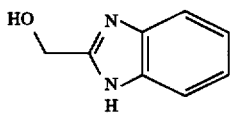

A mixture of 3.24 g (30.0 mmol) of o-phenylenediamine and 3.42 g (45.0 mmol) of glycolic acid in 30 mL of 4N HCl was heated at reflux for 45 min. The resulting solution was cooled to RT and basified (pH=8) with NH₄OH. The resulting suspension was cooled in an ice bath, and the solid filtered, rinsed with cold H₂O and recrystallized from H₂O to afford 2.70 g (61%) of Compound 93a as a tan solid.

(b) Compound 93b

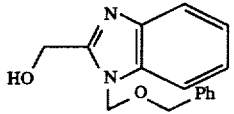

To a solution of 500 mg (3.37 mmol) of Compound 93a in 5 mL of DMF were added 357 mg (3.37 mmol) of Na₂CO₃ and 0.58 mL (3.37 mmol; 80% pure) of benzyl chloromethyl ether. The mixture was stirred at 0° C. for 1 h and at RT for 24 h. The mixture was partitioned between EtOAc and H₂O, and the combined organic extracts dried over Na₂SO₄, filtered, and concentrated in vacuo to give 945 mg of crude material. Flash chromatography on silica 10 gel (25–100% EtOAc-hexane; then, 5% CH₃OH-EtOAc) provided 339 mg (39%) of Compound 93b.

(c) Compound 93c

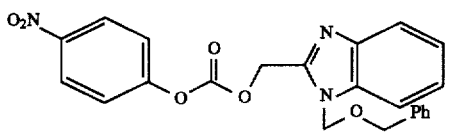

To a solution of 260 mg (1.01 mmol) of Compound 93b in 3 mL of CH₂Cl₂ and 1.5 mL of pyridine at 0° C. was added 214 mg (1.06 mmol) of p-nitrophenylchloroformate in 1.5 mL of CH₂Cl₂. The mixture was stirred at 0° C. for 1 h and at RT for 3 h, diluted with 100 mL of EtOAc and washed with 1M NaOH (3×25 mL), H₂O (2×25 mL), and brine (25 mL). The organic layer was dried over MgSO₄, filtered, and concentrated in vacuo affording 396 mg of Compound 93c.

(d) Compound 93d

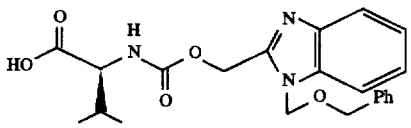

To a solution of 105 mg (0.893 mmol) of L-valine in 0.9 mL of 1.0N NaOH was added a solution of 387 mg (0.893 mmol) of Compound 93c in 3 mL of dioxane and 0.2 mL of Et₃N. The mixture was stirred at RT for 18 h and partitioned between EtOAc and H₂O. The aqueous layer was acidified to pH=4 with 5% KHSO₄ and extracted with EtOAc (2×25 mL). The combined organic extracts were dried over Na₂SO₄, filtered, and evaporated in vacuo to provide 0.79 g of crude acid. Flash chromatography on silica gel, eluting with 50% EtOAc-hexane and then 10% MeOH-CHCl₃, afforded 151 mg (41%) of Compound 93d.

(e) Compound 93e

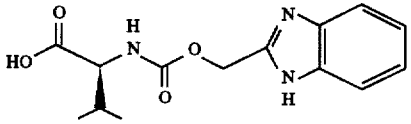

To a solution of 242 mg (0.588 mmol) of Compound 93d in 3 mL of MeOH was added a solution of HCl (0.74 mmol) in 5 mL of MeOH and 200 mg of Pd(OH)₂. The mixture was stirred under a H₂ atmosphere (balloon) for 4 h at which time an additional 0.1 mL of 1N HCl and 50 mg of Pd(OH)₂ was added. The mixture was stirred under a H₂ atmosphere for

137 another 2.5 h and then filtered and evaporated in vacuo. Re-evaporation in vacuo from CHCl$_3$/Et$_2$O afforded 326 mg of crude Compound 93e as an HCl salt.

(f) Compound 93f

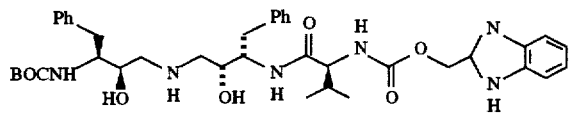

To a solution of 270 mg (~0.488 mmol; ca. 60% pure, contaminated with solvent) of Compound 93e in 3 mL of dry DMF at 0° C. were added 228 mg (0.488 mmol) of Compound 54, 99 mg (0.73 mmol) of HOBT, 110 µL of N-methylmorpholine, and 104 mg (0.54 mmol) of EDC. The mixture was stirred at RT for 18 h, diluted with 100 mL of EtOAc, and washed with saturated NaHCO$_3$, H$_2$O, and brine. The organic layer was dried over Na$_2$SO$_4$, filtered and evaporated in vacuo to give 0.41 g of crude material. Flash chromatography on silica gel (5% CH$_3$OH/CHCl$_3$, then 5–7.5% CH$_3$OH/CHCl$_3$ with 0.5% NH$_4$OH) followed by precipitation from hot MeOH with Et$_2$O provided 150 mg of the title Compound 93f.

mp 161°–165° C.; Mass Spec. 717 (M+H)$^+$

EXAMPLE 94

Preparation of [1S-[1R* [1R*,2S* (2S*,3R*)]]]-[2-[[3-[[(1,1-Dimethylethoxy)carbonyl]amino]-2-hydroxy-4-phenylbutyl]amino]-2-hydroxy-1-(phenylmethyl)propyl]amino]-2-oxo-1-phenylethyl] carbamic acid, phenylmethyl ester (Compound 94)

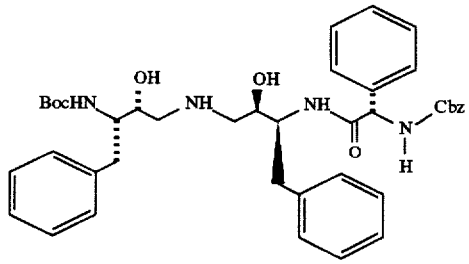

The title Compound 94 was prepared from Compound 54 and Cbz-L-phenylglycine by a procedure analogous to that used for the preparation of Compound 55 (DMF only used along with 2 eq. N-methyl morpholine).

| m.p. 203.5–205° C.; [α]$_D$ = +16.2° (c 0.22, AcOH) Elemental Analysis (%) for C$_{41}$H$_{50}$N$_4$O$_7$·0.24 H$_2$O | | |
|---|---|---|
| | Calc. | Found |
| C | 68.86 | 68.98 |
| H | 7.11 | 7.13 |
| N | 7.83 | 7.71 |

138

EXAMPLE 95

Preparation of [S-[1r*,2S*(2S*,3R*)]]-N-[[3-[[(1,1-Dimethylethoxny)carbonyl]amino]-2-hydroxy-4-phenylbutyl]amino]-2-hydroxy-1(phenylmethyl)propyl]-N$_2$-[N-[(phenylmethoxy)carbonyl]-L-alanyl]-L-valinamide (Compound 95)

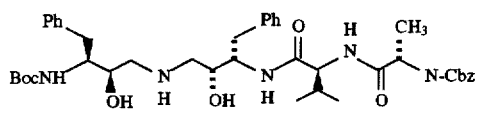

The title Compound 95 was prepared from Compound 61 and Cbz-alanine by a procedure analogous to that used for the two-step conversion of Compound 48 to Compound 52.

EXAMPLE 96

Preparation of [S-[1R*,2S*(2S*,3R*)]-N-]3-[[3-[[(1,1-Dimethylethoxy)carbonyl]amino]-2-hydroxy-4-phenylbutyl]amino]-2-hydroxy-1(phenylmethyl)propyl]-N$^2$-(L-alanyl)-L-valinamide, fumarate salt (Compound 96)

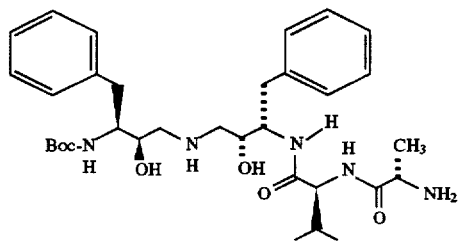

Fumaric acid salt

Compound 95 was converted into Compound 96 by a procedure analogous to the one used for the synthesis of Compound 84.

mp 168°–174° C.; [α]$_D$$^{22}$=19° (c 0.15, CH$_3$OH); High Resolution Mass Spec. (FAB): C$_{33}$H$_{52}$N$_5$O$_6$=614.3908$^+$; Δ=1.6 ppm.

EXAMPLE 97

Preparation of [S-[1R*,2S*(2S*,3R*)]]-N-[3-[[3-[[(1,1-Dimethylethoxy)carbonyl]amino]-2-hydroxy-4-phenylbutyl]amino]-2-hydroxy-1-(phenylmethyl)propyl]-N$^2$-[N-[(phenylmethoxy)carbonyl]-L-leucyl]-L-valinamide (Compound 97)

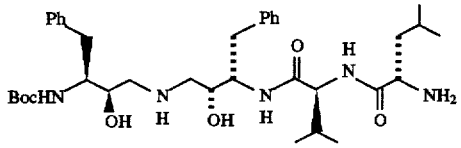

The title Compound 97 was prepared from Compound 61 and Cbz-L-leucine by a procedure analogous to that used for the two-step conversion of Compound 48 to Compound 52.

EXAMPLE 98

Preparation of [S-[1R*,2S*(2S*,3R*)]]-N-[3-[[3-[[(1,1-Dimethylethoxy)carbonyl]amino]-2-hydroxy-4-phenylbutyl]amino]-2-hydroxy-1(phenylmethyl)propyl]-N²-(L-leucyl)-L-valinamide, fumarate salt (Compound 98)

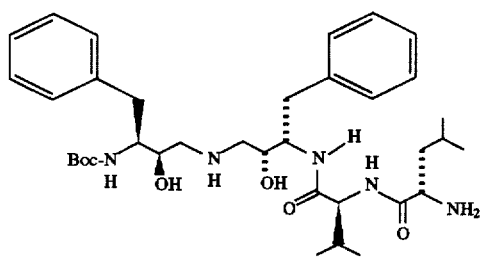

fumarate salt

Compound 97 was converted into Compound 98 by a procedure analogous to the one used for the synthesis of Compound 84.

mp 184°–190° C.; $[\alpha]_D^{22}=-12°$ (c 0.16, CH$_3$OH); High Resolution Mass Spec. (FAB): C$_{36}$H$_{57}$N$_5$O$_6$=656.4382$^+$; Δ=0.8 ppm.

EXAMPLE 99

Preparation of [S-(1R*,2S*)]-N,N'-[Iminobis[2-hydroxy-1-(phenylmethyl)-3,1-propanediyl]]bis [N²-[[[1,1-dimethylethoxy)carbonyl]-amino]acetyl]-L-valinamide](Compound 99)

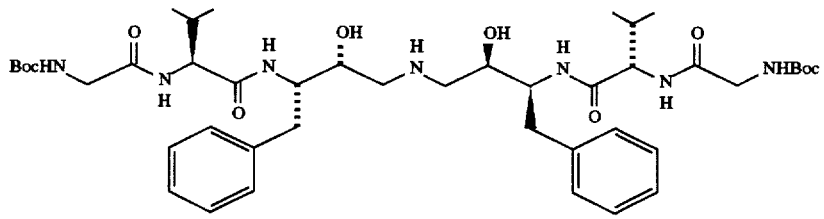

The title Compound 99 was prepared from Compound 90 and Boc-glycine by a procedure analogous to the one used for the synthesis of 75f.

m.p. 212–215° C.; $[\alpha]_D = -26.2°$ (c 0.1, AcOH)

Elemental Analysis (%)
for C$_{44}$H$_{69}$N$_7$O$_{10}$·0.78 H$_2$O

| | Calc. | Found |
|---|---|---|
| C | 60.74 | 60.81 |
| H | 8.17 | 8.08 |
| N | 11.27 | 11.20 |

EXAMPLE 100

Preparation of [S-[1R*,2S*(2S*,3R*)]]-N-[3-[[3-[[(1,1-Dimethylethoxy)carbonyl]amino]-2-hydroxy-4-phenylbutyl]amino]-2-hydroxy-1-(phenylmethyl)-propyl]-N²[(phenylmethoxy)carbonyl]-L-threoninamide (Compound 100)

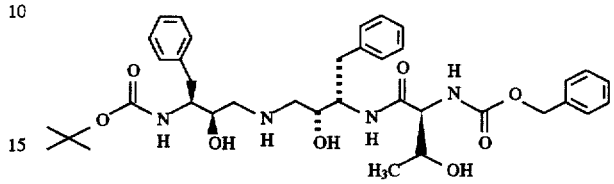

The title Compound 100 (white solid) was prepared from Compound 54 and Cbz-L-threonine by a procedure analogous to that used for the synthesis of 55 (DMF only used).

m.p. 150–155° C.; $[\alpha]_D = -17.8°$ (C 0.18, MeOH)
Mass spec.: 679 (M + H)
Elemental Analysis (%)
for C$_{37}$H$_{50}$N$_4$O$_8$·0.75 H$_2$O

| | Calc. | Found |
|---|---|---|
| C | 64.20 | 64.25 |
| H | 7.50 | 7.34 |
| N | 8.09 | 8.04 |

EXAMPLE 101

Preparation of [S-[1R*,2S*(2S*,3R*)]]-N-[3-[[3-[[(1,1-Dimethylethoxy)carbonyl]amino]-2-hydroxy-4-phenylbutyl]amino]-2-hydroxy-1-(phenylmethyl)propyl]-N²-[(1H-benzimidazol-2-yl)-carbonyl]-L-valinamide](Compound 101b)

(a) Compound 101a

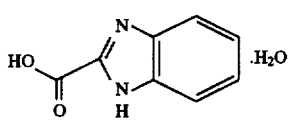

To a solution of 0.500 g (3.37 mmol) of Compound 93a in 10 mL of boiling H$_2$O was added 10 drops of 3M NaOH. The resulting solution was kept at 100° C. during the addition (10 min) of a solution of 0.8 g (5.0$_5$ mmol) of KMnO$_4$ in 50 mL of water. Heating at 100° C. was continued for 30 min. The hot mixture was filtered through celite, cooled to RT and acidified with HOAc. The white precipitate was collected by suction filtration and recrystallized from H₂O to afford 185 mg (34%) of Compound 101a.

mp 170°–172° C. (—CO₂).

(b) Compound 101b

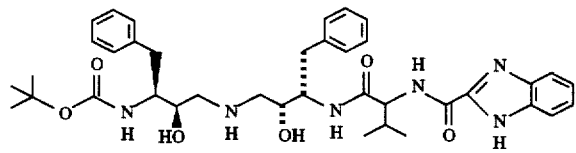

The title Compound 101b was prepared from Compounds 61 and 101a by a two-step procedure analogous to that used for the conversion of Compound 48 to Compound 52.

m.p. 210–215° C.; $[\alpha]^{20}_D = -30°$ (c 0.32, CH₃OH)
Mass spec. 687 (M = H)⁺
Elemental Analysis (%) C₃₈H₅₀N₆O₆

|   | Calc. | Found |
|---|-------|-------|
| C | 66.45 | 66.53 |
| H | 7.34  | 7.38  |
| N | 12.24 | 12.21 |

EXAMPLE 102

Preparation of [S-[1R*.2S*(2S*,3R*)][]-N-[[[3-[[3-[[(1,1-Dimethylethoxy)carbonyl]amino]-2-hydroxy-4-phenylbutyl]amino]-2-hydroxy-1-(phenylmethyl)-propyl]-N²-[phenylmethoxy)carbonyl]-L-prolinamide (Compound 102)

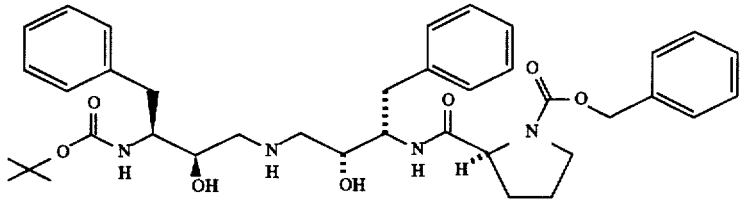

The title Compound 102 (white solid) was prepared from Compound 54 and Cbz-L-proline by a procedure analogous to that used for the synthesis of Compound 55 (used DMF only).

m.p. 142–146° C.; $[\alpha]_D = -31.7°$ (C 0.81, MeOH)

Mass spec. 675 (M + H)

Elemental Analysis (%)

for C₃₈H₅₀N₄O₇·0.69 H₂O

|   | Calc. | Found |
|---|-------|-------|
| C | 66.42 | 66.29 |
| H | 7.53  | 7.41  |
| N | 8.15  | 8.28  |

EXAMPLE 103

Preparation of [S-[1R*.2S*(2S*,3R*)]-N²-[3-(1H-Benzimidazol-2-yl)-1-oxo-propyl]-N-[3-[[3-[[(1,1-di-methylethoxy)carbonyl]amino-4-phenylbutyl]amino]-2-hydroxy-1-(phenylmethyl)propyl]-L-valinamide (Compound 103b)

(a) Compound 103a

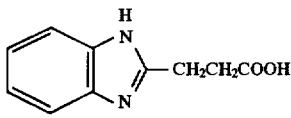

A mixture of o-phenylenediamine (2.70 g, 25 mmol) and succinic acid (5.02 g, 42.5 mmol) was heated at reflux in 150 ml of 5N HCl for 3 hrs.

The mixture was allowed to stand overnight at RT, filtered and then the pH was adjusted to 5 with 5N NaOH. The aqueous mixture was saturated with NaOAc and stored overnight at 0° C. The crude product precipitated as a tan solid and was crystallized from H₂O/EtOH (9:1) affording 968 mg (20%) of the Compound 103a. See Chemical Abstracts CA: 19953g (1961); French Patent 1,179,933 (May 29, 1959).

(b) Compound 103b

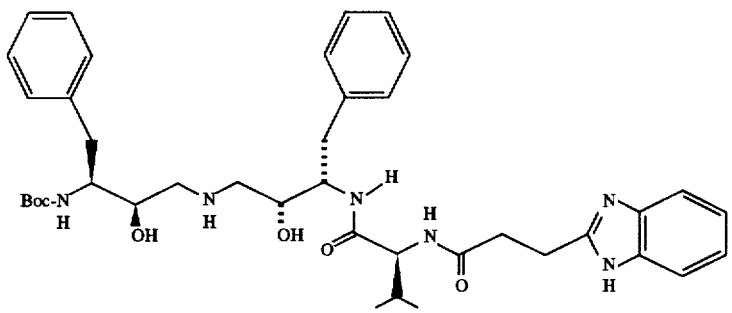

The title Compound 103b was prepared from Compounds 61 and 103a by a two-step procedure analogous to that used for the conversion of Compound 48 to Compound 52.

mp 182°–185° C.; $[\alpha]_D^{22}$=–20° (c 0.25, CH$_3$OH); Analysis calc. for C$_{40}$H$_{54}$N$_6$O$_6$•2.5 mole H$_2$O: C, 63.22; H, 7.80; N, 11.06; Found: C, 63.06; H, 7.47; N, 10.90.

EXAMPLE 104

Preparation of [1R*,2S*(2S*,3R*)]-N-[3-[[3-[[(1,1-dimethylethoxy)carbonyl]amino]-2-hydroxy-4-phenylbutyl]amino]-2-hydroxyl-1-(phenylmethyl)propyl]-N$^2$-[(1H-indol-2-ylmethoxy)carbonyl]-L-valinamide (Compound 104e)

(a) Compound 104a

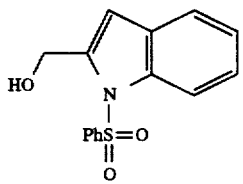

A solution of LiBH$_4$ (1.6M in THF, 2.4 mL, 3.8 mmol) was added at –78° C. to a stirred solution of 1.0 g, 3.5 mmol, of 2-formyl-1-phenylsulfonyl indole (Saulnier et al., *J. Org. Chem.*, 47, 757 (1982)) in 30 mL of Et$_2$O. The mixture was allowed to come to RT and stirred for 30 min. The reaction mixture was carefully quenched by adding sat. NaHCO$_3$, diluted with EtOAc and stirred for 30 min. The organic layer was separated, dried over MgSO$_4$ and concentrated to afford 0.975 g (97%) of Compound 104a.

(b) Compound 104b

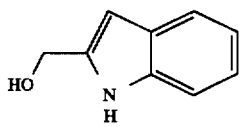

To a solution of Compound 104a (0.97 g, 3.38 mmol) in 15 mL 2-methoxyethanol was added 3 mL 20% aq. KOH. The mixture was heated under reflux for 3 h, allowed to come to RT and partitioned between EtOAc and brine. The organic layer was washed with brine, dried over sodium sulfate and concentrated to afford a crude brown oil which was purified by flash chromatography (silica gel/hexane-EtOAc 5:1 to 1:1) giving 0.45 g (91%) of Compound 104b as a yellow solid.

(c) Compound 104c

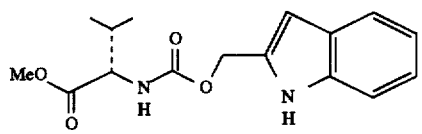

Trichloromethyl chloroformate (1.08 mL) was added to a stirred suspension of L-valine methyl ester hydrochloride (3.0 g, 17.9 mmol) in 10 mL dry dioxane. The mixture was refluxed for 1.5 h, concentrated, and the residue flash distilled (bath temperature 100°–125° C., 0.5 mm vacuum) to afford 1.0 g of L-valine methyl ester isocyanate. A solution of 0.55 g (3.5 mmol) of L-valine methyl ester isocyanate in 7.5 mL dry toluene was treated with 4M HCl in dioxane (79 mL, 0.315 mmol) at RT and stirred for 5 min. The resulting mixture was treated with 1.0 g solid K$_2$HPO$_4$ for 5 min, followed by the addition of Compound 104b (0.464 g, 3.15 mmol). The mixture was refluxed for 9 h, diluted with EtOAc and washed with sat. NaHCO$_3$ followed by brine. The organic phase was dried (MgSO$_4$), concentrated, and the crude product purified by flash chromatography (silica gel/hexane to EtOAc-hexane 1:9 to 1:4, stepwise gradient) to afford 0.51 g (53%) of Compound 104c as a yellow gummy solid.

(d) Compound 104d

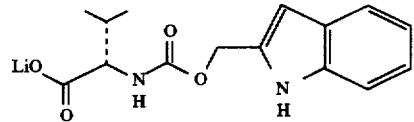

To a solution of Compound 104c (0.5 g, 1.64 mmol) in 7 mL dioxane was added 0.54M aq. LiOH (3.05 mL, 1.64 mmol), stirred at RT for 12 h, concentrated and the residue chased 3 times with toluene. The resulting off-white Li salt (0.5 g) of the acid was used as such for the next step.

(e) Compound 104e

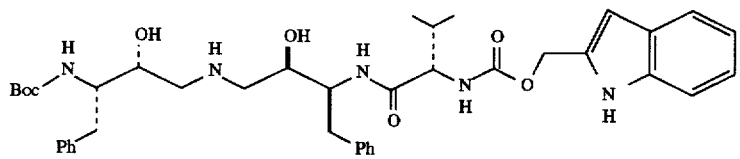

To a solution of Compound 104d (0.15 g, 0.51 mmol) and HOBT (0.101 g, 0.66 mmol) in 1.5 mL dry DMF at 0° C. was added EDC (0.108 g, 0.56 mmol) and N-methyl morpholine (0.111 mL, 1.02 mmol), and the resulting mixture was stirred at 0° C. for 1 h. The mixture was treated with Compound 54 (0.226 g, 0.51 mmol), and stirred at RT for 12 h, concentrated, and the residue partitioned between EtOAc and sat. NaHCO$_3$. The organic layer was washed with brine, dried over MgSO$_4$, concentrated, and the crude product was purified by flash chromatography (silica gel/CHCl$_3$-MeOH-NH$_4$OH 99:1:0.5 to 90:10:1) followed by preparative HPLC (Waters Prep Nova-Pack HR C18, 6 micron, 30×300 mm; eluent: MeOH-H$_2$O-TFA 75:25:0.05 to 80:20:0.05; UV 254 nm). The desired fractions were made basic with sat. NaHCO$_3$, concentrated, and the residue partitioned between EtOAc/1:1 brine-sat. NaHCO$_3$. The organic phase was dried over MgSO$_4$, concentrated and the resulting white solid was triturated from 10:1 hexane-Et$_2$O to afford 0.181 g (50%) of the title Compound 104e as a white solid.

$[\alpha]_D$=+3.0° (c=0.5, CH$_2$Cl$_2$); m.p. 115°–120° C. High Resolution Mass Spectrum: (M+H)$^+$=716.4010, $\Delta$1.8 ppm error (theoretical: (M+H)$^+$: 716.5023).

EXAMPLE 105

Preparation of S-[1R*,2S*(2S*,3R*)]-N-[3-[[3-[[(1,1-Dimethylethoxy)carbonyl]amino]-2-hydroxy-4-phenylbutyl]amino]-2-hydroxy-1-(phenylmethyl)-propyl]-N$^2$-(1H-benzimidazol-2-ylacetyl)-L-valinamide (Compound 105)

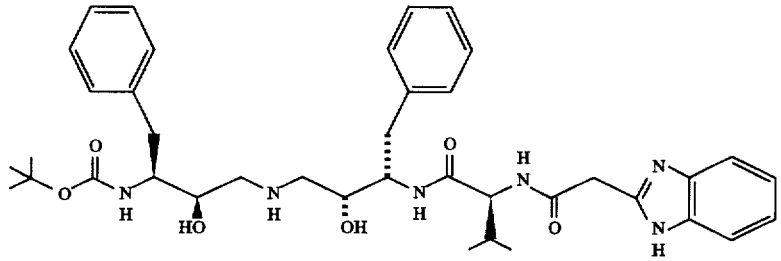

The title Compound 105 was prepared from Compound 61 and 2-benzimidazoleacetic acid (Copeland et al., *J. Am. Chem. Soc.*, 65, 1072 (1943)) by a two-step procedure analogous to that used for the conversion of Compound 48 to Compound 52.

m.p. 177°–182° C.; Mass spec (FAB) 701 (M+H); Elemental Analysis; Calc. for C$_{39}$H$_{52}$N$_6$O$_6$•0.78 H$_2$O; C, 65.52; H, 7.55; N, 11.75 ; Found C, 65.52; H, 7.40; N, 11.68

EXAMPLE 106

Preparation of [1S-[1R*,2S* (2S*,3R*)]]-3-[[3-[[3,3-Dimethyl-1-oxo-2-(phenylmethoxy)butyl)butyl]amino]-2-hydroxy-4-phenylbutyl]amino]-2-hydroxy-1-(phenyl-methyl)propyl]carbamic acid, 1,1-dimethylethyl ester (Compound 106e)

(a) Compound 106a

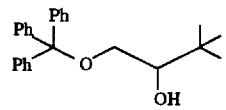

A solution of 1.18 g (10 mmoles) of 3,3-dimethyl-2-hydroxy-1-butanol and 3.1 g of triphenylmethyl chloride in 25 ml of pyridine was stirred at RT overnight. The reaction mixture was evaporated to dryness and the residue diluted with EtOAc and washed with 1N HCl, brine, saturated NaHCO$_3$ and brine. After drying (MgSO$_4$), removal of solvent gave an oily residue which was purified by flash chromatography on a 400 cc column of silica gel. Elution with 5% ether-hexane afforded 3.0 g (8.5 mmoles, 85% yield) of Compound 106a as a clear colorless oil which crystallized on standing.

(b) Compound 106b

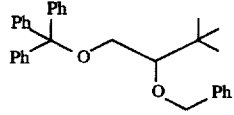

To a solution of 750 mg (2.1 mmoles) of Compound 106a in 9 ml of dry THF, at −10° C. was added dropwise 4.6 ml (2.3 mmoles) of 0.5M KN(TMS)$_2$ in toluene. Cooling was removed and the clear solution stirred for 0.5 hr. The reaction was ice cooled and 309 µl (2.6 mmoles) of benzyl bromide was added dropwise, neat. Stirring was continued at RT for 1 hr. The reaction was diluted with brine and

147 extracted with EtOAc. The extracts were washed with brine, dried (MgSO₄) and the solvent evaporated to yield an oily residue which was purified by flash chromatography on a 450 cc column of silica gel. Elution with 20% $CH_2Cl_2$-hexane gave 880 mg (1.95 mmoles, 94% yield) of Compound 106b as a colorless oil.

(c) Compound 106c

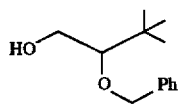

A solution of 0.8 g (1.8 mmoles) of Compound 106b and 40 mg of p-toluenesulfonic acid in 20 ml of MeOH was stirred at RT for 3 hr. The reaction was evaporated to dryness and the residue placed on a 400 cc column of silica gel. Elution with 20% Et₂O-hexane, followed by 30% Et₂O-hexane gave 233 mg (1.12 mmole, 63%) of Compound 106c as a clear colorless oil.

(d) Compound 106d

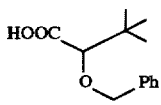

To a solution of 5.8 g (16.8 mmoles) of pyridinium dichromate in 8 ml of DMF at RT was added dropwise a solution of 1.0 g (4.8 mmoles) of Compound 106c in 2 ml of DMF. The dark solution was stirred overnight, poured into 80 ml of ice/water and extracted with Et₂O. The extracts were filtered through a Celite-MgSO₄ mixture and extracted with saturated NaHCO₃, and H₂O. The combined aqueous fractions were washed once with Et₂O, acidified with 6N HCl, and extracted with Et₂O. The combined extracts were washed with brine, dried (MgSO₄) and the solvent removed to yield 480 mg of clear colorless oil. Distillation (kugelrohr, 140° C., 0.05 mm) gave 410 mg (1.8 mmoles, 38%) of Compound 106d as a clear colorless oil.

(e) Compound 106e

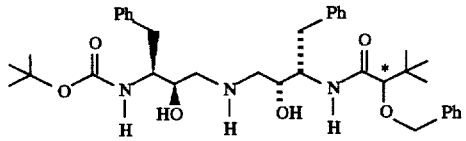

The title Compound 106e was prepared as a white solid from Compounds 54 and 106d by a procedure analogous to that used for the synthesis of Compound 55 (DMF only; 2 eq. of N-methyl-morpholine used).

m.p. 114°–117° C.; Mass spec. (M+H) 648; Elemental Analysis; Calc. for $C_{38}H_{53}N_3O_6$: C, 70.45; H, 8.25; N, 6.49; Found: C, 70.09; H, 8.27; N, 6.57

148

EXAMPLE 107

Preparation of [1S-[1R*,2S*(2S*,3R*)]]-[[3-[[3-[[(1,1-Dimethylethoxy)carbonyl]amino]-2-hydroxy-4-phenylbutyl][(9H-fluoren-9-ylmethoxy)carbonyl]amino]-2-hydroxy-1-(phenyl-methyl)propyl] carbamic acid, phenylmethyl ester (Compound 107)

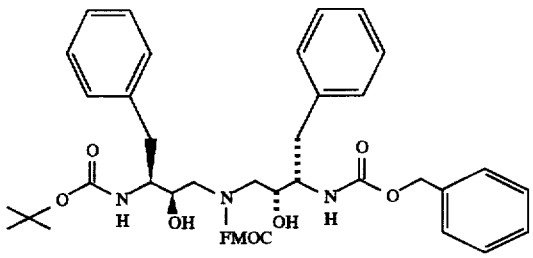

Compound 45 was converted to the title Compound 107 by a procedure analogous to the one used for the synthesis of Compound 39.

¹H NMR (CD₃OD): δ 1.23 (m, 9H), 2.42 (m, 1H), 2.59 (m, 1H), 2.91 (m, 1H), 3.07 (m, 1H), 3.18 (m, 1H), 3.28 (m, 1H), 3.44–3.88 (m's, 6H), 4.27 (m, 1H), 4.52 (m, 2H), 4.87 (m, 2H), 7.05–7.47 (m's, 19H), 7.64 (m, 2H), 7.78 (m, 2H).

EXAMPLE 108

Preparation of [1S-[1R*,2S*(2S*,3R*)]]-[3-[(3-Amino-2-hydroxy-4-phenylbutyl)-[(9H-fluoren-9-ylmethoxy)carbonyl]amino]-2-hydroxy-1-(phenyl-methyl)propyl]carbamic acid, 1,1-dimethylethyl ester (Compound 108)

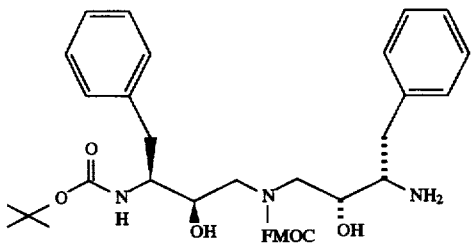

Compound 107 was converted to the title Compound 108 by a procedure analogous to that used for the synthesis of Compound 61 (EtOH was employed in place of MeOH). Compound 108 was used without further purification in the preparation of Compound 109 following.

EXAMPLE 109

Preparation of [S-[1R*,2S*(2S*,3R*)]]-N-[3-[[3-[[(1,1-Dimethylethoxy)carbonyl]amino]-2-hydroxy-4-phenylbutyl][(9H-fluoren-9-ylmethoxy)carbonyl]-amino]-2-hydroxy-1-(phenylmethyl)propyl]-N²-[(phenylmethoxy)carbonyl]-L-valinamide (Compound 109)

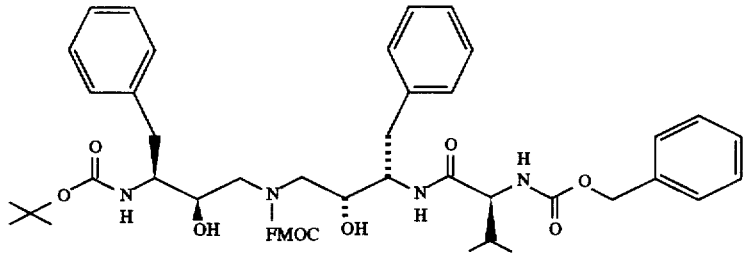

Compound 108 was coupled with Cbz-valine by a procedure analogous to that used for the preparation of Compound 51 to give the title Compound 109.

Mass Spec. (FAB): 899 (M+H)⁺.

EXAMPLE 110

Preparation of [S-[1R*,2S*(2S*,3R*)]]-N-[3-[(3-Amino-2-hydroxy-4-phenylbutyl)-[(9H-fluoren-9-ylmethoxy)carbonyl]amino]-2-hydroxy-1-(phenylmethyl)propy]-N²-](phenylmethoxy)carbonyl]-L-valinamide, monohydrochloride (Compound 110)

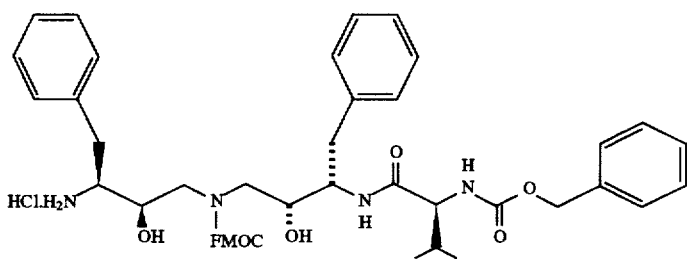

Acetyl chloride (39.8 µL, 56.0 mmol, 10 eq.) was added at 0° C. to MeOH (560 µL) followed by Compound 109 (50 mg, 0.56 mmol). The viscous solution was diluted with 1 mL MeOH and an additional solution of acetyl chloride (39.8 µL) in MeOH (2 mL) was added. The white turbid mixture was allowed to warm to RT, stirred for 4 hrs, and then gently warmed to 40° C. After 1 h, the volatiles were removed in vacuo to yield 46 mg (99%) of Compound 110 which was used without further purification.

EXAMPLE 111

Preparation of [S-[1R*,2S*(2S*, 3R*)]]-N-[2-Hdroxy-3-[[2-hydroxy-4-phenyl-3-[[N-[(phenylmethoxy)-carbonyl]-L-valyl]amino]butyl-] [(9H-fluoren-9-yl-methoxy)carbonyl]amino]-1-(phenylmethyl)propyl]-N²-[(phenylmethoxy)carbonyl]-L-asparaginamide (Compound 111)

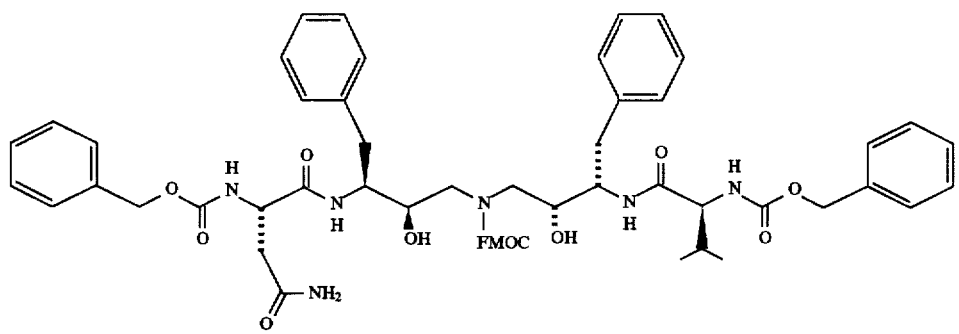

Compound 110 and Cbz-L-asparagine were reacted by a procedure analogous to that used for the preparation of Compound 51 to give the title Compound 111.

Mass Spec.: (FAB): 1047.5 (M+H)$^+$.

EXAMPLE 112

Preparation of [S-[1R*,2S*(2S*,3R*)]]-N-[2-Hydroxy-3-[[2-hydroxy-4-phenyl-3-[[N-[(phenylmethoxy)carbonyl]-L-valyl]amino]butyl]amino]-1-(phenylmethyl)propyl]-N$^2$-[(phenylmethoxy)carbonyl]-L-asparaginamide, monohydrochloride (compound 112)

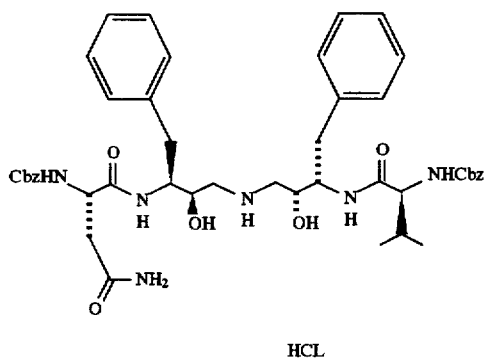

Compound 111 was converted to the title Compound 112 by a procedure analogous to that used for the synthesis of Compound 42. Compound 112 was isolated as the HCl salt which was recrystallized from MeOH/Et$_2$O.

mp 198°–200° C.; [α]$_D$=−31° (c 0.2, AcOH). Mass Spec.: (FAB): 825 (M+H)$^+$. Analysis calculated for C$_{45}$H$_{56}$N$_6$O$_9$.HCl.2.30 H$_2$O: C, 59.93; H, 6.77; N, 9.32; Found: C, 60.26; H, 6.56; N, 8.99;

EXAMPLE 113

Preparation of [1S-[1R*,2S*(2R*,3R*)]-[3-[[3-[[(1,1-Dimethylethoxy)carbonyl]amino]-2-hydroxy-4-phenylbutyl]amino]-2-hydroxy-1-(phenyl-methyl)propyl]carbamic acid, phenylmethyl ester (Compound 113c)

(a) Compound 113a

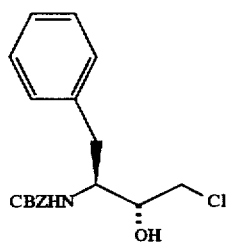

Compound 113a was prepared during the reduction procedure in which Compound 44a above was prepared and isolated.

(b) Compound 113b

Compound 113b was prepared from Compound 113a by a procedure analogous to that used for the synthesis of Compound 1b(ii).

(c) Compound 113c

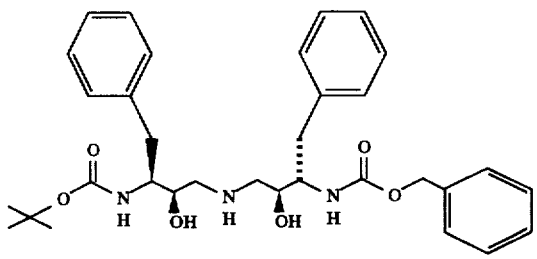

Compounds 113b and 16b (1 eq. of each) were reacted by a procedure analogous to that used for the synthesis of Compound 4b to give the title Compound 113c (white solid).

¹H NMR (CD₃OD): δ 1.29 (s, 9H), 2.56 (dd, J=10.5, 14 Hz, 1H), 2.66 (m, 2H), 2.80 (m, 3H), 2.91 (dd, J=5.5, 13.5 Hz, 1H), 3.09 (dd, J=3.5, 14 Hz, 1H), 3.60 (m, 2H), 3.80 (m, 1H), 3.86 (m, 1H), 4.99 (m, 2H), 7.20 (m, 15H).

EXAMPLE 114

Preparation of [1S-[1R*,2S*(2R*,3R*)]-[3-[(3-Amino-2-hydroxy-4-phenylbutyl)amino]-2-hydroxy-1-(phenylmethyl)propyl]carbamic acid, 1,1-dimethylethyl ester (Compound 114)

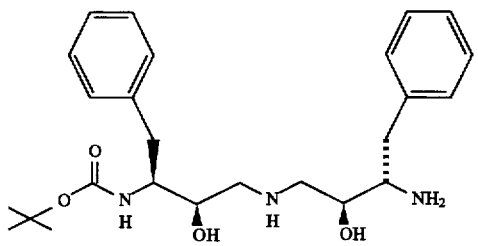

Compound 113c was converted to the title Compound 114 (white foam) using conditions analogous to those used for the synthesis of Compound 7.

¹H NMR (CD₃OD): δ 1.29 (s, 9H), 2.54 (dd, J=10.5, 14 Hz, 1H), 2.63 (dd, J=7.5, 12 Hz, 1H), 2.71 (m, 2H), 2.85 (dd, J=9.5, 12.5 Hz, 1H), 2.91 (m, 2H), 3.10 (m, 2H), 3.62 (m, 3H), 7.28 (m, 10H).

EXAMPLE 115

Preparation of [S-[1R*,2R*(2S*,3R*)]-N-[3-[[3-[[(1,1-Dimethylethoxy)carbonyl]amino]-2-hydroxy-4-phenylbutyl]amino]-2-hydroxy-1-phenylmethyl)propyl]-N²-[(phenylmethoxy)-carbonyl]-L-valinamide (compound 115)

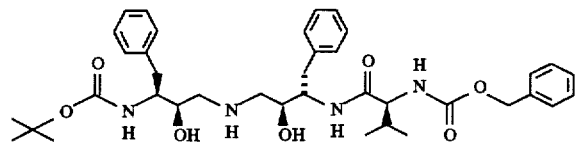

Compound 114 and Cbz-valine were reacted by a procedure analogous to that used for the synthesis of Compound 55 (DMF only as solvent) to give the title Compound 115.

mp 183°–186° C.; [α]$_D$=–38.7° (c 0.23, MeOH). Mass Spec. FAB: M+H=677. Analysis calc. for C₃₈H₅₂N₄O₇•0.81 H₂O: C, 66.01; H, 7.82; N, 8.10; Found C, 65.95; H, 7.72; N, 8.16.

EXAMPLE 116

Preparation of [S-(R*,R*)]-[Iminobis[2-hydroxy-1-(phenylmethyl)-3,1-propanediyl]biscarbamic acid, 1,1-dimethylethyl phenylmethyl ester (Compound 116)

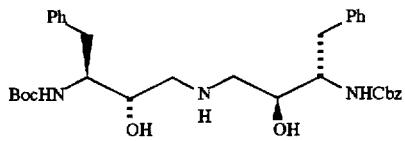

Compounds 27a and 113b (1 eq. of each) were reacted by a procedure analogous to that used for the synthesis of Compound 4b to give the title Compound 116 (white foam).

¹H NMR (CD₃OD): δ 1.34 (s, 9H), 2.52 (m, 4H), 2.75 (m, 2H), 2.87 (m, 2H), 3.69 (m, 3H), 3.82 (m, 1H), 4.98 (s, 2H), 7.22 (m, 15H).

EXAMPLE 117

Preparation of [S-[1R*,2R*(2R*,3R*)]]-N-[3-[[3-[[(1,1-Dimethylethoxy)carbonyl]amino]-2-hydroxy-4-phenylbutyl]amino]-2-hydroxy-1-(phenylmethyl) propyl]-N²-[(phenylmethoxy)-carbonyl]-L-valinamide (Compound 117)

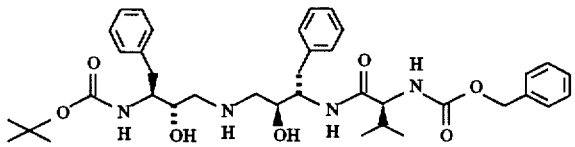

Compound 116 was converted to the title Compound 117 by a two-step procedure analogous to that used for the synthesis of Compound 115 (removal of the Cbz group using conditions analogous to those for Compound 7, and coupling of the resulting product with Cbz-valine analogous to Compound 55 [DMF only]).

mp 170°–175° C.; [α]$_D$=–51.5° (c 0.20, MeOH). Mass Spec. FAB+ions: M+H=677. Analysis calc. for C₃₈H₅₂N₄O₇•0.59 H₂O: C, 66.38; H, 7.80; N, 8.15; Found C, 66.25; H, 7.61; N, 8.28.

EXAMPLE 118

Preparation of [S-(R*,R*)]-1,1'-Iminobis(3-amino-4-phenyl-2-butanol) (Compound 118)

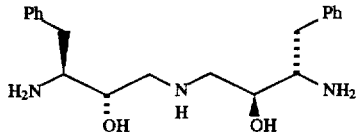

Compound 3 was converted to the title Compound 118 (which was used without further purification in the following Example as the tri-HCl salt) by a procedure analogous to that used for the synthesis of Compound 32. R$_f$=0.035 (20:2:78 MeOH:NH₄OH:CHCl₃).

EXAMPLE 119

Preparation of [S-(1R*,2R*)]-N,N'-[Iminobisr[2-hydroxy-1-(phenylmethyl)-3,1-propanediyl]]bis[N²-[phenylmethyloxy)carbonyl]-L-valinamide] (Compound 119)

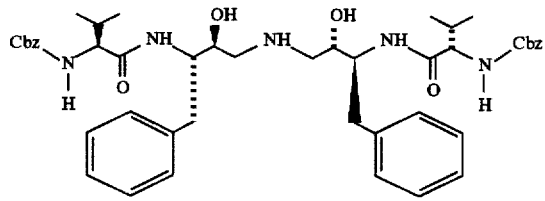

Compound 118 and Cbz-L-valine were reacted by a procedure analogous to that used for the synthesis of Compound 75f to give the title Compound 119.

m.p. dec. 206°–208° C.; $[\alpha]_D^{25}$=–42.8° (c 0.14, DMSO). MS: (FAB): 810 (M+H). Anal. Cac. for $C_{46}H_{59}N_5O_8 \cdot 1.08$ $H_2O$: C, 66.62; H, 7.43; N, 8.44; Found: C, 66.71; H, 7.33; N, 8.35

EXAMPLE 120

Preparation of [S-[1R*,2S*(2S*,3R*)]]-N-[3-[(3-Amino-2-hydroxy-4-phenylbutyl)amino]-2-hydroxy-1-(phenylmethyl)-propyl]-N²-[(phenyl-methoxy)carbonyl]-L-valinamide (Compound 120)

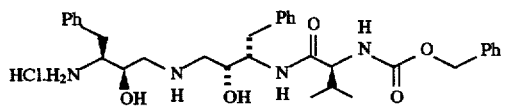

Compound 52 was converted to the title Compound 120 (used without further purification in the next Example) by a procedure analogous to that used for the synthesis of Compound 110.

¹H NMR (CD₃OD): δ 0.52 (d, J=6.6 Hz, 3H) 0.56 (d, J=6.6 Hz, 3H), 1.70 (m, 1H), 2.70 (m, 1H), 2.95 (m, 1H), 3.05 (m, 4H), 3.17 (m, 2H), 3.57 (d, J=7.2 Hz, 1H), 3.72 (m, 1H), 3.80 (m, 1H), 4.07 (m, 1H), 4.28 (m, 1H), 5.11 (s, 2H), 7.12–7.42 (m's, 15H).

EXAMPLE 121

Preparation of [S-[1R*,2S*(2S*,3R*)]]-N²-[(1-Dimethylethoxy)carbonyl]-N-[2-hydroxy-3-[[2-hydroxy-4-phenyl-3-[[N-[(phenylmethoxy)carbonyl]-L-valyl]amino]butyl]amino]-1-(phenylmethyl)-propyl]-L-asparaginamide (Compound 121)

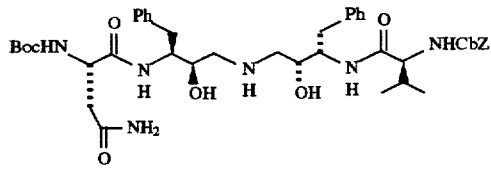

Compound 120 was reacted with Boc-L-asparagine by a procedure analogous to that used for the synthesis of Compound 55 (DMF only; 2 eq. of N-methylmorpholine added) to give the title Compound 121.

mp 199°–202° C.; $[\alpha]_D$=–31° (c 0.2, AcOH). Mass Spec.: FAB (M+H)⁺791. Analysis calculated for $C_{42}H_{58}N_6O_9 \cdot 0.61$ $H_2O$: C, 62.90; H, 7.44; N, 10.48; Found: C, 63.04; H, 7.33; N, 10.34.

EXAMPLE 122

Preparation of [R-(R*,S*)]-[[(Phenylmethyl)-imino] bis[2-hydroxy-1-(phenylmethyl)-3,1-propanediyl] biscarbamic acid, bis(1-methyl-ethylester (Compound 122)

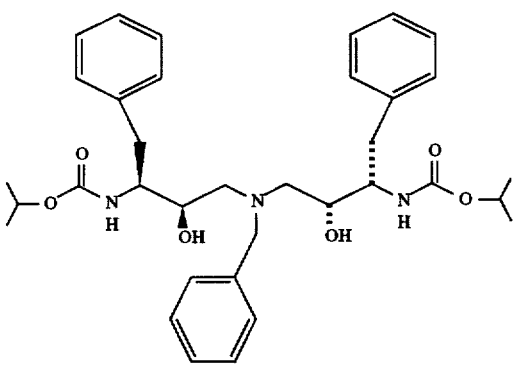

To a solution of Compound 32 (165 mg; 0.35 mmol) and 0.27 mL (1.56 mmol) of i-Pr₂NEt in 0.35 mL of dry DMF at 0° C. was added 0.78 mL (0.78 mmol) of isopropyl chloroformate. The reaction mixture was stirred at RT for 72 h, at which point it was quenched with saturated aqueous NaHCO₃ and extracted with Et₂O. The organic layer was washed with brine and dried (Na₂SO₄). The salts were filtered and the solvents removed in vacuo to give a residue, which was purified on silica gel (gradient of 75:25 to 50:50 hexane:EtOAc) to give 100 mg of Compound 122 (white solid).

¹H NMR (CDCl₃): δ 1.11 (d, 6H), 1.70 (1H), 1.17 (d, 6H), 2.50–2.59 (m, 4H), 2.70–2.83 (m, 4H), 3.40–3.51 (m, 2H), 3.60–3.83 (m, 5H), 4.69 (m, 2H), 4.76–4.82 (m, 2H), 7.13–7.35 (m, 15H).

EXAMPLE 123

Preparation of [R-(R*,S*)]-[Iminobis[2-hydroxy-1-(phenylmethyl)-3,1-propandiyl]biscarbamic acid, bis (1-methylethyl)ester (Compound 123)

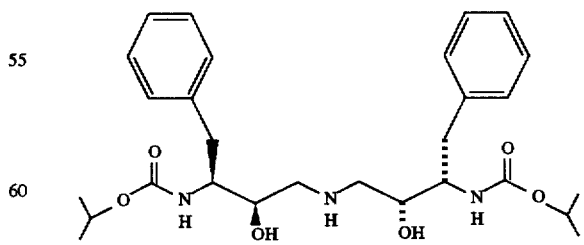

Compound 122 was converted to the title Compound 123 by a procedure analogous to that used for the synthesis of Compound 2.

| | Calc. | Found |
|---|---|---|
| C | 65.22 | 64.00 |
| H | 8.01 | 7.88 |
| N | 8.15 | 7.80 | m.p. 195–200° C.; [α]_D = −13.2° (c, 0.09, MeOH)
Mass spec. (CI) (M + H) 516
Elemental Analysis (%)
$C_{28}H_{41}N_3O_6 \cdot 0.63\ H_2O$

EXAMPLE 124

Preparation of [1S-[1R*,2R*(2S*,3R*)]]-[3-[[3-[[(1,1-Dimethylethoxy)carbonyl]amino]-2-hydroxy-4-phenylbutyl]amino]-2-hydroxy-1-(1phenyl-methyl)proyl]carbamic acid, phenylmethyl ester (Compound 124)

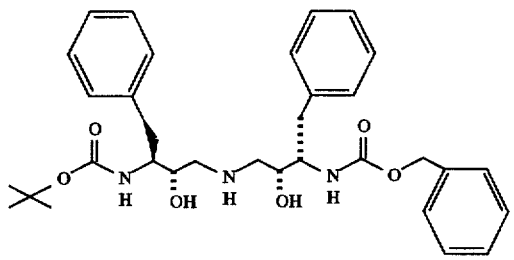

Compounds 27a and 44a (1 eq. of each) were reacted by a procedure analogous to that used for the synthesis of Compound 4b (white powder) to give the title Compound 124.

$^1$H NMR (DMSO-d$^6$): δ 1.30 (s, 9H), 2.57 (m, 6H), 2.80 (dd, J=5.5, 13.5, 1H), 3.01 (d, J=11 Hz, 1H), 3.41 (m, 1H), 3.50 (m, 1H), 3.60 (m, 1H), 3.70 (m, 1H), 4.73 (m, 1H), 4.85 (m, 1H), 4.88 (d, J=13 Hz, 1H), 4.93 (d, J=13 Hz, 2H), 6.40 (d, J=9 Hz, 1H), 7.27 (m, 15H).

EXAMPLE 125

Preparation of [S-[1R*,2S*(2R*,3R*)]-N-[3-[[3-[[(1,1-Dimethylethoxy)carbonyl]amino]-2-hydroxy-4-phenylbutyl]amino]-2-hydroxy-1-(phenylmethyl)propyl]-N$^2$[(phenylmethoxy)carbonyl]-L-valinamide (Compound 125)

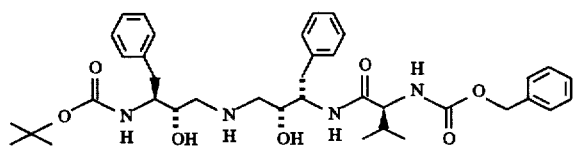

Compound 124 was converted to the title Compound 125 by a two-step procedure analogous to that used for the synthesis of Compound 115 (removal of Cbz group using conditions analogous to those used for Compound 7 (AcOH used in place of MeOH), and coupling of the resulting product with Cbz-valine analogous to Compound 55 (DMF only).

mp 175°–180° C.; [α]_D=−26.0° (c 0.15, MeOH). Mass Spec. FAB+ions: M+H=677. Analysis calc. for $C_{38}H_{52}N_4O_7 \cdot 0.95\ H_2O$: C, 65.77; H, 7.83; N, 8.07; Found C, 65.55; H, 7.59; N, 8.29.

EXAMPLE 126

Preparation of [1S-[1R*,2S*(2S*,3R*)]]-[3-[[3-[(3,3-Dimethylbutyl)amino]-2-hydroxy-4-phenylbutyl][[2-(trimethylsilyl)ethoxy]carbonyl]amino]-2-hydroxy-1-(phenylmethyl)propy-1]carbamic acid, 1,1-dimethylethyl ester (Compound 126)

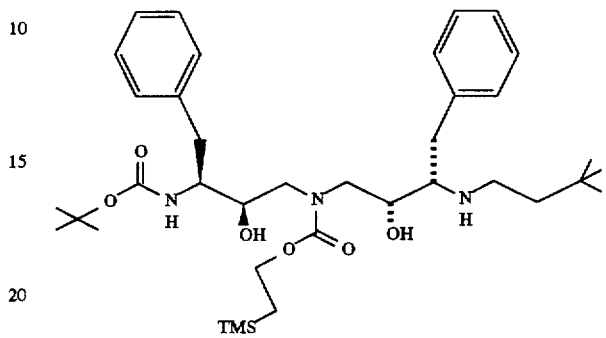

To a solution of Compound 48 (300 mg, 0.51 mmol) in 1.55 mL MeOH (adjusted to pH 6 with AcOH) was added 3,3-dimethylbutylraldehyde (70 μl, 0.56 mmol, 1.1 eq.) and a small amount of pulverized 4 Å molecular sieves. To this mixture at RT was added NaCNBH$_3$ (48 mg, 0.77 mmol) in two portions. The reaction was quenched after 2 h with 10 mL saturated NaHCO$_3$ solution and extracted with CH$_2$Cl$_2$. The combined extracts were washed with brine, dried over MgSO$_4$, filtered, concentrated, and dried in vacuo to yield 330 mg crude oil. The residue was purified by chromatography on a 3×16 cm silica gel column, eluting with CH$_2$Cl$_2$, then 98.9:1:0.1 and 97.8:2:0.2 CH$_2$Cl$_2$:MeOH:NH$_4$OH to afford 238 mg (69%) of Compound 126.

Mass Spec: 672 (M+H)$^+$.

EXAMPLE 127

Preparation of [1S-[1R*,2S*(2S*,3R*)]]-[3-[[3-[(3,3-Dimethylbutyl)amino]-2-hydroxy-4-phenylbutyl]amino]-2-hydroxy-1-(phenylmethyl)propyl]carbamic acid, 1,1-dimethylethyl ester (Compound 127)

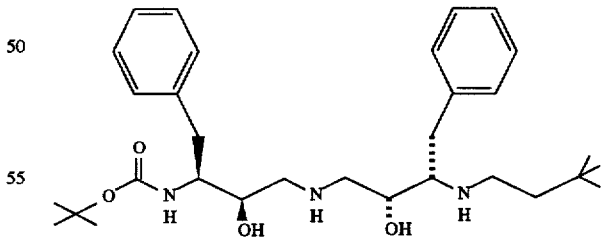

Compound 126 was converted to the title Compound 127 by a procedure analogous to the one used for the synthesis of Compound 21.

mp 89°–91° C.; [α]_D=+9° (c 0.24, MeOH). Mass Spec: Fab (M+H)$^+$: 528. Analysis calculated for $C_{31}H_{49}N_3O_4 \cdot 0.74\ H_2O$: C, 68.82; H, 9.40; N, 7.77; Found: C, 68.57; H, 9.16; N, 8.02.

EXAMPLE 128

Preparation of [1S-[1R*,2S*(2S*,3R*)]]-[3-[[3-Amino-2-hydroxy-4-phenylbutyl][(9H-fluoren-9-ylmethoxy)carbonyl]amino]-2-hydroxy-1-(phenylmethyl)propyl]carbamic acid, 1,1-dimethylethyl ester, monoacetate salt (Compound 128)

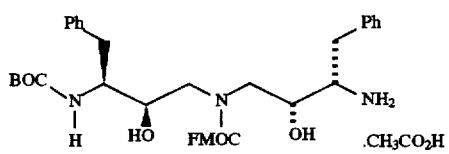

A solution of 1.69 g (2.1 mmoles) of Compound 107 and 2.0 ml of 1,4-cyclohexadiene in 60 ml of EtOH containing 225 mg of 10% Pd/C catalyst was stirred under a hydrogen atmosphere for 3.5 hr. The catalyst was removed by filtration through Celite and 0.5 ml of HOAc added. Evaporation to dryness gave 1.8 g (assumed 100% yield) of Compound 128 as a white solid. [TLC: $R_f$=0.38, 10% MeOH—$CH_2Cl_2$].

Mass Spec. 666 (M+H).

EXAMPLE 129

Preparation of [1S-[1R*,2S*(2S*,3R*)]]-[3-[[(9H-Fluoren-9-ylmethoxy)carbonyl][3-(formylamino)-2-hydroxy-4-phenylbutyl]amino]-2-hydroxy-1-(phenylmethyl)propyl]carbamic acid, 1,1-dimethylethyl ester (Compound 129)

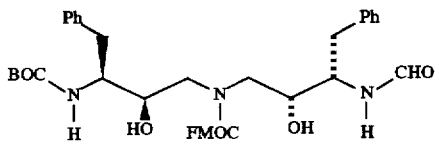

Formic acetic anhydride was prepared by the addition of 260 μl of formic acid to 745 μl of acetic anhydride at 0° C. and the resulting solution then heated at 50° C. for 2 h. The anhydride was dissolved in 5 ml of THF and added to a slurry of 1.8 g (assumed 2.1 mmoles) of Compound 128 in 20 ml of THF. The reaction was stirred at 0° C. for 30 min, then at RT for 30 min, and then evaporated to dryness to yield the crude product as a white foam. This material was purified by flash chromatography on a 75 cc column of silica gel. Elution with 50% EtOAc-hexane, followed by 100% EtOAc gave 1.16 g (1.67 mmole, 80% yield over two steps) of Compound 129 as a solid white foam. [TLC: $R_f$=0.29, EtOAc] Mass Spec. 694 (M+H).

EXAMPLE 130

Preparation of [1S-[1R*,2S*(2S*,3R*)]]-[3-[[(9H-Fluoren-9-ylmethoxy)carbonyl][2-hydroxy-3-(methylamino)-4-phenylbutyl]amino]-2-hydroxy-1-(phenylmethyl)propyl]carbamic acid, 1,1-dimethylethyl ester, monoacetate salt (Compound 130)

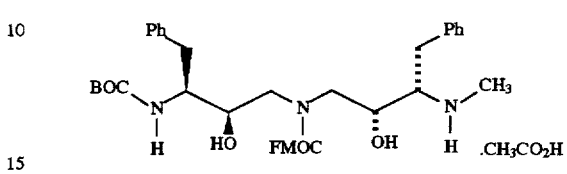

To a solution of 785 mg (1,13 mmoles) of Compound 129 in 10 ml of THF at 0° C. was added dropwise 2.85 ml of 2 M borane-methyl sulfide in THF. After foaming ceased the reaction mixture was heated at 50° C. for 1 h then cooled to 0° C. and excess borane hydrolyzed by the dropwise addition of approx. 10 ml of MeOH. After reaction ceased, 0.5 ml of HOAc was added and the solution heated at 50° C. for 6 h to destroy the amine-boron complex. The solution was evaporated to dryness and the residue purified by flash chromatography on a 35 cc column of silica gel (elution with 100% EtOAc, 10% MeOH-EtOAc, and 20% MeOH-EtOAc). After the appropriate fractions were combined, 0.5 ml of HOAc was added and the solvent removed to yield 625 mg (0.84 mmole, 75% yield) of Compound 130 as a solid white foam. This material contained approximatly 3 equivalents of HOAc by $^1$H NMR. [TLC: $R_f$=0.43, 10% MeOH—$CH_2Cl_2$].

Mass Spec. 690 (M+H).

EXAMPLE 131

Preparation of [S-[1R*,2S*(2S*,3R*)]]-[3-[3-[[(1,1-Dimethylethoxy) carbonyl]amino]-2-hydroxy-4-phenylbutyl][(9H-fluoren-9-ylmethoxy)-carbonyl]amino]-2-hydroxy-1-(phenyl-methyl)propyl]methylcarbamic acid, 1,1-dimethylethyl ester (Compound 131)

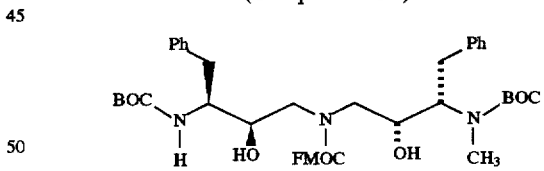

To a solution of 160 mg (0.166 mmole, based on 3 eq of HOAc) of Compound 130 and 137 mg (0.63 mmole) of di-t-butyl dicarbonate in 1 ml of DMF at 0° C. was added, dropwise, 146 μl of $Et_3N$. After 30 min an additional 65 mg of di-t-butyl dicarbonate and 75 μl of $Et_3N$ were added and stirring continued for an additional 30 min. The reaction was diluted with EtOAc and washed with water and brine, dried (MgSO$_4$), and the solvent removed to yield a residue which was purified by flash chromatography on a 20 cc column of silica gel (elution with 25% EtOAc/hexane, followed by 50% EtOAc/hexane) to give 129 mg (0.166 mmole, 89% yield) of Compound 131 as a solid white foam. [TLC: $R_f$=0.30, 50% EtOAc/Hexane]

Mass Spec. 780 (M+H).

EXAMPLE 132

Preparation of [1S-[1R*,2S*(2S*,3R*)]]-3-[[(1,1-Dimethylethoxy)carbonyl]amino]-2-hydroxy-4-phenylbutyl]amino]-2-hydroxy-1-(phenylmethyl)-propyl]methylcarbamic acid, 1,1-dimethylethyl ester (Compound 132)

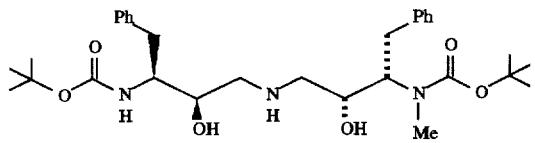

Compound 131 was converted to the title Compound 132 by a procedure analogous to the procedure used for the synthesis of Compound 42 (CH$_2$Cl2 used in place of DMF).

[α]$_D$=−19.6° (c=0.6, MeOH). MS: (M+H)$^+$=558; MW=557; Anal. Calc. for C$_{31}$H$_{47}$N$_3$O$_6$•0.33 H$_2$O: C, 66.06; H, 8.52; N, 7.46. Found: C, 66.00; H, 8.47; N, 7.52.

EXAMPLE 133

Preparation of [S-[1R*,2S*(2S*,3R*)]]-N-[3-[[(1 1-Dimethylethoxy)carbonyl]-amino]-2-hydroxy-4-phenylbutyl][(9H-fluoren-9-ylmethoxy)carbonyl]amino]-2-hydroxy-1-(phenylmethyl)propyl]-N-methyl-N$^2$-[(phenylmethoxy)carbonyl]-L-valinamide (Compound 133)

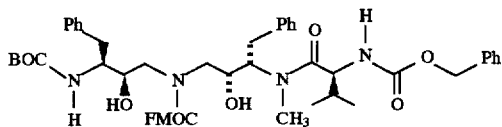

To a solution of 75 mg (0.087 mmole) of Compound 130 in 0.5 ml of MeOH was added a solution of 6.2 μl (0.087 mmole) of AcCl in 1 ml of MeOH. The solution was evaporated to dryness and the residue co-evaporated from toluene to remove traces of HOAc. The residue was dried under high vacumn for 2 h to give 68 mg of the hydrochloride salt as a white solid. This material was diluted with 1 ml of CH$_2$Cl$_2$, cooled to 0° C. and 44 mg (0.174 moles) Cbz-L-valine and 49 mg (0.192 mmole) of BOP-Cl added as solids, followed by 46 μl (0.261 mmole) of i-Pr$_2$NEt. The solution was stirred at 0° C. for 4.5 hr and then placed directly on a 16 cc column of silica gel (elution with 50% EtOAc/hexane afforded 70 mg (0.077 mmole, 88% yield) of the title Compound 133 as a white foam. [TLC: R$_f$=0.27, 50% EtOAc-hexane].

Mass Spec.: 913 (M+H).

EXAMPLE 134

Preparation of [S-[1R*,2S*(2S*,3R*)]]-N-[3-[[(1,1-Dimethylethoxy)carbonyl]amino]-2-hydroxy-4-phenylbutyl]amino]-2-hydroxy-1-(phenylmethyl)-propyl]-N-methyl-N$^2$-[(phenylmethoxy)carbonyl]-L-valinamide (Compound 134)

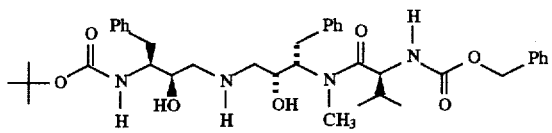

Compound 133 was converted to the title Compound 134 (solid white foam) by a procedure analogous to the procedure used for the synthesis of Compound 42 (CH$_2$Cl$_2$ used in place of DMF).

[α]$_D$=−35.6° (c 0.82, MeOH). Mass Spec.: 691 (M+H). Elemental Analysis (%); for C$_{39}$H$_{54}$N$_4$O$_7$·0.36 H$_2$O; C; 67.18; H; 7.91; N; 8.03; Found: C; 67.12; H; 7.83; N; 8.09

EXAMPLE 135

Preparation of [1S-[1R*,2S*(2S*,3R*)]]-[3-[[[(1,1-Dimethylethyl)amino]-carbonyl]methylamino]-2-hydroxy-4-phenylbutyl][(9H-fluoren-9-ylmethoxy)-carbonyl]amino]-2-hydroxy-1-(phenylmethyl)propyl]-carbamic acid, 1,1-dimethylethyl ester (Compound 135)

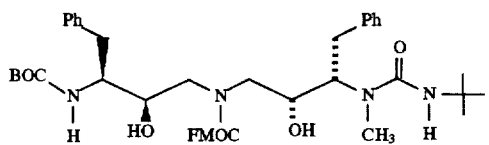

A solution of 110 mg of Compound 130 (0.13 mmole, material contained 3 eq. of HOAc by NMR) and 14.5 μl (0.16 mmole) of t-butyl isocyanate in 2 ml of CH$_2$Cl$_2$ was stirred at RT for 3 hr. An additional 7 μl of t-butyl isocyanate was added and stirring continued for 2.5 hr. The solution was evaporated to dryness to give 112 mg of a white foam which was combined with material from a similar reaction (total 130 mg) and purified by flash chromatography on a 20 cc column of silica gel (elution with 50% EtOAc/hexane) to afford 110 mg (0.14 mmole, 88% yield) of the title Compound 135 as a solid white foam. [TLC: R$_f$=0.66, 100% EtOAc].

Mass Spec. 799 (M+H).

EXAMPLE 136

Preparation of [1S-[1R*,2S*(2S*,3R*)]]-[3-[[3-[[[(1,1-Dimethylethyl)amino]carbonyl]methylamino]-2-hydroxy-4-phenylbutyl]amino]-2-hydroxy-1-(phenylmethyl))propyl]carbamic acid, 1,1-dimethylethyl ester (Compound 136)

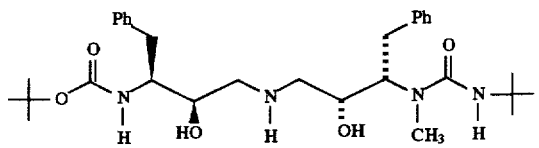

Compound 135 was converted to the title Compound 136 (solid white foam) by a procedure analogous to the procedure used for the synthesis of Compound 42 (CH₂Cl₂ used in place of DMF).

[TLC: $R_f$=0.31, CH$_2$Cl$_2$—MeOH—NH$_4$OH, 90:10:1]; $[\alpha]_D$=−15.2° (c=0.27, MeOH); Mass Spec.: 557 (M+H). Calc. for C$_{31}$H$_{48}$N$_4$O$_5$·0.28 H$_2$O (561.79): C,66.28; H, 8.71, N, 9.97. Found: C, 66.40; H, 8.59, N, 9.85.

EXAMPLE 137

Preparation of [1S-[1R*,2S*(2S*,3R*)]]-[3-[[3-[[[(1,1-Dimethylethyl)amino]thioxomethyl]amino]-2-hydroxy-4-phenylbutyl]amino]-2-hydroxy-1-(phenylmethyl))propyl]carbamic acid, 1,1-dimethylethyl ester (Compound 137)

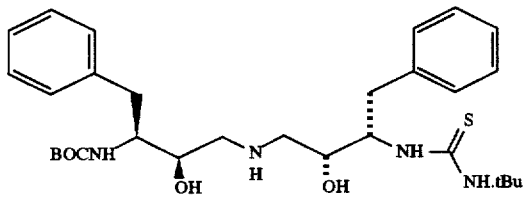

Compound 48 was converted to the title Compound 137 (white solid) by a two-step procedure analogous to that used for the preparation of Compound 50 (t-butylisothiocyanate used in place of t-butylisocyanate).

m.p. 85°–87° C. ("softening" at 75–85° C.). $[\alpha]_D$=−12.8° (c=0.40, MeOH)

COMPOUND 138

Preparation of [R-(R*,S*)]-[Iminobis[2-hydroxy-1-(phenylmethyl)-3,1-propandiyl]]biscarbamic acid, bis(1,1-dimethylpropyl)ester (Compound 138b)

(a) Compound 138a

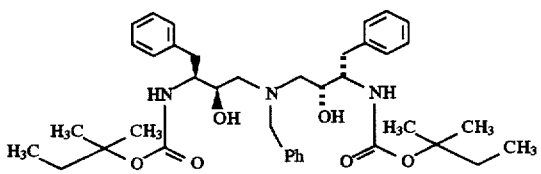

Compound 138a was obtained as a white solid by reaction of Compound 32 with di-tert-amyldicarbonate using conditions analogous to those used for the synthesis of Compound 131 (i-Pr₂NEt used instead of Et₃N).

Mass Spec. 662 (M+H)

(b) Compound 138b

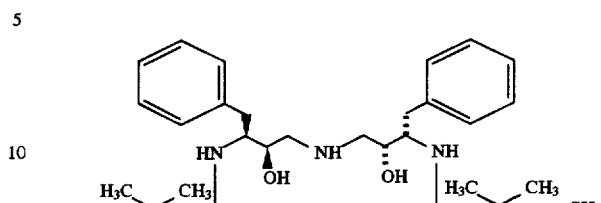

Compound 138a was converted to Compound 138b (white solid) by a procedure analogous to that used for the preparation of Compound 2.

| m.p. 161–163° C.; $[\alpha]_D$ = +1.47° (c = 0.2, CH$_2$Cl$_2$) Elemental Analysis (%) for C$_{32}$H$_{49}$N$_3$O$_6$·0.52 H$_2$O | | |
|---|---|---|
| | Calc. | Found |
| C | 66.13 | 66.42 |
| H | 8.68 | 8.73 |
| N | 7.23 | 6.94 |

EXAMPLE 139

Preparation of [1S-(1R*,2S*)]-[Iminobis[2-hydroxy-1-(phenylmethyl)-3,1-propanediyl]] biscarbamic acid, bis(2,2-dimethylpropyl)ester (Compound 139)

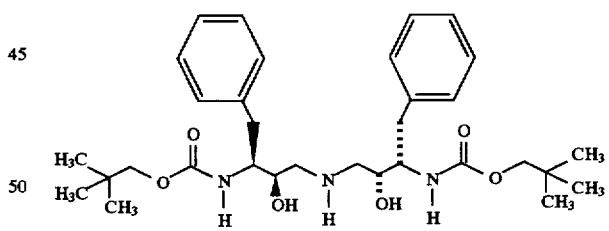

Compound 139 was obtained as a solid by reaction of Compound 32 with neopentyl chloroformate (J. Org. Chem. 49, 1174 (1984)), and subsequent deprotection analogous to the two step procedure used for the synthesis of Compound 123.

m.p. 152° 154° C.; $[\alpha]^{20}_D$=−12.5° (c=0.1, CH$_3$OH); TLC:$R_f$=0.43 (silica gel); Solvent:90:9:1; CH$_2$Cl$_2$:MeOH:NH$_4$OH.

EXAMPLE 140

Preparation of [1S-[1R*,2S*(2S*,3R*)]]-[3-[[3-(5,5-Dimethyl-2-oxo-3-oxazolidinyl)-2-hydroxy-4-phenylbutyl]amino]-2-hydroxy-1-(phenylmethyl)-propyl]carbamic acid, 1,1-dimethylethyl ester (Compound 140f)

(a) Compound 140a

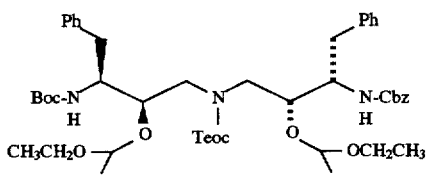

To a solution of the Cbz-intermediate formed during the first step of the synthesis of Compound 48 (100 mg, 0.138 mmol) in dry $CH_2Cl_2$ (1 mL) at 0° C. was added ethyl vinyl ether (300 μL, 3.14 mmol), followed by pyridinum p-toluene sulfonate (10.7 mg, 0.042 mmol) and the reaction stirred at RT for 18 h. The reaction mixture was diluted with EtOAc and washed with saturated $NaHCO_3$. The combined organic extracts were dried ($MgSO_4$), filtered and concentrated in vacuo to yield a gummy white solid which was purified by silica gel chromatography, eluting with EtOAc (10 to 40%)/hexane to afford 105 mg of Compound 140a (88% yield) as a white residue.

TLC (silica gel/ Hexanes:EtOAc 1:1): $R_f$=0.7

(b) Compound 140b

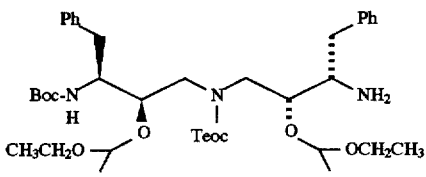

Compound 140a was converted to Compound 140b (colorless oil) by a procedure analogous to that used for the synthesis of Compound 54.

Mass Spec.: 732 (M+H)

(c) Compound 140c

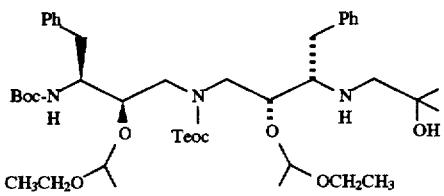

To a solution of Compound 140b (175 mg, 0.24 mol) in EtOH (2 mL) in a pressure tube was added isobutylene oxide (0.66 mL, 7.17 mmol) and the tube sealed under argon and heated at 110° C. for 4 h, and then at 150° C. for 2 h. The solvents were removed in vacuo, and the oily residue purified by silica gel chromatography, eluting with $CH_3OH$ (1 to 10%)/$CHCl_3$ to give 138 mg of Compound 140c (71% yield) as a colorless gummy residue.

Mass Spec. 805 (M+H)

(d) Compound 140d

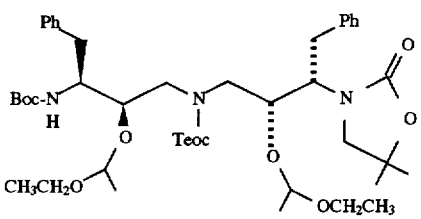

To a solution of Compound 140c (103 mg, 0.13 mmol) in dry $CH_2Cl_2$ (375 μL) at 0° C. was added pyridine (125 μL, 1.54 mmol), followed by 20% $COCl_2$ in toluene (166 μL, 1.93M) and the mixture stirred at 0° C. for 25 min. The reaction mixture was quenched with saturated $NaHCO_3$, extracted with EtOAc, the organic phase dried ($MgSO_4$), filtered and concentrated in vacuo to afford 98 mg of Compound 140d (ca. 91% crude yield) as yellow foamy residue.

TLC (silica gel/$CHCl_3$:MeOH 98:2): $R_f$=0.26

(e) Compound 140e

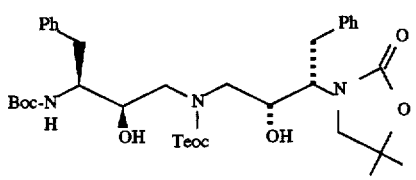

To a solution of Compound 140d (98 mg, 0.12 mmol) in 1.5 mL acetone was added pyridinum p-toluene sulfonate (98 mg, 0.12 mmol) and the yellow solution stirred at RT for 18 h. The solvent was removed and the residue taken into EtOAc (10 mL) and washed with saturated $NaHCO_3$. The organic extracts were dried (anhydrous $Na_2SO_4$), filtered and concentrated to dryness. The crude product was purified by silica gel chromatography, eluting with $CH_3OH$ (1 to 10%)/$CHCl_3$ to afford 68 mg of Compound 140e (81% yield) as a yellow residue.

Mass Spec. 686 (M+H)

(f) Compound 140f

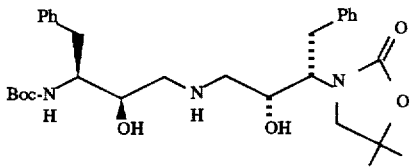

Compound 140e was converted to the title Compound 140f (yellow solid) by a procedure analogous to that used for the synthesis of Compound 21.

m.p. 55°–58° C., $[\alpha]_D$=–3.96° (c=0.2, $CH_2Cl_2$). Analysis for: $C_{30}H_{43}N_3O_6 \cdot 2.19\ H_2O$; Calculated: C, 62.00; H, 8.22; N, 7.23; Found: C, 62.25; H, 7.63; N, 6.98.

EXAMPLE 141

Preparation of [S-[1R*,2S*(2S*,3R*)]]-N-[3-[[3-[[(1,1-Dimethylethoxy)carbonyl]methylamino]-2-hydroxy-4-phenylbutyl]amino]-2-hydroxy-1-(phenylmethyl)propyl]-N²-[(phenylmethoxy)-carbonyl]-L-valinamide] (Compound 141e)

(a) Compound 141a

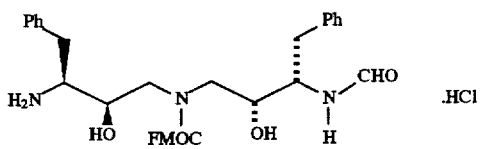

Compound 129 was converted to Compound 141a (yellow solid) by a procedure analogous to that used for the synthesis of Compound 32.

(b) Compound 141b

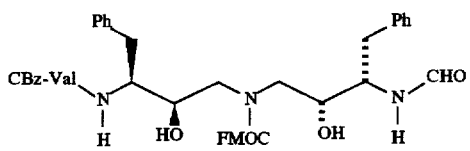

Compound 141a was converted to Compound 141b (white solid) by a procedure analogous to that used for the synthesis of Compound 51 (CH$_2$Cl$_2$ was used as solvent). TLC: R$_f$=0.21, 100% EtOAc.

(c) Compound 141c

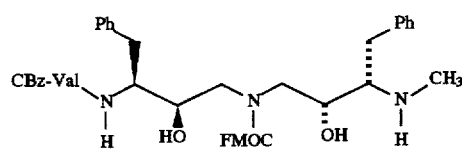

Compound 141b was converted to Compound 141c (white foam) by a procedure analogous to that used for the synthesis of Compound 130. TLC: R$_f$=0.42, CH$_2$Cl$_2$—MeOH—NH$_4$OH, 90:10:1.

(d) Compound 141d

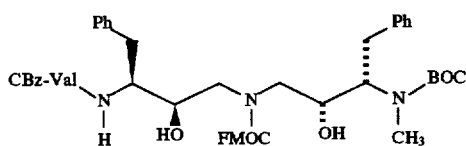

Compound 141c was converted to Compound 141d (white foam) by a procedure analogous to that used for the synthesis of Compound 131.

(e) Compound 141e

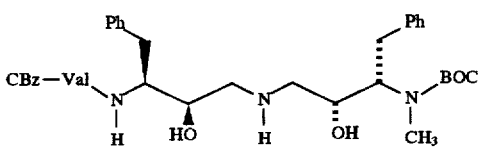

Compound 141d was converted to Compound 141e (white foam) by a procedure analogous to that used for the synthesis of Compound 42. TLC: R$_f$=0.38, CH$_2$Cl$_2$:MeOH:NH$_4$OH, 90:10:0.1 (UV detection).

| | | [α]$_D$ = −27.9° (c 0.72, MeOH) Elemental Analysis (%) C$_{30}$H$_{54}$N$_4$O$_7$ | |
|---|---|---|---|
| | | Calc. | Found |
| | C | 67.80 | 67.51 |
| | H | 7.88 | 7.94 |
| | N | 8.11 | 8.14 |

EXAMPLE 142

Preparation of [1S-[1R*,2S*(2S*,3R*)]]-[3-[[3-[[(1,1-Dimethylethoxy) carbonyl]amino]-2-hydroxy-4-phenylbutyl]amino]-2-methoxy-1-(phenylmethyl) propyl]carbamic acid 1,1-dimethylethyl ester (Compound 142d)

(a) Compound 142a

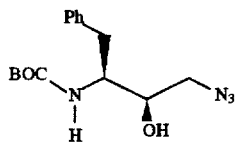

A solution of 300 mg (1.14 mmole) of Compound 1b(i), 186 mg (2.85 mmoles) of NaN$_3$ and 111 mg (2.05 mmoles) of NH$_4$Cl in 6 ml of MeOH was stirred at reflux overnight. The white solid residue obtained on removal of solvent was dissolved in EtOAc and washed with H$_2$O and brine. Drying (MgSO$_4$) and concentration gave 300 mg (0.98 mmole, 86%) of Compound 142a as a white solid. TLC: R$_f$=0.21, 25% EtOAc-hexane.

(b) Compound 142b

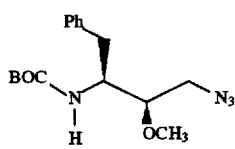

To a suspension of 48 mg (1.2 mmoles) of 60% NaH (hexane washed) in 1 ml of dry THF at RT was added a solution of 295 mg (0.96 mmole) of Compound 142a in 4 ml of THF. The reaction was stirred for 2 hr at which time 89 µl (1.44 moles) of methyl iodide was added. Stirring was continued for 1 hr then the reaction was diluted with EtOAc and washed with H$_2$O, 10% Na$_2$S$_2$O$_3$, and brine. After drying (MgSO$_4$), removal of solvent gave a white solid residue which was purified by flash chromatography on a 130 cc column of silica gel (elution with 20% EtOAc/hexane) to give 206 mg (0.64 mmole, 67%) of Compound 142b as a white solid. TLC: R$_f$=0.55, 25% EtOAc-hexane.

(c) Compound 142c

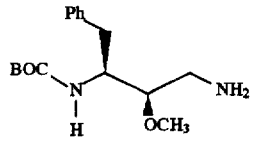

A solution of 150 mg (0.47 mmole) of Compound 142b in 3 ml of MeOH containing 45 mg of 10% Pd/C was hydrogenated at RT for 1.5 hr (balloon). The reaction was diluted with additional MeOH. 0.5 ml of NH₄OH was added, and stirring was continued for 15 min. The catalyst was removed by filtration through Celite (MeOH wash) and the filtrate concentrated. The residue was taken up in CH₂Cl₂, dried (MgSO₄), and the solvent evaporated to afford 122 mg (0.41 mmole, 88%) of Compound 142c as a white solid. TLC: $R_f$=0.28, CH₂Cl₂:MeOH:NH₄OH, (90:10:1).

(d) Compound 142d

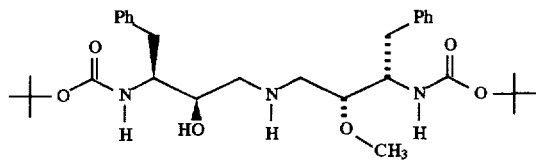

Compounds 142c and 1b(i) were reacted by a procedure analogous to that used for the synthesis of Compound 4b to give the title Compound 142d (white foam). TLC: $R_f$=0.37, CH₂Cl₂:MeOH:NH₄OH, 90:10:0.1

| | [α]_D = –3.9° (c 0.67, MeOH) Elemental Analysis (%) C₃₁H₄₇N₃O₆·0.78 H₂O | |
|---|---|---|
| | Calc. | Found |
| C | 65.11 | 64.75 |
| H | 8.56 | 8.22 |
| N | 7.35 | 7.71 |

EXAMPLE 143

Preparation of [1S-[1R*,2S*)]][[[[2-(Trimethyl-silyl)ethoxy]carbonyl]imino]bis[2-hydroxy-1-(phenylmethyl)-3,1-propanediyl]-biscarbamic acid, 1,1-dimethylethyl 2,3-dihydro-1H-inden-1-yl ester (Compound 143)

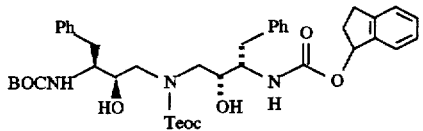

To a solution of 53 mg (0.0924 mmol) of Compound 48 in 200 μL of CH₃CN at RT were added 29 mg of Compound 67a and 26 μL of Et₃N. After 22 h, an additional 3 mg of Compound 67a and 5 μL of Et₃N were added to the reaction mixture. After 48 h, the mixture was diluted with 50 mL of CH₂Cl₂ and washed with 10% citric acid and saturated NaHCO₃. The organic layer was dried over Na₂SO₄, filtered and concentrated in vacuo. Flash chromatography on silica gel eluting with 10–50% EtOAc-hexane provided 57 mg (84%) of Compound 143.

EXAMPLE 144

Preparation of [1S-(1R*,2S*)]-[Iminobis[2-hydroxy-1-(phenylmethyl)-3,1-propanediyl)]-bis [carbamic acid], 1,1-dimethylethyl-2,3-dihydro-1H-inden-1-yl ester (Compound 144)

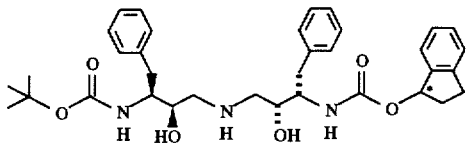

Compound 143 was converted to the title Compound 144 by a procedure analogous to that used for the synthesis of Compound 21. (1:1 mixture R:S at *)

| | mp 157–166° C.; [α]²⁰_D = –11° (c = 0.35, CH₃OH) Mass spec. 604 (M + H)⁺ Elemental Analysis (%) C₃₅H₄₅N₃O₆·0.71 H₂O | |
|---|---|---|
| | Calc. | Found |
| C | 68.18 | 68.40 |
| H | 7.59 | 7.55 |
| N | 6.81 | 6.59 |

EXAMPLE 145

Preparation of [1S-(1R*,2S*)]-[Iminobis[2-hydroxy-1-(phenylmethyl)-3,1-propanediyl)] biscarbamic acid, 1,1-dimethylethyl(R)-2,3-dihydro-1H-inden-1-yl ester (Compound 145)

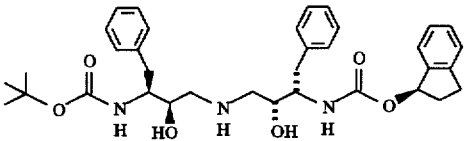

Compound 48 was converted to the title Compound 145 by a two-step procedure analogous to that used for the synthesis of Compound 144 except that the p-nitrophenyl carbonate of R-(–)-indanol was used.

| | mp 187–190° C.; [α]²⁰_D = –4.9° (c = 0.35, DMSO) Mass spec. 604 (M + H)⁺ Elemental Analysis (%) C₃₅H₄₅N₃O₆ + 0.51 H₂O | |
|---|---|---|
| | Calc. | Found |
| C | 68.58 | 68.24 |
| H | 7.57 | 7.29 |
| N | 6.86 | 7.20 |

EXAMPLE 146

Preparation of [1S-(1R*,2S*)]-[Iminobis[2-hydroxy-1-(phenylmethyl)-3,1-propanediyl)] biscarbamic acid, 1,1-dimethylethyl(S)-2,3-dihydro-1H-inden-1-yl ester (Compound 146)

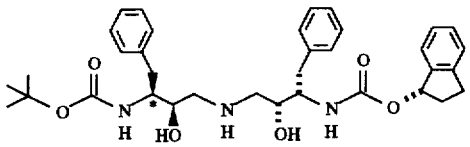

Compound 48 was converted to the title Compound 146 by a two-step procedure analogous to that used for the synthesis of Compound 144 except that the p-nitrophenyl carbonate of S-(+)-indanol was used.

mp 175–178° C.; $[\alpha]^{20}_D = -26°$ (c = 0.12, $CH_3OH$)
Mass spec. 604 (M + H)$^+$
Elemental Analysis (%)
$C_{35}H_{45}N_3O_6 \cdot 0.25\ H_2O$

|   | Calc. | Found |
|---|-------|-------|
| C | 69.12 | 68.96 |
| H | 7.54  | 7.62  |
| N | 6.91  | 7.07  |

EXAMPLE 147

Preparation of [1S-(1R*,2S*)]-[[Iminobis[2-hydroxy-1-(phenylmethyl)-3,1-proanediyl]] biscarbamic acid, 1,1-dimethylethyl 2,3-dihydro-2-[(1,1-dimethylethyl)dimethylsilyl]oxy]-1H-inden-1-yl-ester, 1:1 mixture of 1R,2R- and 1S,2S-diastereomers on indane ring (Compound 147d)

(a) Compound 147a

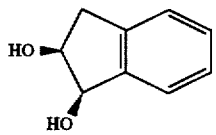

To a solution of 200 mg of $OsO_4$ in 100 mL of dry $CH_2Cl_2$ were added 14.6 g (125 mmol) of N-methylmorpholine oxide and 15.2 g (125 mmol) of phenylboronic acid. To the resulting solution was added a solution of 11.6 g of indene in 200 mL of $CH_2Cl_2$ over 10 min. The resulting orange solution was stirred at RT for 45 min and the reaction quenched with 10% sodium thiosulfate (RT, 1 hr). The mixture was diluted with EtOAc, washed with brine and the organic layer dried over $Na_2SO_4$, filtered, and concentrated to give 27 g of a phenylboronate intermediate. The solid was dissolved in 250 mL of THF and 300 mL of 2N NaOH was added. The mixture was cooled to 0° C. and treated dropwise with 200 mL of 30% $H_2O_2$. The mixture was stirred at RT for 2 h and at 50° C. for 1 h. After cooling to RT, the aqueous layer was saturated with NaCl, diluted with 500 mL of EtOAc and the organic layer separated and concentrated in vacuo. The aqueous layer was extracted with EtOAc and the combined organics washed with brine. The organic layer was dried over $Na_2SO_4$, filtered, and concentrated in vacuo to give 13.3 g of a residue. Flash chromatography of the residue on silica gel, eluting with 10–100% EtOAc-hexane, provided 6.64 g (44%) of Compound 147a.

(b) Compound 147b(i)

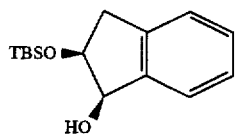

and
Compound 147b(ii)

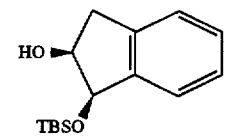

To a solution of the diol Compound 147a in 70 mL of DMF were added 6.4 g (42 mmol) of t-butyl-dimethylsilyl chloride and 3.6 g (53 mmol) of imidazole. The mixture, containing Compounds 147b(i) and 147b(ii), was stirred at RT for 24 h and the solvent removed in vacuo. The residue was taken up in $Et_2O$ and washed with saturated $NaHCO_3$. The organic layer was dried over $Na_2SO_4$, filtered, and concentrated in vacuo to give 9.27 g of a colorless oil. Flash chromatography on silica gel, eluting with 0–10% $Et_2O$-hexane, provided 1.38 g (26%) of Compound 147b(i) as a colorless oil.

(c) Compound 147c

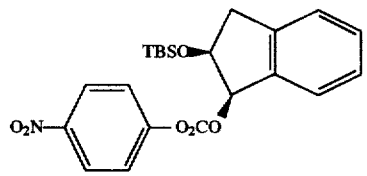

Compound 147b(i) was converted to Compound 147c by a procedure analogous to that used for the synthesis of Compound 67a [pyridine was used as base and co-solvent (3:1 $CH_2Cl_2$/pyridine)].

(d) Compound 147d

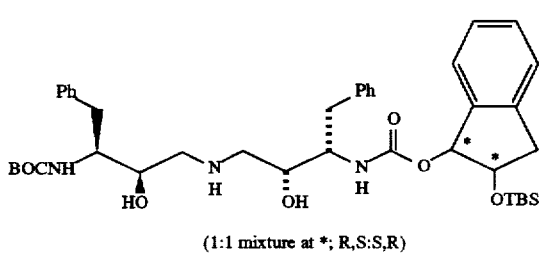

(1:1 mixture at *; R,S:S,R)

To a solution of 211 mg (0.476 mmol) of Compound 54 in 2 mL DMF at RT were added 0.26 mL of i-$Pr_2NEt$ and then a solution of 225 mg (0.523 mmol) of Compound 147c in 2 mL of $CH_2Cl_2$. The mixture was stirred at RT for 72 h then diluted with EtOAc and washed with 0.1N NaOH and brine. The organic layer was dried over $Na_2SO_4$, filtered and concentrated in vacuo to give 381 mg of crude material. Flash chromatography on silica gel, eluting with 95:5:0.25 $CHCl_3/CH_3OH/NH_4OH$, provided 144 mg (41%) of the title Compound 147d.

EXAMPLE 148

Preparation of [1S-(1R*, 2S*)]-[Iminobis[2-hydroxy-1-(phenylmethyl)-3,1-propanediyl)] biscarbamic acid, 1,1-dimethylethyl 2,3-dihydro-2-hydroxy-1H-inden-1-yl ester (Compound 148)

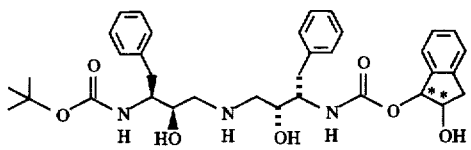

*1:1 Mixture of diastereomers (R,S:S,R)

To a solution of 143 mg (0.195 mmol) of Compound 147d in 1.0 mL of dry THF at 0° C. was added 5 mL of a cold (0° C.) HF-pyridine solution (prepared by adding 1 mL of HF-pyridine to an ice cold solution of 2 mL pyridine in 7 mL of dry THF). The resulting solution was stirred at 0° C. for 2 h and at RT for 2 h. The mixture was diluted with $CHCl_3$ and washed with saturated $NaHCO_3$ and brine. The organic layer was dried over $Na_2SO_4$, filtered, and concentrated in vacuo to give 123 mg (~100%) of the title Compound 148. The compound was triturated with $Et_2O$ and lyophilized from dioxane.

mp 135–140° C. (soft at 75° C.); $[\alpha]^{20}_D = -3°$ (c 0.20, $CH_3OH$)
Mass spec. 620 $(M + H)^+$
Elemental Analysis (%)
$C_{35}H_{45}N_3O_7 \cdot 0.054\ H_2O$

|   | Calc. | Found |
|---|-------|-------|
| C | 66.78 | 66.86 |
| H | 7.38  | 7.28  |
| N | 6.67  | 6.59  |

EXAMPLE 149

Preparation of [1S-(1R*,2S*)]-[[[[2-(Trimethylsilyl)ethoxylcarbonyl]imino]bis-[2-hydroxy-1-(phenylmethyl)-3,1-propanediyl]]biscarbamic acid, 1,1-dimethylethyl 1,1-dimethyl-4-[[(phenylmethoxy)carbonyl]amino]butyl ester (Compound 149e)

(a) Compound 149a

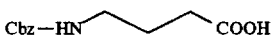

Compound 149a was prepared from 4-aminobutyric acid using a procedure analogous to that used for the synthesis of Compound 85a.

(b) Compound 149b

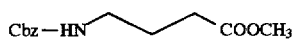

Thionyl chloride (2.91 ml; 40 mmol) was added dropwise to a solution of Compound 149a (4.74 g; 20 mmol) in 65 ml of MeOH at −20° C. After warming to RT, the reaction mixture was stirred for 18 hr then diluted with $Et_2O$ and the resulting organic layer washed with saturated $NaHCO_3$ and brine. After drying over $MgSO_4$, the organic layer was concentrated to afford 4.475 g (89%) of crude Compound 149b as a colorless oil. A 3.5 g portion of this material was chromatographed on a 5×15 cm silica gel column using hexane:EtOAc, 85:15 and hexane:EtOAc, 75:25 as the mobile phase to afford 3.28 g (84% yield) of Compound 149b as a colorless liquid.

(c) Compound 149c

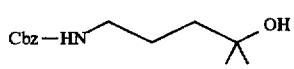

A solution of Compound 149b (500 mg; 2 mmol) in 4 ml of THF was added to a solution of MeLi (5.7 ml 1.4M in Et2O; 8 mmol) in 6 ml of THF at −78° C. After stirring 5 h at −78° C., the reaction mixture was quenched with saturated $NH_4Cl$ and the resulting mixture extracted with $Et_2O$. The organic layer was washed with $H_2O$ and brine. After drying over $MgSO_4$, the organic layer was concentrated and the resulting liquid purified on a 2.5×25 cm silica gel column using hexane:EtOAc, 6:4 as the mobile phase to afford 294 mg (59%) of Compound 149c as a colorless liquid.

(d) Compound 149d

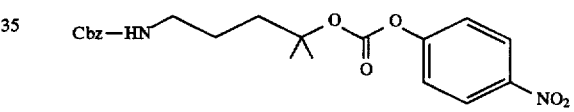

4-Nitrophenylchloroformate (350 mg; 1.70 mmol) in 1 ml of $CH_2Cl_2$ was added dropwise to a solution of Compound 149c (280 mg; 1.11 mmol) in 2.5 ml of $CH_2Cl_2$ and 0.5 ml pyridine. After stirring for 2 h at 0° C., an additional 0.25 ml of pyridine and 4-nitrophenylchloroformate (225 mg; 1.10 mmol) were added. The reaction mixture was stirred an additional 2 h at 0° C. after which time 75 ml of $Et_2O$ was added. The organic layer was washed with $H_2O$, 0.1N NaOH, $H_2O$, 5% cupric sulfate solution, $H_2O$, and brine. Drying ($MgSO_4$) and concentration afforded a solid residue which was purified on a 2.5×20 cm silica gel column using hexane:EtOAc, 75:25 to afford 370 mg (80%) of Compound 149d as a light yellow oil.

(e) Compound 149e

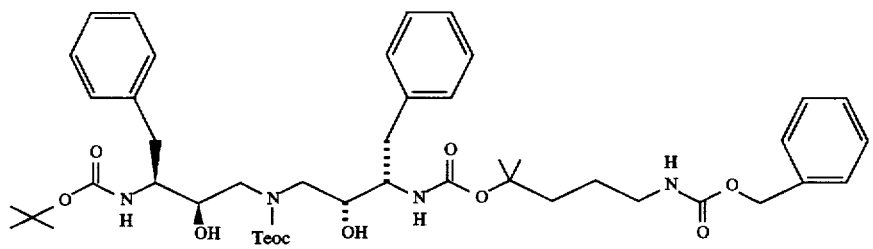

A mixture of Compound 48 (447 mg; 0.76 mmol), Compound 149d (357 mg; 0.84 mmol) and i-Pr$_2$NEt (0.29 ml; 1.70 mmol) in 1.5 ml of CH$_3$CN was stirred 72 h at RT. An additional quantity of i-Pr$_2$NEt (0.15 ml; 0.86 mmol) was added and the reaction mixture was heated to 45° C. for 18 h. The volatiles were removed in vacuo and the residue was partitioned between EtOAc and H$_2$O. The organic layer was washed with H$_2$O, 0.1N NaOH, H$_2$O, saturated aq. KHSO$_4$, H$_2$O, and brine. Dying (MgSO$_4$) and concentration afforded a residue which was purified on a 2.5×15 cm silica gel column using 4% MeOH/CH$_2$Cl$_2$ to afford 540 mg (82%) of Compound 149e as a white foamy solid.

$^1$H NMR (DMSO-d$^6$; 70° C.): δ0.01 (s, 9H) 0.93 (t, J=8, 8.5 Hz, 2H), 1.19 (s, 6H), 1.23 (s, 9H), 1.32 (m, 2H), 1.53 (m, 2H), 2.56 (m, 2H), 3.15 (m, 2H), 3.57 (m, 4H), 3.68 (m, 2H), 4.07 (m, 2H), 4.79 (m, 2H), 5.00 (s, 2H), 6.27 (brs, 2H), 6.90 (brs, 1H), 7.11 (m, 2H), 7.18 (m, 8H), 7.31 (m, 5H).

EXAMPLE 150

Preparation of [1S-(1R*,2S*)]-[Iminobis[2-hydroxy- 1-(phenylmethyl)-3,1-propanediyl)] biscarbamic acid, 1,1-dimethylethyl 1,1-dimethyl-4-[[(phenylmethoxy) carbonyl]amino]butyl ester (Compound 150)

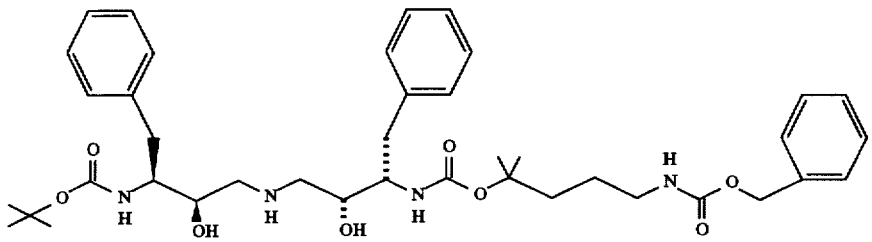

Compound 149e was converted to the title Compound 150 (white solid) by a procedure analogous to that of Example 21.

mp 153°–155° C.; [α]$_{365}$=–18.0° (c 0.10, MeOH). Mass Spec. FAB+ion: (M+H)=721. Analysis calc. for C$_{40}$H$_{56}$N$_4$O$_8$: C, 66.64; H, 7.83; N, 7.77; Found: C, 66.36; H, 7.81; N, 7.75.

EXAMPLE 151

Preparation of [1S-(1R*,2S*)]-[[[[2-(Trimethylsilyl) ethoxy]carbonyl]imino]-bis [[2-hydroxy-1-(phenylmethyl)-3,1-propanediyl]]biscarbamic acid, 1,1-dimethylethyl 4-amino-1,1-dimethylbutyl ester (Compound 151)

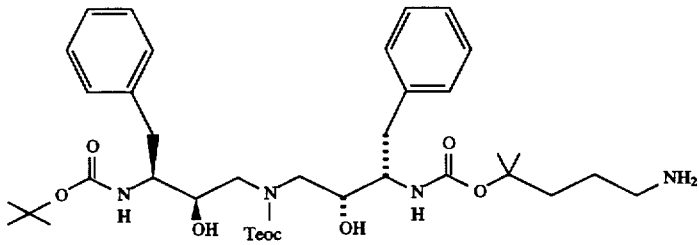

Compound 149e was converted to the title Compound 151 (colorless oil) using conditions analogous to those used for the synthesis of Compound 7.

$^1$H NMR (DMSO-d$^6$; 70° C.): δ 0.01 (s, 9H), 0.93 (t, J=9, 8 Hz, 2H), 1.20 (s, 6H), 1.22 (m; buried under large singlets, 2H), 1.23 (s, 9H), 2.43 (m, 2H), 2.55 (m, 2H), 2.93 (dd, J=3.5, 14 Hz, 2H), 3.05 (m, 4H), 3.53 (m, 4H), 3.65 (m, 2H), 4.02 (m, 2H), 6.23 (brs, 2H), 7.12 (m, 10H).

EXAMPLE 152

Preparation of [1S-(1R*,2S*)]-[[[[2-(Trimethylsilyl) ethoxy]carbonyl]imino]-bis[[2-hydroxy-1-(phenylmethyl)-3,1-propanediyl]]biscarbamic acid, 1,1-dimethylethyl 1,1-dimethyl-4-[(phenyl-methyl) amino]butyl ester (Compound 152)

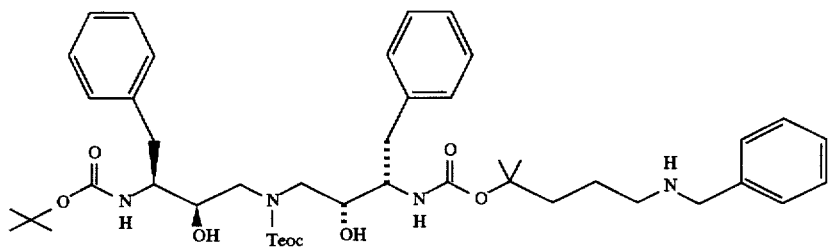

NaHB(OAc)₃ (57 mg; 0.26 mmol) was added to a solution of Compound 151 (125 mg; 0.178 mmol) and benzaldehyde (18 μl; 0.178 mmol) in 1.2-dichloroethane at RT. After stirring for 3 h the solvent was removed in vacuo and the residue was partitioned between EtOAc and saturated NaHCO₃. The organic layer was washed with H₂O and brine, dried over MgSO₄ and concentrated to afford a crude residue which was purified on a 2.5×8 cm silica gel column, using CH₂Cl₂:MeOH:NH₄OH, 94.5:5.0:0.5 to give 125 mg (86%) of the title Compound 152 as a white foam.

$^1$H NMR (DMSO-d$^6$; 70° C.): δ 0.01 (s, 9H), 0.93 (t, J=9, 8 Hz, 2H), 1.21 (s, 6H), 1.23 (s, 9H), 1.33 (m, 2H), 1.58 (m, 2H), 2.48 (m, 2H), 2.57 (m, 2H), 2.94 (dd, J=3, 14 Hz, 2H), 3.15 (m, 2H), 3.54 (m, 4H), 3.68 (m, 2H), 3.72 (s, 2H), 4.05 (m, 2H), 4.80 (m, 2H), 6.26 (brs, 2H), 7.17 (m, 10H), 7.30 (m, 5H).

EXAMPLE 153
Preparation of [1S-(1R*,2S*)]-[Iminobis[2-hydroxy-1-(phenylmethyl)-3,1-propanediyl] biscarbamic acid, 1,1-dimethylethyl 1,1-dimethyl-4-[(phenylmethyl)-amino]butyl ester (Compound 153)

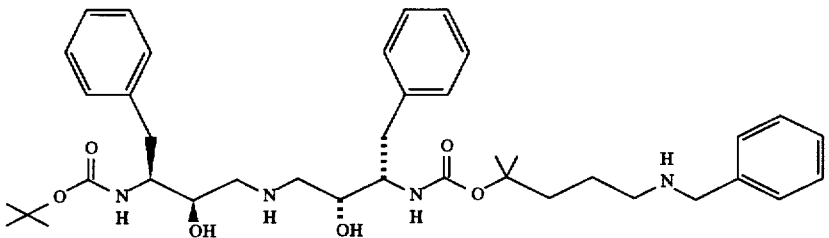

Compound 152 was converted to the title Compound 153 (white solid) by a procedure analogous to that used for the synthesis of Compound 21. mp 128°–132° C.; [α]$_D$=–4.8° (c 0.42, MeOH).

Mass Spec. FAB +ion: (M+H)=677. Analysis calc. for C₃₉H₅₆N₄O₆·0.52 H₂O: C, 68.27; H, 8.38; N, 8.16; Found: C, 68.14; H, 8.25; N, 8.29.

EXAMPLE 154

Preparation of [R-(R*,S*)]-Iminobis[2-hydroxy-1-(phenylmethyl)-3,1-propanediyl)]biscarbamic acid, 1,1-dimethylethyl 1,1-dimethyl-2-phenylethyl ester (Compound 154)

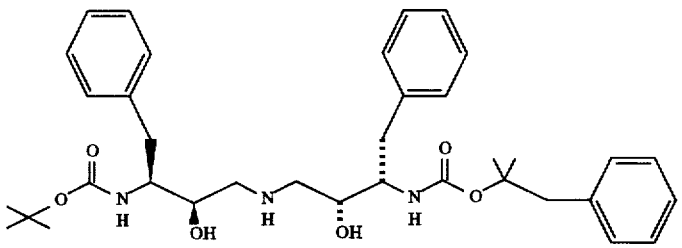

α,α-Dimethylphenethyl alcohol was converted to the title Compound 154 (white solid) by a three-step procedure analogous to that used for the conversion of Compound 149c to Compound 150 (Et₃N and DMF used in the coupling of the p-nitrophenyl carbonate to Compound 48).

m.p. 161°–164° C.

EXAMPLE 155

[1S-(1R*,2S*)]-[Iminobis[2-hydroxy-1-(phenylmethyl )-3,1-propanediyl]biscarbamic acid, 1,1-dimethylethyl 1,1-dimethyl-5-phenyl-2-pentynyl ester (Compound 155b)

(a) Compound 155a

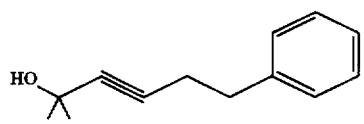

To a −78° C. solution of 4-phenyl-1-butyne (1.00 g, 7.68 mmol) in THF (4.40 mL) was added dropwise a solution of n-BuLi/hexane (3.24 mL of a 2.49M solution) and the resulting solution stirred at −78° C. for 1 h. A solution of acetone (0.59 mL, 8.07 mmol) in THF (1.0 mL) was added dropwise at −78° C. and the resulting solution stirred at −78° C. for 3 h at which point a solution of aqueous NH$_4$Cl (9 mL of a 1M solution) was added. The aqueous layer was extracted with EtOAc and the combined organic extracts dried (anhydrous Na$_2$SO$_4$) and concentrated in vacuo to give a yellow oil. This crude material was chromatographed on silica gel (100 mL) eluting with 10:1 hexane:EtOAc to give Compound 155a (1.36 g, 94%) as a clear colorless oil.

(b) Compound 155b

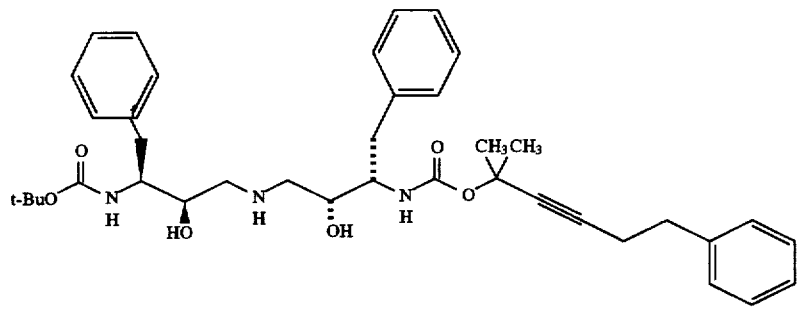

Compound 155a was converted to the title Compound 155b (white solid) by a three-step procedure analogous to that used for the conversion of Compound 149c to Compound 150 (DMF used in the coupling of the p-nitrophenyl carbonate to Compound 48).

m.p. 140–142° C.; α$_D$ = +2.0° (c = 0.2, MeOH)

Elemental Analysis (%)
for C$_{39}$H$_{51}$N$_3$O$_6$·0.87 H$_2$O

|   | Calc. | Found |
|---|-------|-------|
| C | 69.55 | 69.40 |
| H | 7.89  | 7.73  |
| N | 6.24  | 6.39  |

EXAMPLE 156

Preparation of [1S-(1R*,2S*)]-2-hydroxy-1-(phenylmethyl )-3,1-propanediyl)biscarbamic acid, 1,1-dimethylethyl-1-methyl-1-phenylethyl ester (Compound 156)

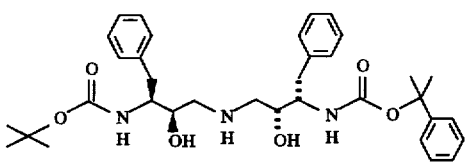

Dimethylphenyl carbinol was converted to the title Compound 156 (white solid) by a three-step procedure analogous to that used for the conversion of Compound 149c to Compound 150 (Et$_3$N and DMF used in the coupling of the p-nitrophenyl carbonate to Compound 48).

m.p. 89°–92° C.

EXAMPLE 157

Preparation of [1S-(1R*,2S*)]-[Iminobis[2-hydroxy-1-(phenylmethyl)-3,1-propanediyl)] biscarbamic acid, 1,1-dimethylethyl 1,1-dimethyl-2-(phenylmethoxy)-ethyl ester (Compound 157b)

(a) Compound 157a

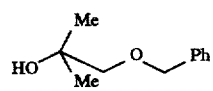

Compound 157a was prepared from benzyloxyacetyl chloride by a procedure analogous to that used for the synthesis of Compound 149c.

(b) Compound 157b

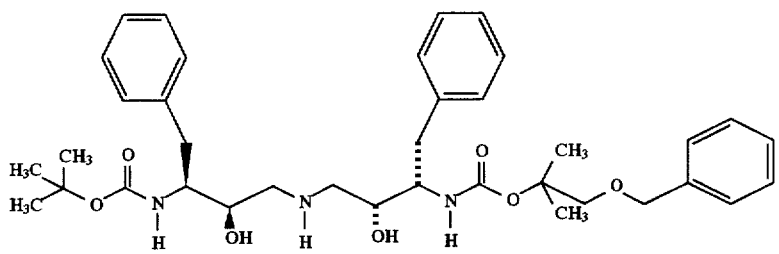

Compound 157a was converted to the title Compound 157b (white solid) by a three-step procedure analogous to that used for the conversion of Compound 149c to Compound 150 (DMF used in the coupling of the p-nitrophenyl carbonate to Compound 48).

m.p. 129-135° C.; $[\alpha]^{20}_D = -3.5°$ (c 0.5, $CH_3OH$)
Elemental Analysis (%)
Calculated for $C_{37}H_{51}N_3O_7 \cdot 1.37\ H_2O$

|   | Calc. | Found |
|---|-------|-------|
| C | 65.89 | 65.52 |
| H | 8.03  | 7.64  |
| N | 6.23  | 6.60  |

EXAMPLE 158

Preparation of [1S-(1R*,2S*)]-[Iminobis[2-hydroxy-1-(phenylmethyl)-3,1-propanediyl] biscarbamic acid, 1,1-dimethylethyl 1,1-dimethyl-3-(phenylmethoxy)-propyl ester (Compound 158b)

(a) Compound 158a

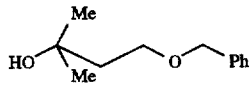

To a solution of 3M MeMgCl in THF (5 mL, 15 mmol) at −20° C. was added 5 mL of THF and a solution of 4-benzyloxy-2-butanone (1.735 mL, 10 mmol) in 5 mL of THF. After the addition was complete, the reaction mixture was warmed to RT and quenched with 10 mL of water. The mixture was extracted with $CH_2Cl_2$ and the organic phase was separated, dried ($MgSO_4$) and concentrated to provide the Compound 158a (1.8 g, 92%) as a colorless oil.

(b) Compound 158b

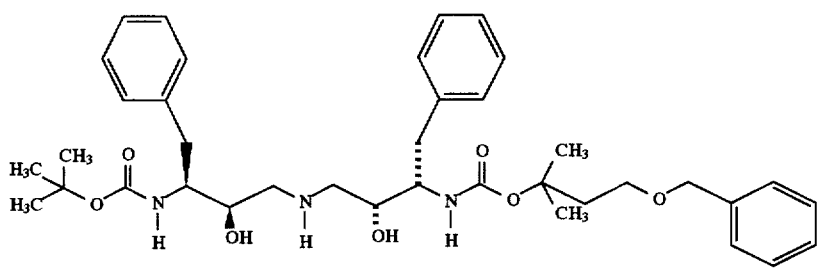

Compound 158a was converted to the title Compound 158b (white solid) by a three-step procedure analogous to that used for the conversion of Compound 149c to Compound 150 ($Et_3N$ and DMF used in the coupling of the p-nitrophenyl carbonate to Compound 48).

m.p. 122-125° C.; $[\alpha]^{20}_D = -4.8°$ (c = 0.5, $CH_3OH$)
Elemental Analysis (%)
Calculated for $C_{38}H_{53}N_3O_7 \cdot 1.30\ H_2O$

|   | Calc. | Found |
|---|-------|-------|
| C | 66.41 | 66.58 |
| H | 8.15  | 7.89  |
| N | 6.11  | 5.94  |

EXAMPLE 159

Preparation of [1S-(1R*,2S*)]-[Iminobis[2-hydroxy-1-(phenylmethyl)-3,1-propanediyl]]bis-[carbamic acid], 1,1-dimethylethyl 1-methyl-cyclopentyl ester (Compound 159)

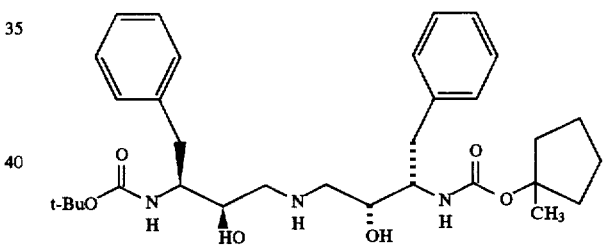

1-Methyl-1-cyclopentanol was converted to the title Compound 159 by a three-step procedure analogous to that used for the conversion of Compound 149c to Compound 150 (DMF used in the coupling of the p-nitrophenyl carbonate to Compound 48).

| m.p. 160–162° C.; [α]$_D$ = −4.3° (c 0.21) Elemental Analysis (%) for C$_{32}$H$_{47}$N$_3$O$_6$·1.54 H$_2$O | | |
|---|---|---|
| | Calc. | Found |
| C | 64.34 | 64.15 |
| H | 8.45 | 8.03 |
| N | 7.03 | 7.22 |

EXAMPLE 160

Preparation of [1S-(1R*,2S*)]-[Iminobis[2-hydroxy-1-(phenylmethyl)-3,1-propanediyl]]bis[carbamic acid], 1,1-dimethylethyl-1-methylcyclobutyl ester (Compound 160)

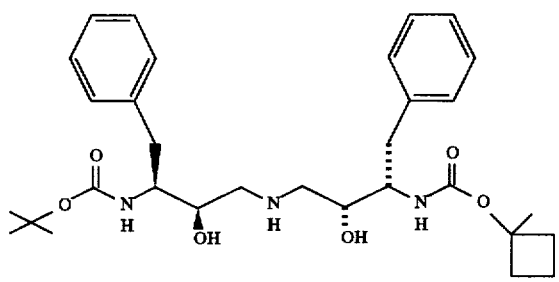

1-Methyl-1-cyclobutanol was converted to the title Compound 160 (white solid) by a three-step procedure analogous to that used for the conversion of Compound 149c to Compound 150 (Et$_3$N and DMF used in the coupling of the p-nitrophenyl carbonate to Compound 48).

| m.p. 179–182° C. Elemental Analysis (%) C$_{31}$H$_{45}$N$_3$O$_6$·0.47 H$_2$O | | |
|---|---|---|
| | Calc. | Found |
| C | 66.00 | 65.89 |
| H | 8.21 | 8.00 |
| N | 7.45 | 7.56 |

EXAMPLE 161

Preparation of [R-(R*,S*) ]-[Iminobis[2-hydroxy-1-(phenylmethyl)-3,1-propanediyl]]1biscarbamic acid, 1,1-dimethylethyl 2-[[(1,1-dimethylethyl)dimethylsilyl]oxy]-1,1-dimethylethyl ester (Compound 161g)

(a) Compound 161a

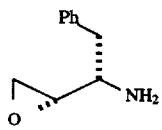

A mixture of Compound 44a (1.0 g, 3.36 mmol) and 5% Pd on CaCO$_3$, poisoned with Pb (0.1 g, Aldrich) in 40 mL of MeOH was stirred under 1 atm H$_2$ for 2 h. The catalyst was filtered off through a pad of Celite and the filtrate concentrated. The crude product was purified by chromatography on a column of silica gel (2.5×35cm) eluting with a gradient of CH$_2$Cl$_2$—MeOH-aqueous NH$_4$OH (98.0-1.8-0.2 to 95.0-4.5-0.5) to afford 170 mg (31% yield) of Compound 161a as a clear oil.

(b) Compound 161b

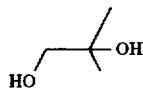

To 26.25 mL of 0.1M HClO$_4$ was slowly added 9.45 g (0.131 mol) of isobutylene oxide and the reaction mixture stirred at RT for 30 mins. Water from the reaction mixture was distilled off first, followed by the product which distilled at 80° C. (10 mm Hg). Collection of pure distillate afforded Compound 161b as a colorless oil (6.4 g, 54%).

(c) Compound 161c

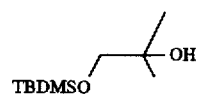

To a cooled (0° C.) solution of Compound 161b (2.0 g, 22.22 mmol) in 10ML of CH$_2$Cl$_2$ was added Et$_3$N (6.2 mL, 44.44 mmol) followed by t-butyldimethylsilyl chloride (3.684 g, 24.44 mmol). The reaction mixture was warmed to RT and after 2 h of stirring, N,N-dimethylaminopyridine (0.056 g, 0.44 mmol) was added. After stirring the reaction mixture overnight, it was diluted with EtOAc and washed with saturated NaHCO$_3$ followed by brine. The organic phase was dried (MgSO$_4$) and concentrated. The crude product obtained was chromatographed on silica gel eluting with a stepwise gradient of. hexane to 50% EtOAc-hexane to afford Compound 161c (4.2 g, 92%) as a colorless oil.

(d) Compound 161d

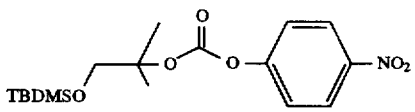

To a solution of Compound 161c (1.0 g, 4.9 mmol) in 10 mL of dry CH$_2$Cl$_2$ cooled to 0° C. was added 5.0 mL of pyridine followed by slow addition of a solution of p-nitrophenylchloroformate (1,185 g, 5.88 mmol) in 6 mL of CH$_2$Cl$_2$. The resulting suspension was stirred at 5° C. overnight. The reaction mixture was diluted with EtOAc and washed with saturated NaHCO$_3$ and brine. The organic phase was dried (MgSO$_4$) and concentrated to obtain the crude product which was flash chromatographed on silica gel eluting with a stepwise gradient of hexane to 10% EtOAc-hexane to afford Compound 161d (1.05 g, 58%) as a viscous oil.

(e) Compound 161e

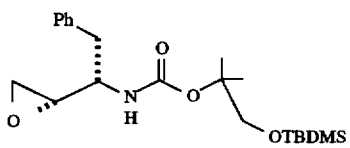

A solution of Compound 161a (70 mg, 0.429 mmol), Compound 161d (174 mg, 0.472 mmol), and i-Pr$_2$NEt (90 ∞L, 66.5 mg, 0.515 mmol) in 0.5 mL DMF was stirred at RT for 72 h. The crude mixture was combined with the crude mixture of a second, similar reaction run on exactly twice

185 the scale. The combined crude mixture was concentrated and chromatographed on a column of silica gel (2.5X30cm) eluting with 10% EtOAc-hexane to afford 423 mg (83% yield) of Compound 161e as a clear oil.

(f) Compound 161f

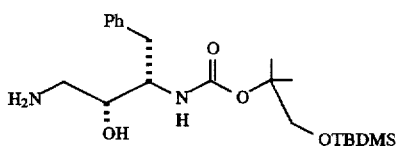

A stream of $NH_3$ was bubbled into a 5° C. solution of Compound 161e (420 mg, 1.07 mmol) in 5 mL EtOH and 5 mL 30% aqueous $NH_4OH$ for 30 min. The resulting solution was stirred at 5° C. for 15 min and then at RT for 18 h. Argon was bubbled through the mixture for a few minutes and the solvents were removed. The crude product was chromatographed on a column of silica gel (2.5×15 cm) eluting with a gradient of $CH_2Cl_2$—MeOH-aqueous $NH_4OH$ (98.0-1.8-0.2 to 92.0-7.2-0.8) to afford 373 mg (85% yield) of Compound 161f as a white solid.

(g) Compound 161g

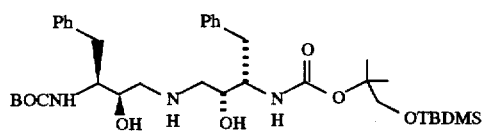

A solution of Compound 161f (223 mg, 0.543 mmol) and Compound 1b(i) (129 mg, 0.489 mmol) was stirred in 1 mL of DMF at 115° C. for 3.5 h. The mixture was cooled to RT, concentrated to remove the bulk of the DMF, and the crude product was chromatographed on a column of silica gel (2.5X25cm) eluting with a gradient of $CH_2Cl_2$—MeOH-aqueous $NH_4OH$ (98.0-1.8-0.2 to 92.0-7.2-0.8) to afford 176 mg (53% yield) of Compound 161g as a white solid.

186

Example 162

Preparation of [R-(R*,S*)]-[Iminobis[2-hydroxy-1-(phenylmethyl)-3,1-propanediyl)biscarbamic acid, 1,1-dimethylethyl-2-hydroxy-1,1-dimethylethyl ester (Compound 162)

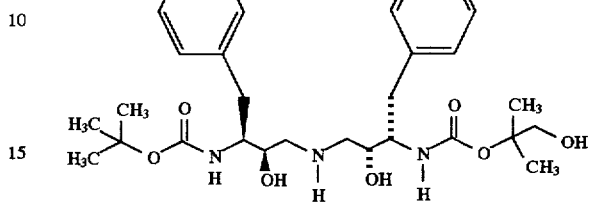

To a solution of Compound 161g (170 mg, 0.252 mmol) in 1 mL THF was added 3 mL HOAc followed by 1 mL of $H_2O$. The resulting mixture was stirred at RT for 32 h. Solvents were removed and the crude product was chromatographed on a column of silica gel (2.5X25cm) eluting with a gradient of $CH_2Cl_2$—MeOH-aqueous $NH_4OH$ (98.0-1.8-0.2 to 92.0-7.2-0.8) to afford 107 mg (76% yield) of the title Compound 162 as a white solid. (Alternatively, Compound 157b was converted to Compound 162 by a procedure analogous to that used for the synthesis of Compound 2.)

| m.p. 153–155° C.; $[\alpha]_D = -6.5°$ (c 0.54) Elemental Analysis (%) for $C_{30}H_{45}N_3O_7$ | | |
|---|---|---|
|  | Calc. | Found |
| C | 64.38 | 64.07 |
| H | 8.10 | 8.16 |
| N | 7.51 | 7.91 |

EXAMPLE 163

Preparation of [R-(R*,S*)]-[[[(Trimethylsilyl)-ethoxy]carbonyl]iminobis[2-hydroxy-1-(phenylmethyl)-3,1-propanediyl]]biscarbamic acid, 1,1-dimethylethyl 2-[[(1,1-dimethylethyl) dimethylsilyl]-oxy]-1,1-dimethylethyl ester (Compound 163)

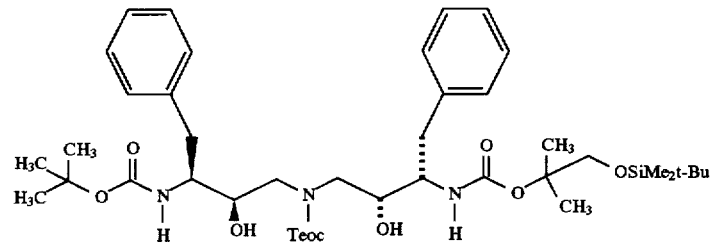

Compounds 161d and 48 were reacted by a procedure analogous to that used for the synthesis of Compound 143 (i-$Pr_2NEt$ used as base) to give the title Compound 163 (white solid).

¹H NMR (CD₃OD) δ7.23–7.08 (m, 10H) 4.13 (m, 2H) 3.81–3.60 (m, 6H) 3.5–3.36 (m, 2H) 3.30 (m, 2H) 3.03 (m, 2H) 2.59 (m, 2H) 1.30–1.08 (15H) 0.98 (m, 2H). Mass Spec (FAB)—(M+H)+ =704

EXAMPLE 164

Preparation of [R-(R*,S*)]-[[[(Trimethylsilyl)-ethoxy]carbonyl]iminobis[2-hydroxy-1-(phenylmethyl)-3,1-propanediyl]]biscarbamic acid, 1,1-di-methylethyl 2-hydroxy-1,1-dimethylethyl ester (Compound 164)

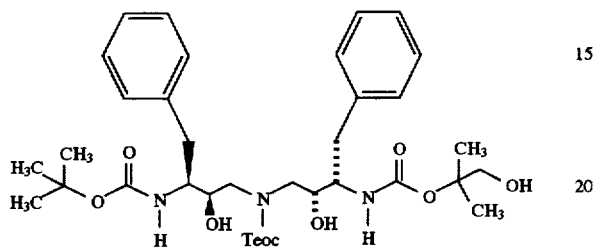

Compound 163 was converted to the title Compound 164 (white foam) by a procedure analogous to that used for Compound 162. TLC (SiO₂) R_f=0.22 (50% EtOAc/Hexanes—PMA). Compound 164 was converted to Compound 162 in 20% yield by a procedure analogous to that used for Compound 21.

EXAMPLE 165

Preparation of [R-(R*,S*)]-[Iminobis[2-hydroxy-1-(phenylmethyl )-3,1-propanediyl)biscarbamic acid, bis(2-hydroxy-1,1-dimethylethyl) ester (Compound 165c)

(a) Compound 165a

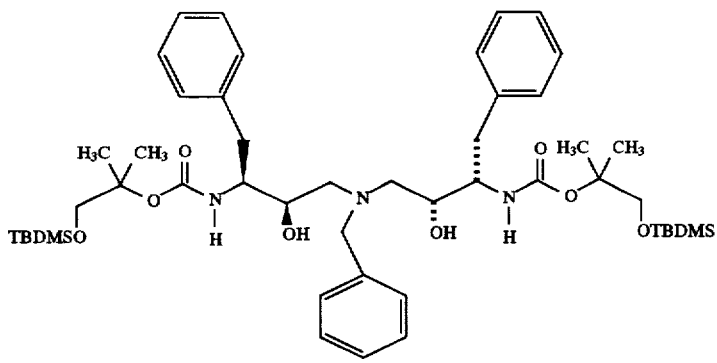

Compounds 32 and 161d (2 eq.) were reacted by a procedure analogous to that used for the synthesis of Compound 161e to give Compound 165a.

(b) Compound 165b

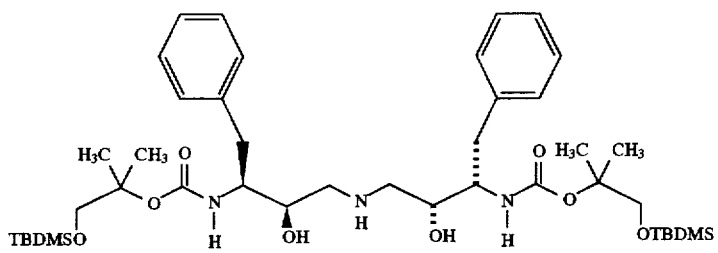

Compound 165a was converted into Compound 165b (white solid) by a procedure analogous to that used for the synthesis of Compound 2.

(c) Compound 165c

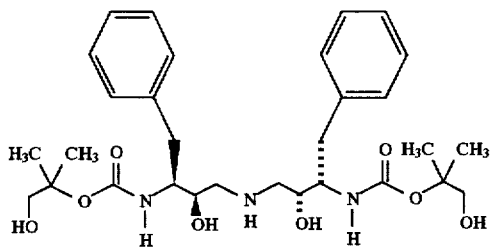

Compound 165b was converted to Compound 165c by a procedure analogous to that used for the synthesis of Compound 162.

mp 140°–142° C.; $[\alpha]_D = -2.3°$ (c=0.2, $CH_3OH$). Mass Spec. (FAB) $(M+H)^+ = 576$; Analysis calc. for $C_{30}H_{45}N_3O_8 \cdot 1.42H_2O$: Calculated C, 59.93; H, 8.02; N, 6.99; Found: C, 60.14; H, 7.68; N, 6.78.

EXAMPLE 166

Preparation of [1S-(1R*,2S*)]-[Iminobis[2-hydroxy-1-(phenylmethyl)-3,1-propanediyl]]bis [carbamic acid], 1,1-dimethylethyl-4-methyltetrahydropyran-4-yl-ester (Compound 166b)

(a) Compound 166a

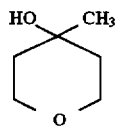

Tetrahydro-4H-pyran-4-one was converted to Compound 166a by a procedure analogous to that used for the synthesis of Compound 149c.

(b) Compound 166b

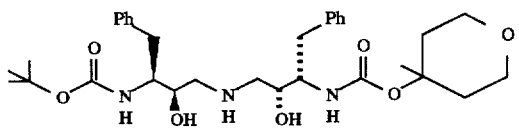

Compound 166a was converted to the title Compound 166b (white solid) by a three-step procedure analogous to that used for the conversion of Compound 149c to Compound 150 (DMF used in the coupling of the p-nitrophenyl carbonate to Compound 48).

| m.p. 144–146° C. Elemental Analysis (%) $C_{32}H_{47}N_3O_7 \cdot 0.54 H_2O$ | | |
|---|---|---|
| | Calc. | Found |
| C | 64.55 | 64.64 |
| H | 8.14 | 8.02 |
| N | 7.06 | 6.97 |

EXAMPLE 167

Preparation of [1S-(1R*,2S*)]-[Iminobis[2-hydroxy-1-(phenylmethyl)-3,1-propanediyl] biscarbamic acid, 1,1-dimethylethyl 1,1]-dimethyl-5-phenyl-3-pentynyl ester (Compound 167b)

(a) Compound 167a

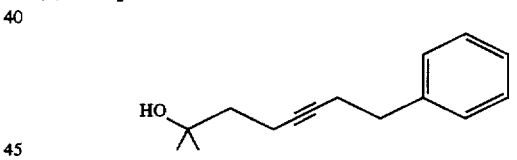

To a –78° C. solution of 3-phenyl-1-propyne (4.00 g; 34.4 mmol) in THF (16 mL) was added a solution of n-BuLi (14.10 mL of a 2.52M solution in hexanes) followed 30 min later by $BF_3 \cdot Et_2O$ (4.24 mL; 34.5 mmol). The resulting solution was stirred at –78° C. for 1 h at which point a solution of isobutylene oxide (2.55 g; 35.4 mmol) in THF (5 mL) was added. After 2 hr. a saturated aqueous $NaHCO_3$ solution was added and the mixture was allowed to warm to RT. The mixture was partitioned between $H_2O$ and $Et_2O$ and the combined organic extracts washed with $H_2O$ and brine, dried (anhydrous $Na_2SO_4$) and concentrated in vacuo to give an orange-yellow oil. This material was chromatographed on silica gel (200 mL) using 10:1 hexane:EtOAc as eluent to give Compound 167a (4.32 g; 67%) as a pale yellow oil.

(b) Compound 167b

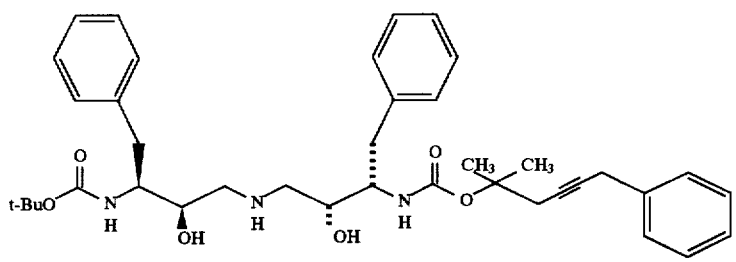

Compound 167a was converted to the title Compound 167b (white solid) by a three-step procedure analogous to that used for the conversion of Compound 149c to Compound 150 (DMF used in the coupling of the p-nitrophenyl carbonate to Compound 48).

m.p. 120°–124° C.; $[\alpha]_D = -3.2°$ (c 0.25, MeOH) Mass spec (CI) 658 (M+H)

EXAMPLE 168

Preparation of [R-(R*,S*)]-[Iminobis[2-hydroxy-1-(phenylmethyl)- 3,1-propanediyl)biscarbamic acid, 1,1-dimethylethyl 2-methoxy-1,1-dimethylethyl ester (Compound 168b)

(a) Compound 168a

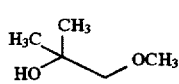

Methylmethoxy acetate was converted to Compound 168a by a procedure analogous to that used for the synthesis of Compound 149c.

(b) Compound 168b

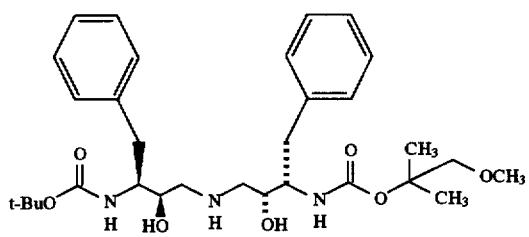

Compound 168a was converted to the title Compound 168b (white solid) by a three-step procedure analogous to that used for the conversion of Compound 149c to Compound 150 (DMF used in the coupling of the p-nitrophenyl carbonate to Compound 48).

m.p. 151°–155° C.; $[\alpha]_D = -5.8°$ (c 0.32, MeOH) Mass spec (CI) 574 (M+H)

EXAMPLE 169

Preparation of [1S-(1R*,2S*)]-Iminobis[2-hydroxy-1-(phenylmethyl)-3,1-propanediyl]]biscarbamic acid, 1,1-dimethylethyl-3-hydroxy-1,1-dimethylpropyl ester (Compound 169)

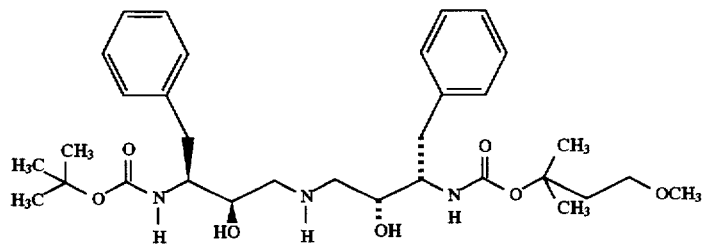

Compound 169 was obtained as a white solid from Compound 158b by a procedure analogous to that used for the synthesis of Compound 2.

m.p. 133° C.; $[\alpha]^{20}_D = -5.0°$ (c 0.2, CH$_3$OH)

Elemental Analysis (%)

Calculated for $C_{31}H_{47}N_3O_7 \cdot 0.95 H_2O$

|   | Calc. | Found |
|---|-------|-------|
| C | 63.02 | 62.98 |
| H | 8.34  | 8.18  |
| N | 7.11  | 7.15  |

EXAMPLE 170

Preparation of [S-[1R*,2S*(2S*,3R*)]-N-[3-[[3-[[(1 1-Dimethylethoxy)carbonyl]amino]-2-hydroxy-4-phenylbutyl]amino]-2-hydroxy-1-(phenylmethyl)-propyl ]-N²-[[(1-methyl-1H-benzimidazol-2-yl)-methoxy]carbonyl]-L-valinamide (Compound 170b)

(a) Compound 170a

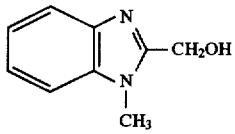

A mixture of 2-hydroxymethylbenzimidazole (500 mg, 3.38 mmol), anhydrous $K_2CO_3$ (467 mg, 3.38 mmol) and MeI (210 μL, 3.38 mmol) in 5 ml of DMF was heated at 50° C. for 6 hr. The reaction was diluted with $H_2O$ and extracted with EtOAc. The extracts were washed with brine, dried ($Na_2SO_4$) and concentrated. The crude product was purified on a 30 ml silica column eluting with MeOH:EtOAc (1:9) to give 146 mg (27%) of Compound 170a.

(b) Compound 170b

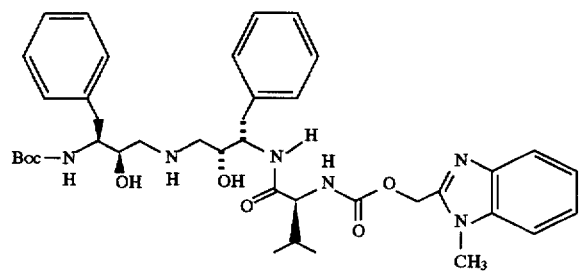

Compound 170a was converted into the title Compound 170b by a three-step sequence analogous to that used for the synthesis of Compound 67c (pyridine was used in the formation of the p-nitrophenyl carbonate; no t-BuOH was used in the coupling of the p-nitrophenyl carbonate with L-valine; and no $CH_2Cl_2$ was used in the reaction of the resulting acid with Compound 54).

m.p. 148°–152° C.; $[\alpha]_D = -18.6°$ (c=0.22, MeOH). High Res. Mass Spec. (FAB): $C_{40}H_{55}N_6O_7 = 731.4142^+$; Δ=1.4 ppm.

EXAMPLE 171

Preparation of S-[1R*,2S*(2S*,3R*)]-N²-[[(2-Benzo-xazolyl) methoxy]carbonyl]-N-[3-[[3-[[(1,1-dimethylethoxy) carbonyl]amino]-2-hydroxy-4-phenylbutyl ]amino]-2-hydroxy-1-(phenylmethyl)-propyl]-L-valinamide (Compound 171b)

(a) Compound 171a

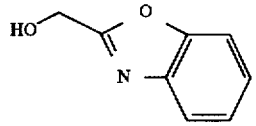

To a mixture of 2.50 g (22.9 mmol) of o-aminophenol and 1.74 g (22.9 mmol) of glycolic acid in 50 mL of toluene was added 150 mg of p-toluenesulfonic acid. The mixture was heated at reflux for 18 h with azeotropic removal of water. The resulting solution was cooled to RT, diluted with EtOAc and washed with 1N NaOH. The organic layer was dried ($Na_2SO_4$), filtered through a pad of silica gel, and concentrated in vacuo to give 1.57 g (47%) of an orange solid which was recrystallized from EtOAc-hexane to afford 647 mg of Compound 171a (yellow solid).

(b) Compound 171b

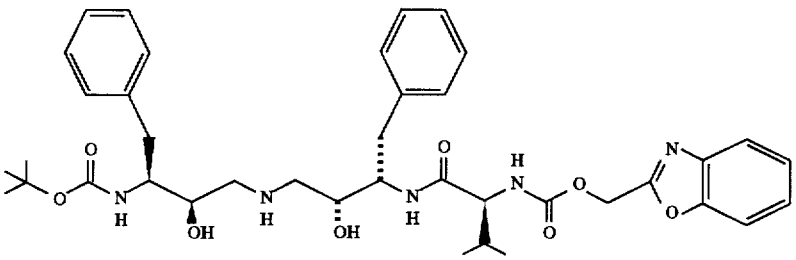

Compound 171a was converted into the title Compound 171b by a three-step sequence analogous to that used for the synthesis of Compound 67c (pyridine was used in the formation of the p-nitrophenyl carbonate; no t-BuOH was used in the coupling of the p-nitrophenyl carbonate with L-valine; and no $CH_2Cl_2$ was used in the reaction of the resulting acid with Compound 54).

m.p. 186°–188° C.; Elemental Analysis; Calc. for $C_{39}H_{51}N_5O_8 \cdot 0.82$ H2O; C, 63.93; H, 7.24; N, 9.56; Found C, 64.02 H, 7.13 N, 9.47; Mass spec (FAB) 718 (M+H)

EXAMPLE 172

Preparation of [4S-4δ, 5δ(4R*,5S*)]-5-[[[[3-[(1,1-Dimethylethoxy) carbonyl]-4-[(4-hydroxyphenyl)-methyl ]-2,2-dimethyl-5-oxazolidinyl]methyl][[2-(trimethylsilyl) ethoxy]carbonyl]amino]methyl]-2,2-dimethyl-4-(phenylmethyl)-3-oxazolidinecarboxylic acid, 1,1-dimethylethyl ester (Compound 172)

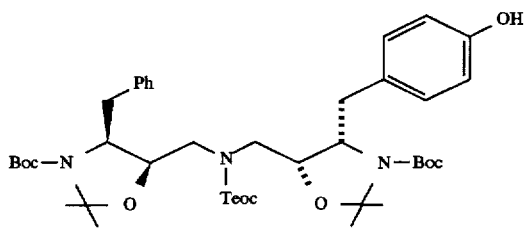

The mixture of Compound 20 (211 mg, 0.30 mmol), 2,2-dimethoxypropane (250 mg, 2.4 mmol) and p-TsOH (1.5 mg) in dry benzene (1.6 ml) was refluxed for 3.0 hrs with azeotropic removal of H₂O, then stirred at RT overnight. The mixture was diluted with EtOAc then washed with saturated NaHCO₃ and brine and dried over anhydrous Na₂SO₄. Concentration in vacuo followed by flash chromatography (hexane/EtOAc 10:1 to 6:1) on a silica gel column (190×20 mm) afforded 230 mg (98%) of Compound 172 as a white foam.

¹H-NMR (400MHz, CDCl₃): 6.65–7.40 (m, 11H), 4.04–4.38 (m, 6H), 3.20–3.64 (m, 4H), 2.81–3.06 (m, 4H), 1.25–1.94 (m, 30H), 0.95 (m, 2H), 0.00 (s, 9H).

EXAMPLE 173

Preparation of [4S-4α, 5α(4R*,5S*)]-5-[[[[3-[(1,1-Dimethylethoxy) carbonyl]-2,2-dimethyl-4-[[4-[2-(4-morpholinyl) ethoxy]phenyl]methyl]-5-oxazolidinyl]methyl][[2-(trimethylsilyl)ethoxy]carbonyl]amino]methyl]-2,2-dimethyl-4-(phenylmethyl)-3-oxazolidinecarboxylic acid, 1,1-dimethylethyl ester (Compound 173)

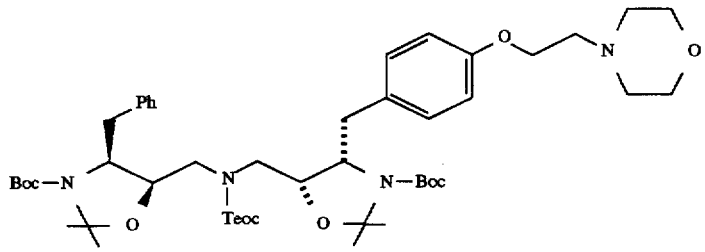

The mixture of Compound 172 (200 mg, 0.255 mmol), 4-(2-chloroethyl)morpholine (191 mg, 1.28 mmol) and K₂CO₃ (88 mg, 0.638 mmol) in dry DMF (1.0 ml) was heated at 100° C. for 14 hrs. The mixture was diluted with EtOAc then washed with water, saturated NaHCO₃ and brine and dried over anhydrous Na₂SO₄. Concentration in vacuo followed by flash chromatography (100% CHCl₃ to CHCl₃—MeOH—NH₄OH: 99:1:0.1) on a silica gel column (200×20 mm) afforded 163 mg (71%) of Compound 173 as a colorless oil.

¹H-NMR (400MHz, CDCl₃): 7.10–7.40 (m, 7H), 6.84 (m, 2H), 4.02–4.39 (m, 8H), 3.76 (t, J=4.70, 4H), 3.20–3.60 (m, 4H), 2.73–3.03 (m, 6H), 2.60 (m, 4H), 1.24–1.83 (m, 30H), 0.95 (m, 2H), 0.00 (s, 9H).

EXAMPLE 174

Preparation of [1S-[1R*,2S*(2S*,3R*)]]-[3-[[3-[[(1,1-Dimethylethoxy)carbonyl]amino]-2-hydroxy-4-[4-[2-(4-morpholinyl)ethoxy]phenyl]butyl][[2-(trimethylsilyl)ethoxy]carbonyl]amino]-2-hydroxy-1-(phenylmethyl)propyl]carbamic acid, 1,1-dimethylethyl ester (Compound 174)

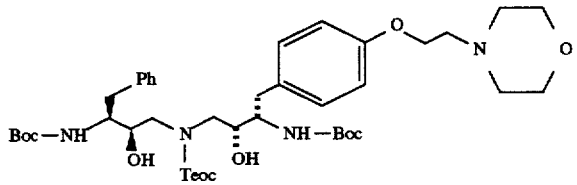

To Compound 173 (160 mg, 0.178 mmol) was added pre-cooled (10° C.) 96% formic acid (8.0 ml). The mixture was stirred at 5° C. for 15 min then was frozen (dry ice-acetone) and lyophilized overnight. The residue was taken into CHCl₃ and washed with saturated NaHCO₃ and dried over anhydrous Na₂SO₄. Concentration in vacuo followed by flash chromatography (100% CHCl₃ to CHCl₃—MeOH—NH₄OH: 98:2:0.2) on a silica gel column afforded 112 mg (77%) of Compound 174 as a colorless oil.

¹H—NMR (400MHz, CD₂Cl₂): 7.10–7.30 (m, 7H), 6.78 (m, 2H), 4.45–4.85 (m, 3H), 4.13 (t, J=8.76, 2H), 4.00 (t, J=5.77, 2H), 3.55–3.90 (m, 4H), 3.63 (t, J=4.70, 4H), 3.10–3.55 (m, 4H), 2.60–2.95 (m, 4H), 2.70 (t, J=5.77, 2H), 2.48 (m, 4H), 1.31 and 1.30 (both s, 18H), 0.96 (m, 2H), 0.00 (S, 9H).

EXAMPLE 175

Preparation of[1S-[1R*,2S*(2S*,3R*)]]-[3-[[3-[[(1,1-Dimethylethoxy)carbonyl]amino]-2-hydroxy-4-(4-[2-(4-morpholinyl)ethoxyl-phenyl]butyl]amino]-2-hydroxy-1-(phenylmethyl)propyl]carbamic acid, 1,1-dimethylethyl ester (Compound 175e)

(a) Compound 175a

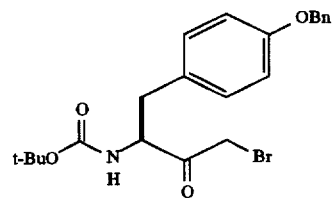

To a solution of N-Boc-o-benzyl-L-tyrosine (25 g, 67.3 mmol) in dry THF (90 ml) cooled at −20° C. to −25° C. was added isobutyl chloroformate (8.7 ml, 67.3 mmol) followed by 4-methylmorpholine (6.8 ml, 67.3 mmol) and the mixture was stirred for 20 min. The precipitate was filtered and washed with dry THF. The filtrate was cooled to −5° C. and poured into a diazomethane in ether solution (prepared from 1-methyl-3-nitro-1-nitrosoguanidine (29.7 g, 202 mmol) as described in Example 1a(i)) at 0° C. The resulting yellow solution was kept at 0° C. for 2.0 h, then at RT overnight. Nitrogen was then bubbled through the solution for 30 min, the solution diluted with Et₂O (500 ml) and then washed with H₂O, sat'd NaHCO₃, and brine, and dried (MgSO₄). Concentration in vacuo afforded a yellow residue, which was triturated with hexane (500 ml) to give 24.5 g (92%) of the corresponding α-diazoketone as an off-white solid. A solution of 48% aqueous HBr (5.8 ml, 51.4 mmol) was added dropwise to the α-diazoketone (20.3 g, 51.4 mmol) in 500 ml of 1,4-dioxane-DME (2:1) cooled at −5° C. After 30 min, saturated NaHCO₃ was added until pH=7.0 and the solvent was removed under reduced pressure. The mixture was diluted with H₂O and extracted with EtOAc. The combined organic extracts were washed with H₂O and brine and dried (Na₂SO₄). Concentration in vacuo followed by recrystallization from EtOAc-hexane gave 20.9 g (91%) Compound 175a as an off-white solid.

(b) Compound 175b

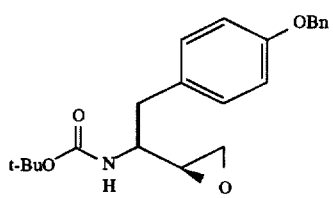

To a solution of Compound 175a (23.3 g, 50.0 mmol) in 250 ml of MeOH-THF (1:1) cooled at −5° C. was added, portionwise, NaBH₄ (2.0 g, 50.0 mmol). After 1 h, 10% KHSO₄ (75 ml) was added at 0° C. and the mixture was allowed to warm to RT. The mixture was extracted with hot EtOAc and the combined organic extracts were washed with H₂O and brine, and dried (Na₂SO₄). Concentration in vacuo followed by recrystallization from EtOAc (350 ml) afforded 14.5 g (62%) of the syn bromohydrin as a white solid. HPLC analysis showed the diastereomeric ratio as 95:5. To a solution of the syn bromohydrin, prepared as above (115.2 g, 0.256 mole), in 1.5 L of THF and 1.5 L of 100% EtOH was added a solution of KOH (17.2 g of 87.6% pellets, 0.269 mole) in 300 mL of 100% EtOH at RT. After 15 min, 1 L of sat. aq. NH₄Cl was added and the mixture then diluted with 6 L of H₂O to give a precipitate. The solid was filtered, washed with H₂O, and extracted into 1 L of EtOAc. The organic phase was dried (Na₂SO₄) and concentrated in vacuo to give a solid which was triturated with 1 L of hexane, to afford 79.3 g (84%) of Compound 175b as a white solid.

(c) Compound 175c

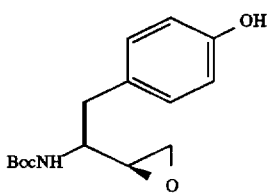

The mixture of Compound 175b (5.0 g, 13.5 mmol) and Pd(OH)₂ (500 mg) in 100 ml EtOH and 25 ml of EtOAc was stirred under hydrogen atmosphere for 4.5 hrs. The catalyst was removed by filtration and the filter cake was washed with EtOH, MeOH, and EtOAc. The combined washes were concentrated in vacuo to give a 3.8 g (99%) of Compound 175c as a white solid.

(d) Compound 175d

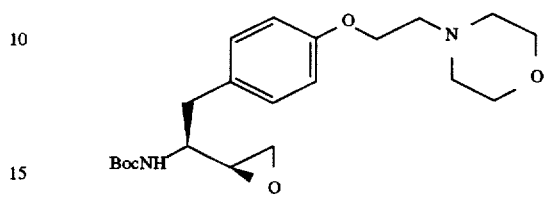

To the mixture of Compound 175c (150 mg, 0.54 mmol), 4-(2-hydroxyethyl)morpholine (141 mg, 1.07 mmol) and PPh₃ (282 mg, 1.07 mmol) in 1.5 ml of dry THF was added DEAD (169 μl, 1.07 mmol). The resulting mixture was stirred at RT overnight. Concentration in vacuo followed by flash chromatography (CHCl₃-i-PrOH—NH₄OH: 99:1:0.1 to 98:2:0.2) afforded 190 mg (90%) of Compound 175d as a white foam.

(e) Compound 175e

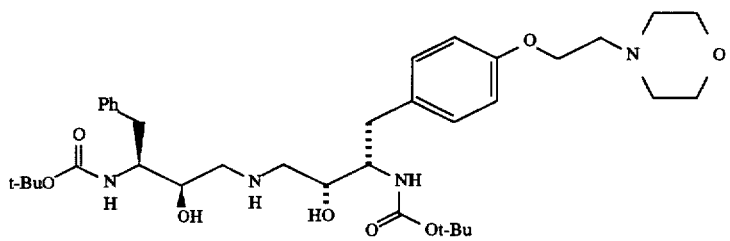

A mixture of Compound 175d (126 mg, 0.32 mmol) and Compound 16b (90 mg, 0.32 mmol) in 0.64 ml of dry DMF was heated at 100° C. for 4.0 hrs. Concentration in vacuo followed by flash chromatography (CHCl₃—MeOH—NH₄OH: 99:1:0.1 to 96:4:0.4) afforded, after trituration with chloroform/hexane, 90 mg (44%) of Compound 175e. m.p.: 140.0°–141.0° C.; [α]$_D$=−3.25° (c 0.246, MeOH).

MS (FAB): 673⁺ (M+H)⁺. Anal. Calc. for C₃₆H₅₆N₄O₈·0.42H₂O: C, 63.55; H, 8.42; N, 8.24. Found: C, 63.73; H, 8.43; N, 8.06.

Alternatively, Compound 175e was prepared as follows. Compound 174 was converted to the title Compound 175e by a procedure analogous to that used for the synthesis of Compound 21. Flash chromatography (100% CHCl₃ to CHCl₃—MeOH—NH₄OH: 100:4.5:0.5) on a silica gel column gave Compound 175e as a white solid which was lyophilized from 1,4-dioxane to give a white lyophilate.

EXAMPLE 176

Preparation of [4S-4α, 5α(4R*,5S*)]-5-[[[[3-[(1,1-Dimethylethoxy) carbonyl]-2,2-dimethyl-4-phenylmethyl-5-oxazolidinyl]methyl][[2-(trimethylsilyl) ethoxy]carbonyl]amino]methyl]-2,2-dimethyl-4-[[4-[2-(2-pyridinyl) ethoxy]phenyl] methyl]]-3-oxazolidinecarboxylic acid, 1,1-dimethylethyl ester (Compound 176)

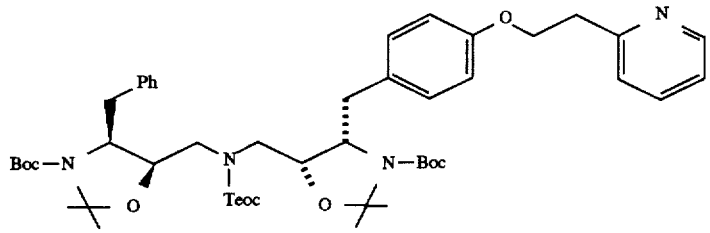

To the mixture of Compound 172 (184 mg, 0.235 mmol), 2-(2-hydroxyethyl)pyridine (40 μl, 0.352 mmol) and PPh₃ (93 mg, 0.352 mmol) in dry THF (0.5 ml) was added DEAD (55 μl, 0.352 mmol). The resulting yellow solution was stirred at RT overnight. Concentration in vacuo followed by flash chromatography (hexane/EtOAc 4:1) on a silica gel column afforded 143 mg (69%) of Compound 176 as a colorless oil.

$^1$H-NMR (400MHz, CD$_3$OD): 8.49 (d, J=5.13, 1H), 7.79 (m, 1H), 7.44 (d, J=7.69, 1H), 7.13–7.38 (m, 8H), 6.87 (d, J=7.69, 1H), 4.34 (t, J=6.41, 2H), 4.03–4.35 (m, 6H), 3.30–3.55 (m, 4H), 3.26 (t, J=6.41, 2H), 2.75–3.00 (m, 4H), 1.30–1.79 (m, 30H), 0.93 (m, 2H), 0.00 (s, 9H).

EXAMPLE 177

Preparation of [1S-[1R*,2S*(2S*,3R*)]]-[3-[[3-[[(1,1-Dimethylethoxy)carbonyl]amino]-2-hydroxy-4-phenylbutyl ][[2-(trimethylsilyl)ethoxy]carbonyl]-amino ]-2-hydroxy-1-[[4-2-(2-pyridinyl)ethoxy]-phenyl ]methyl]propyl]carbamic acid, 1,1-dimethylethyl ester (Compound 177)

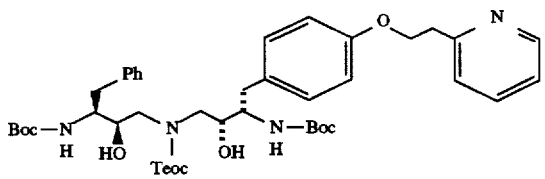

a) Removal of bis-acetonide

To Compound 176 (143 mg, 0.161 mmol) was added pre-cooled (10° C.) 96% formic acid (4.0 ml). The mixture was stirred at 5° C. for 15 min then was frozen (dry ice-acetone) and lyophilized overnight to give an oily residue.

b) The above residue was dissolved in MeOH (2.3 ml). To this solution was added Et$_3$N (40 μl, 0.242 mmol) and di-t-butyldicarbonate (20 μl, 0.08 mmol). The mixture was stirred at RT overnight. Concentration in vacuo followed by flash chromatography (100% CHCl$_3$ to CHCl$_3$—MeOH—NH$_4$OH: 97:3:0.3) on a silica gel column afforded 106 mg (81%) of Compound 177 as a white foam.

$^1$H-NMR (400MHz, CD$_3$OD): 8.42 (m, 1H), 7.72 (m, 1H), 7.36 (m, 1H), 7.03–7.25 (m, 8H), 6.75 (d, J=7.69, 2H), 4.24 (t, J=6.41, 2H), 4.12 (t, J=8.55, 2H), 3.50–3.80 (m, 6H), 3.17 (t, J=6.41, 2H), 2.88–3.30 (m, 4H), 2.35–2.64 (m, 2H), 1.25 (s, 18H), 0.99 (t, J=8.55, 2H), 0.00 (s, 9H).

EXAMPLE 178

Preparation of [1S-[1R*,2S*(2S*,3R*)]]-[3-[[3-[[(1,1-Dimethylethoxy)carbonyl]amino]-2-hydroxy-4-(4-[2-(2-pyridinyl)ethoxy]phenyl]butyl]amino]-2-hydroxy-1-(phenylmethyl)-propyl]carbamic acid, 1,1-dimethyl-ethyl ester (Compound 178)

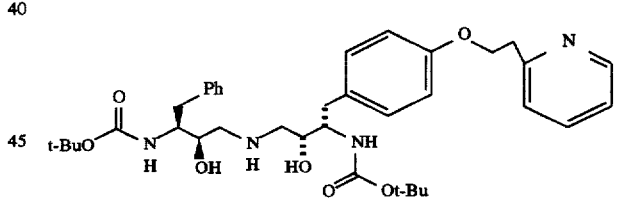

A mixture of Compound 177 (0.106 g; 0.131 mmol) and solid n-Bu$_4$NF·nH$_2$O (0.103 g; 0.393 mmol) in 0.56 ml THF was stirred at 50° C. for 4 h. After cooling to RT, 1 g of celite was added and the solvent removed in vacuo. Flash chromatography (CHCl$_3$—MeOH—NH$_4$OH: 98:2:0.2 to 95:5:0.5) on a silica gel column followed by trituration with Et$_2$O-hexane gave 0.04 g-of Compound 178 as a light yellow solid.

m.p.: 125.0°–126.5° C.; [α]$_D$=−4.84° (c 0.248, MeOH). MS (FAB): 665⁺ (M+H)⁺. Anal. Calc. for C$_{37}$H$_{52}$N$_4$O$_7$·0.53H$_2$O: C, 65.89; H, 7.93; N, 8.13. Found: C, 66.07; H, 7.85; N, 8.13.

EXAMPLE 179

Preparation of [1S-[1R*,2S*(2S*,3R*)]]-[3-[[3-[[(1,1-Dimethylethoxy)carbonyl]amino]-2-hydroxy-4-phenylbutyl]amino]-2-hydroxy-1-[[4-(phenylmethoxy)-phenyl]methyl]propyl]carbamic acid, 1,1-dimethylethyl ester (Compound 179c)

(a) Compound 179a

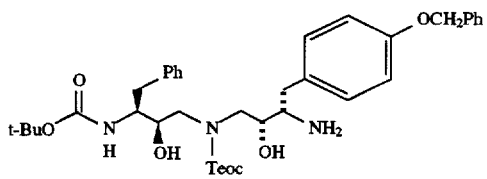

Compound 18 was converted to Compound 179a in 27% yield by a procedure analogous to that used for the synthesis of Compound 19 except that the reaction was only allowed to proceed to partial completion.

(b) Compound 179b

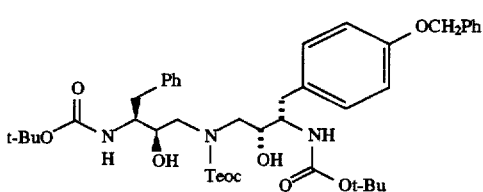

Compound 179a was converted to Compound 179b by a procedure analogous to that used for the synthesis Compound 131 except that MeOH was used in place of DMF and the reaction was run at RT overnight.

(c) Compound 179c

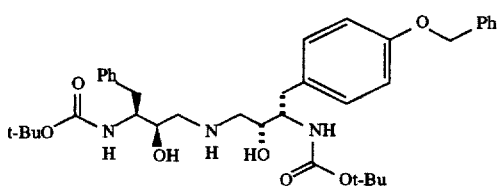

Compound 179c was obtained as a white solid from Compound 179b by a procedure analogous to that used for the synthesis of Compound 21.

m.p. 159°–161° C.; [α]$_D$=–8.97° (c 0.245, DMSO); M.S. (FAB): 650⁺ (M+H)⁺

EXAMPLE 180

Preparation of [1S-(1R*,2S*)]-[Iminobis[2-hydroxy-1-(phenylmethyl)-3,1-propanediyl] biscarbamic acid, 4-amino-1,1-dimethylbutyl 1,1-dimethylethyl ester, fumarate (2:3) salt (Compound 180)

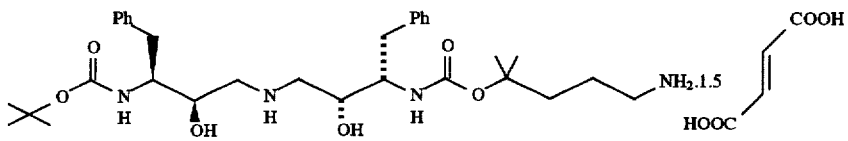

Compound 180 was obtained as a white powder from Compound 150 by a procedure analogous to that used for the synthesis of Compound 84.

mp 123°–130° C.; [α]$_{365}$=–12.7 (c 0.15, MeOH). Mass Spec. FAB +ions: (M+H)=587. Analysis calc. for $C_{32}H_{50}N_4O_6 \cdot 1.5\ C_4H_4O_4 \cdot 2.96\ H_2O$:

C, 56.06; H, 7.66; N, 6.88; Found: C, 56.21; H, 7.42; N, 6.73.

EXAMPLE 181

Preparation of [1S-[1R*,2S*(2S*,3R*)]]-[3-[[3-[[(2,2-Dimethylpropyl)sulfonyl]amino]-2-hydroxy-4-phenylbutyl]amino]-2-hydroxy-1-(phenylmethyl) propyl]carbamic acid 1,1-dimethylethyl ester (Compound 181b)

(a) Compound 181a

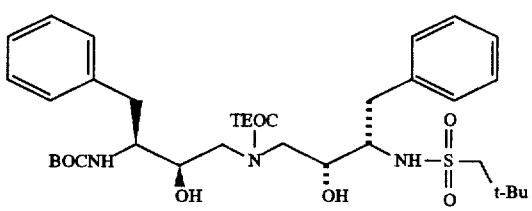

To a stirred solution of Compound 48 (300 mg, 0.51 mmol) in 2 ml of dry CH$_3$CN at –20° C. under argon was added 2,2-dimethylpropyl-1-sulfonylchloride (Synthesis, 489 (1974)) (96 mg, 0.56 mmol) followed by i-Pr$_2$NEt (79 mg, 0.61 mmol). After approximately 2 hr at –5° C., additional sulfonylchloride (48 mg, 0.28 mmol) and i-Pr$_2$NEt (40 mg, 0.31 mmol) was added at –20° C. The mixture was re-warmed to ca. –5° C. and stirred at that temperature for 4 hr, at which time the solution was adsorbed onto celite and chromatographed on a column (2.5X30cm) of silica gel eluting with a gradient of hexane and EtOAc to afford 101 mg (27% yield) of Compound 181a as a clear solid foam.

(b) Compound 181b

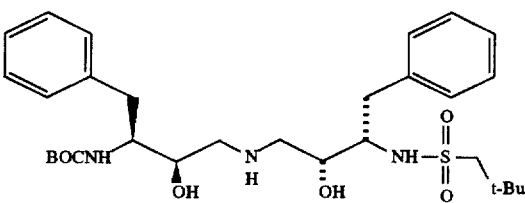

Compound 181b was obtained as a white lyophilate from Compound 181a by a procedure analogous to that used for the synthesis of Compound 21.

m.p. 134–137° C. ("shrinkage" at 65–134° C.);
[α]$_D$ = –11.0° (c 0.77, MeOH)
Elemental Analysis (%)
Calc. for C$_{30}$H$_{47}$N$_3$O$_6$S·0.7 H$_2$O

|   | Calc. | Found |
|---|-------|-------|
| C | 61.03 | 61.05 |
| H | 8.26  | 8.17  |
| N | 7.12  | 7.10  |

EXAMPLE 182

Preparation of [1S-[1R*,2S*(2S*,3R*)]]-[3-[[(1,1-Dimethylethyl)-sulfinyl]amino-2-hydroxy-4-phenylbutyl]amino]2-hydroxy-1-(phenylmethyl)propyl]carbamic acid, 1,1- dimethylethyl ester
(Compound 182c)

(a) Compound 182a

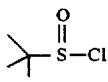

To a solution of t-butyl disulfide (4.8 mL, 25 mmol) in 25 mL of HOAc at 0° C. was added 3.18 mL (31.25 mmol) of 30% aqueous H$_2$O$_2$. The reaction mixture was stirred at 5° C. for 24 h and then poured into 100 mL of ice water. The product was extracted with CH$_2$Cl$_2$ and the combined extracts washed with sat. NaHSO$_3$, sat. NaHCO$_3$ and H$_2$O. The organic phase was dried (MgSO$_4$) and concentrated to obtain a colorless oil. Cl$_2$ gas (1.93 g, 27.18 mmol) was condensed at –78° C. and cannulated into a cooled solution (0°–10° C.) of the above oil in 25 mL of dry CH$_2$Cl$_2$. The resulting yellow solution was allowed to warm to RT and concentrated to obtain a dark yellow oil which was distilled at 47°–48° C. (9 mm Hg) to obtain pure Compound 182a (0.72 g, 20%) as a colorless oil.

(b) Compound 182b

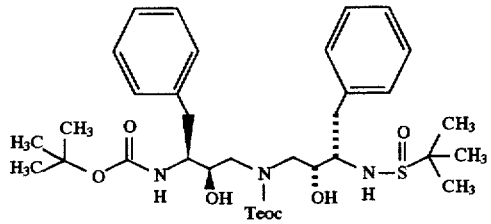

Compound 182a was converted to Compound 182b by a procedure analogous to that used for the synthesis of Compound 181a except that Et$_3$N/CH$_2$Cl$_2$ was used.

(c) Compound 182c

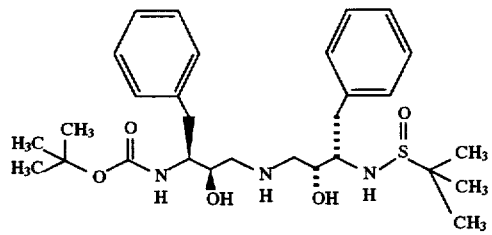

Compound 182c was prepared as a white solid from Compound 182b by a procedure analogous to that used for Compound 21.

m.p. 152°–155° C. ("shrinkage" at 55°–70° C.)

EXAMPLE 183

Preparation of [1S-[1R*,2S*(2S*,3R*)]]-[3-[[3-[[(2,2-Dimethylethyl)sulfonyl]amino]-2-hydroxy-4-phenylbutyl]amino]-2-hydroxy-1-(phenylmethyl)proyl]carbamic acid, 1,1-dimethylethyl ester
(Compound 183b)

(a) Compound 183a

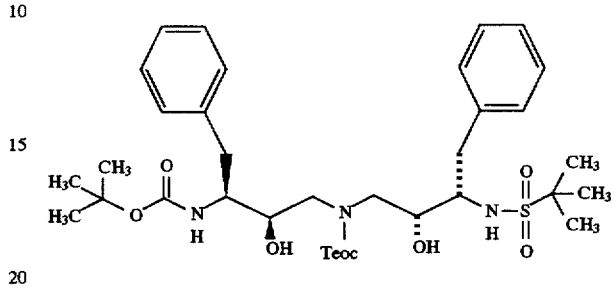

To a solution of Compound 182b (0.22 g, 0.318 mmol) in 2.5 mL of CH$_2$Cl$_2$ cooled to 0° C. was added 1.5 mL of saturated aq. NaHCO$_3$. The suspension was vigorously stirred and a solution of 75% m-CPBA (80 mg, 0.35 mmol) in 2.5 mL of CH$_2$Cl$_2$ was added dropwise. The reaction mixture was stirred for 90 min after which time it was warmed to RT, diluted with CH$_2$Cl$_2$ and washed with sat. NaHSO$_3$ followed by sat. NaHCO$_3$. The organic phase was dried (MgSO$_4$) and concentrated. The crude material was flash chromatographed on silica eluting with a step-wise gradient of 25% EtOAc-hexane to 80% EtOAc-hexane to obtain 0.193 g (85%) of Compound 183a as a white solid.

(b) Compound 183b

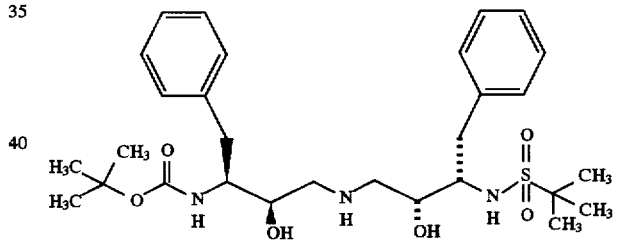

Compound 183b was prepared as a white solid by a procedure analogous to that used for the synthesis of Compound 21.

m.p. 86°–90° C. ("softening" at 75°–86° C.); [α]$^{20}_D$= 18.7° (c=0.2, CH$_3$OH).

EXAMPLE 184

Preparation of [1S-[1R*,2S*(2S*,3R*)]]-[3-[[3-[[[(1,1-Dimethylethyl)thio)carbonyl]amino]-2-hydroxy-4-phenylbutyl]amino]-2-hydroxy-1-(phenylmethyl)-propyl]carbamic acid, 1,1-dimethylethyl ester
(Compound 184b)

(a) Compound 184a

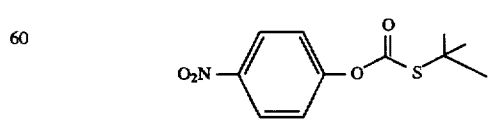

Compound 184a was prepared from t-butyl mercaptan by a procedure analogous to that used for the synthesis of Compound 67a (pyridine was used).

(b) Compound 184b

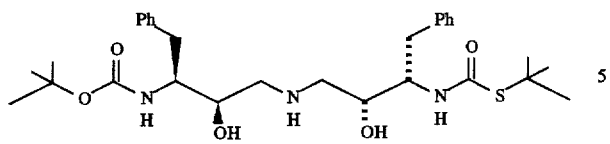

Compounds 184a and 54 were reacted by a procedure analogous to that used for the synthesis of Compound 147d to afford Compound 184b as a white solid.

m.p. 140°–141° C. ("softening" at 134°–140° C.); $[\alpha]^{20}_D = -20.0°$ (c=0.05, CH$_3$OH).

EXAMPLE 185

Preparation of [2S-[2R*,3S*(2S*,3R*)]]-[3-[[3-[[(1,1-Dimethylethoxy) carbonyl]amino-2-hydroxy-4-phenylbutyl]amino-2-hydroxy-4-phenylbutyl ]carbamnic acid, phenylmethyl ester (Compound 185d)

(a) Compound 185a

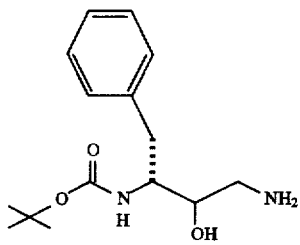

A 3:2 mixture of Compounds 26a(i) and 26a(ii) was converted into Compound 185a by a procedure analogous to that used for the synthesis of Compound 16b (except that the reaction was performed in NH$_3$ saturated MeOH at 50°–60° C. in a sealed vessel).

(b) Compound 185b

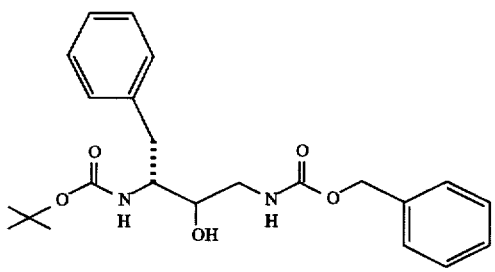

Compound 185a was reacted with Cbz chloride by a procedure analogous to that used for the synthesis of Compound 122 to give Compound 185b (CH$_2$Cl$_2$ used in place of DMF).

(c) Compound 185c

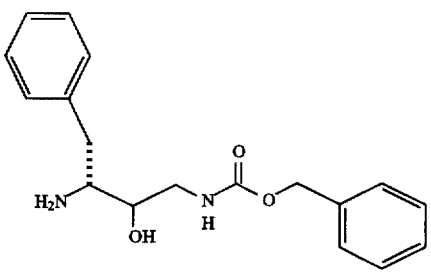

Compound 185b was converted to Compound 185c by a procedure analogous to that used for the synthesis of Compound 32.

(d) Compound 185d

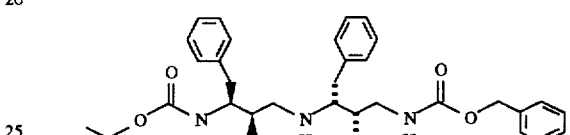

Compounds 185c and 1b(i) were reacted by a procedure analogous to that used for the synthesis of Compound 4b to give the title Compound 185d as a white solid after silica gel chromatography (28 g) eluting the column with a stepwise gradient of CH$_2$Cl$_2$:MeOH:NH$_4$OH (98.9:1.0:0.1) to CH$_2$Cl$_2$:MeOH:NH$_4$OH (94.5:5.0:0.5), using 1% increments for MeOH and 0.1% increments for NH$_4$OH and trituration with Et$_2$O to separate the isomers.

mp 120°–121° C.; $[\alpha]_D = -5.0°$ (c 0.10, MeOH). MS: (M+H)$^+$@578$^+$. Analysis calc. for C$_{33}$H$_{43}$N$_3$O$_6$. 0.01H$_2$O: C, 68.59; H, 7.50; N, 7.27; Found: C, 68.52; H, 7.65; N, 7.34.

EXAMPLE 186

Preparation of [3S-[3R*,2(R*,S*) [2S*,3R*)]-3-[[3-(1,1-Dimethylethoxy)carbonyl]amino]-2-hydroxy-4-phenylbutyl]amino]-2-hydroxy-4-phenylbuty 1] carbamic acid, phenylmethyl ester (Compound 186)

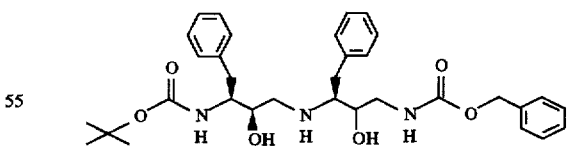

Compound 186 was prepared as a colorless solid from a 1:1 mixture of 1b(i) and 1b(ii) by a procedure analogous to that used for the synthesis of Compound 185d.

mp 90°–95° C.; $[\alpha]_D = -4.0°$ (c 0.10, MeOH). MS: (M+H)$^+$@578$^+$ Analysis calc. for C$_{33}$H$_{43}$N$_3$O$_6$. 0.96H$_2$O: C, 68.40; H, 7.81; N, 7.25; Found: C, 68.39; H, 7.57; N, 7.26.

EXAMPLE 187

Preparation of [2S-[2R*,3S*(2S*,3R*)]]-[3-[[3-[[(1,1-Dimethylethoxy)carbonyl]amino]-2-hydroxy-4-phenylbutyl]amino]-2-hydroxy-4-phenylbutyl] carbamic acid, 1,1-dimethylethyl ester (Compound 187)

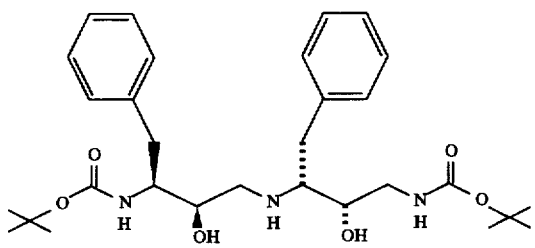

Compound 187 was obtained as a white solid from the (S)-hydroxyl diastereomer of Compound 185d by removing the Cbz group using reaction conditions analogous to those used for the synthesis of Compound 7 and putting on the Boc group using a procedure analogous to that used for the synthesis of Compound 20 (CH$_2$Cl$_2$/DMF used as solvent).

m.p. 143° C.-144° C.; [α]$_D$ = −4.0° (c = 0.09, MeOH)
Elemental Analysis (%)
C$_{33}$H$_{44}$N$_3$O$_6$, calculated for 0.44 H$_2$O

|   | Calc. | Found |
|---|-------|-------|
| C | 65.31 | 65.09 |
| H | 8.38  | 8.22  |
| N | 7.62  | 7.83  |

EXAMPLE 188

Preparation of [3S-[3R*(2S*,3R*)]]-[3-[[3-[[(1,1-Dimethylethoxy)carbonyl]amino]-2-hydroxy-4-phenyl-butyl]amino]-2-hydroxy-4-phenylbutyl] carbamic acid, 1,1-dimethylethyl ester, 2:1 diastereomer mixture (Compound 188)

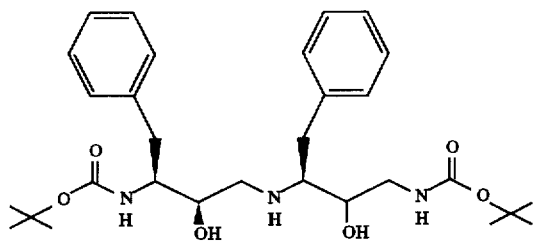

Compound 188 was obtained as a white solid from Compound 186 by removing the Cbz group using reaction conditions analogous to those used for the synthesis of Compound 7 and putting on the Boc group using a procedure analogous to that used for the synthesis of Compound 20 (CH$_2$Cl$_2$/DMF used as solvent).

m.p. 93° C.-94° C.; [α]$_D$ = +4.0° (c = 0.10, MeOH)
Elemental Analysis (%)
C$_{30}$H$_{45}$N$_3$O$_6$, calculated for 0.2 moles H$_2$O

|   | Calc. | Found |
|---|-------|-------|
| C | 65.84 | 65.74 |
| H | 8.36  | 8.39  |
| N | 7.68  | 7.78  |

EXAMPLE 189

Preparation of [2R-[2R*,3R*(2R*,3S*)]]-[3-[[3-[[(1,1-Dimethylethoxy)carbonyl]amino]-2-hydroxy-4-phenylbutyl]amino]-2-hydroxy-4-phenylbutyl]-carbamic acid, phenylmethyl ester (Compound 189)

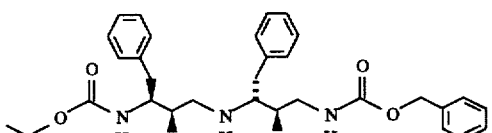

Compound 189 was obtained as a white solid from the (R)-hydroxyl diastereomer of Compound 185a by a procedure analogous to that of Example 185d.

m.p. 112° C.-113° C.; [α]$_D$ = +3.0° (c = 0.09, MeOH)
Elemental Analysis (%)
C$_{33}$H$_{43}$N$_3$O$_6$, calculated for 0.27 H$_2$O

|   | Calc. | Found |
|---|-------|-------|
| C | 68.03 | 67.94 |
| H | 7.53  | 7.35  |
| N | 7.21  | 7.30  |

EXAMPLE 190

Preparation of [2R-[2R*,3R*(2R*,3S*)]]-[3-[[3-[[(1,1-Dimethylethoxy)carbonyl]amino]-2-hydroxy-4-phenyl-butyl]amino]-2-hydroxy-4-phenylbutyl] carbamic acid, 1,1-dimethylethyl ester (Compound 190)

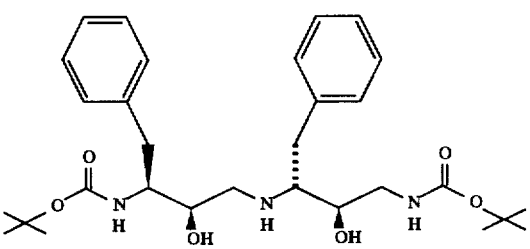

Compound 190 was obtained as a white solid from Compound 189 by a two-step procedure analogous to that used for the synthesis of Compound 187.

| Elemental Analysis (%) $C_{30}H_{45}N_3O_6$, calculated for 1.34 moles $H_2O$ | | |
|---|---|---|
| | Calc. | Found |
| C | 65.63 | 65.27 |
| H | 7.96 | 7.83 |
| N | 6.96 | 7.32 |

EXAMPLE 191

Preparation of [1S-(1R*,2S*)]-[3-[[3-[[(1,1-Dimethylethoxy)carbonyl]amino]-2-hydroxy-2-(phenylmethyl)propyl]amino]-2-hydroxy-1-(phenylmethyl)propyl]carbamic acid, 1,1-dimethylethyl ester (Compound 191e)

(a) Compound 191a

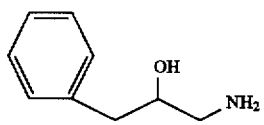

Compound 191a was prepared from epoxypropyl benzene by a procedure analogous to that used for the synthesis of Compound 16b except that $NH_3$ saturated MeOH was used at 90° C. in a sealed vessel.

(b) Compound 191b

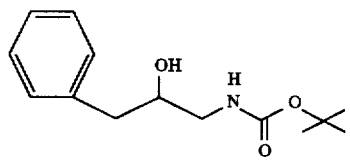

Compound 191b was prepared from Compound 191a by a procedure analogous to that used for the synthesis of Compound 131 (THF/$H_2O$ used).

(c) Compound 191c

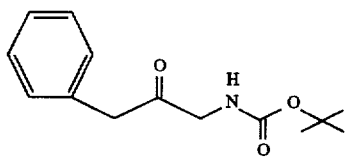

DMSO (0.17 ml, 2.40 mmol) was added to a stirred solution of $(COCl)_2$ (0.104 ml, 1.20 mmol) in dry $CH_2Cl_2$ (5.0 ml) at −78° C. After 15 min, a solution of Compound 191b (0.10 g, 0.40 mmol) in $CH_2Cl_2$ (5.0 ml) was added. The reaction mixture remained at −78° C. for 40 min before adding $Et_3N$ (0.39 ml, 2.80 mmol), and warming to 0° C. for 4 min. The yellow reaction mixture was then quenched with saturated $NH_4Cl$ and the aqueous layer extracted with EtOAc. The organic layer was washed with saturated $NaHCO_3$, dried ($Na_2SO_4$) and concentrated in vacuo to afford 0.109 g of Compound 191c as a yellow oil.

(d) Compound 191d

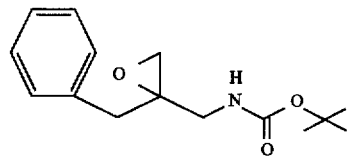

To a solution of Compound 191c (0.10 g, 0.40 mmol) in THF (30 ml) was added the ylide (0.60 ml, 0.962M) freshly prepared by refluxing trimethylsulfoxonium chloride (3.75 g, 29.16 mmoles) and NaH (0.693 g, 28.88 mmol, 60% oil dispersion washed with hexane) in dry THF (30 ml) for 3.5 h. After stirring at 0° C. for 75 seconds, saturated $NaHCO_3$ was added and the reaction mixture was partitioned between EtOAc and $NaHCO_3$ solution. The volatiles were evaporated to afford a yellow oil which is a mixture of Compounds 191c and 191d (1:1). The oil was dried by azeotroping with toluene three times and placing under high vacuum, then resubmitting to the reaction conditions. The isolated crude material was purified on a silica gel column (10 g), eluting the column with $CH_2Cl_2$:MeOH:$NH_4OH$ (98.9:1.0:0.1, 97.8:2.0:0.2 and 96.7:3.0:0.3) to afford 0.69 g (66%) of Compound 191d as a yellow oil.

(e) Compound 191e

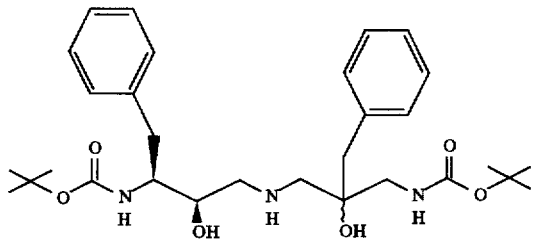

Compounds 191d and 16b were reacted by a procedure analogous to that of Example 4b (except in MeOH at 50° C.) to give Compound 191e as a colorless foam.

| m.p. 65–67° C.; $[\alpha]_D = -3.0°$ (c 0.10, MeOH) Calculated for $C_{30}H_{45}N_3O_6 \cdot 0.35\ H_2O$ | | |
|---|---|---|
| | Calc. | Found |
| C | 65.52 | 65.36 |
| H | 8.37 | 8.42 |
| N | 7.64 | 7.80 |

EXAMPLE 192

Preparation of [1S-[1R*.2S*(3R*)]]-[3-[[3-[[(1,1-Dimethylethoxy)carbonyl]amino]- 2-hydroxy-2-methyl-4-phenylbutyl]amino]-2-hydroxy-1-(phenylmethyl)propyl]amino]carbamic acid, 1,1-dimethylethyl ester (Compound 192c)

(a) Compound 192a

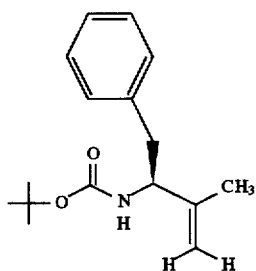

KN(TMS)₂ (6.08 ml, 3.04 mmol) was added dropwise to a mixture of MePPh₃⁺Br⁻ (1.19 g, 3.34 mmol) in toluene (8 ml) at −78° C. After 5 min, the mixture was warmed to RT and stirred for 15 min. After recooling the reaction to −78° C., a solution of 3S-3-[(1,1-dimethylethoxycarbonyl)amino]-4-phenyl-2-butanone [Godfrey et al., Tetrahedron Letters, 28, 1603 (1987)] (0.40 g, 1.52 mmol) in toluene (2 ml) was added. The reaction was quenched after 35 min with pH 7 buffer and the aqueous layer extracted with EtOAc. The combined extracts were dried (Na₂SO₄) and concentrated in vacuo to afford 0.159 g of Compound 192a as a white solid (42% yield).

(b) Compound 192b

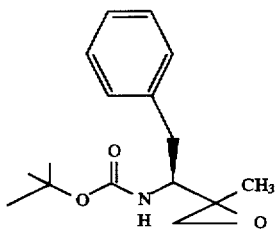

m-CPBA (0.13 g, 0.61 mmole) was added to a stirred solution of Compound 192a (0.16 g, 0.61 mmol) in CH₂Cl₂ (2 ml) at 0° C. After 30 min, the reaction mixture was warmed to RT and stirred for an additional 30 min before quenching with pH 7 buffer and partitioning between aq. NaHCO₃ and EtOAc. The organic extracts were dried (Na₂SO₄) and concentrated in vacuo to afford 0.17 g of a white solid. This crude material was purified by silica gel chromatography (20 g), eluting the column with 10% EtOAc/hexane to afford 0.129 g of Compound 192b as a white solid (87% yield).

(c) Compound 192c

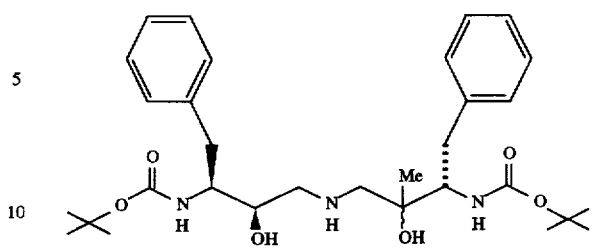

Compounds 192b and 16b were reacted by a procedure analogous to that of Example 4b (except that the reaction was run in MeOH at 50° C.) to give the title Compound 192c as a colorless foam.

| | Elemental Analysis (%) Calc. for C₃₁H₄₇N₃O₆·0.42 H₂O | |
|---|---|---|
| C | 65.98 | 66.15 |
| H | 8.37 | 8.52 |
| N | 7.45 | 7.28 |

EXAMPLE 193

Preparation of [1S-[1R*.2S*(3R*)]]-[3-[[3-[[(1,1-Dimethylethoxy)carbonyl]amino]-2-oxo-4-phenylbutyl]amino]-2-hydroxy-1-(phenylmethyl)propyl]carbamic acid, 1,1-dimethylethyl ester (Compound 193b)

(a) Compound 193a

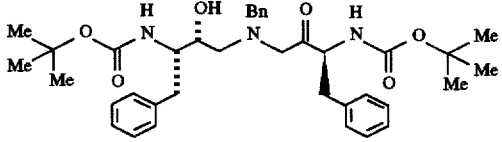

To a solution of Compound 1a(iii) (197 mg, 0.68 mmol), Compound 4a (250 mg, 0.66 mmol), and NaI (99 mg, 0.66 mmol) in DMF (1.8 mL) was added NaHCO₃ (200 mg, 2.38 mmol). The suspension was stirred at RT for 18.5 h and then partitioned between EtOAc and H₂O. The organic extracts were dried (Na₂SO₄) and concentrated in vacuo to give an oily-solid residue which was purified by flash chromatography (silica gel, 3 by 11 cm), eluting with MeOH:NH₄OH:CH₂Cl₂ (0.5:0.05:99.45 and then 1:0.1:98.9) to give Compound 193a (130 mg, 31% yield) as a colorless solid.

R_f=0.36 (4:0.4:95.6; MeOH:NH₄OH:CH₂Cl₂); Mass Spec. (FAB): 632 (M+H).

(b) Compound 193b

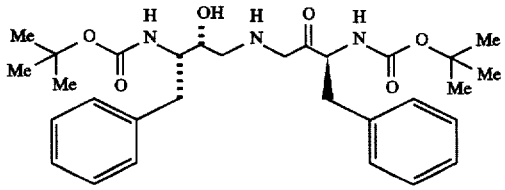

Compound 193b was prepared as a colorless solid from Compound 193a by a procedure analogous to that of Example 7 (1:1 THF:MeOH used).

m.p. dec. 116°–120° C.

Mass Spec. (CI/NH₃): 542 (M+H).

Anal. Calc. for $C_{30}H_{43}N_3O_6 \cdot 0.26\ H_2O$: C, 65.94; H, 8.03; N, 7.69

Found: C, 66.00; H, 8.05; N, 7.63

EXAMPLE 194

Preparation of [2S-(2R*,2R*)]-[[(Phenylmethyl)-imino ]bis[2-hydroxy-4-phenyl-3,1-butanediyl]] biscarbamic acid, bis(1,1-dimethylethyl)ester (Compound 194b)

(a) Compound 194a

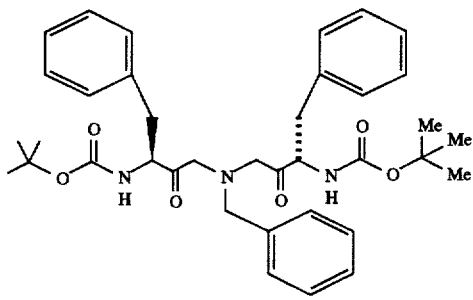

Compound 194a was prepared from 1 eq. of benzyl amine and 2.2 eq. of Compound 1a(iii) by a procedure analogous to that used in Example 193a.

(b) Compound 194b

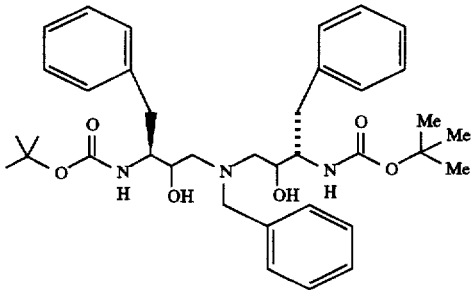

Compound 194b was prepared as a white foam from Compound 194a by a procedure analogous to that used for the synthesis of Compounds 1a(iv) and 1a(v) except that 95% EtOH was used.

| m.p. 60.0–62.0° C. Elemental Analysis (%) $C_{37}H_{51}N_3O_6$ | | |
|---|---|---|
| | Calc. | Found |
| C | 70.11 | 69.67 |
| H | 8.11 | 8.05 |
| N | 6.63 | 6.43 |

EXAMPLE 195

Preparation of [1S-[1R*(3R*)]]-[3-[[3-[[(1,1-Dimethylethoxy)carbonyl]amino]-2-hydroxy-4-phenylbutyl]-(phenylmethyl)amino]-2-oxo-1-(phenylmethyl)propyl]-carbamic acid, 1,1-dimethylethyl ester (Compound 195)

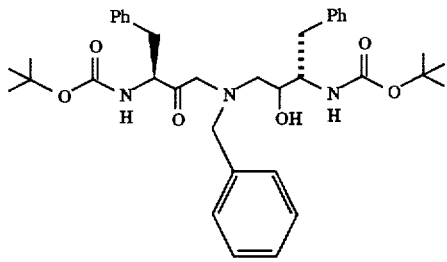

Compound 195 was also isolated as a white solid from the reaction mixture of Example 194b.

| m.p. (161.0° C. softens) 176.0°–177.0° C. Elemental Analysis (%) $C_{37}H_{49}N_3O_6$ | | |
|---|---|---|
| | Calc. | Found |
| C | 70.34 | 69.85 |
| H | 7.82 | 7.86 |
| N | 6.65 | 6.77 |

EXAMPLE 196

Preparation of (3S,3S')-[[(Phenylmethyl)nitrilo]-bis (2-hydroxy-5-methyl-3,1-hexandiyl)]-biscarbamic acid, bis(1,1-dimethylethyl)ester (Compound 196b)

(a) Compound 196a

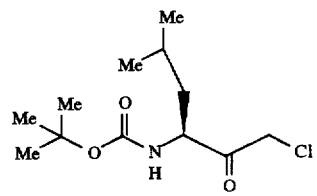

Compound 196a was prepared from Boc-L-leucine by a procedure analogous to that used for the synthesis of Compound 1a(iii).

(b) Compound 196b

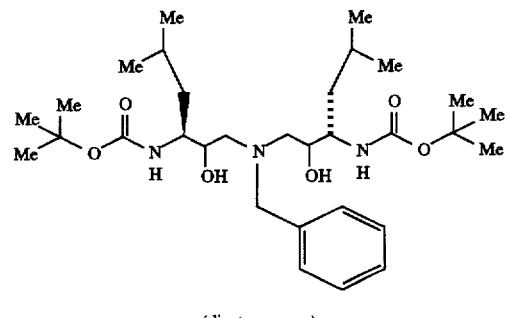

(diastereomers)

Compound 196b was prepared as a white foam by a two-step procedure analogous to that of Example 194b.

| m.p. 54.0–55.0° C. Elemental Analysis (%) $C_{31}H_{45}N_3O_6.0.53 H_2O$ | | |
|---|---|---|
| | Calc. | Found |
| C | 64.72 | 64.63 |
| H | 9.82 | 9.27 |
| N | 7.30 | 7.39 |

EXAMPLE 197

Preparation of [1S-[1R*(2S*,3R*)]]-[3-[[3-[[(1,1-Dimethylethoxy)carbonyl]-amino]-2-hydroxy-4-phenylbutyl]-methylamino]-2-oxo-1-(phenylmethyl) propyl]carbamic acid, 1,1-dimethylethyl ester (Compound 197b)

(a) Compound 197a

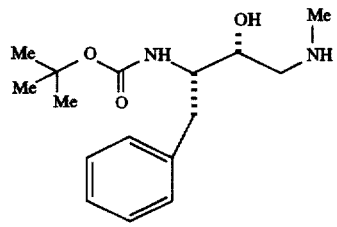

Compound 197a was prepared from Compound 1b(i) and MeNH₂ by a procedure analogous to that used for the synthesis of Compound 4a except that the reaction was run in EtOH at RT.

(b) Compound 197b

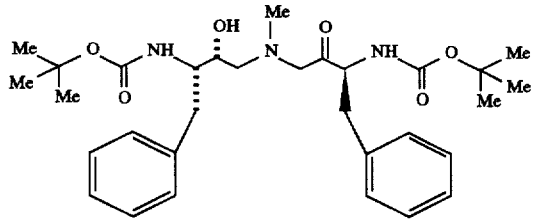

Compound 197b was prepared as a white foam from Compounds 197a and 1a(iii) by a procedure analogous to that of Example 193a.

| m.p. 120.0–122.0° C. Elemental Analysis (%) $C_{31}H_{45}N_3O_6.0.40 H_2O$ | | |
|---|---|---|
| | Calc. | Found |
| C | 66.14 | 66.01 |
| H | 8.20 | 8.08 |
| N | 7.46 | 7.28 |

EXAMPLE 198

Preparation of [1S-[1R*,2S*(3R*)]]-[3-[[3-[[(1,1-Dimethylethoxy)carbonyl]-amino]-2-hydroxy-4-phenylbutyl]-methylamino]- 2-hydroxy-1-(phenylmethyl)propyl]-carbamic acid, 1,1-dimethylethyl ester (Compound 198)

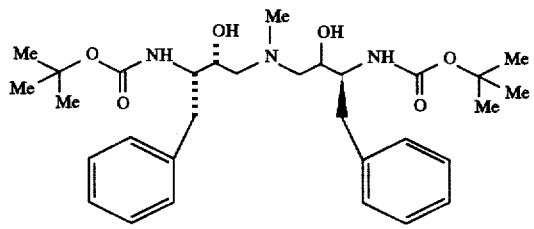

Compound 198 was prepared as a white foam from Compound 197b by a procedure analogous to that used for the synthesis of Compounds 1a(iv) and 1a(v) except that 95% EtOH was used.

| m.p. 62.0–70.0° C. Elemental Analysis (%) $C_{31}H_{47}N_3.0.18 H_2O$ | | |
|---|---|---|
| | Calc. | Found |
| C | 66.76 | 66.37 |
| H | 8.49 | 8.70 |
| N | 7.53 | 7.27 |

EXAMPLE 199

Preparation of [1S-[1R*(2R*,3R*)]]-3-[[3[[-(1,1-Dimethylethoxy)carbonyl]-amino]-2-hydroxy-4-phenylbutyl]-methylamino]-2-oxo-1-(phenylmethyl) -propyl]carbamic acid, 1,1-dimethylethyl ester (Compound 199)

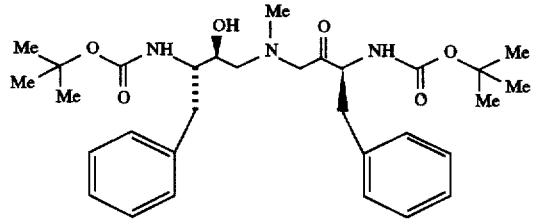

Compound 199 was prepared as a white foam from Compound 1b(ii) by a procedure analogous to that of Example 197b.

| m.p. 72.0–80.0° C. Elemental Analysis (%) $C_{31}H_{45}N_3O_6$ | | |
|---|---|---|
| | Calc. | Found |
| C | 67.00 | 66.84 |
| H | 8.16 | 8.14 |

EXAMPLE 200

Preparation of [1S-[1R*,2R*(1R*)]]-[3-[[3-[[(1,1-Dimethylethoxy)carbonyl]-amino]-2-hydroxy-4-phenylbutyl]-methylamino]-2-hydroxy-1-(phenylmethyl)propyl]-carbamic acid, 1,1-dimethylethyl ester (Compound 200)

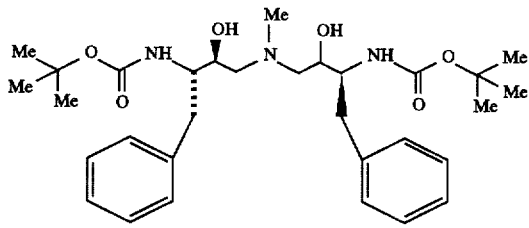

Compound 200 was prepared as a white foam from Compound 199 by a procedure analogous to that used for the synthesis of Compounds 1a(iv) and 1a(v) except that 95% EtOH was used.

| | m.p. 70.0–75.0° C. Elemental Analysis (%) C₃₁H₄₇N₃O₆·0.85 H₂O | |
|---|---|---|
| | Calc. | Found |
| C | 64.98 | 65.31 |
| H | 8.57 | 8.30 |
| N | 7.33 | 7.00 |

EXAMPLE 201

Preparation of [1S-[1R*,2S*(2S*,3R*)]]-[3-[[3-[[(1,1-Dimethylethoxy)carbonyl]aminol-2-hydroxy-4-[4-[3-(4-morpholinyl)propoxy]phenyl]butyl]amino]-2-hydroxy-1-(phenylmethyl)propyl]carbamic acid, 1,1-dimethylethyl ester (Compound 201d)

(a) Compound 201a

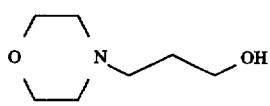

Ethyl-3-bromoproprionate (3.20 ml; 25 mmol) was added to a mixture of morpholine (2.20 ml; 25 mmol) and Na₂CO₃ (2.78 g; 26 mmol) in 4.5 ml of EtOH at RT. The mixture was stirred for 30 min at RT and 4 h at reflux. After cooling to RT and filtering, the filtrate was concentrated and the residue was dissolved in H₂O. The pH was adjusted to ~1.5 with saturated KHSO₄ and the acidic mixture was washed with Et₂O. Solid K₂CO₃ was added to the aqueous layer until a pH of ~9 was reached. The basic mixture was extracted with CH₂Cl₂, dried (MgSO₄) and concentrated to afford 4.75 g (100+%; contained trace solvent) of ethyl-3-morpholinoproprionate as a colorless liquid. A solution of this ester (935 mg; 5 mmol) in 20 ml of Et₂O was added to a suspension of LiAlH₄ (400 mg; 10 mmol) in 80 ml of Et₂O at 0° C. After stirring for 30 min at 0° C., the reaction was quenched by the careful addition of 0.42 ml of H₂O followed by 0.42 ml of 15% NaOH and 1.26 ml of H₂O. MgSO₄ was added and the suspension was filtered and concentrated to afford 531 mg (73%) of Compound 201a as a colorless liquid.

(b) Compound 201b

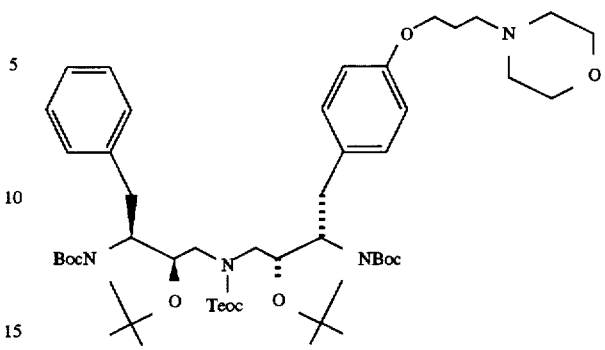

Compounds 172 and 201a were reacted by a method analogous to that described in Example 176 to give Compound 201b.

(c) Compound 201c

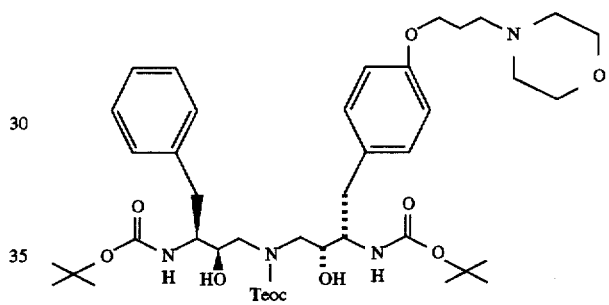

Compound 201b was converted into Compound 201c (white foam) by the method described for Compound 177.

(d) Compound 201d

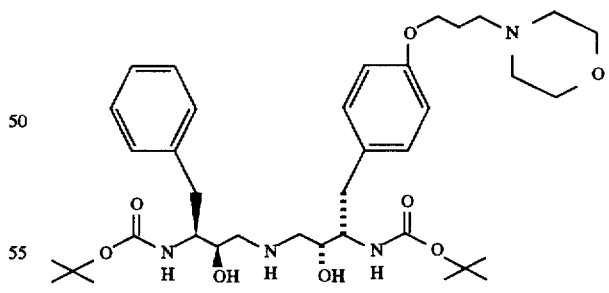

Compound 201c was converted to the title Compound 201d (white solid) by the method described in Example 21.

mp 122°–124° C.; [α]_D=–4.7° (c 0.30, MeOH). Mass Spec. FAB+ions: M+H=687. Analysis calc. for C₃₇H₅₈N₄O₈·0.39 H₂O: C, 64.05; H, 8.54; N, 8.07; Found: C, 64.10; H, 8.50; N, 8.02.

EXAMPLE 202

Preparation of [[1R*,2S*(2S*,3R*)],N²-(R*)]-N²-[(2,3-Dihydroxypropoxy)carbonyl]-N-[3-[[3-[[(1,1-dimethylethoxy) carbonyl]amino]-2-hydroxy-4-phenylbutyl]amino]-2-hydroxy-1-(phenylmethyl) propyl]-L-valinamide (Compound 202e)

(a) Compound 202a

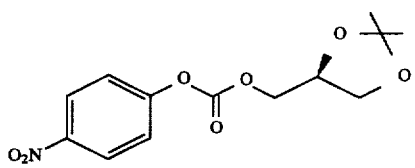

(R)-2,2-Dimethyl-1,3-dioxolane-4-methanol was converted to Compound 202a (pale yellow oil) by a method analogous to that of Example 161d.

(b) Compound 202b

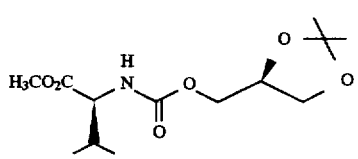

Compound 202a and valine methyl ester hydrochloride were reacted by a method analogous to that described for Example 161e to give Compound 202b (yellow oil).

(c) Compound 202c

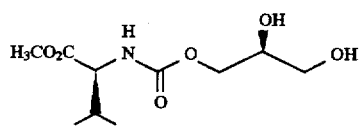

Crude Compound 202b was dissolved in a solution of glacial HOAc (10 mL) and H₂O (2.50 mL) and heated at 40°–45° C. in an oil bath for 3 h. Volatiles were removed in vacuo to afford an orange oil, which was chromatographed on silica gel (100 mL) using a gradient from 1:1 hexane:EtOAc to 100% EtOAc as eluent to afford Compound 202c (0.552 g, 74% over 2 steps) as a pale yellow oil.

(d) Compound 202d

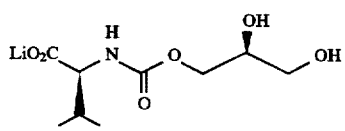

Compound 202c was converted to Compound 202d (white solid) by a method analogous to that used for the preparation of Compound 70c (THF used as solvent).

(e) Compound 202e

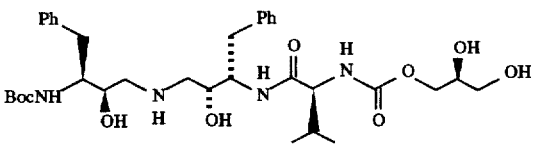

Compounds 54 and 202d were reacted by a method analogous to that described for Compound 55 (2 eq. N-methylmorpholine added; DMF only used) to give the title Compound 202e. This material was purified by preparative HPLC on a Waters Delta Prep 4000, with a Waters Novapak C-18 (6 μm particle size; 30×300 mm) column using as eluent a gradient from 50:50 A:B to 100% A (A=90:10:0.05 MeOH:H₂O:TFA; B=90:10:0.05 H₂O:MeOH:TFA) to give 47 mg (21%) of pure Compound 202e as a white powder.

m.p.=167°–170° C.; $[\alpha]_D=-15.90°$ (c=0.23; MeOH) High resolution MS (FAB): Calculated (M+H)⁺ (for $C_{34}H_{53}O_9N_4$) =661.3813; Observed (M+H)⁺=661.3798 Δ=2.3 ppm

EXAMPLE 203

Preparation of [1R*,2S*(2S*,3R*)]-N-[3-[[3-[[(1,1-Dimethylethoxy) carbonyl]amino]-2-hydroxy-4-phenylbutyl]amino]-2-hydroxy-1-(phenylmethyl) propyl]-N²-[[2-(phenylamino) ethoxy]carbonyl]-L-valinamide (Compound 203e)

(a) Compound 203a

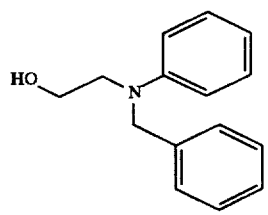

2-Anilinoethanol, benzaldehyde and NaCNBH₃ were reacted by a method analogous to that of Example 126 (MeOH/1% HOAc used) to give Compound 203a (clear oil).

(b) Compound 203b

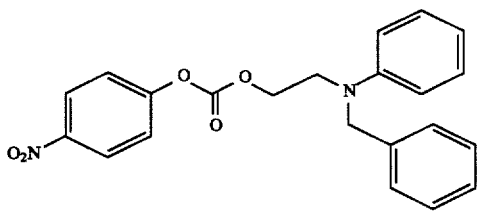

Compound 203a was converted to Compound 203b (yellow oil which solidified upon standing) by a method analogous to that described in Example 161d.

(c) Compound 203c

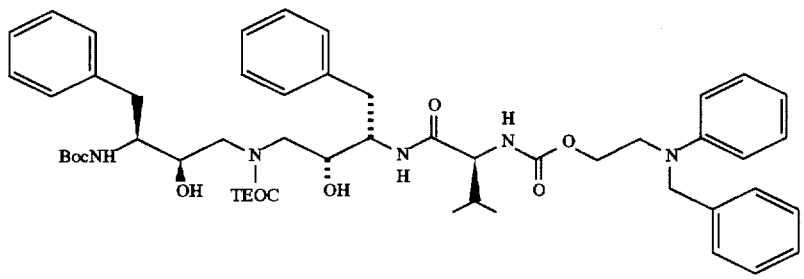

Compounds 203b and 61 were reacted by a method analogous to that described in Example 161e to give 238 mg of Compound 203c (white solid).

(d) Compound 203d

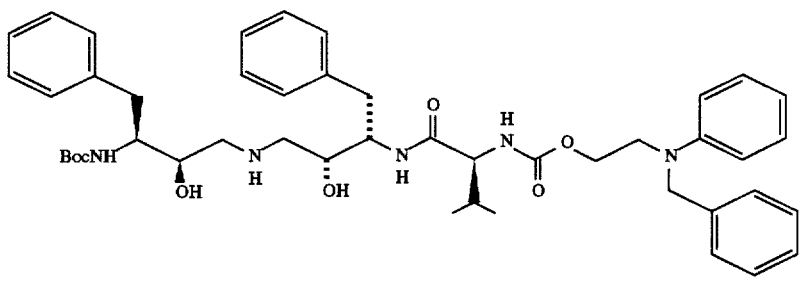

Compound 203c was converted into Compound 203d (white solid) by a method analogous to that described in Example 21.

(e) Compound 203e

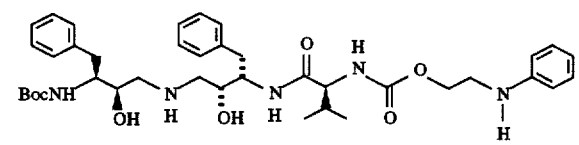

Compound 203d was converted into the title Compound 203e (white solid) by a method analogous to that of Example 2.

mp 162°–167° C. ("softening" at 150°–162° C.); $[\alpha]_D=$ –15.5° (c=0.69, MeOH). Mass spectrum (FAB): 706 (M+H$^+$); Analysis calculated for $C_{39}H_{55}O_7N_5 \cdot 1.85H_2O$: C, 63.37 H, 8.00 N, 9.47; Found: C, 63.32 H, 7.91 N, 9.52

EXAMPLE 204

Preparation of [1R*,2S*(2S*,3R*)]-N-[3-[[3-[[(1,1-Dimethylethoxy) carbonyl]amino]-2-hydroxy-4-phenylbutyl]amino]-2-hydroxy-1-(phenylmethyl) propyl]-N²-[[1,4-dioxo-4-(phenylamino) butyl]-L-valinamide (Compound 204b)

(a) Compound 204a

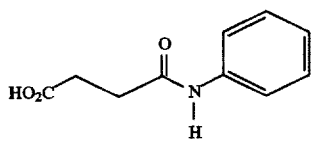

Compound 204a was prepared by a procedure analogous to that described in *Liebigs Ann. Chem.*, 306, 326 (1899).

(b) Compound 204b

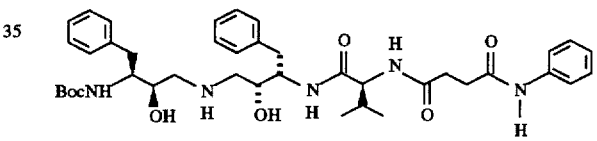

Compound 204b (white solid) was prepared starting from Compounds 61 and 204a by a two-step method analogous to that used for the conversion of Compound 48 to Compound 52.

mp 218°–220° C. ("softening" at 210°–218° C.); $[\alpha]_D=$ –3.7° (c=0.47, MeOH). mass spectrum (FAB): 718 (M+H$^+$); Analysis calculated for $C_{40}H_{55}O_7N_5 \cdot 0.94 H_2O$: C, 65.38 H, 7.80 N, 9.53; Found: C, 65.44 H, 7.65 N, 9.47.

EXAMPLE 205

Preparation of [1R*,2S*(2S*,3R*)]-N-[3-[[3-[[(1,1-Dimethylethoxy) carbonyl]amino]-2-hydroxy-4-phenylbutyl]amino]-2-hydroxy-1-(phenylmethyl) propyl]-N²-[(phenylmethoxy)carbonyl]-L-allothreoninamide (Compound 205b)

(a) Preparation of Cbz-L-allothreonine (Compound 205a)

Benzylchloroformate (0.35 ml; 2.3 mmol) was added to a mixture of L-allothreonine (0.25 g; 2.1 mmol) and NaHCO₃ (435 mg; 5.18 mmol) in 2.5 ml of H₂O at RT. After 3 h, the reaction mixture was partitioned between Et₂O and H₂O. The aqueous layer was washed with Et₂O, acidified to pH <2 with 6N HCl, and extracted with CH₂Cl₂. The organic layer was dried (MgSO₄) and concentrated to afford 320 mg (63%) of Cbz-L-allothreonine.

(b) Compound 205b

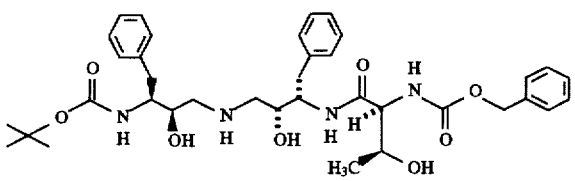

Compounds 205a and 54 were reacted by a method analogous to that described in Example 55 (DMF only) to give the title Compound 205b (white solid).

mp 155°–157° C.; $[\alpha]_D$=–21.0° (c 0.45, MeOH). Mass Spec. FAB+ions: M+H=679. Analysis calc. for $C_{37}H_{50}N_4O_8 \cdot 0.61\ H_2O$: C, 64.43; H, 7.48; N, 8.12; Found C, 64.46; H, 7.35; N, 8.09.

EXAMPLE 206

Preparation of [4S-[4α, 5α(4R*,5S*)]]-5-[[[[3-[(1,1-Dimethylethoxy)carbonyl]-4-[[4-[2-(phenylmethoxy) ethoxy]phenyl]methyl]-2,2-dimethyl-5-oxazolidinyl]methyl][[2-(trimethylsilyl)ethoxylcarbonyl]]amino]methyl]-2,2-dimethyl-4-(phenylmethyl)-3-oxazolidinecarboxylic acid, 1,1-dimethylethyl ester (Compound 206)

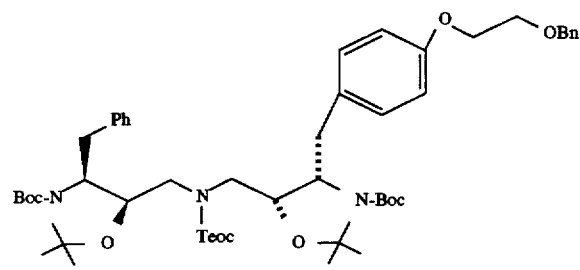

To a mixture of Compound 172 (250 mg, 0.32 mmol), 2-benzyloxyethanol (91 μl, 0.64 mmol) and Ph₃P (167 mg, 0.64 mmol) in dry THF (0.64 ml) was added DEAD (100 μl, 0.64 mmol). The mixture was stirred at RT overnight. Concentration in vacuo followed by flash chromatography (hexane/EtOAc 10:1 to 8:1) afforded 251 mg (86%) of Compound 206 as a white foam.

¹H NMR (400 MHz, CDCl₃): 7.10–7.55 (m, 12H), 6.85 (m, 2H), 4.66 (s, 2H), 4.02–4.38 (m; 8H), 3.85 (m, 2H), 3.20–3.60 (m, 4H), 2.70–3.05 (m, 4H), 1.20–180 (m, 30H), 0.92 (m, 2H), 0.00 (s, 9H).

EXAMPLE 207

Preparation of [1R*,2S*(2S*,3R*)]-[3-[[3-[[(1,1-Dimethylethoxy) carbonyl]amino]-2-hydroxy-4-[4-[2-(phenylmethoxy) ethoxyl]phenyl]butyl]][[2-(trimethylsilyl) ethoxy]carbonyl]]amino]-2-hydroxy-1-(phenylmethyl) propyl]carbamic acid, 1,1-dimethylethyl ester (Compound 207)

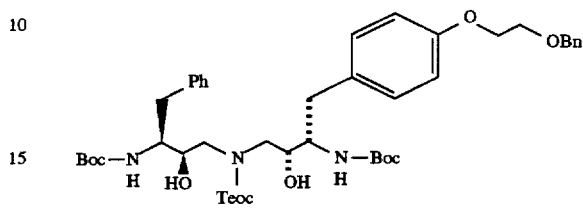

To Compound 206 (251 mg, 0.274 mmol) was added pre-cooled (10° C.) 96% formic acid (6.0 ml). The mixture was stirred at 5° C. for 20 min and then frozen (dry ice-acetone) and lyophilized (overnight). The residue was taken into MeOH (5 ml). To this solution was added Et₃N (115 μl, 0.822 mmol), followed by di-tert-butyldicarbonate (60 mg, 0.274 mmol). The mixture was stirred at RT overnight. Concentration in vacuo followed by flash chromatography (100% CHCl₃ to CHCl₃—MeOH—NH₄OH: 95:5:0.5) afforded 219 mg (97%) of Compound 207 as a white foam.

¹H NMR (400 MHz, CD₃OD): 7.05–7.35 (m, 12H), 6.79 (d, J=8.12, 2H), 4.55 (s, 2H), 4.12 (m, 2H), 4.06 (t, J=4.70, 2H), 3.75 (t, J=4.70, 2H), 3.54–3.85 (m, 6H), 3.10–3.30 (m, 2H, N-CH₂), 2.54 and 3.00 (both m, 4H), 1.25 and 1.26 (both s, 18H), 0.99 (m, 2H), 0.00 (s, 9H).

EXAMPLE 208

Preparation of [1R*,2S*(2S*,3R*)]-[3-[[3-[[(1,1-Dimethylethoxy) carbonyl]amino]-2-hydroxy-4-[4-(2-hydroxyethoxy) phenyl]butyl][[2-(trimethylsilyl) ethoxy]carbonyl]]amino]-2-hydroxy-1-(phenylmethyl) propyl]carbamic acid, 1,1-dimethylethyl ester (Compound 208)

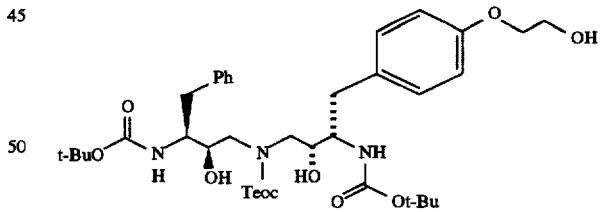

To a solution of Compound 207 (219 mg, 0.265 mmol) in 4.0 ml of MeOH was added 75 mg Pd(OH)₂. The mixture was stirred under a H₂ atmosphere overnight. The catalyst was removed by filtration and the filtrate was concentrated under reduced pressure to give 195 mg of Compound 208 as a colorless oil, which was used immediately for the next Example.

¹H NMR (400 MHz, CD₃OD): 7.05–7.25 (m, 7H), 6.79 (d, J=7.69, 2H), 4.12(m, 2H), 3.95 (t, J=4.91, 2H), 3.79 (t, J=4.91, 2H), 3.50–3.80 (m, 6H), 3.10–3.32 (m, 2H), 2.52 and 3.00 (both m. 4H), 1.25 and 1.27 (both s, 18H), 0.99 (t, J=8.55, 2H), 0.00 (s, 9H).

EXAMPLE 209

Preparation of [1S-[1R*,2S*(2S*,3R*)]]-[3[[-3-[[(1,1-Dimethylethoxy)carbonyl]amino]-2-hydroxy-4-[4-(2-hydroxyethoxy)phenyl]butyl]amino]-2-hydroxy-1-(phenylmethyl) propyl]-carbamic acid, 1,1-dimethylethyl ester (Compound 209)

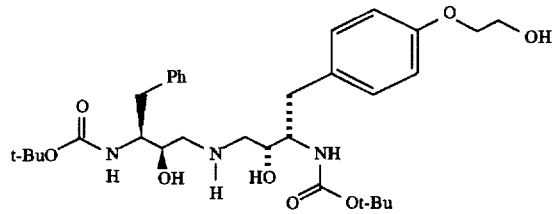

A mixture of Compound 208 (195 mg, 0.265 mmol) and solid n-Bu$_4$NF·nH$_2$O (208 mg, 0.795 mmol) in dry THF (1.2 ml) was heated at 50° C. for 4.0 h. After cooling to RT, Celite (1.0 g) was added and the solvent was removed under reduced pressure. Flash chromatography (100% CHCl$_3$ to CHCl$_3$—MeOH—NH$_4$OH: 94:6:0.6) on silica gel afforded 122 mg (76%) of Compound 209 as a white solid.

M.P.: 152°–154° C.; [α]$_D$=−2.9° (c 0.49, MeOH). MS (FAB): 604$^+$ (M+H)$^+$. Anal. Calc. for C$_{32}$H$_{49}$N$_3$O$_8$·1.16 H$_2$O: C, 61.52; H, 8.28; N, 6.73. Found: C, 61.44; H, 7.90; N, 6.81.

EXAMPLE 210

Preparation of [1S-(1R*,2S*)]-[Iminobis[2-hydroxy-1-(phenylmethyl)-3,1-propanediyl]] biscarbamic acid, 1,1-dimethylethyl-4-(phenylmethoxy)-1,1-dimethylbutyl ester (Compound 210b)

(a) Compound 210a

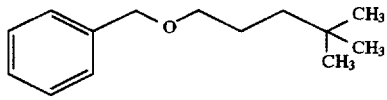

Compound 210a (viscous oil) was prepared from 5-benzyloxy-2-pentanone (Jiang et al., *J. Org. Chem*, 48, 2001 (1983)) by a procedure analogous to that described in Example 158a.

(b) Compound 210b

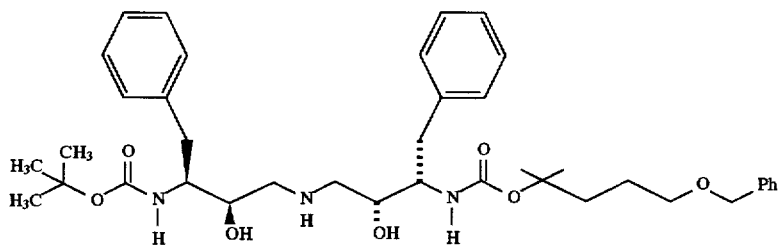

Compound 210a was converted into Compound 210b (white solid) by a three-step procedure analogous to that used for the conversion of Compound 149c to Compound 150 (DMF used in the coupling of the p-nitrophenyl carbonate with Compound 48).

mp 139°–142° C. ("shrinkage" at 120°–135° C.); [α]$_D$=−3.4° (c 0.23, CH$_3$OH). Mass Spec.(High Res.) (M+H)$^+$= 678.4092 (Δppm=3.8)

EXAMPLE 211

Preparation of [1R*,2S*(2S*,3R*)]-N-[3-[[3-[[(1,1-Dimethylethoxy) carbonyl]amino]-2-hydroxy-4-phenylbutyl]amino]-2-hydroxy-1-(phenylmethyl) propyl]-N$^2$-(2-hydroxyoxyphenylalanyl)-L-valinamide, fumarate (2:3) salt (Compound 211c)

(a) Compound 211a

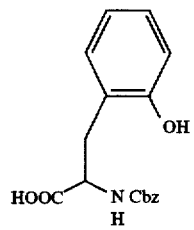

DL-o-Tyrosine was converted to Compound 211a (colorless solid) by a method analogous to that described in Example 85a.

(b) Compound 211b

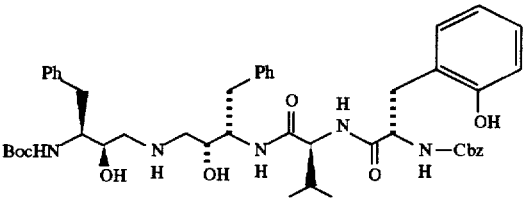

Compounds 211a and 61 were converted to Compound 211b (colorless solid) by a two-step procedure analogous to that used for the conversion of Compound 48 to Compound 52.

(c) Compound 211c

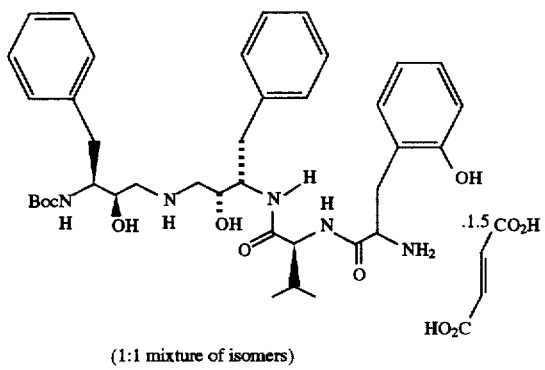

(1:1 mixture of isomers)

Compound 211b was converted into Compound 211c (colorless solid) by a method analogous to that described in Example 84.

High Res. Mass Spec. (FAB): $C_{39}H_{56}N_5O_7$ (M+H)$^+$= 706.4180$^+$ Δ=3.7 ppm. [α]$_D$=−12° (c=0.2, MeOH).

EXAMPLE 212

Preparation of [1R*,2S*(2S*,3R*)]-N-[N-[3-[[3-[[ (1,1-Dimethylethoxy)carbonyl]amino]-2-hydroxy-4-phenylbutyl]amino]-2-hydroxy-1-(phenylmethyl) propyl]-L-valyl]-L-serinamide, fumarate (2:3) salt (Compound 212b)

(a) Compound 212a

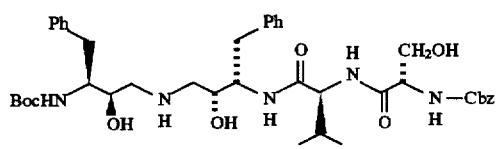

Compound 61 and N-Cbz-L-serine were converted to Compound 212a (colorless solid) by a two-step procedure analogous to that used for the conversion of Compound 48 to Compound 52.

(b) Compound 212b

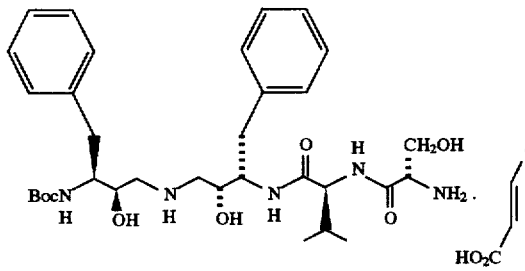

Compound 212a was converted into Compound 212b (colorless solid) by a method analogous to that described in Example 84.

m.p. 178°–184° C. High Res. Mass Spec. (FAB): $C_{33}H_{52}N_5O_7$ (M+H)$^+$=630.3850$^+$; Δ=2.7 ppm.

EXAMPLE 213

Preparation of [1S-[1R*,2S*(2S*,3R*)]]-[3-[[3-[(3, 3-Dimethyl-1,2-dioxobutyl)amino]-2-hydroxy-4-phenylbutyl]amino]-2-hydroxy-1-(phenylmethyl) propyl]carbamic acid, 1,1-dimethylethyl ester (Compound 213c)

(a) Compound 213a

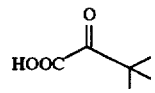

7 ml of 1N aqueous KOH was added to 600 mg (3.8 mmoles) of t-butyl ethyl oxylate [J. Org. Chem, 35, 3726 (1970)] in 7 ml of MeOH. After 3 h, the reaction was evaporated to near dryness and the residue dissolved in $H_2O$ and washed with $Et_2O$. The aqueous layer was acidified to pH 1, saturated with solid NaCl and extracted with $Et_2O$. The combined extracts were washed with brine, dried (MgSO4) and the solvent evaporated to yield a colorless oil residue. Distillation (kugelrohr, 165°–175° C., 50 mm) afforded 427 mg (86% yield) of Compound 213a as a colorless oil which crystallized on standing.

(b) Compound 213b

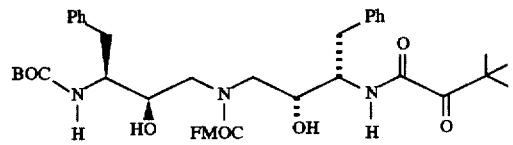

1 eq. of HCl/MeOH was added to Compound 128 in MeOH. Filtration and evaporation gave the hydrochloride salt which was reacted with Compound 213a by a procedure analogous to that described in Example 51 to give Compound 213b as a viscous foam.

(c) Compound 213c

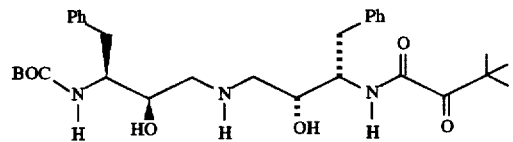

Compound 213b was converted to Compound 213c (white solid) by a procedure analogous to that described in Example 42.

m.p. 133°–134° C.; [α]$_D$=−14.3° (c 0.96, MeOH). Mass Spec.: 556 (M+H); Anal. Calc. for $C_{31}H_{45}N_3O_6$ (555.7): C, 67.00; H, 8.16; N, 7.56. Found: C, 66.87; H, 8.01; N, 7.37.

EXAMPLE 214

Preparation of [1S-[1R*,2S*(2S*,3R*)]]-[3-[[3-[(3,3-Dimethyl-1,2-dioxobutyl)amino]-2-hydroxy-4-phenylbutyl]amino]-2-hydroxy-1-(phenylmethyl)propyl]carbamic acid, 1,1-dimethylethyl ester (Compound 214b)

(a) Compound 214a

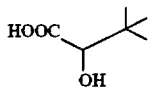

Compound 106d was converted to Compound 214a (white solid) by a procedure analogous to that described in Example 7 (EtOH used).

(b) Compound 214b

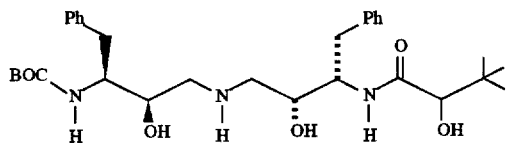

Compounds 54 and 214a were reacted by a procedure analogous to that described in Example 55 (2 eq. of N-methylmorpholine was added; DMF only used) to give the title Compound 214b (white foam).

Anal. Calc. for $C_{31}H_{47}N_3O_6 \cdot 1.75\ H_2O$: C, 63.20; H, 8.64; N, 7.13. Found: C, 63.71; H, 8.36; N, 6.62. HRMS: (M+H)$^+$=558.3533$^+$

EXAMPLE 215

Preparation of [1S-(1R*,2S*)(trans)]-[Iminobis[2-hydroxy-1-(phenylmethyl)-3,1-propanediyl]] biscarbamic acid, 1,1-dimethylethyl 2,3-dihydro-2-hydroxy-1H-inden-1-yl ester (Compound 215d)

(a) Compound 215a

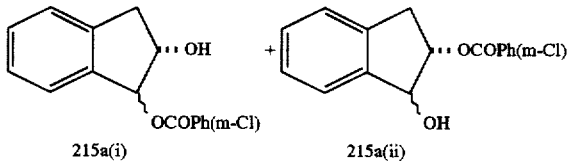

215a(i)  215a(ii)

To a solution of indene (1 ml, 8.57 mmol) in CH$_2$Cl$_2$ (28 mL) was added m-CPBA (2.1 g, 9.13 mmol). After stirring for 21.5 h, the mixture was filtered and the volatiles evaporated in vacuo. The resulting residue was partitioned between CH$_2$Cl$_2$ and saturated NaHCO$_3$, the aqueous layer back-extracted with CH$_2$Cl$_2$, and the combined organic layers dried (Na$_2$SO$_4$). Evaporation in vacuo gave an oil containing Compounds 215a(i) and 215a(ii) (1.9 g total) which was used in the next reaction.

(b) Compound 215b

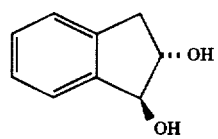

To a cloudy solution of crude Compounds 215a(i) and 215a(ii) (<1.9 g, ≦6.89 mmol) in MeOH (50 mL) was added NaOMe (1.9 mL, 8.31 mmol, 25% in MeOH). The solution was stirred at RT for 1 h, the volatiles removed in vacuo, and the residue partitioned between EtOAc and brine. The combined organic layers were dried (Na$_2$SO$_4$) and concentrated in vacuo. The residue was purified by flash chromatography (silica gel, 5 by 17 cm), eluting with EtOAc:CH$_2$Cl$_2$ (3:2 then 2:1) to give Compound 215b (140 mg) as a colorless solid. A somewhat contaminated fraction of Compound 215b was crystallized from hot EtOAc to give a further 74 mg (214 mg, 20.7% total).

(c) Compound 215c

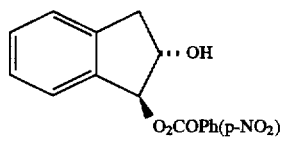

Compound 215b was converted to Compound 215c by a procedure analogous to that used for the synthesis of Compound 161d. Compound 215c was separated from its regioisomer by flash chromatography (silica gel, 5×10 cm) eluting with Et$_2$O:pentane (1:1 then 3:2).

(d) Compound 215d

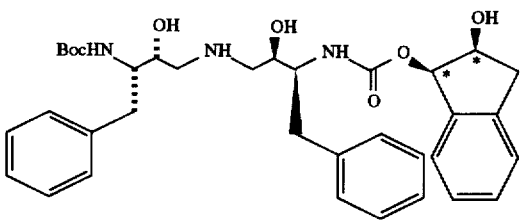

1:1 mixture of diastereomers at . (S,S:R,R)

Compounds 215c and 54 were reacted by a procedure analogous to that used in Example 147d (DMF only used) to give Compound 215d (colorless solid).

m.p. 131°–133° C.; [α]$_D$=−12.3° [c 0.20, MeOH]. MS: (CI): 620 (M+H). Anal. Calc. for $C_{35}H_{45}N_3O_7 \cdot 1.42\ H_2O$: C,65.14; H,7.47; N,6.51 ; Found: C,65.22; H,7.10; N,6.43.

EXAMPLE 216

Preparation of [1S-(1R*,2S*)]-[Iminobis[2-hydroxy-1-(phenylmethyl)-3,1-propanediyl]] biscarbamic acid, 2-amino-1,1-dimethylethyl-1,1-dimethylethyl ester (Compound 216e)

(a) Compound 216a

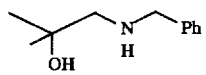

Isobutylene oxide was reacted with benzyl amine by a procedure analogous to that used in Example 4a except that MeOH at 105° C. was used (sealed tube)

(b) Compound 216b

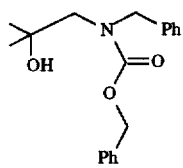

Compound 216a was reacted with carbobenzyloxy chloride using a procedure analogous to that of Example 122 (except that CH₂Cl₂ was used and the reaction was run at RT) to give Compound 216b.

(c) Compound 216c

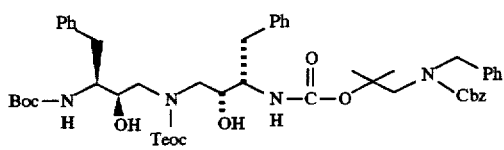

Compound 216b was converted to Compound 216c by a two-step procedure analogous to that used for the conversion of Compound 149c to 149e (DMF was used in coupling of p-nitrophenyl carbonate to Compound 48).

(d) Compound 216d

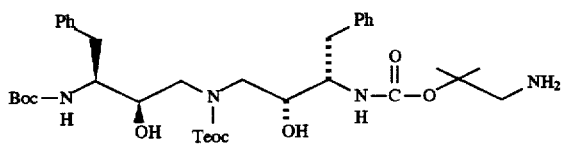

Compound 216c was converted to Compound 216d by a procedure analogous to that of Example 54.

(e) Compound 216e

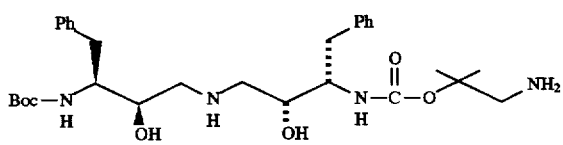

Compound 216d was converted to the title Compound 216e (white solid) by a procedure analogous to that of Example 21.

m.p. 118°–120° C.; Analysis calculated for: $C_{30}H_{46}N_4O_6 \cdot 1.12\ H_2O$; C, 62.24; H, 8.40; N, 9.68. Found: C, 62.65; H, 8.19; N, 9.27.

EXAMPLE 217

Preparation of [1S-[1R*,2S*(2S*,3R*)]]-[3-[[3-[[(1,1-Dimethylethoxy)carbonyl]amino]-2-hydroxy-4-[4-[2-methyl(4-methylphen-yl)amino]-ethoxyl]phenyl]butyl]amino]-2-hydroxy-1-(phenylmethyl) propyl] carbamic acid, 1,1-dimethylethyl ester (Compound 217b)

(a) Compound 217a

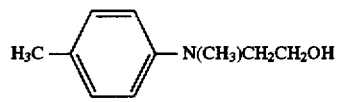

A mixture of N-methyl-p-toluidine (3.5 g; 29 mmol) and ethylene carbonate (4 g) was heated to 100° C. for 3 h and 150° C. for 10 h. After cooling to 0° C., 15 ml of 4N HCl was added and the resulting mixture was partitioned between CH₂Cl₂ and 4N HCl. After adjusting the pH of the aqueous layer to ~9 with solid K₂C)₃, the aqueous layer was extracted with CH₂Cl₂, dried (MgSO₄) and concentrated to dryness. The residue was chromatographed on a 5×20 cm silica gel column, using 25% EtOAc/Hex as the mobile phase to afford 2.63 g (55%) of Compound 217a as a light yellow liquid.

(b) Compound 217b

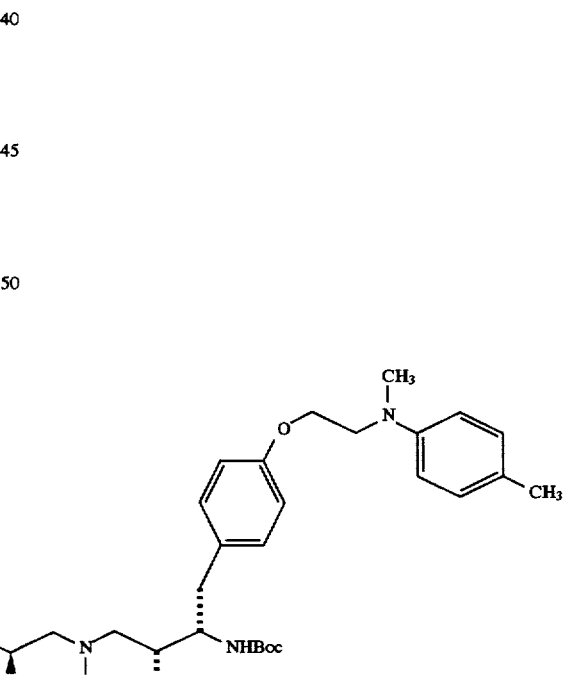

Compound 217a and Compound 172 were reacted by a four-step procedure analogous to that used for the conversion of Compound 172 to Compound 178 to give the title Compound 217b (white solid).

mp 120°–127° C.; $[\alpha]_D = -5.6°$ (c 0.27, MeOH). Mass Spec. FAB+ions: M+H=707; Analysis calc. for $C_{40}H_{58}N_4O_7 \cdot 1.27\ H_2O$: C, 65.83; H, 8.36; N, 7.68; Found: C, 66.05; H, 8.09; N, 7.46.

EXAMPLE 219

Preparation of [[1R*,2S*(2S*,3R*)],$N^2$-(S*)]-$N^2$-[(2,3-Dihydroxypropoxy)carbonyl]-N-[3-[[3-[[(1,1-dimethylethoxy) carbonyl]-amino]-2-hydroxy-4-phenylbutyl]amino]-2-hydroxy-1-(phenylmethyl) propyl]-L-valinamide (Compound 219)

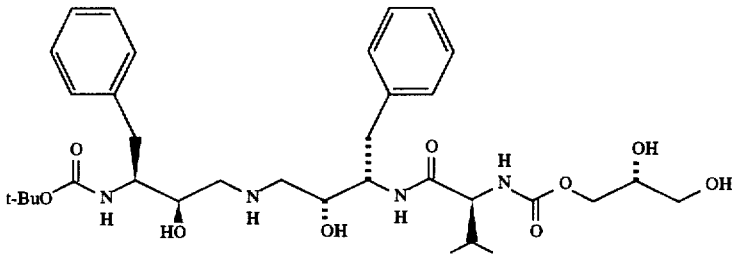

Starting from (S)-(+)-2,2 dimethyl-1,3-dioxolane-4-methanol, the title Compound 219 (white solid) was prepared by a procedure analogous to that used for the preparation of Compound 202e.

m.p.=200°–205° C. (decomposes); $[\alpha]_D = -3.3°$ (c=0.30; MeOH). High resolution MS (FAB): Calculated (M+H)$^+$ (for $C_{34}H_{53}O_9N_4$)=661.3831; Observed (M+H)$^+$=661.3798 Δ=2.3 ppm

EXAMPLE 218

Preparation of [1R*,2S*(2S*,3R*)]-N-[3-[[3-[[(1,1-Dimethylethoxy) carbonyl]amino]-2-hydroxy-4-phenylbutyl]amino]-2-hydroxy-1-(phenylmethyl) propyl]-$N^2$-[(2-hydroxyethoxy) carbonyl]-L-valinamide (Compound 218c)

(a) Compound 218a

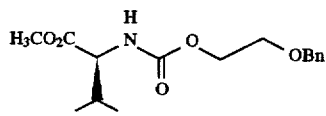

Benzyloxyethanol and valine methyl ester hydrochloride were converted to Compound 218a by a two-step procedure analogous to that used for the conversion of Compound 161c to Compound 161e.

(b) Compound 218b

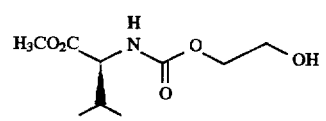

Compound 218a was converted to Compound 218b by a procedure analogous to that of Example 2.

(c) Compound 218c

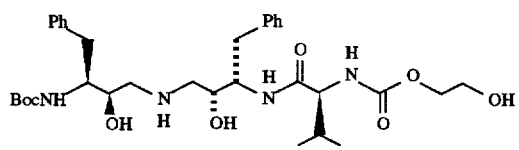

Compounds 218b and 54 were converted to the title Compound 218c (white solid) by a two-step procedure analogous to that used for the conversion of Compound 202c to Compound 202e.

m.p.=174°–179° C.; $[\alpha]_D = -16.1°$ (c=0.23; MeOH) High resolution MS (FAB): Calculated (M+H)$^+$ (for $C_{33}H_{51}N_4O_8$) =631.3707; Observed (M+H)$^+$=631.3709 Δ=0.3 ppm

EXAMPLE 220

Preparation of [1R*,2S*(2S*,3R*)]-$N^2$-[[(2-Benzimidazolyl) methoxy]carbonyl]-N-[3-[[3-[[(1,1-dimethylethoxy) carbonyl]amino]-2-hydroxy-4-phenylbutyl]amino]-2-hydroxy-1-(phenylmethyl) propyl]-L-alaninamide (Compound 220d)

(a) Compound 220a

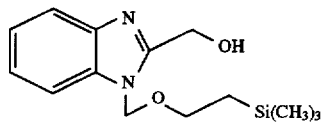

Compound 93a and 2-(trimethylsilyl)-ethoxymethyl chloride was converted to Compound 220a by a procedure analogous to that of Example 93b (reaction was run at 70° C.). (b) Compound 220b

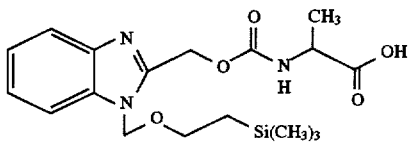

Compound 220a and alanine were reacted by a two-step procedure analogous to that used for the conversion of Compound 93b to Compound 93d to give Compound 220b.

(c) Compound 220c

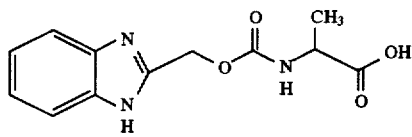

Compound 220b in a 4M HCl/dioxane solution (23ml) was stirred at 50° C. for 2.5 h then cooled to RT and stirred overnight. The reaction was concentrated and the resulting yellow foam was purified by silica gel chromatography, eluting the column with a stepwise gradient of EtOAc, EtOAc:AcOH (98:2), and EtOAc:MeOH:AcOH (78:20:2) to afford 0.498 g (70%) of Compound 220c.

(d) Compound 220d

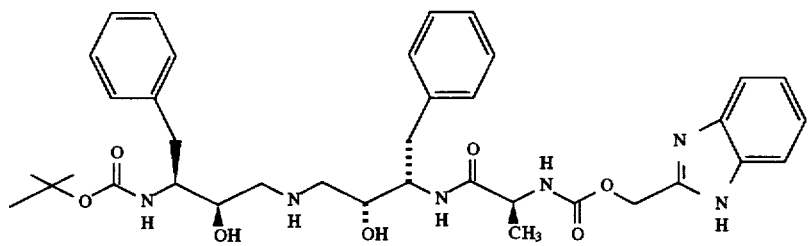

Compounds 220c and 54 were reacted by a procedure analogous to that used for the preparation of Compound 93f to give the title Compound 220d (white solid).

m.p. 106°–108° C.; $[\alpha]_D = -1.00$ (C, 0.10 MeOH). Mass Spec. FAB: $(M+H)^+$ @689$^+$. Analysis calc. for $C_{37}H_{48}N_6O_7 \cdot 0.65 H_2O$: C, 63.63; H, 6.83; N, 12.03; Found: C, 63.66; H, 7.13; N, 11.99.

EXAMPLE 221

Preparation of [1S-[[1R*,2S*(2S*,3R*)],N²-(S*) ]]-N-[3-[[3-[[(1,1-Dimethylethoxy) carbonyl]amino]-2-hydroxy-4-phenylbutyl]amino]-2-hydroxy-1-(phenylmethyl) propyl]-N²-(2-hydroxy-1-oxopropyl)-L-valinamide (Compound 221)

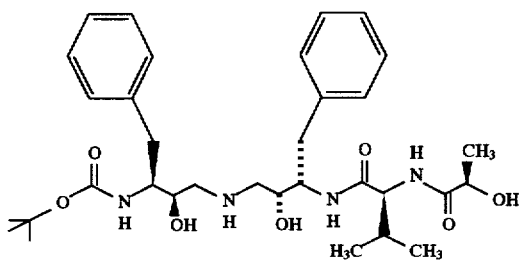

Compound 61 and D-lactic acid were reacted by a two-step procedure analogous to that used for the conversion of Compound 48 to Compound 52 to give the title Compound 221 (white solid).

mp 213°–219° C.; $[\alpha]_D = -56.8°$ (c 0.19, AcOH). Mass Spec. FAB+ion: M+H=615. Analysis calc. for $C_{33}H_{50}N_4O_8 \cdot 1.34 H_2O$: C, 62.04; H, 8.31; N, 8.77; Found: C, 62.02; H, 7.87; N, 8.79.

EXAMPLE 222

Preparation of [1R*,2S*(2S*,3R*)]-N²-[[(3,4-Dyhydro-4-oxo-2-quinazolinyl)methoxy]carbonyl]-N-[3-[[3-[[(1,1-dimethylethoxy)carbonyl]amino]-2-hydroxy-4-phenylbutyl]amino]-2-hydroxy-1-(phenylmethyl) propyl]-L-valinamide (Compound 222d)

(a) Compound 222a

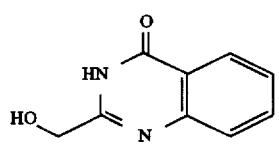

Compound 222a was prepared according to the procedure of Bergman et al., Tetrahedron, 46, 1296 (1990).

(b) Compound 222b

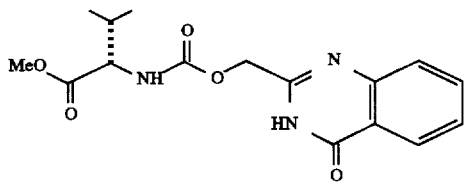

Compound 222a and L-valine methyl ester hydrochloride were reacted by a two-step procedure analogous to that used for the conversion of Compound 161c to Compound 161e to give Compound 222b.

(c) Compound 222c

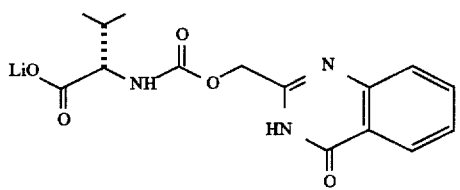

Compound 222b was converted to Compound 222c by a procedure analogous to that of Example 70c.

(d) Compound 222d

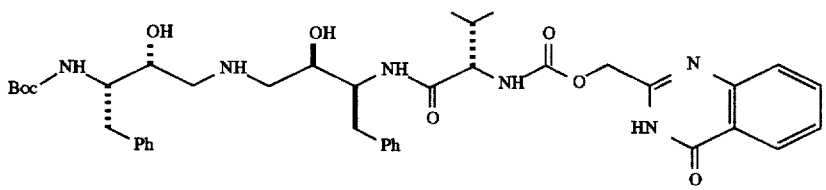

Compounds 222c and 48 were reacted by a two-step procedure analogous to that used for the conversion of Compound 48 to Compound 52 (no N-methylmorpholine was used in the EDCI coupling step) to give the title Compound 222d (white solid).

m.p. 105°–107° C. $[\alpha]_D$=+1.8° (c=0.5, MeOH). High Res Mass Spectrum: (M+H)$^+$=745.3925, theoretical: (M+H)$^+$= 745.3925 (Δ0.0 ppm error).

EXAMPLE 223

Preparation of [1S-[1R*,2S*(2S*,3R*)]]-[3-[[3-[[(2, 3-Dihydro-3-oxo-1H-isoindol-1-yl) carbonyl]amino] -2-hydroxy-4-phenylbutyl]amino]-2-hydroxy-1- (phenylmethyl)propyl]carbamic acid, 1,1- dimethylethyl ester (Compound 223b)

(a) Compound 223a

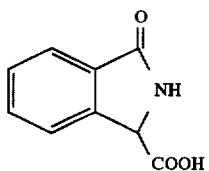

To a MeOH (50 mL) solution of 2-carboxybenzaldehyde (5.0 g, 0.033 mol) in a cool water bath (~18° C.) was added NH$_3$ gas for 15 min, and the solution stirred at RT for 1 h. Aqueous NaCN (1.63 g, 0.033 mol in 50 mL H$_2$O) was then added dropwise over 15 min. After 1 h, the volatiles were concentrated in vacuo and the resulting yellow solution was treated with 6N HCl (40 mL). A precipitate formed after several mls of HCl had been added and the reaction slowly became homogeneous. The reaction mixture was heated at 100° C. for 1.45 h, then placed in a cool water bath (~18° C.). A yellow solid quickly formed and was removed by filtration, washing with H$_2$O and acetone. The filtrate was allowed to stand at RT for several days and the resulting solid was collected by filtration, washing with H$_2$O and acetone to give slightly impure Compound 223a (2.2 g, ~38% yield). A portion (670 mg) of this material was crystallized from hot H$_2$O, washing the solid with more H$_2$O and drying in vacuo to give Compound 223a (359 mg) as a colorless solid.

(b) Compound 223b

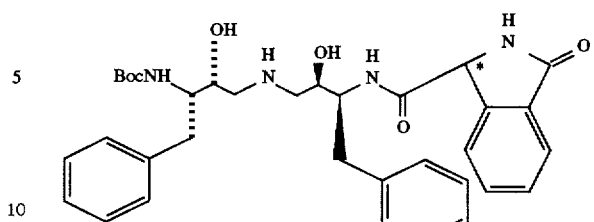

(1:1 mixture of diastereomers at ·)

Compounds 223a and 54 were reacted by a procedure analogous to that of Example 93f to give the title Compound 223b (colorless solid).

m.p. dec. 141°–152° C.; $[\alpha]_D^{25}$=–1.2° (c 0.16, AcOH). MS: (FAB): 603 (M+H). Anal. Calc. for $C_{34}H_{42}N_4O_6 \cdot 0.82$ H$_2$O: C, 66.14; H, 7.12; N, 9.07 Found: C, 66.10; H, 6.88; N, 9.11.

EXAMPLE 224

Preparation of [1S-[1R*,2S*(2S*,3R*)]]-[3-[[3-[[(1, 1-Dimethylethoxy)carbonyl]amino]-2-hydroxy-4-[4- (2-methoxyethoxy)phenyl]butyl]amino]-2-hydroxy- 1-(phenylmethyl) propyl]carbamic acid, 1,1- dimethylethyl ester (Compound 224c)

(a) Compound 224a

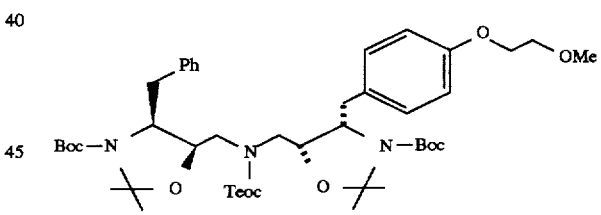

To a mixture of Compound 172 (250 mg, 0.32 mmol), 2-methoxyethanol (50 μl, 0.64 mmol) and PPh$_3$ (167 mg, 0.64 mmol) in dry THF (0.64 ml) was added DEAD (100 μl, 0.64 mmol). The mixture was stirred at RT overnight. Concentration in vacuo followed by flash chromatography (hexane/EtOAc 10:1 to 7:1) afforded 225 mg (84%) of Compound 224a as a white foam.

(b) Compound 224b

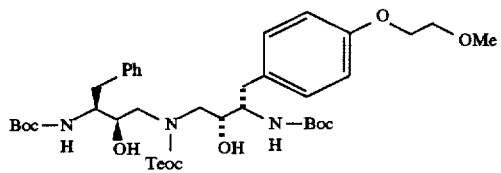

To Compound 224a (225 mg, 0.267 mmol) was added pre-cooled (10° C.) 96% formic acid (5.0 ml). The mixture was stirred at 5° C. for 20 min and was then frozen (dry ice-acetone) and lyophilized (overnight). The residue was taken into MeOH (5 ml) and Et$_3$N (112 μl, 0.80 mmol) was added followed by di-tert-butyldicarbonate (88 mg, 0.40 mmol). The mixture was stirred at RT overnight. Concentration in vacuo followed by flash chromatography (100% CHCl$_3$ to CHCl$_3$—MeOH—NH$_4$OH: 96:4:0.4) afforded 203 mg (100%) of Compound 224b as a white foam.

(c) Compound 224c

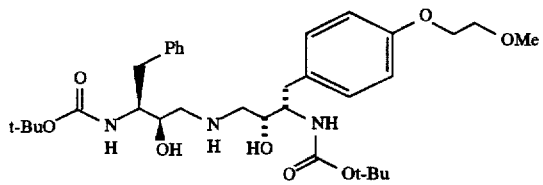

A mixture of Compound 224b (203 mg, 0.27 mmol) and solid n-Bu$_4$NF·nH$_2$O (223 mg, 0.85 mmol) in dry THF (1.3 ml) was heated at 50° C. for 4.0 h. After cooling to RT, Celite (1.0 g) was added and the solvent was removed under reduced pressure. Flash chromatography (100% CHCl$_3$ to CHCl$_3$—MeOH—NH$_4$OH: 94:6:0.6) on silica gel afforded 128 mg (73%) of the title Compound 224c as a gel, which upon trituration with Et$_2$O-hexane afforded the product as a white solid.

m.p.: 136°–138° C.; [α]$_D$=–2.3°, [α]$_{Hg(436)}$=–6.1°, [α]$_{Hg(365)}$=–14.2°, (c 0.53, MeOH). Mass Spec. (FAB): 618$^+$ (M+H)$^+$. Anal. Calc. for C$_{33}$H$_{51}$N$_3$O$_8$·0.83H$_2$O:C, 62.65; H, 8.39; N, 6.64. Found: C, 62.52; H, 8.12; N, 6.77.

EXAMPLE 225

Preparation of [1S-[[1R*,2S*(2S*,3R*)],N$^2$-(R*)]- N-[3-[[3-[[(1,1-Dimethylethoxy)carbonyl]amino]-2- hydroxy-4-phenylbutyl]amino]-2-hydroxy-1- (phenylmethyl)propyl]-N$^2$-(2-hydroxy-1-oxo-propyl) -L-valinamide (Compound 225)

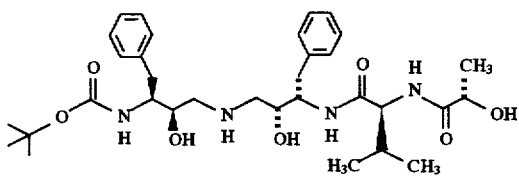

Compound 61 and L-lactic acid were reacted by a two-step procedure analogous to that used for the conversion of Compound 48 to Compound 52 to give the title Compound 225 (white solid).

m.p. 210°–214° C.; [α]$_D$=–24.8° (c 0.31, MeOH). Mass Spec. (FAB+ion): M+H=615. Analysis calc. for C$_{33}$H$_{50}$N$_4$O$_8$·1.00 H$_2$O: C, 62.63; H, 8.28; N, 8.85; Found: C, 62.37; H, 7.84; N, 8.74.

EXAMPLE 226

Preparation of [1S-[1R*,2S*(2S*,3R*)]]-[3 -[[3- [[(1,1-Dimethylethoxy)carbonyl]amino]-2-hydroxy-4- (4-[2-(4-morpholinyl)-2-oxo-ethoxy]phenyl]butyl] amino]-2-hydroxy-1-(phenylmethyl)propyl]carbamic acid, 1,1-dimethylethyl ester (Compound 226b)

(a) Compound 226a

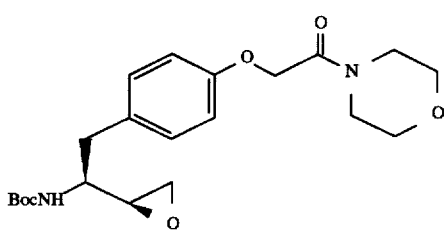

NaH (48 mg, 60% dispersion in mineral oil, 1.2 mmol) was washed twice with hexane and suspended in 1.0 ml of dry DMF. The suspension was cooled to 0° C. and a solution of Compound 175c (280 mg, 1.0 mmol) in 1.5 ml of dry DMF was added. The mixture was stirred at 0° C. for 30 min and then 4-(2-bromoacetyl)morpholine (J. Med. Chem., 35, 1685 (1992); 270 mg, 1.3 mmol) was added in one portion, followed by n-Bu$_4$NI (185 mg, 0.5 mmol). The resulting mixture was stirred at RT overnight. After cooling to 10° C., H$_2$O was added and the mixture extracted with EtOAc. The combined extracts were washed with H$_2$O and brine, dried (NaHCO$_3$) and concentrated in vacuo to give a crude product which was purified by flash chromatography (hexane-EtOAc: 1:1 to 1:4) on silica gel to give 392 mg (96%) of Compound 226a as a white solid.

(b) Compound 226b

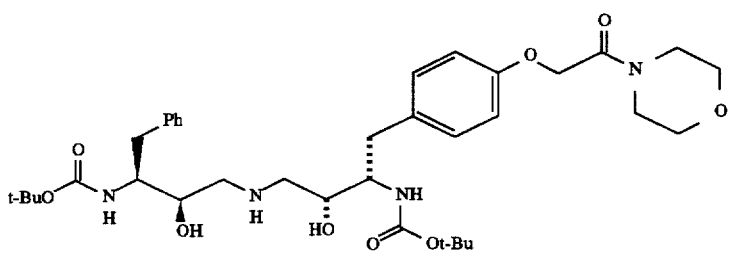

A mixture of Compounds 226a (407 mg, 1.0 mmol) and 16b (280 mg, 1.0 mmol) in 1.0 ml of dry DMF was heated at 100° C. for 4.0 h. Concentration in vacuo followed by flash chromatography (CHCl$_3$—MeOH—NH$_4$OH: 98:2:0.2 to 95:5:0.5) on silica gel afforded 501 mg (73%) of Compound 226b as a white solid.

m.p. 118°–120° C.; $[\alpha]_D$=–4.7, $[\alpha]_{365(Hg)}$=–23.6° (c 1.0, MeOH). Mass Spec. (FAB): 687$^+$ (M+H)$^+$. Anal. Calc. for $C_{36}H_{54}N_4O_9 \cdot 0.30 H_2O$: C, 62.46; H, 7.95; N, 8.09. Found: C, 62.46; H, 7.91; N, 8.28.

EXAMPLE 227

Preparation of [1S-(1R*,2S*),(R*)]-[Iminobis[2-hydroxy-1-(phenylmethyl)-3,1-propanediyl]] biscarbamic acid, 2,3-dihydroxy-1,1-dimethylpropyl 1,1-dimethylethyl ester (Compound 227c)

(a) Compound 227a

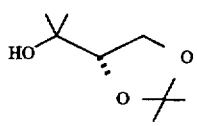

Methyl (S)-(-)-2,2-dimethyl-1,3-dioxolane-4-carboxylate was converted to Compound 227a by a procedure analogous to that of Example 158a.

(b) Compound 227b

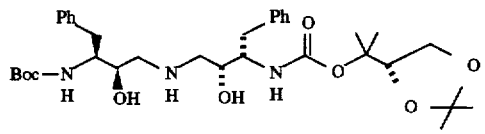

Compound 227a was converted to Compound 227b by a three-step procedure analogous to that used for the conversion of Compound 149c to Compound 150 (DMF was used in the coupling of the p-nitrophenyl carbonate with Compound 48).

(c) Compound 227c

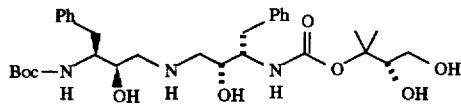

Compound 227b was converted to Compound 227c (white solid) by a procedure analogous to that of Example 202c.

m.p. 104°–105° C.

High Res Mass Spectrum: (M+H)$^+$=590.3463, theoretical: (M+H)$^+$=590.3441 (Δ 4 ppm error).

EXAMPLE 228

Preparation of [1S-(1R*,2S*),(S*)]-[Iminobis[2-hydroxy-1-(phenylmethyl)-3,1-propanediyl]] biscarbamic acid, 2,3-dihydroxy-1,1-dimethylpropyl 1,1-dimethylethyl ester (Compound 228)

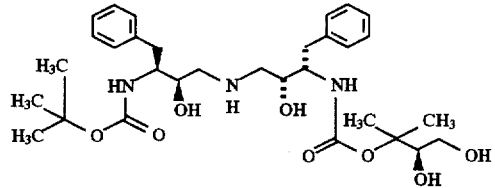

Methyl (R)-(+)-2,2-dimethyl-1,3-dioxolane-4-carboxylate was converted to the title Compound 228 (white solid) by a procedure analogous to that used for the synthesis of Compound 227c.

m.p. 69°–72° C.; $[\alpha]_D$=–6.0° (c=0.2, CD$_3$OD) Analysis Calculated for: $C_{31}H_{47}N_3O_8 \cdot 1.03 H_2O$ C, 61.20; H, 8.13; N, 6.91. Found: C, 61.26; H, 7.93; N, 6.85.

EXAMPLE 229

Preparation of [R-(R*,S*)]-[Iminobis[2-hydroxy-1-(phenylmethyl)-3,1-propanediyl)]biscarbamic acid, 4-hydroxy-1,1-dimethyl-butyl 1,1-dimethylethyl ester (Compound 229)

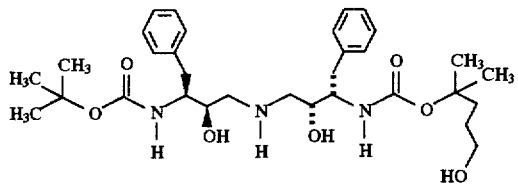

Compound 210b was converted to the title Compound 229 (white solid) by a procedure analogous to that of Example 2.

m.p. 80°–84° C.; $[\alpha]_D$=–2.6° (c 0.2, CH$_3$OH). High Res Mass Spec (M+H)$^+$=588.3649 (Δ ppm=1.2) Analysis calc. for $C_{32}H_{49}N_3O_7 \cdot 2.69 H_2O$: Calculated C, 60.42; H, 8.61; N, 6.60; Found: C, 60.46; H, 8.22; N, 6.56.

EXAMPLE 230

Preparation of [1S-(1R*,2S*),(R*)]-[Iminobis[2-hydroxy-1-(phenylmethyl)-3,1-propanediyl]] biscarbamic acid, 2,3-dihydroxypropyl 1,1-dimethylethyl ester (Compound 230)

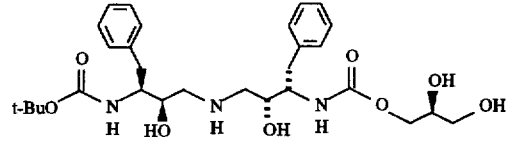

(R)-2,2-Dimethyl-1,3-dioxolane-4-methanol was converted to the title Compound 230 (white solid) by a three-step procedure analogous to that used for the conversion of Compound 149c to Compound 150 (DMF was used in the coupling of the p-nitrophenyl carbonate with Compound 48).

m.p.=151°–154° C. (decomposes); $[\alpha]_D$=–5.3° (c=0.30; MeOH). High resolution MS (FAB): Calculated (M+H)$^+$ (for $C_{29}H_{44}O_8N_3$)=562.3128; Observed (M+H)$^+$=562.3147 Δ=3.4 ppm; Analysis for $C_{29}H_{43}N_3O_8 \cdot 1.31 H_2O$: Calculated: C, 59.51; H, 7.86; N, 7.48 ; Found: C, 59.19; H, 7.47; N, 7.18.

EXAMPLE 231

Preparation of [1S-(1R*,2S*),(S*)]-[Iminobis[2-hydroxy-1-(phenylmethyl)-3,1-propanediyl]] biscarbamic acid, 2,3-dihydroxypropyl 1,1-dimethylethyl ester (Compound 231)

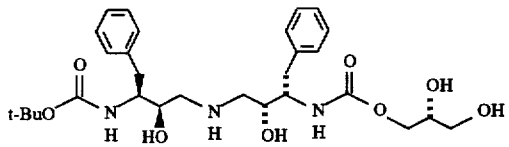

(S)-2,2-Dimethyl-1,3-dioxolane-4-methanol was converted to the title Compound 231 (white solid) by a three-step procedure analogous to that used for the conversion of Compound 149c to Compound 150 (DMF was used in the coupling of the p-nitrophenyl carbonate with Compound 48).

m.p.=157°–160° C.; $[\alpha]_D$=–8.7° (c=0.31; MeOH). High resolution MS (FAB): Calculated (M+H)$^+$ (for $C_{29}H_{44}O_8N_3$) =562.3128; Observed (M+H)$^+$=562.3127; Δ=0.2 ppm; Analysis for $C_{29}H_{43}N_3O_8 \cdot 0.45$ $H_2O$: Calculated: C, 61.13; H, 7.77; N, 7.38 ; Found: C, 60.94; H, 7.62; N, 7.57

EXAMPLE 232

Preparation of [1S-(1R*,2S*),(R*)]-[Iminobis[2-hydroxy-1-(phenylmethyl)-3,1-propanediyl]] biscarbamic acid, 1,1-dimethylethyl 2-hydroxy-1,1-dimethylpropyl ester (Compound 232d)

(a) Compound 232a

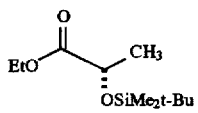

To a solution of 0.5 g (0.48 ml; 4.23 mmol) of (S)-Ethyl lactate in 8.5 ml of $CH_2Cl_2$ at 0° C. was added 1.13 ml (1.2 eq; 5.07 mmol) of 2,6-di-t-butylpyridine followed by 1.16 ml (1.2 eq; 5.07 mmol) of t-butyldimethylsilyl triflate. After 1 h at 0° C., $Et_2O$ and 1N HCl were added and the organic layer washed with $H_2O$, saturated $NaHCO_3$, and brine. The extracts were dried ($MgSO_4$) and evaporated in vacuo to give a crude liquid which was purified by flash chromatography (25 mm×7"; elution with 2% EtOAc/Hexanes then 5% EtOAc/Hexanes) to give 0.89 g (90%) of Compound 232a as a colorless liquid.

(b) Compound 232b

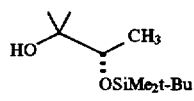

Compound 232a was converted to Compound 232b by a procedure analogous to that used in Example 149c.

(c) Compound 232c

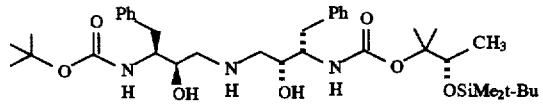

Compound 232b was converted to Compound 232c by a two-step procedure analogous to that used for the conversion of Compound 147b(i) to Compound 147d.

(d) Compound 232d

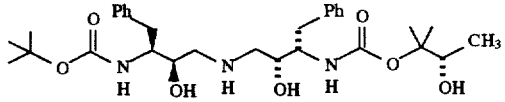

Compound 232c was converted to Compound 232d (white solid) by a procedure analogous to that of Example 162.

m.p. 129°–131° C. (softens at 90° C.); $[\alpha]_D$=–20.9° (c 0.32, MeOH).

Mass Spec.: FAB+ions: M+H=574. Analysis calc. for $C_{31}H_{47}N_3O_7 \cdot 0.15$ $H_2O$: C, 64.59; H, 8.27; N, 7.29; Found: C, 64.47; H, 8.25; N, 7.41.

EXAMPLE 233

Preparation of [1S-[1R*,2S*(2S*,3R*)]]-[3-[[3-[[(1,1-Dimethylethoxy)carbonyl]amino]-2-hydroxy-4-(4-hydroxyphenyl)butyl]amino]-2-hydroxy-1-(phenylmethyl)propyl]carbamic acid,2-hydroxy-1,1-dimethylethyl ester (Compound 233c)

(a) Compound 233a

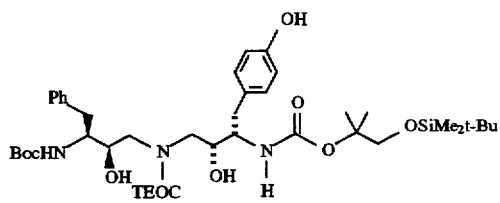

Compounds 19 and 161d were reacted by a procedure analogous to that of Example 143 (i-Pr$_2$NEt and DMF were used) to give Compound 233a.

(b) Compound 233b

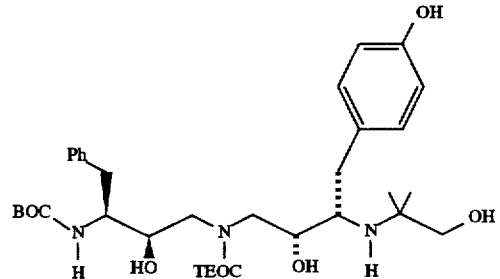

Compound 233a was converted to Compound 233b by a procedure analogous to that of Example 162.

(c) Compound 233c

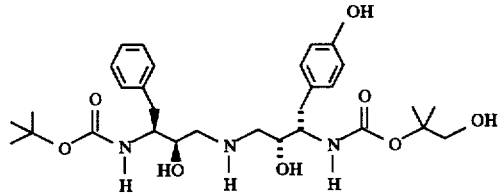

Compound 233b was converted to Compound 233c (white solid) in 28% yield by a procedure analogous to that of Example 21.

m.p. 135°–137° C.; $[\alpha]_D$=–4.9° (c 0.55, MeOH). MS: (M+H)$^+$ 576.3290$^+$ (High res). Anal. Calc for $C_{30}H_{45}N_3O_8$: C, 62.59; H, 7.88; N, 7.30. Found: C, 62.20; H, 7.86; N, 7.38.

EXAMPLE 234

Preparation of [1S-[1R*,2S*(2S*,3R*),(R*)]]-[3-[[3-[[3,3-Dimethyl-2-(formylamino)-1-oxobutyl]amino]-2-hydroxy-4-phenylbutyl]amino]-2-hydroxy-1-(phenylmethyl) propyl]carbamic acid, 1,1-dimethylethyl ester (Compound 234c)

(a) Compound 234a

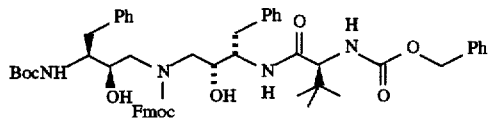

To a mixture of Compound 88b (286 mg, 0.414 mmol) and i-Pr$_2$NEt (94 µl, 0.538 mmol) in 2.5 ml of dry DMF at 0° C. was added 9-fluorenylmethyl-chloroformate (124 mg, 0.48 mmol). The mixture was stirred at 0° C. for 1.0 hr and H$_2$O was added. The mixture was extracted with EtOAc and the extracts were washed with sat'd NaHCO$_3$ and brine and dried over Na$_2$SO$_4$. Concentration in vacuo followed by flash chromatography (hexane/EtOAc 4:1 to 1:1) on a silica gel column afforded 341 mg (90%) of Compound 234a as a white solid.

TLC(SiO$_2$)R$_f$=0.51. (CHCl$_3$—MeOH 95:5—PMA).

(b) Compound 234b

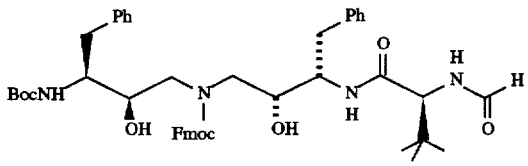

A mixture of Compound 234a (341 mg, 0.374 mmol), 1,4-cyclohexadiene (356 µl) and 10% Pd-C (40 mg) in 11 ml of EtOH was stirred under a H$_2$ atmosphere for 2 h. An additional 25 mg of 10% Pd-C was added after 2 and 4 h. After 6 h total, the catalyst was removed by filtration through a short pad of Celite. 90 µl of HOAc was added to the filtrate and the mixture was evaporated to dryness to yield 308 mg of the amine acetate salt as a white solid.

Formic acetic anhydride was prepared by addition of 46.3 µl of HCO$_2$H to 133 µl of ice-cooled Ac$_2$O. The solution was then stirred at 50° C. for 2 h. This material dissolved in 1 ml of dry THF was added to an ice-cooled solution of 308 mg of the amine acetate salt in 2.5 ml of dry THF. The mixture was stirred at 0° C. for 1.0 h and then at RT for 15 min. The reaction mixture was partitioned between H$_2$O and EtOAc and the organic extracts were washed with brine and dried (Na$_2$SO$_4$). Concentration in vacuo followed by purification by prep HPLC (Nova-Pak HR silica 60Å) with 60% EtOAc in hexane as eluent, afforded 123 mg (41% for two steps) of Compound 234b as a white solid.

TLC(SiO$_2$)R$_f$=0.17. (CHCl$_3$—MeOH 95:5—PMA).

(c) Compound 234c

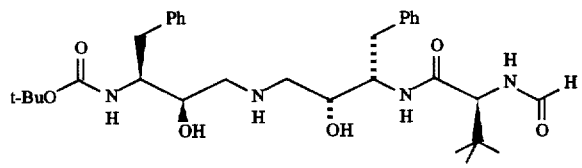

To a solution of Compound 234b (123 mg, 0.152 mmol) in 2.7 ml of dry CH$_2$Cl$_2$ was added piperidine (132 µl, 1.34 mmol). The mixture was stirred at RT for 1.5 h. Concentration in vacuo followed by flash chromatography (CHCl$_3$—MeOH—NH$_4$OH: 99:1:0.1 to 92:8:0.8) on silica gel gave, after trituration with CHCl$_3$-hexane, 84 mg (94%) of the title Compound 234c as a white solid.

m.p.: 166°–168° C.; [α]$_D$=−23.80°, [α]$_{436(Hg)}$=−54.8° (c 0.21, MeOH). Mass Spec. (FAB): 585$^+$ (M+H)$^+$. Anal. Calc. for C$_{32}$H$_{49}$N$_4$O$_6$·0.34H$_2$O:C, 64.93; H, 8.46; N, 9.47. Found: C, 64.99; H, 8.20; N, 9.41.

EXAMPLE 235

Preparation of [1S-[1R*,2S*[2S*,3R*(E)]]]-[3-[[3-[[(1,1-Dimethylethoxy)carbonyl]amino]-2-hydroxy-6-(4-hydroxyphenyl)-5-hexenyl]amino]-2-hydroxy-1-(phenylmethyl)propyl]carbamic acid, 1,1-dimethylethyl ester (Compound 235e)

(a) Compound 235a

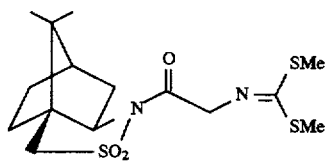

Compound 235a was prepared according to the procedure of Oppolzer et al., *Tetrahedron Lett.*, 30 (44), 6009 (1989).

(b) Compound 235b

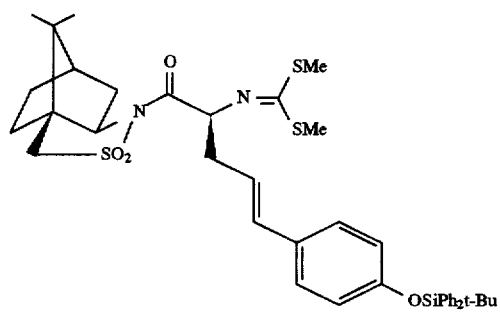

To a solution of n-BuLi (4.4 ml; 11.0 mmol; 2.5M in hexanes) in 25 ml of dry THF cooled at −78° C. was added a solution of Compound 235a (3.77 g; 10.0 mmol) in 15 ml of dry THF. The mixture was stirred at −78° C. for 1 h, followed by addition of a solution of 4-t-butyldiphenylsilyloxycinnamyl bromide (Young et al., *J. Med. Chem.*, 35, 1702 (1992)); 6.8 g, 15.0 mmol) in 10 ml of 1:1 THF-HMPA, dropwise over 10 min. n-Bu$_4$NI (200 mg) was then added and the reaction was warmed from −78° C. to RT over 2 hours. The reaction mixture was cooled back to −20° C. and H$_2$O was added. The mixture was extracted with EtOAc and the combined extracts washed with H$_2$O and brine and dried over MgSO$_4$. Concentration in vacuo gave an oily residue which was purified by flash chromatography (10:1 hexane-chloroform to 100% chloroform) on silica gel to afford 5.2 g (69%) of Compound 235b as a colorless oil which solidified upon standing.

(c) Compound 235c

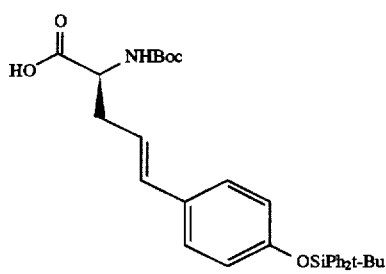

To a solution of Compound 235b (14.7 g, 19.7 mmol) in 280 ml of THF and 125 ml of DME was added a solution of 1.0N HCl (125 ml). The homogeneous mixture was then heated at 40° C. overnight. H$_2$O (200 ml) was added and the pH was adjusted to 12 with 6N KOH. The mixture was extracted with EtOAc and the combined organic extracts washed with H$_2$O, saturated NaHCO$_3$, brine and dried over Na$_2$SO$_4$. Removal of solvent under reduced pressure afforded 13.9 g of crude amine as an off-white foam which was used without further purification.

To the suspension of the crude amine (13.9 g) in 85 ml of dry CH$_3$CN cooled at 0° C. was added di-t-butyl dicarbonate (7.7 g, 32.5 mmol). The reaction mixture was stirred at RT overnight. The solvent was removed under reduced pressure and the residue was purified by flash chromatography (hexane-EtOAc: 4:1) on silica gel to afford 13.7 g of the N-Boc carbamate as an off-white foam.

To a solution of LiOH·H$_2$O (1.5 g, 36.8 mmol) in H$_2$O (36 ml) cooled at 0° C. was added a solution of 30% H$_2$O$_2$ (11.3 ml, 110 mmol). The mixture was stirred at 0° C. for 1 h and added at 0° C. to a solution of the above prepared N-Boc carbamate (13.7 g, 18.4 mmol) in 380 ml of 3:1 THF-H$_2$O. The reaction mixture was stirred at 0° C. for 15 min and a solution of 1.5N Na$_2$SO$_3$ (85 ml) was added. After stirring for another 30 min, the mixture was acidified to pH=2 with 3N HCl and extracted with EtOAc. The combined extracts were washed with brine and dried over Na$_2$SO$_4$. Concentration in vacuo followed by flash chromatography (CHCl$_3$—MeOH—AcOH: 95:5:1) on silica gel afforded 7.74 g (77%) of Compound 235c as a white solid.

(d) Compound 235d

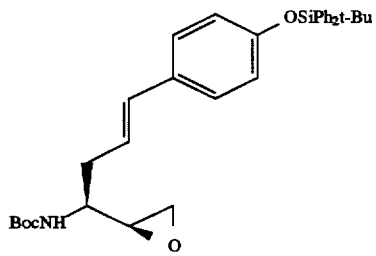

Compound 235c was converted to Compound 235d by a procedure analogous to that used for the preparation of Compound 175b.

(e) Compound 235e

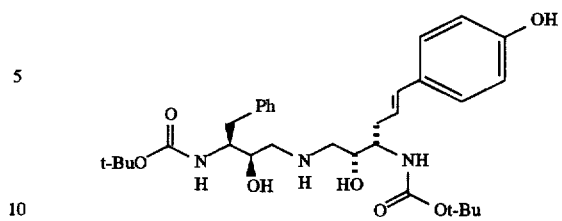

Compounds 235d and 16b were reacted by a procedure analogous to that used for the synthesis of Compound 4b to give the title Compound 235e (off-white solid).

m.p.: 110°–112° C.; [α]$_D$=+1.6° (c 0.25, MeOH). Mass Spec. (FAB): 586$^+$ (M+H)$^+$. Anal. Calc. for C$_{32}$H$_{47}$N$_3$O$_7$·0.82 H$_2$O: C, 64.00; H, 8.16; N, 7.00. Found: C, 64.15; H, 8.05; N, 6.85.

EXAMPLE 236

Preparation of [1S-(1R*,2S*)]-[Iminobis[2-hydroxy-1- (phenylmethyl)-3,1-propanediyl]] biscarbamic acid, 2-(formylamino)-1,1-dimethylethyl 1,1-dimethylethyl ester (Compound 236b)

(a) Compound 236a

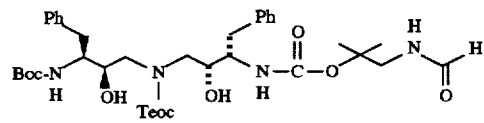

Compound 216d was reacted with formylacetic anhydride in THF by a procedure analogous to that of Example 129 to give Compound 236a.

(b) Compound 236b

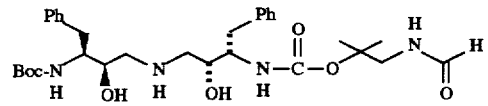

Compound 236a was converted to the title Compound 236b (white solid) by a procedure analogous to that of Example 21. The final product was purified by reverse phase HPLC (19×300 mm C18 column) eluted with a continuous gradient (30:70 A:B to 80:20 A:B; A=90% CH$_3$OH/H$_2$O+0.05% TFA; B=10% CH$_3$OH/H$_2$O+0.05% TFA). The resulting foamy white solid was lyophlized from CH$_3$OH/H$_2$O.

m.p. 78°–81° C.; [α]$_D$=–7.8° (c=0.2, CH$_3$OH). Analysis calculated for:C$_{31}$H$_{46}$N$_4$O$_7$·1.89 H$_2$O; C, 59.98; H, 8.08; N, 9.02. Found: C, 60.45; H, 7.73; N, 8.55.

EXAMPLE 237

Preparation of [1S-[1R*,2S*[2S*,3R*(trans)]]]-[3-[[3-[[(2,3-Dihydro-2-hydroxy-1H-inden-1-yl)carbonyl]amino]-2-hydroxy-4-phenylbutyl]amino]-2-hydroxy-1-(phenylmethyl)propyl]carbamic acid, 1,1-dimethylethyl ester (Compound 237c)

(a) Compounds 237a(i) and 237a(ii)

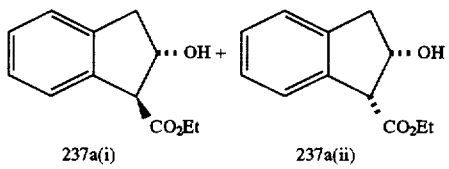

237a(i)  237a(ii)

To a mixture of NaBH$_4$ (230 mg, 6.08 mmol) in aqueous EtOH (30 mL, 95%) at 0° C. was added 1-carboethoxy-2-indanone (0.62 g, 3.03 mmol, prepared as in *J. Chem. Soc.*, 121, 1562–1571 (1922)). After stirring for 1 h, solid NH$_4$Cl (140 mg, 2.61 mmol) was added and the mixture was brought to RT. More solid NH$_4$Cl (440 mg, 8.22 mmol) was added after 2 h, followed by NaBH$_4$ (59 mg, 1.56 mmol). Further amounts of NH$_4$Cl (995 mg over 11.5 h), and then NaBH$_4$ (573 mg over 11.5 h), were added periodically over the next 11.5 h. The mixture was evaporated in vacuo, the resulting residue suspended in saturated NH$_4$Cl and extracted with EtOAc. The combined organic layers were dried (Na$_2$SO$_4$) and evaporated in vacuo to an oil which was purified by flash chromatography (silica gel, 3 by 20 cm), eluting with EtOAc:CH$_2$Cl$_2$ (1, 2, 3, and then 5% EtOAc) to give Compounds 237a(i) and 237a(ii) (350 mg, 3:2 ratio by $^1$H NMR, 56% yield) as a colorless oil.

(b) Compound 237b

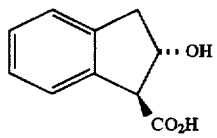

To neat Compounds 237a(i) and 237a(ii) (350 mg, 1.70 mmol) was added 1N NaOH (3 mL, 3 mmol). After 1.5 h, the solution was brought to pH 1 with 1N HCl. The resulting solution was extracted with Et$_2$O, the combined organic layers dried over Na$_2$SO$_4$ and concentrated in vacuo to give an oily solid. This residue was dissolved in hot EtOAc, diluted with hot pentane and allowed to slowly cool. After storing overnight at −20° C., the solid was triturated twice with cold pentane/EtOAc (4:1) to give after drying in vacuo Compound 237b (219 mg, 72% yield) as a slightly orange colored solid.

(c) Compound 237c

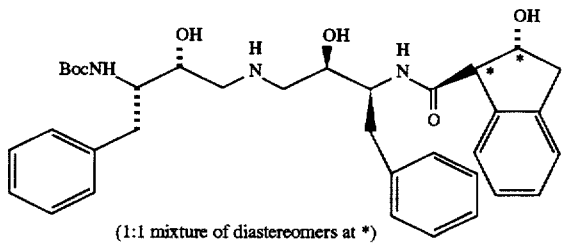

(1:1 mixture of diastereomers at *)

Compounds 237b and 54 were reacted by a procedure analogous to that of Example 55 (DMF only used) to give the title Compound 237c (colorless solid).

m.p. (shrink 141° C.) dec. 161°–165° C.; [α]$_D$=+10.7° (c 0.41, HOAc). MS: (CI): 604 (M+H). Anal. Calc. for C$_{35}$H$_{45}$N$_3$O$_6$·0.51 H$_2$O; C, 68.58; H, 7.57; N, 6.86 Found: C, 68.53; H, 7.41; N, 6.91

EXAMPLE 238

Preparation of [1S-[1R*,2S*(2S*,3R*)]]-[3-[[3-[[2-[3-(2-Benzimidazolyl)propoxy]-3,3-dimethyl-1-oxobutyl]amino]-2-hydroxy-4-phenylbutyl]amino]-2-hydroxy-1-(phenylmethyl)propyl]carbamic acid, 1,1-dimethylethyl ester (Compound 238e)

(a) Compound 238a

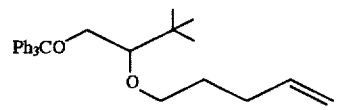

The triflate of 4-pentene-1-ol was prepared by the addition of 5.5 ml (33 mmol) of triflic anhydride in 50 ml of CH$_2$Cl$_2$, over a period of 1 hr, to a solution of 3.1 g (30 mmol) of 4-pentene-1-ol and 3.6 ml (45 mmol) of pyridine in 150 ml of CH$_2$Cl$_2$, at −10° C. After the addition was complete, the cold reaction was washed twice with 1N HCl, twice with brine, sat NaHCO$_3$, and twice with brine. The solution was dried (MgSO$_4$) and the solvent removed to yield 6.6 g (assumed 30 mmol, 100%) of the triflate as a pale yellow oil. This material was used immediately in the next step.

To a suspension of 1.7 g (15 mmol) of 35% KH suspension (hexane washed) in 50 ml of THF, at RT was added dropwise a solution of 4.8 g (13.3 mmoles) of Compound 106a in 25 ml of THF. After 2 h the solution was ice cooled and diluted with 75 ml of DMF. To this solution was added a solution of the freshly prepared pre-cooled (−78° C.) 4-pentene-1-ol triflate in 10 ml of THF. After stirring for 0.5 h at 0° C. and RT for 1 h, the reaction was diluted with brine and extracted twice with Et$_2$O. The extracts were washed with brine, dried (MgSO$_4$), the solvent removed and the resulting oil purified by flash chromatography on a 400 cc column of silica gel (elution with 25% CH$_2$Cl$_2$/hexane) to afford 2.9 g (51%) of Compound 238a as a colorless oil.

(b) Compound 238b

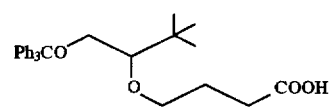

A solution of 1.7 g (4 mmoles) of Compound 238a, 1.9 g (12 mmoles) of KMnO$_4$, and 75 mg of n-Bu$_4$NBr in 20 ml of toluene, 20 ml of H$_2$O and 4 ml of HOAc was stirred for 2 h. To the resulting slurry was added sat. NaHSO$_3$ with stirring until the reaction became colorless. The suspension was extracted with EtOAc and the combined extracts washed with brine, dried (MgSO$_4$) and the solvent removed to yield a crude product which was purified by flash chromatography on a 125 cc column of silica gel (elution with 25% EtOAc/hexane) to afford 1.1 g (62%) of Compound 238b as a colorless oil.

(c) Compound 238c

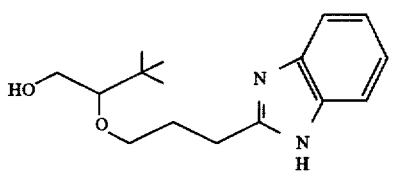

To a solution of 1.0 g (2.2 mmol) of Compound 238b and 0.42 ml (3 mmol) of Et₃N in 10 ml of THF, at −10° C. was added dropwise 0.32 ml (2.5 mmol) of i-butylchloroformate. After 0.5 h, a solution of 270 mg (2.5 mmol) of o-phenylenediamine in 5 ml of THF was then added. After 1.5 h at −10° C., the reaction was diluted with EtOAc and washed with H₂O, sat. NaHCO₃, and brine, dried (MgSO₄) and the solvent removed to give 1.3 g of a white foam. This material was dissolved in 25 ml of HOAc and heated at 65° C. for 3.5 hr. After cooling, the solution was evaporated to dryness. The residue was taken into EtOAc and washed with sat NaHCO₃ and brine. After drying (MgSO₄), removal of solvent gave a residue which was purified by flash chromatography on a 125 cc column of silica gel (elution with 100% EtOAc) to give 266 mg (44%) of Compound 238c as a solid foam.

(d) Compound 238d

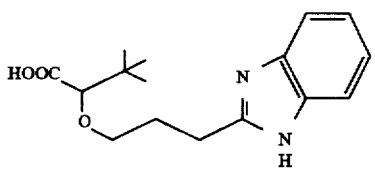

75 mg (0.27 mmol) of Compound 238c was converted to the corresponding aldehyde by a procedure analogous to that of Example 191c. To 50 mg of the intermediate aldehyde in 0.5 ml of THF and 0.9 ml (1.8 mmoles) of a 2M THF solution of 2-methyl-2-butene was added dropwise a solution of 23 mg (0.2 mmol) of sodium chlorite (80%) in 0.5 ml of pH 3.95 acetate buffer. After 1 h, the reaction was evaporated to dryness and the residue taken into 1 ml of H₂O saturated with solid NaCl and the pH adjusted to 5.0 by the addition of HOAc. After extraction with EtOAc, the combined organic layers were washed once with minimal brine, dried (MgSO₄), and the solvent removed to give a crude product which was purified by flash chromatography on a 15 cc column of silica gel (elution with 5%, 10% and 20% MeOH/CHCl₃) to afford 35 mg (45%) of Compound 238d as a white solid.

(e) Compound 238e

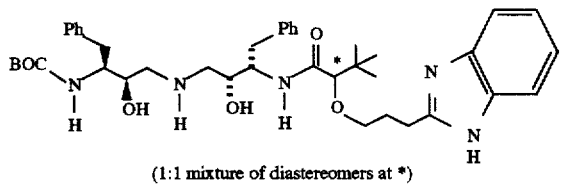

(1:1 mixture of diastereomers at *)

Compounds 238d and 54 were reacted by a procedure analogous to that of Example 93f to give the title Compound 238e (solid foam) as a 1:1 mixture of diastereomers.

High Res Mass Spec.: (M+H)⁺=716.4375; calc. 716.4387. Calc. for C₄₁H₅₇N₅O₆·H₂O (733.9): C, 67.09; H, 8.10; N, 9.54. Found: C, 67.01; H, 8.00; N, 9.21.

EXAMPLE 239

Preparation of [1S-[1R*,2S*(2S*,3R*)]]-[3-[[3-[[(5, 5-Dimethyl-2-oxo-4-oxazolidinyl) carbonyl]amino]-2-hydroxy-4-phenylbutyl]amino]-2-hydroxy-1-(phenylmethyl) propyl]carbamic acid, 1,1-dimethylethyl ester, isomer A (Compound 239d)

(a) Compound 239a

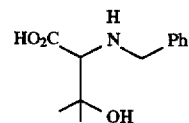

Dimethylacrylic acid and sodium tungstate were suspended in H₂O (0.67 ml/g acid) the pH of which was adjusted to 6.5 with aq. NaOH. At RT, 35% aq. H₂O₂ (4.1 mol eq.) was added dropwise maintaining the pH with additional aq. NaOH. After the addition was complete, the reaction was stirred for 1 h at 40° C. at which time Na₂SO₃ was added to destroy excess peroxide. Benzylamine was added (1.2 eq.) and the resulting mixture stirred at reflux for 2 h. The reaction was partially concentrated and then brought to pH 6 with concentrated HCl. The reaction was cooled to RT and the solid product Compound 239a filtered off and washed with cold H₂O and EtOH (28%).

(b) Compound 239b

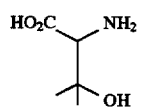

Compound 239a was stirred in MeOH (10 ml/g) along with 10% Pd/C under a H₂ atmosphere for 1 h (35° C.). After filtering off the catalyst, the reaction was partially concentrated and then cooled to 0° C. Acetone (7 ml/g Compound 239a) was added and the resulting solid Compound 239b filtered and washed with acetone (100%).

(c) Compound 239c

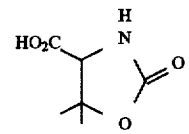

To a solution of Compound 239b (1.33 g, 10.0 mmol) in 12.5% aq. KOH (37 ml) cooled at 0° C. was added a solution of phosgene (1.93M) in toluene (11.7 ml). The mixture was stirred at 0° C. for 1.0 h and the toluene layer was separated. The aqueous layer was washed with Et₂O, acidified to pH=3 with 3N HCl and concentrated in vacuo to afford a solid residue. This residue was extracted into hot methanol (200 ml) and the solid removed by filtration. The filtrate was concentrated in vacuo and then partitioned between 5% KHSO₄ and EtOAc. The aqueous layer was extracted with hot EtOAc and the combined organic layers were dried (Na₂SO₄) and concentrated to afford 1.38 g (87%) of Compound 239c as an off-white solid.

(d) Compound 239d

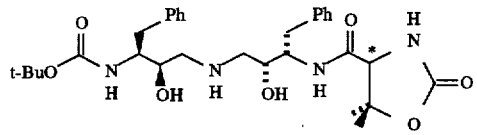

Compounds 54 and 239c were reacted by a procedure analogous to that of Example 93f to give Compound 239d along with its diastereomer Compound 240 as a 1:1 mixture. HPLC purification (S-10 C18; 120Å ODS; MeOH—H$_2$O-TFA 60:40:0.1) gave the title Compound 239d (white solid) as the slower moving isomer.

m.p. 108°–110° C.; $[\alpha]_D$ −5.0° (c 0.2, MeOH). Mass Spec. (FAB): 585$^+$ (M+H)$^+$. Analysis Calc. for C$_{31}$H$_{44}$N$_4$O$_7$: C, 63.68; H, 7.58; N, 9.51. Found: C, 63.75; H, 7.79; N, 9.51.

EXAMPLE 240

Preparation of [1S-[1R*,2S*(2S*,3R*)]]-[3-[[3-[[(5,5-Dimethyl-2-oxo-4-oxazolidinyl) carbonyl]amino]-2-hydroxy-4-phenylbutyl]amino]-2-hydroxy-1-(phenylmethyl) propyl]carbamic acid, 1,1-dimethylethyl ester, isomer B (Compound 240)

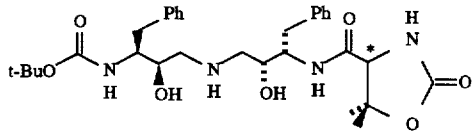

Compound 240 (white solid) was isolated by preparative HPLC (the faster moving isomer) as described in Example 239.

m.p. 120°–122° C.; $[\alpha]_D$=−18.3° (c 0.25, MeOH). Mass Spec. (FAB): 585$^+$(M+H)$^+$. Analysis Calc. for C$_{31}$H$_{44}$N$_4$O$_7$·1.08H$_2$O: C, 61.63; H, 7.70; N, 9.27. Found: C, 61.70; H, 7.62; N, 9.20.

EXAMPLE 241

Preparation of [R-(R*,S*)]-[Iminobis[2-hydroxy-1-(phenylmethyl)-3,1-propanediyl)]biscarbamic acid, 1,1-dimethylethyl-2-hydroxyethyl ester (Compound 241c)

(a) Compound 241a

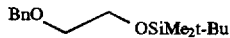

Benzyloxyethanol was converted to Compound 241a by a procedure analogous to that of Example 161c.

(b) Compound 241b

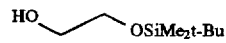

Compound 241a was converted to Compound 241b by a procedure analogous to that of Example 7.

(c) Compound 241c

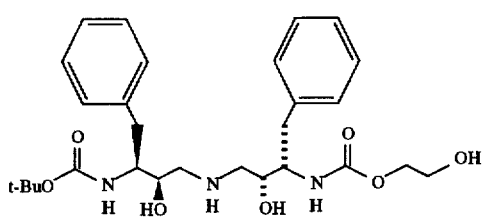

Compounds 241b and 48 were converted to the title Compound 241c (white solid) by a three-step procedure analogous to that used for the conversion of Compound 149c to Compound 150 (DMF was used as the solvent in the coupling reaction of Compound 48 with the p-nitrophenyl carbonate of Compound 241b).

m.p.=168°–172° C.; $[\alpha]_D$=−8.3° (c=0.32; MeOH). MS (FAB): (M+H)$^+$=532; Elemental Analysis: (for C$_{28}$H$_{41}$N$_3$O$_7$·0.27 H$_2$O); Calculated: C, 62.68; H, 7.80; N, 7.83; Found: C, 62.69; H, 7.68; N, 7.82.

EXAMPLE 242

Preparation of [1S-[1R*,2S*(2S*,3R*)]]-[3-[[4-[4-[(2-Benzoxazolyl)methoxy]phenyl]-3-[[(1,1-dimethylethoxy) carbonyl]amino]-2-hydroxybutyl] amino]-2 -hydroxy-1-(phenylmethyl) propyl] carbamic acid, 1,1-dimethylethyl ester (Compound 242)

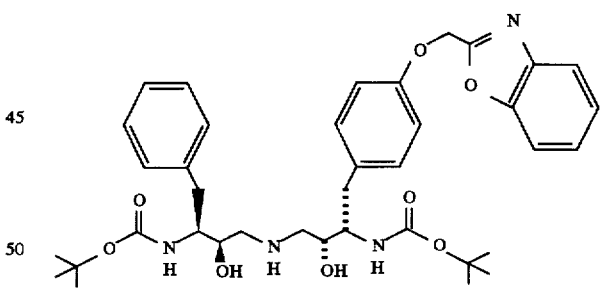

Compounds 171a and 172 were reacted by a four-step procedure analogous to that used for the conversion of Compound 172 to Compound 178 to give the title Compound 242 (white solid).

mp 145°–150° C.; $[\alpha]_{365}$=−21.7° (c 0.27, MeOH). Mass Spec. FAB+ions: M+H=691; Analysis calc. for C$_{38}$H$_{50}$N$_4$O$_8$·109 H$_2$O: C, 64.24; H, 7.40; N, 7.89; Found: C, 64.16; H, 7.14; N, 7.97.

EXAMPLE 243

Preparation of [1R*,2S*(2S*,3R*)]-N-[3-[[3-[[(1,1-Dimethylethoxy) carbonyl]amino]-2-hydroxy-4-phenylbutyl]-2-hydroxy-1-(phenylmethyl)propyl]-N²-[(phenylmethoxy)carbonyl]-L-alaninamide (Compound 243)

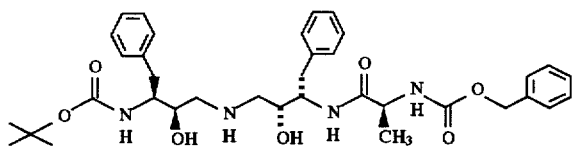

Compound 54 and N-carbobenzyloxy-L-alanine were reacted by a procedure analogous to that of Example 55 (DMF only used) to give the title Compound 243 (white solid).

mp 156°–157° C., $[\alpha]_D$=–10° (c 0.10, MeOH). Mass Spec. IONSPRAY+ion; (M+H)⁺=649⁺. Analysis calc. for $C_{36}H_{48}N_4O_7 \cdot 0.25 H_2O$: C, 66.18; H, 7.48; N, 8.58; Found: C, 66.21; H, 7.47; N, 8.55.

EXAMPLE 244

Preparation of [1S-[1R*,2S*(2S*,3R*)]]-[3-[[3-[[(1,1-Dimethylethoxy)carbonyl]amino]-2-hydroxy-4-[4-[3-[(2-benzoxazolyl)-propoxy]phenyl]butyl]amino]-2-hydroxy-1-(phenylmethyl)propyl]carbamic acid, 1,1-dimethylethyl ester (Compound 244b)

(a) Compound 244a

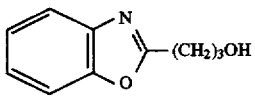

A mixture of o-aminophenol (2.5 g; 23 mmol), 4-pentenoic acid (2.33 ml; 23 mmol) and p-toluenesulfonic acid (150 mg) in 50 ml of toluene was refluxed with azeotropic removal of $H_2O$ for 30 hours. After cooling to RT, the reaction mixture was partitioned between EtOAc and 1N NaOH and the organic layer washed with 1N NaOH, $H_2O$ and brine. After drying over $MgSO_4$ and decolorizing over charcoal (Darco), the organic layer was filtered and concentrated to afford 793 mg (20%) of the intermediate, benzoxazole-2-prop-3-ene, as a yellow liquid. Ozone was bubbled through a solution of this intermediate (492 mg; 2.8 mmol) in 13 ml of MeOH at –78° for ~3 min. The reaction was stopped when starting material was consumed by TLC (EtOAc:Hex, 1:1). After purging with oxygen, the reaction mixture was warmed to –35° C. and 1.5 ml of $H_2O$, followed by $NaBH_4$ (163 mg; 4.2 mmol), was added. The reaction mixture was warmed to 0° C. over 1 h, at which time saturated aqueous $NH_4Cl$ (3 ml) was added. Most of the MeOH was removed in vacuo and the residue was partitioned between EtOAc and saturated aqueous $NH_4Cl$. The organic layer was washed with saturated aqueous $NH_4Cl$ and brine. After drying over $MgSO_4$ and concentrating, the residue was chromatographed on a 2.5×5 cm silica gel column using EtOAc as the mobile phase to afford 400 mg (81%) of Compound 244a as an orange solid.

(b) Compound 244b

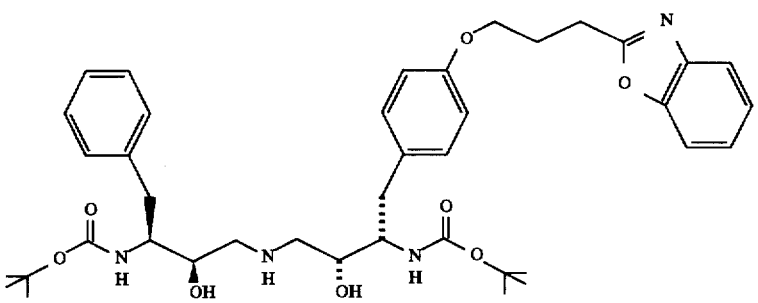

Compounds 244a and 172 were reacted by a four-step procedure analogous to that used for the conversion of Compound 172 to Compound 178 to give the title Compound 244b (white solid).

mp 121°–126° C.; $[\alpha]_{365}$=–3.6° (c 0.48, MeOH). Mass Spec. FAB+ions: M+H=719; Analysis calc. for $C_{40}H_{54}N_4O_8 \cdot 1.28 H_2O$: C, 64.75; H, 7.68; N, 7.55; Found: C, 64.59; H, 7.43; N, 7.71.

EXAMPLE 245

Preparation of [1R*,2S*(2S*,3R*)]-N-[3-[[3-[[(1,1-Dimethylethoxy)carbonyl]amino]-2-hydroxy-4-phenylbutyl]amino]-2-hydroxy-1-(phenylmethyl)propyl]-N²-[[(1H-benzimidazol-2-yl-methyl)methylamino]carbonyl]-L-valinamide (Compound 245d)

(a) Compound 245a

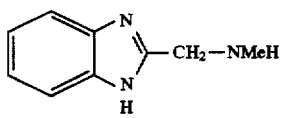

To a 40% aqueous solution of methylamine (100 ml) cooled to 0° C. was slowly added 2-chloromethyl benzimidazole (6.0 g, 36 mmol). After 1 additional h at 0° C. the reaction was diluted with H₂O and extracted with CH₂Cl₂. The combined extracts were dried (Na₂SO₄) and the solvent was evaporated in vacuo to give a crude product which was purified on a silica column eluting with a gradient from 5 to 10% MeOH/CH₂Cl₂+0.1 % NH₄OH to afford 680 mg (12%) Compound 245a as a colorless solid.

(b) Compound 245b

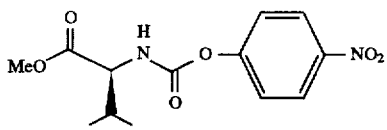

Pyridine (1.19 g; 15 mmol) was added to a suspension of L-valine methyl ester hydrochloride (1 g; 6 mmol) in CH₂Cl₂ at 0° C. p-Nitrophenyl-chloroformate (1.33 g; 6.6 mmol) was added and the mixture stirred at 0° C. for 2 h and at RT for 1 h. The reaction was diluted with EtOAc and washed with 10% KHSO₄, sat. NaHCO₃, H₂O and brine. The organic layer was dried (Na₂SO₄) and concentrated to afford 1.4 g (80%) of Compound 245b as a pale-yellow solid.

(c) Compound 245c

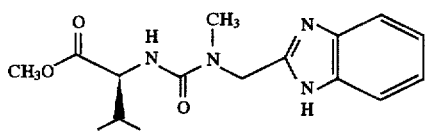

A mixture of Compound 245a (282 mg, 1.75 mmol), Compound 245b (518 mg, 1.75 mmol), and Et₃N (354 mg, 3.5 mmol) in 9 ml of dry CH₃CN was stirred overnight at RT. The volatiles were evaporated to give a crude product which was purified on a silica column eluting with a gradient from 2 to 5% MeOH/CH₂Cl₂+0.1% NH₄OH to afford 136 mg (24%) of Compound 245c as a colorless solid.

(d) Compound 245d

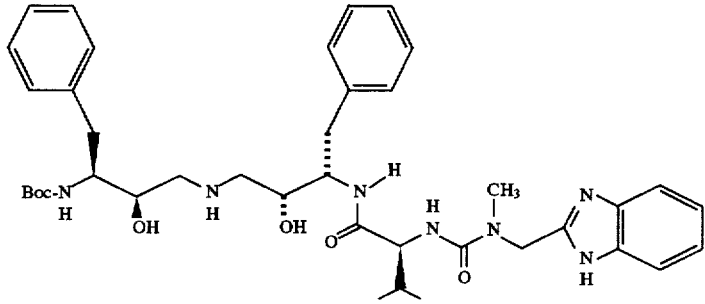

Compounds 245c and 54 were reacted by a two-step procedure analogous to that used for the conversion of Compound 70b to Compound 70d (DMF only; no N-methyl morpholine was added) to give the title Compound 245d (colorless solid).

m.p. 184°–188° C. (dec); $[\alpha]_D$=−18.5° (c=0.25, MeOH). High Res. Mass Spec. (FAB): (M+H)⁺=730.4292⁺; C₄₀H₅₆N₇O₆ Δ=1.5 ppm.

EXAMPLE 246

Preparation of [1R*,2S*(2S*,3R*)]-N-[3-[[3-[[(1,1-Dimethylethoxy)carbonyl]amino]-2-hydroxy-4-phenylbutyl]amino]-2-hydroxy-1-(phenylmethyl) propyl]-N²-(2-methoxycarbonyl)-3-methyl-L-valinamide (Compound 246b)

(a) Compound 246a

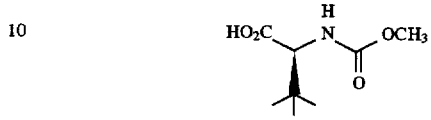

To a 0° C. solution of (L)-t-leucine (0.600 g, 4.57 mmol) in aqueous NaOH (2.80 mL of a 2.0N solution) were added in alternate portions methyl chloroformate (0.388 mL, 5.03 mmol) and aqueous NaOH (2.20 mL of a 2.0N solution) over 5 min. The solution was stirred at 0° C. for 30 min and for 1 h at RT. The aqueous solution was washed with Et₂O, acidified with aqueous 3M HCl solution to pH 1 and extracted with EtOAc. The combined organic extracts were dried (Na₂SO₄) and concentrated in vacuo to give the Compound 246a (0.867 g, ≦100%) as a colorless glass, which was used in the next step without purification.

(b) Compound 246b

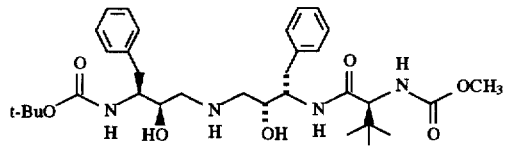

To a 0° C. solution of Compound 246a (0.094 g, 0.496 mmol) and HOBT.H₂O (0.114 g, 0.744 mmol) in DMF (1.0 mL) was added EDC (0.095 g, 0.496 mmol). The solution was stirred at 0° C. for 1 h. Compound 54 (200 mg, 0.451 mmol) in 1 ml DMF was added followed by N-methyl morpholine (0.165 mL, 1.50 mmol). The solution was allowed to warm to RT and stir for 36 h at which time volatiles were removed in vacuo. The residue was partitioned between aqueous 50% NaHCO₃ and EtOAc. The combined organic extracts were washed with brine, dried (Na₂SO₄), and concentrated in vacuo to give solid, which was chromatographed on silica gel (100 mL) using a gradient from 99:1:0.1 to 90:10:1 CH₂Cl₂:MeOH:NH₄OH as eluent to afford Compound 246b as a white solid (135 mg; 49%).

m.p.=153°–156° C.; $[\alpha]_D$=−16.10 (c=0.33; MeOH). MS (FAB): (M+H)⁺=615; Elemental Analysis: (for C₃₃H₅₀N₄O₇·1.09 H₂O); Calculated: C, 62.48; H, 8.29; N, 8.83; Found: C, 62.48; H, 8.06; N, 8.83.

EXAMPLE 247

Preparation of [1R*,2S*,3R*)]-N-[3-[[3-[[(1,1-Dimethylethoxy) carbonyl]amino]-2-hydroxy-4-phenylbutyl]amino]-2-hydroxy-1-(phenylmethyl)propyl]-N²-(methoxycarbonyl)-L-valinamide (Compound 247)

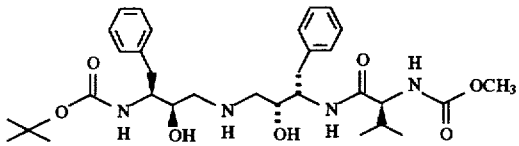

Compound 54 and L-valine were converted into the title Compound 247 (white solid) by a two-step procedure analogous to that of Example 246.

m.p. 202°–205° C.; [α]$_D$=–33.3° (c 0.06, MeOH). Analysis Calc. for C$_{32}$H$_{48}$O$_7$N$_4$·0.28 H$_2$O: C, 63.44; H, 8.08; N, 9.25; Found: C, 63.51; H, 8.03; N, 9.18.

EXAMPLE 248

Preparation of [1R*,2S*,(2S*,3R*)]-N-[3-[[3-[[(1,1-Dimethylethoxy)carbonyl]amino]-2-hydroxy-4-phenylbutyl]amino]-2-hydroxy-1-(phenylmethyl)propyl]-N²-(1-oxopropyl)-L-valinamide (Compound 248)

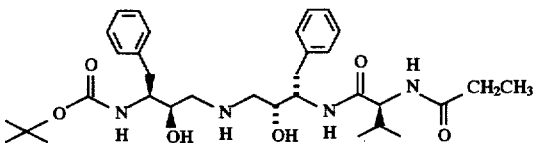

Compound 61 and propionic acid were converted into the title Compound 248 (white solid) by a two-step procedure analogous to that used for the conversion of Compound 48 to Compound 52.

m.p. 222°–225° C.; [α]$_D$=–28.5° (c 0.07, MeOH). Analysis Calc. for C$_{32}$H$_{50}$O$_6$N$_4$·0.64 H$_2$O: C, 64.95; H, 8.47; N, 9.18; Found: C, 64.90; H, 8.31; N, 9.23.

EXAMPLE 249

Preparation of [1R*,2S*(2S*,3R*)]-N-[3-[[3-[[(1,1-Dimethylethoxy)carbonyl]amino]-2-hydroxy-4-phenylbutyl]amino]-2-hydroxy-1-(phenylmethyl)propyl]-N²-[(1H-imidazol-2-ylmethoxy)carbonyl]-L-valinamide, acetate (2:3) salt (Compound 249c)

(a) Compound 249a

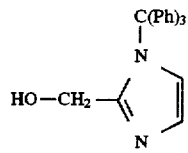

To a solution containing 1-trityl-2-formyl imidazole (1.54 g, 4.55 mmol; *J. Org. Chem.*, 43, 4381 (1978)) in a mixture of 12 mL of THF and 12 mL of EtOH cooled to 0° C. was added portionwise NaBH$_4$ (300 mg, 7.93 mmol). After 45 min at 0° C., the cold reaction mixture was quenched with pH 4 phosphate buffer and extracted with CH$_2$Cl$_2$. The combined organic extracts were washed with brine, dried (MgSO$_4$) and concentrated in vacuo to afford 1.47 g of Compound 249a as a waxy solid (95%, crude yield).

(b) Compound 249b

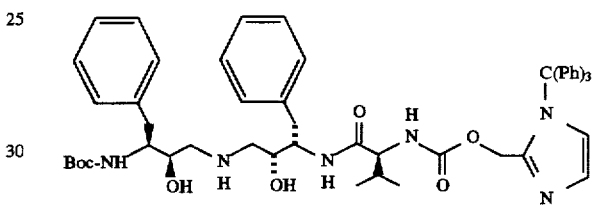

Compound 249a and 61 were converted into Compound 249b by a three-step procedure analogous to that used for the conversion of Compound 149c to Compound 150 (Et$_3$N was used in the coupling of Compound 61 with the p-nitrophenyl carbonate of Compound 249a).

(c) Compound 249c

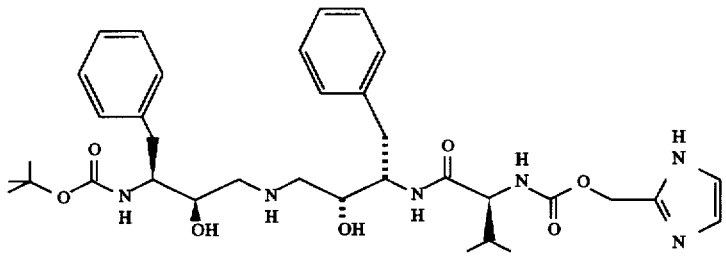

Compound 249b (250 mg, 0.275 mmol) was dissolved in a mixture of 3 mL of absolute EtOH and 12 mL of HOAc. The reaction mixture was heated at 40° C. for 3.5 h in a stoppered flask, then concentrated in vacuo and triturated with CH$_2$Cl$_2$—hexanes to afford the title Compound 249c (180 mg, 83%) as a white solid.

m.p. (softens 129° C.), 135–152° C.; [α]$_{D=+}$1.2° (c=0.21, MeOH). MS (FAB): (M+H)$^+$=667$^+$; Elemental Analysis: Calcd for C$_{35}$H$_{50}$N$_6$O$_7$·1.5; C$_2$H$_4$O$_2$·1.8 H$_2$O: C, 57.82; H, 7.61; N, 10.65. Found: C, 57.77; H, 7.27; N, 11.04.

EXAMPLE 250

Preparation of [1R*,2S*(2S*,3R*)]-N²-[3-(1, 3-Dihydro-3-oxo-2H-indazol-2-yl)-1-oxopropyl]-N-[3-[[3-[[(1,1-dimethylethoxy)carbonyl]amino]-2-hydroxy-4-phenylbutyl]amino]-2-hydroxy-1-(phenylmethyl)propyl]-L-valinamide (Compound 250e)

(a) Compound 250a

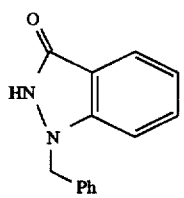

To a solution of 0.380 mg (16.5 mmol) of Na metal in 25 mL of anhydrous EtOH was added 2.01 g (15.0 mmol) of indazolinone. The resulting suspension was heated at reflux for 15 min at which point 1.9 mL (16.5 mmol) of benzyl chloride was added over 15 min. The resulting mixture was heated at reflux for 7 h, cooled to RT, concentrated in vacuo, and the residue diluted with 150 mL of 1N NaOH. The mixture was extracted with Et₂O. The aqueous layer was acidified to pH=5 with HOAc and then extracted with Et₂O. The Et₂O extracts were dried (Na₂SO₄), filtered, and concentrated in vacuo and the solid recrystallized from H₂O/MeOH to give 990 mg (29%) of Compound 250a.

(b) Compound 250b(i)

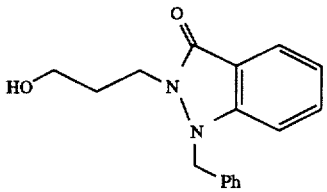

250b(i)

-continued

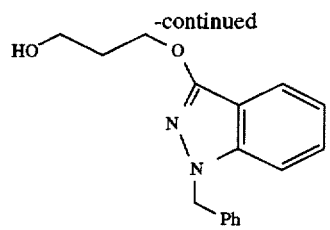

250b(ii)

To a solution of 0.253 mg (11.0 mmol) of Na metal in 20 mL of anhydrous EtOH was added 2.29 g (10.2 mmol) of Compound 250a. The mixture was heated at reflux for 15 min at which point 1.13 mL (12.0 mmol) of 3-bromopropanol in 5 mL of toluene was added over 10 min. After 4 h, an additional 0.38 mL (1.1 mmol; 21% wt in ethanol) of sodium ethoxide and 0.1 mL of 3-bromopropanol were added. The mixture was heated at reflux for 2 h, and then stirred at RT for 12 h. The cooled mixture was concentrated in vacuo, and the residue was diluted with 150 mL of 1N NaOH. The mixture was extracted with Et₂O and the extracts washed with brine dried (Na₂SO₄), filtered, and concentrated in vacuo. Flash chromatography on silica gel (10–50% EtOAc-CH₂Cl₂; then, 5% CH₃OH-CH₂Cl₂) provided 634 mg (22%) of Compound 250a(i) [TLC Rf=0.10 (10% EtOAc-CH₂Cl₂)] and 2 g of Compound 250b(ii) [TLC Rf=0.37 (10% EtOAC-CH₂Cl₂)].

(c) Compound 250c

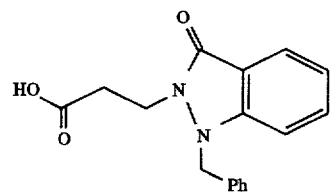

To a solution of 200 mg (0.708 mmol) of Compound 250b(i) in 3.5 mL of dry DMF was added 1.03 g (2.73 mmol) of pyridinium dichromate. The mixture was stirred at RT for 18 h then poured into 1:1 H₂O/brine (100 mL) and extracted with Et₂O. The organic layer was dried (Na₂SO₄), filtered, and evaporated in vacuo to give 130 mg (62%) of Compound 250c.

(d) Compound 250d

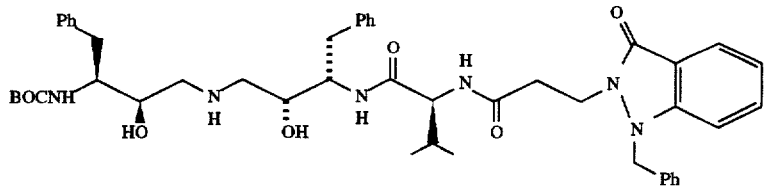

To a solution of 238 mg (0.439 mmol) of Compound 59, 130 mg (0.439 mmol) of Compound 250c, and 119 mg (0.88 mmol) of HOBT in 2.5 mL of dry DMF at 0° C. was added 93 mg (0.483 mmol) of EDCI. The mixture was stirred at 0° C. for 3 h and at RT for 18 h then concentrated in vacuo. The residue was diluted with EtOAc, and washed with saturated NaHCO₃, H₂O, and brine. The organic layer was concentrated in vacuo, and purified by flash chromatography on silica gel [2–10% CH₃OH/CH₂Cl₂ with 1.0% NH₄OH] to provide 265 mg [74% yield (88% pure by HPLC)] of Compound 250d.

(e) Compound 250e

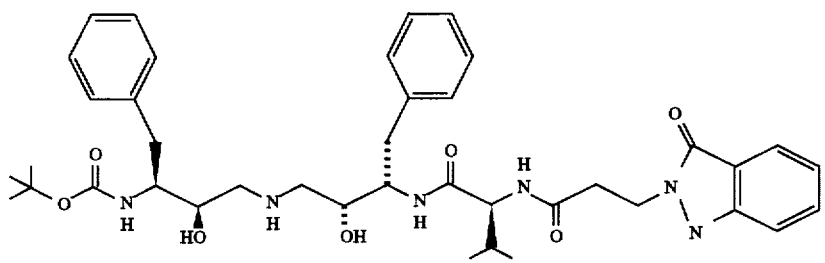

A solution of 185 mg (0.225 mmol) of Compound 250d in 12 mL of hot MeOH was cooled to RT, and treated with 100 mg of 10% Pd/C. The mixture was stirred under a $H_2$ atmosphere for 24 h then an additional 100 mg of 10% Pd/C was added and the mixture was stirred under a $H_2$ atmosphere for another 12 h. The mixture was filtered, rinsed with hot MeOH, and evaporated in vacuo. Flash chromatography of the residue on silica gel [2% $CH_3OH/CH_2Cl_2$, then 3–10% $CH_3OH/CH_2Cl_2$ (with 0.3–1.0% $NH_4OH$)] provided 81 mg (49%) of the title Compound 250e (colorless solid).

mp 187°–192° C. (dec.); $[\alpha]_D = -22°$ (c 0.32, $CH_3OH$); Mass Spec: 731 (M+H)$^+$; Elemental Analysis: Calcd for $C_{40}H_{54}N_6O_7 \cdot 0.32\ H_2O$: C, 65.21; H, 7.48; N, 11.41. Found: C, 65.31; H, 7.53; N, 11.31.

EXAMPLE 251

Preparation of [R-(R*,S*)]-[Iminobis[2-hydroxy-1-(phenylmethyl)-3,1-propanediyl)]biscarbamic acid, 1,1-bis(hydroxymethyl)ethyl 1,1-dimethylethyl ester (Compound 251d)

(a) Compound 251a

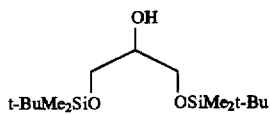

Compound 251a was prepared by the method described in Curran et al., Synthetic Comm. 20, 3575 (1990).

(b) Compound 251b

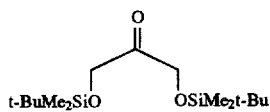

To a slurry of (1,1,1-triacetoxy-1,1-dihydro-1,2-benziodoxol-3(1H)-one) (3.8 g, 8.96 mmol) in 10 mL of dry $CH_2Cl_2$ was added t-BuOH (0.929 mL, 9.856 mmol). The mixture was cooled to 0° C. and a solution of Compound 251a (1.434 g, 4.48 mmol) in 5 mL of $CH_2Cl_2$ was added. The reaction mixture was warmed to RT and stirred for 2 h after which time the mixture was diluted with 75 mL of EtOAc and 90 mL of 1:1:1 sat. $NaHCO_3$—10% $Na_2SO_3$—brine was added. The mixture was stirred vigorously for 1 h, the two phases separated and the organic phase washed with brine, dried ($MgSO_4$) and concentrated. The crude residue was purified by flash chromatography on silica, eluting with a stepwise gradient of hexane to 50% EtOAc-hexane to obtain Compound 251b (0.775 g, 54%) as a colorless oil.

(c) Compound 251c

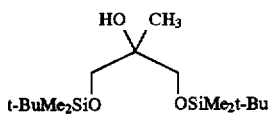

To 1.95 mL (2.681 mmol) of a 1.4M MeLi solution in $Et_2O$ was added 5 mL of THF. The solution was cooled to –78° C. and a solution of Compound 251b (0.775 g, 2.437 mmol) in 5 mL of THF was slowly added. An additional 1 mL of MeLi solution was added twice at intervals of 1 h and the mixture slowly warmed to –40° C. After 1 additional h, the reaction was quenched by adding 0.4 mL of HOAc in 5 mL of THF, warmed to RT and diluted with $H_2O$. The mixture was extracted with EtOAc and the extracts washed with sat. $NaHCO_3$ and brine, dried ($MgSO_4$) and concentrated. The crude residue was purified by flash chromatography on silica gel eluting with a stepwise gradient of hexane to 75% EtOAc-hexane to afford Compound 251c (0.475 g, 58%) as a colorless oil.

(d) Compound 251d

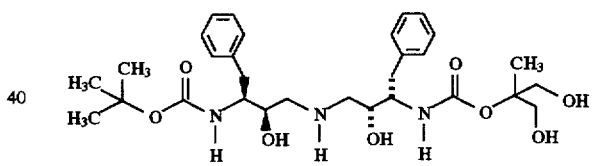

Compounds 161a and 251c were reacted by a five-step procedure analogous to that used for the conversion of Compound 161c to Compound 162 ($Et_3N$ was used in the coupling of the p-nitrophenyl carbonate of Compound 251c with Compound 161a) to give the title Compound 251d (off-white solid). High Res. Mass Spec.(M+H)$^+$=576.3285 (Δppm =2.2).

EXAMPLE 252

Preparation of [1S-(1R*,2S*)]-[Iminobis[2-hydroxy-1-(phenylmethyl)-3, 1-propanediyl]] biscarbamic acid 2-fluoro-1,1-dimethylethyl 1,1-dimethylethyl ester (Compound 252d)

(a) Compound 252a

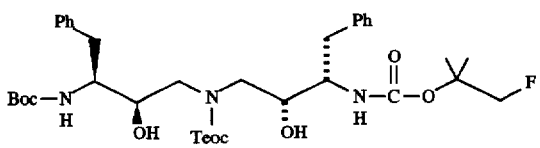

Compound 48 and 2-methyl-1-fluoro-2-propanol (Bergmann et al., J. Chem. Soc., 2259 (1958)) were converted to Compound 252a by a two-step procedure analogous to that used for the conversion of Compound 149c to 149e.

(b) Compound 252b

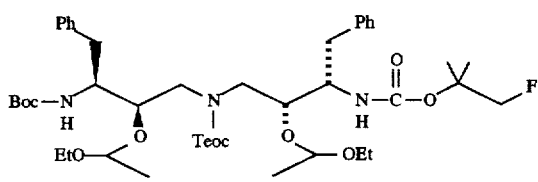

Compound 252a was converted to Compound 252b by a procedure analogous to that of Example 140a.

(c) Compound 252c

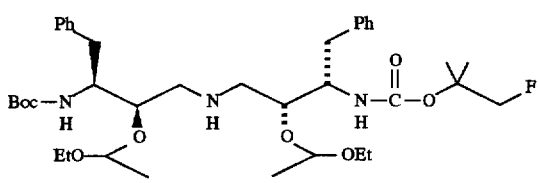

Compound 252b was converted to Compound 252c by a procedure analogous to that of Example 21.

(d) Compound 252d

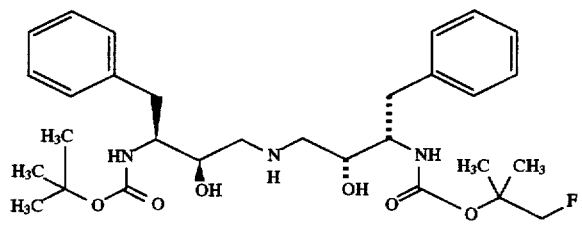

Compound 252c was converted to the title Compound 252d (white solid) by a procedure analogous to that of Example 140e except that the reaction was run at RT for 18 h and at reflux for 2 h.

m.p. 174°–176° C.; $[\alpha]_D = -6.0°$ (c=0.2, CH$_3$OH); Analysis calculated for:C$_{30}$H$_{44}$N$_3$O$_6$F; C, 64.15; H, 7.90; N, 7.48; F, 3.38. Found: C, 63.99; H, 7.96; N, 7.81; F, 3.35.

EXAMPLE 253

Preparation of [R-(R*,S*)]-[Iminobis[2-hydroxy-1-(phenylmethyl)-3,1-propanediyl)]biscarbamic acid, 1,1-dimethylethyl(4-phenyl-1H-imidazol-2-yl) methyl ester (Compound 253e)

(a) Compound 253a

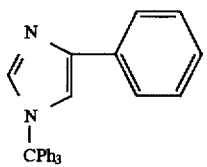

4-Phenylimidazole (2.5 g, 17.3 mmol) was stirred with trityl chloride (4.8 g, 17.2 mmol) in acetone (37 ml) and Et$_3$N (2.9 ml, 20.8 mmol) for 3 h. The mixture was concentrated, dissolved in CH$_2$Cl$_2$ and washed with H$_2$O, brine, dried (Na$_2$SO$_4$) and concentrated. The product crystallized and was dried in vacuo to yield Compound 253a (6.49 g, 97%, mp 185°–188° C.).

(b) Compound 253b

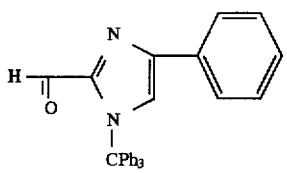

Compound 253a (2.0 g, 5.17 mmol) in 50 ml of dry THF was cooled to –45° C. and tert-butyl lithium (1.7M in hexanes, 6.1 ml, 10.34 mmol) was added dropwise and the reaction was stirred for 30 min. DMF (1.9 ml, 25.85 mmol) was added and the reaction was stirred for 1.5 h at which point saturated aq. NH$_4$Cl was added and product was extracted with EtOAc. The EtOAc solution was washed with H$_2$O, brine, dried (Na$_2$SO$_4$), and concentrated in vacuo to yield crystalline Compound 253b (2.09 g, 94%, mp 185°–188° C.).

(c) Compound 253c

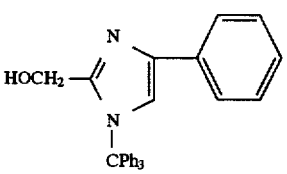

Compound 253b (2.09 g, 5.0 mmol) was dissolved in THF:EtOH:CHCl$_3$ (15 ml:15 ml:20 ml), cooled to 0° C. and NaBH$_4$ (0.33 g, 8.57 mmol) was added portionwise. After 1 h, the reaction mixture was diluted with CH$_2$Cl$_2$ and washed with H$_2$O, brine, dried (Na$_2$SO$_4$) and concentrated. The product crystallized from Et$_2$O to yield Compound 253c (1.8 g, 86%, mp 183°–190° C.).

(d) Compound 253d

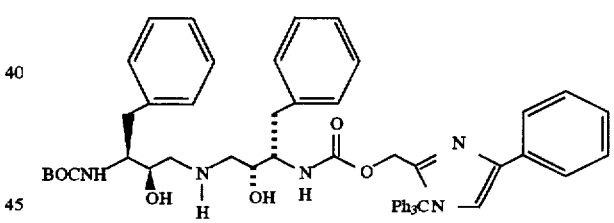

Compounds 253c and 48 were reacted by a three-step procedure analogous to that used for the conversion of Compound 149c to 150 (Et$_3$N and DMF were used in the reaction of the p-nitrophenyl carbonate of Compound 253c with Compound 48) to give Compound 253d.

(e) Compound 253e

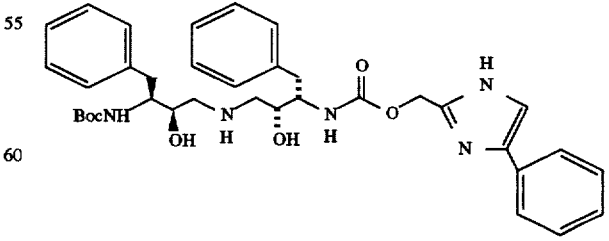

Compound 253d was dissolved in EtOH (4.7 mL) and HOAc (19 mL) and the reaction mixture was stirred at 40° C. for 2 h, concentrated in vacuo and the residue triturated with Et$_2$O. The resulting solid was chromatographed through 80 g of silica gel eluting with CHCl$_3$:MeOH:NH$_4$OH (89:10:1) to afford the title Compound 253e (0.12 g, 54%) as a white solid.

m.p. 109°–115° C.; [α]$_D$=–5.6° (c=0.85, MeOH). Analysis Calc. for C$_{36}$H$_{45}$N$_5$O$_6$·1.13 H$_2$O: C, 65.11;H, 7.17; N, 10.55; Found: C, 65.12;H, 6.99; N, 10.54

EXAMPLE 254

Preparation of [1R*,2S*(2S*,3R*)]-N-[3-[[3-[[(1,1-Dimethylethoxy) carbonyl]amino]-2-hydroxy-4-phenylbutyl]amino]-2-hydroxy-1-(phenylmethyl) propyl]-N$^2$-(3,4-dihydroxy-1-oxobutyl)-L-valinamide (Compound 254f)

(a) Compound 254a

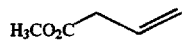

To a 0° C. solution of diazomethane/Et$_2$O (see Compound 1a(i) for preparation) was added dropwise 3-butenoic acid (4.94 mL, 58.0 mmol) over 5 min. The solution was swirled until colorless, then washed with aqueous NaHCO$_3$ and dried (Na$_2$SO$_4$). The Et$_2$O was distilled off to give Compound 254a (4.32 g, 74%).

(b) Compound 254b

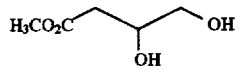

To a solution of Compound 254a (4.25 g, 42.4 mmol) and N-methylmorpholine N-oxide (8.07 mL of a 60% solution by weight in H$_2$O) in acetone (30 mL) and H$_2$O (20 mL) was added OsO$_4$ (70.0 mg, 0.275 mmol) and the resulting solution stirred at RT for 18 h. A solution of NaHSO$_3$ (0.50 g in 5 mL H$_2$O) was then added, the resulting black solution stirred at RT for 30 min, then filtered through Celite (acetone wash). The volatiles were removed and the residual aqueous solution was saturated with NaCl and extracted with EtOAc. The combined organic extracts were dried (Na$_2$SO$_4$), concentrated and purified on silica gel (150 mL) using a gradient from 1:1 hexane:EtOAc to 100% EtOAc to give Compound 254b (3.15 g, 55%) as a slightly yellow oil.

(c) Compound 254c

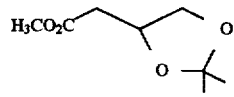

To a solution of Compound 254b (1.00 g, 7.46 mmol) in acetone (10 mL) and 2,2-dimethoxypropane (10 mL) was added p-toluenesulfonic acid hydrate (7 mg, 0.037 mmol) and the solution was stirred at RT for 18 h. Saturated aqueous NaHCO$_3$ solution was added and the mixture was concentrated in vacuo. The residue was partitioned between H$_2$O and EtOAc and the combined organic extracts were washed with H$_2$O dried (Na$_2$SO$_4$), and concentrated in vacuo. The oil was purified on silica gel (150 mL) using 10:1 hexane:EtOAc to give Compound 254c (1.260 g, 97%) as a colorless oil.

(d) Compound 254d

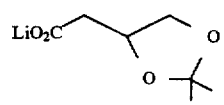

Compound 254c was converted to Compound 254d by a procedure analogous to that of Example 70c (THF used as solvent).

(e) Compound 254e

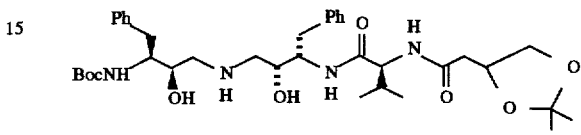

Compounds 254d and 61 were reacted by a two step procedure analogous to that used for the conversion of Compound 48 to Compound 52 to give Compound 254e (white foam).

(f) Compound 254f

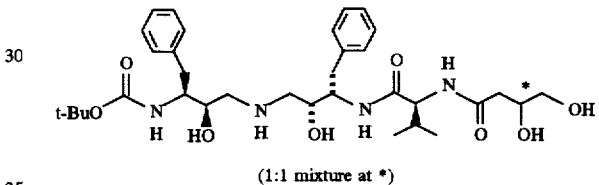

(1:1 mixture at *)

Compound 254e was converted to the title Compound 254f (white solid; mixture of diastereomers at *) by a procedure analogous to that of Example 202c.

m.p.=156°–160° C.; [α]$_D$=–11.1° (c=0.28; MeOH) High resolution Mass Spec. (FAB): Calculated (M+H)$^+$ (for C$_{34}$H$_{53}$N$_4$O$_8$)=645.3861; Observed (M+H)$^+$=645.3862 Δ=0.2 ppm

EXAMPLE 255

Preparation of [1S-[1R*,2S*(2S*,3R*)]]-[3-[[3-[(3, 4-Dihydroxy-1-oxo-butyl)amino]-2-hydroxy-4-phenylbutyl]amino]-2-hydroxy-1-(phenylmethyl) propyl]carbamic acid, 1,1-dimethylethyl ester (Compound 255b)

(a) Compound 255a

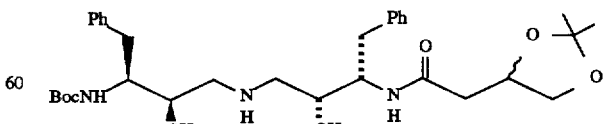

Compounds 254d and 48 were reacted by a two-step procedure analogous to that used for the conversion of Compound 48 to 52 to give Compound 255a (white solid).

(b) Compound 255b

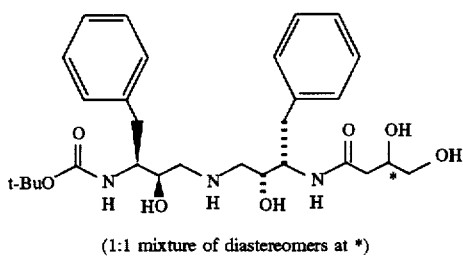

(1:1 mixture of diastereomers at *)

Compound 255a was converted to the title Compound 255b (white solid; mixture of diastereomers) by a procedure analogous to that of Example 202c.

m.p.=145°–150° C.; $[\alpha]_D$=+5.0° (c=0.20; MeOH) Mass Spec. (FAB): $(M+H)^+$=546; Elemental Analysis: (for $C_{29}H_{43}N_3O_7 \cdot 1.19 H_2O$) Calculated: C, 61.42; H, 8.07; N, 7.41; Found: C, 61.20; H, 7.83; N, 7.63;

EXAMPLE 256

Preparation of [R-(R*,S*)]-[Iminobis[2-hydroxy-1-(phenylmethyl)-3, 1-propanediyl)]biscarbamic acid. 1,1-dimethylethyl-3-pyridinylmethyl ester (Compound 256)

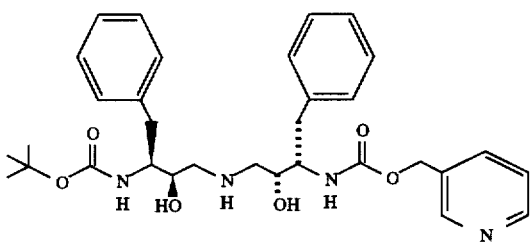

3-Pyridine carbinol and Compound 48 were converted to the title Compound 256 (colorless solid) by a three-step procedure analogous to that used for the conversion of Compound 149c to 150 (DMF was used in the coupling of the p-nitrophenyl carbonate of 3-pyridine carbinol to Compound 48).

m.p. 167°–170° C.; $[\alpha]_D$=−16° (c 0.24, CH$_3$OH); Mass Spec. 579 (M+H)$^+$; Analysis Calc. for $C_{32}H_{42}N_4O_6 \cdot 0.37 H_2O$: C, 65.66; H, 7.36;N, 9.57; Found: C, 65.65; H, 7.39;N, 9.58

EXAMPLE 257

Preparation of [S-[1R*,2S*(2S*,3R*)]]-[2,2-Dimethyl-1-[[[3-[[3-[[(1,1-dimethylethoxy)carbonyl]amino]-2-hydroxy-4-phenylbutyl]-amino]-2-hydroxy-1-(phenylmethyl)propyl]amino]-carbonyl]propyl]carbamic acid, (2-benzoxazolyl)methyl ester (Compound 257c)

(a) Compound 257a

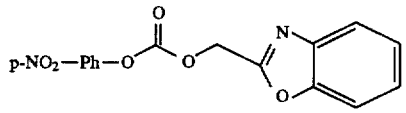

To a solution of 350 mg (2.35 mmol) of Compound 171a in 5 mL of CH$_2$Cl$_2$ and 2.5 mL of pyridine at 0° C. was added 475 mg (2.35 mmol) of p-nitrophenylchloroformate in 2.5 mL of CH$_2$Cl$_2$. The mixture was stirred at 0° C. for 2 h. The mixture was diluted with EtOAc and washed with 1M NaOH, H$_2$O, and brine. The organic layer was dried (Na$_2$SO$_4$), filtered, and concentrated in vacuo. Flash chromatography of the residue (20–40% EtOAc-hexane) afforded 567 mg (77%) of Compound 257a.

(b) Compound 257b

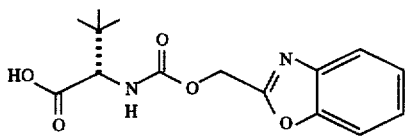

To neat tert-L-leucine (146 mg, 1.11 mmol) was added aqueous 1N NaOH (1.1 mL). After stirring for several minutes, a dioxane (3 mL) solution of Compound 257a (140 mg, 2.61 mmol) was added, followed by Et$_3$N (0.23 mL, 1.65 mmol). The reaction mixture was stirred for 26 h, diluted with H$_2$O, and brought to pH 4 with 5% KHSO$_4$. The aqueous solution was extracted with EtOAc, the aqueous layer brought back to pH 3 with more 5% KHSO$_4$ and extracted with EtOAc. The combined organic layers were dried (Na$_2$SO$_4$) and evaporated in vacuo to an oil. The residue was purified by flash chromatography (silica gel, 3 by 15 cm), eluting with EtOAc:CH$_2$Cl$_2$ (1:1), then 10% MeOH:CH$_2$Cl$_2$ to give Compound 257b (227.7 mg, 67% yield) as a colorless oily solid.

(c) Compound 257c

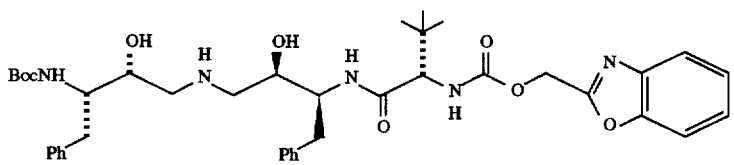

To a solution of Compound 257b (152 mg, 0.50 mmol) in DMF (2.5 mL) at 0° C. under argon was added HOBT (105 mg, 0.78 mmol), and then EDCI (95 mg, 0.50 mmol). After 45 min, solid Compound 54 (226 mg, 0.51 mmol) was added and the mixture was brought to RT. After stirring 24 h, the reaction mixture was partitioned between EtOAc and saturated NaHCO$_3$. The combined organics were dried (Na$_2$SO$_4$) and evaporated in vacuo to give an oily solid which was purified by flash chromatography (silica gel, 3 by 15 cm), eluting with MeOH:NH$_4$OH:CH$_2$Cl$_2$ (5:0.5:94.5, 6:0.6:93.4, and then 7:0.7:92.3) to give the title Compound 257c (151 mg, 42% yield) as a colorless solid. m.p. 149°–159° C.; [α]$_D^{25}$=−18.2° (c 0.28, MeOH).

Mass Spec.: (FAB): 732 (M+H). Anal. Calc. for C$_{40}$H$_{53}$N$_5$O$_8$: C, 65.64; H, 7.30; N, 9.57; Found: C, 65.79; H, 7.54; N, 9.66

EXAMPLE 258

Preparation of [R-(R*,S*)]-[Iminobis[2-hydroxy-1-(phenylmethyl)-3,1-propanediyl)]biscarbamic acid, 1,1-dimethylethyl-1-(3-pyridinyl)ethyl ester (Compound 258b)

(a) Compound 258a

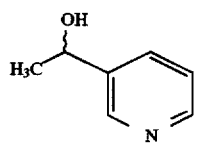

To a solution of 536 mg (5.00 mmol) of 3-pyridinecarboxaldehyde in 16.5 mL of dry THF at −78° C. was added 3.4 mL (5.5 mmol) of methyllithium (1.6M in Et$_2$O) (internal temperature <−55° C.). The resulting yellow solution was warmed to 0° C. and quenched by the addition of 30 mL of saturated NH$_4$Cl. The reaction mixture was extracted with Et$_2$O and the organic layer dried (Na$_2$SO$_4$), filtered, and concentrated in vacuo to provide 458 mg of Compound 258a. The aqueous layer was saturated with NaCl and extracted with Et$_2$O. Concentration in vacuo provided an additional 74 mg (total 532 mg) of product.

(b) Compound 258b

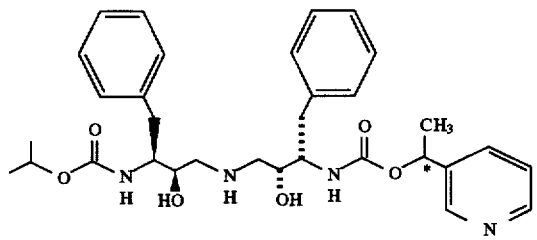

(1:1 mixture of stereoisomers at *)

Compounds 258a and 48 were converted to the title Compound 258b (colorless solid) by a three-step procedure analogous to that used for the conversion of Compound 149c to 150 (DMF was used in the coupling of the p-nitrophenyl carbonate of Compound 258a to Compound 48).

m.p. 161°–170° C.; [α]$_D$=−14° (c 0.21, CH$_3$OH); Mass Spec. 593 (M+H)$^+$; Anal. Calc. for C$_{33}$H$_{44}$N$_4$O$_8$: C, 66.87; H, 7.48; N, 9.45; Found: C, 66.54; H, 7.64; N, 9.28

EXAMPLE 259

Preparation of [1R*, 2S* (2S*, 3R*)]-N-[3-[[3-[[(1,1-Dimethylethoxy)carbonyl]amino]-2-hydroxy-4-phenylbutyl] amino]-2-hydroxy-1-(phenylmetyl) propyl]-N$^2$-(hydroxyacetyl)-L-valinamide (Compound 259)

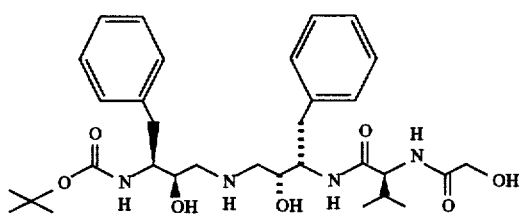

Compound 61 and glycolic acid were reacted by a two-step procedure analogous to that used for the conversion of Compound 48 to Compound 52 to afford the title Compound 259 (white solid).

m.p. 208°–210° C.; Mass Spec. High resolution 601.3595, error 1.0 ppm, theory 601.3601; Analysis Calc. for C$_{32}$H$_{48}$O$_7$N$_4$·1.34 H$_2$O: C, 61.50; H, 8.17; N, 8.97; Found: C, 61.77; H, 8.15; N, 8.70

EXAMPLE 260

Preparation of [1R*,2S*(2S*,3R*)]-N-[3-[[3-[[(1,1-Dimethylethoxy)carbonyl]amino]-2-hydroxy-4-phenylbutyl]amino]-2-hydroxy-1-(phenylmethyl) propyl]-N$^2$-[3-(1H-indol-3-yl)-1-oxo-propyl]-L-valinamide (Compound 260)

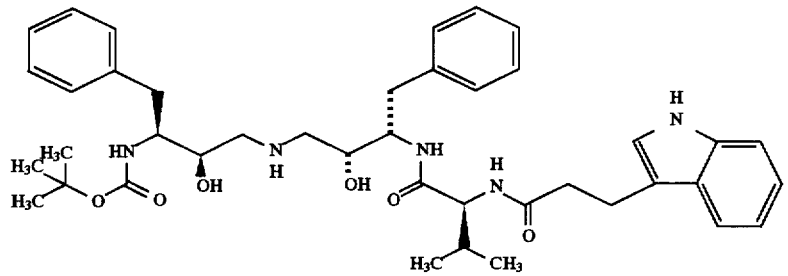

Compound 61 and 3-indolpropionic acid were reacted by a two-step procedure analogous to that used for the conversion of Compound 48 to Compound 52 to afford the title Compound 260 (white solid).

EXAMPLE 261

Preparation of [1S-[1R*,2S*[2R*,3R*(R*)]]]-[3-[[3-[(2-Hydroxy-2,3,3-trimethyl-1-oxobutyl) amino]-2-hydroxy-4-phenylbutyl]amino]-2-hydroxy-1-(phenylmethyl)propyl]carbamic acid, 1,1-dimethylethyl ester (Compound 261c)

(a) Compound 261a

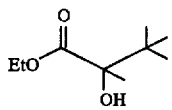

A solution of t-butyl magnesium chloride (2M in Et$_2$O, 21.55 mL, 43.1 mmol) was added to a stirred solution of ethyl pyruvate (5 g, 43.1 mmol) in THF (75 mL) at −78° C. The reaction mixture was stirred at −78° C. for 15 min, RT for 1 h, diluted with EtOAc, and washed with 1N HCl followed by sat. NaHCO$_3$. The organic layer was dried (MgSO$_4$), concentrated, and the resulting oil was fractionally distilled under vacuum affording 3.5 g (47%) of Compound 261a as a colorless oil (b.p. 45–50° C. at 1.2 mm).

(b) Compound 261b

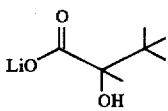

A 0.5M aq. solution of LiOH (10.64 mL) was added to a solution of Compound 261a (1.0 g, 5.75 mmol), stirred at 75° C. for 8 h, concentrated in vacuo, and the residue concentrated from toluene. The residue was triturated from Et$_2$O to afford 0.9 g (ca. 100%) of Compound 261b.

(c) Compound 261c

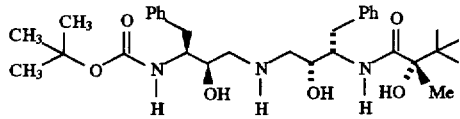

To a solution of Compound 261b (0.114 g, 0.75 mmol), HOBT monohydrate (0.135 g, 0.88 mmol) in 2 mL dry DMF at 0° C. was added N-methyl morpholine (0.1634 mL, 1.49 mmol), EDCI hydrochloride (0.1434 g, 0.75 mmol) and the resulting mixture was stirred at 0° C. for 15 min. The mixture was treated with Compound 54 (0.3 g, 0.68 mmol) and stirred at RT for 20 h, concentrated, and the residue partitioned between EtOAc and sat. NaHCO$_3$. The organic layer was dried (MgSO$_4$), concentrated, and the crude product was subjected to flash chromatography (silica gel/CH$_2$Cl$_2$—MeOH—NH$_4$OH 95:5:0.5) affording 0.193 mg (50%) of a mixture of the two diastereomeric products. This mixture was subjected to prep. HPLC (Waters Prep Nova-Pack HR C18, 6 micron, 30×300 mm; eluent: MeOH-water-TFA 30:70:0.05 to 90:10:0.05; UV 254 nm). The fractions from the slower moving isomer were made basic with sat. NaHCO$_3$, concentrated, and the residue partitioned between EtOAc/1:1 brine-sat. NaHCO$_3$. The organic phase was dried (MgSO$_4$), concentrated, the resulting white solid was triturated from 10:1 hexane-Et$_2$O to afford 19 mg (5%) of the title Compound 261c as a white solid.

m.p. 212°–214° C.; [α]$_D$=−38.1° (c=0.2, CH$_3$OH) Analysis for:C$_{41}$H$_{55}$N$_5$O$_8$·0.65 H$_2$O; Calculated:C, 67.86; H, 7.82; N, 9.65. Found: C, 67.95; H, 7.77; N, 9.56.

EXAMPLE 262

Preparation of [1S-[1R*,2S*[2S*,3R*(S*)]]]-[3-[[3-[(2-Hydroxy-2,3,3-trimethyl-1-oxobutyl)amino]-2-hydroxy-4-phenylbutyl]amino]-2-hydroxy-1-(phenylmethyl)propyl]carbamic acid, 1,1-dimethylethyl ester (Compound 262f)

(a) Compound 262a

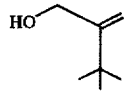

A 70% solution of t-butyl hydroperoxide in water (340.5 ml, 2.38 mol) was extracted with 300 ml CH$_2$Cl$_2$. The organic layer was added to a stirred mixture of SeO$_2$ (3.67 g, 33.1 mmol) and benzoic acid (8.1 g, 66.2 mmol) in 50 ml CH$_2$Cl$_2$. The mixture was cooled to 0° C. and 2,3,3-trimethylbutene (65 g, 0.662 mol) was added and the mixture stirred at RT for 14 h. The mixture was washed with 5% aq. KOH, brine and dried (MgSO$_4$). The volatiles were removed by distillation and the residue was cooled to ca. 0° C. 100 ml HOAc was added followed by 100 ml Me$_2$S added dropwise over 15 min. The reaction was stirred at RT for 3 h, cooled to 0° C. and made basic with 20% aq. K$_2$CO$_3$. The mixture was extracted with Et$_2$O and the organic extracts washed with sat. NaHCO$_3$, dried (MgSO$_4$), and the solvent removed by distillation at atmospheric pressure followed by distillation of the product (90°–100° C., 25 mm) to afford 20 g (26.5%) of Compound 262a.

(b) Compound 262b

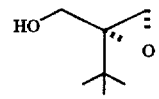

Diethyl D-tartrate (618 mg, 3 mmol) and Ti(iPrO)$_4$ (0.744 ml, 2.5 mmol) were added to a stirred suspension of 4 Å activated powdered molecular sieves in 175 ml dry CH$_2$Cl$_2$ at 0° C. The mixture was cooled to −20° C. and a 5.5M solution of t-butyl hydroperoxide in 2,2,4-trimethylpentane (18.2 ml, 100 mmol) was added. After 20 min, a solution of Compound 262a (5.7 g, 50 mmol) in 25 ml CH$_2$Cl$_2$ was added and the mixture stirred at −20° C. for 14 h. After warming to 0° C., 15 ml H$_2$O was added, the mixture stirred at RT for 30 min, 30% aq. NaOH saturated with NaCl (3 ml) was added and the reaction stirred at RT for 25 min. The aqueous layer was extracted with CH$_2$C$_{12}$, the combined extracts dried (MgSO$_4$) and concentrated by distillation at atmospheric pressure followed by distillation of Compound 262b (105°–107° C., 25 mm; 4.75 g, 73%).

(c) Compound 262c

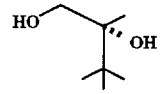

A solution of Compound 262b (2.3 g, 17.7 mmol) in 10 ml Et$_2$O was added to a suspension of LiAlH$_4$ (1.477 g, 38.9 m.p. 97°–100° C.; [α]$_D$=−5.2° (c=0.91, MeOH). High resolution Mass Spec.: (M+H)$^+$=572.3688, theoretical: (M+H)$^+$=572.3699 (Δ 1.9 ppm error). Similar work-up of the fractions from the faster moving peak afforded 23 mg (6%) of Compound 262f.

mmol) in 100 ml Et₂O at −5° C. and stirred at RT for 30 min. The mixture was cooled to 0° C., and quenched with 10% aq. H₂SO₄ saturated with Na₂SO₄. The aqueous layer was extracted with EtOAc and the combined extracts washed with sat. NaHCO₃ and brine and dried (MgSO₄). Concentration in vacuo followed by recrystallization from hexane gave 1.5 g (64%) of Compound 262c as a white solid.

(d) Compound 262d

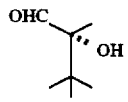

A solution of DMSO (2.578 ml, 36.3 mmol) in 3 ml CH₂Cl₂ was added dropwise at −78° C. to a stirred solution of oxalyl chloride (1.585 ml, 18.2 mmol) over 5 min. and stirred at −78° C. for 10 min. A solution of Compound 262c (2.18 g, 16.5 mmol) in 25 ml CH₂Cl₂, was added dropwise and stirred for 15 min. at −78° C. Et₃N (11.51 ml, 82.6 mmol) was added and the reaction allowed to come to RT. The mixture was diluted with additional CH₂Cl₂, washed with 10% H₂SO₄, the combined aqueous phase extracted with CH₂Cl₂, and the combined organic layer washed with sat. NaHCO₃, dried (MgSO₄), and concentrated by distillation at atmospheric pressure to afford 2.15 g (100%) of Compound 262d as a pale gummy solid.

(e) Compound 262e

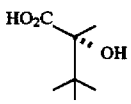

NaClO₂ (1.81 g, 20 mmol) and sulfamic acid (1.94 g, 20 mmol) were added in succession to a stirred solution of Compound 262d (2.0 g, 15.4 mmol) in 30 ml 1:1 THF-water at 0° C. The mixture was allowed to warm to RT, stirred for 30 min., diluted with CH₂Cl₂ and ca. 1 ml Me₂S was added followed by a small quantity of H₂O. The organic layer was separated, the aqueous layer was extracted with CH₂Cl₂, the combined organic layer was dried (MgSO₄) and concentrated to afford a yellow gummy solid which was recrystallized from hexanes to afford 1.45 g (64.5%) of Compound 262e as a pale solid.

(f) Compound 262f

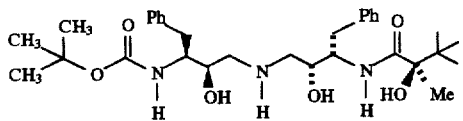

N-methylmorpholine (0.037 ml, 0.34 mmol) and BOP-reagent (150 mg, 0.34 mmol) were added at RT in succession to a stirred mixture of Compound 262e (45 mg, 0.31 mmol) and Compound 54 (137 mg, 0.31 mmol) in 0.5 ml dry DMF. The mixture was stirred at RT for 60 h, concentrated in vacuo, the residue partitioned between EtOAc and sat. NaHCO₃, and the organic layer dried (MgSO₄) and concentrated in vacuo. The residue was purified by flash chromatography (1"×12" silica gel/CH₂Cl₂ to CH₂Cl₂.MeOH:aq.NH₄OH 99:1:0.1 stepwise to 92.5:7.5:0.75) to afford 120 mg (68%) of the title Compound 262f as a white solid.

m.p. 204°–205° C. Anal. Calcd. for C₃₂H₄₉N₃O₆·1.22 H₂O: C, 64.73; H, 8.73; N, 7.08; Found: C, 64.73; H, 8.42;N, 7.10.

EXAMPLE 263

Preparation of [1R*,2S*(2S*,3R*)]-N-[3-[[3-[[(1,1-Dimethylethoxy)carbonyl]amino]-2-hydroxy-4-phenylbutyl]amino]-2-hydroxy-1-(phenylmethyl)propyl]-N²-[(methylamino)carbonyl]-3-methyl-L-valinamide (Compound 263d)

(a) Compound 263a

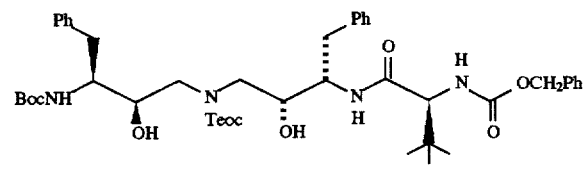

Compounds 88a and 48 were reacted by a procedure analogous to that of Example 51 to give Compound 263a (white foam).

(b) Compound 263b

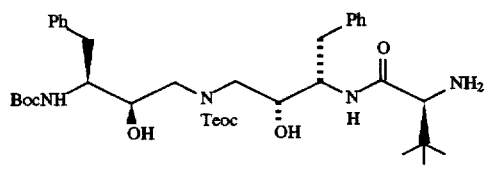

Compound 263a was converted to Compound 263b (white foam) by a procedure analogous to that of Example 61.

(c) Compound 263c

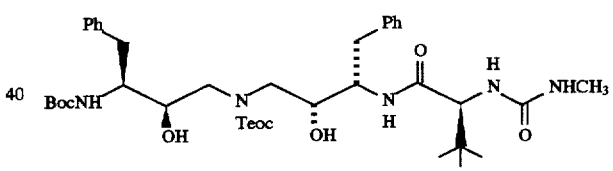

Compound 263b and methyl isocyanate were reacted by a procedure analogous to that of Example 46 to give Compound 263c (colorless oil).

(d) Compound 263d

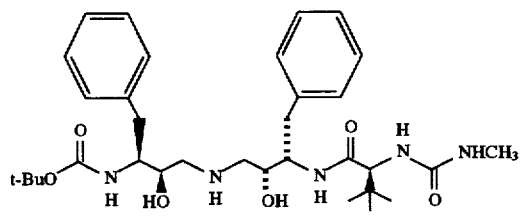

Compound 263c was converted to the title Compound 263d (white solid) by a procedure analogous to that of Example 21.

m.p.=174°–178° C. ; [α]_D=−15.0° (c=0.28; MeOH) High resolution Mass Spec. (FAB): Calculated (M+H)⁺ (for C₃₃H₅₂O₆N₅)=614.3917; Observed (M+H)⁺=614.3936 Δ=3.1 ppm.

EXAMPLE 264

Preparation of [1R*2S*(2S*,3R*)]-N-[3-[[3-[[(1,1-Dimethylethoxy) carbonyl]amino]-2-hydroxy-4-phenylbutyl]amino]-2-hydroxy-1-(phenylmethyl) propyl]-$N^2$-[(phenylmethoxy)carbonyl]-L-homoserinamide (Compound 264d)

(a) Compound 264a

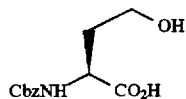

To a solution of L-homo-serine (596 mg, 5.0 mmol) and NaHCO$_3$ (420 mg, 5.0 mmol) in 14 ml of H$_{20}$-acetone (1:1) was added N-benzyloxycarbonyloxy succinimide (1.25 g, 5.0 mmol). The mixture was stirred overnight at RT. Acetone was removed under reduced pressure. The aqueous solution was washed with CH$_2$Cl$_2$ and then acidified to pH 2.5 with 6N HCl solution and extracted with EtOAc. The combined extracts were washed with H$_2$O and brine and dried (Na$_2$SO$_4$). Concentration in vacuo afforded 980 mg (77%) of Compound 264a.

(b) Compound 264b

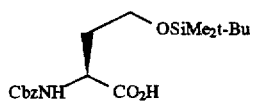

To a stirred solution of Compound 264a (506 mg, 2.0 mmol) in 10 ml of dry DMF was added tert-butyldimethylsilyl chloride (1.81 g, 12.0 mmol), followed by imidazole (1.63 g, 24.0 mmol). The mixture was stirred for 24 h at RT. CH$_3$OH (35 ml) was added and the mixture was stirred for another 14 h. The solvent was removed under reduced pressure and the residue was dissolved in EtOAc. The organic layer was washed with 10% citric acid and brine and dried over Na$_2$SO$_4$. Concentration in vacuo followed by flash chromatography (CHCl$_3$—EtOAc-HOAc: 60:40:1) afforded 638 mg (87%) of Compound 264b as a colorless oil.

(c) Compound 264c

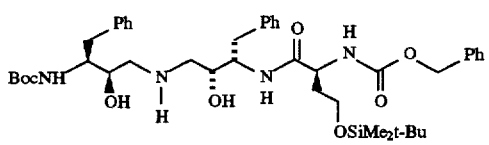

Compounds 54 and 264b were reacted by a procedure analogous to that of Example 93f to give Compound 264c.

(d) Compound 264d

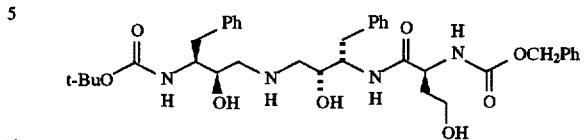

Compound 264c was converted to the title Compound 264d (white solid) by a procedure analogous to that of Example 162.

m.p. 168°–170° C.; $[\alpha]_D$=−25.6° (c 0.36, MeOH). Mass Spec. (FAB): 679$^+$ (M+H)$^+$. Analysis Calc. for C$_{37}$H$_{50}$N$_4$O$_8$·0.20H$_2$O: C, 65.12; H, 7.44; N, 8.21. Found: C, 65.04; H, 7.48; N, 8.29.

EXAMPLE 265

Preparation of [1R*,2S*(2S*,3R*)]-N-[3-[[3-[[(1,1-Dimethylethoxy)carbonyl]amino]-2-hydroxy-4-phenylbutyl]amino]-2-hydroxy-1-(phenylmethyl) propyl]-$N^2$-[[(4-phenyl-1H-imidazol-2-yl) methoxylcarbonyl]-L-valinamide (Compound 265b)

(a) Compound 265a

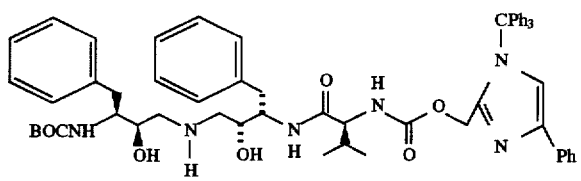

Compounds 253c and 61 were reacted by a three-step procedure analogous to that used for the conversion of Compound 149c to 150 (Et$_3$N and DMF were used in the reaction of the p-nitrophenyl carbonate of Compound 253c with Compound 61) to give Compound 265a.

(b) Compound 265b

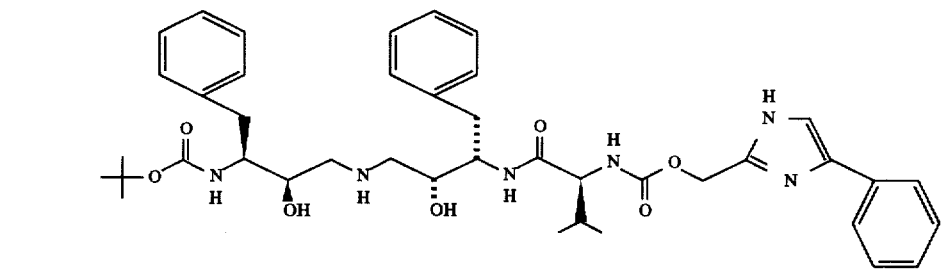

Compound 265a was converted to Compound 265b (white solid) by a procedure analogous to that of Example 253e.

m.p. 140°–145° C.; $[\alpha]_D$=−1.8° (MeOH, c=0.5); Analysis Calc. for C$_{41}$H$_{54}$N$_6$O$_7$·1.61 H$_2$O: C, 63.80; H, 7.47; N, 10.89. Found: C, 63.75; H, 7.39; N, 10.94.

EXAMPLE 266

Preparation of [1S-[1R*,2S*(2S*,3R*)]]-[3-[[3-[[(3,3-Dimethyl-5-oxo-2-pyrrolidinyl)carbonyl]amino]-2-hydroxy-4-phenylbutyl]amino]-2-hydroxy-1-(phenylmethyl)propyl]carbamic acid, 1,1-dimethylethyl ester (Compound 266c)

(a) Compound 266a

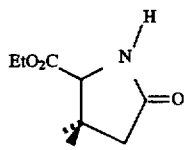

Compound 266a was prepared by the method of Yamazaki et al., Chem. Pharm. Bull., 24, 3011 (1976).

(b) Compound 266b

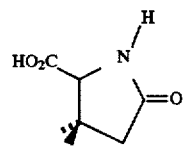

Compound 266a was converted to Compound 266b by a procedure analogous to that of Example 70c (except THF:H$_2$O:DME (2:1:0.5) was used).

(c) Compound 266c

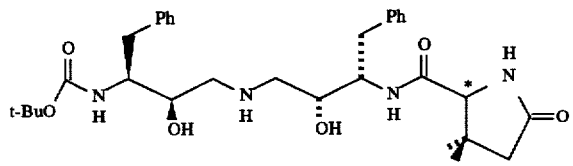

(single isomer at *)

Compounds 266b and 54 were reacted by a procedure analogous to that of Example 93f to give the title Compound 266c along with its diastereomer Compound 267 (1:1). Compound 266c (white lyophilate) was isolated by flash chromatography (CHCl$_3$—MeOH—NH$_4$OH 95:5:0.5 to 90:10:1) on silica gel followed by preparative HPLC (CH$_3$CN—H$_2$O—TFA 62:38:0.1) purification (YMC SH ODS-365-10, S-10 column).

$^1$H-NMR (400 MHz, CD$_3$OD): δ 7.10–7.30 (m, 10H), 4.27 (m, 1H), 3.70 (s, 1H), 3.58–3.75 (m, 3H), 3.14 (m, 2H), 2.50–2.84 (m, 6H), 2.26 (d, J=16.7, 1H), 1.93 (d, J=16.7, 1H), 1.29 (s, 9H), 0.79 (s, 3H), 0.76 (s, 3H). High resolution Mass Spec. Calc. for C$_{32}$H$_{47}$N$_4$O$_6$: 583.3496; Found: 583.3506, Δ=1.7 ppm.

EXAMPLE 267

Preparation of [1S-[1R*,2S*(2S*,3R*)]]-[3-[[3-[[(3,3-Dimethyl-5-oxo-2-pyrrolidinyl)carbonyl]amino]-2-hydroxy-4-phenylbutyl]amino]-2-hydroxy-1-(phenylmethyl)propyl]carbamic acid, 1,1-dimethylethyl ester (Compound 267)

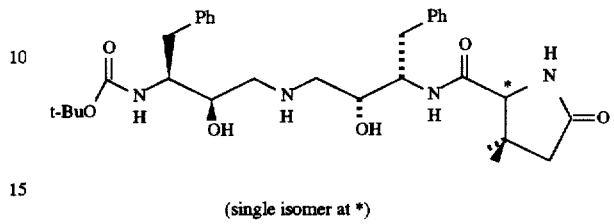

(single isomer at *)

Compound 267, the diastereomer of Compound 266c, was isolated by preparative HPLC as described in Example 266c. $^1$H-NMR (400 MHz, CD$_3$OD):δ 7.10–7.30 (m, 10H), 4.16 (m, 1H), 3.63 (s, 1H), 3.56–3.73 (m, 3H), 3.10 (m, 2H), 2.63–2.80 (m, 5H), 2.58 (m, 1H), 2.47 (d, J=16.7, 1H), 2.38 (d, J=16.7, 1H), 1.29 (s, 9H), 0.97 (s, 3H), 0.93 (s, 3H). High resolution Mass Spec. Calc. for C$_{32}$H$_{47}$N$_4$O$_6$: 583.3496; Found: 583.3505, Δ=1.7 ppm.

EXAMPLE 268

Preparation of [R-(R*,S*)]-[Iminobis[2-hydroxy-1-(phenylmethyl)-3,1-propanediyl)]biscarbamic acid, (1H-imidazol-2-yl)-methyl 1,1-dimethylethyl ester (Compound 268b)

(a) Compound 268a

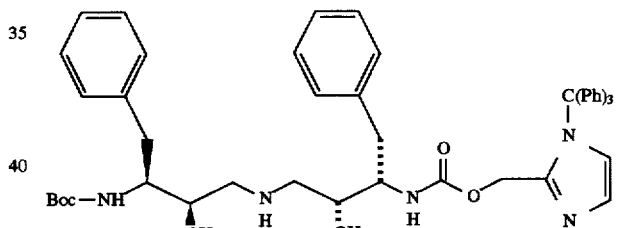

Compounds 249a and 48 were reacted by a three-step procedure analogous to that used for the conversion of Compound 149c to 150 (Et$_3$N and DMF were used in the reaction of the p-nitrophenyl carbonate of Compound 249a with Compound 48) to give Compound 268a.

(b) Compound 268b

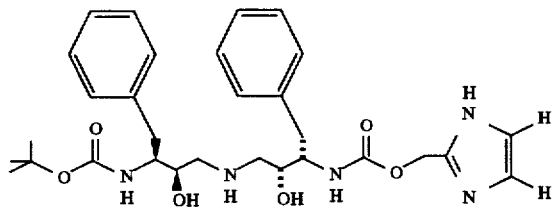

Compound 268a was converted to Compound 268b (white solid) by a procedure analogous to that of Example 253e.

m.p. 143°–147° C. (dec.); [α]$_D$=−5.9° (c=0.16, MeOH). Analysis Calcd. for C$_{30}$H$_{41}$N$_5$O$_6$·0.45 H$_2$O (575.79): C, 62.58; H, 7.34; N, 12.16. Found: C, 62.57; H, 7.35; N, 12.08. Mass Spec. (FAB): (M+H)$^+$=568$^+$

EXAMPLE 269

Preparation of [1S-[1R*,2S*(2S*,3R*)]]-[3-[[3-[(2,2-Dimethyl-1-oxo-propyl)amino]-2-hydroxy-4-phenylbutyl]amino]-2-hydroxy-1-(phenylmethyl)propyl]carbamic acid, 1,1-dimethylethyl ester (Compound 269)

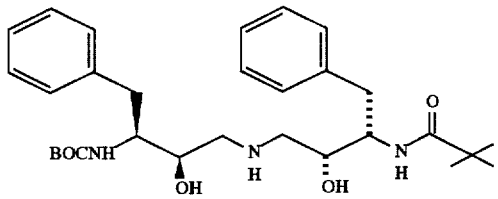

Compound 54 and trimethylacetic acid were converted to the title Compound 269 (white solid) by a procedure analogous to that of Example 262f except that a mixture of DMF and CH$_2$Cl$_2$ was used and no N-methylmorpholine was added.

m.p. 100°–104° C. ("softening" at 84°–99° C.); [α]$_D$=+10.1° (c=0.8.5, MeOH). High resolution Mass Spec. 528.3428$^+$ for C$_{30}$H$_{46}$O$_5$N$_3$; (calc. 528.3437$^+$) Δ=1.7ppm.

EXAMPLE 270

Preparation of [1S-[1R*,2S*(2S*,3R*)]]-[3-[[3-[[(2-Formyl-2,3-dihydro-1H-isoindol-1-yl)carbonyl]amino]-2-hydroxy-4-phenylbutyl]amino]-2-hydroxy-1-(phenylmethyl)-propyl]carbamic acid 1,1-dimethylethyl ester (Compound 270g)

(a) Compound 270a

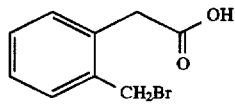

A solution of benzoyl peroxide (97%; 0.043 g), N-bromosuccinimide (11.74 g, 0.066 mol) and o-tolylacetic acid (10.0 g, 0.066 mol) in CCl$_4$ (600 ml) was heated at 90° C. for 3.5 h. Upon cooling, the reaction was filtered to remove a yellow precipitate, and the filtrate was concentrated in vacuo to a yellow solid. This solid was recrystallized from CCl$_4$ to afford 9.20 g (64%) of Compound 270a as a white crystalline solid.

(b) Compound 270b

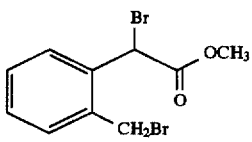

After heating a solution of Compound 270a (9.0 g, 0.04 mol) in SOCl$_2$ (9.0 ml) at 50° C. for 3 h, the excess reagent was removed at reduced pressure, and the resulting yellow oil heated to 80° C. under a 250 watt lamp. Br$_2$ (2.5 ml) was added and the reaction continued at 80° C. for 4 h before cooling and removing the excess reagent under reduced pressure. The resulting brown residue was stirred in MeOH for 30 min at RT then concentrated in vacuo to an orange oil which was chromatographed on a silica gel column, eluting the column with toluene to afford 8.0 g (65%) of Compound 270b as a yellow oil.

(c) Compound 270c

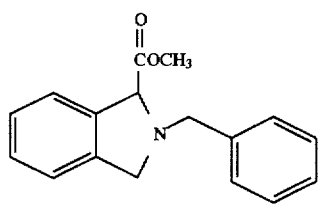

Benzylamine (2.04 ml, 18.69 mmol) was added to a stirred solution of Compound 270b (2.0 g, 6.23 mmol) in toluene (13 ml) at 0° C. The reaction was warmed to RT where it remained for 72 h before filtering off a yellow precipitate under Ar. The solid was washed thoroughly with toluene and the filtrate diluted with a solution of anhydrous Et$_2$O saturated with HCl gas. The mother liquor was decanted and the remaining yellow gum dried under high vacuum to afford 1.35 g (50%) of Compound 270c as a green foam.

(d) Compound 270d

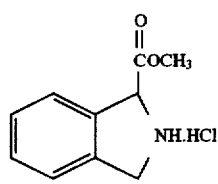

Compound 270c was converted to Compound 270d by a procedure analogous to that of Example 2.

(e) Compound 270e

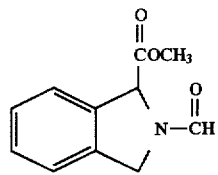

Compound 270d was converted to Compound 270e by a procedure analogous to that of Example 129 (except 1.1 eq. of N-methylmorpholine was also added to the reaction mixture).

(f) Compound 270f

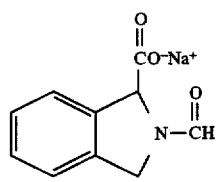

A solution of aqueous NaOH (0.736 ml, 1N) was added at RT to a rapidly stirred solution of Compound 270e in THF (1 ml). After 20 min, the solution was concentrated in vacuo then dried under high vacuum to afford 0.136 g (51%) of Compound 270f as a brown/green solid.

(g) Compound 270g

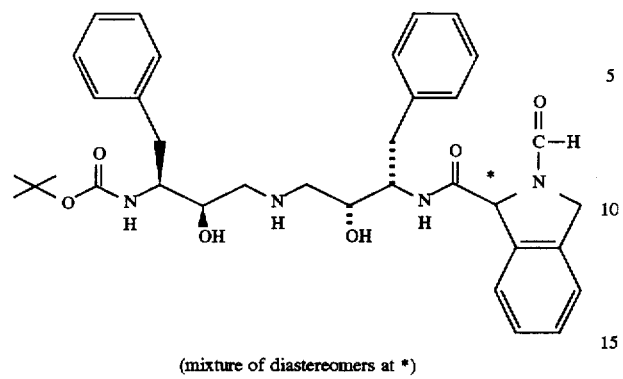

(mixture of diastereomers at *)

Compounds 270f and 54 were reacted by a procedure analogous to that of Example 55 (DMF only used) to give the title Compound 270g (white solid) as a mixture of diastereomers.

m.p. 174°–176° C.; $[\alpha]_D=-30°$ (c 0.1, MeOH). Mass spec: HRMS $C_{35}H_{45}O_6N_4$: 617.3328+: calculated 617.3339+, Δ=1.8 ppm.

EXAMPLE 271

Preparation of [1S-[1R*,2S*(2S*,3R*)]]-[2-Hydroxy-1-(phenylmethyl)-3-[[2-hydroxy-4-phenyl-3-[(3,3,3-trifluoro-2-hydroxy-1-oxopropyl) amino] butyl]amino]-propyl]carbamic acid, 1,1-dimethylethyl ester (isomer A) (Compound 271)

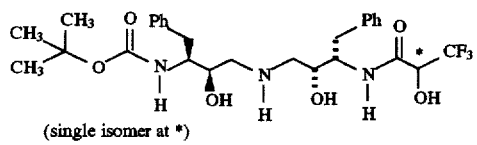

(single isomer at *)

To a solution of trifluorolactic acid (0.107 g, 0.75 mmol, prepared as described in Burstein, Can. J. Chem., 39, 1848 (1961)), HOBT monohydrate (0.135 g, 0.88 mmol) in 2.1 mL dry DMF at RT was added in succession N-methylmorpholine (0.163 mL, 1.49 mmol), Compound 54 (0.3 g, 0.68 mmol) and EDCI hydrochloride (0.143 g, 0.75 mmol). The resulting mixture was stirred at RT for 16 h, concentrated, and the residue partitioned between EtOAc and sat. NaHCO₃. The organic layer was dried (MgSO₄), concentrated, and the crude product was purified by flash chromatography (silica gel/CH₂Cl₂ to CH₂Cl₂—MeOH—NH₄OH 90:10:1, stepwise gradient) affording 0.21 g (54%) of a mixture of the two diastereomeric products. This mixture was subjected to preparative HPLC (Waters Prep Nova-Pack HR C18, 6 micron, 30×300 mm; eluent: MeOH-water-TFA 20:80:0.05 to 90:10:0.05; UV 254 nm). The desired fractions containing the faster eluting component on C18 were made basic with sat. NaHCO₃, concentrated, and the residue partitioned between EtOAc/brine. The organic phase was dried (MgSO₄), concentrated, and the resulting solid was triturated from 5:1 pentane-Et₂O to afford 51 mg (13%) of the title Compound 271 as a white solid.

m.p. 160°–163° C.; $[\alpha]_D=+2.25°$ (c=0.2, MeOH). High resolution Mass Spec.: (M+H)⁺=570.2809, theoretical: (M+H)⁺=570.2791 (Δ 3.1 ppm error).

EXAMPLE 272

Preparation of [1S-[1R*,2S*(2S*,3R*)]]-[2-Hydroxy-1-(phenylmethyl)-3-[[2-hydroxy-4-phenyl-3-[(3,3,3-trifluoro-2-hydroxy-1-oxopropyl)amino] butyl]amino]propyl]carbamic acid,1,1-dimethylethyl ester (isomer B) (Compound 272)

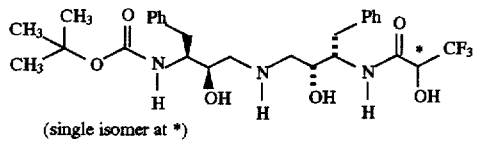

(single isomer at *)

Compound 272 (white solid), the diastereomer of Compound 271, was isolated by preparative HPLC (work up of the fraction from the slower moving peak) as described in Example 271.

m.p. 127°–130° C.; $[\alpha]_D=+5.0°$ (c=0.3, MeOH). High resolution mass spectrum: (M+H)⁺=570.2786, theoretical: (M+H)⁺=570.2791 (Δ 0.9 ppm error).

EXAMPLE 273

Preparation of [1R*,2S*(2S*,3R*)]-N²-[[(1H-Benzimidazol-2-ylmethyl)amino]carbonyl]-N-[3-[[3-[[(1,1-dimethylethoxy)carbonyl]amino]-2-hydroxy-4-phenylbutyl]amino]-2-hydroxy-1-(phenylmethyl) propyl]-L-valinamide (Compound 273b)

(a) Compound 273a

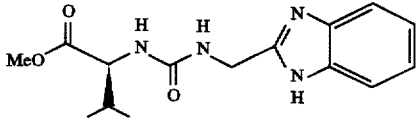

2-Aminomethylbenzimidazole and Compound 245b were reacted by a procedure analogous to that of Example 245c to give Compound 273a.

(b) Compound 273b

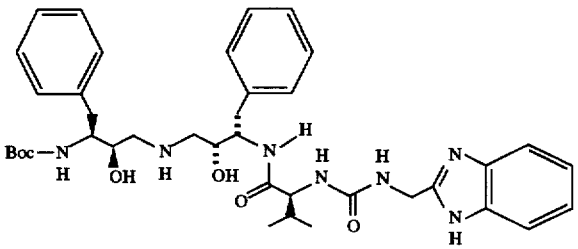

Compounds 273a and 54 were reacted by a two-step procedure analogous to that used for the conversion of Compound 70b to Compound 70d (DMF only; no N-methylmorpholine was added) to give the title Compound 273b (white solid) along with its valine diastereomer Compound 274. The diastereomers were separated on a 30 ml silica column eluting with 2–8% MeOH/CH₂Cl₂ which was increased in 0.5% units with 0.1% NH₄OH. TLC(SiO₂)R_f= 0.40 (CH₂Cl₂.MeOH: NH₄OH 90:10:1);

m.p. 182°–186° C. (dec); $[\alpha]_D=-22°$ (c=0.25, MeOH) Analysis Calcd. for: $C_{39}H_{53}N_7O_6\cdot 2.5\ H_2O$; C, 61.57 H, 7.68 N, 12.89; Found: C, 61.23 H, 7.33 N, 12.78.

EXAMPLE 274

Preparation of [1S*,2R*(2R*,3S*)]-N²-[[(1H-Benzimidazol-2-ylmethyl)amino]carbonyl]-N-[3-[[3-[[(1,1-dimethylethoxy)carbonyl]amino]-2-hydroxy-4-phenylbutyl]amino]-2-hydroxy-1-(phenylmethyl)propyl]-D-valinamide (Compound 274)

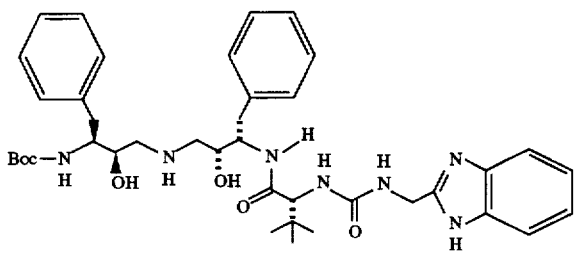

Compound 274 (white solid) was isolated as the slower moving isomer by the procedure described in Example 273b.

TLC(SiO₂)R$_f$=0.35 (CH₂Cl₂:MeOH:NH₄OH 90:10:1); m.p. 186°–189° C. (dec); [α]$_D$=10.5° (c=0.25, MeOH). Analysis Calcd. for: C₃₉H₅₃N₇O₆2.4 H₂O; C, 61.77 H, 7.67 N, 12.93; Found: C, 61.54 H, 7.28 N, 13.03

EXAMPLE 275

Preparation of [1S-[1R*,2S*),(S*)]-[Iminobis [2-hydroxy-1-(phenylmethyl)-3,1-propanediyl]] biscarbamic acid, 1,1-dimethylethyl 2-hydroxy-1,1-dimethylpropyl ester (Compound 275h)

(a) Compound 275a

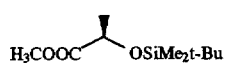

Compound 275a was prepared from (R)-methyl lactate by a procedure analogous to that of Example 232a.

(b) Compound 275b

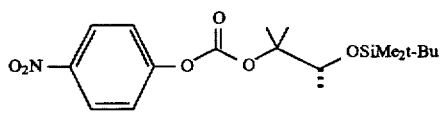

Compound 275a was converted to Compound 275b by a two-step procedure analogous to that used for the conversion of Compound 149b to Compound 149d.

(c) Compound 275c

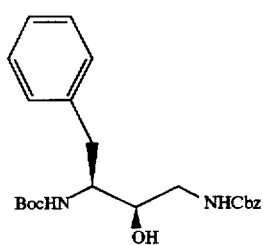

Compound 16b was reacted with benzylchloroformate by a procedure analogous to that used in Example 122 (reaction run at 0° C. for 2 h) to give Compound 275c.

(d) Compound 275d

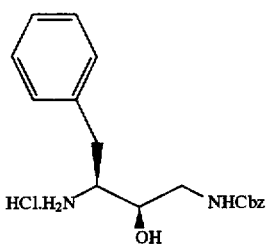

Solid Compound 275c (1.21 g; 2.91 mmol) was added to a saturated solution of HCl gas in 45 ml of EtOAc at 0° C. The reaction was stoppered and stirred for 3 h at 0° C. The solution was purged with N₂ for 15 min and the volatiles were removed in vacuo to afford 1.03 g (~100%; contained trace solvent) of Compound 275d as a white solid.

(e) Compound 275e

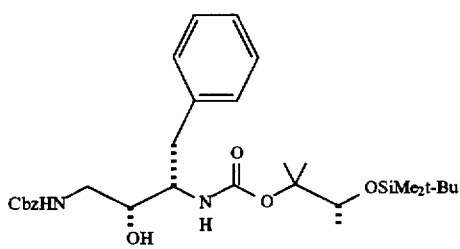

Compounds 275b and 275d were reacted by a procedure analogous to that of Example 161e to give Compound 275e.

(f) Compound 275f

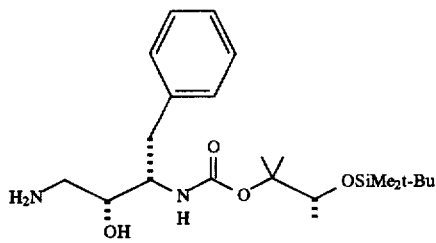

Compound 275e was converted to Compound 275f by a procedure analogous to that of Example 61.

(g) Compound 275g

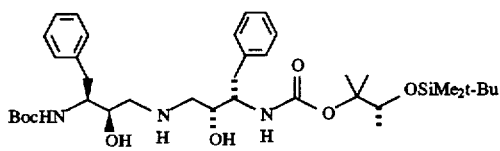

Compounds 1b(i) and 275f were reacted by a procedure analogous to that of Example 4b to give Compound 275g.

(h) Compound 275h

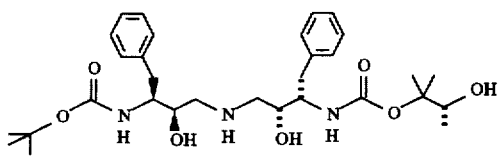

Compound 275g was converted to the title Compound 275h (white solid) by a procedure analogous to that of Example 162.

m.p. 77°–87° C. (dec.); $[\alpha]_D = -8.5°$ (c 0.27, MeOH). Mass Spec. FAB: M+H=574 (M+H); Analysis calc. for $C_{31}H_{47}N_3O_7 \cdot 0.64\ H_2O$: C, 63.62; H, 8.31; N, 7.18; Found: C, 63.57; H, 8.33; N, 7.23.

EXAMPLE 276

Preparation of [1S-[1R*,2S*(2S*,3R*)]]-[3-[[3-[[(1,1-Dimethylethoxy)carbonyl]amino]-2-hydroxy-6-[4-[2-(4-morpholinyl)-2-oxoethoxy]phenyl]-5-hexenyl]amino]-2-hydroxy-1-(phenylmethyl)propyl]carbamic acid, 1,1-dimethylethyl ester (Compound 276d)

(a) Compound 276a

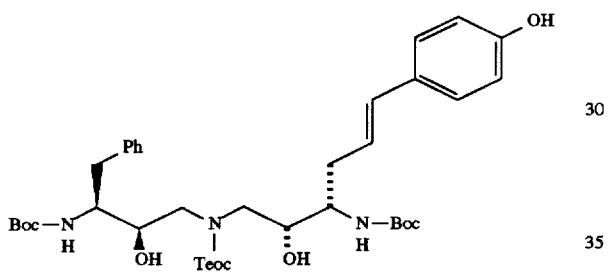

Compound 235e was converted to Compound 276a by a procedure analogous to that of Example 18.

(b) Compound 276b

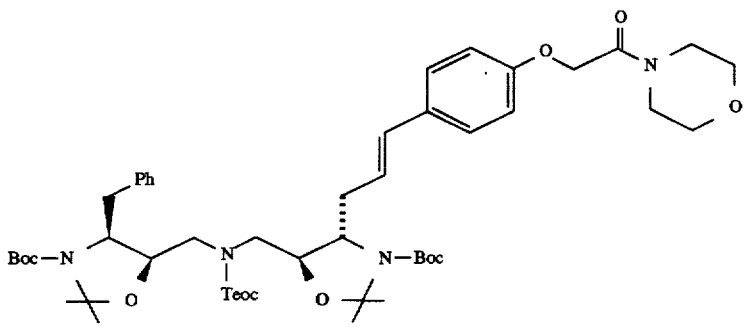

Compound 276a and 4-(2-bromoacetyl)-morpholine (J. Med. Chem., 35, 1685 (1992)) were converted to Compound 276b by a two-step procedure analogous to that used for the conversion of Compound 20 to Compound 173.

(c) Compound 276c

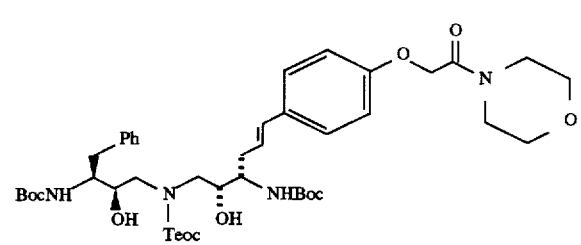

Compound 276b was converted to Compound 276c by a two-step procedure analogous to that of Example 177.

(d) Compound 276d

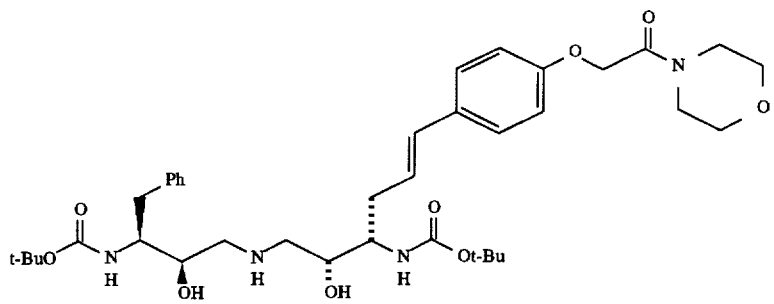

Compound 276c was converted to the title Compound 276d (white solid) by a procedure analogous to that of Example 21.

m.p. 115°–116° C.; [α]Hg (365)=−27.1° (c 0.14, MeOH). Mass Spec. (FAB): 713⁺ (M+H)⁺. Analysis Calcd. for $C_{38}H_{56}N_4O_9$: C, 64.00; H, 7.92; N, 7.86. Found: C, 63.78; H, 7.93; N, 8.08.

EXAMPLE 277

Preparation of [R-(R*,S*)]-[Iminobis[2-hydroxy-1-(phenylmethyl)-3,1-propanediyl]]biscarbamic acid, 1,1-dimethylethyl-2-hydroxy-1-(3-pyridinyl)ethyl ester (Compound 277e)

(a) Compound 277a

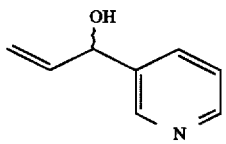

To a 0° C. solution of vinyl magnesium bromide (41.0 mL of a 1.0M solution in THF) was added dropwise over 1 h a solution of pyridine 3-carboxaldehyde (4.00 g, 37.3 mmol) in THF (50 mL). The resulting orange-yellow solution was allowed to warm to RT and stirred for 24 h under argon. The reaction mixture was cooled to 0° C., then was quenched by slow addition of aqueous NH₄Cl (55 mL of a 1M solution). EtOAc was added and the resulting emulsion was filtered through Celite in a sintered glass funnel under vacuum. The aqueous layer was extracted with EtOAc and the combined organic extracts were dried (Na₂SO₄) and concentrated in vacuo to give a red oil which was purified on silica gel (500 mL) using a stepwise gradient from 1:1 to 1:5 hexanes:ethyl acetate as eluent to give Compound 277a (3.89 g; 77%) as a pale yellow oil.

(b) Compound 277b

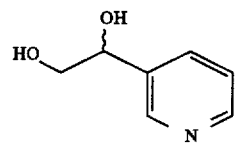

Ozone was bubbled through a solution of 1.00 g (7.40 mmol) of Compound 277a in 25 mL of CH₃OH at −78° C. for 20 min. After purging with N₂ and warming to 0° C., the reaction mixture was diluted with 3 mL of H₂O and NaBH₄ (420 mg, 11.1 mmol) was added. The mixture was stirred for 30 min at 0° C. and for 1 h at RT then quenched by the addition of 10 mL of saturated NH₄Cl. The pH was adjusted to 4 with 20 mL of 1M HCl, and the reaction mixture was concentrated in vacuo. Flash chromatography on silica gel [2% CH₃OH/CH₂Cl₂, then 3–10% CH₃OH/CH₂Cl₂ (with 1.0% NH₄OH)] provided 717 mg (70%) of Compound 277b.

(c) Compound 277c

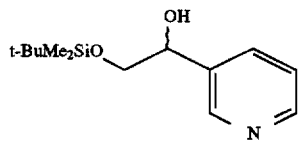

To a solution of 677 mg (4.86 mmol) of Compound 277b in 20 mL of dry CH₂Cl₂ at 0° C. were added 0.75 mL (5.4 mmol) of Et₃N, 30 mg DMAP, and 769 mg (5.10 mmol) of t-butyldimethylsilylchloride. The reaction mixture was warmed to RT over 4 h and then stirred for 4 days. The reaction mixture was diluted with 75 mL of EtOAc, and washed with saturated NaHCO₃ and brine. The organic layer was dried (Na₂SO₄), filtered, and concentrated in vacuo to provide, after flash chromatography on silica gel (25–100% EtOAc-hexane), 1.12 g (91%) of Compound 277c.

(d) Compound 277d

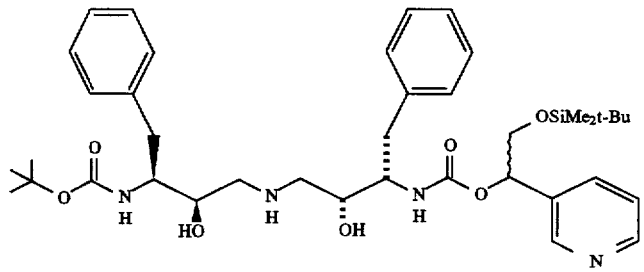

Compounds 277c and 54 were reacted by a two-step procedure analogous to that used for the conversion of Compound 147b to Compound 147d to give Compound 277d.

(e) Compound 277e

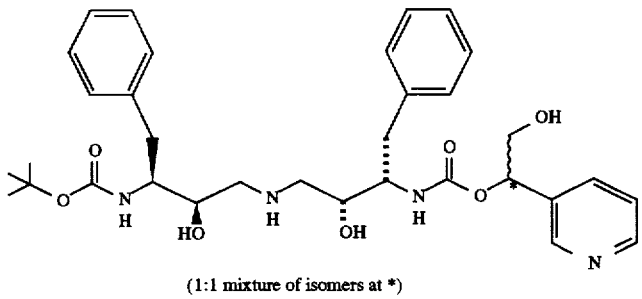

(1:1 mixture of isomers at *)

Compound 277d was converted to the title Compound 277e (white solid) by a procedure analogous to that of Example 162.

m.p. 75°–85° C.; $[\alpha]_D=-13°$ (c 0.28, $CH_3OH$); Mass Spec. 609 (M+H)$^+$; Analysis Calcd. for $C_{33}H_{44}N_4O_7 \cdot 1.03$ $H_2O$: C, 63.18; H, 7.40; N, 8.93. Found: C, 63.28; H, 7.28; N, 8.83.

EXAMPLE 278

Preparation of [1S-[1R*,2S*(2S*,3R*)]]-[2-Hydroxy-3-[[2-hydroxy-3-[(2-hydroxy-2-methyl-1-oxoproply)amino]-4-phenylbutyl]amino]-1-(phenylmethyl)propyl]carbamic acid, 1,1-dimethylethyl ester (Compound 278)

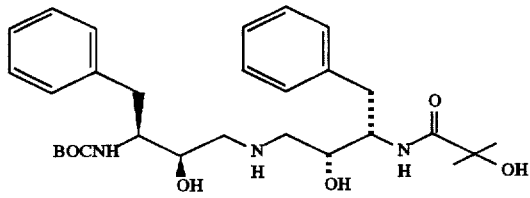

Compound 54 and 2-hydroxyisobutyric acid were reacted by a procedure analogous to that of Example 269 to give the title Compound 278 (white solid).

m.p. 162°–166° C. ("softening" at 156°–161° C.); $[\alpha]_{Hg}$ 365=−2.90° (c=0.99, $CH_3OH$). Mass Spec. (FAB), 530 (M+H)$^+$; Analysis Calcd. for $C_{29}H_{43}N_3O_6 \cdot 0.48$ $H_2O$: C, 64.70; H, 8.23; N, 7.81. Found: C, 64.72; H, 8.32; N, 7.79.

EXAMPLE 279

Preparation of [1S-[1R*,2S*(2S*,3R*)]]-[2-Hydroxy-3-[[2-hydroxy-3-[[2-(hydroxymethyl)-2-methyl-1-oxopropyl]amino]-4-phenylbutyl]amino]-1-(phenylmethyl)propyl]carbamic acid, 1,1-dimethylethyl ester (Compound 279)

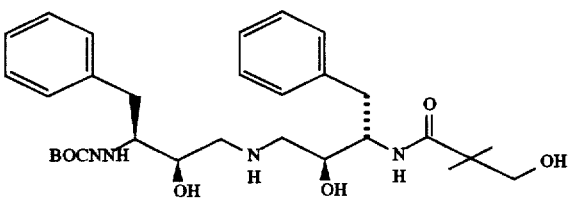

Compound 54 and 2,2-dimethyl-3-hydroxypropionic acid were reacted by a procedure analogous to that of Example 269 ($CH_2Cl_2$ only used) to give the title Compound 279 (white solid).

m.p. 73°–76° C. ("softening" at 66°–72° C.); $[\alpha]_D=+3.6°$; (c=0.76, $CH_3OH$). Mass Spec. (FAB), 544 (M+H)$^+$; Analysis Calcd. for $C_{30}H_{45}N_3O_6 \cdot 0.29$ $H_2O$: C, 65.64; H, 8.37; N, 7.65. Found: C, 65.64; H, 8.33; N, 7.81.

EXAMPLE 280

Preparation of [1R*, 2S* (2S*, 3R*)]-N-[3-[[3-[[(1,1-Dimethylethoxy)carbonyl]amino]-2-hydroxy-4-phenylbutyl]amino]-2-hydroxy-1-(phenylmethyl) propyl]-N$^2$-[[(1H-inden-2-yl)methoxy]carbonyl]-L-valinamide (Compound 280b)

(a) Compound 280a

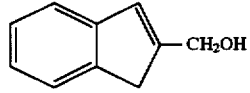

A solution of 2-carboethoxyindene (1.0 g, 6.24 mmol; see Treibs, Chem. Ber., 93, 545 (1960)) in 15 ml of dry toluene was treated with 4 eq. of a 1M solution of diisobutylaluminum hydride in toluene (24.96 ml) at RT. After 4 h at RT, the reaction was cooled in an ice-bath and MeOH was added. The mixture was filtered and the solvents evaporated yielding the crude product as a colorless oil which was purified by chromatography on silica column eluting with 60%

EtOAc/hexane to afford 593 mg (77%) of Compound 280a as a colorless solid.

(b) Compound 280b

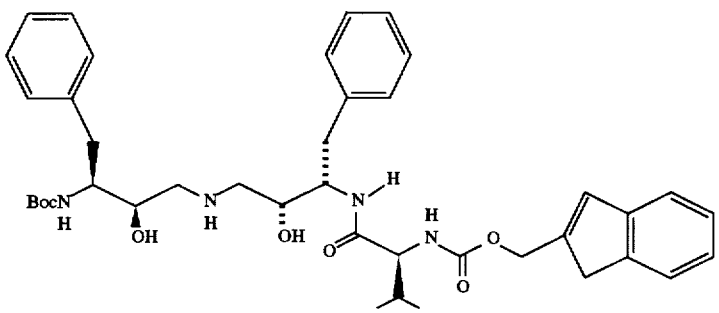

L-Valine and Compounds 280a and 54 were reacted by a three-step procedure analogous to that described for the conversion of Compound 171a to Compound 257c to give the title Compound 280b (colorless solid).

m.p. 148°–154° C. (dec); $[\alpha]_D = -18.50°$ (c 0.22, MeOH). Mass Spec. (FAB):715⁺ (M+H)⁺; Analysis Calcd. for: $C_{41}H_{54}N_4O_7 + 0.75\ H_2O$: C, 67.61; H, 7.68; N, 7.69; Found: C, 67.62; H, 7.52; N, 7.68.

EXAMPLE 281

Preparation of [1R*,2S*(2S*,3R*)]]-N-[3-[[1,1-Dimethylethoxy)carbonyl]amino]-2-hydroxy-4-phenylbutyl]amino]-2-hydroxy-1-(phenylmethyl)-proyl]-N²-[(2-quinolinylmethoxy)carbonyl]-L-valinamide (Compound 281c)

(a) Compound 281a

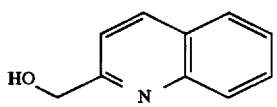

A solution of 7.25 mL (7.25 mmol; 1.0M in Et₂O) of LiAlH₄ was diluted with 4 mL of dry Et₂O and cooled to −60° C. To this was added, over 30 min, a solution of 1.15 g of methyl quinaldate in 7 mL of dry Et₂O. The mixture was warmed to −25° C., stirred for 15 min, and treated with 10 mL of Et₂O which was saturated with H₂O. The mixture was warmed to 0° C. and quenched by the addition of a solution of 360 mg of NaOH in 2 mL of H₂O. The mixture was diluted with 100 mL of Et₂O and washed with H₂O and brine. The organic layer was dried (Na₂SO₄), filtered, and concentrated in vacuo to give crude material which was purified by flash chromatography on silica gel (25–100% EtOAc-hexane) to afford 445 mg (46%) of Compound 281a.

(b) Compound 281b

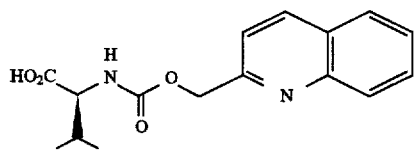

Compound 281a and L-valine were reacted by a two-step procedure analogous to that described for the conversion of Compounds 70a(i) and 70a(ii) to Compound 70c to give Compound 281b.

(c) Compound 281c

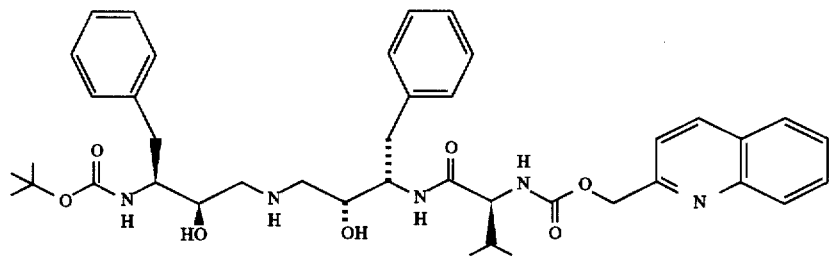

Compounds 281b and 54 were reacted by a procedure analogous to that of Example 55 (DMF only used) to give the title Compound 281c (white solid).

m.p. 177°–190° C. (dec.); $[\alpha]_D = -12°$ (c 0.33, CH₃OH); Mass Spec. 728 (M=H)⁺; Analysis Calcd. for: $C_{41}H_{53}N_5O_7 \cdot 0.85\ H_2O$: C, 66.25; H, 7.42; N, 9.42; Found: C, 66.10; H, 7.28; N, 9.57

EXAMPLE 282

Preparation of [1S-[1R*,2S*(2S*,3R*)]]-[3-[[3-[[(1,1-Dimethylethoxy)carbonyl]amino]-2-hydroxy-4-phenylbutyl]amino]-2-hydroxy-1-[[4-[2-(2-pyridinyl)ethoxy]phenyl]methyl]propyl]carbamic acid, 2-hydroxy-1,1-dimethylethyl ester (Compound 282a)

(a) Compound 282a

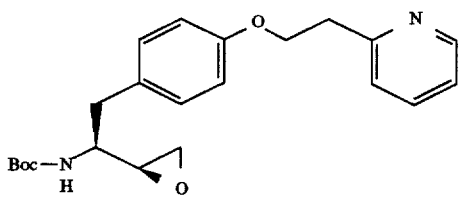

To a suspension of Compound 175c (400 mg, 1.43 mmol) in THF (1.5 mL) was added PPh$_3$ (0.564 g, 2.15 mmol), followed by 2-(2-hydroxyethyl)pyridine (256.5 mg, 2.15 mmol) and DEAD (0.374 g, 2.15 mmol). The resulting solution was stirred at RT for 18 h. The reaction mixture was concentrated in vacuo and purified by silica gel chromatography, eluting with EtOAc (10% to 100%)-hexane to afford Compound 282a (0.254 g, 45% yield).

(b) Compound 282b

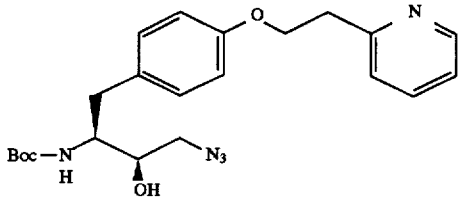

To a solution of Compound 282a (200 mg, 0.52 mmol) in MeOH (ca. 8 mL) was added NaN$_3$ (101.45 mg, 1.56 mmol) and NH$_4$Cl (50 mg, 0.93 mmol) and the mixture heated at reflux for 18 h. The solution was cooled to RT, and the solvent removed under vacuum. The residue was taken in EtOAc and washed with H$_2$O and brine. The combined organic phase was dried (MgSO$_4$), and concentrated in vacuo to yield Compound 282b (187 mg, 71%) as a gummy white residue.

(c) Compound 282c

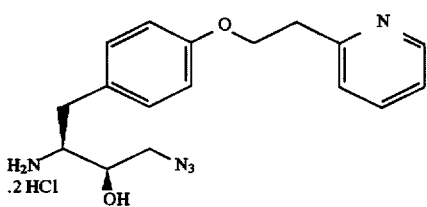

Compound 282b (180 mg, 0.421 mmol) in 4M HCl in dioxane (3.36 mL) was stirred at RT for 1 h, and concentrated in vacuo to yield a yellow residue which was azeotroped from CHCl$_3$ and then toluene to yield Compound 282c as a foamy yellow solid (197 mg, ca. 100% yield, crude).

(d) Compound 282d

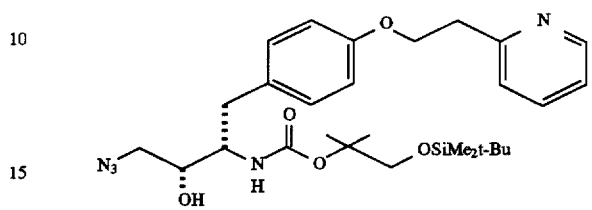

To Compound 282c (195 mg, 0.595 mmol) in DMF (0.5 mL) was added i-Pr$_2$NEt (0.72 mL, 4.16 mmol), followed by a solution of the Compound 161d (242 mg, 0.655 mmol) in DMF (ca. 0.5 mL) and the mixture stirred at RT for 18 h. The reaction mixture was concentrated in vacuo and the residue taken in EtOAc and washed with 1:1 saturated NaHCO$_3$:brine. The combined organic layer was dried (MgSO$_4$), filtered and concentrated in vacuo to yield a yellow gummy residue which was purified by flash chromatography, eluting with CH$_3$OH (1% to 30%)—CH$_2$Cl$_2$ to afford Compound 282d (250 mg, 75% yield) as a yellow solid.

(e) Compound 282e

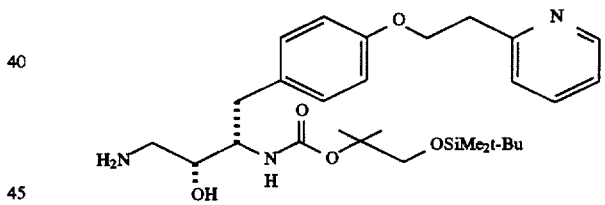

To a solution of Compound 282d (235 mg, 0.421 mmol) in THF (2.5 mL) was added H$_2$O (12 μL), followed by triphenylphosphine (122 mg, 0.463 mmol) and the mixture stirred at RT for 18 h. The reaction mixture was concentrated in vacuo, and purified on silica gel, eluting with CH$_2$Cl$_2$:CH$_3$OH:aq. NH$_4$OH (99:1:0.02 to 85:15:0.1) to afford Compound 282e (145 mg, 65% yield) as a gummy white solid.

(f) Compound 282f

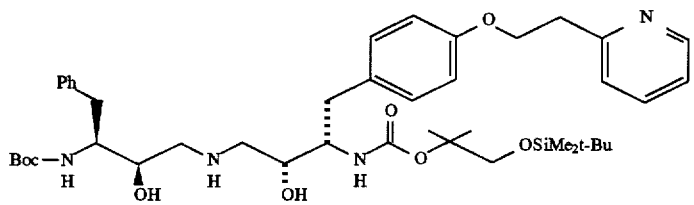

To a solution of Compound 282e (134 mg, 0.252 mmol) in DMF (0.5 mL) was added the Compound 1b(i) (66.36 mg, 0.252 mmol) and the mixture heated at 110° C. for 6 h, and concentrated in vacuo. The crude product was purified by silica gel chromatography, eluting with $CH_2Cl_2$:$CH_3OH$:aq. $NH_4OH$ (99:1:0.02 to 90:10:1) to afford Compound 282f (114 mg, 57% yield) as a white residue. TLC($SiO_2$) $R_f$=0.22 (9:1:0.1 $CH_2Cl_2$:MeOH:aq. $NH_4OH$—Rydon)

(g) Compound 282g

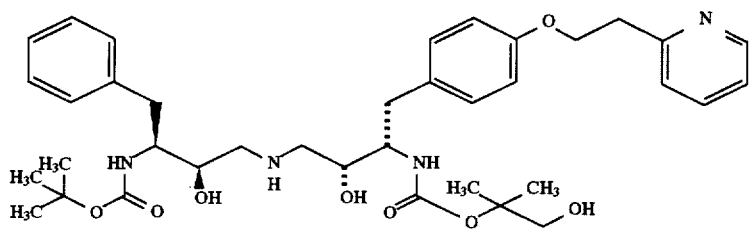

Compound 282f (114 mg, 0.143 mmol) in a mixture of HOAc:THF:$H_2O$ (3:1:1, 1.5 mL) was stirred at RT for 40 h, and then heated at 50° C. for 4 h. The reaction mixture was concentrated in vacuo and the residue purified by silica gel chromatography, eluting with $CH_2Cl_2$:$CH_3OH$:aq. $NH_4OH$ (97.5:2.5:0.025 to 90:10:1) to afford the title Compound 282g (50 mg, 51% yield) as a foamy white solid.

m.p. 106°–108° C.; $[\alpha]_D$=−4.0° (c=0.2, $CH_3OH$). Analysis for: $C_{37}H_{52}N_4O_8$·0.84 $H_2O$; Calculated: C, 63.85; H, 7.77; N, 8.05. Found: C, 63.86; H, 7.58; N, 8.04.

EXAMPLE 283

Preparation of [1S-[1R*,2S*(2S*,3R*)]]-[3-[[3-[[(1,1-Dimethylethoxy)carbonyl]amino]-2-hydroxy-4-phenylbutyl]amino]-2-hydroxy-1-[[4-(2-methoxyethoxy) phenyl]methyl]propyl]carbamic acid, 2-hydroxy-1,1-dimethylethyl ester (Compound 283)

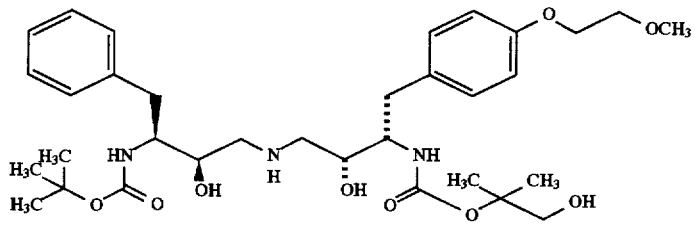

Compound 175c and 2-methoxyethanol were converted to the title Compound 283 (white solid) by a seven-step procedure analogous to that used in Example 282.

m.p. 118°–120° C.; $[\alpha]_D$=−3.90° (c=0.2, $CH_3OH$). Analysis for: $C_{33}H_{51}N_3O_9$·0.38 $H_2O$; Calculated: C, 61.87; H, 8.14; N, 6.56. Found: C, 61.88; H, 8.08; N, 6.55.

EXAMPLE 284

Preparation of [1R*,2S*(2S*,3R*)]-N-[3-[[(1,1-Dimethylethoxy)carbonyl]amino]-2-hydroxy-4-phenylbutyl]amino]-2-hydroxy-1-(phenylmethyl)propyl]-$N^2$-(N-formyl-L-alanyl)-3-methyl-L-valinamide (Compound 284d)

(a) Compound 284a

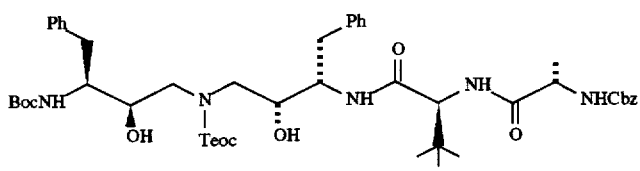

Compound 263b and N-carbobenzyloxy-L-alanine were reacted by a procedure analogous to that of Example 51 to give Compound 284a.

(b) Compound 284b

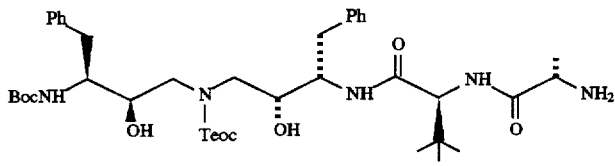

Compound 284a was converted to Compound 284b by a procedure analogous to that of Example 61 (EtOH was used instead of MeOH).

(c) Compound 284c

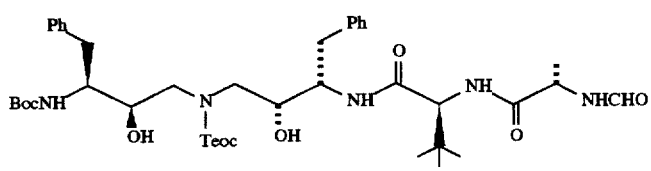

Compound 284b was reacted with formic acetic anhydride by a procedure analogous to that of Example 129 to give Compound 284c.

(d) Compound 284d

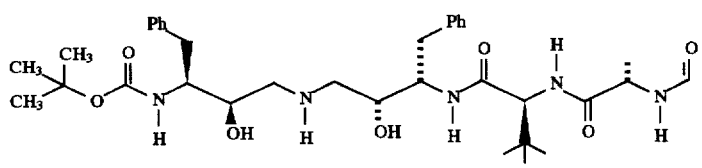

Compound 284c was converted to the title Compound 284d (white solid) by a procedure analogous to that of Example 21.

m.p. 167°–170° C., $[\alpha]_D = -25.7°$ (MeOH, C=0.6). Mass Spec. 656 (M +H)$^+$

EXAMPLE 285

Preparation of [1R*,2S*(2S*,3R*)]-N-[3-[[(1,1-Dimethylethoxy)carbonyl]amino]-2-hydroxy-4-phenylbutyl]amino]-2-hydroxy-1-(phenylmethyl) propyl]-N$^2$-(N-formyl-L-phenylalanyl)-3-methyl-L-valinamide (Compound 285)

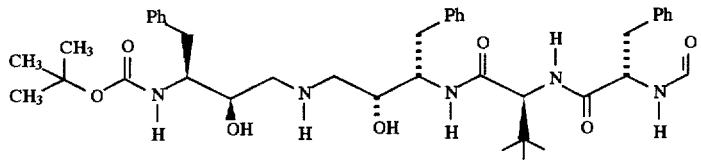

Compound 263b and N-carbobenzyloxy-L-phenylalanine were converted to the title Compound 285 (white solid) by a four-step procedure analogous to that described in Example 284.

m.p. 117°–119° C., [α]$_D$=–9.6° (MeOH, c 1.12). Mass Spec. 732 (M+H)$^+$

EXAMPLE 286

Preparation of [1R*,2S*(2S*,3R*)]-N-[3-[[(1,1-Dimethylethoxy)carbonyl]amino]-2-hydroxy-4-phenylbutyl]amino]-2-hydroxy-1-(phenylmethyl) propyl]-N$^2$-(N-formylglycyl)-3-methyl-L-valinamide (Compound 286b)

(a) Compound 286a

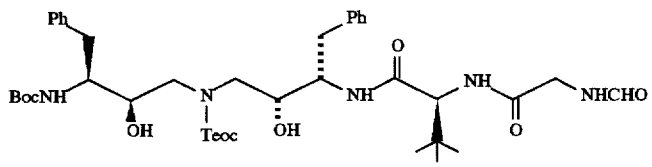

Compound 263b and N-formylglycine were reacted by a procedure analogous to that of Example 51 to give Compound 286a.

(b) Compound 286b

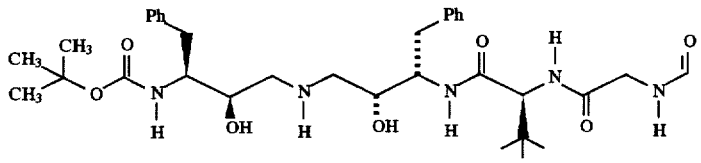

Compound 286a was converted to the title Compound 286b (white solid) by a procedure analogous to that of Example 21.

m.p. 180°–183° C.

EXAMPLE 287

Preparation of [1S-[1R*,2S*(2S*,3R*)]]-[3-[[3-[[3,3-Dimethyl-2-[[(methylamino)carbonyl]oxy]-1-oxobutyl]amino]-2-hydroxy-4-phenylbutyl]amino]-2-hydroxy-1-(phenylmethyl)propyl]-carbamic acid, 1,1-dimethylethyl ester (Compound 287d)

(a) Compound 287a

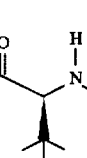

Vinyl magnesium bromide was added to pivaldehyde by a procedure analogous to that of Example 277a to give Compound 287a as a yellow-orange oil.

(b) Compound 287b

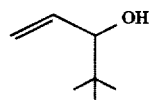

To a 0° C. suspension of THF-washed NaH (0.116 g of an 80% oil dispersion) in anhydrous THF (5 mL) was added dropwise a solution of Compound 287a (0.400 g; 3.50 mmol) in THF (10 mL). The reaction mixture was allowed to warm to RT and stirred for 1 h. After recooling to 0° C., a solution of methyl isocyanate (0.25 mL; 4.20 mmol) in THF (1.5 ML) was added dropwise. The reaction was allowed to warm to RT and stirred for 4 h. Aqueous NH$_4$Cl (10 mL of a 1M solution) and EtOAc (20 mL) were added. The aqueous layer was saturated with NaCl and extracted with EtOAc. The combined organic extracts were dried (Na$_2$SO$_4$) and concentrated in vacuo to give Compound 287b (0.302 g; 50%) as a yellow oil.

(c) Compound 287c

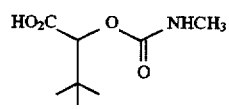

Compound 287b was converted to Compound 287c by a procedure analogous to that of Example 238b.

(d) Compound 287d

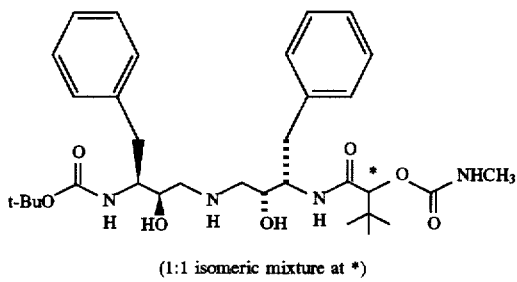

(1:1 isomeric mixture at *)

Compound 287c was converted to the title Compound 287d (white solid) by a procedure analogous to that of Example 93f.

m.p.=85°–89° C. (softens at 65°–70° C.); $[\alpha]_D$=−5.8° (c 0.12, MeOH) Mass Spec. (M+H)$^+$=615; Analysis Calculated for $C_{33}H_{50}N_4O_7 \cdot 0.80\ H_2O$: C, 63.00; H, 8.27; N, 8.91; Found: C, 63.00; H, 8.20; N, 8.63

EXAMPLE 288

Preparation of [1R*,2S*(2S*,3R*)]-N$^2$-[[(2-Benzoxazolyl)methoxy]carbonyl]-N-[3-[[3-[[(1,1-dimethylethoxy)carbonyl]amino]-2-hydroxy-4-phenylbutyl]amino]-2-hydroxy-1-[(4-hydroxyphenyl)methyl]propyl]-L-valinamide (Compound 288f)

(a) Compound 288a

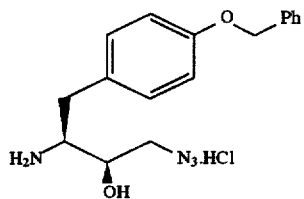

Compound 175b was converted to Compound 288a by a two-step procedure analogous to that described for the conversion of Compound 282a to Compound 282c.

(b) Compound 288b

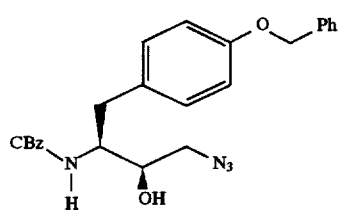

Compound 288a was converted to Compound 288b by a procedure analogous to that of Example 122 except that benzylchloroformate was used.

(c) Compound 288c

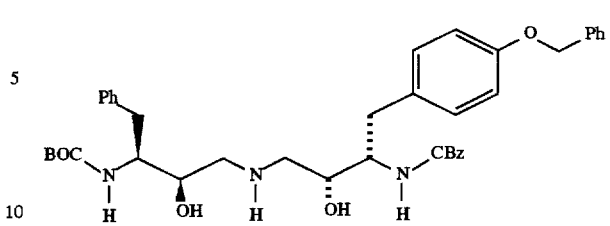

Compounds 288b and 1b(i) were converted to Compound 288c by a two-step procedure analogous to that used for the conversion of Compound 282d to Compound 282f (except that the second step was performed in i-PrOH at 80° C.).

(d) Compound 288d

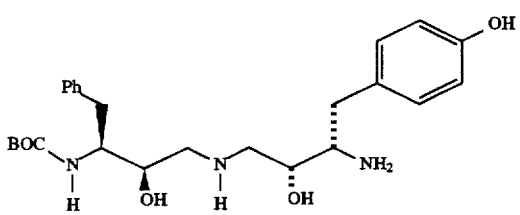

Hydrogenation (balloon) of 120 mg (0.175 mmole) of Compound 288c in 10 ml of MeOH over 30 mg of 10% Pd/C catalyst afforded 80 mg (0.174 mmole, 100%) of Compound 288d as a solid foam.

(e) Compound 288e

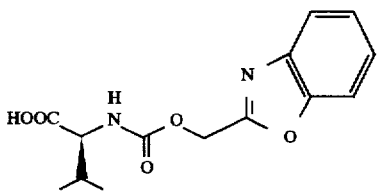

Compound 288e was prepared as described in Example 171.

(f) Compound 288f

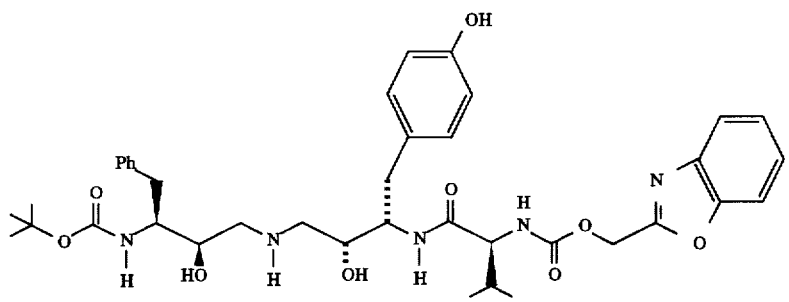

Compounds 288d and 288e were reacted by a procedure analogous to that of Example 93f to give the title Compound 288f (white solid).

m.p. 175°–177° C.; [α]$_D$=–20.1 (c. 0.92, MeOH). Mass Spec.: (M+H)$^+$ 734$^+$; Analysis Calc. for C$_{39}$H$_{51}$N$_5$O$_9$·0.33 H$_2$O: C, 63.32; H, 7.04; N, 9.47. Found: C, 63.32; H, 7.03,N, 9.27.

EXAMPLE 289

Preparation of [R-(R*,S*)]-[Iminobis[2-hydroxy-1-(phenylmethyl)-3,1-propanediyl)]biscarbamic acid, (1H-benzimidazol-2-yl)methyl 1,1-dimethylethyl ester (Compound 289e)

(a) Compound 289a

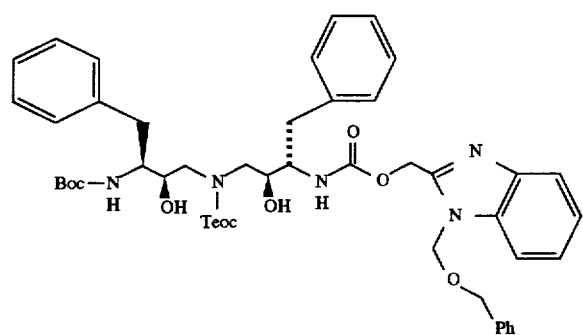

Compounds 93c and 48 were reacted by a procedure analogous to that of Example 149e (DMF used) to give Compound 289a.

(b) Compound 289b

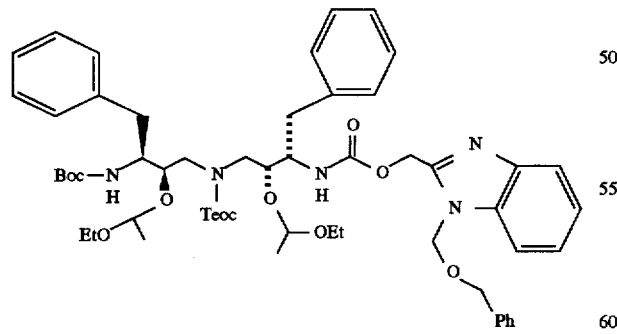

Compound 289a was converted to Compound 289b by a procedure analogous to that of Example 140a.

(c) Compound 289c

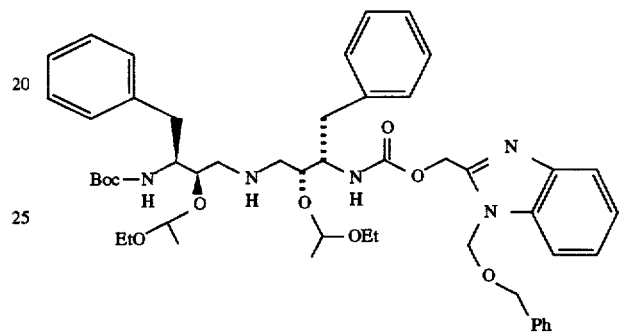

Compound 289b was converted to Compound 289c by a procedure analogous to that of Example 21.

(d) Compound 289d

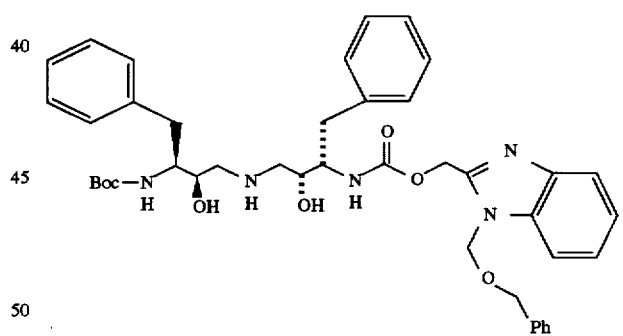

Compound 289c was converted to Compound 289d by a procedure analogous to that of Example 140e.

(e) Compound 289e

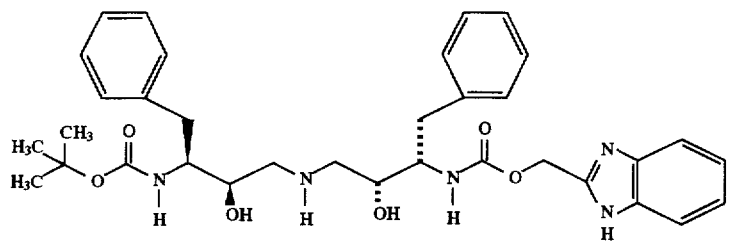

Compound 289d was converted to the title Compound 289e (white solid) by a procedure analogous to that of Example 7 (1 eq. of hydrazine monohydrate was added).

m.p. 95°–105° C.; $[\alpha]_D=-9.3°$ (c=0.2, $CH_3OH$). Mass Spec. (FAB) $(M+H)^+=618$; Analysis calc. for $C_{34}H_{43}N_5O_6 \cdot 1.02H_2O$: C, 64.19; H, 7.14; N, 11.01; Found: C, 64.39; H, 6.89; N, 10.81.

EXAMPLE 290

Preparation of [1S-[1R*,2S*(2S*,3R*)]]-[3-[[3-[[(1,1-Dimethylethoxy)carbonyl]amino]-2-hydroxy-4-[4-[2-(1H-imidazol-1-yl)-ethoxy]phenyl]butyl]amino]-2-hydroxy-1-(phenylmethyl)-propyl]carbamic acid, 1,1-dimethylethyl ester (Compound 290d)

(a) Compound 290a

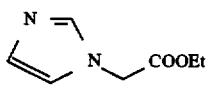

A mixture of imidazole (2 g; 29 mmol), ethyl bromoacetate (3.2 ml; 29 mmol) and $K_2CO_3$ (8.1 g; 58 mmol) in 30 ml of DMF was heated to 65° C. for 18 h. After cooling to RT, the reaction mixture was filtered through a glass-fritted funnel and the filtrate was concentrated in vacuo. The residue was purified on a 5×15 cm silica gel column, using 5% $MeOH/CH_2Cl_2$ as the mobile phase to afford 2.10 g (49%) of Compound 290a as a light orange oil.

(b) Compound 290b

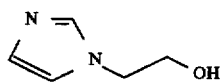

Compound 290a was converted to Compound 290b by a procedure analogous to that of Example 281a.

(c) Compound 290c

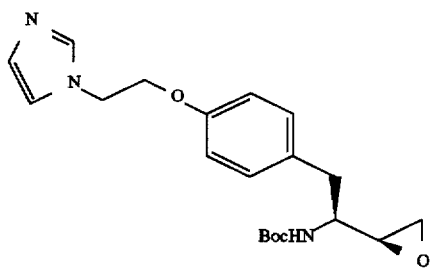

Compounds 290b and 175c were reacted by a procedure analogous to that of Example 282a to give Compound 290c.

(d) Compound 290d

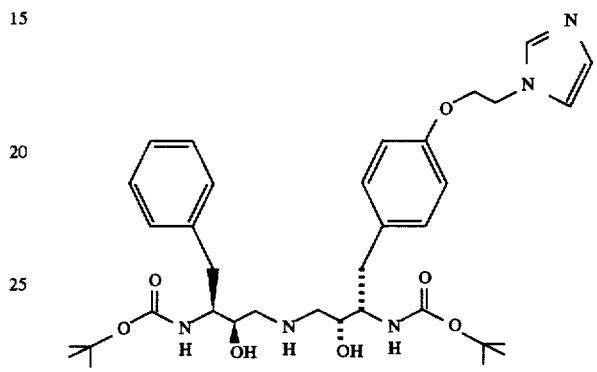

Compounds 290c and 16b were reacted by a procedure analogous to that of Example 226b to give the title Compound 290d (white solid).

m.p. 130°–135° C. (dec.); $[\alpha]_{365}=-14.1°$ (0.33, MeOH). Mass Spec. CI: (M+H) 654; Analysis calc. for $C_{35}H_{51}N_5O_7 \cdot 0.52 H_2O$: C, 63.38; H, 7.91; N, 10.56; Found: C, 63.31; H, 7.97; N, 10.63.

EXAMPLE 291

Preparation of [1S-[1R*,2S*(2S*,3R*)]]-[2-Hydroxy-3-[[2-hydroxy-3-[(4-hydroxy-2,2-dimethyl-1-oxobutyl)amino]-4-phenylbutyl]amino]-1-(phenylmethyl)propyl]carbamic acid, 1,1-dimethylethyl ester (Compound 291d)

(a) Compound 291a

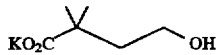

Compound 291a was prepared as described in U.S. Pat. No. 4,732,902.

(b) Compound 291b

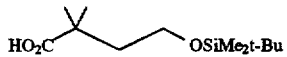

To a solution of Compound 291a (2.0 g, 11.76 mmol) in DMF was added t-butyldimethylsilyl chloride (10.635 g, 70.56 mmol) and imidazole (8.006 g, 117.6 mmol). The resulting mixture was stirred at RT for 24 h. MeOH (100 mL) was added and the reaction mixture was stirred at RT for 24 h. The mixture was diluted with EtOAc and washed with 10% citric acid (until aqueous phase had pH=2) followed by $H_2O$ and brine. The organic phase was separated, dried ($MgSO_4$) and concentrated. The crude residue was purified by flash chromatography on silica gel eluting with 90:9:1 followed by 80:19:1 hexane-EtOAc-HOAc to afford Compound 291b (1.8 g, 62%) as a colorless oil.

(c) Compound 291c

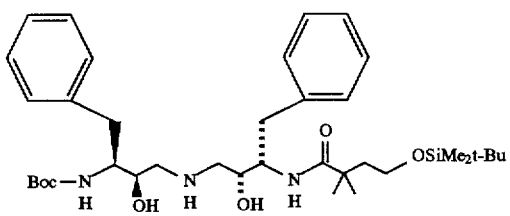

Compounds 291b and 54 were reacted by a procedure analogous to that of Example 55 to give Compound 291c.

(d) Compound 291d

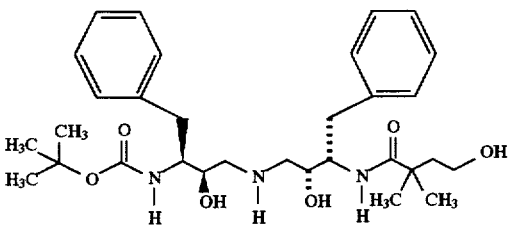

Compound 291c was converted to Compound 291d (white solid) by a procedure analogous to that of Example 162.

m.p. 70°–74° C. (softening at 60°–65° C.); [α]$_D$=−1.2° (c=1.0, CH$_3$OH). Mass Spec. (FAB) (M+H)$^+$=558; Analysis calc. for C$_{31}$H$_{47}$N$_3$O$_6$·0.35H$_2$O: Calculated C, 66.01; H, 8.52; N, 7.45; Found: C, 65.91; H, 8.55; N, 7.55.

EXAMPLE 292

Preparation of [S-[1R*,2S*(2S*,3R*)]]-[2,2-Dimethyl-1-[[[3-[[3-[[(1,1-dimethylethoxy)carbonyl]amino]-2-hydroxy-4-phenylbutyl]amino]-2-hydroxy-1-(phenylmethyl)propyl]amino]carbonyl]propyl]carbamic acid, (2-benzothiazolyl)methyl ester (Compound 292b)

(a) Compound 292a

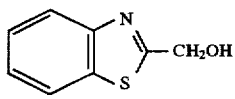

2-Aminothiophenol and glycolic acid were reacted by a procedure analogous to that of Example 171a to give Compound 292a.

(b) Compound 292b

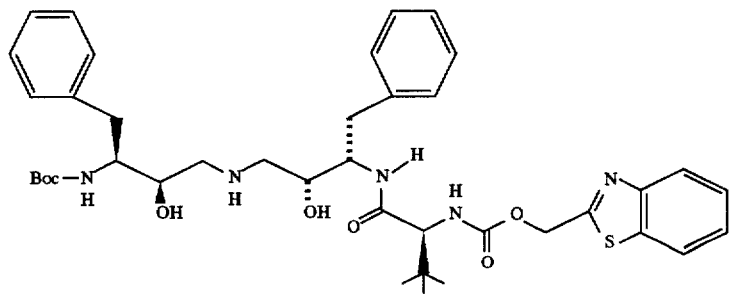

Compound 292a and L-tert-leucine were reacted by a three-step procedure analogous to that used for the conversion of Compound 171a to Compound 257c to give the title Compound 292b (colorless solid).

m.p. 148°–154° C. (dec); [α]$_D$=−14.5° (c=0.25, MeOH). Mass Spec. (FAB): (M+H)$^+$=748$^+$; Analysis Calcd. for C$_{40}$H$_{53}$N$_5$SO$_7$·1.78 H$_2$O: C, 61.60; H, 7.31; N, 8.98; S, 4.11; Found: C, 61.62; H, 6.96; N, 8.96; S, 4.01

EXAMPLE 293

Preparation of [1S-[1R*,2S*(2S*,3R*)]]-[2-Hydroxy-3-[2-hydroxy-1-oxo-2-(trifluoromethyl)-propyl]amino]-4-phenylbutyl]amino]-1-(phenylmethyl)propyl]carbamic acid, 1,1-dimethylethylester (isomer A) (Compound 293b)

(a) Compound 293a

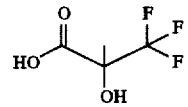

1,1,1-Trifluoroacetone cyanohydrin (5 g, 39.4 mmol) was added to 5 mL conc. H$_2$SO4 with stirring at RT. The mixture was heated at 120° C. for 15 min and 20 mL ice cold water was added. After refluxing for 15 h, the reaction was cooled to RT, saturated with Na$_2$SO$_4$ and extracted with Et$_2$O. The combined Et$_2$O extracts were dried (MgSO$_4$), the Et$_2$O distilled off with a vigruex column at atmospheric pressure and the residue sublimed (0.5 mm at 150°–200° C.) to afford 4.3 g (69%) of the Compound 293a as a white solid.

(b) Compound 293b

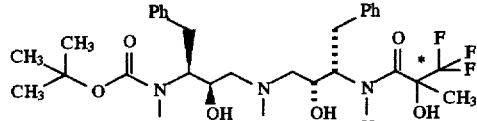

To a solution of Compound 293a (117.5 mg, 0.75 mmol) and HOBT monohydrate (0.135 g, 0.88 mmol) in 2 mL dry DMF at RT was added in succession Compound 54 (0.3 g, 0.68 mmol), N-methylmorpholine (0.1634 mL, 1.49 mmol), and EDCI hydrochloride (0.1434 g, 0.75 mmol). The resulting mixture was stirred at RT for 14 h, concentrated, and the residue partitioned between EtOAc and sat. NaHCO$_3$. The organic layer was dried over MgSO$_4$, concentrated, and the crude product was purified by flash chromatography (silica gel/CH$_2$Cl$_2$ to CH$_2$Cl$_2$—MeOH—NH$_4$OH 90:10:1, continuous gradient) affording 0.3 g (76%) of a mixture of the two diastereomeric products (at *). This mixture was subjected to prep. HPLC (Waters Prep Nova-Pack HR C18, 6 micron, 40×300 mm; eluent: MeOH-water-TFA 50:50:0.05 to 100:0:0.05; UV 254 nm). The desired fractions containing the faster eluting component were made basic with sat. NaHCO₃, concentrated, and the residue partitioned between EtOAc/1:1 brine-sat. NaHCO₃. The organic phase was dried (MgSO₄) and concentrated to afford 100 mg (25%) of the title Compound 293b (single diastereomer) as a white solid.

m.p. 203°–204° C.; [α]$_D$=+1.5° (c=1.2, MeOH). Mass Spec. 584 (M+H)⁺. Analysis calcd. for C$_{29}$H$_{40}$N$_3$O$_6$F$_3$·0.55H$_2$O: C, 58.69; H, 6.98; N, 7.08; F, 9.60. Found: C, 58.55; H, 6.81; N, 7.22; F, 10.04.

EXAMPLE 294

Preparation of [1S-[1R*,2S*(2S*,3R*)]]-[2-Hydroxy-3-[2-hydroxy-1-oxo-2-(trifluoromethyl) propyl]amino]-4-phenylbutyl]amino]-1-(phenylmethyl)propyl]carbamic acid, 1,1-dimethylethylester (isomer B) (Compound 294)

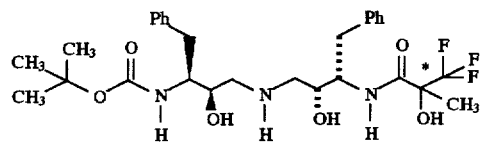

Preparative HPLC separation as described in Example 293b and work up of the fraction from the slower moving peak afforded 95 mg (24%) of the title Compound 294 (single diastereomer) as a white solid.

m.p. 92°–95° C.; [α]$_D$=−2.5° (c 0.75, MeOH). Mass Spec. 584 (M+H)⁺. Analysis calcd. for C$_{29}$H$_{40}$N$_3$O$_6$F$_3$·1.23 H$_2$O: C, 57.50; H, 7.06; N, 6.94; F, 9.41. Found: C, 57.70; H, 6.70; N, 6.74; F, 9.67.

EXAMPLE 295

Preparation of [1S-[1R*,2S*(2S*,3R*)]]-[2-Hydroxy-3-[[2-hydroxy-3-[[2-(hydroxyimino)-3,3-dimethyl-1-oxobutyl]amino]-4-phenylbutyl]amino]-1-(phenylmethyl)propyl]carbamic acid, 1,1-dimethylethyl ester (Compound 295)

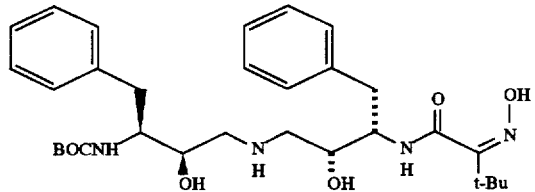

A solution of Compound 213c (60 mg, 91% pure, 0.10 mmol), hydroxylamine hydrochloride (22.5 mg, 0.324 mmol) and 3 drops of pyridine in 1.0 ml absolute EtOH was stirred at RT for 2 h. The reaction mixture was concentrated in vacuo to provide an oily residue which was purified by chromatography on a silica gel column (11mm×20cm) eluting with CH$_2$Cl$_2$—MeOH-aq. NH$_4$OH in a gradient from 98–1.8–0.2 to 92–7.2–0.8 to provide 36 mg (63% yield) of Compound 295 (white solid) as a single isomer (oxime geometry not determined).

m.p. 100°–104° C. ("softening" at 87°–100° C.); [α]$_D$= −12.4°; (c=1.1, CH$_3$OH); Mass Spec. (FAB): 571 (M+H⁺);

Analysis calc. for C$_{31}$H$_{46}$N$_4$O$_6$·0.87 H$_2$O: C, 63.49; H, 8.21; N, 9.55; Found: C, 63.47; H, 8.02; N, 9.57

EXAMPLE 296

Preparation of [1S-[1R*,2S*(2S*,3R*)]]-[2-Hydroxy-3-[[2-hydroxy-3-[[2-(methoxyimino)-3,3-dimethyl-1-oxobutyl]amino]-4-phenylbutyl]amino]-1-(phenylmethyl)propyl]carbamic acid, 1,1-dimethylethyl ester (Compound 296)

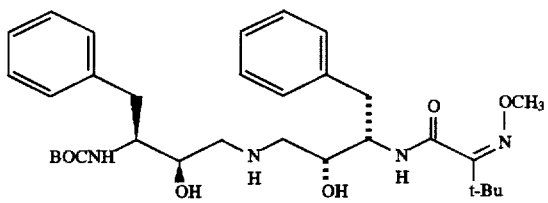

Compound 213c was reacted with methoxyamine hydrochloride by a procedure analogous to that of Example 295 to give the title Compound 296 (white solid).

m.p. 199°–201° C. ("softening" at 175°–198° C.); [α]$_D$= −13.5°; (c=0.38, CH$_3$OH); Mass Spec. (FAB): 585 (M+H⁺)

EXAMPLE 297

Preparation of [1R*,2S*(2S*,3R*)]-N-[3-[[3-[[(1,1-Dimethylethoxy)carbonyl]amino]-2-hydroxy-4-phenylbutyl]amino]-2-hydroxy-1-[[4-[r2-(2-pyridinyl)ethoxy]phenyl]methyl]propyl]-N²-(2-methoxycarbonyl)-3-methyl-L-valinamide (Compound 297a)

(a) Compound 297a

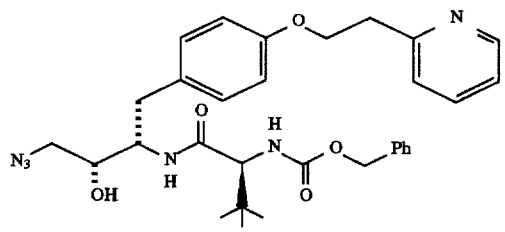

A solution of Compound 282c (410 mg, 1.25 mmol) in CH$_2$Cl$_2$ (40 mL) and CH$_3$OH (5 mL) was stirred with K$_2$CO$_3$ (3 g) at RT for 1 h, filtered, and the filtrate concentrated in vacuo to yield the free amine (390 mg, ca. 95% yield) as a gummy yellow residue. This material was coupled to Compound 88a (350 mg, 1.31 mmol) in 2 mL DMF, along with 251 mg (1.31 mmol) EDCI, 177 mg (1.31 mmol) HOBT and 170 μl (1.55 mmol) N-methylmorpholine, using a procedure analogous to that described in Example 93f, to give Compound 297a (421 mg, 61%).

(b) Compound 297b

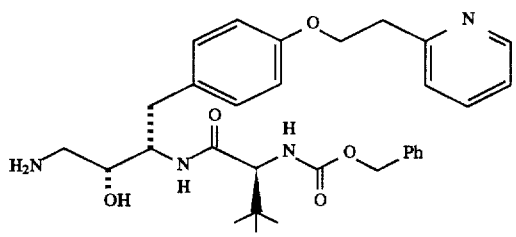

Compound 297a (420 mg, 0.729 mmol) was treated with triphenylphosphine (210.5 mg, 0.802 mmol) in THF (4.5 mL) and water (20 μL), using a procedure analogous to that of Example 282e to afford Compound 297b (318 mg, 79%) as a gummy residue.

(c) Compound 297c

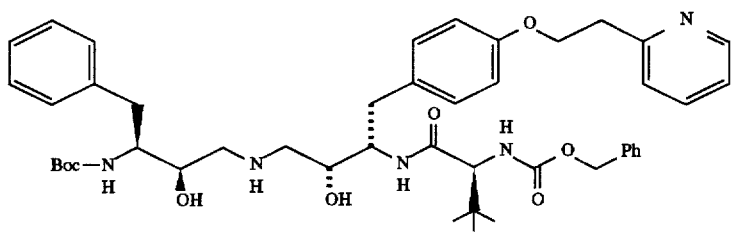

Compound 297b (314 mg, 0.571 mmol) was taken in DMF (1.0 mL) and heated with the Compound 1b(i) (150.2 mg, 0.571 mmol) using a procedure analogous to that of Example 282f to afford Compound 297c (296 mg, 63% yield) as a yellow residue. TLC(SiO$_2$) R$_f$=0.28 (9:1:0.1 CH$_2$Cl$_2$:CH$_3$OH: aq. NH$_4$OH-Rydon)

(d) Compound 297d

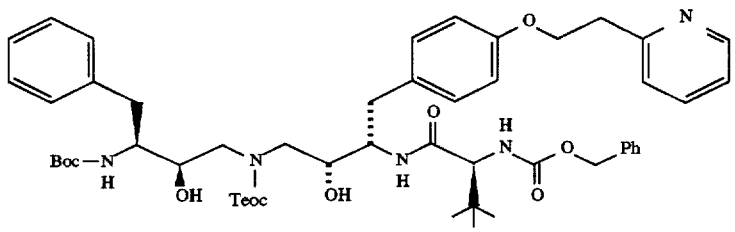

To a solution of Compound 297c (291 mg, 0.358 mmol) in DMF (1 mL), was added i-Pr$_2$NEt (130 μL, 0.752 mmol) and 2-trimethylsilyl-ethylchloroformate (72 mg, 0.394 mmol) at 0° C., and the mixture stirred for 2.5 h. The reaction mixture was diluted with EtOAc and poured into a 1:1 mixture of saturated NaHCO$_3$:H$_2$O. The organic layer was washed with brine, dried (MgSO$_4$) and concentrated under vacuum to yield a gummy residue which was purified by silica gel chromatography, eluting with CH$_3$OH (3% to 8%)—CH$_2$Cl$_2$ to afford Compound 297d (305 mg, 89% yield) as a foamy white residue.

TLC(SiO$_2$) R$_f$=0.53 (8% CH$_3$OH-CH$_2$Cl$_2$-Rydon)

(e) Compound 297e

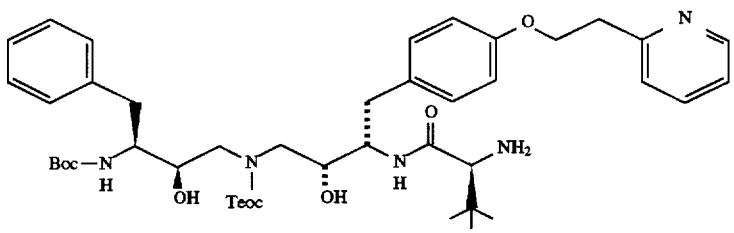

Compound 297d (303 mg, 0.316 mmol) in EtOH (4 mL) was treated with 20% Pd(OH)$_2$/C (104 mg) under a H$_2$ atmosphere for 18 h. The catalyst was filtered and the filtrate concentrated. The crude product was purified by silica gel chromatography, eluting with CH₃OH (2.5% to 7.5%)—CH₂Cl₂, to afford Compound 297e (185 mg, 71% yield) as a yellow solid.

TLC(SiO₂) R_f=0.27 (8% CH₃OH—CH₂Cl₂—Rydon)

(f) Compound 297f

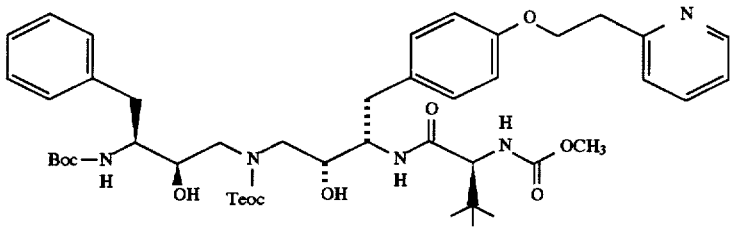

To a solution of Compound 297e (85 mg, 0.103 mmol) in p-dioxane (0.8 mL) was added a 1:1 mixture of saturated NaHCO₃:H₂O (400 uL), followed by methyl chloroformate (0.114 mmol, 8.7 uL) and the mixture stirred at RT for 30 min. Additional methyl chloroformate was added (3.3 eq.; 27 μl total in small portions), and stirred at RT for a total of 3.5 h. The reaction mixture was diluted with EtOAc and washed with saturated NaHCO₃ and brine and the organic layer was dried and concentrated in vacuo to yield crude Compound 297f (86 mg, 94% yield) as gray solid.

TLC(SiO₂) Rhd f=0.25 (5% CH₃OH/CH₂Cl₂-PMA)

(g) Compound 297g

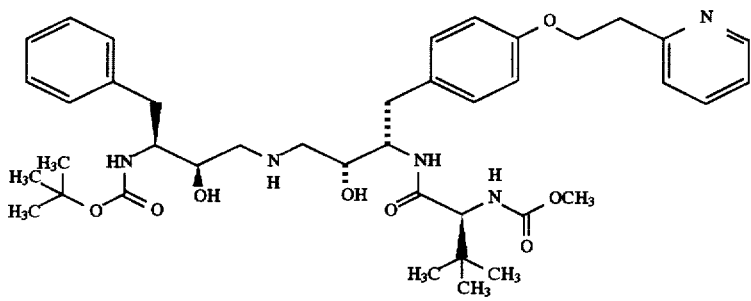

To a solution of Compound 297f (86 mg, 0.097 mmol) in dry THF (1 mL) was added n-Bu₄NF (76.6 mg, 0.293 mmol) and the reaction mixture heated at 45° C. for 4 h. The mixture was concentrated in vacuo and chromatographed on silica gel, eluting with CH₃OH (2.5% to 6.5%)—CH₂Cl₂ with aq. NH₄OH (0.25% to 0.6%) to afford the title Compound 297g (44 mg, 62%) as a white solid m.p. 127°–130° C.; [α]_D=–16° (c=0.2, CH₃OH). Analysis Calc. for C₄₀H₅₇N₅O₈0.52 H₂O; Calculated: C, 64.46; H, 7.85; N, 9.40 Found: C, 64.31; H, 7.49; N, 9.55

EXAMPLE 298

Preparation of [1S-[1R*,2S*(2S*,3R*)]]-[2 Hydroxy-3-[[2-hydroxy-3-[[(2-hydroxy-1,1-dimethylethoxy)carbonyl]amino]-4-phenylbutyl] amino]-1-[[4-[2-(2-pyridinyl)ethoxy]phenyl]methyl] propyl]carbamic acid, 1,1-dimethylethyl ester (Compound 298e)

(a) Compound 298a

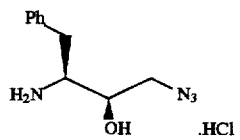

To a solution of 1.4 g (4.6 mmol) of Compound 142a in 10 ml of dioxane was added 10 ml of 4N HCl in dioxane and stirred at RT for 4 hr. Removal of solvent afforded 1.24 g (≦100%) of Compound 298a as a white foam.

(b) Compound 298b

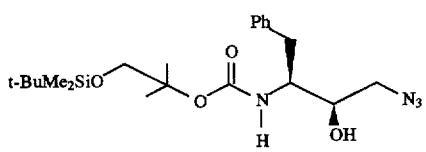

A solution of 381 mg (1.57 mmol) of Compound 298a, 579 mg (1.57 mmol) of Compound 161d, and 1.48 ml (8.65 mmol) of i-Pr$_2$NEt in 10 ml of dry DMF was stirred at RT for 5 days. After removal of solvent the residue was taken into EtOAc and washed with 1N HCl and brine. The oil residue obtained after drying (MgSO$_4$) and removal of solvent was purified by flash chromatography on silica gel (10% EtOAc-hexane) to afford 589 mg (86%) of Compound 298b as a white solid.

(c) Compound 298c

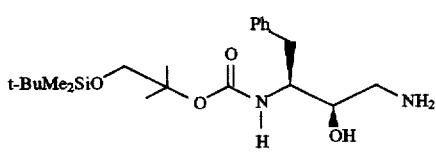

A solution of 550 mg (1.26 mmol) of Compound 298b was hydrogenated (balloon) over 55 mg 10% Pd/C catalyst in 10 ml of MeOH at RT for 2 hr. After filtration of catalyst through Celite, removal of solvent gave 423 mg (82%) of Compound 298c as a white foam.

(d) Compound 298d

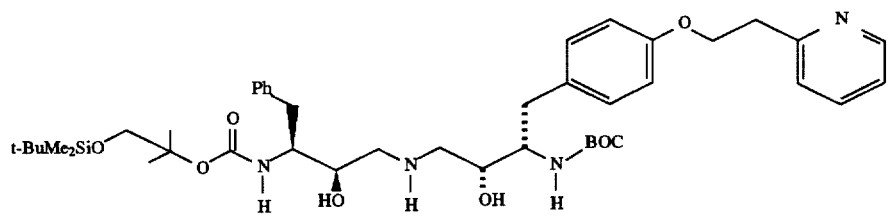

A solution of 184 mg (0.45 mmol) of Compound 298c and 165 mg (0.43 mmol) of Compound 282a in 1 ml of dry DMF was heated at 100° C. for 7 h. After removal of solvent, the residue was purified by flash chromatography on a 35 cc column of silica gel. Elution with CHCl$_3$:MeOH:NH$_4$OH (95:5:0.5) afforded 113 mg (33%) of Compound 298d as a solid foam.

TLC(SiO$_2$) R$_f$=0.32 (CHCl$_3$:MeOH:NH$_4$OH 90:10:1)

(e) Compound 298e

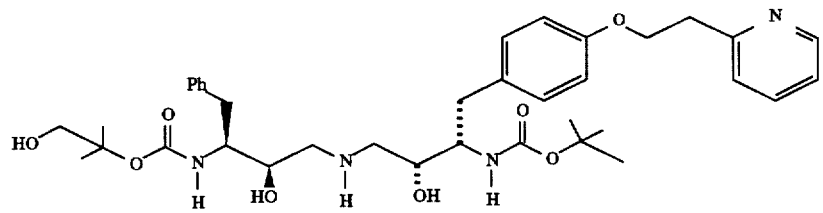

A solution of 110 mg (0.14 mmol) of Compound 298d in 1 ml HOAc:H$_2$O:THF (3:1:1) was stirred at RT for 48 h.

After removal of solvent, the residue was purified by flash chromatography on a 35 cc column of silica gel. Elution with CHCl$_3$:MeOH:NH$_4$OH (95:5:0.5) afforded 67 mg of material which was further purified by trituration with Et$_2$O to afford 60 mg (63%) of the title Compound 298e as a white powder; m.p. 125°–126° C.; [α]$_D$=–3.4° (c 0.82, MeOH)

Mass Spec: (M+H)$^+$681$^+$; Analysis Calc. for C$_{37}$H$_{52}$N$_4$O$_8$·0.87 H$_2$O: C, 63.81; H, 7.78; N, 8.04. Found: C, 63.88; H, 7.53; N, 8.04.

EXAMPLE 299

Preparation of [1S-[1R*, 2S*(2S*,3R*)]-[3-[[(1,1-Dimethylethoxy)carbonyl]amino]-2-hydroxy-4-[4-(2-methoxyethoxy)phenyl]butyl]amino]-2-hydroxy-1-(phenylmethyl)propyl]carbamic acid, 1-(hydroxymethyl)-1-methylethyl ester (Compound 299b)

(a) Compound 299a

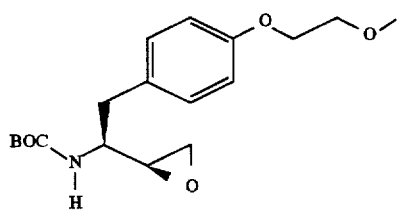

To a solution of 200 mg (0.72 mmol) of Compound 175c, 113 µl (1.44 mmol) of 2-methoxyethanol and 377 mg (1.44 mmol) of PPh$_3$ in 3 ml of dry THF at RT, was added 226 µl (1.44 mmol) of DEAD. Stirring was continued overnight.

After removal of solvent, flash chromatography of the oil residue on silica gel (25% EtOAc-hexane) afforded 198 mg (81%) of Compound 299a as a white solid.

(b) Compound 299b

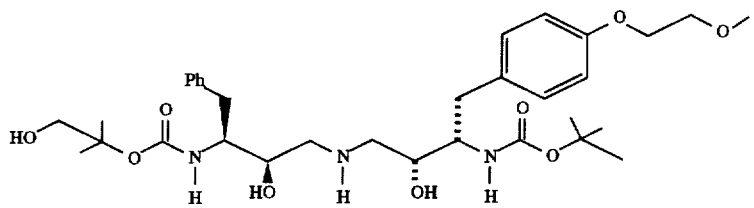

Compounds 298c and 299a were reacted by a two-step procedure analogous to that used for the conversion of Compound 298c to Compound 298e to give the title Compound 299b (white solid).

m.p. 128°–130° C.; $[\alpha]_D$=–4.0° (c 0.89, MeOH). Mass Spec.: (M+H)$^+$634$^+$; Analysis Calc. for $C_{33}H_{51}N_3O_9 \cdot 0.42$ $H_2O$: C, 61.81; H, 8.15; N, 6.55. Found: C, 61.88; H, 8.21; N, 6.48.

EXAMPLE 300

Preparation of [1S-[1R*,2S*(2S*,3R*)]]-[3-[[3-[[(1,1-Dimethylethoxy)-carbonyl]amino]-2-hydroxy-4-[4-(4-methoxybutoxy)phenyl]butyl]amino]-2-hydroxy-1-(phenylmethyl)propyl]carbamic acid, 1,1-dimethylethyl ester (Compound 300d)

(a) Compound 300a

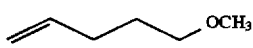

4-Penten-1-ol (1.80 ml; 17.5 mmol) was added dropwise over 1 h to a suspension of pentane washed NaH (770 mg 60% in oil; 19.2 mmol) in 35 ml of DMF at 0° C. After stirring at 0° C. for 30 min, methyl iodide (1.40 ml; 21.8 mmol) was added dropwise over 15 min and the reaction mixture was allowed to warm to RT. After stirring 18 h at RT, the excess methyl iodide was pumped off (dry ice trap). $H_2O$ was then added and the mixture was extracted with $Et_2O$. The organic layer was washed with $H_2O$ and brine, dried ($MgSO_4$) and most of the $Et_2O$ was removed at atmospheric pressure to give a concentrated solution of Compound 300a in $Et_2O$ which was used without further purification.

(b) Compound 300b

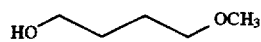

Compound 300a was converted to Compound 300b by a procedure analogous to that of Example 277b.

(c) Compound 300c

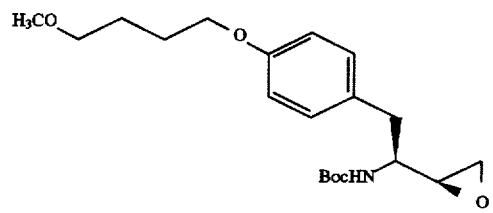

Compounds 175c and 300b were reacted by a procedure analogous to that of Example 282a to give Compound 300c.

(d) Compound 300d

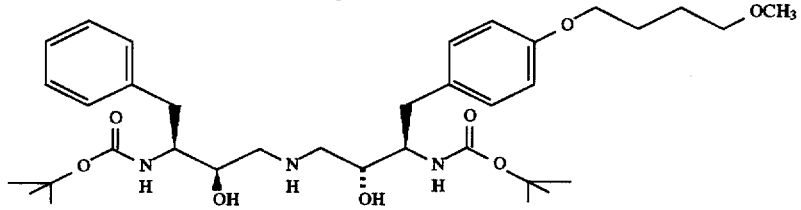

Compounds 300c and 16b were reacted by a procedure analogous to that of Example 226b to give the title Compound 300d (white solid).

m.p. 118°–125° C.; $[\alpha]_D$=+1.4° (0.59, MeOH). Mass Spec. FAB: M+H=646. Analysis calc. for $C_{35}H_{55}N_3O_8 \cdot 1.39$ $H_2O$: C, 62.67; H, 8.68; N, 6.26; Found: C, 62.50; H, 8.43; N, 6.43.

EXAMPLE 301

Preparation of [1S-[1R*,2S*(2S*,3R*)]]-[1-[[[3-[[(1,1-Dimethylethoxy)carbonyl]amino]-2-hydroxy-4-phenylbutyl]amino]-2-hydroxy-1-(phenylmethyl)propyl]amino]carbonyl]-2-hydroxy-2-methylpropyl]carbamic acid, phenylmethyl ester, isomer A (Compound 301b)

(a) Compound 301a

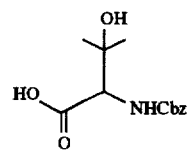

Compound 239b was converted to Compound 301a by a procedure analogous to that of Example 205a.

(b) Compound 301b

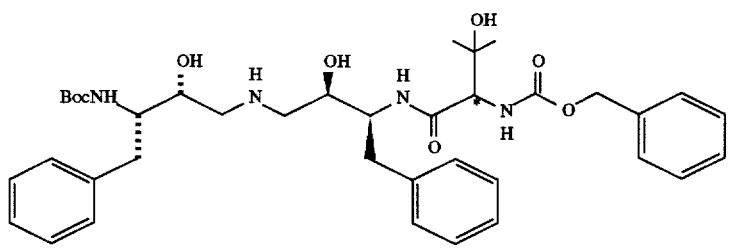

Compounds 301a and 54 were reacted by a procedure analogous to that of Example 55 (DMF only used) to give the Compound 301b along with its diastereomer (at ·) Compound 302. Flash chromatography (silica gel, 5 by 10.5 cm), eluting with a step-wise gradient of MeOH:NH$_4$OH:CH$_2$Cl$_2$ (5:0.5:94.5 to 8:0.8:91.2) followed by trituration of the faster moving isomer with hot Et$_2$O gave the title Compound 301b (53 mg, 17% yield) as a colorless solid.

$R_f$=0.39 (10:1:89 MeOH:NH$_4$OH:CH$_2$Cl$_2$); m.p. 164°–166° C.; $[\alpha]_D$=+7.89° (c 0.34, MeOH). Anal. Calc. for C$_{38}$H$_{52}$N$_4$O$_8$·0.58 H$_2$O; C, 64.90; H, 7.62; N, 7.97 Found: C, 64.97; H, 7.55; N, 7.90

EXAMPLE 302

Preparation of [1S-[1R*,2S*(2S*,3R*)]]-[1-[[[3-[[(1,1-Dimethylethoxy)carbonyl]amino]-2-hydroxy-4-phenylbutyl]amino]-2-hydroxy-1-(phenylmethyl)propyl]amino]carbonyl]-2-hydroxy-2-methylpropyl] carbamic acid, phenylmethyl ester, isomer B (Compound 302)

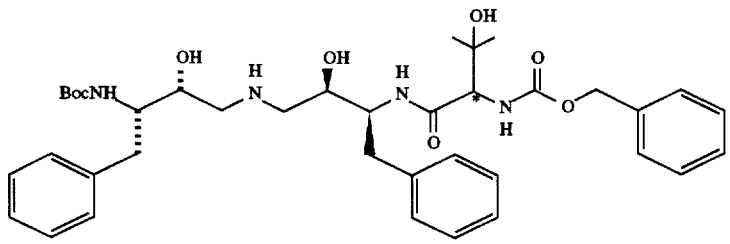

Flash chromatography of the diastereomeric mixture described in Example 301 followed by trituration of the slower moving isomer with hot Et$_2$O and with hot EtOAc gave Compound 302 (48 mg, 15% yield) as a colorless solid. $R_f$=0.33 (10:1:89 MeOH:NH$_4$OH:CH$_2$Cl$_2$); m.p. 185°–189° C.; $[\alpha]_D$=–17.30 (c 0.15, MeOH).

Anal. Calc. for C$_{38}$H$_{52}$N$_4$O$_8$·0.26 H$_2$O; C, 65.44; H, 7.59; N, 8.03 Found: C, 65.54; H, 7.53; N, 7.93

EXAMPLE 303

Preparation of [1S-(1R*,2S*)]-[Iminobis[2-hydroxy-1-(phenylmethyl)-3,1-propanediyl]]bis-[[carbamic acid], 1-(hydroxymethyl)cyclobutyl 1,1-dimethylethyl ester (Compound 303e)

(a) Compound 303a

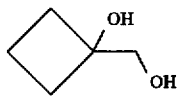

Compound 303a was prepared as described in J. Am. Chem. Soc., 71, 3925 (1949).

(b) Compound 303b

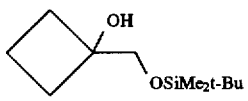

Compound 303a was converted to Compound 303b by a procedure analogous to that of Example 277c.

(c) Compound 303c

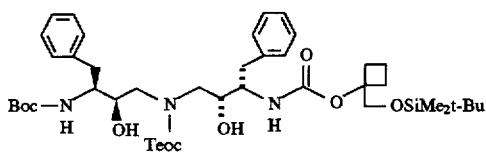

Compounds 303b and 48 were converted to Compound 303c by a two-step procedure analogous to that used for the conversion of Compound 149c to Compound 149e (DMF was used in the coupling of the p-nitrophenylcarbonate of Compound 303b with Compound 48).

(d) Compound 303d

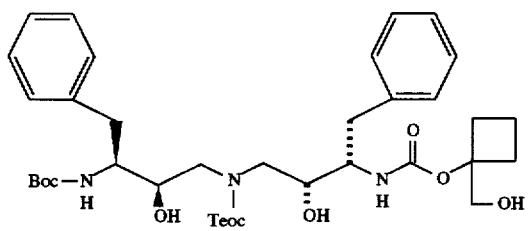

Compound 303c was converted to Compound 303d by a procedure analogous to that of Example 162.

(e) Compound 303e

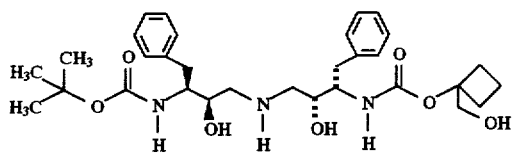

Compound 303d was converted to the title Compound 303e (light-brown solid) by a three-step procedure analogous to that used for the conversion of Compound 289a to Compound 289d.

m.p. 139°–145° C.; $[\alpha]_D$=–5.10 (c 0.2, $CH_3OH$). Mass Spec. (FAB) $(M+H)^+$=572; Analysis calc. for $C_{31}H_{45}N_3O_7$·2.05 $H_2O$: C, 61.17; H, 8.13; N, 6.90; Found: C, 60.95; H, 7.70; N, 7.12.

EXAMPLE 304

Preparation of [1S-[1R*,2S* (2S*, 3R*)]]-[3-[[3-[[(1,1-Dimethylethoxy)carbonyl]amino]-2-hydroxy-4-[4-[2-(3-pyridinyloxy)ethoxylphenyl]butyl]amino]-2-hydroxy-1-(phenylmethyl)propyl]carbamic acid, 1,1-dimethylethyl ester (Compound 304c)

(a) Compound 304a

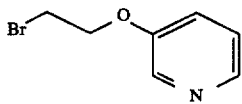

To a 0° C. suspension of 3-hydroxypyridine (1.00 g; 10.5 mmol), $Ph_3P$ (7.08 g; 27.0 mmol), and bromoethanol (1.91 mL; 27.0 mmol) in anhydrous THF (30 mL) was added dropwise DEAD (4.25 mL; 27.0 mmol) over 15 min. The resulting yellow solution was allowed to warm to RT and stirred for 36 h. Volatiles were removed in vacuo to give a yellow-brown residue, which was dissolved in EtOAc and $Et_2O$ (1:1). This solution was extracted with aqueous 1N HCl and the aqueous extracts basified at 0° C. with excess 1M aq. NaOH. Extraction with EtOAc followed by drying ($MgSO_4$) and evaporation in vacuo gave an oil which was purified on silica gel (150 mL) using a stepwise gradient from 3:1 to 1:2 hexanes:EtOAc to afford Compound 304a (1.27 g; 60%) as a yellow oil.

(b) Compound 304b

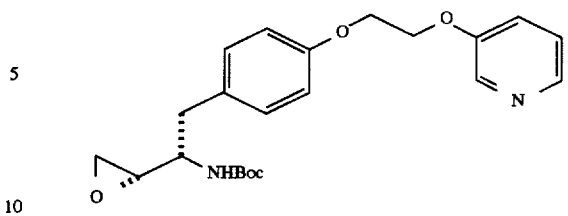

To a 0° C. suspension of NaH (0.032 g of a 60% suspension in oil) in anhydrous DMF (1.0 mL) was added dropwise a solution of Compound 175c (0.200 g; 0.716 mmol) in DMF (1.0 mL). The solution was stirred at RT for 1 h, then recooled to 0° C. A solution of Compound 304a (0.167 g; 0.827 mmol), n-$Bu_4$NI (0.015 g; 0.039 mmol) and 15-crown-5 (0.159 mL; 0.80 mmol) in DMF (1.0 mL) was added dropwise. The reaction was stirred at RT for 24 h. Volatiles were removed in vacuo, and the residue was partitioned between $H_2O$ and EtOAc. The organic extracts were washed with $H_2O$, dried ($Na_2SO_4$) and concentrated in vacuo to give an oil, which was purified on silica gel (100 mL) using a gradient from 3:1 to 1:3 hexane:EtOAc as eluent to give Compound 304b (0.168 g; 59%) as a white solid.

(c) Compound 304c

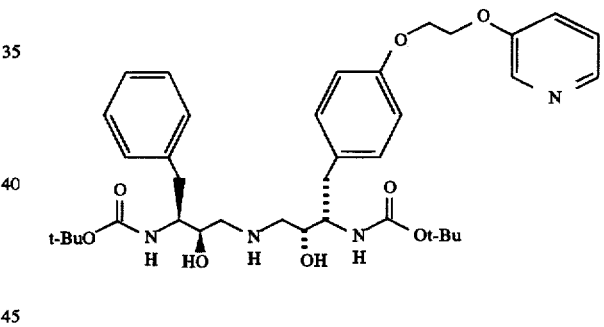

Compound 304b (0.160 g; 0.400 mmol) was reacted with Compound 16b (0.112 g; 0.400 mmol) in DMF at 100° C. for 5 h. Volatiles were removed in vacuo and the residue was chromatographed on silica gel (100 mL) using as eluent a stepwise gradient from 99:1:0.1 to 90:10:1 $CH_2Cl_2$:MeOH:$NH_4OH$ to afford a white solid (0.125 g, 46%). This material was further purified by preparative HPLC on a C-18 column (6 μm- 30×300 cm; using a stepwise gradient from 50:50 to 75:25 A:B; A=90:10:0.05 MeOH:$H_2O$:TFA; B=90:10:0.05 $H_2O$:MeOH:TFA) followed by basification with saturated aq. $NaHCO_3$, extraction with EtOAc, concentration and lyphilization from dioxane-$H_2O$ to afford the title Compound 304c (0.091 g; 34%) as a white solid.

m.p.=127°–130° C.; $[\alpha]_D$=–3.5° (c=0.34; MeOH). Mass Spec. (CI): $(M+H)^+$ =681; Analysis calc. for $C_{37}H_{52}N_4O_8$·0.80 $H_2O$: C, 63.92; H, 7.77; N, 8.06 Found: C, 64.24; H, 7.72; N, 7.74

EXAMPLE 305

Preparation of [1R*,2S* (2S*,3R*)]-N-[3-[[(1,1Dimethylethoxy)carbonyl]amino]-2-hydroxy-4-phenylbutyl]amino]-2-hydroxy-1-(phenylmethyl) propyl]-N²-[(dimethylamino)carbonyl]-3-methyl-L-valinamide (Compound 305b)

(a) Compound 305a

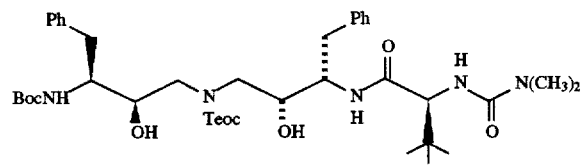

To a 0° C. solution of Compound 263b (0.271 g; 0.387 mmol) in anhydrous CH₂Cl₂ (4.0 mL) was added dimethyl carbamyl chloride (0.050 g; 0.464 mmol) dropwise, followed by dry Et₃N (0.129 mL, 0.930 mmol). The reaction was allowed to warm to RT and stirred for 24 h. Additional dimethyl carbamyl chloride (0.040 g; 0.372 mmol) and Et₃N (0.100 mL; 0.718 mmol) were added and the reaction was stirred for another 24 h. Aqueous NaHCO₃ (10 mL of a 50% saturated solution) was added and extracted with CH₂Cl₂. The combined organic extracts were dried (Na₂SO₄) and concentrated in vacuo to give an oil, which was chromatographed on silica gel (150 mL) with a stepwise gradient from 2:1 to 1:4 hexanes:EtOAc to afford Compound 305a (0.193 g; 65%) as a white foam.

(b) Compound 305b

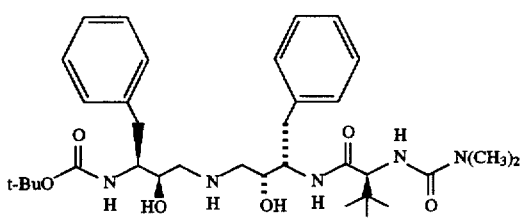

Compound 305a was converted to the title Compound 305b (white solid) by a procedure analogous to that of Example 21.

m.p.=146°–150° C. (dec.); [α]$_D$=−12.5° (c=0.20; MeOH). Mass Spec. (FAB): (M+H)⁺=628.

EXAMPLE 306

Preparation of [1S-[1R*, 2S* (2S*, 3R*)]-[3-[[(1,1-Dimethylethoxy)carbonyl]amino]-2-hydroxy-4-[4-(2-hydroxypropoxy)phenyl]butyl]amino]-2-hydroxy-1-(phenylmethyl)propyl]carbamic acid, 1,1-dimethylethyl ester (Compound 306e)

(a) Compound 306a

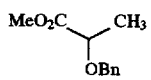

To a 0° C. suspension of THF-washed NaH (1.0 g of a 60% suspension in oil) was added dropwise a solution of methyl lactate (2.10 mL; 22.0 mmol) in 10 mL of dry THF over 15 min. The reaction mixture was allowed to warm to 20° C. and stirred for 30 min. The solution was cooled to 0° C. and benzyl bromide (2.97 mL;25 mmol) in 5 mL of dry THF was added, followed by Bu₄NI (0.092 g; 0.25 mmol). The reaction solution was allowed to warm to RT and stirred for 24 h. The reaction mixture was partitioned between H₂O and EtOAc and the combined organic extracts were washed with H₂O and brine and dried over Na₂SO₄. Volatiles were removed in vacuo to give an oil, which was purified on silica gel using a gradient from hexane to 10% EtOAc/hexane to afford Compound 306a (2.46 g; 57%) as a clear, colorless oil.

(b) Compound 306b

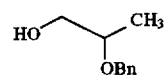

Compound 306a was converted to Compound 306b by a procedure analogous to that of Example 281a (reaction was run at 0° C. to RT).

(c) Compound 306c

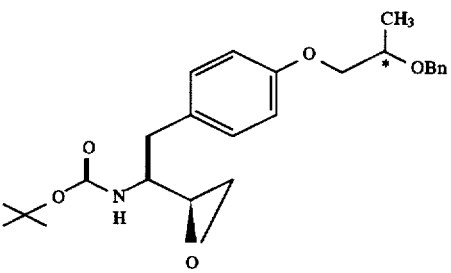

Compounds 306b and 175c were reacted by a procedure analogous to that of Example 282a to give Compound 306c.

(d) Compound 306d

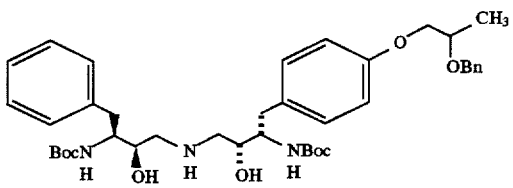

Compounds 306c and 16b were reacted by a procedure analogous to that of Example 226b to give the Compound 306d.

(e) Compound 306e

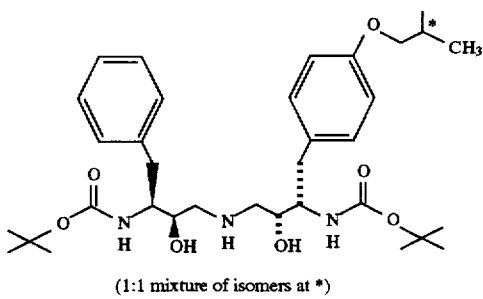

(1:1 mixture of isomers at *)

To a suspension of 10% Pd/C (60 mg) in MeOH (2.5 mL) was added Compound 306d (64 mg; 0.09 mmol) followed by aq. HCl (900 μL of a 0.1N solution) and the reaction was placed under an atmosphere of H₂. After 1 h, the reaction mixture was neutralized with 900 μL of 0.1N NaOH, filtered through a Celite plug and concentrated in vacuo. The crude product was purified on silica gel using a stepwise gradient from 98:2:0.2 to 92:8:0.8 CH₂Cl₂:MeOH: NH₄OH to afford Compound 306e (35 mg; 65%) as a white solid.

m.p.=145–147° C.; Mass Spec. (CI): (M+H)=618; Analysis calc. for $C_{33}H_{51}N_3O_8 \cdot 0.94\ H_2O$: C, 62.44; H, 8.40; N, 6.62; C, 62.89; H, 8.17; N, 6.17

EXAMPLE 307

Preparation of [1S-[1R*,2S*(2S*,3R*)]]-[1-[[[3-[[(1,1-Dimethylethoxy)carbonyl]amino]-2-hydroxy-4-phenylbutyl]amino]-2-hydroxy-1-(phenylmethyl)-propyl]amino]carbonyl]-3-[[(1,1-dimethylethyl)-dimethylsilyl]oxy]-2,2-dimethylpropyl]carbamic acid, phenylmethyl ester, isomer A (Compound 307e)

(a) Compound 307a

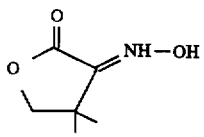

To a solution of dihydro-4,4-dimethyl-2,3-furandione (0.5 g, 3.76 mmol) in HOAc (20 mL) was added KOAc (1.0 g, 0.01 mol) and then $H_2NOH \cdot HCl$ (0.70 g, 0.01 mol). After 1.2 h, the reaction mixture was partitioned between EtOAc and $H_2O$, and the aqueous layer extracted with EtOAc. The combined organic extracts were dried ($Na_2SO_4$) and evaporated in vacuo to give Compound 307a (1.28 g, 89% yield) as a colorless solid.

(b) Compound 307b

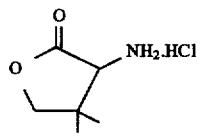

A solution of Compound 307a (710 mg, 4.96 mmol) in EtOH (3 mL) was added to a suspension of 180 mg of 5% Pd/C in EtOH (10 mL) and 2N HCl (5 mL) and the mixture stirred under a $H_2$ atmosphere. After 4 h, the reaction mixture was filtered through a Nylon plug and the filtrate evaporated in vacuo to give Compound 307b (826 mg, ≦100% crude yield) as an oily solid after co-evaporation from MeOH.

(c) Compound 307c

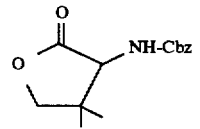

To a 0° C. solution of Compound 307b (≦0.82 g, ≦3.47 mmol) in aqueous 0.83M $NaHCO_3$ (10 mL) was added Cbz-Cl (0.50 mL, 3.26 mmol). After 15 min, the reaction mixture was brought to RT for 3 h and a second portion of Cbz-Cl (0.10 mL, 0.65 mmol) was added. After a total of 5 h, the reaction mixture was filtered, washing the solid with $H_2O$ and hexanes. The solid residue was purified by flash chromatography (silica gel, 5 by 10 cm), eluting with 2% EtOAc:$CH_2Cl_2$ to give Compound 307c (567 mg, 61% yield for the 2 steps) as a colorless solid.

(d) Compound 307d

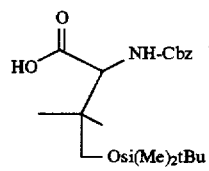

To a solution of Compound 307c (500 mg, 1.90 mmol) in THF (15 mL) was added an aqueous solution of LiOH (80 mg, 1.91 mmol). After 1.45 h the volatiles were evaporated in vacuo to give the lithium salt (826 mg, ≦100% crude yield) as an oily solid after co-evaporation with dry THF and with dry DMF. The crude residue (≦1.90 mmol) was dissolved in DMF (7 mL) and imidazole (320 mg, 4.7 mmol) and then t-butyldimethylsilyl chloride (630 mg, 4.18 mmol) was added. After stirring 23 h, MeOH (8 mL) was added and the mixture was stirred for 21 h, then stored at –80° C. After warming, the volatiles were removed in vacuo and the oily residue was partitioned between EtOAc and saturated $NH_4Cl$. The combined organic extracts were dried over $Na_2SO_4$ and concentrated in vacuo to give an oil which was purified by flash chromatography (silica gel, 5 by 9 cm), eluting with EtOAc:$CH_2Cl_2$ (6, 7 and then 20% EtOAc containing 1% AcOH) to give Compound 307d (450 mg, 60% yield for the 2 steps) as an oily solid after co-evaporation with heptane.

(e) Compound 307e

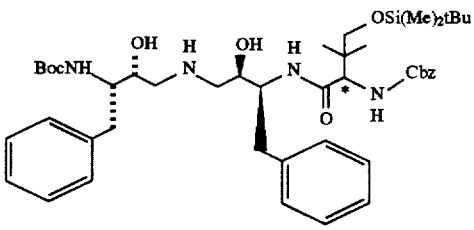

(single isomer at *)

To a solution of Compound 307d (345 mg, 0.873 mmol) and Compound 54 (410 mg, 0.925 mmol) in DMF (6 mL) at 0° C. under argon was added HOBT (190 mg, 1.41 mmol), EDCI (170 mg, 0.887 mmol), and then N-methylmorpholine (0.1 mL, 0.91 mmol). The mixture was allowed to come to RT and stirred for 20 h. The reaction mixture was partitioned between EtOAc and saturated $NaHCO_3$, and the combined organic extracts were washed with brine, dried over $Na_2SO_4$ and evaporated in vacuo to leave an oil. The residue was purified by flash chromatography (silica gel, 5 by 10 cm), eluting with a gradient of MeOH:$NH_4OH$:$CH_2Cl_2$ (2:0.2:97.8, 3:0.3:96.7, 3.5:0.35:96.15, 4:0.4:95.6, 4.5:0.45:95.05, 5:0.5:94.5, and then 6:0.6:93.4) to give the title Compound 307e (170 mg, 47%) as a colorless glass (single isomer). $R_f$ ($SiO_2$)=0.45 (10:1:89 MeOH:$NH_4OH$:$CH_2Cl_2$); Compound 309a was also isolated.

EXAMPLE 308

Preparation of [1S-[1R*,2S*(2S*,3R*)]]-1-[[[3-[[(1,1-Dimethylethoxy)carbonyl]amino]-2-hydroxy-4-phenylbutyl]amino]-2-hydroxy-1-(phenylmethyl)propyl]amino]carbonyl -2-(hydroxymethyl)-2-methylpropyl] carbamic acid, phenylmethyl ester, isomer A (Compound 308)

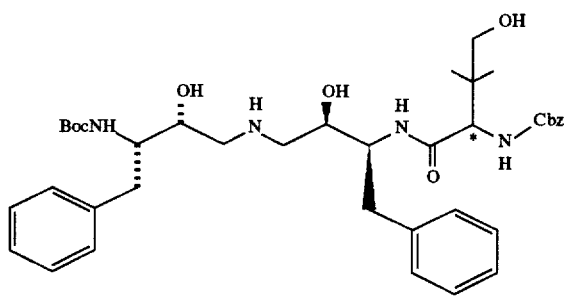

(single isomer at *)

A solution of Compound 307e (162 mg, 0.197 mmol) in AcOH:THF:H₂O (5 mL, 3:1:1) was stirred at RT for 59.5 h and the volatiles were removed in vacuo. The oily residue was co-evaporated once with heptane and then twice with heptane/CH₂Cl₂ to leave an oily solid residue. The residue was purified by flash chromatography (silica gel, 2.5 by 18 cm), eluting with MeOH:NH₄ $_{OH:CH2}$Cl₂ (6:0.6:93.4 and then 7:0.7:92.3) to give the title Compound 308 (98 mg, 70%) as a colorless solid.

R$_f$ (SiO₂)=0.29 (10:1:89 MeOH:NH₄OH:CH₂Cl₂); m.p. 68°–70° C.; [α]$_D$=–19.8° (c 0.19, MeOH). (FAB): 707 (M+H). Analysis Calc. for C₃₉H₅₄N₄O₈·0.46 H₂O: C, 65.51; H, 7.74; N, 7.83 Found: C, 65.45; H, 7.62; N, 7.89

EXAMPLE 309

Preparation of [1S-[1R*,2S*(2S*, 3R*)]]-1-[[[3-[[(1,1-Dimethylethoxy)carbonyl]amino]-2-hydroxy-4-phenylbutyl]amino]-2-hydroxy-1-(phenylmethyl)-propyl]amino]carbonyl]-2-(hydroxymethyl)-2-methylpropyl]carbamic acid, phenylmethyl ester, isomer B (Compound 309b)

(a) Compound 309a

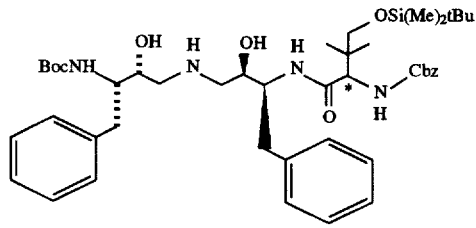

Flash chromatography of the reaction mixture from Example 307e gave Compound 309a, the diastereomer at * of Compound 307e. R$_f$ (SiO2)=0.43 (10:1:89 MeOH:NH₄OH:CH₂Cl₂).

(b) Compound 309b

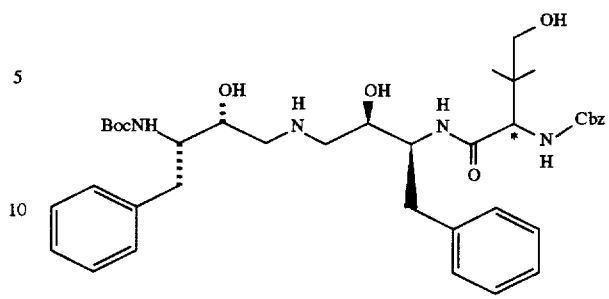

Compound 309a was converted to the title Compound 309b (colorless solid) by a procedure analogous to that of Example 308.

R$_f$ (SiO₂)=0.35 (10:1:89 MeOH:NH₄OH:CH₂Cl₂); m.p. 72°–76° C.; [α]$_D$=–9.720 (c 0.26, AcOH). Mass Spec.: (FAB): 707 (M+H). Anal. Calc. for C₃₉H₅₄N₄O₈·0.47 H₂O: C, 65.49; H, 7.74; N, 7.83; Found: C, 65.50; H, 7.64; N, 7.82

EXAMPLE 310

Preparation of [1S-(1R*,2S*)]1-[Iminobis[2-hydroxy-1-(phenylmethyl)3,1-propanediyl]]bis[carbamic acid], 3-tetrahydrofuranyl 1,1-dimethylethyl ester (Compound 310)

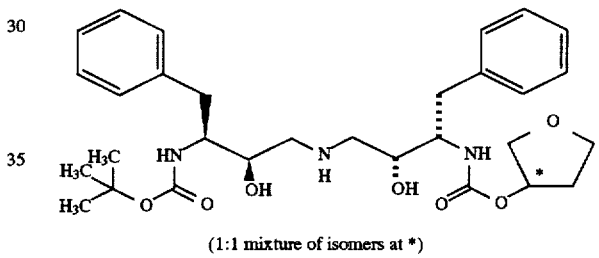

(1:1 mixture of isomers at *)

3-Hydroxytetrahydrofuran and Compound 48 were reacted by a three-step procedure analogous to that used for the conversion of Compound 149c to Compound 150 (DMF was used in the coupling of the p-nitrophenylcarbonate with Compound 48) to give the title Compound 310 (white solid).

m.p. 200°–203° C.; [α]$_D$=–11° (c=0.2, CH₃OH); Analysis calc.for C₃₀H₄₃N₃O₇·0.26 H₂O: C, 63.84; H, 8.13; N, 7.44 Found: C, 63.89; H, 7.70; N, 7.39

EXAMPLE 311

Preparation of [S-[1R*,2S*(2S*,3R*)]]-[2,2-Dimethyl-1-[[[3-[[(1,1-dimethylethoxy)carbonyl]amino]-2-hydroxy-4-phenylbutyl]amino]-2-hydroxy-1-(phenylmethyl)-propyl]aminocarbonyl]propyl] carbamic acid, (2-quinoxalinyl)methyl ester (Compound 311c)

(a) Compound 311a

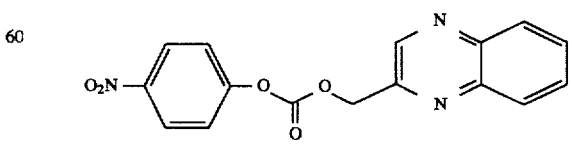

A solution of 2-hydroxymethyl quinoxaline (Lindquist, *J. Chem. Soc.*, 2052-8 (1956)) (160.2 mg, 1.0 mmol) in 4 ml of CH₂Cl₂ was cooled to 0° C. and pyridine (87 mg, 1.1 mmol) was added followed by the addition of p-nitrophenylchloroformate (222 mg, 1.1 mmol) in 2 ml of CH₂Cl₂. The mixture was stirred at 0° C. for 3 h and slowly warmed to RT and stirred overnight. The reaction was diluted with EtOAc and washed with H₂O and brine. After drying over Na₂SO₄ the solvents were evaporated yielding the crude product as a yellow solid. The product was purified by chromatography on CC-7 (buffered silica, pH 6.8) eluting with EtOAc/hexane (1:1) to afford 304 mg (93%) of Compound 311a as a colorless solid.

(b) Compound 311b

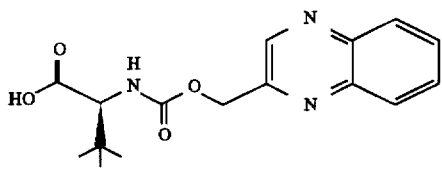

L-tert-Leucine (112 mg, 0.85 mmol) was dissolved in 0.85 ml of 1 N NaOH and a solution of Compound 311a (275 mg, 0.85 mmol) in 1.5 ml of dioxane was added at RT followed by the addition of Et₃N (91 mg, 1.55 mmol). The reaction was stirred overnight, diluted with 5% KHSO₄ and extracted with EtOAc. The combined EtOAc extracts were washed with H₂O and brine and the solvents evaporated yielding the crude product as a pale yellow solid. The crude material was purified on a silica column eluting with 5–10% MeOH/CH₂Cl₂ to afford 198 mg (73%) of the Compound 311b as a colorless solid.

(c) Compound 311c

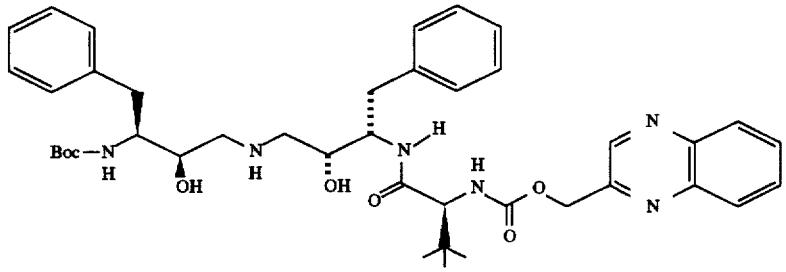

A mixture of Compound 54 (273 mg, 0.6 mmol), Compound 311b (195 mg, 0.6 mmol) and HOBT (94 mg, 0.6 mmol) was dissolved in 2 ml of dry DMF and the mixture cooled to 0° C. EDCI (118 mg, 0.6 mmol) was added and the mixture stirred at 0° C. for 3 h and then slowly allowed to warm to RT and stir overnight. The reaction was diluted with EtOAc and washed with 5% KHSO₄, NaHCO₃, H₂O and brine. The solvents were evaporated and the crude residue was purified on a silica column eluting with 3–5% MeOH/CH₂Cl₂+0.1% NH₄OH to afford 198 mg (44%) of the title Compound 311c as a colorless solid.

m.p. 178°–184° C. (dec); [α]$_D$=−14.5° (c=0.25, MeOH). Mass Spec. (FAB): (M+H)⁺=743⁺; Analysis Calcd. for C₄₁H₅₄N₆O₇·0.45 H₂O: C, 65.58 H, 7.37 N, 11.1; Found C, 65.62 H, 7.41 N, 11.15

EXAMPLE 312

Preparation of [1S-[1R*, 2S* (2S*, 3R*)]]-[3-[[3-[[2-(1,1-Dimethylethyl)-4-hydroxy-1-oxobutyl]amino]-2-hydroxy-4-phenylbutyl]amino]-2-hydroxy-1-(phenylmethyl)propyl]carbamic acid, 1,1-dimethylethyl ester, isomer A (Compound 312d)

(a) Compound 312a

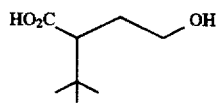

Compound 312a was prepared as described in *Chem. Ber.* 123, 2167–2172 (1990).

(b) Compound 312b

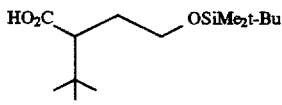

Compound 312a was converted to Compound 312b by a procedure analogous to that of Example 291b.

(c) Compound 312c

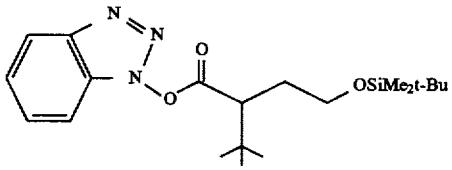

To a 5° C. mixture of Compound 312b (250 mg, 0.91 mmol) and HOBT hydrate (149 mg, 1.1 mmol) in CH₂Cl₂ (1 mL) and DMF (0.5 mL) was added EDCI hydrochloride (192 mg, 1.0mmol). The mixture was allowed to warm to RT and was stirred overnight. The mixture was concentrated to remove most of the DMF and the residue was partitioned between EtOAc and sat'd. aq. NaHCO₃. The combined organic extracts were washed with H₂O and brine, dried (Na₂SO₄) and concentrated to afford a crude residue which was purified by column chromatography on silica gel eluting with EtOAc-hexane (80-20) to afford 324 mg (91% yield) of Compound 312c as a white solid.

(d) Compound 312d

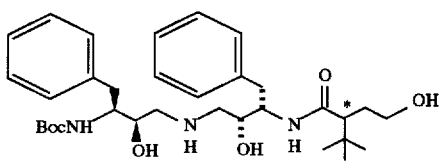

A mixture of Compound 54 (365 mg, 0.82 mmol) and Compound 312c (269 mg, 0.69 mmol) in 1.2 mL dry DMF was heated at 75°–80° C. for 4 hr. The mixture was cooled to RT and concentrated to remove most of the DMF. This residue was dissolved in EtOAc and the solution was washed with sat'd. aq. NaHCO$_3$, H$_2$O, and brine, and was dried over Na$_2$SO$_4$. The solution was concentrated to afford 600 mg of a semisolid which was dissolved in 3 mL THF and 3 mL H$_2$O followed by the addition of 9 mL HOAc. The clear solution was stirred overnight at RT. The reaction mixture was concentrated and the crude product was purified by chromatography on silica gel eluting with a gradient of CH$_2$Cl$_2$—MeOH—aq. NH$_4$OH (98:1.8:0.2 to 92:7.2:0.8) to afford the semipure diastereomers (at *) Compounds 312d and 313. The faster moving diastereomer was repurified by preparative TLC on silica gel eluting with CH$_2$Cl$_2$—MeOH—aq. NH$_4$OH (90:9:1) to afford 57 mg (14% yield) of the title Compound 312d (white solid).

TLC R$_f$ $_{(SiO2)}$=0.19 (CH$_2$Cl$_2$—MeOH—aq. NH$_4$OH 90:9:1); m.p. 158°–162° C. ("softening" at 150°–157° C.); [α]$_D$=–0.570; (c=1.23, CH$_3$OH); Mass Spec. (FAB), 586 (M+H$^+$); Analysis calc. for C$_{33}$H$_{51}$N$_3$O$_6$·0.05 H$_2$O: C, 67.56; H, 8.78; N, 7.16; Found: C, 67.45; H, 8.69; N, 7.27.

EXAMPLE 313

Preparation of [1S-[1R*, 2S* (2S*, 3R*)]]-[3-[[3-[[2-(1,1-Dimethylethyl)-4-hydroxy-1-oxobutyl]-amino]-2-hydroxy-4-phenylbutyl]amino]-2-hydroxy-1-(phenylmethyl)propyl]carbamic acid, 1,1-dimethylethyl ester, isomer B (Compound 313)

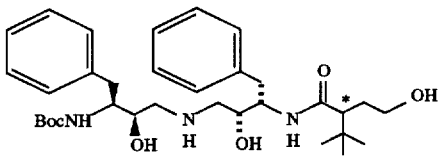

Compound 313 (white solid) was prepared as the slower moving isomer as described in Example 312.

TLC R$_f$ $_{(SiO2)}$=0.13 (CH$_2$Cl$_2$—MeOH—aq. NH$_4$OH 90:9:1); mp 140°–143° C.; [α]$_D$=–5.620; (c=1.30, CH$_3$OH); Mass Spec. (FAB), 586 (M+H$^+$); Analysis calc. for C$_{33}$H$_{51}$N$_3$O$_6$·0.52 H$_2$O: C, 66.61; H, 8.81; N, 7.06; Found: C, 66.53; H, 8.87; N, 7.14.

EXAMPLE 314

Preparation of [1S-(1R*,2S*)]-[Iminobis[2-hydroxy-1-(phenylmethyl)-3,1-propanediyl]]bis [carbamic acid], 1,1-dimethylethyl-3-methyl-3-tetrahydrofuranyl ester (Compound 314c)

(a) Compound 314a

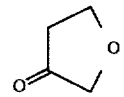

To the suspension of pyridinium chlorochromate (32 g, 0.15 mol) and activated 4 Åmolecular sieves (40 g, powder) in 200 ml of dry CH$_2$Cl$_2$ cooled at 10° C. was added a solution of 3-hydroxytetrahydrofuran (8.9 g, 0.1 mol) in 50 ml of dry CH$_2$Cl$_2$. The mixture was stirred at RT for 2.5 h and then filtered through a short column of Florisil. The filtrate was evaporated by careful distillation of the solvent. Short-path distillation of the residue (bp: 136°–137° C.) afforded 4.9 g (56%) of Compound 314a as a colorless liquid.

(b) Compound 314b

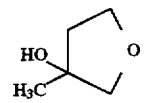

Compound 314a was converted to Compound 314b by a procedure analogous to that of Example 258a.

(c) Compound 314c

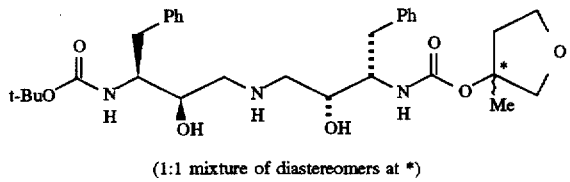

(1:1 mixture of diastereomers at *)

Compounds 314b and 48 were converted to the title Compound 314c (white solid) by a three-step procedure analogous to that used for the conversion of Compound 149c to Compound 150 (DMF was used in the coupling of the p-nitrophenyl carbonate of Compound 314b with Compound 48).

m.p.: 166°–167° C. Mass Spec. (FAB): 572$^+$(M+H)$^+$. Analysis Calc. for C$_{31}$H$_{45}$N$_3$O$_7$·0.18 H$_2$O: C, 64.75; H, 7.95; N, 7.31. Found: C, 64.77; H, 8.00; N, 7.29.

EXAMPLE 315

Preparation of [S-[1R*,2S*(2S*,3R*)]]-[2,2-Dimethyl-1-[[[3-[[3-[[(1,1-dimethylethoxy)carbonyl] amino]-2-hydroxy-4-phenylbutyl]amino]-2-hydroxy-1-(phenylmethyl)-propyl]amino]carbonyl]propyl] carbamic acid, (2-oxo-4-oxazolidinyl)methyl ester (Compound 315b)

(a) Compound 315a

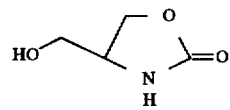

To a stirring solution of 2-amino-1,3-propanediol (1.58 g, 0.017 mol) in aqueous 1.73M KOH at 0° C. (20 mL) was added a toluene solution of phosgene (11 mL, 0.021 mol). After warming to RT slowly overnight, the reaction mixture was extracted with hexanes and the aqueous layer evaporated at ~30° C. to give an oily solid residue. The residue was repeatedly washed with hot EtOAc and the combined washes were evaporated in vacuo. The resulting solid residue was co-evaporated with heptane to afford Compound 315a as a colorless solid (1.28 g, 63%).

(b) Compound 315b

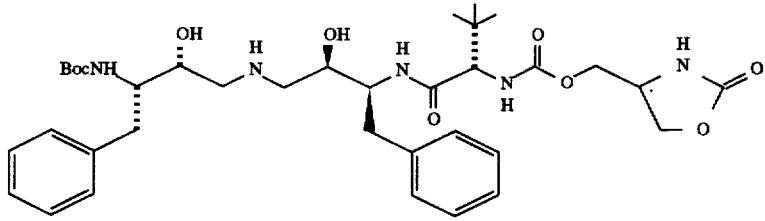

(1:1 mixture of isomers at .)

tert-Leucine and Compounds 315a and 54 were reacted by a three-step procedure analogous to that used for Example 257a through 257c to give the title Compound 315b (colorless solid).

m.p. 104°–114° C.; $[\alpha]_D$=−16.6° (c 0.22, MeOH). Mass Spec.: (FAB): 700 (M+H). Analysis Calc. for $C_{36}H_{53}N_5O_9$: C, 61.78; H, 7.63; N, 10.01 Found: C, 61.62; H, 7.91; N, 9.65.

EXAMPLE 316

Preparation of [1S-(1R*,2S*), (3S-trans)]-[Iminobis [2-hydroxy-1-(phenylmethyl)-3,1-propanediyl]]bis [carbamic acid], 4-hydroxy-3-tetrahydrofuranyl 1,1-dimethylethyl ester (Compound 316)

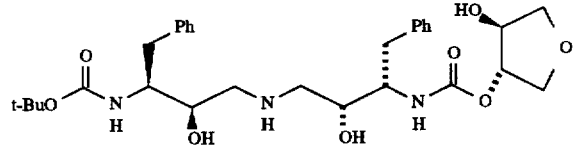

1,4-Anydro-L-threitol was converted to its mono-p-nitrophenyl carbonate which was reacted with Compound 48 by a procedure analogous to that used for the conversion of Compound 149c to 150 (DMF was used in the coupling of the p-nitrophenyl carbonate with Compound 48) to give the title Compound 316 (white solid).

m.p.: 183°–184° C.; $[\alpha]_{365}$=−27.2° (c 0.2, MeOH). Mass Spec. (FAB): 574⁺(M+H)⁺. Analysis Calc. for $C_{30}H_{43}N_3O_8$: C, 62.81; H, 7.55; N, 7.32. Found: C, 62.77; H, 7.72; N, 7.25.

EXAMPLE 317

Preparation of [1S-(1R*,2S*), (3R-trans)]-[Iminobis [2-hydroxy-1-(phenylmethyl)-3,1-propanediyl]]bis [carbamic acid], 4-hydroxy-3-tetrahydrofuranyl 1,1-dimethylethyl ester (Compound 317)

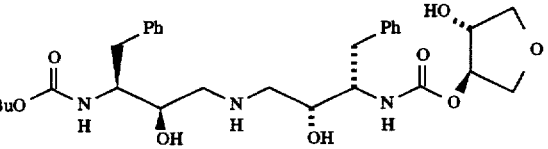

1,4-Anydro-D-threitol (prepared from D-threitol [Terfort, Synthesis, 951 (1992)] according to Otey et al., J. Org. Chem., 26, 1673 (1961)) was converted to its mono-p-nitrophenyl carbonate which was reacted with Compound 48 by a procedure analogous to that used for the conversion of Compound 149c to 150 (DMF was used in the coupling of the p-nitrophenyl carbonate with Compound 48) to give the title Compound 317 (white solid).

m.p.: 181°–182° C.; $[\alpha]_D$=−31.3° (c 0.63, MeOH). Mass Spec. (FAB): 574⁺(M+H)⁺. Analysis Calc. for $C_{30}H_{43}N_3O_8$·0.45 $H_2O$: C, 61.93; H, 7.61; N, 7.22. Found: C, 62.01; H, 7.55; N, 7.14.

EXAMPLE 318

Preparation of [1S-(1R*,2S*)]-[Iminobis[2-hydroxy-1-(phenylmethyl)-3,1-propanediyl)]bis[carbamic acid], 1,1-dimethylethyl-3-tetrahydropyranyl ester (Compound 318)

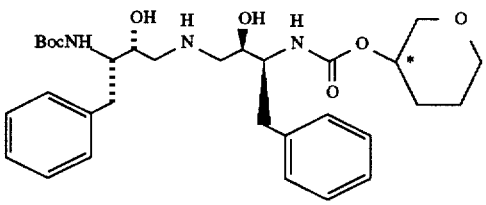

(1:1 mixture of isomers at .)

3-Hydroxytetrahydropyran (Zweifel et al., *J. Org. Chem.*, 35, 898–902 (1970)) and Compound 48 were reacted by a procedure analogous to that used for the conversion of Compound 149c to 150 (DMF was used in the coupling of the p-nitrophenyl carbonate with Compound 48) to give the title Compound 318 (colorless solid).

m.p. 185°–187° C.; $[\alpha]_D$=–1.80° (c 0.36, CHCl$_3$). MS: (FAB): 572 (M+H). Anal. Calc. for C$_{31}$H$_{45}$N$_3$O$_7$·0.09 H$_2$O; C, 64.95; H, 7.94; N, 7.35; Found: C, 64.68; H, 8.00; N, 7.33.

EXAMPLE 319

Preparation of [1S-(1R*,2S*)]-[Iminobis[2-hydroxy-1-(phenylmethyl)3,1-propanediyl)]bis[carbamic acid], 1,1-dimethylethyl 4-oxetanyl ester (Compound 319c)

(a) Compound 319a

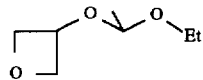

Compound 319a was prepared as described in Baum et al., *J. Org. Chem.*, 48, 2953–2956 (1983).

(b) Compound 319b

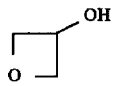

To a solution of Compound 319a (670 mg, 4.58 mmol) in MeOH (7 mL) was added pyridinium p-tosylate (277 mg, 5 mmol). After 4 h NaHCO$_3$ (150 mg) was added and the volatiles were evaporated in vacuo to give an oily solid residue which was purified by flash chromatography (silica gel, 3 by 15 cm), eluting with MeOH:CH$_2$Cl$_2$ (3 and then 3.5% MeOH) to give Compound 319b (148 mg, 44%) as an oil.

(c) Compound 319c

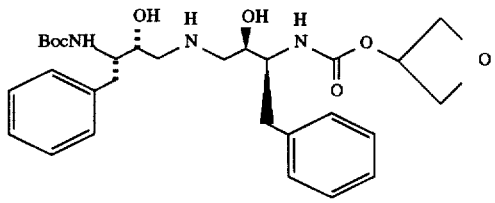

Compounds 319b and 48 were reacted by a procedure analogous to that used for the conversion of Compound 149c to 150 (DMF was used in the coupling of the p-nitrophenyl carbonate with Compound 48) to give the title Compound 319c (colorless solid).

m.p. 196°–199° C.; $[\alpha]_D$=–9.06° (c 0.23, MeOH). Mass Spec.: (FAB): 544 (M+H). Analysis Calc. for C$_{29}$H$_{41}$N$_3$O$_7$: C, 64.07; H, 7.60; N, 7.73; Found: C, 63.99; H, 7.74; N, 7.63.

EXAMPLE 320

Preparation of [1S-[1R*,2S*,(2S*,3R*)]-[2,2-Dimethyl-1-[[[3-[[3-(1,1-dimethylethoxy)-carbonyl]amino]-2-hydroxy-4-phenylbutyl]amino]-2-hydroxy-1-(phenylmethyl)propyl]amino]-carbonyl]propyl]methylcarbamic acid, methyl ester (Compound 320c)

(a) Compound 320a

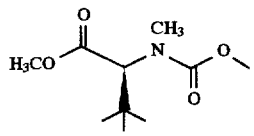

Compound 246a was converted to Compound 320a by a procedure analogous to that of Example 66a.

(b) Compound 320b

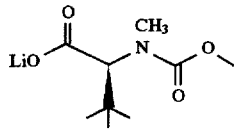

Compound 320a was converted to Compound 320b by a procedure analogous to that of Example 70c (no acid work-up).

(c) Compound 320c

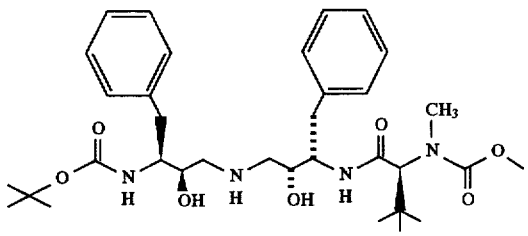

Compounds 320b and 54 were reacted by a procedure analogous to that of Example 93f to give the title Compound 320c (white solid).

m.p.=78°–81° C.; Mass Spec. (CI): (M+H)=629; Analysis Calc. for C$_{34}$H$_{52}$N$_4$O$_7$·1.35 H$_2$O: C,62.52; H,8.44; N,8.58; Found: C,62.74; H,8.27; N,8.36.

EXAMPLE 321

Preparation of [1S-[1R*,2S*(2S*,3R*)]]-[3-[[3-[[2,2-Dimethyl-1-hydroxycyclopentyl)-carbonyl]amino]-2-hydroxy-4-phenylbutyl]amino]-2-hydroxy-1-(phenylmethyl)propyl]carbamic acid, 1,1-dimethylethyl ester, isomer A (Compound 321d)

(a) Compound 321a

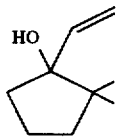

A suspension of anhydrous cerium (III) chloride (4.25 g; 17 mmol) in freshly distilled THF was stirred at RT for 2 h. After cooling this suspension to −78° C., vinylmagnesium bromide (17 ml 1.0M in THF; 17 mmol) was added dropwise over ~15 min. The resulting light orange suspension was stirred at −78° C. for 1.5 h. After this time 2,2-dimethylcyclopentanone (1.27 g; 11 mmol) was added and the reaction mixture was stirred for 1.5 h at −78° C. Saturated NH₄Cl solution (50 ml) was added and the mixture was allowed to warm to RT with stirring. The mixture was partitioned between Et₂O and H₂O. The organic layer was washed with H₂O and brine, dried (MgSO₄), and most of the solvent removed in vacuo to afford 3.38 g of a light yellow liquid. This liquid was ~50% by wt. a solution of Compound 321a in THF and was used in the subsequent step without further purification.

(b) Compound 321b

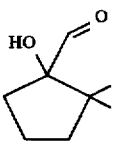

Ozone/oxygen was bubbled through a solution of Compound 321a (1.6 g; 50% by wt. in THF; 5.6 mmol) and NaHCO₃ (42 mg) in 50 ml of MeOH at −78° C. for ~10 min. After purging the solution for 15 min, Me₂S (4.5 ml) was added. After warming to RT, the mixture was stirred for 1 h and the volatiles removed in vacuo. The residue was partitioned between Et₂O and H₂O and the organic layer washed with brine and dried (MgSO₄). Concentration afforded 760 mg (96%) of Compound 321b as a colorless liquid.

(c) Compound 321c

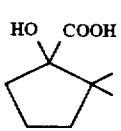

Sodium chlorite (746 mg; 6.6 mmol; 80% pure) was added to a rapidly stirring mixture of Compound 321b (720 mg; 5.06 mmol) and sulfamic acid (641 mg; 6.6 mmol) in 5 ml of H₂O and 5 ml of THF at 0° C. After stirring at 0° C. for 30 min, 0.5 ml of Me₂S was added followed by 20 ml of 1N NaOH. This mixture was extracted with Et₂O and the aqueous layer acidified to pH ~1.5 with saturated KHSO₄, saturated with NaCl, and extracted with EtOAc. The combined organic extracts were washed with brine and dried (MgSO₄). Concentration afforded a solid which was recrystallized from hexane to afford 456 mg (57%) of Compound 321c as a colorless solid.

(b) Compound 321d

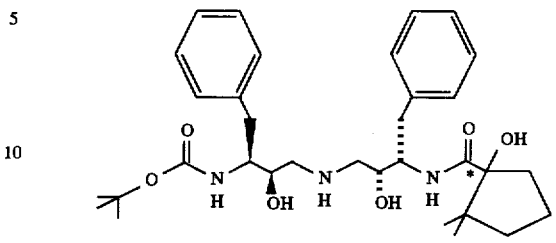

BOP-reagent (265 mg; 0.60 mmol) was added in one portion to a solution of Compound 321c (90 mg; 0.569 mmol), Compound 54 (252 mg; 0.569 mmol) and N-methylmorpholine (66 μl; 0.60 mol) at 0° C. in 1 ml of DMF. The reaction mixture was allowed to warm to RT and stir 16 h. After diluting with EtOAc, the organic phase was washed with H₂O, saturated aq. NaHCO3 and brine. After drying (MgSO₄), the solvent was removed in vacuo. The residue was chromatographed on a 5×12 cm silica gel column eluting with 2% MeOH/CH₂Cl₂ followed by a gradient of 3–7% MeOH/CH₂Cl₂+0.3–0.7% NH₄OH in 0.5% and 0.05% increments respectively. The slower moving isomer (at *) was rechromatographed on a 2.5×15 cm silica gel column with elution as above followed by trituration with Et₂O which afforded 23 mg (7%) of Compound 321d as a white solid.

$R_f$=0.25, CH₂Cl₂:MeOH:NH₄OH, 90:9:1 (UV and PMA detection); m.p. 108°–111° C.; $[\alpha]_D$=−15.2° (c 0.25, MeOH). Mass Spec. FAB M+H=584. Analysis calc. for C₃₃H₄₉N₃O₆·0.57 H₂O: C, 66.73; H, 8.51; N, 7.07; Found C, 66.66; H, 8.44; N, 7.14.

EXAMPLE 322

Preparation of [1S-[1R*,2S*(2S*,3R*)]]-[3-[[3-[[2,2-Dimethyl-1-hydroxycyclopentyl)-carbonyl]amino]-2-hydroxy-4-phenylbutyl]amino]-2-hydroxy-1-(phenylmethyl)-propyl]carbamic acid, 1,1-dimethylethyl ester, isomer B (Compound 322)

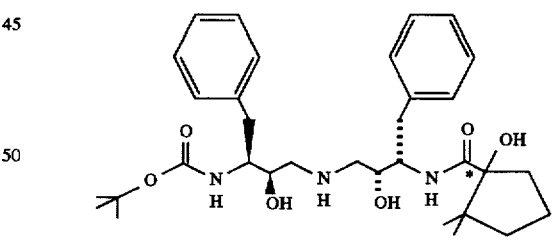

The faster moving isomer from Example 321d was rechromatographed on a 2.5×25 cm silica gel column using 1% MeOH/CH₂Cl₂ followed by 2% MeOH/CH₂Cl₂ then 2.5% MeOH/CH₂Cl₂ and finally a gradient of 3–5% MeOH/CH₂Cl₂+0.3–0.5% NH₄OH in 0.25% and 0.025% increments respectively. Concentration and trituration with Et₂O afforded 41 mg (12%) of Compound 322 as a white solid.

$R_f$=0.28, CH₂Cl₂:MeOH:NH₄OH, 90:9:1 (UV and PMA detection); m.p. 185°–190° C.; $[\alpha]_D$=−15.5° (c 0.33, MeOH). Mass Spec. FAB: M+H=584. Analysis calc. for C₃₃H₄₉N₃O₆·1.17 H₂O: C, 65.53; H, 8.56; N, 6.95; Found C, 65.45; H, 8.25; N, 7.03.

EXAMPLE 323

Preparation of [S-[1R*,2S*(2S*,3R*)]]-[r2,2-Dimethyl-1-[[[3-[[3-[[(1,1-dimethylethoxy)carbonyl]amino]-2-hydroxy-4-phenylbutyl]amino]-2-hydroxy-1-(phenylmethyl)propyl]amino]carbonyl]propyl]carbamic acid, (2-furo[3,2-b]pyridinyl)methyl ester (Compound 323f)

(a) Compound 323a

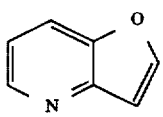

Compound 323a was prepared as described in Shiotani et al., J. Het. Chem., 23, 665 (1986).

(b) Compound 323b

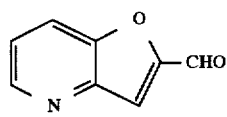

Compound 323a was converted to Compound 323b by the method described in Morita et al., J. Heter. Chem. 24, 373, (1987).

(c) Compound 323c

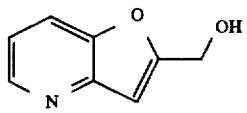

To a solution of Compound 323b (1.5 g, 10.195 mmol) in 100 mL of 3:3:4 THF—EtOH—CHC$_3$ cooled to 0° C. was added NaBH$_4$ (0.675 g, 17.841 mmol) in portions. After the addition was complete, the mixture was stirred at 0° C. for 30 min, diluted with H$_2$O and extracted with CH$_2$Cl$_2$. The combined extracts were dried (MgSO$_4$) and concentrated. The crude residue was flash chromatographed on silica gel eluting with a stepwise gradient of 25% to 100% EtOAc-hexane to afford Compound 323c (1.42 g, 93%) as a beige solid.

(d) Compound 323d

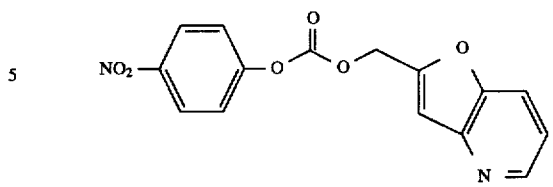

To a solution of Compound 323c (0.745 g, 5 mmol) in 30 mL of CH$_2$Cl$_2$ cooled to 0° C. was added 2 mL of pyridine followed by p-nitrophenyl-chloroformate (1.008 g, 5 mmol) as a solid. The reaction mixture was stirred for 16 h at RT, diluted with EtOAc and washed with sat. NaHCO$_3$ and brine. The organic phase was dried (MgSO$_4$) and concentrated to obtain Compound 323d (1.56 g, 99%; crude yield) containing traces of p-nitro-phenylchloroformate and p-nitrophenol.

(e) Compound 323e

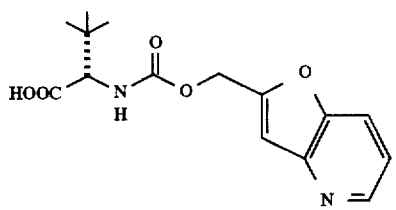

Compound 323d (0.75 g; 2.38 mmol) in 5 mL of dioxane was added to a solution of L-tert-leucine (0.314 g; 2.38 mmol) in 2.4 mL of 1N NaOH at RT followed by the addition of Et$_3$N (365 µL; 2.62 mmol). After 5 h at RT, the reaction mixture was diluted with 10% KHSO$_4$ and extracted with EtOAc. The organic extracts were washed with H$_2$O and brine, dried (MgSO$_4$) and concentrated. Flash chromatography on silica gel of the crude residue (CH$_2$Cl$_2$ followed by 5% then 10% MeOH/CH$_2$Cl$_2$+0.5% HOAc) afforded 0.28 g (38%) of Compound 323e as a beige solid.

(f) Compound 323f

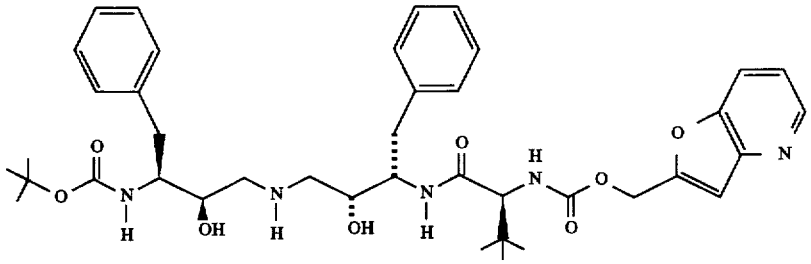

To a 0° C. solution of Compound 323e (0.173 g; 0.56 mmol) in 3 mL of CH$_2$Cl$_2$ was added HOBT (0.115 g; 0.84 mmol) followed by EDCI (0.114 g; 0.59 mmol). After 30 min, Compound 54 (0.25 g; 0.56 mmol) was added followed by 0.5 mL of DMF. The reaction mixture was stirred at 0° C. for 30 min and at RT for 40 h, at which time it was diluted with CH₂Cl₂, and washed with H₂O, sat. aq. NaHCO₃ and brine. The organic extracts were dried (MgSO₄), concentrated, and the resulting residue purified by flash chromatography on silica gel, eluting with a gradient of 98.9:1:0.1 to 89:10:1 CH₂Cl₂:MeOH:NH₄OH, to afford 0.26 g (65%) of the title Compound 323f as a white solid.

m.p. 108°–112° C. (softening at 95°–105° C.); $[\alpha]_D$=−16.5° (c=0.2, CH₃OH). Mass Spec. (FAB) (M +H)+=732; Analysis calc. for $C_{40}H_{53}N_5O_8 \cdot 1.77 H_2O$: C, 62.91; H, 7.46; N, 9.17; Found: C, 62.91; H, 7.17; N, 9.17.

EXAMPLE 324

Preparation of 1S-(1S*,2R*)-N, N'-Iminobis[2-hydroxy-1-(phenylmethyl)-3,1-propanediyl]bis (imino)bis[1-(1,1-dimethylethyl)-2-oxo-2,1-ethanediyl]]biscarbamic acid, dimethyl ester (Compound 324)

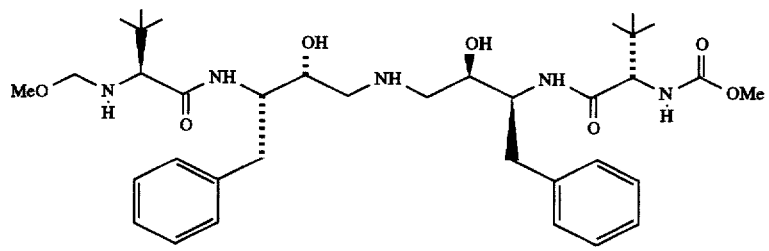

Compounds 74 and 246a were reacted by a procedure analogous to that of Example 75f to give the title Compound 324 (colorless solid).

m.p. 98°–102° C.; $[\alpha]_D$=−37.7° (c 0.25, CHCl₃). Mass Spec.: (FAB): 686 (M+H). Anal. Calc. for $C_{36}H_{55}N_5O_8 \cdot 0.73 H_2O$: C, 61.86; H, 8.14; N, 10.02; Found: C, 61.86; H, 8.09; N, 10.06

EXAMPLE 325

Preparation of [1S-[1R*,2S*(2S*,3R*)]]-[2-Hydroxy-3-[[2-hydroxy-3-[(2-methoxy-3,3-dimethyl-1-oxobutyl)amino]-4-phenylbutyl]amino]-1-(phenylmethyl)-propyl]carbamic acid, 1,1-dimethylethyl ester (Compound 325b)

(a) Compound 325a

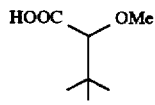

Through a solution of 4,4-dimethyl-3-methoxy-1-pentene (*J. Am. Chem. Soc.*, 109, 3353, (1987); 0.512 g, 4 mmol) in 10 mL of CH₂Cl₂ cooled to −78° C. was bubbled O₃ for a period of 2 h until a light blue color persisted. To the mixture was added Me₂S (1.468 mL, 20 mmol) and the yellow solution stirred at RT for 2 h at which point most of the solvent was distilled off. The resulting aldehyde was then converted to Compound 325a by a procedure analogous to that of Example 262e.

(b) Compound 325b

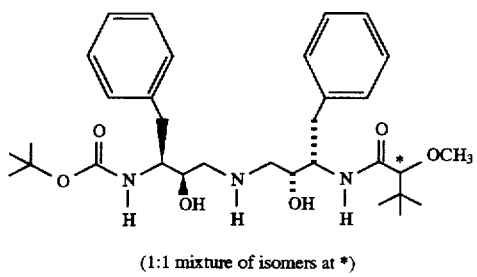

(1:1 mixture of isomers at *)

Compounds 325a and 54 were reacted by a procedure analogous to that of Example 55 to give the title Compound 325b (white solid).

m.p. 153°–162° C.; Mass Spec. (FAB) (M+H)⁺=572; Analysis calc. for $C_{32}H_{49}N_3O_6 \cdot 0.58 H_2O$: C, 66.02; H, 8.68; N, 7.22; Found: C, 65.99; H, 8.56; N, 7.25.

EXAMPLE 326

Preparation of [S-[1R*,2S*(2S*,3R*)]]-[2,2-Dimethyl-1-[[[3-[[3-[[(1,1-dimethylethoxy)carbonyl]amino]-2-hydroxy-4-phenylbutyl]amino]-2-hydroxy-1-(phenylmethyl)propyl]amino]carbonyl]propyl] carbamic acid, (2-(phenyloxy)ethyl ester (Compound 326)

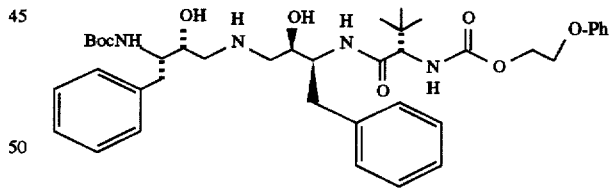

2-Phenoxyethanol was converted to its p-nitrophenyl carbonate which was reacted with tert-leucine and the resulting product coupled with Compound 54 by a three-step procedure analogous to that used for Example 257a through 257c to give the title Compound 326 (colorless solid).

m.p. 138°–140° C. (shrinks 120° C.); $[\alpha]_D$=20.4° (c 0.3, CHCl₃). Mass Spec.: (FAB): 721 (M+H). Anal. Calc. for $C_{36}H_{53}N_5O_9 \cdot 0.31 H_2O$; C, 66.13; H, 7.86; N, 7.71; Found: C, 66.09; H, 7.85; N, 7.75.

EXAMPLE 327

Preparation of [1R*,2S*(2S*,3R*)-N-[3-[[3-[[(1,1-Dimethylethoxy)carbonyl]amino]-2-hydroxy-4-[4-[2-(2-pyridinyl)ethoxyl]phenyl]butyl]amino]-2-hydroxy-1-(phenylmethyl)propyl]-N²-(methoxycarbonyl)-3-methyl-L-valinamide (Compound 327c)

(a) Compound 327a

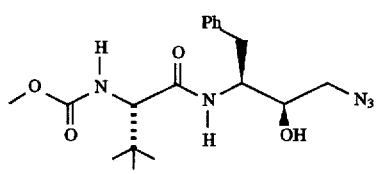

To an ice cooled solution, under argon, of 608 mg (2.5 mmol) of Compound 298a, 520 mg (2.75 mmol) of Compound 246a, 371 mg (2.75 mmol) of HOBT and 905 µl of N-methylmorpholine in 12.5 ml of DMF was added 528 mg (2.75 mmol) of EDCI. Stirring was continued with cooling for 1 h, then at RT overnight. The solution was evaporated to dryness (30° C., high vacuum) and the residue taken into EtOAc and washed with brine, 1N HCl , brine, sat. NaHCO₃, and brine. After drying (MgSO₄), removal of solvent afforded 1.03 g of Compound 327a as a solid white foam.

(b) Compound 327b

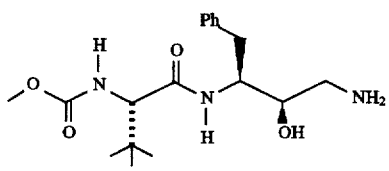

A solution of 250 mg (0.66 mmol) of Compound 327a in 8 ml of EtOH, containing 25 mg of 10% Pd on carbon catalyst, was stirred under an atmosphere of H₂ for 4 h. After removal of catalyst by filtration through Celite, removal of solvent gave a solid foam residue which was recrystallized from CHCl₃ to afford 108 mg (47% yield over 2 steps) of Compound 327b as a white powder.

(c) Compound 327c

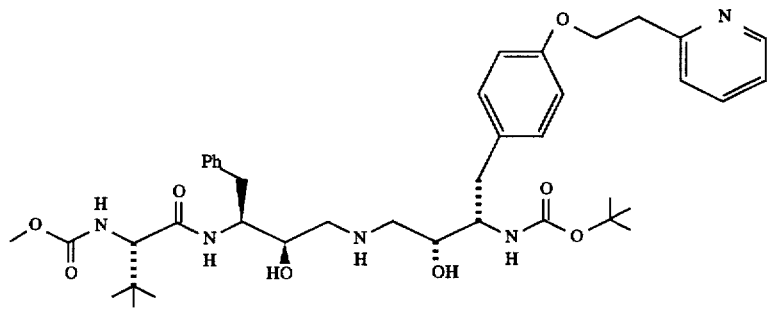

A solution of 246 mg (0.70 mmol) of Compound 327b and 250 mg (0.65 mmol) of Compound 282a in 1 ml of DMF, under argon, was heated at 100° C. for 5 h. The solvent was removed (30° C., high vacuum) and the residue purified by flash chromatography on a 130 cc column of silica gel. Elution with CHCl₃:MeOH:NH₄OH (95:5:0.5) followed by recrystallization from hot EtOAc afforded 170 mg of Compound 327c as a white solid.

m.p. 139°–141° C.; [α]$_D$=−15.9° (c 0.92, MeOH). Mass Spec.: (M+H)⁺736⁺; Analysis Calc. for C₄₀H₅₇N₅O₈·0.46 H₂O: C, 64.56; H, 7.84; N, 9.41. Found: C, 64.82; H, 7.87; N, 9.41.

EXAMPLE 328

Preparation of [1S-[1R*,2S*(2S*,3R*)]]-[2-[[3-[[3-[[(1,1-Dimethylethoxy)carbonyl]amino]-2-hydroxy-4-phenylbutyl]amino]-2-hydroxy-1-(phenylmethyl)propyl]amino]-2-oxo-1-(trifluoromethyl)ethyl] carbamic acid, phenylmethyl ester (Compound 328b)

(a) Compound 328a

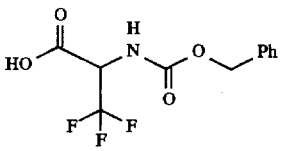

Compound 328a was prepared from D,L-trifluoromethyl alanine by a procedure analogous to that of Example 85a.

(b) Compound 328b

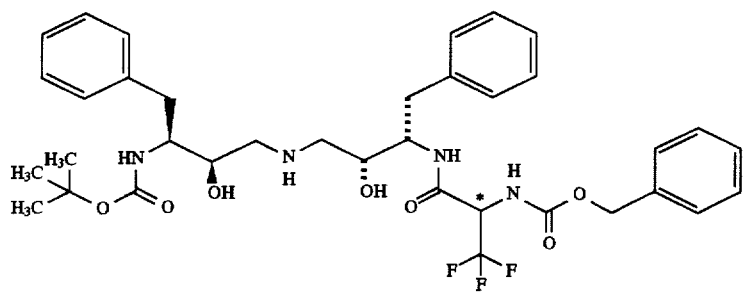

(1:1 mixture of isomers at *)

Compounds 328a and 48 were reacted by a two-step procedure analogous to that used for the conversion of Compound 48 to 52 to give the title Compound 328b (white solid).

m.p. 166°–169° C.; $[\alpha]_D = -5.7°$ (c=0.21, CH$_3$OH); Analysis calculated for: C$_{36}$H$_{45}$N$_4$O$_7$F$_3$·1.21 H$_2$O; C, 59.68; H, 6.60; N, 7.73; F, 7.87; Found: C, 59.74; H, 6.47; N, 7.67; F, 7.81

EXAMPLE 329

Preparation of [1S-[1R*,2S*(2S*,3R*)]]-[3-[[3-[[(1-Amino-2,2,2-trifluoroethyl)carbonyl]amino]-2-hydroxy-4-phenylbutyl]amino]-2-hydroxy-1-(phenylmethyl)propyl]carbamic acid, 1,1-dimethylethyl ester (Compound 329)

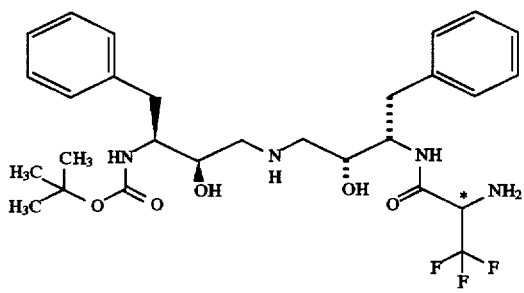

(1:1 mixture of isomers at *)

Compound 328b was converted to the title Compound 329 by a procedure analogous to that of Example 19.
m.p. 152°–155° C.

EXAMPLE 330

Preparation of [1S-[1R*,2S*(2S*,3R*)]]-[2-hydroxy-3-[[2-hydroxy-3-[[(tetrahydro-3-hydroxy-3-furanyl)carbonyl]amino]-4-phenylbutyl]amino]-1-(phenylmethyl)propyl]carbamic acid, 1,1-dimethylethyl ester (Compound 330b)

(a) Compound 330a

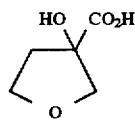

To a solution of Compound 314a (2.02 g, 23.46 mmol) in CH$_2$Cl$_2$ (2.5 mL) was added trimethylsilyl cyanide (4.06 mL, 30.50 mmol), ZnI$_2$ (0.22 g, 0.70 mmol) and the solution stirred at RT for 18 h. The reaction mixture was purged with a stream of nitrogen, concentrated in vacuo and taken in concentrated HCl (6 mL) and heated at reflux for 2 h. After cooling to RT, the mixture was saturated with Na$_2$SO$_4$ and extracted with EtOAc, dried (MgSO$_4$) and concentrated in vacuo to yield a brown gummy oil. The crude product was combined with another batch (1.06 g, 12.3 mmol) of similar crude material and partially purified by silica gel chromatography, eluting with CH$_3$OH (5% to 60%)—CH$_2$Cl$_2$ (with 1 to 2% HOAc). The product was taken in 3N NaOH and washed with Et$_2$O. The aqueous layer was acidified to pH ca. 2 by addition of 6N HCl, saturated with Na$_2$SO$_4$, and extracted repeatedly with EtOAc. The combined organic layer was dried (MgSO$_4$), and concentrated in vacuo to afford Compound 330a (2.5 g, 52% overall yield) as a brown oil.

(b) Compound 330b

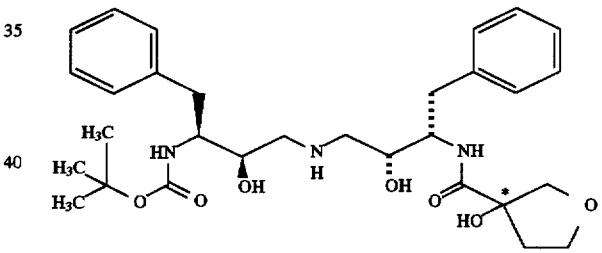

(1:1 mixture of diastereomers at *)

Compounds 330a and 54 were reacted by a procedure analogous to that of Example 262f to give the title Compound 330b.

m.p. 119°–122° C.; $[\alpha]_D = 3.5°$ (c=0.2, CH$_3$OH); Analysis calculated for: C$_{30}$H$_{43}$N$_3$O$_7$·0.45 H$_2$O; C, 63.68; H, 7.82; N, 7.43; Found: C, 63.63; H, 7.79; N, 7.48

EXAMPLE 331

Preparation of [1S-(1R*,2S*,3R*)]-[Iminobis[2-hydroxy-1-(phenylmethyl)-3,1-propanediyl]]bis[carbamic acid], 3-tetrahydrofuranyl 1,1-dimethylethyl ester (Compound 331c)

(a) Compound 331a

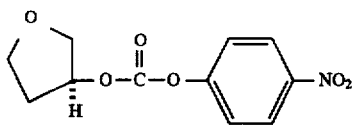

To a solution of (S)-(+)-3-hydroxy-tetrahydrofuran (441 mg, 5.0 mmol) in 15 mL of CH$_2$Cl$_2$-pyridine (5:1) cooled at 0° C. was added a solution of para-nitrophenylchloroformate (1.0 g, 5.0 mmol) in 12.5 mL of CH$_2$Cl$_2$. The reaction was stirred at 0° C. for 1.0 h, then at RT overnight. The reaction mixture was diluted with EtOAc and the organic layer was washed with sat. aq. NaHCO$_3$ and brine, and dried (Na$_2$SO$_4$). Flash chromatography (hexane-EtOAc: 10:1 to 2:1) on silica gel afforded 1.25 g (99%) of Compound 331a as a colorless liquid.

(b) Compound 331b

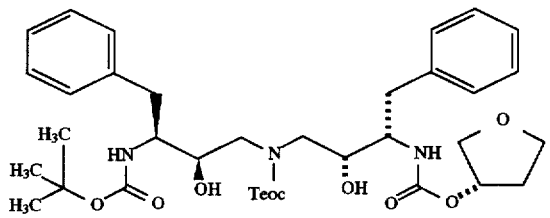

To a solution of Compound 48 (200 mg, 0.340 mmol) in 0.25 mL DMF was added i-Pr$_2$NEt (220 mg; 1.7 mmol), followed by Compound 331a (112 mg, 0.442 mmol) in DMF (0.3 mL). After stirring overnight at RT, the reaction was concentrated in vacuo and diluted with EtOAc. After washing with aq. 1N NaOH, sat. aq. NaHCO$_3$ and brine, the organic phase was dried (MgSO$_4$) and concentrated in vacuo. The crude material was purified by flash chromatography on silica gel, eluting with a gradient from 0.5–5% MeOH/CH$_2$Cl$_2$ to afford 0.2 g (83%) of a yellow foam. Mass Spec. (Fab): (M+H)$^+$702$^+$.

(c) Compound 331c

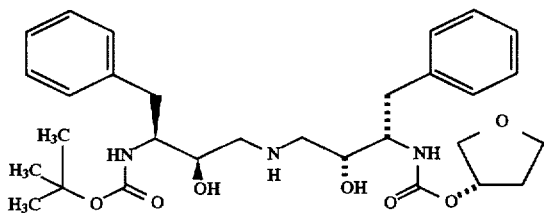

To Compound 331b (200 mg, 0.284 mmol) in THF (2 mL) was added solid n-Bu$_4$NF•nH$_2$O (223 mg, 0.854 mmol) and the mixture stirred at 50° C. for 5h. The reaction was concentrated in vacuo, the residue dissolved in EtOAc, and washed with sat. aq. NaHCO$_3$ and brine. The organic phase was dried (MgSO$_4$) and concentrated in vacuo to give a solid which was purified by flash chromatography on silica gel, eluting with a gradient from 98.5:1.5:0.15 to 92.5:7.5:0.75 CH$_2$Cl$_2$:MeOH:NH$_4$OH, to afford the title Compound 331c (102 mg, 64%) as a white solid.

m.p. 200°–202° C.; [α]$_D$=−14.5° (c=0.2, CH$_3$OH); Mass Spec. (CI): (M+H)$^+$558. Analysis calculated for:C$_{30}$H$_{43}$N$_3$O$_7$·* 1.70 H$_2$O C, 61.08; H, 7.96; N, 7.12. Found: C, 61.10; H, 7.45; N, 7.10.

EXAMPLE 332

Preparation of [1S-[1R*,2S* (2S*,3R*)]]-[3-[[3-[[ (1,1-Dimethylethoxy)carbonyl]amino]-2-hydroxy-4-[4-[2-oxo-2-(1-tetrahydropyranyl) ethoxyl phenyl]butyl]amino]-2-hydroxy-1-(phenylmethyl) propyl]carbamic acid, 1,1-dimethylethyl ester (Compound 332c)

(a) Compound 332a

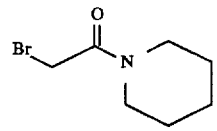

Bromoacetyl bromide (0.87g, 10 mmol) was added dropwise to a stirring solution of piperidine (2.03 ml, 20.60 mmol) in anhydrous Et$_2$O (21 ml) at 0° C. After 20 min, the reaction was filtered, and the solid washed with Et$_2$O. The filtrate was concentrated in vacuo and the crude material chromatographed on a CC$_7$ column, eluting with EtOAc, to afford 1.27g (62%) of Compound 332a as a yellow oil.

(b) Compound 332b

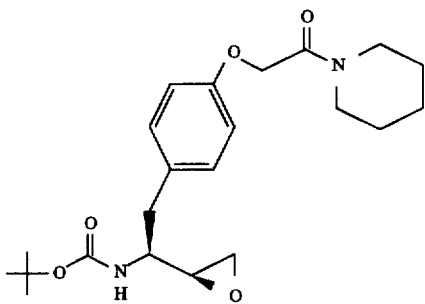

Compounds 175c and 332a were reacted by a procedure analogous to that of Example 226a to give Compound 332b.

(c) Compound 332c

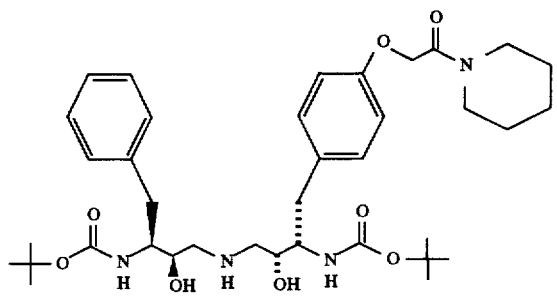

Compounds 16b and 332b were reacted by a procedure analogous to that of Example 226b to give the title Compound 332c (colorless solid).

m.p. 116°–118° C.; [α]$_D$=−6.0° (c, 0.10 MeOH). Mass spec.: (M+H) 685. Analysis calc. for C$_{37}$H$_{56}$N$_4$O$_8$·0.53H$_2$O. C, 64.00; H, 8.28; N, 8.07; Found: C, 64.05; H, 8.43; N, 8.02.

EXAMPLE 333

Preparation of [1S-[1R*,2S*[2S*3R*(S*)]]]-[3-[[3-[(2-Hydroxy-2,3,3-trimethyl-1-oxobutyl)amino]-2-hydroxy-4-phenylbutyl]amino-2-hydroxy-1-(phenylmethyl)propyl]carbamic acid, 2-hydroxy-1,1-dimethylethyl ester (Compound 333d)

(a) Compound 333a

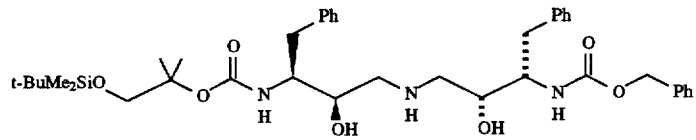

To a solution of Compound 298c (380 mg, 0.93 mmol) in DMF (0.5 mL) was added Compound 44a (276 mg, 0.93 mmol) and the solution heated at 100° C. for 4 h. The reaction mixture was cooled to RT and DMF removed in vacuo. Purification by silica gel chromatography, eluting with a stepwise gradient from 99.5:0.5:0.05 to 90:10:1 $CH_2Cl_2$:$CH_3OH$:aq.$NH_4OH$ afforded Compound 333a (367 mg, 55% yield) as a white residue.

Mass Spec: $(M+H)^+$=708.

(b) Compound 333b

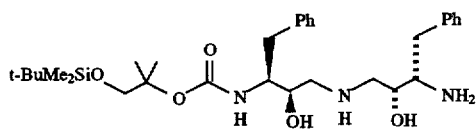

To a solution of Compound 333a (365 mg, 0.52 mmol) in EtOH (14 mL) and EtOAc (3.5 mL) was added 20% Pd(OH)$_2$/C (110 mg total added in three portions over the reaction) and the slurry stirred under a H$_2$ atmosphere overnight. Filtration, evaporation, and trituration of the resulting solid gave Compound 333b (230 mg, 77% yield) as a white solid.

Mass Spec: $(M+H)^+$=574

(c) Compound 333c

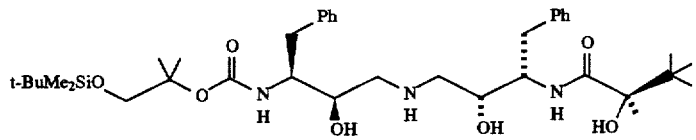

To a solution of Compound 333b (127 mg, 0.22 mmol) in DMF (0.25 mL) was added a solution of Compound 262e (35.6 mg, 0.243 mmol) in 0.25 mL DMF, followed by BOP reagent (107.5 mg, 0.243 mmol) and N-methylmorpholine (53.45 µL) and the reaction stirred for 36 h. The DMF was evaporated in vacuo and the residue dissolved in EtOAc which was washed with satd. NaHCO$_3$ and brine and dried (MgSO$_4$). Silica gel chromatography eluting with a stepwise gradient from 98:2:0.2 to 90:10:1 $CH_2Cl_2$:$CH_3OH$:aq.$NH_4OH$ afforded Compound 333c (105 mg, 67% yield) as a solid.

Mass Spec: $(M+H)^+$=702

(d) Compound 333d

To a solution of Compound 333c (103 mg, 0.146 mmol) in THF (1.5 mL) was added H$_2$O (0.5 mL) and HOAc (0.5 mL) and the reaction mixture stirred at RT for 2 d. Evaporation to dryness, azeotroping with H$_2$O and purification by silica gel chromatography eluting with a stepwise gradient from 98:2:0.2 to 90:10:1 $CH_2Cl_2$:$CH_3OH$:aq.$NH_4OH$ afforded the title Compound 333d (74 mg, 86% yield) as a white solid.

m.p. 185°–188° C.; $[\alpha]_D$=+19.50° (c=0.2, $CH_3OH$); Mass spec. (CI): $(M+H)^+$588$^+$. Analysis calc. for:$C_{32}H_{49}N_3O_7$·0.75 H$_2$O; C, 63.93; H, 8.47; N, 6.99; Found: C, 63.93; H, 8.32; N, 7.11

EXAMPLE 334

Preparation of [1S-[1R*,2S*[2S*,3R*(S*)]]]-[3-[[3-[(2-Hydroxy-3,3-dimethyl-1-oxobutyl)amino]-2-hydroxy-4-phenylbutyl]amino]-2-hydroxy-1-(phenylmethyl)propyl]carbamic acid, 1,1-dimethylethyl ester (Compound 334)

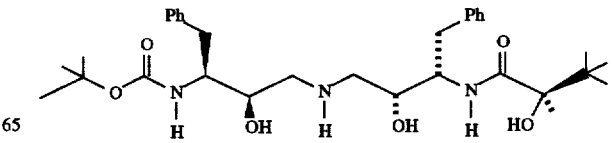

To an ice cooled solution of 73 mg (0.55 mmol) of (R)-3,3-dimethyl-2-hydroxybutanoic acid (Ito et al., Synthesis, 137 (1993)), 244 mg (0.55 mmol) of Compound 54, 111 mg (0.83 mmol) of HOBT and 121 µl (1.1 mmol) of N-methylmorpholine was added 105 mg (0.55 mmol) of EDCI as a solid. Stirring was continued with cooling for 1 h, then at RT overnight. The resulting solution was then added with stirring to an ice-sat. NaHCO$_3$ mixture. The resulting precipitate was filtered and washed with H$_2$O. The crude product was taken into CH$_2$Cl$_2$, dried (MgSO$_4$), and the solution placed on a 50 cc column of silica gel. Elution with CHCl$_3$:MeOH:NH$_4$OH (95:5:0.5) afforded impure product. This material was recrystallized from CH$_2$Cl$_2$ and then rechromatographed on a 100 cc column of silica gel. A gradient elution with CHCl$_3$:MeOH:NH$_4$OH (95:5:0.1 to 0.5) afforded 20 mg of Compound 334 as a white powder.

m.p. 175°–176° C.; [α]$_D$=+1.1° (c 0.08, MeOH). Mass Spec.: (M+H)$^+$558$^+$; Analysis Calc. for C$_{31}$H$_{47}$N$_3$O$_6$·0.25 H$_2$O: C, 66.23; N, 8.52; N, 7.47. Found: C, 66.23, H, 8.46; N, 7.39.

EXAMPLE 335

Preparation of [1S-[1R*,2S*[2S*,3R*(R*)]]]-[3-[[3-[(2-Hydroxy-3,3-dimethyl-1-oxobutyl)amino]-2-hydroxy-4-phenylbutyl]amino]-2-hydroxy-1-(phenylmethyl)propyl]carbamic acid, 1,1-dimethylethyl ester (Compound 335)

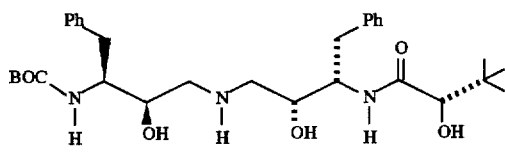

Compound 335 (white solid) was prepared from (S)-3,3-dimethyl-2-hydroxybutanoic acid and Compound 54 by a procedure analogous to that of Example 334.

m.p.: 92°–96° C.; [α]$_D$=–2.7° (c 0.81, MeOH). Mass Spec.: (M+H)$^+$ 558$^+$; Analysis Calc. for C$_{31}$H$_{47}$N$_3$O$_6$·1.0 H$_2$O: C, 64.60; N, 8.58; N, 7.29. Found: C, 64.60, H, 8.57; N, 7.02.

EXAMPLE 336

Preparation of N, N'-[Iminobis[(1S,2R)-2-Hydroxy-1-(Phenylmethyl)-3,1-propanediyl]]bis-[1-hydroxy-2,2-dimethylcyclopentanecarboxamide], isomer A (Compound 336b)

(a) Compound 336a

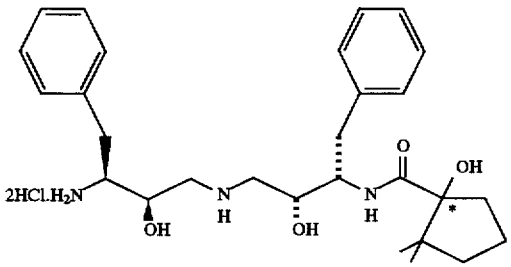

A solution of Compound 321d (115 mg; 0.197 mmol) in 3 ml of HCl saturated EtOAc was stirred 1 h at 0° C. The volatiles were removed in vacuo to afford 109 mg (99%) of Compound 336a as an off-white solid.

$^1$H NMR (CD$_3$OD): δ 0.82 (s, 3H), 0.94 (s, 3H), 1.65 (m, 5H), 2.05 (m, 1H), 2.80 (dd, J=10.5, 13.5 Hz, 1H), 2.91 (dd, J=8.5, 14.5 Hz, 1H), 3.04 (m, 3H), 3.22 (m, 3H), 3.70 (m, 1H), 3.90 (m, 1H), 4.03 (m, 1H), 4.25 (m, 1H), 7.33 (m, 10H).

(b) Compound 336b

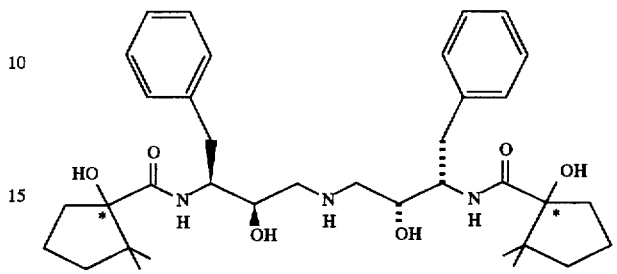

BOP-reagent (89 mg; 0.200 mmol) was added in one portion to a solution of Compound 336a (105 mg; 0.189 mmol), Compound 321c (30 mg; 0.190) and N-methylmorpholine (65 ml; 0.580 mol) at 0° C. in 0.5 ml of DMF. The reaction mixture was allowed to warm to RT and stir 18 h. After diluting with EtOAc, the organic phase was washed with H$_2$O, saturated NaHCO$_3$ solution and brine. After drying (Na$_2$SO$_4$), the solvent was removed in vacuo. The residue was preabsorbed on celite and chromatographed on a 2.5×15 cm silica gel column eluting with CH$_2$Cl$_2$; 1% MeOH/CH$_2$Cl$_2$; 2% MeOH/CH$_2$Cl$_2$; 2.5% MeOH/CH$_2$Cl$_2$; then 3–5% MeOH/CH$_2$Cl$_2$+0.3–0.5% NH$_4$OH in 0.25% and 0.025% increments respectively to afford 14.4 mg (12%) of Compound 336b (white solid) as a single symmetrical isomer of undetermined absolute configuration.

m.p. 135°–145° C.; R$_f$=0.25, CH$_2$Cl$_2$:MeOH:NH$_4$OH, 90:9:1 (UV and PMA detection); [α]$_D$=+28.2° (c 0.38, MeOH). Mass Spec.: M+H=624.

EXAMPLE 337

Preparation of N, N'-[Iminobis[(1S,2R)-2-Hydroxy-1-(Phenylmethyl)-3,1-propanediyl]]bis-[1-hydroxy-2,2-dimethylcyclopentanecarboxamide], isomer B (Compound 337)

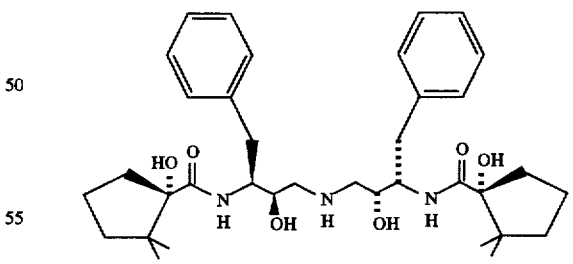

Compound 337 was isolated as the more polar isomer from the reaction described in Example 336. Recrystallization from ether/hexane gave 18 mg (15%) of a white solid.

m.p. 109°–112° C.; R$_f$=0.19, CH$_2$Cl$_2$:MeOH:NH$_4$OH, 90:9:1 (UV and PMA detection); [α]$_{365}$=+25.7° (c 0.33, MeOH). Mass Spec.: M+H=624. Analysis Calc. for C$_{36}$H$_{53}$N$_3$O$_6$·1.35 H$_2$O: C, 66.71; N, 8.66; N, 6.48. Found: C, 66.52, H, 8.52; N, 6.67.

EXAMPLE 338

Preparation of [1S-(1R*,2S*), (R*)]-[Iminobis[2-hydroxy-1-(phenylmethyl)-3,1-propanediyl]]bis[carbamic acid], bis(3-tetrahydrofuranyl)ester (Compound 338b)

(a) Compound 338a

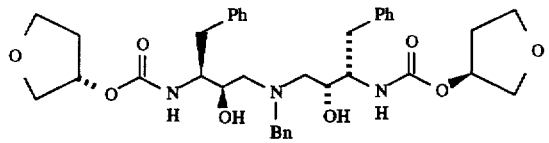

Compound 32 was reacted with 3 eq. of Compound 331a and 10 eq. of iPr₂NEt by a procedure analogous to that of Example 149e (DMF was used in place of CH₃CN) to give Compound 338a.

(b) Example 338b

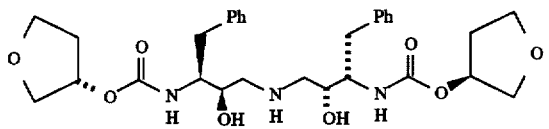

Compound 338a was converted to the title Compound 338b (white solid) by a procedure analogous to that of Example 2.

m.p. 230°–231° C.; $[\alpha]_D$=23.5° (c 0.2, HOAc). Mass Spec. (FAB): 572⁺ (M+H)⁺. Analysis Calc. for $C_{30}H_{41}N_3O_8$: C, 63.03; H, 7.23; N, 7.35. Found: C, 63.19; H, 7.33; N, 7.04.

EXAMPLE 339

Preparation of [S-[1R*,2S*(2S*,3R*)]]-[2,2-Dimethyl-1-[[[3-[[3-[[(1,1-dimethylethoxy)carbonyl]amino]-2-hydroxy-4-phenylbutyl]amino]-2-hydroxy-1-(phenylmethyl)-propyl]amino]carbonyl]propyl]carbamic acid, (2-furo[2,3-c]pyridinyl) methyl ester (Compound 339f)

(a) Compound 339a

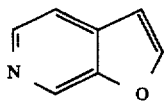

Compound 339a was prepared as described in Shiotani et al., *J. Heter. Chem.*, 19, 1207 (1982).

(b) Compound 339b

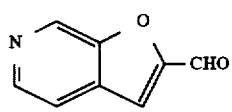

Compound 339b was prepared from Compound 339a as described in Shiotani et al., *J. Heter. Chem.*, 24, 373 (1987).

(c) Compound 339c

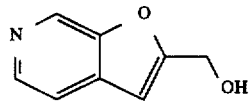

To a solution of Compound 339b (0.66 g, 4.49 mmol) in 50 mL of 3:3:4 THF-EtOH—CHCl₃ cooled to 0° C. was added NaBH₄ (0.298 g, 7.86 mmol) in portions. After addition was complete, the mixture was stirred at 0° C. for 30 min, diluted with H₂O and extracted with CH₂Cl₂. The combined extracts were dried (MgSO₄) and concentrated. The crude residue was flash chromatographed on silica gel eluting with a stepwise gradient of 25% to 100% EtOAc-hexane to afford Compound 339c (0.555 g, 83%) as a white solid.

(d) Compound 339d

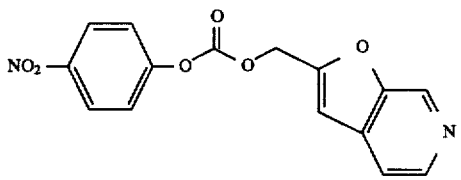

5 To a solution of Compound 339c (0.298 g, 2 mmol) in 15 mL of CH₂Cl₂ cooled to 0° C. was added 1 mL of pyridine followed by p-nitrophenyl-chloroformate (0.403 g, 2 mmol) as a solid. The reaction mixture was stirred for 16 h at RT, diluted with EtOAc and washed with sat. NaHCO₃ and brine. The organic phase was dried (MgSO₄) and concentrated to obtain Compound 339d (0.6 g, 95%; crude yield) containing traces of p-nitrophenylchloroformate and p-nitrophenol.

(e) Compound 339e

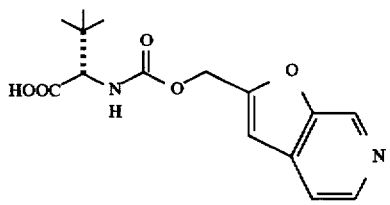

Compound 339d (0.6 g; 1.91 mmol) in 5 mL of dioxane was added to a solution of L-tert-leucine (0.25 g; 1.91 mmol) in 1.92 mL of 1N NaOH at RT followed by the addition of Et₃N (293 μL; 2.1 mmol). After 24 h at RT, the reaction mixture was diluted with 10% KHSO₄ and extracted with EtOAc. The aqueous phase was brought to pH 3.5 with 2N NaOH and extracted with EtOAc. The organic extracts were washed with brine, dried (MgSO₄) and concentrated to afford 0.5 g (85%) of Compound 339e as an off-white solid.

(f) Compound 339f

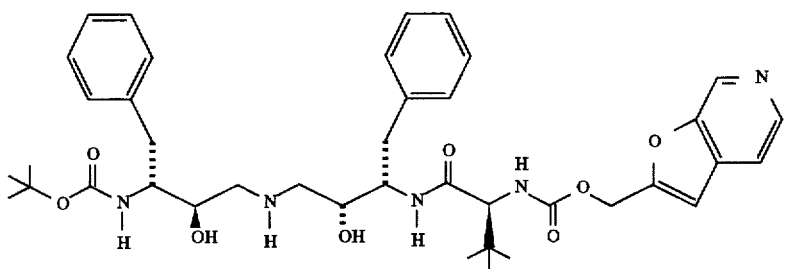

To a 0° C. solution of Compound 339e (0.173 g; 0.56 mmol) in 3 mL of CH$_2$Cl$_2$ was added HOBT (0.115 g; 0.84 mmol) followed by EDCI (0.114 g; 0.59 mmol). After 30 min, Compound 54 (0.25 g; 0.56 mmol) was added followed by 0.5 ML of DMF. The reaction mixture was stirred at 0° C. for 30 min and at RT for 16 h, at which time it was diluted with CH$_2$Cl$_2$, and washed with H$_2$O, sat. aq. NaHCO$_3$ and brine. The organic extracts were dried (MgSO$_4$), concentrated, and the resulting residue purified by flash chromatography on silica gel, eluting with a gradient of 96.7:3:0.3 to 89:10:1 CH$_2$Cl$_2$:MeOH:NH$_4$OH, to afford 0.135 g (33%) of the title Compound 339f as an off-white solid.

m.p. 95°–105° C.; $[\alpha]_D = -19.4°$ (c=0.2, CH$_3$OH). Mass Spec. (FAB) (M+H)$^+$=732; Analysis calc. for C$_{40}$H$_{53}$N$_5$O$_8$·1.39 H$_2$O: C, 63.42; H, 7.43; N, 9.25 Found: C, 63.33; H, 7.23; N, 9.34.

EXAMPLE 340

Preparation of [1S*,2R*(2R*,3S*)]-N-[3-[[3-[[(1,1-Dimethylethoxy)carbonyl]amino]-2-hydroxy-4-phenylbutyl]amino]-2-hydroxy-1-(phenylmethyl)propyl]-N$^2$-(2-methoxycarbonyl)-3-methyl-D-valinamide (Compound 340)

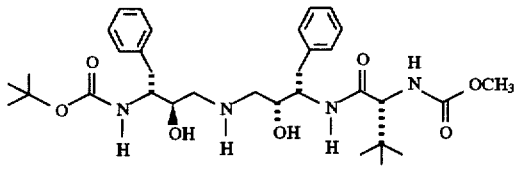

(D)-t-Leucine and Compound 54 were converted to the title Compound 340 by the two-step procedure described in Example 246.

m.p. 135°–143° C.; $[\alpha]_D = +13.4°$ (c=0.2, CH$_3$OH). Mass Spec. (FAB) (M+H)$^+$=615; Analysis calc. for C$_{40}$H$_{53}$N$_5$O$_8$·1.39 H$_2$O: C, 61.95; H, 8.31; N, 8.76 Found: C, 61.95; H, 8.12; N, 8.93.

EXAMPLE 341

Preparation of [1R*,2S*(2S*,3R*)]-N-[3-[[3-[[(1,1-Dimethylethoxy)carbonyl]amino]-2-hydroxy-4-phenylbutyl]amino]-2-hydroxy-1-[[4-[2-(4-morpholinyl)-2-oxoethoxy]phenyl]methyl]propyl]-N$^2$-(2-methoxycarbonyl)-3-methyl-L-valinamide (Compound 341e)

(a) Compound 341a

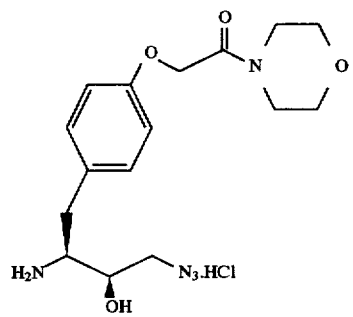

Compound 226a was converted to Compound 341a by a two-step procedure analogous to that used for the conversion of Compound 282a to Compound 282c.

(b) Compound 341b

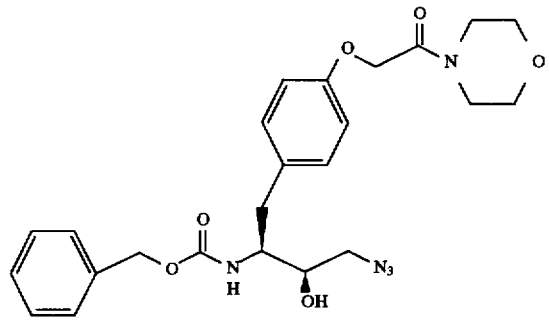

Compound 341a was converted to Compound 341b by a procedure analogous to that of Example 122 except that carbobenzyloxy chloride was used.

(c) Compound 341c

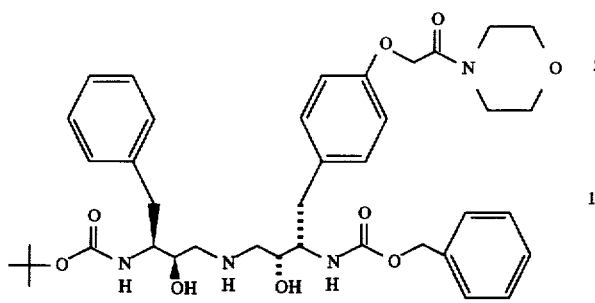

Compounds 341b and 1b(i) were converted to Compound 341c by a two-step procedure analogous to that used for the conversion of Compound 282d to Compound 282f.

(d) Compound 341d

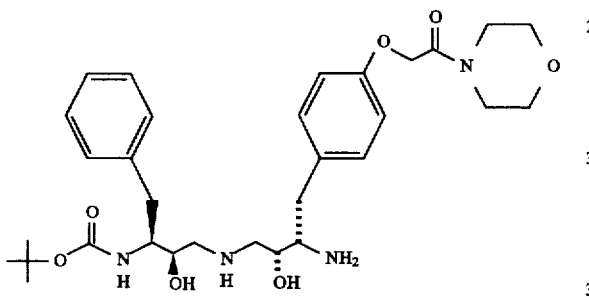

Compound 341c was converted to Compound 341d by a procedure analogous to that of Example 19.

(e) Compound 341e

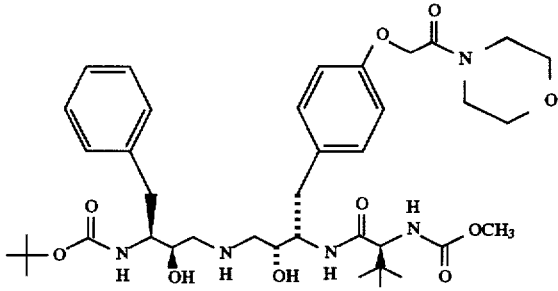

Compounds 341d and 246a were reacted by a procedure analogous to that of Example 246b to give the title Compound 341e (white solid).

m.p. 128°–130° C.; $[\alpha]_D = -12°$ (c=0.07, MeOH). Mass spec.: 758⁺(M+H)⁺. Analysis calc. for $C_{39}H_{59}N_5O_{10}$ 109 0.9 $H_2O$: C, 60.51; H, 7.92; N, 9.05; Found: C, 60.79; H, 8.01; N, 8.65.

EXAMPLE 342

Preparation of [1R*,2S* (2S*, 3R*)]-N-[3-[[3-[[(1,1-Dimethylethoxy)carbonyl]amino]-2-hydroxy-4-phenylbutyl]amino]-2-hydroxy-1-(phenylmethyl)propyl]-$N^2$-[(methylamino)carbonyl]-$N^2$-3-dimethyl-L-valinamide (Compound 342f)

(a) Compound 342a

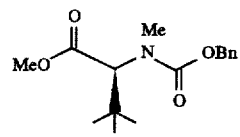

Compound 88a was converted to Compound 342a by a procedure analogous to that of Example 66a (except that DMF was used as solvent instead of THF).

(b) Compound 342b

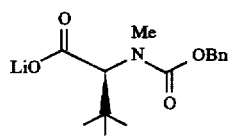

Compound 342a was converted to Compound 342b by a procedure analogous to that of Example 70c except that the reaction was not acidified before evaporation.

(c) Compound 342c

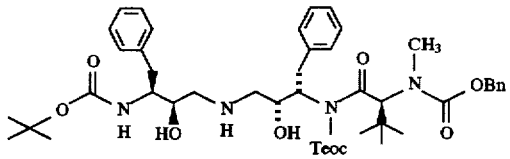

To a 0° C. solution of Compound 48 (200 mg; 0.34 mmol) and Compound 342b (102 mg; 0.35 mmol) in anhydrous DMF (0.68 mL) were successively added BOP reagent (0.154 g; 0.350 mmol) and N-methyl morpholine (0.188 mL; 1.71 mmol). The solution was allowed to warm to RT and stirred for 36 h. Volatiles were removed in vacuo and the residue was partitioned between saturated aqueous $NaHCO_3$ and EtOAc. The combined organic extracts were washed with brine, dried ($Na_2SO_4$), and concentrated in vacuo to give a viscous oil, which was chromatographed on silica gel using a gradient from 10% EtOAc-hexane to 50% EtOAc-hexane to furnish Compound 342c (233 mg; 81%) as a white solid.

(d) Compound 342d

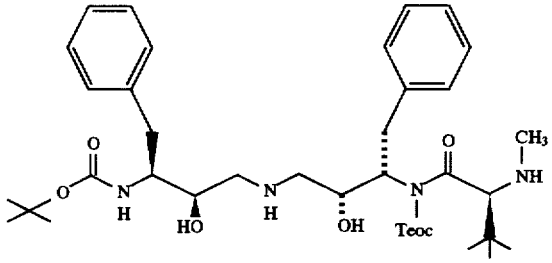

Compound 342c was converted to Compound 342d (white solid) by a procedure analogous to that of Example 19.

(e) Compound 342e

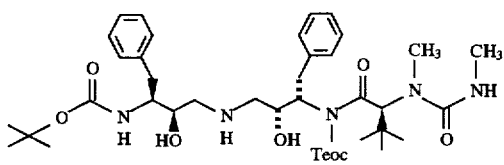

Compound 342d and methyl isocyanate were reacted by a procedure analogous to that of Example 46 to give Compound 342e (colorless oil).

(f) Compound 342f

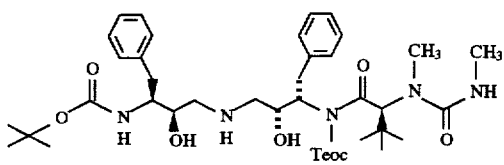

Compound 342e was converted to the title Compound 342f (white solid) by a procedure analogous to that of Example 21.

m.p. 87°–90° C. Mass Spec. (FAB): (M+H)=628

EXAMPLE 343

Preparation of [1S-[1R*,2S*(2S*,3R*)]]-[1-[[[3-[[(1,1-Dimethylethoxy)carbonyl]amino]-2-hydroxy-4-[4-[2-(2-oxo-3-oxazolidinyl)ethoxy]phenyl]butyl]amino]-2-hydroxy-1-(phenylmethyl)propyl]carbamic acid, 1,1-dimethylethyl ester (Compound 343c)

(a) Compound 343a

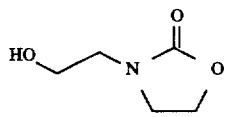

Diethanolamine was converted to Compound 343a by a procedure analogous to that of Example 315a.

(b) Compound 343b

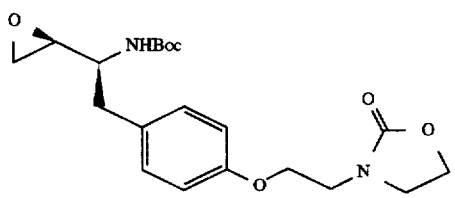

Compounds 175c and 343a were reacted by a procedure analogous to that of Example 282a to give Compound 343b.

(c) Compound 343c

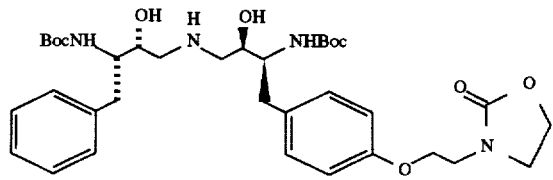

Compounds 16b and 343b were reacted by a procedure analogous to that of Example 226b (except that the reaction was run in MeOH at 60° C.) to ethoxy]afford the title Compound 343c (colorless solid).

m.p. 130.5°–133.5° C.; $[\alpha]_D$=–3.1° (c0.27, MeOH). Mass Spec.: (FAB): 673 (M+H). Anal. Calc. for $C_{35}H_{52}N_4O_9 \cdot 0.25$ $H_2O$ C, 62.07; H, 7.81; N, 8.27; Found: C, 62.04; H, 7.84; N, 8.29.

EXAMPLE 344

Preparation of [2R-[R*(R*,S*)]]-N,N'-[Iminobis[2-hydroxy-1-(phenylmethyl)-3,1-propanediyl]]bis[2-hydroxy-2,3,3-trimethylbutaneamide](Compound 344)

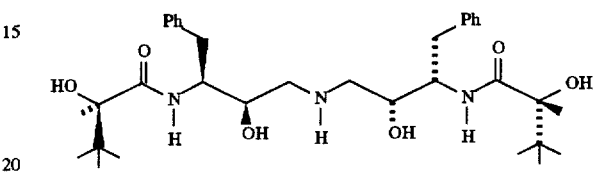

BOP reagent (308 mg, 0.7 mmol) was added to a stirred mixture of Compound 74 (0.15 g, 0.33 mmol), Compound 262e (0.102 g, 0.7 mmol) and N-methylmorpholine (0.254 mL, 2.32 mmol) in 0.75 mL dry DMF. The mixture was stirred at RT for 14 h, concentrated and the residue partitioned between EtOAc and sat. NaHCO3. The organic phase was dried (MgSO$_4$), concentrated, and the residue purified by flash chromatography (silica gel/CH$_2$Cl$_2$ stepwise to 95:5:0.5 CH$_2$Cl$_2$-MeOH-aq NH$_4$OH) followed by preparative HPLC (column: Polymer Labs. PLRP-S 100 Å 10 µm 25×300 mm; eluent: 1:1 A:B, eluent A=H$_2$O—CH$_3$CN—NH$_4$OH 90:10:0.2, eluent B=H$_2$O—CH$_3$CN—NH$_4$OH 10:90:0.2; UV 254 nm) to afford 100 mg (50%) of the title Compound 344 as a white solid.

m.p. 159°–160° C.; $[\alpha]_D$+43.8° (c 0.48, MeOH). Mass Spec.: 600 (M+H)$^+$. Analysis calc. for $C_{34}H_{53}N_3O_6 \cdot 0.59$ $H_2O$: C, 66.90; H, 8.95; N, 6.88. Found: C, 66.89; H, 8.90; N, 6.89.

EXAMPLE 345

Preparation of [S-(1R*,2S*(2S*,3R*)]]-[2,2-Dimethyl-1-[[[3-[[3-[[1,1-dimethylethoxy)-carbonyl]amino]-2-hydroxy-4-phenylbutyl]amino]-2-hydroxy-1-(phenylmethyl)propyl]amino]-carbonyl]propyl] carbamic acid, (4-phenyl-2-oxazolyl)methyl ester (Compound 345b)

(a) Compound 345a

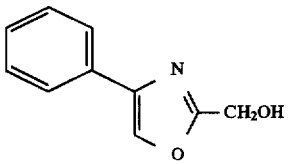

A solution of 4-phenyloxazole (Whitney, J. Org. Chem., 55, 929–935 (1990)) (2.15 g; 14.8 mmol) and 2,2,4,4-tetramethylpiperidine (250 µl; 1.48 mmol) in 30 ml of distilled THF at –78° C. was added 1.3M s-BuLi in cyclohexane (13.7 ml). The mixture was stirred for 30 min at –78° C. and then warmed to 0°0 C. Formaldehyde gas (from paraformaldehyde) was bubbled through the mixture for 5 min and it was allowed to warm to RT and stir overnight. The reaction was quenched with 1N HCl and extracted with CH₂Cl₂. The extracts were washed with brine and dried (Na₂SO₄). Evaporation and purification on a silica gel column eluting with EtOAc/hexane (1:3) and EtOAc/hexane (1:1) gave 1.75 g (68%) Compound 345a.

(b) Compound 345b

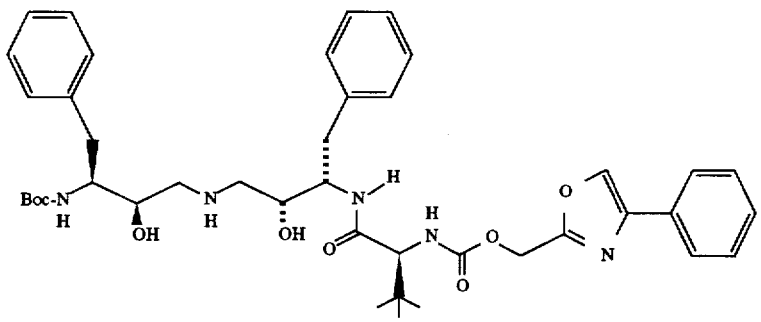

Compound 345a was converted to its p-nitrophenyl carbonate which was reacted with tert-leucine and the resulting product coupled with Compound 54 by a three-step procedure analogous to that used for Example 257a through 257c to give the title Compound 345b (colorless solid).

m.p. 178°–184°0 C. (dec).; [α]_D=–11° (c=0.25, MeOH). Analysis calcd. for: C₄₂H₅₅N₅O₈·0.5 H₂O: C, 65.73; H, 7.36; N, 9.12;

Found: C, 65.73; H, 7.30; N, 9.12; Mass Spec. (FAB): (M+H)⁺=758⁺.

EXAMPLE 346

Preparation of [1S-[1R*.2S*(2S*,3R*)]-[4-[4-(Carboxymethoxy)phenyl)-3-[[3-[[1,1-dimethylethoxy)carbonyl]amino]-2-hydroxy-1-(phenylmeyhyl)propyl) carbamic acid, 1, 1dimethylethyl ester Compound 346c)

(a) Compound 346a

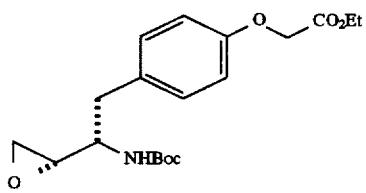

To a 0° C. solution of Compound 175c (0.080 g; 0.286 mmol) in DMF (0.60 ml) was added a solution of NaN (TMS)₂ in THF (0.30 ml of a 1.0M solution; 0.30 mmol). The solution was stirred at 0° C. for 1 h, then ethyl bromoacetate in DMF (0.30 mL of a 1.0M solution; 0.30 mmol) was added dropwise, followed by Bu₄NI (0.011 g; 0.029 mmol). The solution was allowed to warm to RT and stirred for 18 h. Volatiles were removed in vacuo, and the residue was partitioned between H₂O and EtOAc. The combined organic extracts were washed with H₂O, dried (Na₂SO₄) and concentrated in vacuo to give, after chromatography on silica gel (50 mL) using a gradient from 10:1 to 1:2 hexane:EtOAc as eluent, Compound 346a (0.100 g; 95%) as a white solid.

(b) Compound 346b

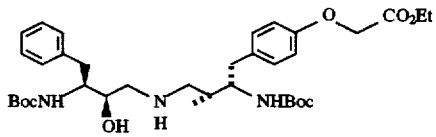

Compounds 346a and 16b were reacted by a 10 procedure analogous to that of Example 226b to give Compound 346b.

Mass Spec. (CI): (M+H)⁺=646

(c) Compound 346c

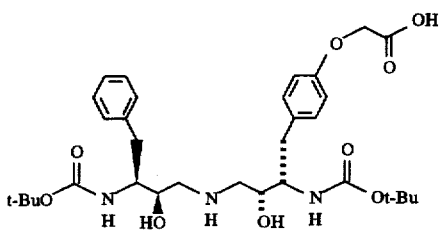

Compound 346b was converted to the title Compound 346c (white solid) by a procedure analogous to that of Example 70c (THF was used instead of dioxane).

m.p.=182°–187° C. (dec); Mass Spec. (FAB): (M+H)⁺= 618.

EXAMPLE 347

Preparation of [S-(1R*,2S*(2S*,3R*)]]-[2,2-Dimethyl-1-[[[3-[[3-[[1,1-dimethylethoxy)-carbonyl]amino]-2-hydroxy-4-phenylbutyl]amino]-2-hydroxy-1-(phenylmethyl)propyl]amino]carbonyl]-propyl]carbamic acid, (5-phenyl-2-oxazolyl)methyl ester (Compound 347b)

(a) Compound 347a

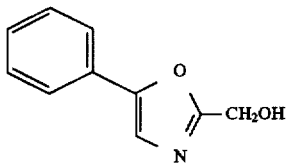

5-Phenyloxazole-2-carboxylic acid ethyl ester (Saito, *J. Pharm. Soc. Japan*, 76, 305 (1956)) was converted to Compound 347a by a procedure analogous to that of Example 281a (except that the reaction was run at 0° C. to RT).

(b) Compound 347b

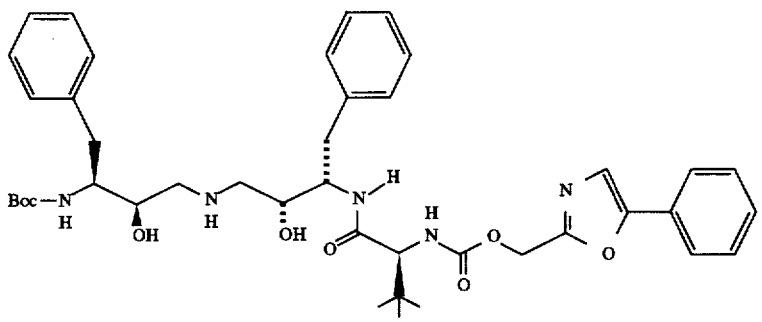

Compound 347a was converted to its p-nitrophenyl carbonate which was reacted with tert-leucine and the resulting product coupled with Compound 54 by a three-step procedure analogous to that used for Example 257a through 257c to give the title Compound 347b (colorless solid).

m.p. 168°–174°0 C. (dec).; $[\alpha]_D = -12.5°$ (c=0.25, MeOH). Mass Spec. (FAB): (M+H)$^+$=758$^+$Analysis calcd. for: $C_{42}H_{55}N_5O_8 \cdot 0.68\ H_2O$: C, 65.50; H, 7.38; N, 9.09; Found: C, 65.46; H, 7.29; N, 9.13.

EXAMPLE 348

Preparation of [1S-[1R*,2S*(2S*,3R*)]]-[3-[[(3-[[(1,1-Dimethylethoxy)carbonyl]amino]-2-hydroxy-4-[2-(phenylmethoxy)phenyl]butyl]amino]-2-hydroxy-1-(phenylmethyl)propyl]carbamic acid, 1,1-dimethylethyl ester (Compound 348d)

(a) Compound 348a

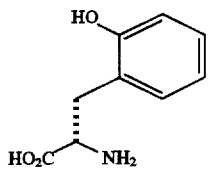

D,L-o-Tyrosine was resolved into the (L) enantiomer, Compound 348a, by the procedure described in *Can. J. Biochem.*, 49, 877 (1971).

(b) Compound 348b

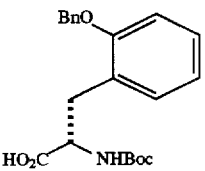

Compound 348a was converted to Compound 348b by a three-step procedure analogous to that used for the conversion of Compound 28b to Compound 28e.

(c) Compound 348c

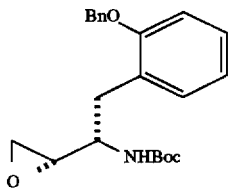

Compound 348b was converted into Compound 348c by procedures analogous to those used for the synthesis of Compound 1b(i).

(d) Compound 348d

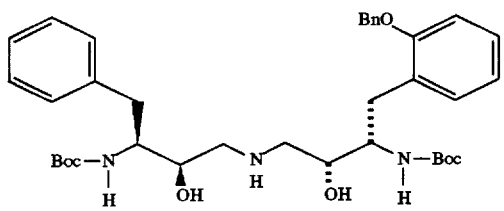

Compounds 348c and 16b were reacted by a procedure analogous to that of Example 226b to give the title Compound 348d (colorless solid).

m.p. 146°–152° C.; $[\alpha]_D = -4°$ (c 0.8, HOAc); Mass Spec. (CI): (M+H)$^+$=650$^+$; Analysis calcd. for: $C_{37}H_{51}N_3O_7 \cdot 1.5\ H_2O$: C, 65.65; H, 8.04; N, 6.41; Found: C, 65.49 H, 7.72; N, 6.66.

EXAMPLE 349

Preparation of [1S-[1R*,2S*(2S*,3R*)]]-[3-[[3-1,1-Dimethylethoxy)-carbonyl]amino]-2-hydroxy-4-(2-methoxyphenyl)butyl]-amino]-2-hydroxy-1-(phenylmethyl)propyl]carbamic acid, 1,1-dimethylethyl ester (Compound 349c)

(a) Compound 349a

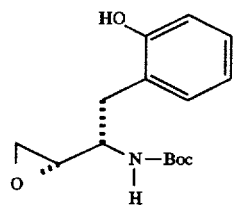

Compound 348c was converted to Compound 349a by a procedure analogous to that of Example 175c.

(b) Compound 349b

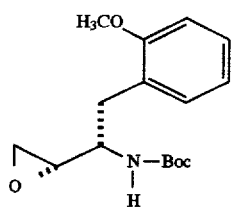

A solution of Compound 349a (70 mg, 0.25 mmol) in 0.5 ml of dry DMF was cooled to 0° C. and 250 µl of a 1M solution of sodium bis(trimethylsilyl)amide in THF (46 mg, 0.25 mmol) was added. After stirring for 15 min, 10 eq. of CH₃I (0.15 ml, 2.5 mmol) was added and the resulting mixture was stirred at 0° C. for 1 h and then allowed to warm to RT and stir overnight. The DMF was evaporated and the crude product purified on a 20 ml silica gel column eluting with 15% EtOAc/hexane yielding 68 mg (93%) of Compound 349b.

(c) Compound 349c

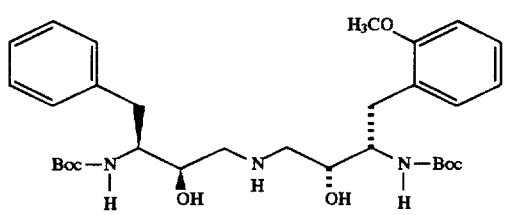

Compounds 349b and 16b were reacted by a procedure analogous to that of Example 226b to give the title Compound 349c (colorless solid).

m.p. 136°–140° C.; [α]$_D$=–3.5° (c 0.5, HOAc); Mass Spec. (CI): (M+H)⁺=574⁺; Analysis calcd. for: C₃₁H₄₇N₃O₇·1.45 H₂O: C, 62.07; H, 8.38; N, 7.01; Found: C, 61.92; H, 8.08; N, 7.16.

EXAMPLE 350

Preparation of [1S-[1R*,2S*(2S*,3R*)]]-[3-[[3-[[(1,1-Dimethylethoxy)carbonyl]amino]-2-hydroxy-4-(2-hydroxyphenyl)butyl]amino]-2-hydroxy-1-(phenylmethyl)propyl]carbamic acid, 1,1-dimethylethyl ester (Compound 350)

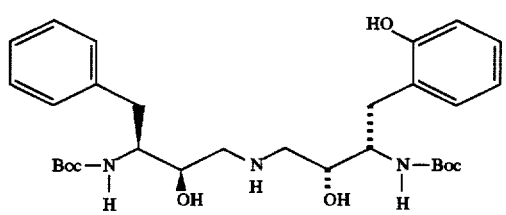

Compound 348d was converted to the title Compound 350 (colorless solid) using conditions analogous to those of Example 43.

m.p. 156°–160° C.; [α]$_D$=–5.2° (c 0.5, HOAc); Mass Spec. (CI): (M+H)⁺=560⁺; Analysis calcd. for: C₃₀H₄₅N₃O₇·1.18 H₂O: C, 62.03; H, 8.22; N, 7.23; Found: C, 61.95; H, 7.79; N, 7.31.

EXAMPLE 351

Preparation of [S-[1R*,2S*(2S*,3R*)]]-[2, 2-Dimethyl-1-[[[3-[[3-[[(1,1-dimethyl-ethoxy)carbonyl]amino]-2hydroxy-4-phenylbutyl]amino-2-hydroxy-1-(phenylmethyll)-propyl]amino]carbonyl]propyl]carbamic acid, 2-(phenylmethoxy) ethyl ester (Compound 351)

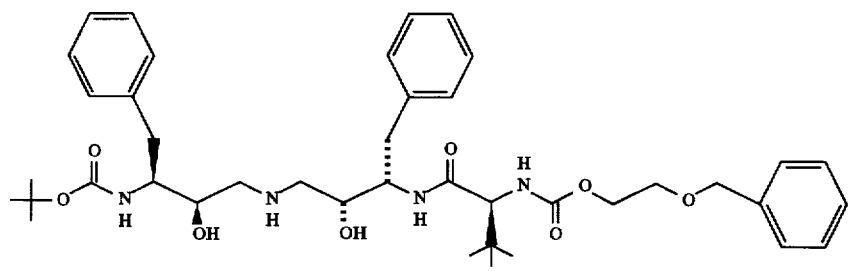

2-Benzyloxyethanol was converted to its p-nitrophenyl carbonate which was reacted with tert-leucine and the resulting product coupled with Compound 54 by a three-step procedure analogous to that used for Example 257a through 257c to give the title Compound 351 (white solid).

m.p. 99°–101° C.; [α]$_D$=–13° (c 0.11, MeOH). Mass spec.: 735⁺ (M+H)⁺. Analysis calc. for $C_{41}H_{58}N_4O_8 \cdot 1.61$ $H_2O$: C, 64.46; H, 8.08; N, 7.33; Found: C, 64.15; H, 7.83; N, 7.51.

EXAMPLE 352

Preparation of [S-[1R*,2S*(2S*,3R*)]]-[2,2-Dimethyl-1-[[[3-[[3-[[(1,1-dimethylethoxy)carbonyl]amino]-2-hydroxy-4-phenylbutyl]amino]-2-hydroxy-1-(phenylmethyl)-propyl]amino]carbonyl]propyl]carbamic acid, (2-furo[2,3-b]pyridinyl)methyl ester (Compound 352h)

(a) Compound 352a

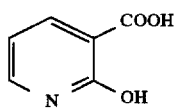

Compound 352a was prepared as described in Sliwa, Bull Soc. Chim. Fr. 631 (1970).

(b) Compound 352b

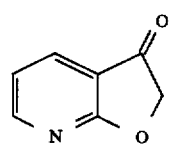

Compound 352a was converted to Compound 352b by the procedure described in Morita et al., J. Heter. Chem., 23, 1465 (1986).

(c) Compound 352c

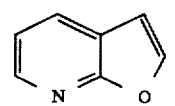

Compound 352b was converted to Compound 352c by the procedure described in Sliwa, Bull Soc. Chim. Fr. 646 (1970).

(d) Compound 352d

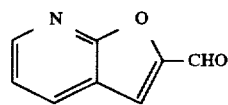

Compound 352c was converted to Compound 352d by the procedure described in Morita et al., J. Heter. Chem., 23, 1465 (1986).

(e) Compound 352e

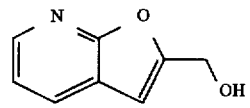

To a solution of Compound 352d (0.26 g, 1.769 mmol; ca. 75% pure) in 20 mL of 3:3:4 THF-EtOH—CHCl₃ cooled to 0° C. was added NaBH₄ (0.117 g, 3.095 mmol) in portions. After addition was complete, the mixture was stirred at 0° C. for 30 min, diluted with $H_2O$ and extracted with $CH_2Cl_2$. The combined extracts were dried ($MgSO_4$) and concentrated. The crude residue was flash chromatographed on silica gel eluting with a stepwise gradient of 25% to 100% EtOAc-hexane to afford Compound 352e (0.16 g, 80%) as a white solid.

(f) Compound 352f

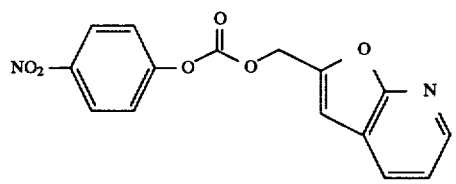

To a solution of Compound 352e (0.160 g, 1.073 mmol) in 8 mL of $CH_2Cl_2$ cooled to 0° C. was added 0.5 mL of pyridine followed by p-nitrophenylchloroformate (0.216 g, 1.073 mmol) as a solid. The reaction mixture was stirred for 20 h at RT, diluted with EtOAc and washed with sat. $NaHCO_3$ and brine. The organic phase was dried ($MgSO_4$) and concentrated to obtain Compound 352f (0.336 g, crude yield) containing traces of p-nitrophenylchloroformate and p-nitrophenol.

(g) Compound 352g

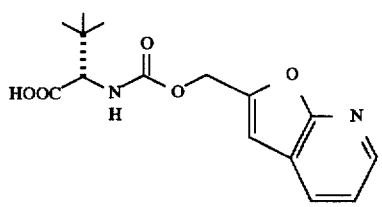

Compound 352f (0.336 g; 1.07 mmol) in 5 mL of dioxane was added to a solution of L-tert-leucine (0.154 g; 1.177 mmol) in 1.17 mL of 1N NaOH at RT followed by the addition of Et₃N (179 μL; 1.284 mmol). After stirring overnight at RT, the reaction mixture was diluted with 10% KHSO₄ and the pH adjusted to 2.0 with 1N NaOH. The mixture was extracted with EtOAc and the combined extracts were washed with brine, dried ($MgSO_4$) and concentrated. Flash chromatography on silica gel of the crude residue ($CH_2Cl_2$ followed by a stepwise gradient from 2% to 10% MeOH/$CH_2Cl_2$+0.5% HOAc) afforded 0.23 g (ca. 80% pure) of Compound 352g.

(h) Compound 352h

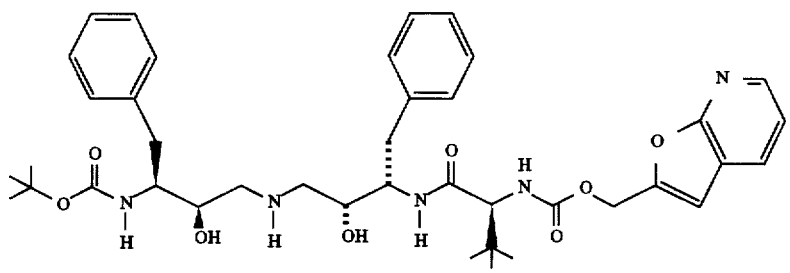

To a 0° C. solution of Compound 352g (0.15 g; 0.40 mmol based on 80% pure material) in 3 mL of $CH_2Cl_2$ was added HOBT (0.092 g; 0.676 mmol) followed by EDCI (0.091 g; 0.474 mmol). After 30 min, Compound 54 (0.20 g; 0.451 mmol) was added followed by 0.5 mL of DMF. The reaction mixture was stirred at 0° C. for 30 min and at RT for 16 h, at which time it was diluted with EtOAc, and washed with $H_2O$, sat. aq. $NaHCO_3$ and brine. The organic extracts were dried ($MgSO_4$), concentrated, and the resulting residue purified by flash chromatography on silica gel, eluting with a gradient of 98.9:1:0.1 to 90.1:9:0.9 $CH_2Cl_2$:MeOH:$NH_4OH$, to afford 0.238 g (72%) of the title Compound 352h as an off-white solid.

m.p. 99°-106° C.; $[\alpha]_D = -15.2°$ (c=0.2, $CH_3OH$). Mass Spec. (FAB) $(M+H)^+ = 732$; Analysis calc. for $C_{40}H_{53}N_5O_8 \cdot 1.28\ H_2O$: C, 63.64; H, 7.42; N, 9.28; Found: C, 63.54; H, 7.37; N, 9.38.

EXAMPLE 353

Preparation of [1S-[1R*,2S*[2S*,3R*(S*)]]]-[3-[[3-[(2-Hydroxy-1-oxo-2-phenylpropyl)amino]-2-hydroxy-4-phenylbutyl]amino]-2-hydroxy-1-(phenylmethyl)propyl]carbamic acid, 1,1-dimethylethyl ester (Compound 353)

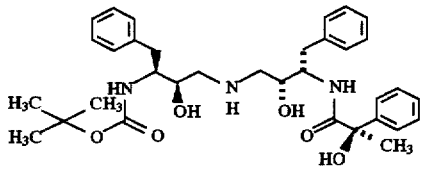

To a solution of Compound 54 (100 mg, 0.225 mmol) in DMF (0.4 ml) was added a solution of (R)-2-hydroxy-2-phenylpropionic acid (41 mg, 0.247 mmol) in 0.3 ml DMF, followed by BOP reagent (109 mg, 0.247 mmol) and N-methylmorpholine (54 µl; 0.49 mmol) to afford 55 mg (41%) the title Compound 353 using a procedure analogous to that of Example 262f.

m.p. 161°-163° C.; $[\alpha]_D = +2.5°$ (c 0.2, $CH_3OH$); Mass spectrum (Fab): $(M+H)^+ 592^+$. Analysis Calc. for:$C_{34}H_{45}N_3O_6$ 109 0.51 $H_2O$: C, 67.95; H, 7.72; N, 6.99; Found: C, 67.92; H, 7.48; N, 7.02.

EXAMPLE 354

Preparation of [1S-[1R*,2S*(2S*,3R*)]]-[3-[[3-[3,3-Dimethyl-2-[(methylamino)carbonyl]-1-oxobutyl]amino]-2-hydroxy-4-phenylbutyl]amino]-2-hydroxy-1-(phenylmethyl)propyl]carbamic acid, 1,1-dimethylethyl ester (Compound 354d)

(a) Compound 354a

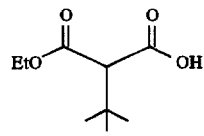

2-tert-Butyl-diethylmalonate was saponified with KOH/EtOH to afford Compound 354a as described in Bajwa et al. J. Amer. Chem. Soc., 104, 6385 (1982).

(b) Compound 354b

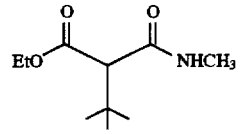

A solution of Compound 354a (1.0 g, 5.31 mmol) in 0.775 ml (10.62 mmol) of $SOCl_2$ was refluxed for 2 h. The excess $SOCl_2$ was removed in vacuo and the residue was dissolved in 20 ml dry $Et_2O$. Anhydrous $CH_3NH_2$ was bubbled into the reaction until no more precipitate formed. The precipitate was filtered off and the filtrate was concentrated to afford 865 mg (81%) of Compound 354b.

(c) Compound 354c

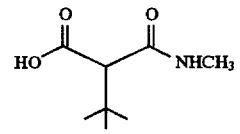

Compound 354c was prepared from Compound 354b by a procedure analogous to that used for the preparation of Compound 354a.

(d) Compound 354d

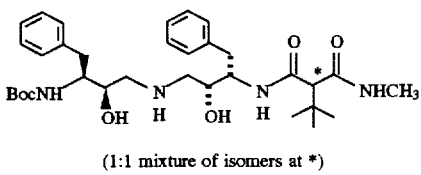

(1:1 mixture of isomers at *)

Compound 354d (white solid) was prepared as a 1:1 mixture of diastereomers from Compounds 354c and 54 by a procedure analogous to that of Example 334.

m.p. 117°–120° C. ("softening" at 114°–117° C.); Mass Spec. (FAB), 599 (M+H$^+$); Analysis Calc. for:$C_{31}H_{50}N_4O_6 \cdot 0.16$ $H_2O$: C, 65.87; H, 8.43; N, 9.31; Found: C, 65.84; H, 8.55; N, 9.34.

EXAMPLE 355

Preparation of [1S-[1R*,2S* (2S*,3R*)]]-[3-[[3-[[(1,1-Dimethylethoxy)carbonyl]amino]-2-hydroxy-4-[4-[2-hydroxy-2-(3-pyridinyl)ethoxy]phenyl]-butyl]amino]-2-hydroxy-1-(phenylmethyl)-propyl]-carbamic acid, 1,1-dimethylethyl ester, Isomer A (Compound 355f)

(a) Compound 355a

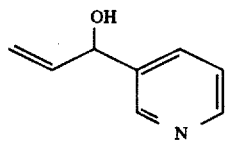

Pyridine 3-carboxaldehyde (4.0 g; 37.3 mmol) in THF (50 mL) was reacted with vinyl magnesium bromide (41.0 mL of a 1.0M solution in THF; 41.0 mmol), first at 0° C. then at RT for 24 h. The reaction mixture was cooled to 0° C. and aqueous NH$_4$Cl (55 mL of a 1M solution) was slowly added, followed by EtOAc (200 mL). The resulting mixture was filtered through Celite and the aqueous layer extracted with EtOAc. The combined organic extracts were dried (Na$_2$SO$_4$) and concentrated in vacuo to give an oil, which was purified by flash chromatography (500 mL SiO$_2$; stepwise gradient from 1:1 to 1:5 hexanes:EtOAc) to give Compound 355a (3.89 g; 77%) as a pale yellow oil.

(b) Compound 355b

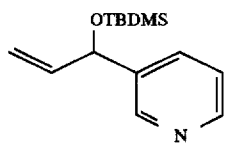

To a 0° C. solution of Compound 355a (0.40 g; 2.96 mmol) in anhydrous DMF (3.0 mL) were successively added tert-butyldimethylsilyl chloride (0.535 g; 3.55 mmol), Et$_3$N (0.467 g; 4.62 mmol) and DMAP (0.036 g; 0.296 mmol). The mixture was allowed to warm to RT and stirred for 24 h. Volatiles were removed in vacuo and the residue was partitioned between aqueous NaHCO$_3$ (20 mL of a 50% saturated solution) and EtOAc (20 mL). The aqueous layer was extracted with EtOAc and the combined organic extracts were washed with H$_2$O, dried, and concentrated in vacuo to give an oil. Flash chromatography (SiO$_2$; 100 mL) using as eluent 10:1 hexane:EtOAc furnished Compound 355b (0.744; 100%) as a pale yellow oil.

(c) Compound 355c

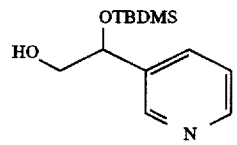

A stream of O$_3$ was bubbled into a –78° C. solution of Compound 355b (0.650 g; 2.61 mmol) in CH$_2$Cl$_2$ (10.0 mL) for 15 min until the solution was faintly blue. After stirring for a further 30 min at –78° C., N$_2$ was bubbled into the solution for 15 min to discharge the blue color. DIBAL-H (10.4 mL of a 1.0M solution in hexane; 10.4 mmol) was added dropwise over 5 min, followed by 10 mL of dry hexane. The solution was stirred at –78° C. for 1 h, then at –20° C. for 2 h. The solution was then recooled to –78° C. and MeOH (3.0 mL) was added dropwise. The solution was allowed to warm to RT and brine (5.0 mL), Et$_2$O (100 mL) and MgSO$_4$ (15 g) were added. The mixture was stirred for 2 h, filtered, and concentrated in vacuo to give a yellow oil, which was flash chromatographed (SiO$_2$; 100 mL) using a stepwise gradient from 1:1 to 1:4 hexane:EtOAc to give Compound 355c (0.234g; 35%) as a slightly yellow oil.

(d) Compound 355d

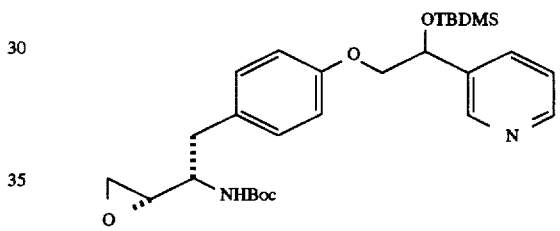

Compound 355c (0.331 g; 1.31 mmol) and Compound 175c (0.183 g; 0.655 mmol) were reacted with DEAD (0.228 g; 1.31 mmol) and Ph$_3$P (0.343 g; 1.31 mmol) in THF for 24 h at RT. The solution was concentrated in vacuo and adsorbed onto Celite. Flash chromatography (100 mL SiO$_2$) using a gradient from 95:5 to 1:1 hexane:EtOAc gave Compound 355d (0.301 g; contaminated with 1,2-dicarbethoxy-hydrazine; only one of two possible diastereomers was isolated) as a pale yellow viscous oil.

(e) Compound 355e

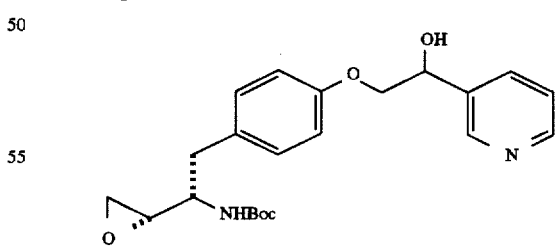

Compound 355d (0.301 g) was dissolved in anhydrous THF and n-Bu$_4$NF.H$_2$O (0.204 g; 0.779 mmol) was added at RT. The yellow solution was stirred for 1.5 h. Volatiles were removed in vacuo and the residue was purified by flash chromatography (SiO$_2$, 100 mL) using a gradient from 1:1 to 1:10 hexane:EtOAc to give Compound 355e (0.096 g; 37% for 2 steps) as a white solid.

(f) Compound 355f

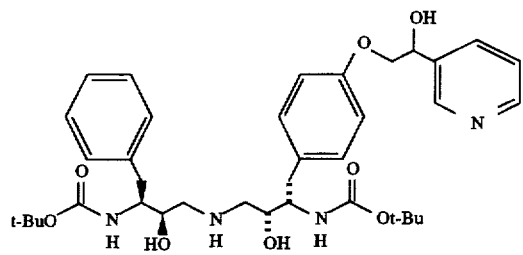

Compound 355e (0.030 g; 0.075 mmol) and Compound 16b (0.025 g; 0.090 mmol) were heated in MeOH (0.20 mL) at 60° C. for 4 h. Volatiles were removed in vacuo and the residue was purified by flash chromatography on SiO$_2$ (100 mL) using as eluent a stepwise gradient from 99:1:0.1 to 92:8:0.8 CH$_2$Cl$_2$: MeOH: NH$_4$OH to afford a white solid (0.026 g, 52%). This material was further purified by preparative HPLC (Polymer Labs PLRP-S column, 25×300 mm, 10 µm particle size, stepwise gradient from 70:30 to 40:60 A:B; A=90:10:0.2 H$_2$O: MeCN: NH$_4$OH, B=90:10:0.2 MeCN:H$_2$O:NH$_4$OH) and then lyophilized from dioxane-H$_2$O to give the title Compound 355f (0.021 g; 41%) as a white solid (single diastereomer of undetermined configuration).

m.p.=68°–72° C. (dec.); [α]$_D$=–4.0° (c=0.10, MeOH). Mass Spec. (FAB): (M+H)$^+$=681.

EXAMPLE 356

Preparation of [1S-[1R*,2S*(2S*,3R*)]]-[3-[3-[2,4-Dihydroxy-2,3,3-trimethyl-1-oxobutyl)amino]-2-hydroxy-4-phenylbutyl]amino]-2-hydroxy-1-(phenylmethyl)propyl]carbamic acid, 1,1-dimethylethyl ester, isomer A (Compound 356b)

(a) Compound 356a

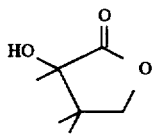

A solution of CH$_3$MgCl (3M in THF, 14.32 mL, 43 mmol) was added to a solution of dihydro-4,4-dimethyl-2,3-furandione (5 g, 39 mmol) in 30 mL THF at –78° C. The mixture was allowed to warm to RT, diluted with Et$_2$O and dilute HCl was added. The organic layer was washed with sat. NaHCO$_3$, dried (MgSO$_4$) and concentrated to afford 3.5 g of a colorless oil. This material was dissolved in 50 mL THF, and a solution of LiOH (583.4 mg, 24.3 mmol) in 25 mL water was added and the mixture was refluxed for 24 h. The mixture was concentrated, the residue dissolved in 30 mL water, washed with Et$_2$O, and the aqueous phase lyophilized to afford 3.0 g of a pale solid. This solid (1.0 g) was dissolved in 5 mL water which was acidified with 10% HCl, extracted with EtOAc, and the organic phase dried (MgSO$_4$), concentrated, and the residue purified by flash chromatography (silica gel/hexane-EtOAc 1:1) to afford 0.815 g of Compound 356a as a colorless oil.

(b) Compound 356b

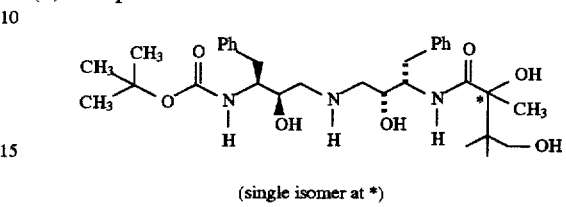

(single isomer at *)

A mixture of Compound 54 (200 mg, 0.45 mmol) and Compound 356a (129.8 mg, 0.90 mmol) in 1 mL dry DMF was heated at 100° C. for 14 h and 145° C. for 2 h, concentrated, and the residue purified by flash chromatography to afford a ca. 1:1 mixture of the two diastereomeric (at *) products. This material was subjected to preparative TLC (0.5 mm silica gel plates/CH$_2$Cl$_2$—MeOH—NH$_4$OH 9:1:0.1, developed twice) to afford, as the faster moving isomer, the title Compound 356b (11 mg, 4.1%) as a white solid.

m.p. 73°–75° C.; [α]$_D$+8° (c=0.15, MeOH). R$_f$ (SiO$_2$); =0.23 (CH$_2$Cl$_2$—MeOH—NH$_4$OH 8:2:0.2). Mass Spec.: 588 (M+H)$^+$.

EXAMPLE 357

Preparation of [1S-[1R*,2S*(2S*,3R*)]]-[3-[[3-[(2,4-Dihydroxy-2,3,3-trimethyl-1-oxobutyl) amino]-2-hydroxy-4-phenylbutyl]amino]-2-hydroxy-1-(phenylmethyl) propyl]carbamic acid, 1,1-dimethylethyl ester, isomer B (Compound 357)

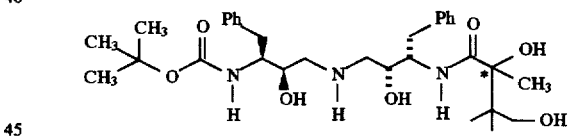

(single isomer at *)

Compound 357 (white solid) was isolated as the slower moving isomer by preparative TLC as described in Example 356b.

m.p. 71°–75° C., R$_f$ (SiO$_2$) =0.20 (CH$_2$Cl$_2$—MeOH—NH$_4$OH 8:2:0.2). Mass Spec. 588 (M+H)$^+$.

EXAMPLE 358

Preparation of [1S-[1R*,2S*(2S*,3R*)]]-[3-[[3-[[(1,1-Dimethylethoxy)carbonyl]amino]-2-hydroxy-4-[4-(2-hydroxy-2-methylpropoxy)phenyl]butyl]amino]-2-hydroxy-1-(phenylmethyl)propyl]carbamic acid, 1,1-dimethylethyl ester (Compound 358b)

(a) Compound 358a

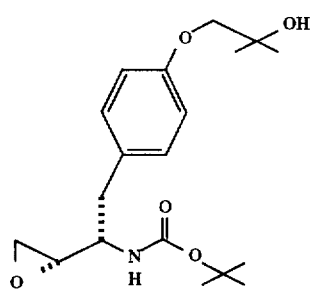

Compound 346a was reacted with CH₃MgBr by a procedure analogous to that of Example 158a to give Compound 358a.

(b) Compound 358b

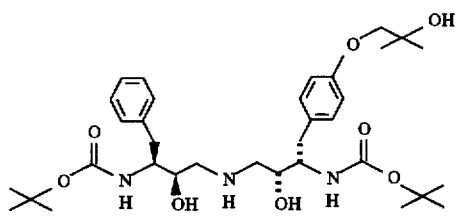

Compounds 358a and 16b were reacted by a procedure analogous to that of Example 226b to give the title Compound 358b (white solid).

m.p. 85°–88° C.; [α]$_D$=–4.5° (c=0.11, CH₃OH); Mass Spec. (FAB): (M+H)=632.

EXAMPLE 359

Preparation of [1R*,2S*(2S*,3R*)]-N-[2-Hydroxy-3-[[2-hydroxy-3-[[(2-hydroxy-1,1-dimethylethoxy)-carbonyl]amino]-4-phenylbutyl]amino]-1-(phenylmethyl) propyl]-N²-(2-methoxycarbonyl)-3-methyl-L-valinamide (Compound 359b)

(a) Compound 359a

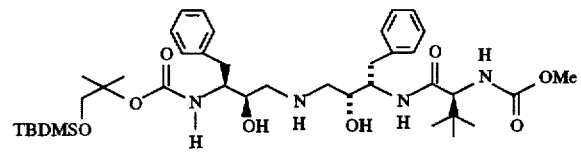

To a 0° C. solution of Compound 246a (0.036 g, 0.191 mmol) in 3 mL of CH₂Cl₂ was added HOBT-hydrate (0.035 g, 0.261 mmol) followed by EDCI (0.037 g, 0.191 mmol). The mixture was stirred at 0° C. for 0.5 h and Compound 333b (0.1 g, 0.174 mL) was added followed by N-methylmorpholine (0.058 mL, 0.522 mmol) and 0.5 mL of DMF. The resulting solution was stirred at RT for 20 h. The mixture was diluted with EtOAc and washed with sat. NaHCO₃ and brine. The organic phase was dried (MgSO₄) and concentrated in vacuo. The residue obtained was flash chromatographed on silica gel eluting with a stepwise gradient of 98.9:1:0.1 to 89:10:1 CH₂Cl₂—MeOH—NH₄OH to afford Compound 359a (0.096 g, 74%) as a white solid.

Mass Spec (FAB)–(M+H)⁺=745.

(b) Compound 359b

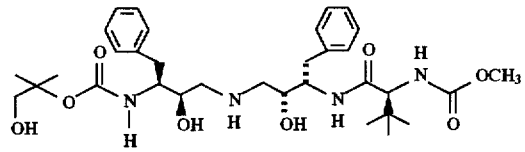

A solution of Compound 359a (0.095 g, 0.127 mmol) in 3 mL of 3:1:1 HOAc-THF-H₂O was stirred at RT for 16 h. The mixture was concentrated in vacuo and flash chromatographed twice on silica gel eluting with a stepwise gradient of 98.9:1:0.1 to 89:10:1 CH₂Cl₂—MeOH—NH₄OH to obtain a solid which was triturated twice with Et₂O to afford Compound 359b (0.07 g, 87%) as a white solid.

m.p. 93°–104° C.; [α]$_D$=–21.2° (c=0.2, CH₃OH). Mass Spec. (FAB): (M+H)⁺=631; Analysis calc. for C₃₃H₅₀N₄O₈·3.03 H₂O: C, 57.83; H, 8.24; N, 8.18; Found: C, 57.92; H, 7.66; N, 8.09.

EXAMPLE 360

Preparation of [1S-(1R*,2S*)]-[Iminobis[2-hydroxy-1-(phenylmethyl)-3,1-propanediyl)]bis[carbamic acid], 1,1-dimethylethyl tetrahydro-1,1-dioxo-3-thienyl ester (Compound 360c)

(a) Compound 360a

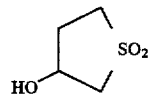

Compound 360a was prepared from tetrahydrothiophene-3-one in two steps employing the procedure described in Dodd et al., J. Heterocyclic. Chem., 27, 1453 (1990).

(b) Compound 360b

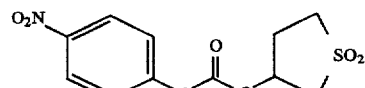

Compound 360a was converted to Compound 360b by a procedure analogous to that of Example 149d.

(c) Compound 360c

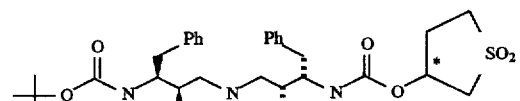

(1:1 mixture of isomers at *)

Compounds 360b and 54 were converted to the title Compound 360c (white solid) in 13% yield by a procedure analogous to that of Example 147d (DMF only used).

m.p. 197°–201° C. Mass Spec. (FAB): 606 (M+H⁺) Analysis calc. for C₃₀H₄₃N₃O₈S: C, 59.49; H, 7.15; N, 6.94; S, 5.29; Found: C, 59.44; H, 7.17; N, 7.07; S, 5.23.

EXAMPLE 361

Preparation of [1S-[1R*,2S*(2S*,3R*)]]-[3-[[3-[[2, 2-Dimethyl-1-hydroxycyclohexyl)carbonyl]amino]-2-hydroxy-4-phenylbutyl]amino]-2-hydroxy-1-(phenylmethyl) propyl]carbamic acid, 1,1-dimethylethyl ester, isomer A (Compound 361b)

(a) Compound 361a

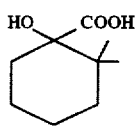

2,2-Dimethylcyclohexanone was converted to Compound 361a by a three-step procedure analogous to that used for the preparation of Compound 321c.

(b) Compound 361b

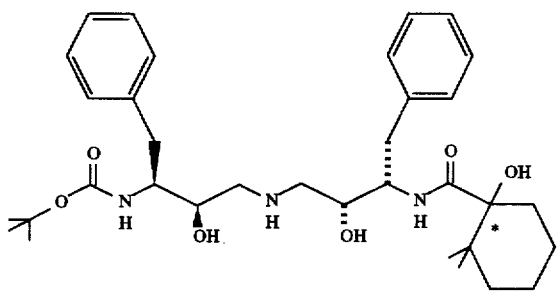

(single isomer of undetermined absolute stereochemistry at *)

Compounds 361a and 54 were reacted by a procedure analogous to that of Example 321d. The crude product was chromatographed on a 2.5×25 cm silica gel column as follows: 1% MeOH/CH$_2$Cl$_2$; 2% MeOH/CH$_2$Cl$_2$; 2.5% MeOH/CH$_2$Cl$_2$; 3–4.75% MeOH/CH$_2$Cl$_2$+0.3–0.75% NH$_4$OH in 0.25% and 0.025% increments respectively. The faster moving isomer was further purified by preparative HPLC (UV 220; YMC S-10 ODS (C-18) 30×500 mm column; stepwise gradient from 76–86% MeOH/H$_2$O+0.1% TFA) followed by chromatography on a 2.5×5 cm silica gel column using 5% MeOH/CH$_2$Cl$_2$+0.5% NH$_4$OH to give 59 mg (17%) of the title Compound 361b as a white solid. m.p 175°–180° C.; R$_f$=0.20, CH$_2$Cl$_2$:MeOH:NH$_4$OH, 90:9:1 (UV and PMA detection); [α]$_D$=+6.2° (C 0.42, MeOH).

Mass Spec. CI+ions: M+H=598. Analysis calc. for C$_{34}$H$_{51}$N$_3$O$_6$: C, 68.31; H, 8.60; N, 7.03; Found C, 68.38; H, 8.80; N, 7.08.

EXAMPLE 362

Preparation of [1S-[1R*,2S*(2S*,3R*)]]-[3-[[3-[[2, 2-Dimethyl-1-hydroxycyclohexyl)carbonyl]amino]-2-hydroxy-4-phenylbutyl]amino]-2-hydroxy-1-(phenylmethyl) propyl]carbamic acid, 1,1-dimethylethyl ester, isomer B (Compound 362)

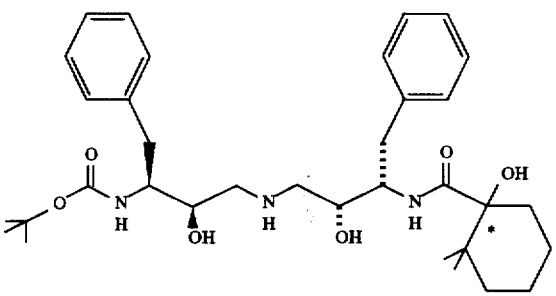

(single isomer of undetermined absolute stereochemistry at *)

The slower moving isomer of Example 361b was further purified by preparative HPLC (UV 220; YMC S-10 ODS (C-18) 30×500 mm column; stepwise gradient from 76–86% MeOH/H$_2$O+0.1% TFA) followed by chromatography on a 2.5×5 cm silica gel column using 5% MeOH/CH$_2$Cl$_2$+0.5% NH$_4$OH to afford 50 mg (15%) of Compound 362 as a white solid.

m.p. 101°–105° C.; R$_f$=0.17, CH$_2$Cl$_2$:MeOH:NH$_4$OH, 90:9:1 (UV and PMA detection); [α]$_D$=-4.1° (C 0.49, MeOH). Mass Spec. FAB+ions: M+H=598. Analysis calc. for C$_{34}$H$_{51}$N$_3$O$_6$·0.28 H$_2$O: C, 67.74; H, 8.62; N, 6.97; Found C, 67.70; H, 8.57; N, 7.01.

EXAMPLE 363

Preparation of [1S-[1R*,2S*(2S*,3R*)]]-[3-[[3-[[(1, 1-Dimethylethoxy)carbonyl]amino]-2-hydroxy-4-[4-[2-(3-methyl-2-oxo-1-imidazolidinyl)-ethoxy] phenyl]butyl]amino]-2-hydroxy-1-(phenylmethyl) propyl]carbamic acid, 1,1-dimethylethyl ester (Compound 363d)

(a) Compound 363a

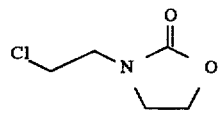

To a solution of Compound 343a (750 mg; 5.72 mmol) in 572 μL of dry benzene was added SOCl$_2$ (417 μL; 5.72 mmol). The solution was heated to reflux for 3 h at which time an additional amount of SOCl$_2$ (83 μL; 1.14 mmol) was added to the reaction. After 30 min, NaHCO$_3$ (576 mg) was added and the mixture was filtered. The solid residue was washed with 50 mL of benzene. The filtrate was treated with charcoal and filtered. The filtrate was concentrated in vacuo to afford Compound 363a as a clear brown oil (580 mg; 68%).

(b) Compound 363b

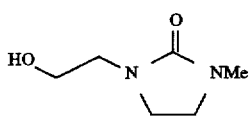

Compound 363a (424 mg; 2.83 mmol) and methylamine (1.95 mL; 56.6 mmol; 40% weight solution in H₂O) were stirred at RT for 6 d. The reaction mixture was concentrated in vacuo and purified on silica gel using a stepwise gradient of 2% to 8% MeOH:CH₂Cl₂ to afford Compound 363b (333 mg; 82%) as a green oil.

(c) Compound 363c

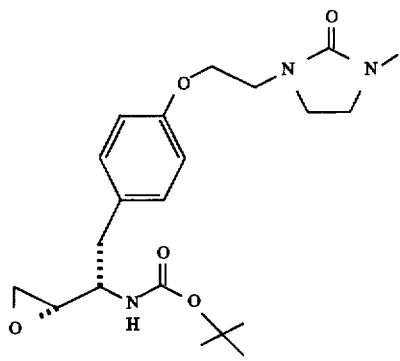

Compounds 175c and 363b were reacted by a procedure analogous to that of Example 282a to afford Compound 363c.

(d) Compound 363d

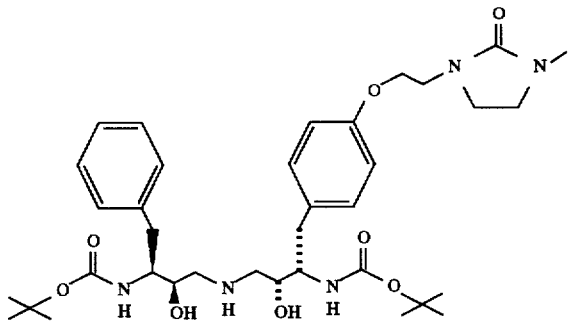

Compounds 363c and 16b were reacted by a procedure analogous to that of Example 226b to give the title Compound 363d as a white solid.

m.p. 63°–66° C.; [α]$_D$=+2.5° (c 0.12, CH₃OH); Mass Spec. (FAB): (M+H)=686

EXAMPLE 364

Preparation of [1S-[1R*,2S*(2S*,3R*)]]-[2-Hydroxy-3-[[tetrahydro-3-hydroxy-4,4-dimethyl-3-furanyl) carbonyl]amino]-4-phenylbutyl]amino]-1-(phenylmethyl)-propyl]carbamic acid, 1,1-dimethylethyl ester, Isomer A (Compound 364f)

(a) Compound 364a

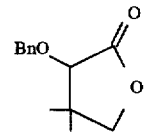

(D,L)-Pantolactone was converted to Compound 364a by a procedure analogous to that of Example 306a.

(b) Compound 364b

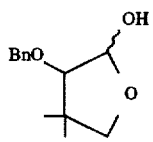

To a −78° C. solution of Compound 364a (7.50 g; 34.0 mmol) in anhydrous toluene and CH₂Cl₂ (75 mL each) was added a solution of DIBAL-H (40.90 mL of a 1.0M solution in hexanes; 40.9 mmol) over 1 h. The solution was stirred at −78° C. for 2 h. MeOH (9.0 mL) was added dropwise. The resulting suspension was allowed to warm to RT. Brine (31 mL) and Et₂O (1 L) were added, followed by MgSO₄ (70 g). The suspension was stirred for 1.5 h, and then filtered. The solids were washed with EtOAc and the combined filtrates were concentrated in vacuo to give a viscous oil, which solidified on standing to give Compound 364b (7.11 g; 94%; 5.4:1 mixture of anomers) as a white solid.

(c) Compound 364c

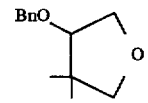

To a −78° C. solution of Compound 364b (5.97 g; 26.8 mmol) in anhydrous CH₂Cl₂ were successively added Et₃SiH (12.84 mL, 80.4 mmol), and BF₃.OEt₂ (3.63 mL; 29.5 mmol) dropwise. The solution was stirred at −78° C. for 2 h, then slowly warmed to 0° C. and stirred for 1 h, then cooled to −78° C. NaHCO₃ (9.0 g) was added and the mixture was stirred at −78° C. for 15 min. Saturated aq. NaHCO₃ was added, and the mixture was allowed to warm to RT over 1 h. The aqueous layer was extracted with EtOAc and the combined organic extracts were dried (MgSO₄), concentrated in vacuo, and purified by flash chromatography (SiO₂; 200 mL) using a stepwise gradient from 99:1 to 90:10 hexanes:Et₂O to give Compound 364c (4.89g; 88%) as a colorless oil.

(d) Compound 364d

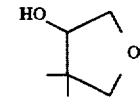

Compound 364c was converted to Compound 364d by a procedure analogous to that described in Example 19.

(e) Compound 364e

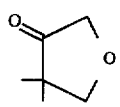

Compound 364d was converted to Compound 364e by a procedure analogous to that of Example 314a.

(f) Compound 364f

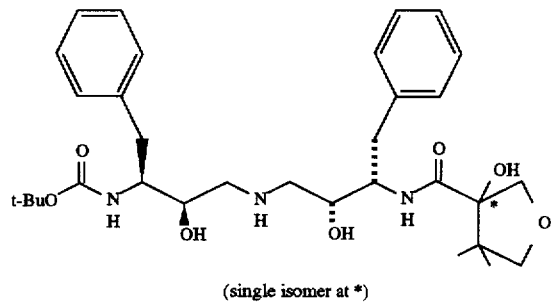

(single isomer at *)

Compounds 364e and 54 were converted to the title Compound 364f by a four-step procedure analogous to that described in Example 321. Flash chromatography (100 mL $SiO_2$; stepwise gradient from 99:1:0.1 to 90:10:1 $CH_2Cl_2$:MeOH:$NH_4OH$) followed by preparative HPLC (Polymer Labs PLRP-S column, 25×300 mm, 10 μm particle size, stepwise gradient from 70:30 to 45:55 A:B (where A=90:10:0.2 $H_2O$:MeCN:$NH_4OH$ and B=90:10:0.2 MeCN:$H_2O$:$NH_4OH$)), and lyophilization from dioxane-$H_2O$ gave 19 mg of Compound 364f as a white solid.

m.p.=84°–87° C.; [α] =+6.8° (c=0.20, MeOH). $R_f$ ($SiO_2$) =0.29 (90:10:1 $CH_2Cl_2$:MeOH:$NH_4OH$). Mass Spec. (CI): (M+H)$^+$=586; Analysis calc. for $C_{32}H_{47}N_3O_7$·0.78 $H_2O$: C, 64.07; H, 8.16; N, 7.01; Found: C, 63.99; H, 7.97; N, 7.09.

EXAMPLE 365

Preparation of [1S-[1R*,2S*(2S*,3R*)]]-[2-Hydroxy-3-[[tetrahydro-3-hydroxy-4,4-dimethyl-3-furanyl) carbonyl]amino]-4-phenylbutyl]amino]-1-(phenylmethyl)-propyl]carbamic acid, 1,1-dimethylethyl ester, Isomer B (Compound 365)

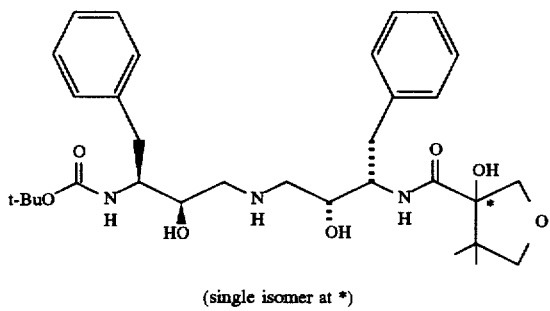

(single isomer at *)

Flash chromatography followed by preparative HPLC as described in Example 364f gave 17 mg of the title Compound 365 (white solid).

m.p.=82°–85° C.; [α]=−13.7° (c=0.16, MeOH). $R_f$ ($SiO_2$) =0.19 (90:10:1 $CH_2Cl_2$:MeOH:$NH_4OH$). Mass Spec. (CI): (M+H)$^+$=586; Analysis calc. for $C_{32}H_{47}N_3O_7$·0.69 $H_2O$: C, 64.25; H, 8.15; N, 7.02; Found: C, 64.24; H, 8.02; N, 7.03.

EXAMPLE 366

Preparation of [1S-[1R*,2S*(2S*,3R*)]]-[3-[[3-[[2-Hydroxy-2-(hydroxymethyl)-3,3-dimethyl-1-oxobutyl]amino]-2-hydroxy-4-phenylbutyl]amino]-2-hydroxy-1-(phenylmethyl) propyl]carbamic acid, 1,1-dimethylethyl ester, isomer A (Compound 366d)

(a) Compound 366a

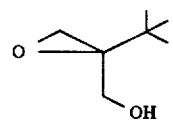

To a solution of 80% m-CPBA (8.5 g, 39.41 mmol) in 160 mL $CH_2Cl_2$ was added Compound 262a (3 g, 26.27 mmol) in 30 mL $CH_2Cl_2$ (40 mL) and the mixture stirred at RT for 20 h. The reaction mixture was cooled to 0° C. and quenched by addition of $Me_2S$ (6 mL) and washed with 10% aq. $Na_2CO_3$. The aqueous phase was extracted with $CH_2Cl_2$, and the combined organic layer dried ($Na_2SO_4$), filtered and the solvent removed by distillation. Fractional distillation (10–23 mm, 70°–90° C.) of the residue afforded Compound 366a (2.63 g, 77% yield) as a light yellow liquid.

(b) Compound 366b

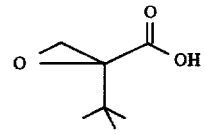

To Compound 366a (2.47 g, 18.97 mmol) in $CH_3CN$ (65 mL), was added 0.85 mL $H_2O$, followed by $NaIO_4$ (12.17 g, 56.92 mmol) and $RuCl_3$ (86.5 mg, 0.417 mmol) and the slurry stirred at RT for 2–3 min, after which another 0.85 mL $H_2O$ was added and the mixture stirred at RT for 2 h. The reaction mixture was diluted with Et2O, filtered through celite and the filtrate concentrated in vacuo. The resulting residue was dissolved in 1N NaOH (pH ca. 12), extracted with $Et_2O$ and the aqueous layer separated and acidified (pH 3.0) by addition of 3N HCl. Saturation of the aqueous phase with $Na_2SO_4$, and extraction with EtOAc afforded Compound 366b (1.58 g, 58% yield) as a brown oil.

(c) Compound 366c

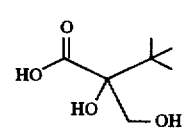

To Compound 366b (1.58 g, 10.97 mmol) in $H_2O$ (55 mL), was added 10% $H_2SO_4$ (25 mL) and the mixture heated at 100°–105° C. for 8 h. The mixture was cooled to RT, saturated with $Na_2SO_4$ and extracted with EtOAc. The organic layer was separated, dried ($MgSO_4$) and concentrated in vacuo. The residue was purified by silica gel chromatography, eluting with 80:20:0.2 to 0:100:1 hexane:EtOAc:HOAc to afford Compound 366c (276 mg, 16% yield) as a white solid.

(d) Compound 366d

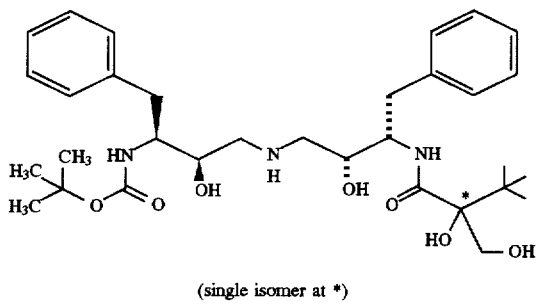

(single isomer at *)

To a solution of Compound 54 (300 mg, 0.676 mmol) in DMF (1.5 mL) was added a solution of Compound 366c (120 mg, 0.743 mmol) in 0.3 mL DMF, followed by BOP reagent (329 mg, 0.743 mmol) and N-methylmorpholine (164 μL, 1.48 mmol) at 0° C. The mixture was heated at 50° C. for 24 h, and then stirred at RT for another 24 h. DMF was removed in vacuo and the residue dissolved in EtOAc, washed with saturated NaHCO$_3$ and then with brine. The organic layer was separated, dried (MgSO$_4$) and concentrated in vacuo to afford the crude product as a mixture of diastereomers. Combination with material from a prior reaction (0.113 mmol scale reaction) and chromatography on silica gel, eluting with 99:1:01 to 92:8:0.8 CH$_2$Cl$_2$:CH$_3$OH:aq. NH$_4$OH gave Compound 366d as the faster moving isomer. Further purification by preparative HPLC (Polymer Labs PLRP-S 100 Å, 10μg column, stepwise gradient [65:35 C:D to 55:45 C:D (1 h); C=10% CH$_3$CN/ H$_2$O+ 0.2% aq. NH$_4$OH; D=90% CH$_3$CN/ H$_2$O+ 0.2% aq. NH$_4$OH]) gave the title Compound 366d (13 mg, 3%) as a white solid.

m.p. 83°–85° C.; R$_f$ (SiO$_2$)=0.4 (90:10:1 CH$_2$Cl$_2$:MeOH:NH$_4$OH). Mass spectrum (Fab): (M+H)$^+$ 588$^+$.

EXAMPLE 367

Preparation of [1S-[1R*,2S*(2S*,3R*)]]-[3-[[3-[[2-Hydroxy-2-(hydroxymethyl)-3,3-dimethyl-1-oxobutyl]amino]-2-hydroxy-4-phenylbutyl]amino]-2-hydroxy-1-(phenylmethyl) propyl]carbamic acid, 1,1-dimethylethyl ester, isomer B (Compound 367)

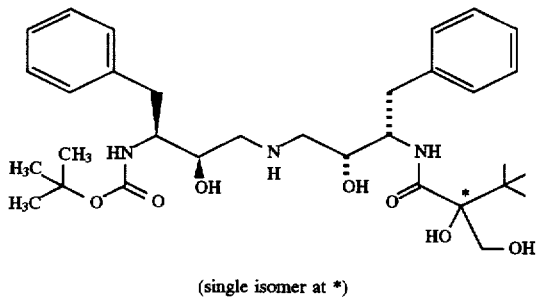

(single isomer at *)

The slower moving isomer from Example 366d was purified by preparative HPLC in analogy to Compound 366d to afford Compound 367 as a white solid.

m.p. 84°–86° C.; R$_f$ (SiO$_2$)=0.3 (90:10:1 CH$_2$Cl$_2$:MeOH:NH$_4$OH). Mass spectrum (Fab): (M+H)$^+$ 588$^+$.

EXAMPLE 368

Preparation of [1S-[1R*,2S*(2S*,3R*)]] -[3-[[3-[[(2,2-Dimethyl-1-hydroxycyclopentyl)-carbonyl]amino] -2-hydroxy-4-phenylbutyl]amino]-2-hydroxy-1-(phenylmethyl) propyl]carbamic acid, 2-hydroxy-1,1-dimethylethyl ester, isomer A (Compound 368f)

(a) Compound 368a

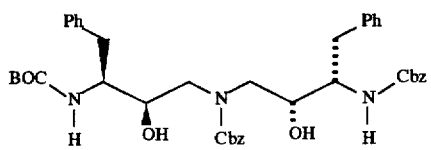

To an ice cooled solution of 1.75 g (3 mmol) of Compound 45 and 1.03 ml (6 mmol) of i-Pr$_2$NEt in 10 ml of DMF was added dropwise 470 μl (3.3 mmoles) of benzyl chloroformate, neat. Stirring was continued with cooling for 0.5 h, then at RT overnight. The solution was evaporated to dryness and the residue purified by flash chromatography on a 1250 cc column of silica gel. Elution with 40% EtOAc—hexane afforded 2.0 g (94%) of Compound 368a as a white solid.

TLC (SiO$_2$) R$_f$=0.14 (1:1 EtOAc/Hexane).

(b) Compound 368b

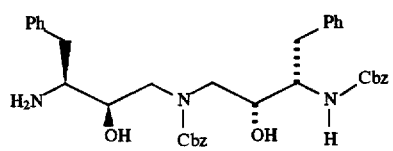

To 1.88 g (2.64 mmol) of Compound 368a at 0° C. was added 10 ml of 4N HCl-dioxane. The reaction was stirred with cooling until solution was obtained, then at RT for an additional 3 h. The reaction mixture was evaporated to dryness and the residue evaporated twice from MeOH to afford 1.54 g (90%) of Compound 368b as a white solid.

TLC (SiO$_2$) R$_f$=0.33 (10% MeOH/CHCl$_3$).

(c) Compound 368c

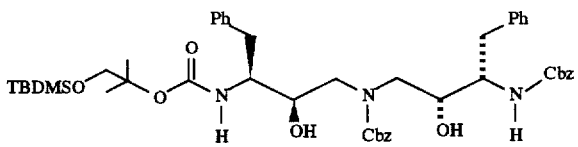

A solution of 1.38 g (2.13 mmol) of Compound 368b, 0.86 g (2.34 mmol) of Compound 161d, and 2.2 ml of i-Pr$_2$NEt in 10 ml of DMF was stirred at RT for 5 d. The solution was evaporated to dryness and the residue dissolved in EtOAc. The solution was washed with 1N HCl, brine, 1N NaOH, and brine and dried (MgSO$_4$). After removal of solvent, the residue was purified by flash chromatography on a 500 cc column of silica gel. Elution with 25 % EtOAc - hexane, followed by 50 % EtOAc—hexane afforded 1.36 g (76 %) of Compound 368c as a solid white foam. TLC (SiO$_2$) R$_f$=0.25 (1:1 EtOAc/hexane).

(d) Compound 368d

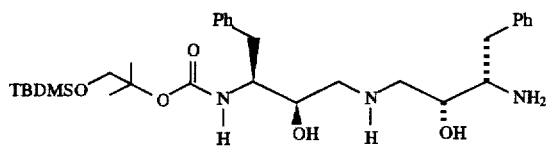

A solution of 1.0 g (1.19 mmol) of Compound 368c in 20 ml of EtOH was hydrogenated over 100 mg of 20 % Pd(OH)₂/C catalyst for 2 h at RT. To the reaction was added 1 ml of NH₄OH and stirring was continued for 0.5 h. The catalyst was removed by filtration through Celite and the filtrate evaporated to dryness to give 717 mg (100 %) of Compound 368d as a solid foam.

TLC (SiO₂) R$_f$=0.21 (CHCl₃:MeOH:aq. NH₄OH 90:10:1).

(e) Compound 368e

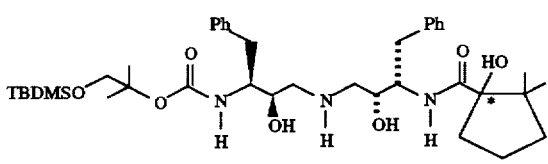

(1:1 mixture of isomers at *)

To a solution of 700 mg (1.22 mmol) of 368d, 193 mg (1.22 mmol) of Compound 321c, and 148 μl (1.35 mmol) of N-methylmorpholine in 5 ml of DMF, with ice cooling, was added 597 mg (1.35 mmol) of BOP reagent. Stirring was continued with cooling for 2 h, then at RT overnight. After removal of the DMF (high vac, 30° C.) the residue, in EtOAc, was washed with brine and dried (MgSO₄). The solvent was removed and the residue purified by flash chromatography on a 125 cc column of silica gel. Elution with CHCl₃:MeOH:NH₄OH (95:5:0.5) afforded 737 mg (85 %) of Compound 368e as a white foam. TLC(SiO₂) R$_f$=0.39 and 0.34 (CHCl₃:MeOH:aq.NH₄OH 90:10:1).

(f) Compound 368f

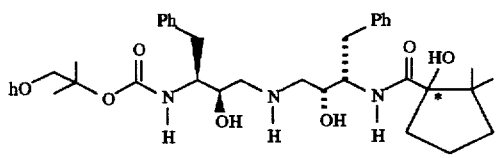

(single isomer at *)

A solution of 720 mg (1 mmol) of Compound 368e in 10 ml HOAc:H₂O:THF (3:1:1) was stirred at RT for 48 h. The reaction was evaporated to dryness and the clear colorless oil residue dissolved in EtOAc and washed with sat. aq. NaHCO₃ and with brine and dried (MgSO₄). Removal of solvent gave 654 mg of crude material which was purified by flash chromatography on a 125 cc column of silica gel. Elution with CHCl₃:MeOH:NH₄OH (95:5:0.5) afforded, as the faster moving isomer, Compound 368f, which was triturated with CHCl₃ to afford 161 mg (0.27 mmole) of the title Compound 368f as a white powder.

m.p. 178°–179° C.; [α]$_D$=+16.0° (c 0.73, MeOH). R$_f$ (SiO₂)=0.20 (CHCl₃:MeOH:NH₄OH, 90:10:1). Mass Spec.: (M+H)⁺600⁺; Analysis calc. for C₃₃H₄₉N₃O₇·0.85 H₂O: C, 64.45; H, 8.31; N, 6.83. Found: C, 64.20; H, 8.09; N, 7.08.

EXAMPLE 369

Preparation of [1S-[1R*,2S*(2S*,3R*)]]-[r3-[[3-[[(2,2-Dimethyl-1-hydroxycyclopentyl)-carbonyl]-amino]-2-hydroxy-4-phenylbutyl]amino]-2-hydroxy-1-(phenylmethyl) propyl]carbamic acid, 2-hydroxy-1,1-dimethylethyl ester, isomer B (Compound 369)

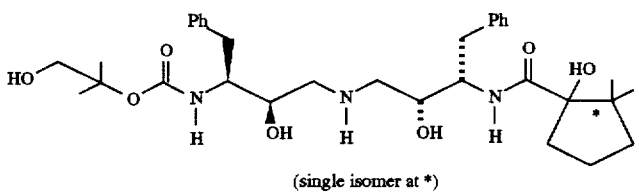

(single isomer at *)

The slower moving isomer from Example 368f was further purified by preparative HPLC on a YMC S-10 ODS (30×500 mm) column. Gradient elution from 60–90% MeOH—H₂O+0.1 % TFA afforded a white foam which was passed through a short column of silica gel (elution with CHCl₃:MeOH:NH₄OH, 90:10:1) to give 71 mg of Compound 369 as a solid white foam.

m.p. 90°–100° C. (softening at 80°); [α]$_D$=–12.9° (c 0.79, MeOH).

R$_f$ (SiO₂)=0.17 (CHCl₃:MeOH:NH₄OH, 90:10:1). Mass Spec.: (M+H)⁺600⁺; Analysis calc. for C₃₃H₄₉N₃O₇·0.40 H₂O: C, 65.30; H, 8.27; N, 6.92. Found: C, 65.39; H, 8.32; N, 6.83.

EXAMPLE 370

Preparation of [1S-[1R*,2S*(2S*, 3R*)]]-[3-[[3-[[(1,1-Dimethylethoxy)carbonyl]amino]-2-hydroxy-4-(2-ethenylphenyl) butyl]amino]-2-hydroxy-1-(phenylmethyl)propxyl]carbamic acid, 1,1-dimethylethyl ester (Compound 370c)

(a) Compound 370a

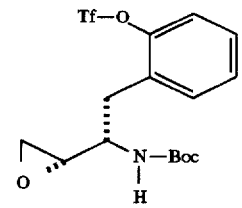

A solution of Compound 349a (1.9 g, 6.8 mmol) in 100 ml of CH₂Cl₂ was cooled at 0° C. and N-phenyltriflimide (2.67 g, 7.47 mmol) was added followed by Et₃N (1.15 ml, 8.25 mmol). The reaction was stirred at 0° C. for 2.5 h and then allowed to warm to RT and stir overnight. Additional quantities of N-phenyltriflimide (800 mg, 2.24 mmol) and Et₃N (345 ml, 2.48 mmol) were added. Stirring was continued for an additional 6 h at RT. The reaction was diluted with Et₂O and washed with H₂O, 1N NaOH, H₂O, and brine. After drying (Na₂SO₄), the solvents were removed and the crude material was purified on a 250 ml silica column eluting with EtOAc/hexanes (1:4) to afford 1.6 g (68%) of Compound 370a as a colorless solid.

(b) Compound 370b

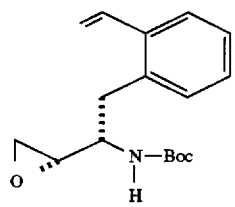

To a solution of the Compound 370a (610 mg, 1.5 mmol) in 10 ml of 1-methyl-2-pyrrolidinone was added LiCl (190 mg, 4.5 mmol) and triphenylarsine (90 mg, 0.3 mmol) and the reaction mixture was degassed with argon. Tris (dibenzylideneacetone)dipalladium (0) (138 mg, 0.15 mmol) was added and the mixture stirred for 5 min. Vinyltributyltin (0.520 ml, 560 mg, 1.8 mmol) was added and the reaction mixture was then stirred for 2.5 h at RT and heated at 55° C. overnight. An additional 20% of triphenylarsine (18mg), Pd° (28 mg) and vinyltributyltin (104 ml) were added and heating was continued for an additional 6 h. The mixture was poured into 1:1 sat. NaHCO$_3$/H$_2$O and extracted with EtOAc. The combined EtOAc extract was washed with H$_2$O and brine and dried (Na$_2$SO$_4$). The solvent was removed and the crude material was purified on a 100 ml silica column eluting with 10 to 20% EtOAc/hexane gradient to afford 190 mg (44%) of Compound 370b as a colorless solid.

(c) Compound 370c

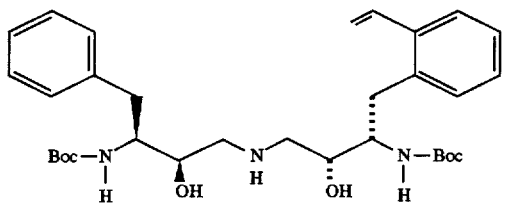

Compounds 370b and 16b were reacted by a procedure analogous to that of Example 304c to afford the title Compound 370c (colorless solid).

m.p. 173°–176° C. (dec); [α]$_D$=–6.0° (c 0.5, MeOH). Mass Spec.: (M+H)$^{30}$ 570$^+$; Analysis calc. for C$_{32}$H$_{47}$N$_3$O$_6$·1.5 H$_2$O: C, 64.40; H, 8.40; N, 7.05. Found: C, 64.21; H, 8.03; N, 7.00.

EXAMPLE 371

Preparation of [1S-[1R*,2S*(2S*, 3R*)]]-[3-[[3-[[(1,1-Dimethylethoxy)carbonyl]amino]-2-hydroxy-4-(2-ethenylphenyl) butyl]amino]-2-hydroxy-1-(phenylmethyl)propxyl]carbamic acid, 1,1-dimethylethyl ester (Compound 371)

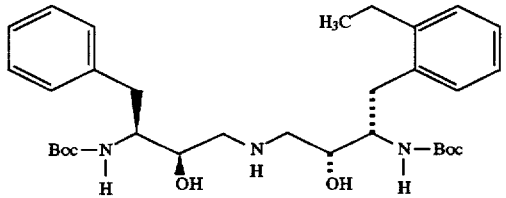

A solution of Compound 370c (68 mg, 0.12 mmol) in 3 ml of MeOH containing 7 mg of 10% Pd/C catalyst was stirred under a hydrogen atmosphere (balloon) for 12 h. The reaction was filtered and the MeOH evaporated to afford 66 mg (98%) of Compound 371 as a colorless solid.

m.p. 178°–181° C. (dec); [α]$_D$=5.6° (c 0.5, MeOH). Mass Spec.: (M+H)$^{30}$ 572$^+$; Analysis calc. for C$_{32}$H$_{49}$N$_3$O$_6$·1.75 H$_2$O: C, 63.61; H, 8.91; N, 7.08. Found: C, 63.71; H, 8.77; N, 6.97.

EXAMPLE 372

Preparation of [1S-[1R*,2S*(2S*, 3R*)[[-]3-]]4-]4-[2-[[(Dimethylamino) carbonyl]oxy]ethoxyl]phenyl]-3-[[(1,1-dimethylethoxy) carbonyl]amino]-2-hydroxybutyl]amino]-2-hydroxy-1-(phenylmethyl) propyl]carbamic acid (Compound 372d)

(a) Compound 372a

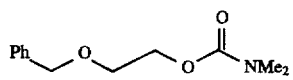

To a stirred solution of phosgene in toluene (8.5 mL of a 1.93M solution; 16.4 mmol) at –60° C. was added a solution of 2-benzyloxyethanol (467 μL, 3.28 mmol) and pyridine (583 μL, 7.22 mmol) in 3 mL CH$_2$Cl$_2$. After adding 20 mL more CH$_2$Cl$_2$, the temperature of the reaction mixture was allowed to rise to 15° C. and was then cooled to –20° C. Excess N,N-dimethylamine was bubbled through the turbid mixture which was stirred at RT overnight. The solution was washed with H$_2$O, dried (Na$_2$SO$_4$), and concentrated to afford the crude product which was purified by chromatography on a column (5 cm×15 cm) of silica gel eluting with EtOAc-hexane (20–80 to 25–75) to afford 490 mg(67%) of Compound 372a.

(b) Compound 372b

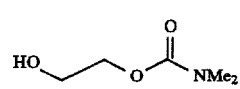

Compound 372a was converted to Compound 372b by a procedure analogous to that of Example 208 (EtOH was used instead of MeOH).

(c) Compound 372c

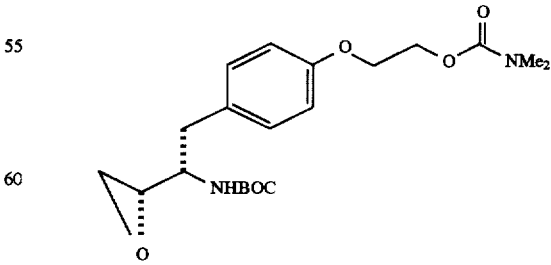

Compounds 372b and 175c were converted to Compound 372c by a procedure analogous to that of Example 282a.

(d) Compound 372d

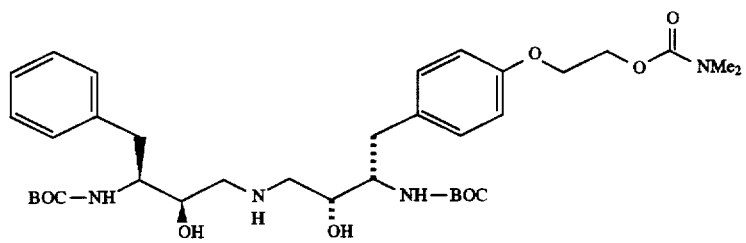

Compounds 372c and 16b were reacted by a procedure analogous to that of Example 304c to give the title Compound 372d (white solid).

m.p. 128°–132° C.; $[\alpha]_D$=–3.1° (c 0.52, MeOH). Mass Spec. (FAB), 675 (M+H)$^+$; Analysis calc. for $C_{35}H_{54}N_4O_9 \cdot 0.54\ H_2O$: C, 61.41; H, 8.11; N, 8.18. Found: C, 61.40; H, 7.95; N, 8.19.

EXAMPLE 373

Preparation of [1S-[1R*,2S*(2S*, 3R*)]]-[1-[[[3-[[3-[[(1, 1-Dimethylethoxy)carbonyl]amino]-2-hydroxy-4-phenylbutyl]amino]-2-hydroxy-1-(phenylmethyl)propyl]amino]carbonyl]-1,2-dimethylpropyl]carbamic acid, methyl ester, isomer A (Compound 373d)

(a) Compound 373a

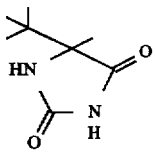

Compound 373a was prepared as described in Obrecht et al., Helv. Chim. Acta, 75, 1666 (1992).

(b) Compound 373b

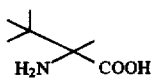

A solution of 1.2 g (7.1 mmol) of 373a in 25 ml of concentrated HCl was heated at 130° C., in a pressure vessel, for 7 d. After cooling to RT, the solution was evaporated to dryness to yield a solid residue which was taken into $H_2O$, washed with $CH_2Cl_2$, and again evaporated to dryness to yield 1.6 g of Compound 373b as a tan solid.

(c) Compound 373c

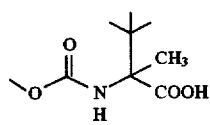

Compound 373b was converted to Compound 373c by a procedure analogous to that of Example 246a.

(d) Compound 373d

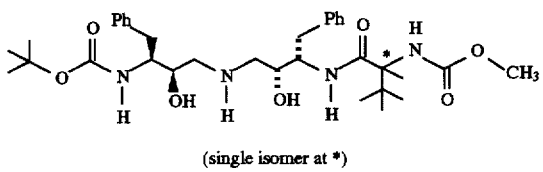

(single isomer at *)

Compounds 373c and 54 were converted to the title Compound 373d by a two-step procedure analogous to that employed for the synthesis of Compound 312d ($CH_2Cl_2$ only used for reaction of HOBT with Compound 373c). The crude product was purified by flash chromatography on a 45 cc column of silica gel. Elution with $CHCl_3$:MeOH:$NH_4OH$ (95:5:0.5) afforded 140 mg of a mixture of isomers which were separated by preparative HPLC on a YMC S-10 ODS (30×500 mm) column. Isocratic elution with 70% MeOH—$H_2O$+0.1% TFA, gave as the faster moving isomer on C-18, Compound 373d, which was passed through a short column of silica gel (elution with $CHCl_3$:MeOH: $NH_4OH$ (90:10:1)) and triturated with $Et_2O$ to afford 42 mg (16%) of the title Compound 373d as a white solid.

m.p. 120°–122° C.; $[\alpha]_D$=–0.9° (c 0.66, MeOH). Mass Spec.: (M+H)$^{30}$ 629$^+$; Analysis calc. for $C_{34}H_{52}N_4O_7$: C, 64.94; H, 8.33; N, 8.91. Found: C, 64.54; H, 8.13; N, 8.57.

EXAMPLE 374

Preparation of [1S-[1R*,2S*(2S*, 3R*)]]-[1-[[[3-[[3-[[(1, 1-Dimethylethoxy)carbonyl]amino]-2-hydroxy-4-phenylbutyl]amino]-2-hydroxy-1-(phenylmethyl)propyl]amino]carbonyl]-1,2-dimethylpropyl]carbamic acid, methyl ester, isomer B (Compound 374)

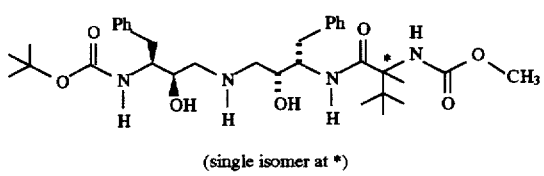

(single isomer at *)

The slower moving isomer on C-18 was isolated by preparative HPLC as described in Example 373d followed by passage through a short column of silica gel (elution with $CHCl_3$:MeOH: $NH_4OH$ (90:10:1)) and trituration with $Et_2O$ to afford 54 mg (20%) of Compound 374 as a white solid.

m.p. 168°–170° C.; $[\alpha]_D$=–21.50° (c 0.75, MeOH). Mass Spec.: (M+H)$^{30}$ 629$^+$; Analysis calc. for $C_{34}H_{52}N_4O_7$: C, 64.94; H, 8.33; N, 8.91. Found: C, 64.75; H, 8.33; N, 8.68.

EXAMPLE 375

Preparation of [1S-[1R*,2S*(2S*, 3R*)]]-[3-[[3-]] (2, 3-Dihydro-1-hydroxy-1H-inden-1-yl)carbonyl] amino]-2-hydroxy-4-phenylbutyl]amino]-2-hydroxy-1-(phenylmethyl)-propyl]carbamic acid, 1,1-dimethylethyl ester, isomer A (Compound 375)

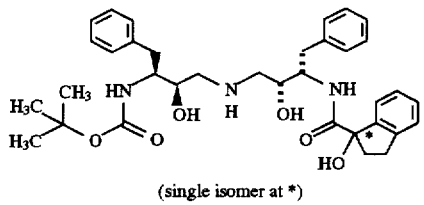

(single isomer at *)

1-Indanone was converted to a 1:1 mixture of Compounds 375 and 376 by a four-step procedure analogous to that used for the synthesis of Compounds 321 and 322. Compound 375 (white solid) was isolated as the faster moving isomer by silica gel chromatography, eluting with 99:1:0.1 to 94:6:0.6 $CH_2Cl_2:CH_3OH:aq. NH_4OH$.

m.p. 189°–192° C.; $[\alpha]_D$=–15.70° (c 0.2, $CH_3OH$); $R_f$ ($SiO_2$)=0.32 (99:1:0.1 $CH_2Cl_2:CH_3OH:aq. NH_4OH$); Mass Spec. (Fab): $(M+H)^{30}$ 604. Analysis calc. for $C_{35}H_{45}N_3O_6$: C, 69.63; H, 7.51; N, 6.96. Found: C, 69.28; H, 7.51; N, 6.97.

EXAMPLE 376

Preparation of [1S-[1R*,2S*(2S*, 3R*)]]-[3-[[3-[[(2,3-Dihydro-1-hydroxy-1H-inden-1-yl)carbonyl]-amino]-2-hydroxy-4-phenylbutyl]amino]-2-hydroxy-1-(phenylmethyl)propyl]carbamic acid, 1,1-dimethylethyl ester, isomer B

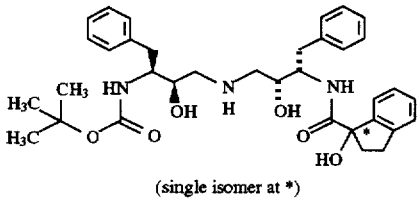

(single isomer at *)

Compound 376 (white solid) was isolated as the slower moving isomer as described in Example 375.

m.p. 100°–102° C.; $[\alpha]_D$=+15.0° (c 0.22, $CH_3OH$); $R_f$ ($SiO_2$)=0.25 (99:1:0.1 $CH_2Cl_2:CH_3OH:aq. NH_4OH$); Mass Spec. (Fab): $(M+H)^{30}$ 604.

EXAMPLE 377

Preparation of [1S-[1R*,2S*[2S*, 3R*(S*)]]]-[3-[[3-[2-Hydroxy-1-oxo-2-phenylethyl) amino]-2-hydroxy-4-phenylbutyl]amino]-2-hydroxy-1-(phenylmethyl)propyl]carbamic acid, 1-dimethylethyl ester (Compound 377)

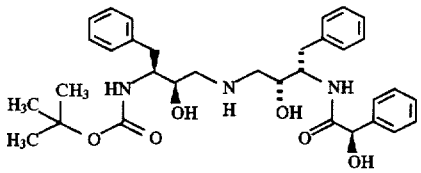

To a solution of (R)-mandelic acid (100 mg, 0.225 mmol) in DMF (0.5 mL) was added Compound 54 (37.6 mg, 0.247 mmol), followed by BOP reagent (241 mg, 0.545 mmol) and N-methylmorpholine (132 µL, 1.20 mmol) at 0° C. The mixture was stirred at RT for 16 h. DMF was removed in vacuo and the residue dissolved in EtOAC, washed with saturated aq. $NaHCO_3$ and then with brine. The organic layer was separated, dried ($MgSO_4$) and concentrated in vacuo and the residue purified by silica gel chromatography, eluting with 99:1:0.1 to 91.5:8.5:0.85 $CH_2Cl_2:CH_3OH:aq. NH_4OH$ to afford Compound 377 (94 mg, 72%) as a white solid.

m.p. 125°–127° C.; $[\alpha]_D$=–13.00° (c 0.2, $CH_3OH$); Mass Spec. (Fab): $(M+H)^{30}$ 578$^+$. Analysis calc. for: $C_{33}H_{43}N_3O_6·0.80 H_2O$; C, 66.93; H, 7.59; N, 7.10. Found: C, 66.76; H, 7.55; N, 7.27.

EXAMPLE 378

Preparation of [1S-[1R*,2S*[2S*, 3R*(R*)]]]-[3-[[3-[2-Hydroxy-1-oxo-2-phenylethyl) amino]-2-hydroxy-4-phenylbutyl]amino]-2-hydroxy-1-(phenylmethyl)propyl]carbamic acid, 1-dimethylethyl ester (Compound 378)

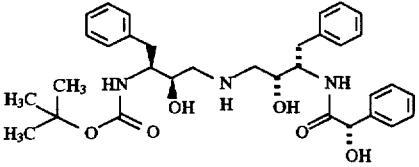

(S)-Mandelic acid and Compound 54 were reacted by a procedure analogous to that of Example 377 to afford the title Compound 378 (white solid).

m.p. 135°–138° C.; $[\alpha]_D$=+9.1° (c 0.22, $CH_3OH$); Mass Spec. (Fab): $(M+H)^{30}$ 578$^+$. Analysis calc. for: $C_{33}H_{43}N_3O_6·0.63 H_2O$; C, 67.28; H, 7.57; N, 7.13. Found: C, 67.12; H, 7.54; N, 7.29.

EXAMPLE 379

Preparation of [1S-(1R*,2S*) (trans)]-[Iminobis[2-hydroxy-1-(phenylmethyl)-3, 1-propanediyl]]bis [carbamic acid], 1,1-dimethylethyl 2-hydroxy-1-methylcyclopentyl ester (Compound 379e)

(a) Compound 379a

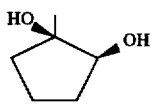

A solution of NaOH (600 mg; 15 mmol) and KMnO$_4$ (2.81 g; 17.8 mmol) in 95 ml of H$_2$O precooled to 0° C. was added to a slurry of 1-methylcyclopentene (1 g; 12 mmol), t-BuOH (120 ml), H$_2$O (25 ml) and ice (60 g) at −10° C. The resulting mixture was stirred 10 min at −10° C. Sodium sulfite (2.3 g) was added and the mixture was filtered through celite. The filtrate was concentrated to ~30 ml by distillation of the solvents at atmospheric pressure. Solid NaCl was added to saturation and the mixture was extracted with EtOAc. After drying (MgSO$_4$), the organic layer was concentrated to afford 1.03 g (74%) of racemic Compound 379a.

(b) Compound 379b

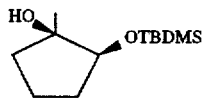

Compound 379a was converted into racemic Compound 379b by a procedure analogous to that of Example 264b.

(c) Compound 379c

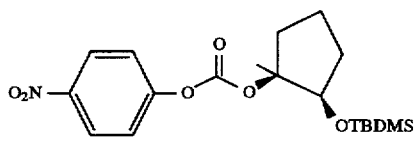

Compound 379b was converted into racemic Compound 379c by a procedure analogous to that of Example 161d.

(d) Compound 379d

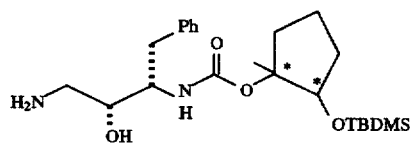

(1:1 mixture of isomers at *; S,R:R,S)

Compounds 379c and 298a were reacted by a two-step procedure analogous that used for the conversion of Compound 282c to Compound 282e to afford Compound 379d.

(e) Compound 379e

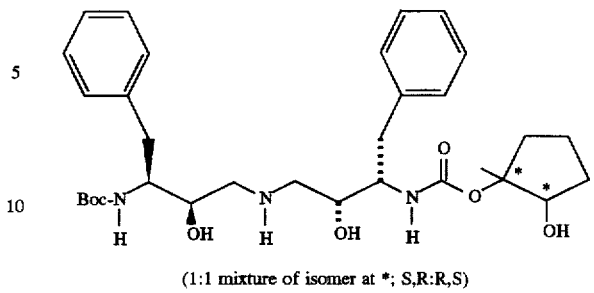

(1:1 mixture of isomer at *; S,R:R,S)

Compounds 379d and 1b(i) were reacted by a two-step procedure analogous to that used for the conversion of Compound 282e to Compound 282g to afford the title Compound 379e (white solid).

m.p. 102°–113° C. ("shrinkage at 68°–87° C.); Mass Spec. (FAB) (M+H)$^{3O}$ =586 Analysis calc. for C$_{32}$H$_{46}$N$_3$O$_7$·0.98 H$_2$O: C, 63.81; H, 8.02; N, 6.98 Found: C, 63.81; H, 8.17; N, 6.98.

EXAMPLE 380

Preparation of [1S-[1R*, 2S*(2S*, 3R*)]]-[3-[[3-[[(1,1-Dimethylethoxy) carbonyl]amino]-2-hydroxy-4-[4-[2-(3-oxo-4-morpholinyl) ethoxy]phenyl]-butyl]amino]-2-hydroxy-1-(phenylmethyl) propyl]-carbamic acid, 1,1-dimethylethyl ester (Compound 380d)

(a) Compound 380a

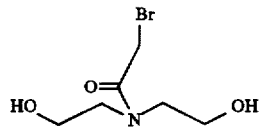

To a 0° C. solution of diethanolamine (2.10 g; 20.0 mmol) in 40 mL of dry CH$_2$Cl$_2$ was added dry Et$_3$N (4.2 mL; 30.0 mmol) and bromoacetyl bromide (2.1 mL; 24.0 mmol). The reaction mixture was stirred at 5° C. for 3 h, then at RT overnight. Volatiles were removed in vacuo and the residue was purified on silica using 100% EtOAc to afford 1.5 g of pure Compound 380a (33%).

(b) Compound 380b

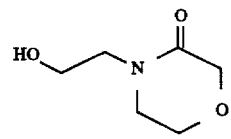

To a suspension of NaH (260 mg; 6.63 mmol; 60% in mineral oil) in 1.0 mL of dry DMF at 0° C. was added a solution of Compound 380a (1.5 g; 6.63 mmol) in 5.5 mL of dry DMF. The solution was allowed to warm to RT. After 6 h another 260 mg (6.63 mmol) of NaH was added and the mixture was stirred overnight. The reaction was quenched with H$_2$O and concentrated in vacuo to give crude material which was purified on silica gel using a stepwise gradient from 2% to 8% MeOH:CH$_2$Cl$_2$:0.1% NH$_4$OH to afford Compound 380b (600 mg; 62%).

(c) Compound 380c

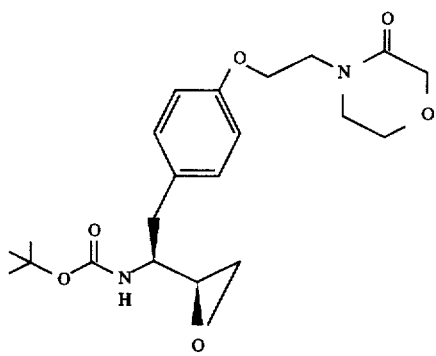

Compounds 175c and 380b were reacted by a procedure analogous to that of Example 282a to give Compound 380c.

(d) Compound 380d

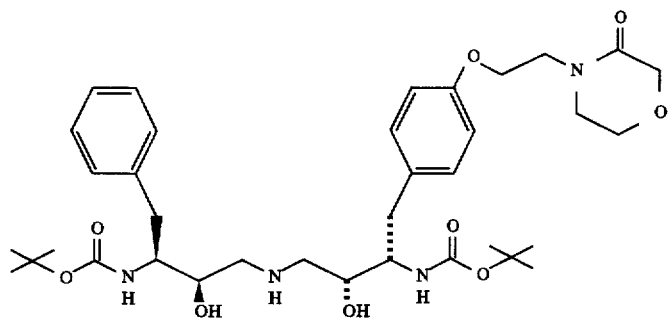

Compounds 16b and 380c were reacted by a procedure analogous to that of 304c to give the title Compound 380d (white solid).

m.p. 108°–111° C.; [α]$_D$=–3.3° (c 0.03, CH$_3$OH); Mass Spec. (FAB): (M+H)=687.

EXAMPLE 381

Preparation of [1S-[1R*,2S*(2S*, 3R*)]]-[2-Hydroxy-3-[[2-hydroxy-3-[[2-hydroxy-1-oxo-2-(2-pyridinyl)propyl]amino]-4-phenylbutyl]amino]-1-(phenylmethyl)propyl]carbamic acid, 1,1-dimethylethyl ester, isomer A (Compound 381b)

(a) Compound 381a

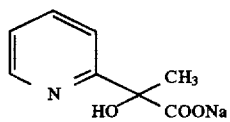

ZnI$_2$ (96 mg; 0.3 mmol) was added to a solution of 2-acetylpyridine (1.10 ml; 9.8 mmol) and trimethylsilylcyanide (1.70 ml; 12.7 mmol) in 20 ml of CH$_2$Cl$_2$ at 20° C. After stirring at RT for 3 h, the solvent was removed in vacuo and the residue was stirred in ~4 ml of concentrated HCl at RT for 40 h. After cooling to 0° C., the pH of the reaction mixture was adjusted to 9 with 6N NaOH. The basic mixture was washed with EtOAc, concentrated to ~15 ml and loaded onto an HP-20 column, eluting with water, to afford 940 mg (50%) of Compound 381a as a white solid.

(b) Compound 381b

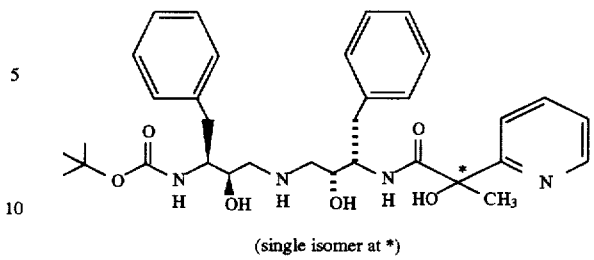

(single isomer at *)

Compounds 54 and 381a were reacted by a procedure analogous to that described in Example 321d to afford a 1:1 mixture of Compounds 381b and 382. The diastereomers were separated by preparative HPLC [YMC S-10 ODS (C-18) 30×500 mm column; stepwise gradient from 56–74% MeOH/H$_2$O+0.1% TFA]. Final isolation of the faster moving isomer by chromatography on a 2.5×10 cm silica gel column using 5% MeOH/CH$_2$Cl$_2$+0.5% NH$_4$OH as the mobile phase gave 88 mg (33%) of the title Compound 381b as a white solid.

m.p. 114°–117° C. (softens at 92° C.); R$_f$ (SiO$_2$)=0.25, CH$_2$Cl$_2$:MeOH:NH$_4$OH, 90:9:1 (UV and PMA detection); [α]$_D$=–7.8 (c 0.32, MeOH). Mass Spec. FAB: M+H=593. Analysis calc. for C$_{33}$H$_{44}$N$_4$O$_6$·0.49 H$_2$O: C, 65.90; H, 7.54; N, 9.31; Found C, 66.10; H, 7.45; N, 9.11.

EXAMPLE 382

Preparation of [1S-[1R*,2S*(2S*, 3R*)]]-[2-Hydroxy-3-[[2-hydroxy-3-[[2-hydroxy-1-oxo-2-(2-pyridinyl)propyl]amino]-4-phenylbutyl]amino]-1-(phenylmethyl) propyl]carbamic acid, 1,1-dimethylethyl ester, isomer B (Compound 382)

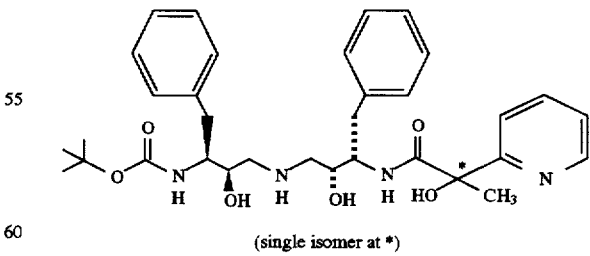

(single isomer at *)

Compound 382 (white solid) was isolated as the slower moving isomer by preparative HPLC followed by silica gel chromatography as described in Example 381b.

m.p. 92°–96° C.; R$_f$ (SiO$_2$)=0.06, CH$_2$Cl$_2$:MeOH:NH$_4$OH, 90:9:1 (UV and PMA detection);

[α]$_D$=−5.7° (c 0.30, MeOH).. Mass Spec. FAB: M+H=593. Analysis calc. for C$_{33}$H$_{44}$N$_4$O$_6$·0.26 H$_2$O: C, 66.34; H, 7.51; N, 9.38; Found C, 66.46; H, 7.65; N, 9.26.

EXAMPLE 383

Preparation of [1R*,2S*[2S*, 3R*(S*)]]-N-[2-Hydroxy-3-[[2-hydroxy-3-[(2-hydroxy-2,3,3-trimethyl-1-oxobutyl) amino]-4-phenylbutyl]amino]-1-(phenylmethyl) propyl]-N$^2$-(2-methoxycarbonyl)-3-methyl-L-valinamide (Compound 383e)

(a) Compound 383a

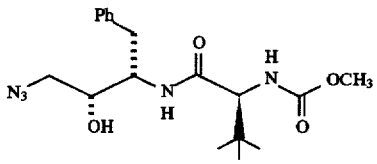

To a solution of Compound 298a (500 mg, 2.42 mmol) in 0.5 mL DMF was added Compound 246a (505 mg, 2.66 mmol), followed by HOBT hydrate (360 mg, 2.66 mmol), N-methylmorpholine (318 mg, 3.15 mmol) and EDCI hydrochloride (510 mg, 2.66 mmol) at 0° C., and the mixture stirred at RT for 21 h. DMF was removed in vacuo and the residue dissolved in EtOAc, washed with sat. NaHCO$_3$ and then brine. The organic layer was separated, dried (MgSO$_4$) and concentrated to yield a residue which was purified by silica gel chromatography, eluting from 99.5:0.5:0.05 to 96.5:3.5:0.35 CH$_2$Cl$_2$:CH$_3$OH:aq. NH$_4$OH to afford Compound 383a (604 mg, 66%) as a white solid.

TLC (SiO$_2$), R$_f$=0.41 (9:1:0.1 CH$_2$Cl$_2$:CH$_3$OH:aq. NH$_4$OH—Rydon).

(b) Compound 383b

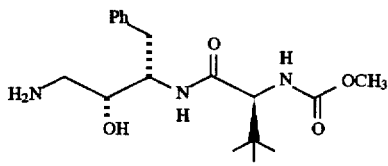

To Compound 383a (604 mg, 1.60 mmol) in THF (7 mL) and H$_2$O (43 µL) was added Ph$_3$P (462 mg, 1.76 mmol) and the solution stirred at RT for 18 h. The solvent was removed in vacuo and the resulting residue purified by flash chromatography on silica gel, eluting with a step wise gradient from 99:1:0.1 to 87:13:1 CH$_2$Cl$_2$:CH$_3$OH:aq. NH$_4$OH to afford Compound 383b (478 mg, 85%) as a white solid.

TLC (SiO$_2$) R$_f$=0.15 (9:1:0.1 CH$_2$Cl$_2$:CH$_3$OH:aq. NH$_4$OH—Rydon).

(c) Compound 383c

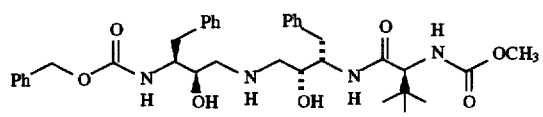

To a solution of Compound 383b (468 mg, 1.33 mmol) in DMF (0.6 mL) was added Compound 44a (396 mg, 1.33 mmol) and the mixture heated at 100° C. for 7 h. DMF was removed in vacuo and the residue purified by flash chromatography on silica gel, eluting with a step wise gradient from 99:1:0.1 to 82:12:1 CH$_2$Cl$_2$:CH$_3$OH:aq. NH$_4$OH to afford Compound 383c (377 mg, 43%) as a white solid.

TLC (SiO$_2$) R$_f$=0.28 (9:1:0.1 CH$_2$Cl$_2$:CH$_3$OH:aq. NH$_4$OH/Rydon).

(d) Compound 383d

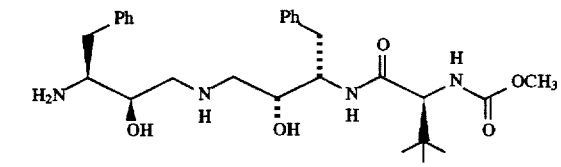

To a solution of Compound 383c (366 mg, 0.564 mmol) in EtOH (12 mL) and EtOAc (4 mL) was added 20% Pd(OH)$_2$/C (108 mg) and the slurry stirred under a H$_2$(g) atmosphere for 18 h. The reaction mixture was filtered and the filtrate concentrated in vacuo. The residue was purified by flash chromatography on silica gel, eluting with a step wise gradient from 97.5:2.5:0.25 to 87:13:1 CH$_2$Cl$_2$:CH$_3$OH:aq. NH$_4$OH to afford Compound 383d (209 mg, 76%) as a white solid.

TLC (SiO$_2$) R$_f$=0.14 (9:1:0.1 CH$_2$Cl$_2$:CH$_3$OH:aq. NH$_4$OH/Rydon).

(e) Compound 383e

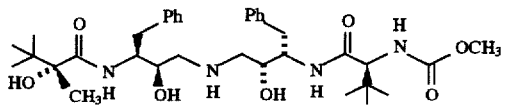

To a solution of Compound 383d (105 mg, 0.204 mmol) in DMF (0.5 mL) was added Compound 262e (34.5 mg, 0.236 mmol), followed by BOP reagent (104 mg, 0.236 mmol) and N-methylmorpholine (52 µL, 0.473 mmol) and the mixture stirred at RT for 18 h. DMF was removed in vacuo, the residue dissolved in EtOAc and washed with sat. NaHCO$_3$ and then brine. The organic layer was separated, dried (MgSO$_4$) and concentrated in vacuo. Purification was achieved by flash chromatography on silica gel, eluting with a step wise gradient from 97.5:2.5:0.25 to 87:13:1 CH$_2$Cl$_2$:CH$_3$OH:aq. NH$_4$OH to afford the title Compound 383e (70 mg, 54% yield) as a white solid.

m.p. 94°–96° C.; [α]$_D^{30}$=+4.54° (c 0.22, CH$_3$OH); Mass Spec. (Fab): (M+H) 643$^+$. Analysis calcd. for C$_{35}$H$_{54}$N$_4$O$_7$·1.00 H$_2$O; C, 63.62; H, 8.54; N, 8.72. Found: C, 63.70; H, 8.43; N, 8.40.

EXAMPLE 384

Preparation of [1S-[1R*,2S*(2S*, 3R*)]]-[3-[[3-[[2-Hydroxy-3, 3-dimethyl-2-[(methylamino)carbonyl]-1-oxobutyl]amino]-2-hydroxy-4-phenylbutyl]-amino]-2-hydroxy-1-(phenylmethyl) propyl]-carbamic acid, 1,1-dimethylethyl ester, isomer A (Compound 384d)

(a) Compound 384a

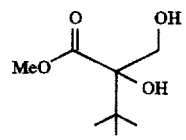

Diazomethane in Et$_2$O (prepared from 5.45 g of 1-methyl-3-nitro-1-nitrosoguanidine as described in Example 1a(i)) was added to a suspension of Compound 366c (3.0 g, 18.5mmol) in 50 mL of Et$_2$O at 0° C. The resulting mixture was quenched with few drops of HOAc and concentrated in vacuo to afford Compound 384a (oil; 3.26 g, 100% crude yield).

(b) Compound 384b

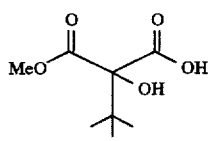

Compound 384a was converted to Compound 384b by a two-step procedure analogous to that used for the synthesis of Compound 262e.

(c) Compound 384c

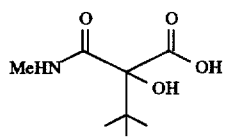

A mixture of methylamine (ca. 5 g) and Compound 384b (0.9 g, 4.74 mmol) in 10 mL of MeOH was heated in a sealed tube at 150° C. for 3 h and concentrated in vacuo. The residue was dissolved in $CH_2Cl_2$, washed with 20% aq. sulfuric acid, the combined aqueous phase was extracted with $CH_2Cl_2$, and the combined organic phase was dried ($MgSO_4$) and concentrated to afford the Compound 384c (0.55 g, 61%) as a colorless oil.

(d) Compound 384d

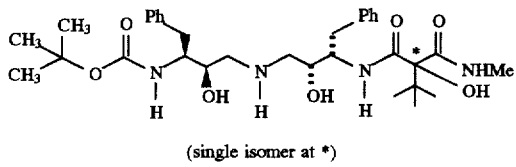

(single isomer at *)

Compounds 384c and 54 were converted to the title Compound 384d and its diastereomer Compound 385 by a two-step procedure analogous to that employed for the synthesis of Compound 312d ($CH_2Cl_2$ only was used for the reaction of HOBT with Compound 384c). The mixture was purified by flash chromatography (silica gel/$CH_2Cl_2$—MeOH—$NH_4OH$ 99:1:0.1 to 95:5:0.5) to afford 115 mg of a 1:1 mixture of diastereomers which were separated by preparative HPLC (column: Polymer Labs. PLRP-S 100 Å 10 μm 25×300 mm; eluent: 30:70 step wise to 1:1 A:B, eluent A=$H_2O$—$CH_3CN$—$NH_4OH$ 90:10:0.2, eluent B =$H_2O$—$CH_3CN$—$NH_4OH$ 10:90:0.2) to afford the title Compound 384d (faster moving isomer on polymer column) as a white solid (25 mg, 9% yield).

$R_f$=0.37 (silica gel/$CH_2Cl_2$—MeOH—$NH_4OH$ 9:1:0.1), m.p. 77°–78° C., $[\alpha]_D$=−7.5° (c 0.6 MeOH). Mass Spec.: 615 (M+H)$^+$. Analysis calcd for $C_{33}H_{50}N_4O_7 \cdot 0.77 H_2O$: C, 63.05; H, 8.26; N, 8.91. Found: C, 63.24; H, 8.17; N. 8.91.

EXAMPLE 385

Preparation of [1S-[1R*,2S*(2S*, 3R*)]]-[3-[[3-[[2-Hydroxy-3, 3-dimethyl-2-[(methylamino)carbonyl]-1-oxobutyl]amino]-2-hydroxy-4-phenylbutyl]-amino]-2-hydroxy-1-(phenylmethyl) propyl]-carbamic acid, 1,1-dimethylethyl ester, isomer B (Compound 385)

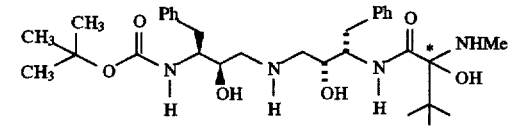

(single isomer at *)

Compound 385 (white solid) was isolated (slower moving isomer on polymer column) by preparative HPLC as described in Example 384d.

$R_f$=0.37 (silica gel/$CH_2Cl_2$—MeOH—$NH_4OH$ 9:1:0.1), m.p. 76°–77° C.; $[\alpha]_D$=−15.1° (c 0.55 MeOH). Mass Spec.: 615 (M+H)$^{30}$.

Other compounds contemplated by the present invention include the following compounds:

1. [R-(R*,S*)]-[Iminobis[2-hydroxy-1-(phenylmethyl)-3, 1-propanediyl]]biscarbamic acid, 1,1-dimethylethyl 3,3,3-trifluoro-2-hydroxy-1, 1-dimethylpropyl ester.
2. [R-(R*,S*)]-[Iminobis[2-hydroxy-1-(phenylmethyl)-3, 1-propanediyl]]biscarbamic acid, 1,1-dimethylethyl (R,R:S,S)-2-hydroxy-1-methylcyclopentyl ester.
3. [R-(R*,S*)]-[Iminobis[2-hydroxy-1-(phenylmethyl)-3, 1-propanediyl]]biscarbamic acid, 1,1-dimethylethyl (R,S:S,R)-tetrahydro-4-hydroxy-3-furanyl ester.
4. [1S-[1R*,2S*(2S*, 3R*)]]-[2-Hydroxy-3-[[2-hydroxy-3-[[(1-hydroxy-2,2-dimethylcyclobutyl) carbonyl]amino]-4-phenylbutyl]amino]-1-(phenylmethyl) propyl]carbamic acid, 1,1-dimethylethyl ester.
5. [1S-[1R*,2S*(2S*, 3R*)]]-[2-Hydroxy-3-[[2-hydroxy-3-[[(4-hydroxyspiro[2.4]hept-4-yl) carbonyl]amino]-4-phenylbutyl]amino]-1-(phenylmethyl) propyl]carbamic acid, 1,1-dimethylethyl ester.
6. [1S-[1R*,2S*(2S*, 3R*)]]-[2-Hydroxy-3-[[2-hydroxy-3-[[(5-hydroxyspiro[3.4]oct-5-yl) carbonyl]amino]-4-phenylbutyl]amino]-1-(phenylmethyl) propyl]carbamic acid, 1,1-dimethylethyl ester.
7. [1S-[1R*,2S*(2S*, 3R*)]]-[2-Hydroxy-3-[[2-hydroxy-3-[[(6-hydroxyspiro[4.4]non-6-yl) carbonyl]amino]-4-phenylbutyl]amino]-1-(phenylmethyl) propyl]carbamic acid, 1,1-dimethylethyl ester.
8. [1S-[1R*,2S*(2S*, 3R*)]]-[2-Hydroxy-3-[[2-hydroxy-3-[[(octahydro-1-hydroxy-1-pentalenyl) carbonyl]amino]-4-phenylbutyl]amino]-1-(phenylmethyl) propyl]carbamic acid, 1,1-dimethylethyl ester.
9. [R-(R*,S*)]-[Iminobis[2-hydroxy-1-(phenylmethyl)-3, 1-propanediyl]]biscarbamic acid, 1,1-dimethylethyl tetrahydro-4,4-dimethyl-3-furanyl ester.
10. [1S-[1R*,2S*(2S*, 3R*)]]-[2-Hydroxy-3-[[2-hydroxy-3-[[(1,5-dihydroxy-2,2-dimethylcyclopentyl) carbonyl] amino]-4-phenylbutyl]amino]-1-(phenylmethyl) propyl] carbamic acid, 1,1-dimethylethyl ester.
11. [1S-[1R*,2S*(2S*, 3R*)]]-[2-Hydroxy-3-[[2-hydroxy-3-[[(1,4-dihydroxy-2,2-dimethylcyclopentyl) carbonyl] amino]-4-phenylbutyl]amino]-1-(phenylmethyl) propyl] carbamic acid, 1,1-dimethylethyl ester.
12. [1S-[1R*,2S*(2S*, 3R*)]]-[2-Hydroxy-3-[[2- hydroxy-3-[[2-hydroxy-1-oxo-2-(3-pyridinyl)-propyl]carbonyl]

amino]-4-phenylbutyl]amino]-1-(phenylmethyl) propyl] carbamic acid, 1,1-dimethylethyl ester.

13. [1S-[1R*,2S*(2S*, 3R*)]]-[2-Hydroxy-3-[[2-hydroxy-3-[[2,3,3-trimethyl-2-[(methylamino)-carbonyl]-1-oxobutyl]carbonyl]amino]-4-phenylbutyl]amino]-1-(phenylmethyl)propyl]carbamic acid, 1,1-dimethylethyl ester.

14. [1S-[1R*,2S*(2S*, 3R*)]]-[2-Hydroxy-3-[[2-hydroxy-3-[[2-cyano-2,3,3-trimethyl-1-oxobutyl]carbonyl]amino]-4-phenylbutyl]amino]-1-(phenylmethyl) propyl] carbamic acid, 1,1-dimethylethyl ester.

15. [1S-[1R*,2S*(2S*, 3R*)]]-[2-Hydroxy-3-[[2-hydroxy-3-[[2-cyano-3,3-dimethyl-1-oxobutyl]carbonyl]amino]-4-phenylbutyl]amino]-1-(phenylmethyl) propyl]carbamic acid, 1,1-dimethylethyl ester.

16. [1S-[1R*,2S*(2S*, 3R*)]]-[2-Hydroxy-3-[[2-hydroxy-3-[[4-hydroxy-2-[(methoxycarbonyl)amino]-3,3-dimethyl-1-oxobutyl]carbonyl]amino]-4-phenylbutyl]amino]-1-(phenylmethyl)propyl]carbamic acid, 1,1-dimethylethyl ester.

17. [1S-[1R*,2S*(2S*, 3R*)]]-[3-[[3-[[(1,1-Dimethylethoxy)carbonyl]amino]-2-hydroxy-4-[2-(hydroxymethyl) phenyl]butyl]amino]-2-hydroxy-1-(phenylmethyl) propyl]carbamic acid, 1,1-dimethylethyl ester.

18. [1S-[1R*,2S*(2S*, 3R*)]]-[3-[[3-[[(1,1-Dimethylethoxy) carbonyl]amino]-2-hydroxy-4-[2-(2-hydroxyethyl) phenyl]butyl]amino]-2-hydroxy-1-(phenylmethyl) propyl]carbamic acid, 1,1-dimethylethyl ester.

19. [1S-[1R*,2S*(2S*, 3R*)]]-[3-[[3-[[(1,1-Dimethylethoxy)carbonyl]amino]-2-hydroxy-4-[2-(3-hydroxypropyl) phenyl]butyl]amino]-2-hydroxy-1-(phenylmethyl) propyl]carbamic acid, 1,1-dimethylethyl ester.

20. [1S-[1R*,2S*(2S*, 3R*)]]-[3-[[3-[[(1,1-Dimethylethoxy)carbonyl]amino]-2-hydroxy-4-[4-[[(4-morpholinylcarbonyl)oxy]methyl]phenyl]butyl]amino]-2-hydroxy-1-(phenylmethyl)-propyl]carbamic acid, 1,1-dimethylethyl ester.

21. [1S-[1R*,2S*(2S*, 3R*)]]-[3-[[3-[[(1,1-Dimethylethoxy)carbonyl]amino]-2-hydroxy-4-[4-[3-(4-morpholinyl)-3-oxopropyl]phenyl]butyl]amino]-2-hydroxy-1-(phenylmethyl) propyl]-carbamic acid, 1,1-dimethylethyl ester.

The above compounds correspond (by number) to the following structures:

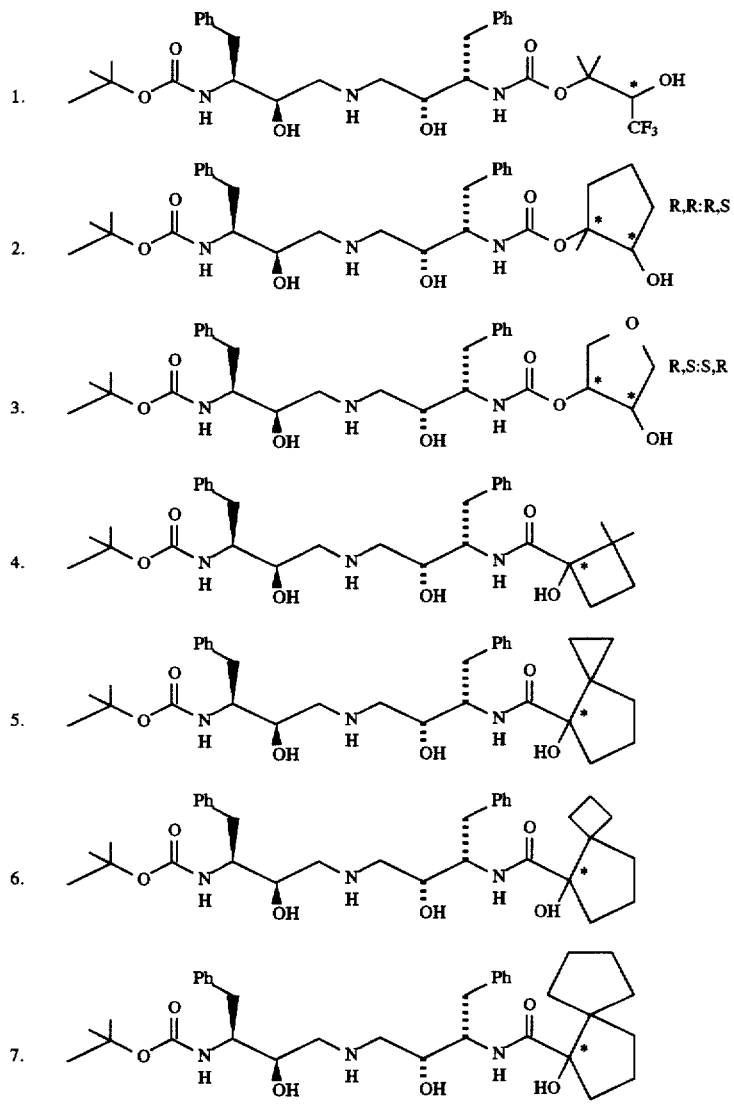

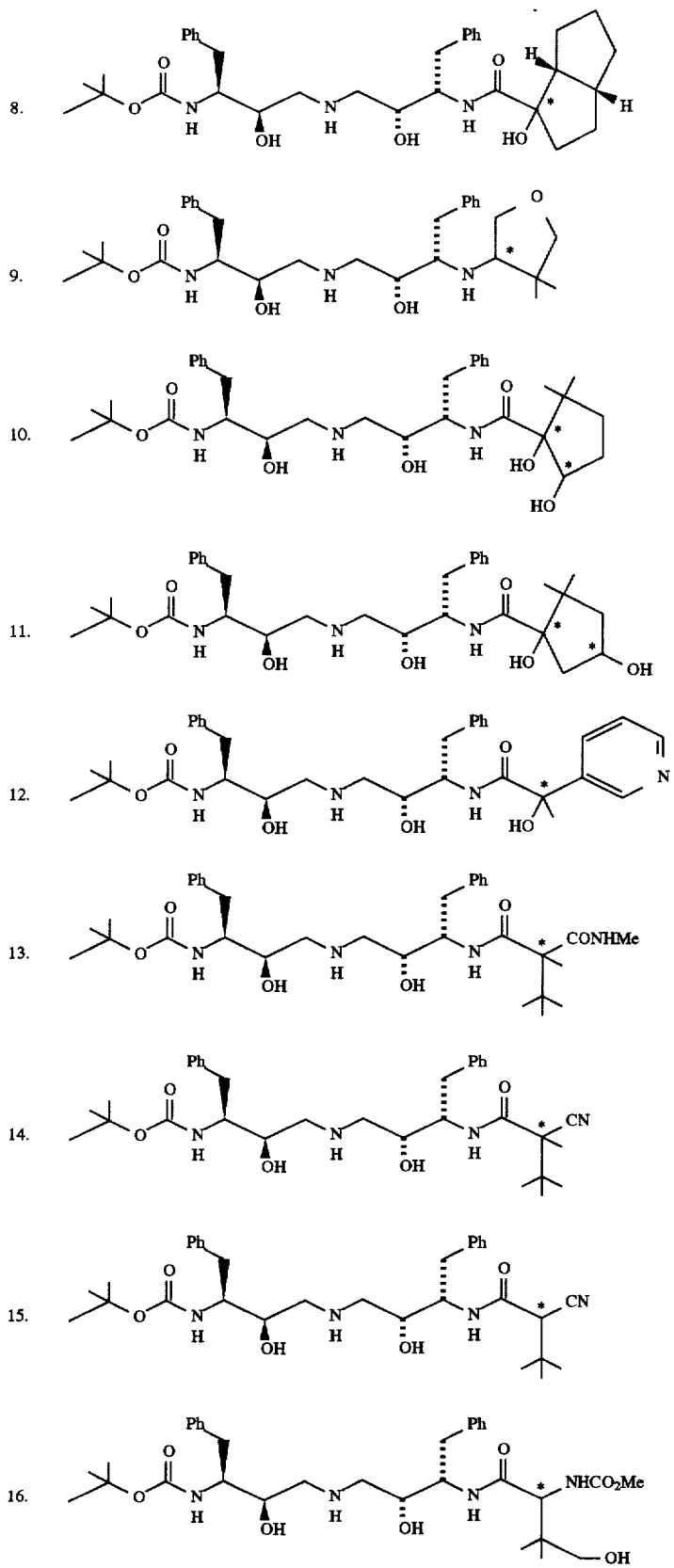

-continued

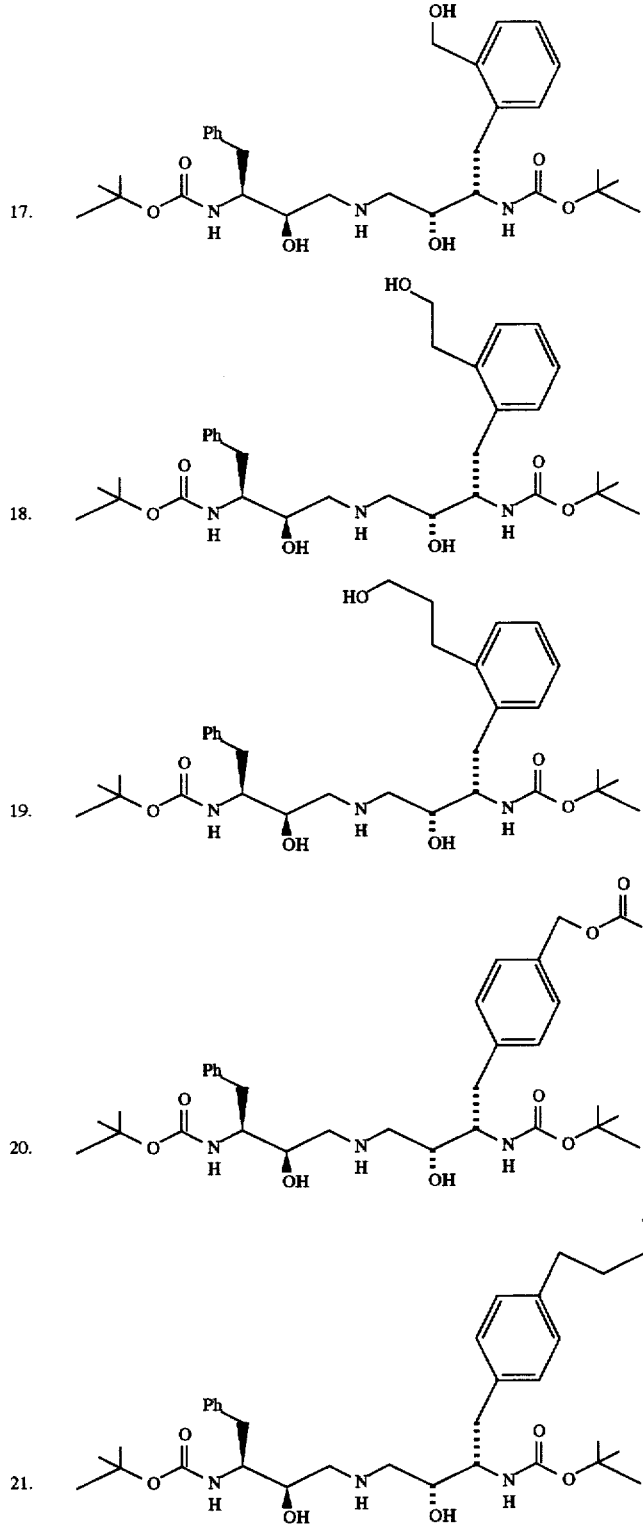

HIV Protease Assay

An HIV protease standard assay was performed in a 60 μl reaction medium containing 50 mM sodium acetate, pH 5.5, 100 μg/ml bovine serum albumen,450 μM substrate ($H_2N$-Val-Ser-Gln-Asn-(β-naphthyl-alanine)-Pro-Val-Ile-OH), and purified protease. The reaction medium was incubated for 30 minutes at 37° C., quenched by the addition of 140 μl 5% $H_3PO_4$, then analyzed by reverse phase HPLC using $UV_{220}$ detection. In a typical control assay, 7% of the substrate was hydrolyzed. Aminediol inhibitors of the present invention, listed in the following Table 1, were then employed in the assay, for which purpose they were prepared as a 0.5 mM solution in DMSO, then diluted to 30 μM with 50 mM sodium acetate/bovine serum albumen. This working stock was then diluted three-fold into the protease reaction medium, for a final concentration of 10 μM inhibitor and 4% DMSO. The results obtained from the assay are shown in the following Table 1.

Cell Culture Anti-HIV Activity

The antiviral activity of aminediol inhibitors of the present invention was evaluated by a microculture method which determines the increase in cell viability of an infected culture when a drug is added. The assay depends on the metabolic reduction of tetrazolium reagent by viable cells to yield a soluble colored formazan product.

The assay was performed as follows: suspensions of CEM-SS cells (5000/well) were infected with the RF strain of HIV at a multiplicity of infection at 0.04 in a 96-well plate. The compounds of the present invention listed in the following Table 1, serially diluted in half-log fashion, were added to the infected and uninfected control cells. Untreated (infected and uninfected) cells were included as controls. Following incubation for 6 days at 37° C., viable cells in each well were quantitated by the visible light absorbance at 450 nm.

The $IC_{50}$ was calculated as the concentration of drug that increased the formazan production in virally infected cells to 50% of that produced by uninfected cells in the absence of drug. The results obtained in the assay are shown in the following Table 1.

TABLE 1

| Compound | HIV Protease % Inhibition at 10 μM | HIV (CEM Cells) $IC_{50}$ (μM) |
|---|---|---|
| 2 | 100 | 0.09 |
| 3 | 0 | >3.2 |
| 5 | 41 | 2.8 |
| 7 | 8 | ND |
| 8 | 2 | ND |
| 10 | 1 | ND |
| 11 | 0 | >6 |
| 12 | 1 | ND |
| 13 | 45 | 5.3 |
| 14 | 100 | 1.1 |
| 15 | 98 | 0.38 |
| 16 | 83 | ≧2.3 |
| 17 | 84 | >1.5 |
| 21 | 99 | 0.09 |
| 22 | 90 | >1.8 |
| 23 | 98 | 0.45 |
| 24 | 78 | 4.5 |
| 25 | 98 | 0.53 |
| 26i | 57 | ND |
| 26ii | 41 | ND |
| 27 | 19 | ND |
| 28 | 100 | 0.09 |
| 29 | 100 | 0.1 |
| 30 | 97 | 0.5 |
| 31 | 100 | 0.03 |
| 34 | 20 | >9 |
| 36 | 36 | >8 |
| 38 | 3 | >4 |
| 42 | 100 | 0.6 |
| 43 | 21 | ND |
| 44 | 58 | >5 |
| 45 | 87 | 0.5 |
| 47 | 81 | 1.1 |
| 50 | 97 | 0.22 |
| 52 | 100 | 0.2 |
| 53 | 99 | 0.54 |
| 55 | 91 | 0.7 |
| 56 | 47 | ND |

TABLE 1-continued

| Compound | HIV Protease % Inhibition at 10 μM | HIV (CEM Cells) $IC_{50}$ (μM) |
|---|---|---|
| 57 | 46 | ND |
| 58 | 57 | 1.0 |
| 59 | 45 | ND |
| 60 | 78 | 1.2 |
| 62 | 98 | 0.05 |
| 63 | 53 | ND |
| 64 | 72 | >5 |
| 65 | 11 | ND |
| 66 | 99 | 0.27 |
| 67 | 100 | 0.04 |
| 68 | 99 | 0.11 |
| 69 | 11 | ND |
| 70 | 100 | 0.5 |
| 71 | 58 | 1.2 |
| 72 | 51> | 3.2 |
| 73 | 99 | 0.6 |
| 75 | 100 | 5.0 |
| 76 | 100 | 0.6 |
| 77 | 99 | 0.2 |
| 78 | 99 | 0.16 |
| 79 | 99 | 0.4 |
| 80 | 98 | 0.3 |
| 82 | 94 | >3 |
| 83 | 19 | ND |
| 84 | 99 | 1.2 |
| 86 | 78 | 1.8 |
| 87 | 92 | >0.88 |
| 88 | 100 | 0.03 |
| 89 | 23 | ND |
| 92 | 100 | 39 |
| 93 | 100 | 0.18 |
| 94 | 80–99 | ND |
| 96 | 100 | >7.6 |
| 98 | 100 | 1.3 |
| 99 | 99 | >100 |
| 100 | 99 | 0.23 |
| 101 | 99 | 0.14 |
| 102 | 47 | ND |
| 103 | 98 | 1.7 |
| 104 | 99 | 0.03 |
| 105 | 99 | 1.6 |
| 106 | 71 | ND |
| 112 | 100 | >8.6 |
| 115 | 58 | ND |
| 117 | 14 | ND |
| 119 | 10 | ND |
| 121 | 73 | >0.3 |
| 123 | 65 | 1.0 |
| 125 | 71 | >1.5 |
| 127 | 15 | ND |
| 132 | 65 | >3 |
| 134 | 87 | >5 |
| 136 | 73 | ND |
| 137 | 92 | >2.6 |
| 138 | 98 | >0.8 |
| 139 | 73 | ND |
| 140 | 61 | ND |
| 141 | 77 | >2.3 |
| 142 | 30 | ND |
| 144 | 88 | 1.0 |
| 145 | 95 | >2.2 |
| 146 | 98 | ≧3.0 |
| 148 | 88 | 2.0 |
| 150 | 93 | >4.0 |
| 153 | 65 | >0.55 |
| 154 | 96 | >1.2 |
| 155 | 95 | >0.2 |
| 156 | 85 | >6.0 |
| 157 | 90 | ND |
| 158 | 97 | >1.8 |
| 159 | 100 | 1.3 |
| 160 | 99 | 0.08 |
| 164 | 99 | 0.04 |
| 165 | 100 | 0.62 |
| 166 | 89 | 1.7 |
| 167 | 97 | >1.8 |

TABLE 1-continued

| Compound | HIV Protease % Inhibition at 10 µM | HIV (CEM Cells) IC$_{50}$ (µM) |
|---|---|---|
| 168 | 61 | 1.4 |
| 169 | 97 | 0.2 |
| 170 | 100 | 0.1 |
| 171 | 99 | 0.05 |
| 175 | 99 | 0.03 |
| 178 | 99 | 0.03 |
| 179 | 99 | 0.17 |
| 180 | 73 | ND |
| 181 | 46 | ND |
| 182 | 41 | ND |
| 183 | 35 | ND |
| 184 | 99 | 1.3 |
| 185 | 5 | ND |
| 186 | 0 | ND |
| 187 | 28 | ND |
| 188 | 21 | ND |
| 189 | 23 | ND |
| 190 | <16 | ND |
| 191 | 13 | ND |
| 192 | 85 | ND |
| 193 | 66 | ND |
| 194 | 0 | >5.0 |
| 195 | 0 | ND |
| 196 | 6 | ND |
| 197 | 10 | >10 |
| 198 | 10 | >14 |
| 199 | 3 | >17 |
| 200 | 5 | >15 |
| 201 | 99 | 0.04 |
| 202 | 95 | 16 |
| 203 | 98 | 0.2 |
| 204 | 99 | 0.17 |
| 205 | 98 | 0.07 |
| 209 | 99 | 0.03 |
| 210 | 81 | >5 |
| 211 | 99 | 0.9 |
| 212 | 99 | 3.8 |
| 213 | 98 | 0.17 |
| 214 | 97 | 0.05 |
| 215 | 66 | ND |
| 216 | 49 | ND |
| 217 | 100 | 0.48 |
| 218 | 96 | 1.1 |
| 219 | 86 | 35 |
| 220 | 100 | 0.77 |
| 221 | 96 | 1.1 |
| 222 | 98 | 0.38 |
| 223 | 89 | 1.4 |
| 224 | 98 | 0.04 |
| 225 | 99 | 0.5 |
| 226 | 98 | 0.05 |
| 227 | 99 | 0.9 |
| 228 | 98 | 0.7 |
| 229 | 82 | 0.6 |
| 230 | 92 | 4.9 |
| 231 | 83 | ND |
| 232 | 99 | 0.05 |
| 233 | 100 | 1.0 |
| 234 | 100 | 0.08 |
| 235 | 97 | 0.35 |
| 236 | 89 | 0.7 |
| 237 | 54 | ND |
| 238 | 64 | 2.3 |
| 239 | 37 | ND |
| 240 | 99 | 2.0 |
| 241 | 95 | 0.28 |
| 242 | 99 | 0.11 |
| 243 | 99 | 0.08 |
| 244 | 100 | 1.5 |
| 245 | 100 | 1.8 |
| 246 | 100 | 0.04 |
| 247 | 99 | 0.1 |
| 248 | 99 | 0.23 |
| 249 | 100 | 0.84 |
| 250 | 100 | 1.5 |
| 251 | 98 | ND |
| 252 | 99 | 0.06 |
| 253 | 85 | ND |
| 254 | 98 | 17 |
| 255 | 86 | ND |
| 256 | 88 | 1.5 |
| 257 | 99 | 0.03 |
| 258 | 91 | 1.5 |
| 259 | 99 | 5.0 |
| 260 | 100 | 0.29 |
| 261 | 94 | 1.1 |
| 262 | 100 | 0.03 |
| 263 | 98 | 0.34 |
| 264 | 99 | 0.16 |
| 265 | 100 | 2.6 |
| 266 | 69 | ND |
| 267 | 97 | 0.18 |
| 268 | 94 | ND |
| 269 | 61 | ND |
| 270 | 27 | ND |
| 271 | 99 | 0.06 |
| 272 | 87 | ND |
| 273 | 100 | 1.7 |
| 274 | 99 | ND |
| 275 | 95 | 0.45 |
| 276 | 97 | 0.13 |
| 277 | 67 | ND |
| 278 | 94 | 0.84 |
| 279 | 54 | ND |
| 280 | 100 | 0.05 |
| 281 | 100 | 0.29 |
| 282 | 100 | 0.06 |
| 283 | 100 | 0.11 |
| 284 | 100 | 4.4 |
| 285 | 100 | 0.65 |
| 286 | 99 | 5.0 |
| 287 | 89 | ND |
| 288 | 100 | 0.47 |
| 289 | 53 | ND |
| 290 | 99 | 0.06 |
| 291 | 73 | ND |
| 292 | 99 | 0.17 |
| 293 | 99 | 0.03 |
| 294 | 89 | ND |
| 295 | 82 | ND |
| 296 | 37 | ND |
| 297 | 100 | 0.05 |
| 298 | 100 | 0.06 |
| 299 | 99 | 0.24 |
| 300 | 99 | 0.03 |
| 301 | 95 | 2.4 |
| 302 | 99 | 0.25 |
| 303 | 98 | 0.07 |
| 304 | 99 | 0.03 |
| 305 | 100 | 0.2 |
| 306 | 100 | 0.06 |
| 308 | 100 | 0.02 |
| 309 | 100 | 1.8 |
| 310 | 100 | 0.18 |
| 311 | 100 | 0.05 |
| 312 | 95 | 3.5 |
| 313 | 65 | ND |
| 314 | 100 | 0.12 |
| 315 | 100 | 1.6 |
| 316 | 97 | 0.62 |
| 317 | 85 | ND |
| 318 | 100 | 0.1 |
| 319 | 93 | 1.37 |
| 320 | 100 | 0.22 |
| 321 | 100 | 0.2 |
| 322 | 100 | 0.02 |
| 323 | 100 | 0.014 |
| 324 | 100 | 0.22 |
| 325 | 90 | 1.54 |
| 326 | 99 | 0.03 |
| 327 | 99 | 0.05 |
| 328 | 99 | 0.54 |

TABLE 1-continued

| Compound | HIV Protease % Inhibition at 10 μM | HIV (CEM Cells) IC$_{50}$ (μM) |
|---|---|---|
| 329 | 84 | ND |
| 330 | 92 | 0.85 |
| 331 | 99 | 0.06 |
| 332 | 100 | 0.07 |
| 333 | 100 | 0.15 |
| 334 | 99 | 0.05 |
| 335 | 89 | ND |
| 336 | 100 | 0.04 |
| 337 | 99 | 0.29 |
| 338 | 99 | 0.93 |
| 339 | 99 | 0.012 |
| 340 | 56 | ND |
| 341 | 99 | 2.1 |
| 342 | 99 | 0.07 |
| 343 | 99 | 0.05 |
| 344 | 99 | 0.03 |
| 345 | 99 | 0.33 |
| 346 | 98 | >50 |
| 347 | 99 | 0.05 |
| 348 | 99 | ND |
| 349 | 98 | 0.37 |
| 350 | 98 | 0.5 |
| 351 | 99 | 0.08 |
| 352 | 99 | 0.1 |
| 353 | 98 | 1.1 |
| 354 | 99 | 0.12 |
| 355 | 99 | 0.07 |
| 356 | 99 | 0.12 |
| 357 | 99 | 0.11 |
| 358 | 99 | 0.1 |
| 359 | 99 | 0.56 |
| 360 | 96 | 0.45 |
| 361 | 97 | ND |
| 362 | 98 | ND |
| 363 | 99 | 0.04 |
| 364 | 98 | 0.22 |
| 365 | 72 | ND |
| 366 | 99 | 0.009 |
| 367 | 50 | ND |
| 368 | 98 | 0.017 |
| 369 | 96 | ND |
| 370 | 96 | ND |
| 371 | 98 | ND |
| 372 | 98 | ND |
| 373 | 85 | ND |
| 374 | 28 | ND |
| 375 | 98 | ND |
| 376 | 63 | ND |
| 377 | 95 | ND |
| 378 | 27 | ND |
| 379 | 98 | ND |
| 380 | 97 | ND |
| 381 | 60 | ND |
| 382 | 89 | ND |
| 383 | 99 | ND |
| 384 | 99 | ND |
| 385 | 99 | ND |

ND = Not Determined

What we claim is:

1. A compound of the following formula I, or a pharmaceutically acceptable salt thereof:

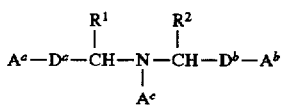

where

A$^c$ id hydrogen or alkyl;

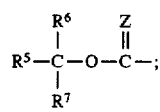

A$^a$ and A$^b$ are independently
where R$^5$, R$^6$ and R$^7$ are independently hydrogen, alkyl, aryl, carbocyclo, fluorenyl, alkynyl or alkenyl, and Z is oxygen or sulfur;

D$^a$ and D$^b$ are independently selected from groups of the formula:

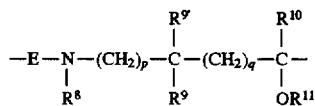

where D$^a$ and D$^b$ are bonded to the groups A$^a$ and A$^b$, respectively, through the moiety —E—N(R$^8$)—, where E is a single bond;

R$^1$ and R$^2$ are independently:
  (1) hydrogen;
  (2) alkyl;
  (3) alkenyl;
  (4) aryl; or
  (5) carbocyclo;

R$^8$ is:
  (a) hydrogen; or
  (b) alkyl;

R$^9$ in one of D$^a$ or D$^b$ is:
  (a) hydrogen;
  (b) alkyl;
  (c) alkenyl;
  (d) alkynyl;
  (e) aryl;
  (f) carbocyclo; or
  (g) arylalkyl;

and, in the other of D$^a$ or D$^b$, R$^9$ is alkyl substituted by aryl, where said aryl is itself substituted by morpholinylcarbonylalkoxy or piperidinylcarbonylalkoxy;

R$^{9'}$ is:
  (a) hydrogen;
  (b) alkyl;
  (c) alkenyl;
  (d) alkynyl;
  (e) aryl; or
  (f) carbocyclo;

R$^{10}$ is:
  (a) hydrogen;
  (b) alkyl;
  (c) alkenyl;
  (d) alkynyl;
  (e) carbocyclo; or
  (f) aryl;

R$^{11}$ is:
  (a) hydrogen; or
  (b) a hydroxyl protecting group;

p and q are, independently, integers from 0 to 4;

the terms "alk" or "alkyl", where they appear alone or as part of another group, denote a straight or branched chain saturated radical containing 1 to 12 carbons in the normal chain;

the term "alkenyl" denotes a straight or branched chain radical containing 2 to 12 carbons in the normal chain which contains at least one carbon to carbon double bond and which is directly attached through one of the carbons composing said double bond;

the term "alkynyl" denotes a straight or branched chain radical containing 2 to 12 carbons in the normal chain which contains at least one carbon to carbon triple bond and which is directly attached through one of the carbons composing said triple bond;

term "carbocyclo" denotes a saturated or partially unsaturated, homocyclic carbon ring system containing from 1 to 3 rings and from 3 to 12 carbons per homocyclic ring; and the term "aryl", where it appears alone or as part of another group, denotes a homocyclic, aromatic group containing 1 or 2 rings and from 6 to 12 carbons.

2. The compound of claim 1, wherein Z is oxygen; $R^5$ is hydrogen, carbocyclo, alkyl, aryl, or alkynyl; and $R^6$ and $R^7$ are hydrogen or alkyl.

3. The compound of claim 2, wherein $R^5$ is hydrogen, alkyl, or aryl, and $R^6$ and $R^7$ are hydrogen or lower alkyl.

4. The compound of claim 1, wherein $R^8$ is hydrogen.

5. The compound of claim 1, wherein p and q are zero.

6. The compound of claim 1, wherein one $R^9$ is alkyl, hydrogen, aryl, alkenyl, carbocyclo, or arylalkyl.

7. The compound of claim 6, wherein the other $R^9$ is alkyl substituted by aryl where said aryl is itself substituted by morpholinylcarbonylalkoxy.

8. The compound of claim 1, wherein $R^{9'}$ is hydrogen.

9. The compound of claim 1, wherein $R^{10}$ is hydrogen or lower alkyl.

10. The compound of claim 9, wherein $R^{10}$ is hydrogen.

11. The compound of claim 1, wherein $R^{11}$ is hydrogen, alkoxyalkyl, or lower alkyl.

12. The compound of claim 11, wherein $R^{11}$ is hydrogen.

13. The compound of claim 1, wherein $R^1$ and $R^2$ are hydrogen.

14. The compound of claim 1, wherein $A^c$ is hydrogen.

15. The compound of claim 1, wherein said compound is selected from the group consisting of [1S-[1R*,2S*,(2S*,3R*)]]-[3-[[3-[[(1,1-dimethylethoxy)carbonyl]amino]-2-hydroxy-4-(4-[2-(4-morpholinyl)-2-oxo-ethoxy]phenyl]butyl]amino]-2-hydroxy-1-(phenylmethyl)propyl]carbamic acid, 1,1-dimethylethyl ester and pharmaceutically acceptable salts thereof.

16. A pharmaceutical composition for the inhibition of HIV protease, comprising a compound of claim 1 in an amount effective therefor, and a pharmaceutically acceptable vehicle or diluent.

* * * * *

UNITED STATES PATENT AND TRADEMARK OFFICE
CERTIFICATE OF CORRECTION

PATENT NO. : 5,760,036

DATED : June 2, 1998

INVENTOR(S) : Eric M. Gordon et al.

It is certified that error appears in the above-identified patent and that said Letters Patent is hereby corrected as shown below:

```
On the title page, first column, item "[75] Inventors", "Chong-Oing"
   should read --Chong-Qing--.
Column 413, line 58, "ceuticlly" should read --ceutically--.
Column 414, lines 1 to 8, "A^C id hydrogen...are independently" should
   read  -- A^C is hydrogen or alkyl;

A^a and A^b are independently
```
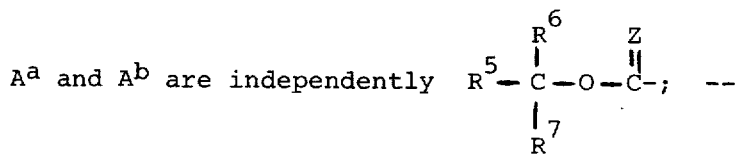

Signed and Sealed this

Fifteenth Day of September, 1998

Attest:

BRUCE LEHMAN

*Attesting Officer*   *Commissioner of Patents and Trademarks*